(12) United States Patent
Chou et al.

(10) Patent No.: US 12,226,769 B2
(45) Date of Patent: *Feb. 18, 2025

(54) SAMPLE MANIPULATION AND ASSAY WITH RAPID TEMPERATURE CHANGE

(71) Applicant: Essenlix Corporation, Monmouth Junction, NJ (US)

(72) Inventors: Stephen Y. Chou, Princeton, NJ (US); Wei Ding, East Windsor, NJ (US); Ji Qi, Skillman, NJ (US); Hua Tan, Princeton Junction, NJ (US); Yufan Zhang, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/121,534

(22) Filed: Mar. 14, 2023

(65) Prior Publication Data

US 2023/0219084 A1 Jul. 13, 2023

Related U.S. Application Data

(63) Continuation of application No. 16/772,396, filed as application No. PCT/US2018/065297 on Dec. 12, (Continued)

(51) Int. Cl.
*B01L 3/00* (2006.01)
*B01L 7/00* (2006.01)
*C12Q 1/686* (2018.01)

(52) U.S. Cl.
CPC .......... *B01L 3/502715* (2013.01); *B01L 7/52* (2013.01); *C12Q 1/686* (2013.01);
(Continued)

(58) Field of Classification Search
CPC ................ B01L 3/502715; B01L 7/52; B01L 2200/021; B01L 2200/10;
(Continued)

(56) References Cited

U.S. PATENT DOCUMENTS 3,368,872 A 2/1968 Natelson
3,447,863 A 6/1969 Patterson
(Continued)

FOREIGN PATENT DOCUMENTS

AU 198813789 A 9/1988
AU 619459 B 1/1992
(Continued)

OTHER PUBLICATIONS

International Report on Patentability for PCT/US18/65297 established by IPEA/US mailed on Feb. 7, 2020.

*Primary Examiner* — Liban M Hassan

(57) ABSTRACT

The disclosure relates to a device and method of using the device for performing biological and chemical assays that require an easy sample manipulation and/or a rapid change or a rapid thermal cycling of a sample temperature (e.g., Polymerase Chain Reaction (PCR) for amplifying nucleic acids). The device includes a first plate, a second plate, a plurality of spacers, and at least one clamp. The method includes obtaining the device, depositing a sample onto a sample contact area of at least one of the first and second plates of the device in an open configuration, closing the two plates into a closed configuration and placing the clamp in the active mode, and rapidly changing the temperature of the sample portion encircled by rings.

24 Claims, 50 Drawing Sheets

A. Before Clamp Activation

B. After Clamp is Activated

Related U.S. Application Data 2018, now Pat. No. 11,648,551, which is a continuation of application No. PCT/US2018/034230, filed on May 23, 2018, and a continuation of application No. PCT/US2018/018405, filed on Feb. 15, 2018, and a continuation of application No. PCT/US2018/018108, filed on Feb. 14, 2018, and a continuation-in-part of application No. PCT/US2018/017307, filed on Feb. 7, 2018.

(60) Provisional application No. 62/772,597, filed on Nov. 28, 2018, provisional application No. 62/597,851, filed on Dec. 12, 2017.

(52) U.S. Cl.
CPC ..... *B01L 2200/021* (2013.01); *B01L 2200/10* (2013.01); *B01L 2300/0816* (2013.01); *B01L 2300/123* (2013.01); *B01L 2300/1805* (2013.01)

(58) Field of Classification Search
CPC ....... B01L 2300/0816; B01L 2300/123; B01L 2300/1805; B01L 2200/025; B01L 2200/0642; B01L 2200/0689; B01L 2300/0851; B01L 2400/0655; B01L 3/502738; C12Q 1/686
See application file for complete search history.

(56) References Cited

U.S. PATENT DOCUMENTS

| | | | |
|---|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |

(56) References Cited

U.S. PATENT DOCUMENTS

| | | |
|---|---|---|
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2003/0215810 A1 | 11/2003 | Lu et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | | |
|---|---|---|---|
| CN | 1299466 | 6/2001 | |
| CN | 1302229 | 7/2001 | |
| CN | 1166950 | 9/2004 | |
| CN | 1188217 | 2/2005 | |
| CN | 102027369 | 4/2011 | |
| EP | 261667 A2 | 3/1988 | |
| EP | 291153 A1 | 11/1988 | |
| EP | 261667 A3 | 5/1989 | |
| EP | 291153 B1 | 6/1992 | |
| EP | 261667 B1 | 2/1993 | |
| EP | 0961110 | 12/1999 | |
| EP | 1949310 A2 | 7/2008 | |
| EP | 2290100 | 3/2011 | |
| EP | 1949310 A4 | 11/2011 | |
| EP | 2439515 | 4/2012 | |
| EP | 2554987 | 2/2013 | |
| EP | 3026433 | 6/2016 | |
| EP | 1949310 B1 | 2/2019 | |
| WO | 1991020009 | 12/1991 | |
| WO | 1999044743 | 9/1999 | |
| WO | 1999045385 | 9/1999 | |
| WO | 2002023154 A2 | 3/2002 | |
| WO | 2003062920 | 7/2003 | |
| WO | 2005114145 | 12/2005 | |
| WO | 2005100539 | 1/2006 | |
| WO | 2007112332 | 10/2007 | |
| WO | 2009117652 | 9/2009 | |
| WO | 2009117664 | 9/2009 | |
| WO | 2009117678 | 9/2009 | |
| WO | 2009117682 | 9/2009 | |
| WO | 2009124186 | 10/2009 | |
| WO | 2009124190 | 10/2009 | |
| WO | 2009126800 | 10/2009 | |
| WO | 2010115026 | 10/2010 | |
| WO | 2014055559 | 4/2014 | |
| WO | 2014089468 | 6/2014 | |
| WO | 2014183049 | 11/2014 | |
| WO | 2014205576 | 12/2014 | |
| WO | WO-2017027643 A1 * | 2/2017 | ............ B01L 3/502 |
| WO | 2017048871 | 3/2017 | |
| WO | 2017048871 A1 | 3/2017 | |
| WO | 2019027963 A1 | 2/2019 | |

* cited by examiner

A. Before Clamp Activation

B. After Clamp is Activated

Top View of the Ring Clamp Jaw

Circular Shaped Ring Clamp Jaw

Rectangle Shaped Ring Clamp Jaw

A. Before Clamp Activation

B. After Clamp is Activated

A. Before Clamp Activation

B. After Clamp is Activated

A. Before Clamp Activation

B. After Clamp is Activated

A. One-spring clamping structure

B. Four-spring clamping structure

10: first plate
20: second plate
100: sample holder
90: fluidic sample
112-1: heating layer
112-2: cooling layer
910: heated volume

- 10: first plate
- 20: second plate
- 100: sample holder
- 90: fluidic sample
- 112: heating/cooling layer
- 115: heating zone
- 910: heated volume
- 210: radiation from heating source

- 10: first plate
- 20: second plate
- 21: inner surface
- 22: outer surface
- 90: fluidic sample
- 102: spacing (i.e. gap) between the two plates
- 112: heating/cooling layer
- 109: first plate thickness
- 209: second plate thickness A. Before clamp activation B. After the clamp is activated A. Before clamp activation B. After the clamp is activated A. Before clamp activation B. After the clamp is activated A. Before clamp activation B. After the clamp is activated A. One-spring clamping structure B. Four-spring clamping structure 10: first plate
20: second plate
100: sample holder
90: fluidic sample
112-1: heating layer
112-2: cooling layer
910: heated volume 10: first plate
20: second plate
100: sample holder
90: fluidic sample
112: heating/cooling layer
115: heating zone
910: heated volume
210: radiation from heating source 10: first plate
20: second plate
21: inner surface
22: outer surface
90: fluidic sample
102: spacing (i.e. gap) between the two plates
112: heating/cooling layer
109: first plate thickness
209: second plate thickness

SAMPLE MANIPULATION AND ASSAY WITH RAPID TEMPERATURE CHANGE

CROSS-REFERENCING

This application is a continuation of U.S. non-provisional application Ser. No. 16/772,396, filed on Jun. 12, 2020, which is a National Stage entry (§ 371) application of International Application No. PCT/US18/65297, filed on Dec. 12, 2018 and issued as U.S. patent Ser. No. 11/648,551 on May 16, 2023, which claims the benefit of U.S. Provisional Patent Application No. 62/597,851 (ESX-014PRV5), filed on Dec. 12, 2017, U.S. Provisional Patent Application No. 62/772,597 (ESX-014-PRV6), filed on Nov. 28, 2018, International Application No. PCT/US2018/017307 (ESXPCT18F15A), filed on Feb. 7, 2018, International Application No. PCT/US2018/018108 (ESXPCT18F14), filed on Feb. 14, 2018, International Application No. PCT/US2018/018405 (ESXPCT18F19), filed on Feb. 15, 2018, International Application No. PCT/US2018/028784 (ESXPCT18AP21), filed on Apr. 23, 2018, and International Application No. PCT/US2018/034230 (ESXPCT18MY22), filed on May 23, 2018, the contents of which are relied upon and incorporated herein by reference in their entirety.

The entire disclosure of any publication or patent document mentioned herein is entirely incorporated by reference.

FIELD

Among other things, the present invention is related to devices and methods of performing biological and chemical assays, particularly an easy sample manipulation and/or a rapid change or a rapid thermal cycling of a sample temperature is needed (e.g. Polymerase Chain Reaction (PCR) for amplifying nucleic acids).

BACKGROUND

In certain chemical, biological, or medical assays, an easy sample manipulation and/or a rapid change or a rapid thermal cycling of a sample temperature is needed (e.g. Polymerase Chain Reaction (PCR) for amplifying nucleic acids).

In certain situation, one would like to quickly isolate a part of the fluidic sample from the rest to do analysis. During thermal cycling, a liquid sample will change in its volume with temperature, and this can cause liquid sample flow between the sample area being heated and the sample area not being heated. Such liquid sample flow can change the sample temperature and increase the time and energy needed to do thermal cycling. Therefore, there is a need to reduce the liquid sample flow during thermal cycling.

One objective of the present invention is to address how to quickly isolate a part of the fluidic sample from the rest to do analysis.

Another objective of the present invention is to address the need to reduce the liquid sample flow between two different temperature areas during thermal cycling. The present invention additionally provides devices and methods for isothermal nucleic acid amplification.

SUMMARY OF INVENTION

The following brief summary is not intended to include all features and aspects of the present invention.

The present invention provides, among other things, the devices and methods that can rapidly change or cycle (i.e. heating and cooling) a sample temperature with high speed, less heating energy, high energy efficiency, a compact and simplified apparatus (e.g. handheld), easy and fast operation, and/or low cost.

The present invention has experimentally achieved a cycling of a sample temperature between 95° C. and 55° C.) in a second or less.

The invention has six novel aspects (1) the devices and methods that allow fast thermal cycling, (2) the devices and methods that allow the sample thickness uniform and sample holder mechanically stable for handling, (3) simple operation, (3) devices and methods for doing real time PCR (4) biochemistry, and (5) smartphone based systems.

To rapid thermal cycle the temperature of a sample or a portion of it, one must reduce the thermal mass and lateral heat.

Radiative heating and cooling are preferred.

BRIEF DESCRIPTION OF THE DRAWINGS

The skilled artisan will understand that the drawings, described below, are for illustration purposes only. The drawings are not intended to limit the scope of the present teachings in any way. In some cases, the drawings are not in scale. In the figures that present experimental data points, the lines that connect the data points are for guiding a viewing of the data only and have no other means.

FIG. 16A illustrates the system before the clamping structure is activated, where the two rings of the clamp are open and hence do not exert a force to push the two plates together. FIG. 16(B) illustrates that the clamp is activated, where a force is applied by the clamping structure to pinch the sample holder area that is pressed by the clamp.

FIG. 18A illustrates the system before the ring clamping structure is activated, where the two rings of the clamp do not assert a force to push the two plates together. FIG. 18B illustrates the system after a force is applied by the clamping structure.

FIG. 19A) illustrates the system before the clamping structure is activated. FIG. 19B illustrates the system after a force is applied by the clamping structure.

FIG. 20A illustrates the system before the clamping structure is activated. FIG. 20B illustrates the system after a force is applied by the clamping structure.

FIG. 21A comprises a support with a one-spring ring structure. FIG. 21B comprises a support with a four-spring ring structure.

DETAILED DESCRIPTION OF EXEMPLARY EMBODIMENTS

Figure 1A:
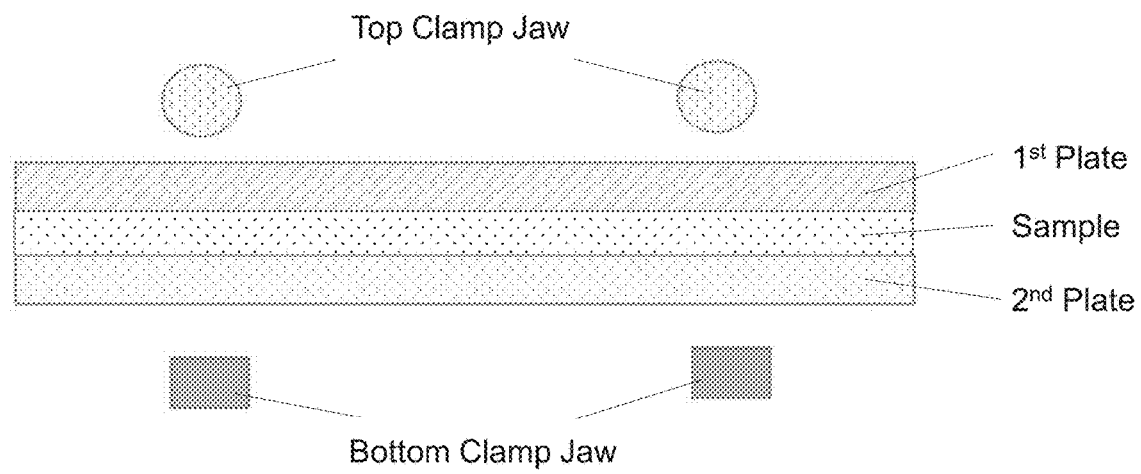
FIG. 1A shows a sectional view of an embodiment of the system of the present invention, comprising a sample holder and a clamping structure. The active clamp. Panel (A) illustrates the system before the clamping structure is activated, where the two rings of the clamp are open and hence does not assert a force to push the two plate together. Panel (B) illustrates that the clamp is activated, where a force is applied by the clamping structure to pinch the sample holder area that is pressed by the claim.
Figure 1A:
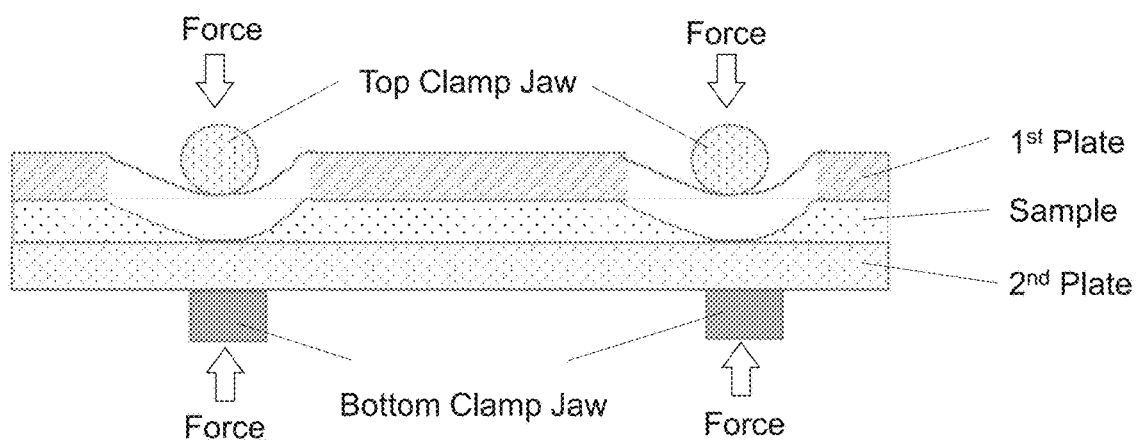

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

The term "sample thermal cycler" or "thermal cycler" refers an apparatus that can raise and cool temperature of a sample, and can, if needed, to repeatedly heat and cool a sample between two temperatures.

The term "sample thermal cycling" or "thermal cycling" refers to a repeatedly raising and cooling temperature of a sample.

The term "a sample thermal cycle" or "a thermal cycle" refers to a cycle that raises the sample temperature to a higher temperature and then cool it back to the original temperature.

The term "sample thermal cycling time" or "thermal cycling time" refers the time for performing a given numbers of thermal cycle.

The term "sample thermal cycling speed" or "thermal cycling speed" refers the speed for performing thermal cycle.

The term "thermal mass" of a material refers to the energy needed to heat up the temperature of that material by one degree when there is no other energy loss. Hence the thermal mass of a material is equal to the specific heat per unit volume multiplies the volume of the material.

The term "thermal conductivity-to-capacity ratio" refers the ratio of the thermal conductivity of a material to its thermal capacity. For examples, at about room temperature, the thermal conductivity-to-capacity ratio is 1.25 $cm^2$/sec (centimeter-square/second) for gold and $1.4 \times 10^{-3}$ $cm^2$/sec for water.

The term "wasted energy" refers the energy supplied to a sample holder that is not used to directly heat the relevant sample.

The terms "a" and "an", as used herein, unless clearly indicated to the contrary, should be understood to mean "at least one".

The term "about," as used herein, generally refers to a range that is 15% greater than or less than a stated numerical value within the context of the particular usage. For example, "about 10" would include a range from 8.5 to 11.5.

The term "sample holder support" refers to a device that a sample holder is physically attached to the device and mechanically supported by the device.

The term "disposable", as used herein, generally refers to devices which are designed to be discarded after a limited use (e.g., in terms of number of reactions, thermal cycles, or time) rather than being reused indefinitely.

The term "nucleic acid amplification" refers to the production of one or more replicate copies of an existing nucleic acid.

The term "nucleic acid amplification cycle" refers to a complete set of steps used to perform a single round of nucleic acid amplification.

The term "template" refers to a nucleic acid that is amplified.

The term "amplification product" refers to replicate copies of an existing nucleic acid produced during nucleic acid amplification from a template.

The term "black paint" refers to a paint that has a black color to human eye when under a day light illumination.

The term "cooling gas" or "cooling liquid" refers to a gas or liquid phase, respectively, which is used to remove thermal energy, for example, from a sample, from a sample holder, from a material, or from a region.

The term "mechanical contact", as used herein, generally refers to contact made between one or more materials wherein the materials are physically touching.

The term "thermal path" refers to the distance through which thermal energy transfers from one location to another location.

The term "relevant sample" or "relevant sample volume" refers to the volume of the sample that is being heated and/or cooled to desired temperatures during a thermal cycling, and the relevant sample can be a portion or an entire volume of a sample on a sample holder, and there is no fluidic separation between the a portion of the sample to the rest of the sample.

The term "high-K material" refers to a material that has a thermal conductivity (K) equal to or larger than 50 W/(m·K) (e.g. gold: ~314 W/(m·K) and graphite ~80 W/(m·K) are high-K material).

The term "low-K material" refers to a material that has a thermal conductivity (K) equal to or less than 1 W/(m·K) (e.g. water (~0.6 W/(m·K)) and plastic (~0.2 W/(m·K)) are low-K material).

The terms "cooling time in a thermal cycle" and "cooling cycle time" are interchangeable.

The terms "heating time in a thermal cycle" and "heating cycle time" are interchangeable.

The term "heating zone" refers to (a) the heating layer when the heating layer is a separate layer from the cooling layer; or (b) the area of heating when the heating and the cooling use the same layer; the heating zone is being directly heated by a heating source.

The term "directly heated" means that an energy being put into that area. For example, for a heating zone by a LED heating source, the LED heating source projects a light over the heating zone. For a heating zone by an electrical heating source, the electrical hearing source sends an electrical current to the heating zone to create heat in the heating zone.

The term "cooling zone" refers to (a) the cooling layer when the cooling layer is a separate layer from the heating layer; or (b) the area of cooling when the cooling and the heating use the same layer. A cooling zone, unless stated otherwise, comprises a material of a thermal conductivity of 50 W/m- or larger.

The term "a heating layer is heated by a heating source" means that "a heating layer or a heating zone of a heating/cooling layer is heated a heating source".

The term "non-sample material" refers to the materials on a sample holder that are outside the relevant sample volume.

The term "wasted heating energy" refers to the energy that must be supplied to the non-sample materials and the non-relevant samples, in order to heat the relevant sample volume to a desired temperature.

The term "average linear dimension" of an area is defined as a length that equals to the area times 4 then divided by the perimeter of the area. For example, the area is a rectangle, that has width w, and length L, then the average of the linear dimension of the rectangle is 4*W*L/(2*(L+W)) (where "*" means multiply and "/" means divide). By this definition, the average line dimension is, respectively, W for a square of a width W, and d for a circle with a diameter d.

The term "lateral" refers to the direction that is parallel to the plates of a sample holder.

The term "vertical" refers to the direction that is normal to the plates of a sample holder.

The term "period" of periodic structure array refers to the distance from the center of a structure to the center of the nearest neighboring identical structure.

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "heating layer", or "heating zone", unless stated otherwise, refers to a material layer that comprises at least a layer of a material that has a thermal conductivity of 50 W/m-K or larger.

The term "heating volume" refers to the volume of a material to be heated.

The term "cooling layer" refers to a thermal radiative cooling layer with a high thermal conductivity and has a large surface thermal radiation capability that is at least 50% of that of a blackbody.

The term "lateral dimension" or "lateral area" of the sample inside the sample holder for heating and cooling, refers lateral dimension or lateral area of the portion of the sample that is being heated to a desired temperature.

The term "plate" refers to a plate this is free standing, except that when two plates are in a "closed configuration" where the two plates are close together and separated by spacers (in this case the pair of the plates are free standing). The term of "free standing" means that the center region of the plate is free of any support. For example, when two plates are in a closed configuration and the sample is between the plate. The central region of the plate pair has no mechanical support, only air touches the outside surface of the plates.

The term "clamp" and "clamping structure" are used interchangeable herein.

I. Sample Manipulation and Assay with Rapid Temperature Change

The present invention provides, among other things, devices and methods to (a) quickly isolate a part of the fluidic sample from the rest to do analysis, and (b) improve the time and energy needed in thermal cycling of a liquid sample by reducing the flow of the liquid sample from the inside to the outside of a thermal cycling sample area.

In certain chemical, biological, or medical assays, a rapid change or a rapid thermal cycling of a sample temperature is needed (e.g. Polymerase chain reaction (PCR) for amplifying nucleic acids).

During thermal cycling, a liquid sample will change in its volume with temperature, and this can cause liquid sample flow. Liquid sample flow can change the sample temperature and increase the time and energy needed to do thermal cycling. Therefore, there is a need to reduce the liquid sample flow during thermal cycling.

One objective of the present invention is to address the need to reduce the liquid sample flow during thermal cycling. The present invention additionally provides devices and methods for isothermal nucleic acid amplification.

A. Quickly Isolating a Portion of a Fluidic Sample

In certain embodiments of the present invention, a device for fluidically isolating a portion of a sample, comprising a first plate, a second plate, and a clamp, wherein:
 i, wherein one or both of the plates is flexible, wherein the plates sandwich a fluidic sample to be analyzed that has a thickness 200 um or less, and has a sample area at last 100 times larger than the sample thickness; and
 ii. the clamp comprises two jaws comprising a top ring and a bottom ring that are movable to each other; and
 iii. the clamp has two operation modes:
 (a) a non-active mode, wherein the top ring and the bottom ring of the clamp do not push the first plate and second plate together; and
 (b) an active mode, wherein the top ring and the bottom ring of the clamp apply force to squeeze the first plate and the second plate and deform the area of the flexible plates that is under the compression of the clamp, thereby reducing the spacing between the two plates in that area, and wherein the reduction of the plate spacing reduces or prevents a fluidic flow between a sample portion encircled by the rings and a sample portion outside the rings.

In certain embodiments of the present invention, device for fluidically isolating a portion of a sample, comprising a first plate, a second plate, spacers, and a clamp, wherein:
 i. the first plate and the second plate are movable relative to each other into different configurations, including an open configuration and a closed configuration, wherein one or both of the plates is flexible, wherein each of the plates comprises, on its respective surface, a sample contact area for contacting a fluidic sample, and wherein at a closed configuration the plates sandwich a sample to be analyzed, that has a thickness 200 um or less, and has an sample area at last 100 times larger than the sample thickness;
 ii. the spacers have a predetermined substantially uniform height that is equal to or less than 200 microns, wherein at least one of the spacers is inside the sample contact area; and
 iii. the clamp has two operation modes:
 (a) a non-active mode, wherein the top ring and the bottom ring of the clamp do not push the first plate and second plate together; and
 (b) an active mode, wherein the top ring and the bottom ring of the clamp are configured to insert force to squeeze the first plate and the second plate and deform the area of the flexible plates that is under the compression of the clamp, thereby reducing the spacing between the two plates in that area, and wherein the reduction of the plate spacing reduces or prevents a fluidic flow between a sample portion encircled by the rings and a sample portion outside the rings.
 wherein in the open configuration the two plates are partially or completely separated apart, the spacing between the plates is not regulated by the spacers, and the clamp is in non-active mode, and the sample is deposited on one or both of the plates;
 wherein in the closed configuration, at least a part of the sample deposited in the open configuration is compressed by the two plates into a layer of substantially uniform thickness, wherein the uniform thickness of the layer is regulated by the plates and the spacers.

One advantage of using a ring (i.e. encircled shape) is that once the rings are clamped on, due to a constant volume of the sample liquid, even the plate thickness is very thin (e.g. 20 um), the two plates will help keeping the spacing of the two plates constant.

Some of the principles of a clamp are shown in the figures. As show, the clamp has two operation modes: a non-active mode and an active mode. When the plates are in the open configuration the clamp is in the non-active mode. When the plates are in the closed configuration and the clamp is activated, the clamp is in the active mode.

In some embodiments, activation of the clamp reduces flow from inside of the clamp ring to outside of the clamp ring. As such, the clamp can be used to create an at least partially isolated reaction chamber in the device. In some embodiments, the device may contain several clamp rings, each capable of creating a separate reaction chamber. In some embodiments, each ring as multiple of smaller diameter rings, that isolate a sample into multiple pockets. For example, in some embodiments, a device may contain at least 2, at least 4, at least 8, at least 16, at least 32 or at least 64 or more top and bottom clamp rings, where the top rings are movable relative to the bottom rings and, when the plates are in the closed position, the rings oppose each other and pinch different areas of the device to produce multiple isolated reaction chambers.

The rings may be of any shape, e.g., circular, oval, rectangular, pentagonal, hexagonal, square, star, or any combination thereof with optional rounded corners. In some embodiments, the clamp ring has a shape of circular, elliptical, oval, rectangular, pentagonal, hexagonal, square, star, polygon, or any superposition of these shapes. In some embodiments, the clamp ring has a preferred shape of circular, elliptical, oval, or any superposition of these shapes.

The parts of the clamp that are in contact with the plate (the rings of the clamp) may have a cross-section of any shape and may be e.g., round, square, triangular, or rectangular with optional rounded corners, for example. As noted below, in some embodiments, the cross-section of the top ring may be of a different shape to the bottom ring. For example, in some embodiments, one of the rings may have a sharp edge that is contact with one of the plates and the other ring may have a flat area in contact with the plates. In this configuration, activation of the clamp may crush the spacers between the rings, thereby creating an at least partially isolated reaction chamber.

The shape and dimensions of the area defined by the rings, i.e., the "ring area" or the area in the interior of the rings, depends on the shape and dimensions of the rings and, as such, may vary greatly depending on how the device is implemented. In some embodiments, the ring area may be less than 10,000 mm$^2$, less than 5,000 mm$^2$, less than 3,000 mm$^2$, less than 1000 mm$^2$, less than 500 mm$^2$, less than 300 mm$^2$, less than 100 mm$^2$, less than 50 mm$^2$, less than 20 mm$^2$, less than 10 mm$^2$, less than 5 mm$^2$, less than 2 mm$^2$, less than 1 mm$^2$, less than 0.5 mm$^2$ or less than 0.1 mm$^2$. The term "ring area" is intended to refer to an area that has a perimeter defined by the ring. If sample flows from inside to outside of the ring area, then there is a net flow of the sample across from within the perimeter of the ring to outside of the perimeter of the ring.

In use, a sample may be deposited onto the sample contact area of at least one of the plates of the device while in the open configuration, closing the plates into the closed configuration and placing the clamp in the active mode; and rapidly changing the temperature of the sample in the clamped area, as described above and below.

Size of Clamp Ring: In some embodiments, the clamp ring has an average lateral size or diameter of 1 mm, 2 mm, 5 mm, 6 mm, 8 mm, 10 mm, 15 mm, 20 mm, 30 mm, 40 mm, 50 mm or in a range between any of the two values. In some embodiments, the clamp ring has a preferred average lateral size or diameter 5 mm, 6 mm, 8 mm, 10 mm, 15 mm, 20 mm, or in a range between any of the two values.

Width of Clamp Ring: In some embodiments, the width of the clamp is 100 um, 300 um, 500 um, 1 mm, 2 mm, 3 mm, 4 mm, 5 mm, 10 mm, 15 mm, or in a range between any of the two values. In some embodiments, the preferred width of the clamp is 1 mm, 2 mm, 3 mm, or in a range between any of the two values.

Contact Curvature of Clamp Ring: In some embodiments, the radius of curvature of one clamp to contact the device is 0.1 mm, 0.2 mm, 0.5 mm, 1 mm, 2 mm, 5 mm, 10 mm, 15 mm, 20 mm, or in a range between any of the two values. In some embodiments, the preferred radius of curvature of one clamp to contact the device is 0.2 mm, 0.5 mm, 1 mm, 2 mm, or in a range between any of the two values.

Width Difference of two Clamp Ring: In some embodiments, for one clamp set, the width of one clamp ring is larger than the other clamp ring for easy alignment. In some embodiments, for one clamp set, the width of one clamp ring is larger than the other clamp ring by 0.2 mm, 0.5 mm, 1 mm, 2 mm, 3 mm, 5 mm, 10 mm. 20 mm, or in a range between any of the two values. In some preferred embodiments, for one clamp set, the width of one clamp ring is larger than the other clamp ring by 0.2 mm, 0.5 mm, 1 mm, or in a range between any of the two values.

Pressure of Clamp Ring: The device, kit, system, or method of any prior embodiments, wherein the pressure provided by clamp on the card is 5 PSI, 10 PSI, 30 PSI, 60 PSI, 90 PSI, 100 PSI, 150 PSI, 200 PSI, 500 PSI 1000 pSI, or in average between any of the two values. The device, kit, system, or method of any prior embodiments, wherein the preferred pressure provided by clamp on the card is less than 30 PSI, less than 60 PSI, and less than 90 PSI.

B. Quickly Isolating a Portion of a Sample and Assay with Rapid Temperature Change According to the present invention, a sample holder comprised a first plate and a second plate, where a liquid sample is sandwiched between the plates. In some embodiments, the two plate are fixed to each other. In some embodiments, the two plates are movable relative to each other. In some embodiments, there are spacers between the two plates to regulate the spacing between the two plates.

According to the present invention, a clamp structure comprises a two rings, wherein the clamp has different configuration: inactive configuration and active configuration. In an inactive configuration, the two rings of the claim are open and the two rings do not insert any compression force on the sample plates. And in an activation configuration, the rings are being pushed towards to each other and insert a compressing force on the areas of a sample holder that are under the rings, and the comprising pinch force pinches the sample holder area under the ring together. In some embodiments, the pinching of the sample holder can reduce the sample in the inside of the clamp ring to flow to the outside of the clamp.

According the present invention, during a thermal cycling, a clamp is used and active, and the use of the clamp reduces the flow of the liquid sample in the inside of the ring to the outside of the ring. The use of the claim reduces the liquid sample flow and hence the energy exchange between the sample in the inside of the ring to the outside of the ring, and reduce the heating energy for heating up the sample inside of the clamp, and increase the thermal cycling time.

According the present invention, during a thermal cycling, the use of a clamp can reduce air bubbles during thermal cycling, which in turn improve thermal cycling quality.

In some embodiments, the method may comprise thermocycling the sample through a plurality of cycles that comprise increasing the temperature of the reaction mix to a temperature of at least 90° C. and then decreasing the temperature of the reaction mix to one or more temperatures in the range of 40° C. to 80° C. In a particular embodiment, the method may comprise thermocycling the sample through a plurality of cycles that comprise increasing the temperature of the reaction mix to a temperature of at least 90° C. and then decreasing the temperature of the reaction mix to one or more temperatures in the range of 40° C. to 65° C., then increasing the temperature of the reaction mix to one or more temperatures in the range of 60° C. to 65° C. The sample may be thermocycled through 10 to 50 cycles, although some protocols can use more or less cycles.

In particular embodiments, the method may be for performing quantitative real-time PCR (qPCR). In these embodiments, the method may comprise thermocycling a reaction mix using a the present device, wherein the reaction mix comprises a pair of PCR primers, a polymerase, a fluorescence-quencher probe oligonucleotide, dNTPs and a template (as well as any other necessary components for PCR, e.g., Mg$^{2+}$); and in each cycle, measuring a fluorescent signal generated by cleavage of a label from the fluorescence-quencher probe oligonucleotide. The fluorescent signal may be a lump-sum signal or may be done by imaging the sample. In these embodiments, the thermocycling may done by activating a heat source configured to radiate electromagnetic radiation towards a ring area. Cleavage of the label may be measured by detecting fluorescence of the reaction mixture during at least some of the cycles. In some embodiments, the fluorescence-quencher probe oligonucleotide comprises a fluorophore and a quencher, and the polymerase cleaves the fluorophore or quencher from the fluorescence-quencher probe oligonucleotide, thereby generating a fluorescent signal. The fluorescent signal over time, and the amount of the template in the sample can be estimated using the plotted signal.

In some embodiments, a subject biosensor can be used to diagnose a pathogen infection by detecting a target nucleic acid from a pathogen in a sample. The target nucleic acid may be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

Other pathogens that may be detected in a diagnostic sample using the present method include, but are not limited to: Varicella zoster, *Staphylococcus epidermidis*, *Escherichia coli*, methicillin-resistant *Staphylococcus aureus* (MSRA), *Staphylococcus aureus*, *Staphylococcus hominis*, *Enterococcus faecalis*, *Pseudomonas aeruginosa*, *Staphylococcus capitis*, *Staphylococcus warneri*, *Klebsiella pneumoniae*, *Haemophilus influenzae*, *Staphylococcus simulans*, *Streptococcus pneumoniae* and *Candida albicans*; gonorrhea (*Neisseria gorrhoeae*), syphilis(*Treponema pallidum*), clamydia(*Clamyda tracomitis*), nongonococcal urethritis (*Ureaplasm urealyticum*), chancroid(*Haemophilus ducreyi*), trichomoniasis(*Trichomonas vaginalis*); *Pseudomonas aeruginosa*, methicillin-resistant *Staphlococccus aureus* (MSRA), *Klebsiella pneumoniae*, *Haemophilis influenzae*, *Staphylococcus aureus*, *Stenotrophomonas maltophilia*, *Haemophilis parainfluenzae*, *Escherichia coli*, *Enterococcus faecalis*, *Serratia marcescens*, *Haemophilis parahaemolyticus*, *Enterococcus cloacae*, *Candida albicans*, *Moraxiella catarrhalis*, *Streptococcus pneumoniae*, *Citrobacter freundii*, *Enterococcus faecium*, *Klebsella oxytoca*, *Pseudomonas fluorscens*, *Neiseria meningitidis*, *Streptococcus pyogenes*, *Pneumocystis carinii*, *Klebsella pneumoniae* *Legionella pneumophila*, *Mycoplasma pneumoniae*, and *Mycobacterium tuberculosis*, etc., as well as others.

FIG. 1A shows a sectional view of an embodiment of the system of the present invention, comprising a sample holder and a clamping structure, wherein a fluidic sample is sandwiched between the two plates. A clamp has two jaws that can, when the clamp is active, push against each other to insert a force on a subject between the two jaws. Panel (A) illustrates that when the clamping structure is not activated, the two jaws of the clamp, which have a ring shape, are open, and hence does not assert a force to push the two plates. Panel (B) illustrates that the clamp is activated, where a force is applied by the clamping structure to pinch the sample holder area that is pressed by the clamp. The activation of the clamping structure, which clamps the area of the sample holder under the clamp, will reduce or prevent a fluid sample from flowing outside the chamber as heat is delivered the heating/cooling layer. In some embodiments, the first plate and the second plate are fixed relative to each other. In some embodiments, the first plate and the second plate are movable relative to each other.

The term "pinch the sample holder", "pinch the two plates" or "the plates get pinched" means that when a sample is sandwiched between two plates wherein at least one of the plates is flexible, and when a ring shaped clamp clamps on the sample holder, the clamp deforms the area of the flexible plates that is compressed by the clamp, hence reducing the spacing between the plates in that area. In some cases, the plate spacing in the compress area is zero, it is termed "the plates get completely pinched". The pinch of the plate will reduce the sample liquid flow from inside of the ring to outside.

Figure 1B:
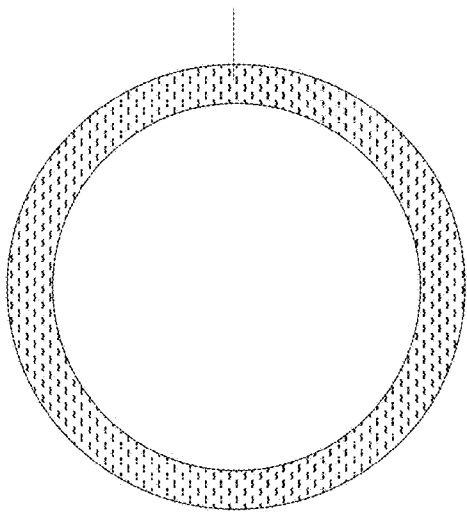
FIG. 1B shows a top view of an embodiment of one side of a ring clamp.
Figure 1B:
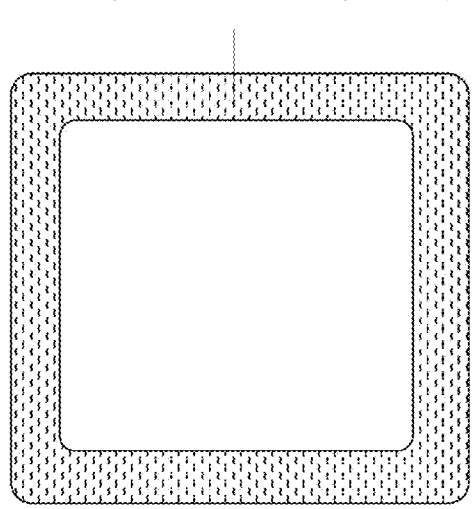

FIG. 1B shows a top view of an embodiment of one side of a ring clamp. Each ring has a width and a circumference. It shows a circular shaped ring clamp and a rectangle shaped ring clamp. As described above, the ring clamp may have another shapes.

Figure 2:
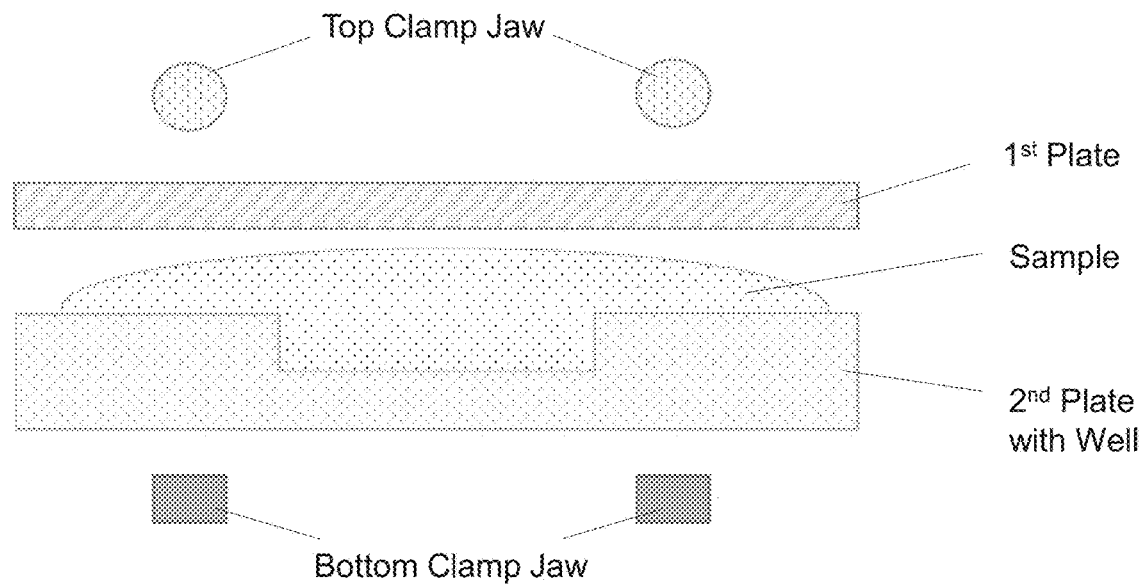
FIG. 2 shows a sectional view of an embodiment of the system of the present invention, comprising a sample holder, and a clamping structure. Panel (A) illustrates the system before the ring clamping structure is activated, where the two rings of the clamp does not assert a force to push the two plate together. Panel (B) illustrates the system after a force is applied by the clamping structure.
Figure 2:
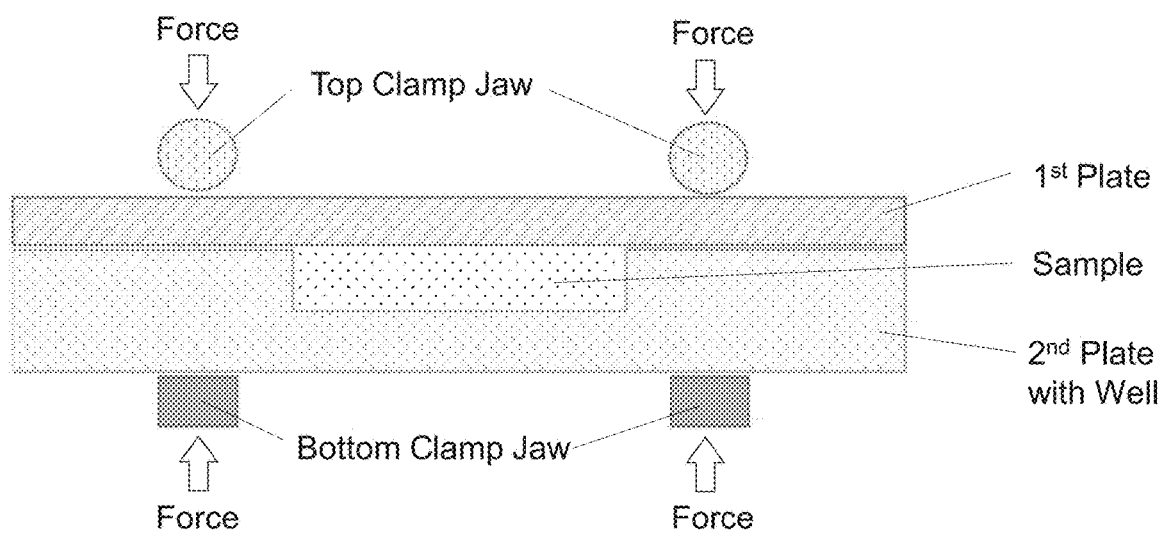

FIG. 2. shows a sectional view of an embodiment of the system of the present invention, comprising a sample holder, and a clamping structure. The sample holder comprises a first plate and a second plate that are movable to each other, where in the second plate a well. Panel (A) illustrates the system before the ring clamping structure is activated, where the two rings of the clamp does not assert a force to push the two plate together. Panel (B) illustrates the system after a force is applied by the clamping structure. The activation of the clamping structure will prevent a fluid sample from flowing outside the chamber as heat is delivered the heating/cooling layer.

Figure 3:
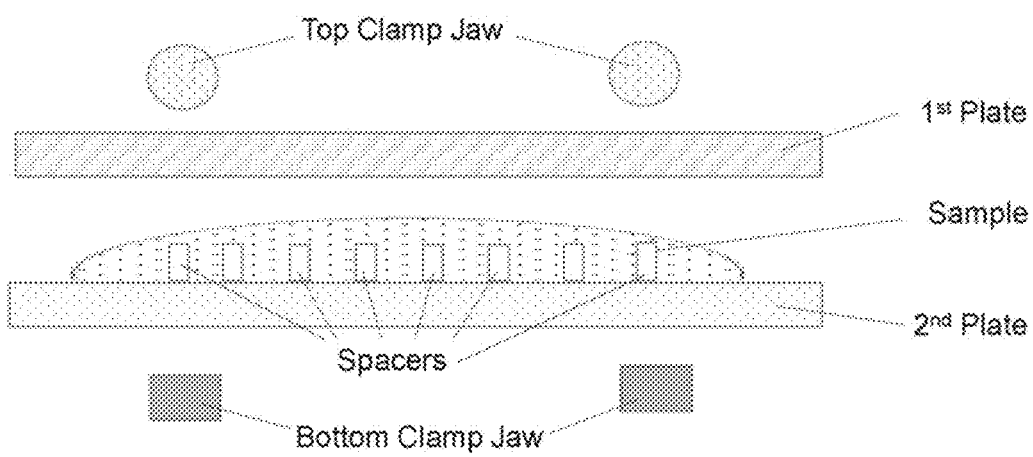
FIG. 3. shows a sectional view of an embodiment of the system of the present invention, comprising a sample holder and a clamping structure. Panel (A) illustrates the system before the clamping structure is activated. Panel (B) illustrates the system after a force is applied by the clamping structure.
Figure 3:
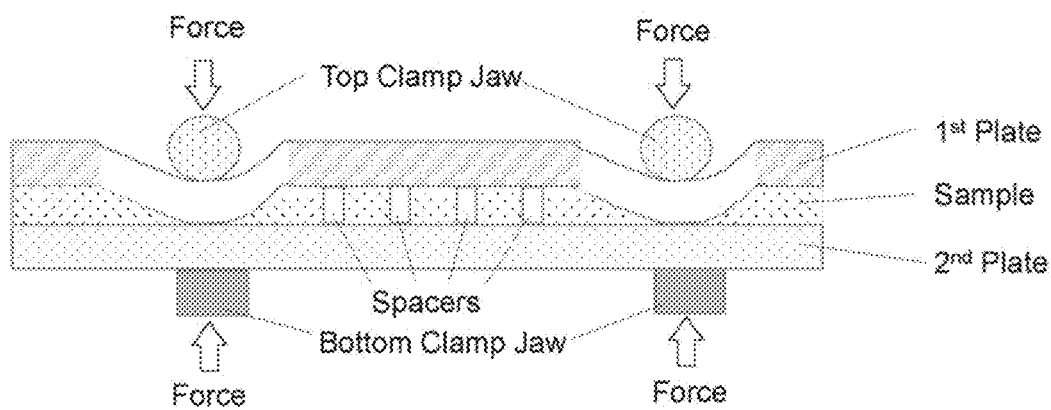

FIG. 3. shows a sectional view of an embodiment of the system of the present invention, comprising a sample holder and a clamping structure. The sample holder comprises a first plate, a second plate with spacers that are fixed on the inner surface. Panel (A) illustrates the system before the clamping structure is activated. Panel (B) illustrates the system after a force is applied by the clamping structure. The activation of the clamping structure will prevent a fluid sample from flowing outside the chamber as heat is delivered the heating/cooling layer.

Figure 4:
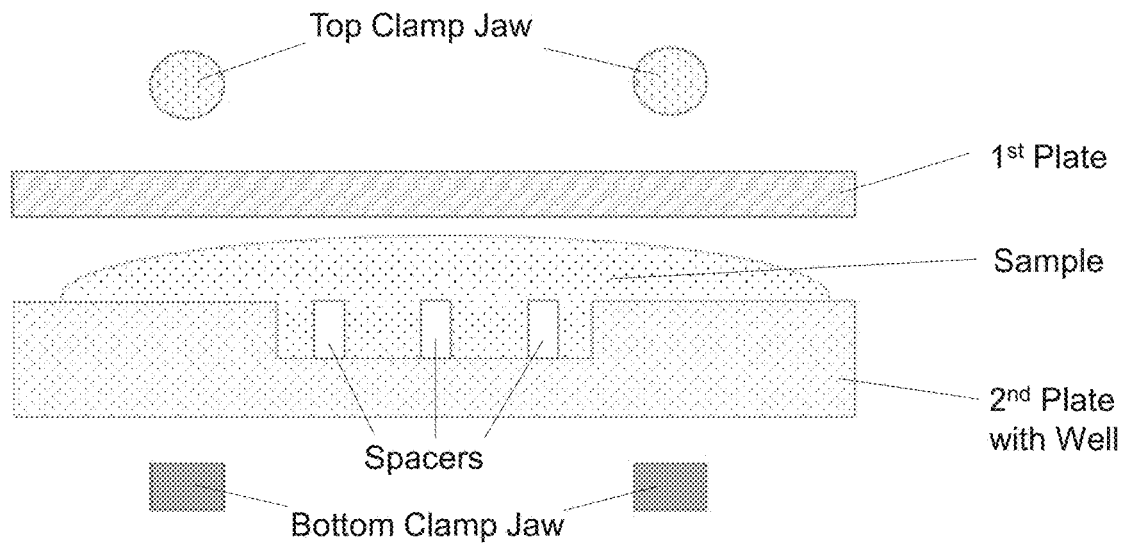
FIG. 4. shows a sectional view of an embodiment of the system of the present invention, comprising a first plate, a second plate with a well and spacers that are fixed on the inner surface, and a clamping structure. Panel (A) illustrates the system before the clamping structure is activated. Panel (B) illustrates the system after a force is applied by the clamping structure.
Figure 4:
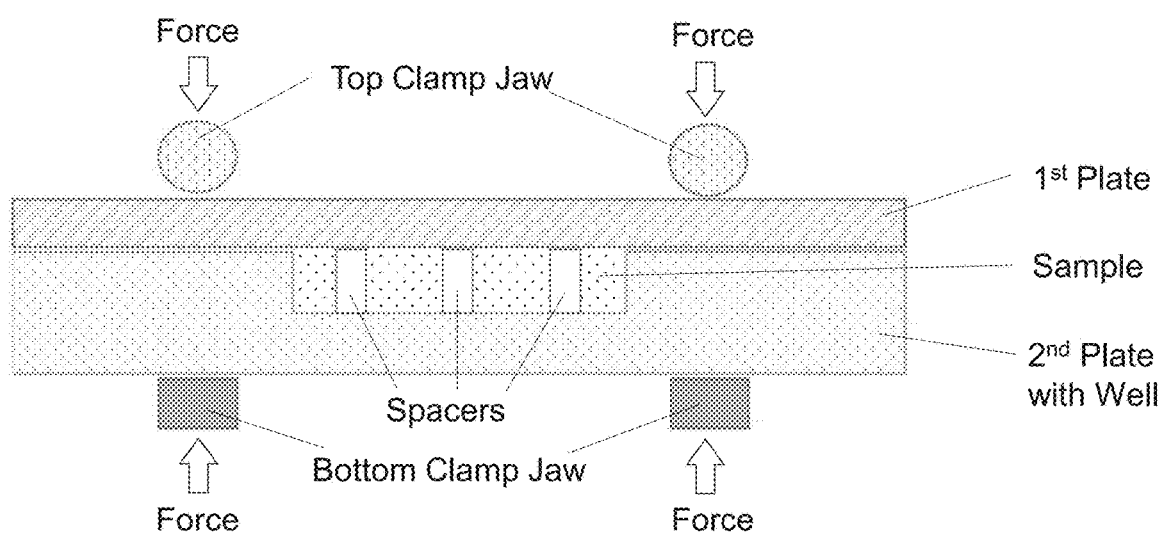

FIG. 4. shows a sectional view of an embodiment of the system of the present invention, comprising a first plate, a second plate with a well and spacers that are fixed on the inner surface, and a clamping structure. Panel (A) illustrates the system before the clamping structure is activated. Panel (B) illustrates the system after a force is applied by the clamping structure. The activation of the clamping structure will prevent a fluid sample from flowing outside the chamber as heat is delivered the heating/cooling layer.

Figure 5:
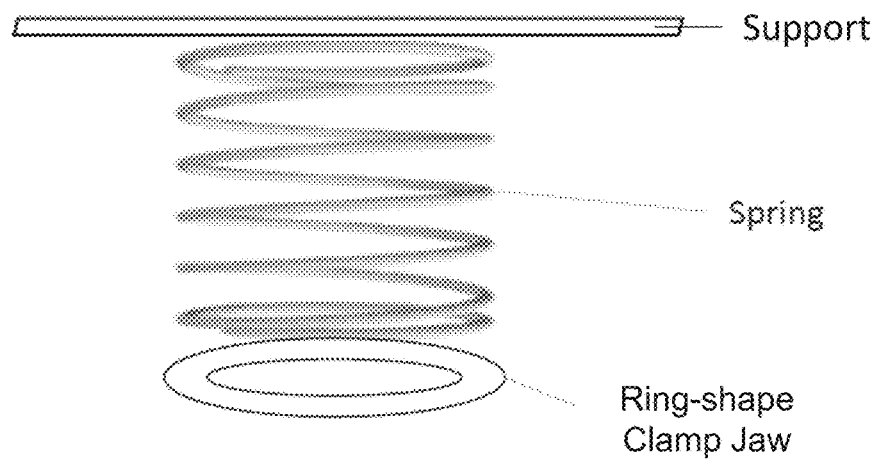
FIG. 5. shows exemplary embodiments of two types of clamping structures. Panel (A) comprises a support with a one-spring ring structure. Panel (B) comprises a support with a four-spring ring structure.
Figure 5:
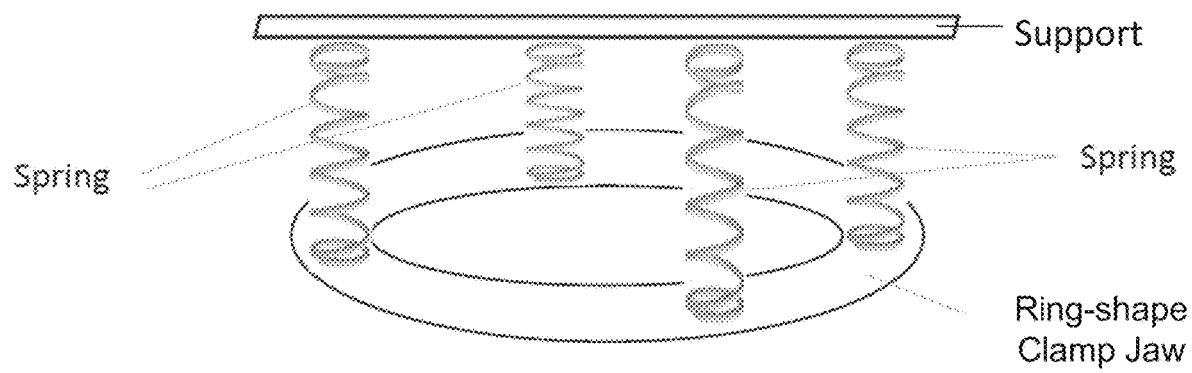

FIG. 5. shows exemplary embodiments of two types of clamping structures. Panel (A) comprises a support with a one-spring ring structure. Panel (B) comprises a support with a four-spring ring structure. In certain embodiments, one or both of the jaws of the clamp are flexible.

In certain embodiments, when a clamp is activated, the two jaws of the clamp are aligned to each other as shown in the image. In certain embodiments, the two jaws of the clamp are misaligned (not on top of each other) at least at certain part of the jaws.

In certain embodiments, at least one jaw of the clamp has a sharp edge in contact with the sample holder, such as the round edges shown in FIGS. 1-5. In certain embodiments, one of the jaws has a sharp edge and the other jaw has a flow surface, as shown in FIG. 1-5; such arrangement makes an alignment between the two jaws easier.

One embodiment of the present invention is a device for rapidly changing the temperature of a fluidic sample, comprising: a first plate, a second plate, and a clamping structure, wherein:
  i. the first plate and the second plate have on their inner surface a sample contact area for contacting a fluidic sample, wherein the sample contact area of the first plate and the second plate face each other, are separated by a separation distance of 200 um or less, and have an area at least times of the separation distance, and are capable of sandwiching the sample between them;
  ii. the clamping structure comprises a top ring and a bottom ring that are movable to each other and comprise:
    a. an open configuration, wherein the top ring and the bottom ring do not push the first plate and second plate together; and
    b. a closed configuration, wherein the top ring and the bottom ring assert a force again each other to push the first plate and the second plate in the closed configuration, deforming an area of the plates that is compressed by the clamp, leading to a reduction of the spacing between the two plate in that area, wherein the reduction of the plate spacing reduces, during thermal cycling or temperature changing, compared to without using a clamping structure, reduces the flow of a sample from the inside to the outside of a ring area.

In another embodiment of the present invention, a device for rapidly changing the temperature of a fluidic sample, comprises: a first plate, a second plate with a well, and a clamping structure, wherein:
  i. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;
  ii. the clamping structure comprises a top ring and a bottom ring that are movable to each other and comprise:
    a. an open configuration, wherein the top ring and the bottom ring do not push the first plate and the second plate with a well together; and
    b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

As illustrated in FIG. 1A (Panel A and Panel B) and FIG. 2 (Panel A and Panel B), the sectional views of the embodiments show an open configuration (before clamp activation) and a closed configuration (after the clamp is activated). In FIG. 1A, the first plate and second plate are flat. In FIG. 2, the second plate comprises a well.

In another embodiment of the present invention, a device for rapidly changing the temperature of a fluidic sample, comprises: a first plate, a second plate, spacers, and a clamping structure, wherein:
  i. the first plate and/or second plate comprise spacers fixed to the inner surface of the first plate and/or second plate,
  ii. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them,
  iii. the clamping structure comprises a top ring and a bottom ring that are movable to each other and comprise:
    a. an open configuration, wherein the top ring and the bottom ring do not push the first plate and the second plate with a well together; and
    b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In yet another embodiment of the present invention, a device for rapidly changing the temperature of a fluidic sample, comprises: a first plate, a second plate with a well, spacers, and a clamping structure, wherein:
  i. the first plate and/or second plate with a well comprise spacers fixed to the inner surface of the first plate and/or second plate,
  ii. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them,
  iii. the clamping structure comprises a top ring and a bottom ring that are movable to each other and comprise:
    a. an open configuration, wherein the top ring and the bottom ring do not push the first plate and the second plate with a well together; and
    b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

As illustrated in FIG. 3 (Panel A and Panel B) and FIG. 4 (Panel A and Panel B), the sectional views of the embodiments show an open configuration (before clamp activation) and a closed configuration (after the clamp is activated)

wherein spacers are positioned between the first plate and the second plate to regulate the distance between the two plates (i.e., the spacing of the first plate and the second plate), to regulate the sample thickness. The spacers allow the thickness of the sample between the first plate and the second plate to be uniform over a large area, even when the first plate and second plate are thin and flexible. In FIG. 3, the first plate and the second plate are flat. In FIG. 4, the second plate comprises a well.

In certain embodiments, the pressure inserted by clamp is configured to completely pinched the flexible plate area that is clamped by the ring clamp. A complete pinch of the plates stops fluidic communication between the liquid sample inside of the ring clamp and outside.

In certain embodiments, the pressure inserted by clamp is configured to crush the spacers to pinch the flexible plate area. A spacer can break into piece when the deformation of a spacer is beyond its elastic deformation limit (metals are an exception of this).

A device for rapidly changing the temperature of a fluidic sample, comprising: a first plate, a second plate, and a clamping structure, wherein:
- i. the first plate and the second plate have on their inner surface a sample contact area for contacting a fluidic sample; wherein the sample contact area of the first plate and the second plate face each other, are separated by a distance of 200 um or less, and are capable of sandwiching the sample between them;
- ii. the clamping structure comprises a top ring and a bottom ring that are movable to each other and comprise:
  - a. an open configuration, wherein the top ring and the bottom ring do not push the first plate and second plate together; and
  - b. a closed configuration, wherein the top ring and the bottom ring assert a force again each other to push the first plate and the second plate in the closed configuration, so the flow of a sample from the inside to the outside of a ring area during thermal cycling is reduced compared to without using a clamping structure.

A device for rapidly changing the temperature of a fluidic sample, comprising: a first plate, a second plate with a well, and a clamping structure, wherein:
- i. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;
- ii. the clamping structure comprises a top ring and a bottom ring that are movable to each other and comprise:
  - a. an open configuration, wherein the top ring and the bottom ring do not push the first plate and the second plate with a well together; and
  - b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

A device for rapidly changing the temperature of a fluidic sample, comprising: a first plate, a second plate, spacers, and a clamping structure, wherein:
- i. the first plate and/or second plate comprise spacers fixed to the inner surface of the first plate and/or second plate,
- ii. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them,
- iii. the clamping structure comprises a top ring and a bottom ring that are movable to each other and comprise:
  - a. an open configuration, wherein the top ring and the bottom ring do not push the first plate and the second plate with a well together; and
  - b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

A device for rapidly changing the temperature of a fluidic sample, comprising: a first plate, a second plate with a well, spacers, and a clamping structure, wherein:
- i. the first plate and/or second plate with a well comprise spacers fixed to the inner surface of the first plate and/or second plate,
- ii. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them,
- iii. the clamping structure comprises a top ring and a bottom ring that are movable to each other and comprise:
  - a. an open configuration, wherein the top ring and the bottom ring do not push the first plate and the second plate with a well together; and
  - b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

A method for rapidly changing the temperature of a fluidic sample, comprising: a first plate, a second plate, and a clamping structure, wherein:
- i. the first plate and the second plate have on their inner surface a sample contact area for contacting a fluidic sample; wherein the sample contact area of the first plate and the second plate face each other, are separated by a distance of 200 um or less, and are capable of sandwiching the sample between them;
- ii. the clamping structure comprises a top ring and a bottom ring that are movable to each other and comprise:
  - a. an open configuration, wherein the top ring and the bottom ring do not push the first plate and second plate together; and
  - b. a closed configuration, wherein the top ring and the bottom ring assert a force again each other to push the first plate and the second plate in the closed configuration, so the flow of a sample from the inside to the outside of a ring area during thermal cycling is reduced compared to without using a clamping structure.

A method for rapidly changing the temperature of a fluidic sample, comprising: a first plate, a second plate with a well, and a clamping structure, wherein:

iii. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;

iv. the clamping structure comprises a top ring and a bottom ring that are movable to each other and comprise:

c. an open configuration, wherein the top ring and the bottom ring do not push the first plate and the second plate with a well together; and a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

A method for rapidly changing the temperature of a fluidic sample, comprising: a first plate, a second plate, spacers, and a clamping structure, wherein:

i. the first plate and/or second plate comprise spacers fixed to the inner surface of the first plate and/or second plate, ii. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them, iii. the clamping structure comprises a top ring and a bottom ring that are movable to each other and comprise:

a. an open configuration, wherein the top ring and the bottom ring do not push the first plate and the second plate with a well together; and b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

A method for rapidly changing the temperature of a fluidic sample, comprising: a first plate, a second plate with a well, spacers, and a clamping structure, wherein:

i. the first plate and/or second plate with a well comprise spacers fixed to the inner surface of the first plate and/or second plate, ii. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them, iii. the clamping structure comprises a top ring and a bottom ring that are movable to each other and comprise:

a. an open configuration, wherein the top ring and the bottom ring do not push the first plate and the second plate with a well together; and b. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

The device or method of any prior embodiments further comprising a heating layer. The device or method of any prior embodiments, wherein the heating layer is positioned on the inner surface, the outer surface, or inside of one of the plates.

The device or method of any prior embodiments, wherein the heating layer is configured to heat a relevant volume of the sample, wherein the relevant volume of the sample is a portion or an entirety of the sample that is being heated to a desired temperature.

The device or method of any prior embodiments further comprising a cooling layer. The device or method of any prior embodiments, wherein the cooling layer is positioned on the inner surface, the outer surface, or inside one of the plates. The device or method of any prior embodiments wherein the cooling layer is configured to cool the relevant sample volume.

The device or method of any prior embodiments, wherein the cooling layer comprises a layer of material that has a thermal conductivity to thermal capacity ratio of 0.6 $cm^2$/sec or larger.

The device or method of any prior embodiments, wherein the clamping structure is attached to either one or both of the first and second plates, and wherein the clamping structure is configured to hold the device and regulate the thickness of the sample layer during the heating of the device.

The device, kit, system, or method of any prior embodiments, wherein the thickness of the clamp is 100 um, 300 um, 500 um, 1 mm, 2 mm, 3 mm, 4 mm, 5 mm, 10 mm, 15 mm, 20 mm, 30 mm or in a range between any of the two values.

The device, kit, system, or method of any prior embodiments, wherein the preferred thickness of the clamp is 1 mm, 2 mm, 10 mm, and 15 mm.

The device, kit, system, or method of any prior embodiments, wherein the circumference of the clamp is 5 mm, 10 mm, 20 mm, 30 mm, 38 mm, 50 mm, 62 mm, 100 mm or in a range between any of the two values.

The device, kit, system, or method of any prior embodiments, wherein the preferred circumference of the clamp is 38 mm and 62 mm.

The device, kit, system, or method of any prior embodiments, wherein the material of clamp includes, but not limited to, glass, quartz, oxides, silicon-dioxide, silicon-nitride, hafnium oxide (HfO), aluminum oxide (AlO), semiconductors: (silicon, GaAs, GaN, etc.).

The device, kit, system, or method of any prior embodiments, wherein the material of clamp includes, but not limited to metals (e.g. gold, silver, coper, aluminum, Ti, Ni, etc.), ceramics, or any combinations of thereof.

The device, kit, system, or method of any prior embodiments, wherein the material of clamp includes, but not limited to, polymers (e.g. plastics) or amorphous organic materials. The polymer materials include, but not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

The device, kit, system, or method of any prior embodiments, wherein the material of clamp includes, but not limited to glass, quartz, oxides, silicon-dioxide, silicon-nitride, hafnium oxide (HfO), aluminum oxide (AlO), semiconductors: (silicon, GaAs, GaN, etc.), plastics, metals (e.g. gold, silver, coper, aluminum, Ti, Ni, etc.), ceramics, or any combinations of thereof.

C. Fast Temperature Changes

Working Principle

One aspect of the present invention is to reduce thermal cycling time, to reduce the heating energy used for such cycling, to increase energy efficiency, and to reduce total power consumption.

The thermal cycling time (speed), heating energy, energy efficiency, and power consumption are related. When more heating energy is needed in raising the temperature of a given sample, the more energy must be removed in cooling the sample, which, in turn, needs more time and/or more energy to perform the cooling.

Many thermal cyclers in prior art require a use of a significant amount of heating energy to the sample holder (e.g. plastic chamber walls) rather than to the sample; a use of lateral thermal conduction through large thermal mass and poor-thermal conduction materials of the sample holder as the major cooling channel to cool the sample (note that a material needs to absorb and release energy to perform a thermal conduction); a use of conductive cooling as major cooling method, and/or a use of an extra cooling gas or a moving cooling block. These approaches lead to issues of long thermal cycling time, high heating energy, low energy efficiency, bulky apparatus, and/or high cost.

Based on theoretical and experimental investigations, the present invention provides solutions to certain drawbacks in a sample thermal cycling in the prior arts.

To illustrate the working principle of the present invention, let us look at the energy components in heating and cooling a sample by a thermal cycler. The heating and cooling share three energy components: (i) one related to thermal mass (i.e. a material's ability to absorb and store energy; larger the thermal mass, more energy needed to be added for heating up and more energy needed to be removed in cooling), (ii) heat loss by thermal radiation, and (iii) heat loss by thermal conduction/convection. To heat fast, all three energy components need to be small. But to cool fast, the first energy component needs to be small, but at least one of the last two energy components needs to be large.

Through theoretical and experimental investigation, the present invention balances and/or optimizes the three energy components for achieving rapid heating and cooling. Particularly, in certain embodiments, the present invention reduces the thermal mass that must be heated in a thermal cycle, limits lateral thermal conduction, and uses radiative heat loss as a primary way to remove energy from the heated sample.

According to the present invention, the cooling of a sample is significantly by thermal radiative cooling, not by thermal conduction cooling. Therefore, in a thermal cycling, most or a significant part of the non-sample materials on a sample holder do not absorb and release as much energy as that in a thermal conduction dominated system.

One aspect of the present invention provides devices and methods that reduce the heating to non-sample materials on the sample holder.

Another aspect of the present invention provides devices and methods that reduce lateral thermal conduction through large thermal mass and poor-thermal conduction materials on the sample holder.

Another aspect of the present invention provides devices and methods that use thermal radiative cooling as the major cooling channel to cool the sample.

Another aspect of the present invention provides devices and methods that place spacers between to plates (i.e. walls) that sandwich a sample. The spacers provides good sample uniformity over a large area, even when the plates are thin (e.g. 25 um thick) and flexible. Without spacers, it can be difficult to achieve a uniform sample thickness, when the two plates that confine the sample become very thin.

Another aspect of the present invention provides devices and methods that make the device operation easier.

According to the present invention, the thermal radiative cooling uses a material layer are configured (in terms of materials and shape) that has good thermal radiative cool properties during the cooling, and a low thermal mass (hence a low heating energy) during heating.

According to the present invention, the sample holder is configured to limit/minimize the thermal conduction cooling.

According to the present invention, the sample thickness, the first plate and the second plate (which are facing each other) of the sample chamber wall thickness are configured to reduce the lateral thermal conduction (i.e. in the direction of the plate).

According to the present invention, in some embodiments, the thermal radiative cooling layer is the same heating/cooling layer of the heating layer, but the ratio of the cooling zone to the heating zone, the material properties, and the material thickness and geometry are configured to make the heating/cooling layer has a low thermal mass in heating and high rate of thermal radiative cooling.

Another objective of the present invention is to make one cycle of a sample temperature change (e.g. from 95° C. to 55° C.) in a few seconds or even sub-second (e.g., 0.7 second).

Another aspect of the present invention is that it provides useful devices and methods for isothermal nucleic acid amplification, where a sample temperature needs to be raised from environment to an elevated temperature (i.e. 65° C.) and keep there for a period of time (i.e., 5-10 min). One aspect of the present invention is to raise the temperature fast, to use less energy, and to make the apparatus compact, lightweight, and portable.

One aspect of the present invention is that the thermal masses of the card as well as the sample are minimized to reduce the energy needed for heating and the energy to be removed for cooling.

Another aspect of the present invention is that in certain embodiments, only a small portion of the sample is heated and/or cooled.

Another aspect of the present invention is that it uses a thin high thermal conductivity layer that has an area size larger than that of the relevant sample area.

Another aspect of the present invention is that it uses a thin high thermal conductivity layer that has an area size larger than the heating zone area.

Another aspect of the present invention provides devices and methods that reduce the heating to non-sample materials on the sample holder.

Another aspect of the present invention provides devices and methods that reduce lateral thermal conduction in large thermal mass and poor-thermal conduction materials on the sample holder.

Another aspect of the present invention provides devices and methods that use thermal radiative cooling as the major cooling channel to cool the sample.

Another aspect of the present invention is that it can achieve fast thermal cycling without using a cooling gas.

Another aspect of the present invention is that the thermal masses of the card as well as the sample are minimized to reduce the energy needed for heating and the energy to be removed for cooling.

Another aspect of the present invention is that the radiative cooling and convention cooling are adjusted for rapid cooling.

Another aspect of the present invention is that heat sink for radiative cooling and/or convention cooling is used for rapid cooling.

Figure 6:
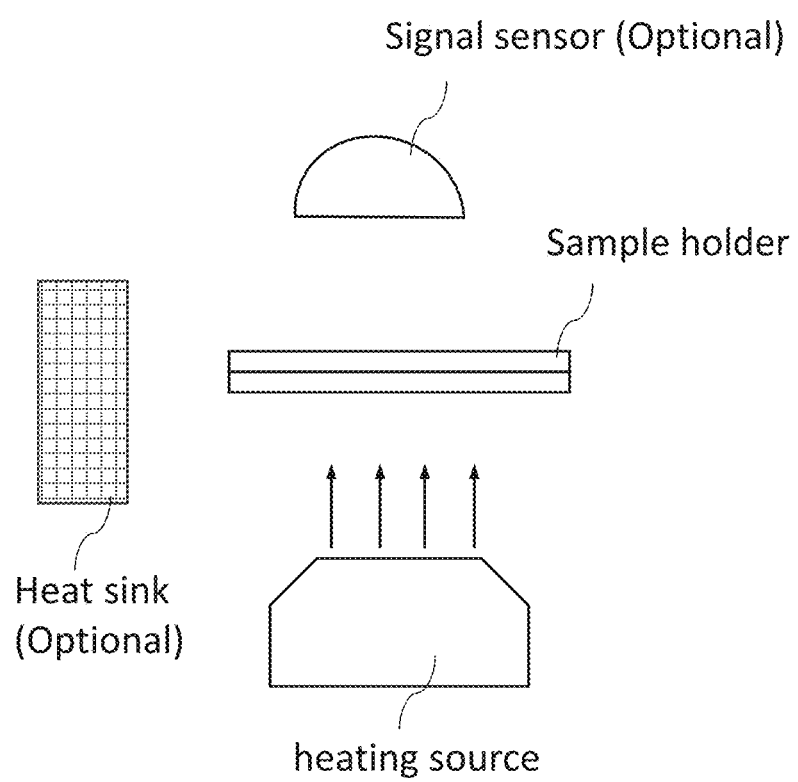
FIG. 6 shows a schematic illustration of certain components of a system for changing the temperature of a sample and for monitoring a signal from the sample, according to some embodiments.

One embodiment of a sample thermal cycling apparatus in the present invention (as illustrated in FIG. 6) comprises: (i) a sample holder, termed "RHC (rapid heating and cooling) Card" or "sample card", that allows a rapid heating and cooling of a sample on the card; (ii) a heating source, (iii) an extra heat sink (optional), (iv) a temperature control system, and (v) a signal monitoring system (optional). The temperature control system and signal monitoring system are not explicitly illustrated in FIG. 6, but may be used to control the output of the heating source. In some embodiments, a signal sensor is included to detect optical signals from samples on the sample holder. Note that certain embodiments of the present invention can have just one or several components illustrated in FIG. 6.

Figure 7A:
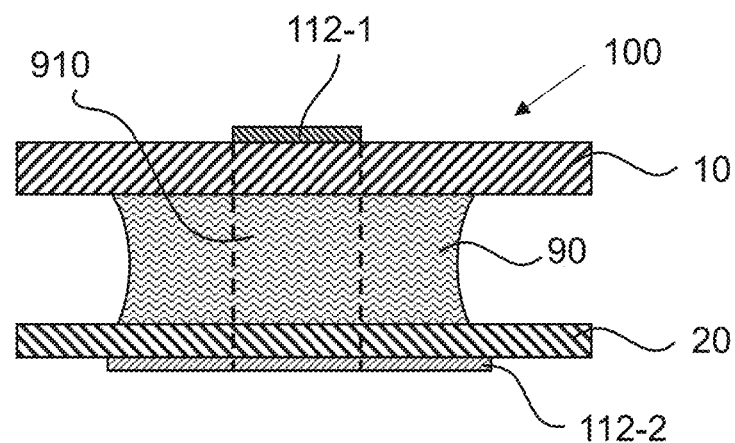
FIG. 7A shows an embodiment of a device with a heating layer separated from a cooling layer, according to some embodiments.
Figure 7B:
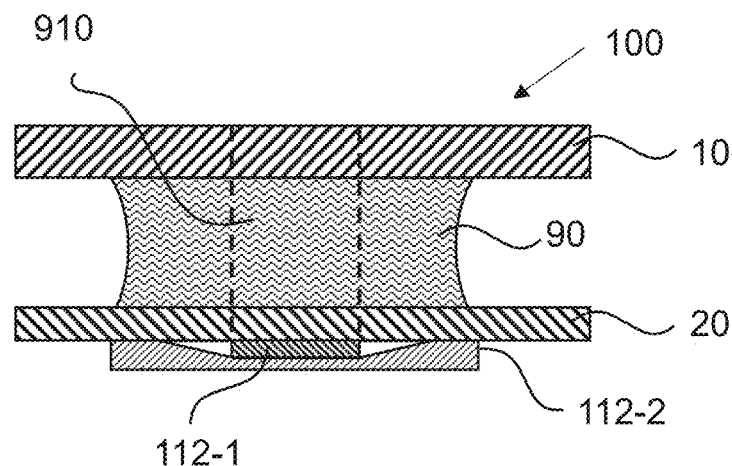
FIG. 7B shows an embodiment having a heating layer contacting a cooling layer, according to some embodiments.
Figure 7C:
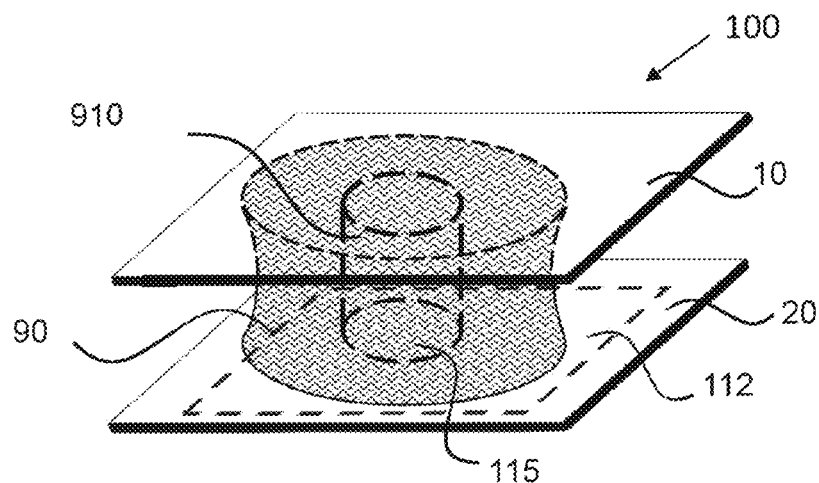
FIG. 7C schematically illustrates a perspective view of an embodiment of a device with a heating/cooling layer, in accordance with an embodiment.
Figure 7D:
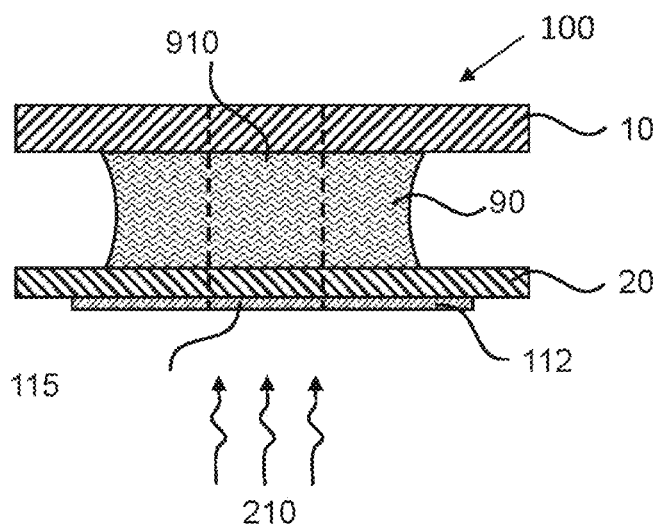
FIG. 7D schematically illustrates a sectional view of an embodiment of a device with a heating/cooling layer, in accordance with an embodiment.

FIGS. 2A and 2B show sectional views of two embodiments of the device of the present invention. FIG. 7A shows an embodiment comprising a separate heating layer (112-1) and a separate cooling layer (112-2), wherein the heating layer (112-1) is on the outer surface of one of the plates and the cooling layer (112-2) is on the outer surface of the other plate. FIG. 7B shows an embodiment comprising a heating layer (112-1) and a cooling layer (112-2), wherein the heating layer (112-1) and the cooling layer (112-2) are structurally distinct but in contact with each other, and the two layers are both on the outer surface of one of the plates.

SH-1 One detailed description of one embodiment of a RHC card in the present invention is that a device for rapidly changing the temperature of a fluidic sample, comprising:

a first plate (10), a second plate (20), a heating layer (112-1), and a cooling layer (112-2), wherein:

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates, and configured to cool the relevant sample volume; and comprises a layer of material that that has a thermal conductivity to thermal capacity ratio of 0.6 cm$^2$/sec or larger;

wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger; and wherein, in some embodiments, the heating layer and cooling layer are the same material layer that have a heating zone and cooling zone, and wherein the heating zone and cooling zone can have the same area or different areas.

SH-2 Another detailed description of one embodiment of a RHC card (sample holder) in the present invention is that a device for rapidly changing the temperature of a fluidic sample, comprising:

A first plate (10), a second plate (20), a heating layer (112-1), and a cooling layer (112-2), wherein:

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates; and configured to cool the relevant sample volume; and comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;

wherein the distance between the cooling layer and a surface of the relevant sample volume is zero or less than a distance that is configured to make the thermal conductance per unit area between the cooling layer and the surface of the relevant sample volume equal to 150 W/(m$^2$·K) or larger; and wherein, in some embodiments, the heating layer and cooling layer are the same material layer that have a heating zone and cooling zone, and wherein the heating zone and cooling can have the same area or different areas.

Figure 8A:
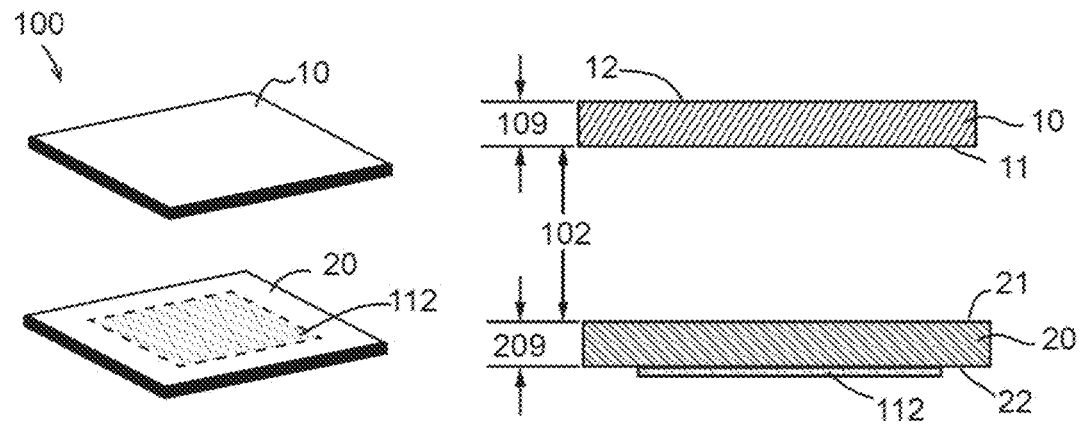
FIGS. 8A and 8B show a prospective view and a sectional view, respectively, of a combination heating/cooling layer on an outer surface of a plate, according to some embodiments.
Figure 8B:
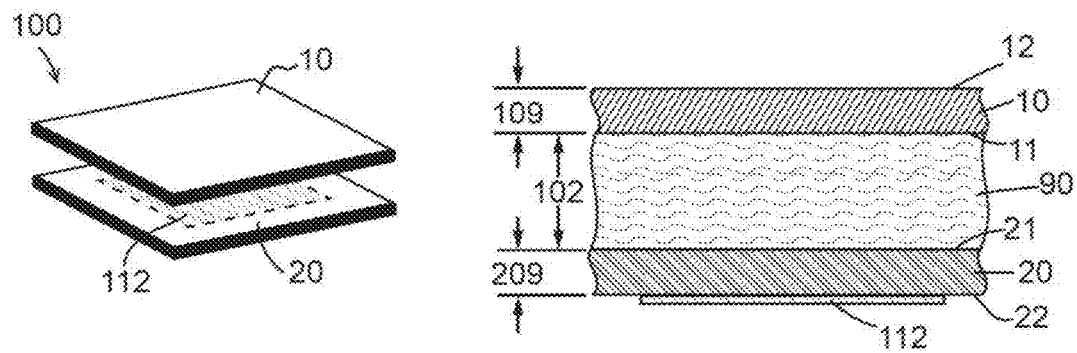

As illustrated in FIGS. 8A and 8B, in some embodiments of the present invention, the heating layer and the cooling layer are combined into one layer (heating/cooling layer) creating a heating zone and cooling zone, where the cooling zone is larger than the heating zone. A sample card 100 (also termed "RHC card") may include two thin plates (10, 20) that sandwich a fluidic sample (90) between them and a heating/cooling layer (112) is under the sample, and the heating/cooling layer (112) is heated by a heat source positioned away from the card. According to an embodiment, at the edge of the sample, there are no walls to contain the sample, but the edge of the sample will not flow due to capillary forces that keep the shape of the fluidic sample edges.

Figure 9A:
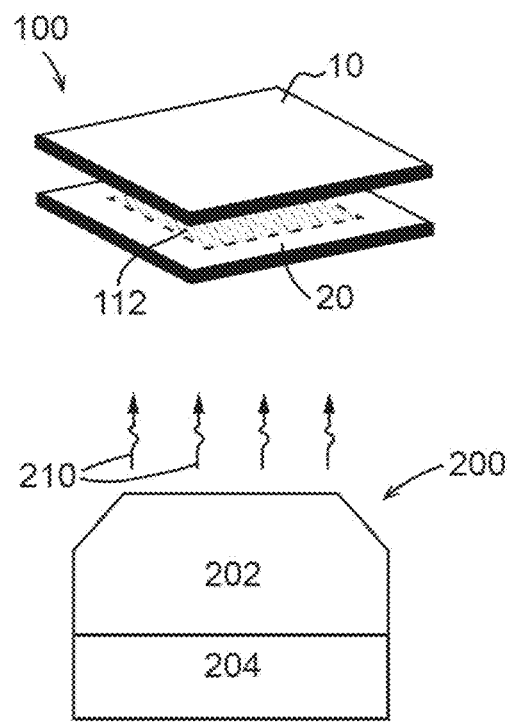
FIG. 9A shows perspective and sectional views of the device in an open configuration, according to some embodiments.
Figure 9B:
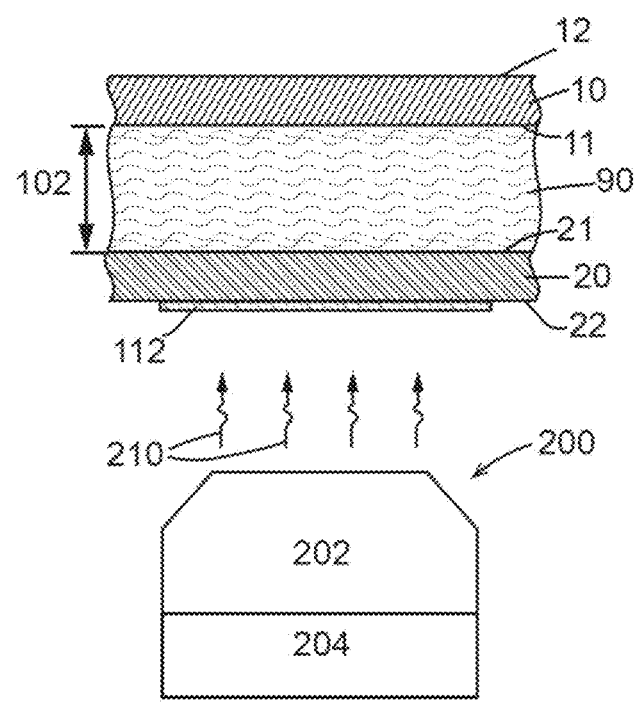
FIG. 9B shows perspective and sectional views of the device when the sample holder is in a closed configuration, according to some embodiments.

As illustrated in FIG. 9A, plates 10 and 20 may have inner surfaces 11 and 21 that are separated by a spacing 102, according to an embodiment. Spacing 102 may be large when the device is ready to receive a sample (e.g., in an open position). FIG. 9B illustrates a closed configuration of device 100 where spacing 102 is made small (e.g., less than about 200 um) to sandwich a sample 90 between plates 10 and 20. In this embodiment, heating/cooling layer 112 is positioned on an outer surface 22 of plate 20.

SH-3 Another detailed description of one embodiment of a RHC card in the present invention is that a device for rapidly changing the temperature of a fluidic sample, comprising:
- a first plate (10), a second plate (20), and a heating/cooling layer (112), wherein:
- the first plate (10) and the second plate (20) face each other, and are separated by a distance from each other;
- each of the plates has, on its respective inner surface (11, 21), a sample contact area for contacting a fluidic sample; wherein the sample contact areas are facing each other, are in contact with the sample, confines a sample between them, and have an average separation distance (102) from each other, and the sample;
- the heating/cooling layer (112) is on the outer surface (22) of the second plate (20); and
- the heating/cooling layer is configured to comprise a heating zone and a cooling zone; wherein the heat zone is configured to heat the fluidic sample, the cooling zone is configured to cool the sample by thermal radiative cooling;
- wherein the heating zone is configured to receive heating energy from a heating source and configured to have an area smaller than the total area of the heating/cooling layer; and
- wherein at least a part of a heating zone of the heating layer overlaps with the sample area.

SH-4 A device for rapidly changing the temperature of a fluidic sample, comprising:
- a first plate (10), a second plate (20), a heating layer (112-1), and a cooling layer (112-2), wherein:
- the first and second plates are movable relative to each other into different configurations;
- each of the first plate and the second plate has, on its respective inner surface, a sample contact area for contacting a fluidic sample; wherein the sample contact areas face each other, are separated by an average separation distance of 200 um or less, and are capable of sandwiching the sample between them;
- the heating layer:
- is positioned on the inner surface, the outer surface, or inside of one of the plates,
- is configured to heat a relevant volume of the sample, wherein the relevant volume of the sample is a portion or an entirety of the sample that is being heated to a desired temperature; and
- the cooling layer is:
- positioned on the inner surface, the outer surface, or inside of one of the plates; and
- configured to cool the relevant sample volume; and
- comprises a layer of material that that has a thermal conductivity to thermal capacity ratio of 0.6 cm$^2$/sec or larger;
- wherein one of the configurations is an open configuration, in which: the two plates are partially or completely separated apart and the average spacing between the plates is at least 300 um;
- wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less.

SH-5 A device for rapidly changing the temperature of a fluidic sample, comprising:
- a first plate (10), a second plate (20), spacers, a heating layer (112-1), and a cooling layer (112-2), wherein:
- the first and second plates are movable relative to each other into different configurations;
- each of the first plate and the second plate has, on its respective inner surface, a sample contact area for contacting a fluidic sample; wherein the sample contact areas face each other, are separated by an average separation distance of 200 um or less, and are capable of sandwiching the sample between them;
- one or both of the plates comprise the spacers and the spacers are fixed on the inner surface of a respective plate;
- the spacers have a predetermined substantially uniform height that is equal to or less than 200 microns, and the inter-spacer-distance is predetermined;
- the heating layer is:
- positioned on the inner surface, the outer surface, or inside of one of the plates, and
- configured to heat a relevant volume of the sample, wherein the relevant volume of the sample is a portion or an entirety of the sample that is being heated to a desired temperature; and
- the cooling layer is:
- positioned on the inner surface, the outer surface, or inside of one of the plates; and
- configured to cool the relevant sample volume; and
- comprises a layer of material that that has a thermal conductivity to thermal capacity ratio of 0.6 cm$^2$/sec or larger;
- wherein one of the configurations is an open configuration, in which: the two plates are partially or completely separated apart, the spacing between the plates is not regulated by the spacers, and the sample is deposited on one or both of the plates; and
- wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In some embodiments, the heating/cooling layer (112) can be on the inner surface (21) or inside the second plate (20), rather than on the outer surface (22) of the second plate (20).

In some embodiments of all embodiments of devices, the RHC card further comprises spacers that are positioned between the first and second plate to regulate the distance between the two plates (i.e. the spacing of the plates), and hence to regulate the sample thickness. The spacers can allow the thickness of the sample between the two plates uniform over a large area, even when the plates are thin and flexible.

In some embodiments, there are more than one heating/cooling layer.

A. Small Relevant Sample Volume (RE Ratio)

Reduction of the sample volume that should be heated or cooled to a desirable temperature can shorten the heating time and cooling time in a thermal cycle as well as heating power. A reduction of the sample volume that will be thermal cycled can be achieved by (a) reducing the entire sample volume or (b) heating just a portion of the sample on the sample holder. The term "relevant sample" or "relevant sample volume" refers to the volume of the sample that is being heated and/or cooled to desired temperatures during a thermal cycling, and the relevant sample can be a portion or an entire volume of a sample on a sample holder, and there is no fluidic separation between the portion of the sample to the rest of the sample.

In some embodiments, the relevant volume of the sample is 0.001 ul, 0.005 ul, 0.01 μl, 0.02 ul, 0.05 ul, 0.1 ul, 0.2 ul, 0.5 ul, 1 ul, 2 ul, 5 ul, 10 ul, 20 ul, 30 uL, 50 ul, 100 ul, 200 μl, 500 ul, 1 ml, 2 ml, 5 ml, or in a range between any of the two values.

In some preferred embodiments, the relevant sample volume is in a range of 0.001 uL to 0.1 uL, 0.1 um to 2 uL, 2 uL to 10 uL, 10 uL to 30 uL, 30 uL to 100 uL, 100 uL to 200 uL, or 200 uL to 1 mL.

In some preferred embodiments, the relevant sample volume is in a range of 0.001 uL to 0.1 uL, 0.1 um to 1 uL, 0.1 uL to 5 uL, or 0.1 uL to 10 uL.

In certain embodiments, the ratio of the relevant sample to entire sample volume (RE ratio) is 0.01%, 0.05%, 0.1%, 0.5%, 0.1%, 0.5%, 1%, 5%, 10%, 20%, 30%, 40%, 50%, 60%, 70%, 80%, 90%, 100%, or in a range between any of the two values.

In some preferred embodiments, the RE ratio is in a range of between 0.01% and 0.1%, 0.1% and 1%, 1% and 10%, 10% and 30%, 30% and 60%, 60% and 90%, or 90% and 100%.

To heat only a portion of the sample, in some embodiments, the area of the heating zone is only a fraction of the sample lateral area, and the fraction (i.e. the ratio of the heating zone to the sample lateral area) is 0.01%, 0.05%, 0.1%, 0.5%, 0.1%, 0.5%, 1%, 5%, 10%, 20%, 30%, 40%, 50%, 60%, 70%, 80%, 90%, 99%, or in a range between any of the two values.

In some preferred embodiments, the ratio of the heating zone area to the sample lateral area is in a range of between 0.01% and 0.1%, 0.1% and 1%, 1% and 10%, 10% and 30%, 30% and 60%, 60% and 90%, or 90% and 99%.

B. Local Heating, High Vertical to Lateral Heat Transfer

When a high-K (high thermal conductivity) layer is (e.g. a metal layer) on the inner surface, the outer surface, or inside of one of the plates of a sample holder (RHC card), to make only a part of the high-K layer and a part of sample volume above the part of the high-K layer to be heated to desired temperatures, while keeping the rest of the high-K layer and the rest of the sample volume at much lower temperatures during a thermal cycling, several conditions must be met. The key conditions are (1) the heat source must directly heat a portion of the high-K layer (the portion is termed "heat zone" e.g., only the portion is directly heated by a LED light or has a local electric heater, while the rest is not), (2) the vertical heating transfer between the heat zone and a portion of the sample should be much larger than the lateral heat transfer within the high-K material (i.e. in the lateral direction of the high-K material), (3) the relevant sample should have a large lateral to vertical size ratio, and (4) the heating power of the heat zone must sufficient to heat up the relevant sample volume in a time frame that lateral heat transfer (i.e., heat conduction) is relatively negligible.

To satisfy the condition (2) above, the scaled thermal conduction ratio (STC ratio) of the vertical heat transfer from the high-K heating zone to the sample through the middle layer that is between the high-K and the sample to the lateral heat transfer inside the high-K layer is defined as:

$$STC \text{ ratio} = \eta = 0.025 \cdot \frac{K_m K_s D^2}{K_k (K_m t_s + K_s t_m) t_k}$$

wherein $K_k$, $K_s$, and $K_m$ is, respectively, the thermal conductivity of the high-K layer, the relevant sample, and the middle layer (i.e. the layer between the high-K and the sample), $t_k$, $t_s$, and $t_m$ is, respectively, the thickness of the high-K layer, the sample, and the middle layer; D is the average lateral dimension of the relevant sample, and 0.025 is a scaling factor.

To locally heat a part of the high-K layer and a part of sample volume above the part of the high-K layer to desired temperatures, while keeping the rest of the high-K layer and the rest of the sample volume at much lower temperatures during a thermal cycling. In some embodiments, the scaled thermal conduction ratio (STM ratio) is 2 or larger, 5 or larger, 10 or larger, 20 or larger, 30 or larger, 40 or larger, 50 or larger, 100 or larger, 1000 or larger, 10000 or larger, 10000 or larger, or in a range between any of the two values.

In some preferred embodiments, the scaled thermal conduction ratio (STM ratio) is in a range of between 10 to 20, 30 to 50, 100 to 1,000, 1,000 to 10,000, or 10,000 to 1,000,000.

To satisfying the condition (2) and (3) above, in some embodiments, the lateral to vertical size (LVS) ratio for relevant sample is 5, 10, 20, 50, 70, 100, 200, 300, 400, 500, 600, 700, 800, 800, 1,000, 2,000, 5,000, 10,000, 100,000, or in a range between any of the two values.

In some preferred embodiments, the LVS ratio for relevant sample is in a range of 5 to 10, 10 to 50, 50 to 100, 100 to 500, 500 to 1,000, 1,000, to 10,000, or 10,000 to 100,000, In certain embodiments, the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

In some preferred embodiments, the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

C. Large Sample to Non-Sample Thermal Mass Ratio (NSTM Ratio)

An increase of the sample-to-non-sample thermal mass ratio can shorten heating time, reduce heating energy, and increase energy efficiency. In an embodiment where a sample is sandwiched between the two plates, a thermal mass ratio can be estimated by only considering the relevant sample volume and the portions of the two plates that sandwich the relevant sample, assuming there are no thermal losses in these volumes. Therefore, one parameter to measure a thermal mass ratio is the ratio of "specific area thermal mass" of the relevant sample to the non-sample (the portions of the plates that sandwich the relevant sample as well as the part heating/cooling layer on the plate portion). The term "specific area thermal mass" of a material refers to as the volume specific heat of the material multiplying its thickness.

The sample to non-sample thermal mass ratio is a ratio of the useful heat energy (which directly heat the relevant sample) to the "wasted heat energy (that heats non-sample materials), assuming that the heat losses by thermal conduction and radiation are negligible. For examples, water has a volume specific heat of 4.2 J/(cm$^3 \cdot ^\circ$ C.), thus the area specific heat for a 30 um thick water layer is $1.26 \times 10^{-2}$ J/(cm$^3 \cdot ^\circ$ C.). A PMMA has a volume specific heat of 1.77 J/(cm$^3 \cdot ^\circ$ C.), thus the area specific heat for a 25 um thick PMMA layer is $4.43 \times 10^{-3}$ J/(cm$^3 \cdot ^\circ$ C.), which is ~2.8 times less than that of 30 um water layer. Gold has a volume specific heat of 2.5 J/(cm^3-C), thus the area specific heat for a 0.5 um thick gold layer is $1.25 \times 10^{-4}$ J/(cm^2-C), which is ~100 times less than that of 30 um water layer, and is negligible. The negligible area specific heat of the Au is due to its thin thickness.

If, in a RHC card embodiment, the relevant sample is sandwiched between two plates of 25 um thick each and the heating/cooling layer is 0.5 um thick, then the sample to non-sample thermal mass ratio for this case is ~1.4. Namely, when the heat losses by thermal conduction and radiation are neglected, the useful energy to the wasted energy ratio is ~1.4, and the useful energy to the total heating energy ratio is 58%.

In some embodiments, the sample to non-sample thermal mass ratio (NSTM ratio) is 0.1, 0.2, 0.3, 0.4, 0.5, 0.6, 0.7, 1, 1.5, 2, 3, 4, 5, 10, 20, 30, 40, 50, 60, 70, 100, 200, 300, 1000, 4000, or in a range between any of the two values.

In preferred embodiments, the sample to non-sample thermal mass ratio (NSTM ratio) is in a range of between 0.1 to 0.2, 0.2 to 0.5, 0.5 to 0.7, 0.7 to 1, 1 to 1.5, 1.5 to 5, 5 to 10, 10 to 30, 30 to 50, 50 to 100, 100 to 300, 300 to 1,000, or 1,000 to 4,000.

To make the sample to non-sample thermal mass ratio high, one needs to keep the area thermal mass of the non-sample low, which in turn, needs to make the plates and the heating/cooling layer thin, and/or the volume specific heat low.

To make the thermal mass ratio large, one embodiment uses a thin material that has multi-layers or mixed materials. For examples, a carbon fiber layer(s) with plastic sheets or carbon mixed with plastics, which can have a thickness of 0.1 um, 0.2 um, 0.5 um, 1 um, 2 um, 5 um, 10 um, 25 um, 50 um, or in a range between any of the two values.

D. Thin Thickness and Large Lateral to Vertical Size Ratio (LVS Ratio) for Relevant Sample The term of "lateral to vertical size ratio for sample" or "LVS ratio for sample" refers to the ratio of the average lateral size of the relevant sample volume to its average vertical size. A larger LVS ratio for sample can reduce the wasted heating energy and increase heating speed and/or cooling speed in the embodiments that the heating and/or cooling is primarily from the vertical direction, and can reduce the lateral thermal conduction loss at the edge of the relevant sample relative to the total thermal energy. All of these can increase and/or can increase cooling time.

In some embodiments, the LVS ratio for relevant sample is 5, 10, 20, 50, 70, 100, 200, 300, 400, 500, 600, 700, 800, 800, 1,000, 2,000, 5000, 10,000, 100,000, or in a range between any of the two values.

In some preferred embodiments, the LVS ratio for relevant sample is in a range of 5 to 10, 10 to 50, 50 to 100, 100 to 500, 500 to 1,000, 1000, to 10,000, or 10,000 to 100,000, For example, a sample has a lateral dimension of 15 mm and a thickness of 30 um, hence an LVS for the sample of 500.

In certain embodiments, the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

In some preferred embodiments, the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

E. Thin Thickness and Large Lateral to Vertical Size Ratio (LVS Ratio) for Non-Samples The term of "lateral to vertical size ratio for non-sample" or "LVS ratio for non-sample" refers to the ratio of the average lateral size of the portions of the two plates that sandwich the relevant sample (which is the same as the average lateral size of the relevant sample volume) to its thickness. A large LVS ratio for non-sample can reduce the lateral thermal conduction loss at the edge of the non-sample relative to the total thermal energy.

In some embodiments, the LVS ratio for non-sample is 5, 10, 20, 50, 70, 100, 200, 300, 400, 500, 600, 700, 800, 800, 1,000, 2000, 5000, 10,000, 100,000, or in a range between any of the two values.

In preferred embodiments, the LVS ratio for non-sample is in a range of 5 to 10, 10 to 50, 50 to 100, 100 to 500, 500 to 1,000, 1000, to 10,000, or 10,000 to 100,000, For example, two 25 um thick plates sandwich a sample of 5 mm or larger lateral dimension of the relevant sample, hence an LVS for the non-sample of 200 or higher for each plate.

To shorten heating time, reduce heating energy, and increase energy efficiency, the lateral thermal conduction through a non-sample material (on the sample holder) should be reduced.

In particularly, when the first and the second plates are made of the materials that are not good thermal materials, the thickness of the plates should be minimized.

In some embodiments, the first plate or the second plate or each of both plates has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

In some preferred embodiments, the first plate or the second plate or each of both plates has a thickness of 10 nm, 100 nm, 200 nm, 300 nm, 400 nm, 500 nm, 1 um, 2.5 um, 5 um, 10 um, 25 um, 50 um, 75 um, or in a range between any of the two values.

The first plate and the second plate can have the same thickness or a different thickness, and can be made of the same materials or different materials.

In some preferred embodiments, the first plate or the second plate or each of both plates has a thickness in a range of between 10 nm and 500 nm, 500 nm and 1 um, 1 um and 2.5 um, 2.5 um and 5 um, 5 um and 10 um, 10 um and 25 um, 25 um and 50 um, 50 um and 100 um, 100 um and 200 um, or 200 um and 500 um, or 500 um and 1,000 um.

In some preferred embodiments, the first plate and second plates are plastic, a thin glass, or a material with similar physical properties. The first plate or second plate has a thickness of 100 nm, 500 nm, 1 um, 5 um, 10 um, 25 um, 50 um, 100 um, 175 um, 250 um, or in a range between any of the two values.

In some preferred embodiments, the first plate and second plates are plastic, a thin glass, or a material with similar physical properties. The first plate has a thickness of 5 um, 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values.

F. Cooling Layer of High K and/or High Thermal Conductivity-to-Capacity Ratio (KC Ratio)

Since any thermal conduction through a non-sample material will waste energy and since lateral thermal conduction has much longer thermal path than vertical thermal conduction, the energy wasted in lateral thermal conduction in non-sample materials should be minimized. One way to minimize this type of wasted energy is to use a high thermal conduction (high-K) or more precisely a high thermal conductivity-to-capacity ratio (KC ratio) materials for the cooling layer. For a given thermal conductivity, a given temperature change, and a given geometry, a high K and/or a high KC ratio material would need much less energy to be heated up than a low K and/or low KC ratio material.

In some embodiments, the KC ratio materials for the cooling layer is equal to or higher than 0.1 $cm^2$/sec, 0.2 $cm^2$/sec, 0.3 $cm^2$/sec, 0.4 $cm^2$/sec, 0.5 $cm^2$/sec, 0.6 $cm^2$/sec, 0.7 $cm^2$/sec, 0.8 $cm^2$/sec, 0.9 $cm^2$/sec, 1 $cm^2$/sec, 1.1 $cm^2$/sec, 1.2 $cm^2$/sec, 1.3 $cm^2$/sec, 1.4 $cm^2$/sec, 1.5 $cm^2$/sec, 1.6 $cm^2$/sec, 2 $cm^2$/sec, 3 $cm^2$/sec, or in a range between any of the two values.

In some preferred embodiments, the KC ratio for the cooling layer is in a range of between 0.5 $cm^2$/sec and 0.7 $cm^2$/sec, 0.7 $cm^2$/sec and 0.9 $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec.

In some embodiments, a high thermal conductivity (i.e. high-K) material is used for the cooling layer, and the high-K material has a thermal conductivity that is equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), 600 W/(m·K), 1000 W/(m·K), 5000 W/(m·K), or in a range between any of the two values.

In some preferred embodiments, a high thermal conductivity (i.e. high-K) material is used for the cooling layer, and the high-K material has a thermal conductivity that is in the range of 50 W/(m·K) to 100 W/(m·K), 110 W/(m·K) to 200 W/(m·K), 200 W/(m·K) to 400 W/(m·K), 400 W/(m·K) to 600 W/(m·K), or 400 W/(m·K) to 5000 W/(m·K).

In some embodiments, the high-K material is selected from metals, semiconductors, and allows of thermal conductivity higher than 50 W/(m·K), and any combinations (including any mixtures). In some embodiments, the high-K material is selected from gold, copper, silver, and aluminum, and any combinations (including any mixtures). In some embodiments, the high-K material is selected from carbon particles, carbon tubes, graphite, silicon, and any combinations (including any mixtures).

G-1. Cooling Zone Area Larger than Lateral Relevant Sample Area and Heating Zone Area To effectively cool a sample while reducing the wasted energy in non-sample materials, in some embodiments, a high K and/or a high KC ratio material (termed "high K material") is used as the major channel for removing the heat from the sample. The area of high-K cooling zone (layer) should be larger than the relevant sample lateral size.

In certain embodiments, the cooling zone (layer) has an area that is larger than the lateral area of the relevant sample by a factor of 1.5, 2, 3, 4, 5, 10, 20, 50, 70, 100, 200, 300, 400, 500, 600, 700, 800, 800, 1,000, 2,000, 5,000, 10,000, 100,000, or in a range between any of the two values.

In preferred embodiments, the cooling zone (layer) has an area that is larger than the lateral area of the relevant sample by a factor in a range of 1.5 to 5, 5 to 10, 10 to 50, 50 to 100, 100 to 500, 500 to 1,000, 1000, to 10,000, or 10,000 to 100,000.

To increase the cooling speed and thermal cycling efficiency, in certain embodiments, the high-K cooling layer (zone) should an area to large than the heating zone area.

In some embodiments, the area of the cooling zone (layer) is larger than the area of the heating zone (layer) by a factor (i.e. the ratio of the cooling zone area to the heating zone area, "CH ratio") of 1.1, 1.5, 2, 3, 4, 5, 10, 20, 30, 40, 50, 70, 100, 200, 300, 400, 500, 600, 700, 800, 800, 1,000, 5000, 10,000, 100,000, or in a range between any of the two values. In preferred embodiments, the cooling zone (layer) has an area that is larger than the lateral area of the hearing zone (layer) by a factor in a range of 1.1 to 1.5, 1.5 to 5, 5 to 10, 10 to 50, 50 to 100, 100 to 500, 500 to 1,000, 1,000, to 10,000, or 10,000 to 100,000.

G-2. Cooling Zone Area and Heating Zone Area are the Same as Lateral Relevant Sample Area In certain embodiments, cooling zone area and heating zone area are the same as lateral relevant sample area, which is much smaller than the total sample area on the plat, and is smaller than the area of the plate. The cooling zone has an area of 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, The cooling zone can have different shape. In certain embodiments, there are more than one cooling zones on one plate, and the cooling zones are separated from each other by a low thermal conductive material such as air or plastic.

H. Heating Zone of High K and/or High Thermal Conductivity-to-Capacity Ratio (KC Ratio)

Since any thermal conduction through a non-sample material that will waste energy and lateral thermal conduction has much longer thermal path than vertical thermal conduction, the energy wasted in lateral thermal conduction in non-sample materials should be minimized. One way to minimize this type of wasted energy is to use high thermal conductivity-to-capacity (KC) ratio materials for the materials in heating zone, which would need much less energy of heating up for a given thermal conductivity, a given temperature change, and a given geometry.

In some embodiments, the KC ratio materials for the heating layer is equal to or higher than 0.1 $cm^{\wedge 2}$/sec, 0.2 $cm^{\wedge 2}$/sec, 0.3 $cm^{\wedge 2}$/sec, 0.4 $cm^{\wedge 2}$/sec, 0.5 $cm^{\wedge 2}$/sec, 0.6 $cm^{\wedge 2}$/sec, 0.7 $cm^{\wedge 2}$/sec, 0.8 $cm^{\wedge 2}$/sec, 0.9 $cm^{\wedge 2}$/sec, 1 $cm^{\wedge 2}$/sec, 1.1 $cm^{\wedge 2}$/sec, 1.2 $cm^{\wedge 2}$/sec, 1.3 $cm^{\wedge 2}$/sec, 1.4 $cm^{\wedge 2}$/sec, 1.5 $cm^{\wedge 2}$/sec, 1.6 $cm^{\wedge 2}$/sec, 2 $cm^{\wedge 2}$/sec, 3 $cm^{\wedge 2}$/sec, or in a range between any of the two values.

In some preferred embodiments, the KC ratio for the heating layer is in a range of between 0.5 $cm^{\wedge 2}$/sec and 0.7 $cm^{\wedge 2}$/sec, 0.7 $cm^{\wedge 2}$/sec and 0.9 $cm^{\wedge 2}$/sec, 0.9 $cm^{\wedge 2}$/sec and 1 $cm^{\wedge 2}$/sec, 1 $cm^{\wedge 2}$/sec and 1.1 $cm^{\wedge 2}$/sec, 1.1 $cm^{\wedge 2}$/sec and 1.3 $cm^{\wedge 2}$/sec, 1.3 $cm^{\wedge 2}$/sec and 1.6 $cm^{\wedge 2}$/sec, 1.6 $cm^{\wedge 2}$/sec and 2 $cm^{\wedge 2}$/sec, or 2 $cm^{\wedge 2}$/sec and 3 $cm^{\wedge 2}$/sec.

In some embodiments, a high thermal conductivity (i.e. high-K) material is used for the heating layer, and the high-K material has a thermal conductivity that is equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), 600 W/(m·K), 1000 W/(m·K), 5000 W/(m·K), or in a range between any of the two values.

In some preferred embodiments, a high thermal conductivity (i.e. high-K) material is used for the heating layer, and the high-K material has a thermal conductivity that is in the range of 50 W/(m·K) to 100 W/(m·K), 110 W/(m·K) to 200 W/(m·K), 200 W/(m·K) to 400 W/(m·K), 400 W/(m·K) to 600 W/(m·K), or 400 W/(m·K) to 5000 W/(m·K).

In some embodiments, the high-K material is selected from metals, semiconductors, and allows of thermal conductivity higher than 50 W/(m·K), and any combinations (including any mixtures). In some embodiments, the high-K material is selected from gold, copper, silver, and aluminum, and any combinations (including any mixtures). In some embodiments, the high-K material is selected from carbon particles, carbon tubes, graphite, silicon, and any combinations (including any mixtures).

To receive light energy by a heating zone (layer), a thermal radiation enhancement surface(s) will be used (on one side or both side of the heating zone). A thermal radiation absorption enhancement surface can be achieved by directly modify the structures of the surface (e.g. patterning nanostructures), coating a high thermal radiation materials (e.g. coating a black paint), or both.

The thermal radiation enhancement surface has a high average light absorptance (e.g. the black paint used in our experiments). In certain embodiments, the heating zone has a surface that has an average light absorptance of 30%, 40%, 50%, 60%, 70%, 80%, 90%, 95%, 100%, or in a range between any of the two values.

In certain preferred embodiments, the heating zone has a surface that has an average light absorptance in a range of 30% to 40%, 40% to 60%, 60% to 80% to 90%, or 90% to 100%.

In some preferred embodiments, the heating zone has a surface that has an average light absorptance in a range of 30% to 100%, 50% to 100%, 70% to 100%, or 80% to 100%. In certain embodiments, the heating zone has a surface that has an average light absorptance of a value given above by averaging over a wavelength range 400 nm to 800 nm, 700 nm to 1500 nm, 900 nm to 2000 nm, or 2000 nm to 20000 nm.

Increasing Thermal Radiative Cooling

In certain embodiments, a fast temperature cycling is achieved by increasing thermal radiative cooling percentage in the total cooling of the sample and the sample holder (i.e. removing heat to the environment) during a thermal cycling, preferably through using high thermal conductivity material as the material for thermal radiative cooling. One reason is that cooling through lateral thermal conduction needs to heat up many non-sample materials, wasting energy. Another reason is that thermal radiation cooling is proportional to the fourth power of the temperature and can be more effective than thermal conduction in a thin film.

To enhancing thermal radiative cooling, in certain embodiments, the thermal radiative cooling uses a cooling layer (cooling zone) that is enhanced for thermal radiative cooling. The enhancement includes (i) increase thermal conductivity of the cooling zone (layer), (ii) enlarging the area of the cooling zone (layer), (iii) enhance the surface thermal radiation of the cooling zone, and (iv) a combination thereof.

Examples of a high thermal conductivity materials are metals (such as gold, silver, coper, aluminum), semimetals, semiconductors (e.g. silicon) or a combination thereof.

To further enhance thermal radiation of a cooling zone (layer), a thermal radiation enhancement surface(s) will be used (on one side or both side of the cooling zone). A thermal radiation enhancement surface can be achieved by directly modify the structures of the surface (e.g. patterning nanostructures), coating a high thermal radiation material (e.g. coating a black paint), or both.

The thermal radiation enhancement surface has a high average light absorptance (e.g. the black paint used in our experiments). In certain embodiments, the cooling zone has a surface that has an average light absorptance of 30%, 40%, 50%, 60%, 70%, 80%, 90%, 95%, 100%, or in a range between any of the two values.

In certain preferred embodiments, the cooling zone has a surface that has an average light absorptance in a range of 30% to 40%, 40% to 60%, 60% to 80% to 90%, or 90% to 100%.

In some preferred embodiments, the cooling zone has a surface that has an average light absorptance in a range of 30% to 100%, 50% to 100%, 70% to 100%, or 80% to 100%.

In certain embodiments, the cooling zone has a surface that has an average light absorptance of a value given above by averaging over a wavelength range 400 nm to 800 nm, 700 nm to 1,500 nm, 900 nm to 2,000 nm, or 2,000 nm to 20,000 nm.

In certain embodiments, the surface thermal radiation enhancement layer is black paint, plasmonic structures, nanostructures, or any combination thereof.

The high thermal radiation materials are polymer mixtures that look black by human eyes (often termed "black paints"). A high thermal radiation material include, but not limited to, a mixture of polymers and nanoparticles. One example of the nanoparticles is black carbon nanoparticle, carbon, nanotubes, graphite particles, graphene, metal nanoparticles, semiconductor nanoparticles, or a combination thereof.

The high thermal radiation material further comprises a material that is deposited or made on the layer surface and look blacks by human eyes. The materials include, but not limited to, black carbon nanoparticle, carbon, nanotubes, graphite particles, graphene, metal nanoparticles, semiconductor nanoparticles, or a combination thereof.

The plasmonic structures include nanostructured plasmonic structures.

In some embodiments, a cooling layer comprise a layer of high thermal conductivity metal (50 W/(m·K) or higher) with a surface thermal radiation enhancement layer. In some embodiments, the surface thermal radiation enhancement layer has a low lateral thermal conductance, which is due to either ultrathin layer, low thermal conductivity, or both.

Percentage of Thermal Radiative Cooling.

In certain embodiments, thermal radiative cooling is achieved by increasing the area of radiative cooling layer (i.e. a high-K material, unless stated otherwise), and the radiative cooling layer area is larger than the lateral area of the relevant sample by a factor of 1.2, 1.5, 2, 3, 4, 5, 10, 20, 30, 40, 50, 60, 70, 80 100, 200, 300, 400, 500, 600, 700, 800, 800, 1,000, 2,000, 5,000, 10,000, 100,000, or in a range between any of the two values.

In preferred embodiments, the radiative cooling zone (layer) has an area that is larger than the lateral area of the relevant sample by a factor in a range of 1.2 to 3, 3 to 5, 5 to 10, 10 to 50, 50 to 100, 100 to 500, 500 to 1,000, 1,000, to 10,000, or 10,000 to 100,000.

In some embodiments, the ratio of the thermal radiation cooling by the cooling zone (layer) to the total cooling of the sample and sample holder during a thermal cycling is 10%, 20%, 30%, 40%, 50%, 60%, 70%, 80%, 90%, 99%, or in a range between any of the two values.

In some preferred embodiments, the ratio of the thermal radiation cooling by the cooling zone (layer) to the total cooling of the sample and sample holder during a thermal cycling is in a range of between 10% and 20%, 20% and 30%, 30% and 40%, 40% and 50%, 50% and 60%, 60% and 70%, 70% and 80%, 80% and 90%, or 90% and 99%.

J. Control of Cooling Layer Thickness

In certain embodiments, the thickness of the cooling layer thickness is configured to facilitate to optimize heating locally and/or energy efficiency. If the cooling zone (layer) is too thick, a significant percentage of the heating energy will be wasted by the cooling layer, lengthening heating time (for a given heating power). On the other hand, if the cooling zone is too thin, the cooling time will be significantly longer. Hence, the cooling layer thickness should be optimized for both fast heating and cooling.

Through our experiments, we found that the thickness of the high-K cooling layer can regulate the cooling rate. By selecting a proper high-K cooling layer thickness and a proper LED power density, a fast heating and cooling can be achieved.

Since a thermal conductance of a layer proportional to a material's thermal conductivity times the layer thickness, so it is this product should be optimized.

In some embodiments, a cooling zone (layer) has thermal conductivity times its thickness of $6\times10^{-5}$ W/K, $9\times10^{-5}$ W/K, $1.2\times10^{-4}$ W/K, $1.5\times10^{-4}$ W/K, $1.8\times10^{-4}$ W/K, $2.1\times10^{-4}$ W/K, $2.7\times10^{-4}$ W/K, $3\times10^{-4}$ W/K, $1.5\times10^{-4}$ W/K, or in a range between any of the two values.

In some preferred embodiments, a cooling zone (layer) has thermal conductivity times its thickness in a range of $6\times10^{-5}$ W/K to $9\times10^{-5}$ W/K, $9\times10^{-5}$ W/K to $1.5\times10^{-4}$ W/K, $1.5\times10^{-4}$ W/K to $2.1\times10^{-4}$ W/K, $2.1\times10^{-4}$ W/K to $2.7\times10^{-4}$ W/K, $2.7\times10^{-4}$ W/K to $3\times10^{-4}$ W/K, or $3\times10^{-4}$ W/K to $1.5\times10^{-4}$ W/K.

In certain preferred embodiments, a cooling zone (layer) has thermal conductivity times its thickness in a range of $9\times10^{-5}$ W/K to $2.7\times10^{-4}$ W/K, $9\times10^{-5}$ W/K to $2.4\times10^{-4}$ W/K, $9\times10^{-5}$ W/K to $2.1\times10^{-4}$ W/K, or $9\times10^{-5}$ W/K to $1.8\times10^{-4}$ W/K.

In one embodiment, a cooling zone comprises a gold layer of a thickness in the range of 200 nm to 800 nm. In another embodiment, a cooling zone comprises a gold layer of a thickness in the range of 300 nm to 700 nm.

K. Large Conductance Between Sample and Heating Zone or Cooling Zone

For a fast heating and cooling a sample, the thermal conduction per unit area between a relevant sample and a heating layer and/or the cooling layer should be large. The thermal conduction per area is equal to the conductivity (unit volume) divided by the material thickness for the materials that are between the HC layer and the sample. For example, for 100 nm thick of PS as the second plate which has the HC layer on one surface and the sample on the other surface, the conductance between the HC layer and the sample is ~1000 $W/(m^2 \cdot K)$ Based on experiments, in some embodiments of a RHC card, the materials between the heating zone and the relevant sample has a thermal conductivity and a thickness configured to be about 1000 $W/(m^2 \cdot K)$ or higher.

In some embodiments of a RHC card, the materials between the heating zone and the relevant sample has a thermal conductivity and a thickness configured to have a conductance per unit area that is equal to or larger than 1000 $W/(m^2 \cdot K)$, 2000 $W/(m^2 \cdot Km^2 \cdot K)$, 3000 $W/(m^2 \cdot Km^2 \cdot K)$, 4000 $W/(m^2 \cdot Km^2 \cdot K)$, 5000 $W/(m^2 \cdot Km^2 \cdot K)$, 7000 $W/(m^2 \cdot Km^2 \cdot K)$, 10000 $W/(m^2 \cdot K)$, 20000 $W/(m^2 \cdot K)$, 50000 $W/(m^2 \cdot K)$, 50000 $W/(m^2 \cdot K)$, 100000 $W/(m^2.K)$, or in a range of any the values.

A preferred conductance per unit area of the material between the heating zone and the relevant sample is in a range of 1000 $W/(m^2 \cdot K)$ to 2000 $W/(m^2 \cdot K)$, 2000 $W/(m^2 \cdot K)$ to 4000 $W/(m^2 \cdot K)$, 4000 $W/(m^2 \cdot K)$ to 10,000 $W/(m^2 \cdot K)$, or 10000 $W/(m^2 \cdot K)$ to 100000 $W/(m^2 \cdot K)$.

In another preferred embodiment, it has zero distance between the heating zone and the relevant sample, and hence an infinity for the conductance per unit area of the material between the heating zone and the relevant sample.

In certain embodiments, the heating layer or the cooling layer is separated from a relevant sample by a thin plastics plate (or film) which has a thermal conductivity in the range of 0.1 to 0.3 W/(m·K), and the thin plastic layer has a thickness of 0 nm, 10 nm, 50 nm, 100 nm, 200 nm, 300 nm, 400 nm, 500 nm, 1 um, 2.5 um, 5 um, 10 um, 25 um, 50 um, 75 nm 100 um, 150 um, or in a range between any of the two values In some preferred embodiments, the thin plastic plate (or film) that separate the relevant sample from the heating layer or the cooling layer has thickness in a range between 0 nm and 100 nm, 100 nm and 500 nm, 500 nm and 1 um, 1 um and 5 um, 5 um and 10 um, 10 um and 25 um, 25 um and 50 um, 50 um and 75 um, 75 um and 100 um, or 100 um and 150 um.

In one preferred embodiment of the RHC card, the thin plastic plate (or film) that separate the relevant sample from the heating layer or the cooling layer has thickness of 1 nm, 10 nm, 0.1 um, 0.5 um, 1 um, 5 um, 10 um, 20 um, 25 um, or a range between any two values.

L. Small Relative Reagent Lateral Diffusion

In order to make a biochemical reaction substantially uniform in the relevant sample volume during a temperature change or a thermal cycling, the average lateral area of the relevant sample should be significantly larger than the lateral diffusion of the nucleic acids and/or other regents used for a molecular amplification and/or reaction. In this way, during the time of temperature change or a thermal cycling, most of the molecules inside the relevant sample volume do not have enough time to diffuse out of the relevant sample volume, while most of the molecules outside the relevant sample volume do not have enough time to diffuse into the relevant sample volume.

Considering a thermal cycling time duration of 3 min and a diffusion constant of $\sim 1\times10^{\wedge}-6$ $cm^2/s$ for a molecule about 600 Da molecular weight, the diffusion length is ~130 um.

In certain embodiments, the ratio of the average lateral size of the relevant sample volume to the diffusion length of the reagent during the time for thermal cycling or a reaction is equal to or larger than 5, 6, 7, 10, 15, 20, 25, 30, 40, 50, 60, 70, 80, 90, 100, 150, 200, 500, 1000, 5000, 10000, 100000, or in a range between any two values.

In some preferred embodiments, the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1000, 1000 to 5000, 5000 to 10,000, or 10,000 to 100,000.

In some preferred embodiments, the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1,000, 1,000 to 5,000, 5,000 to 10,000, or 10,000 to 100,000.

In certain preferred embodiments, the average lateral dimension of the relevant volume is 1 mm, 2 mm, 3 mm, 5 mm, 6 mm, 7 mm, 8 mm, 9 mm 10 mm, 12 mm, 15 mm, 20 mm, 30 mm, 40 mm, 50 mm, 70 mm, 100 mm, 200 mm, or in a range between any two values.

In some preferred embodiments, the average lateral dimension of the relevant volume is in a range of 1 mm to 5 mm, 5 mm to 10 mm, 10 mm to 20 mm, 20 mm to 40 mm, 40 mm to 70 mm, 70 mm to 100 mm, or 100 mm to 200 mm.

In another preferred embodiments, the average lateral dimension of the relevant volume is in a range of 1 mm to 5 mm, 1 mm to 10 mm, or 5 mm to 20 mm.

M. Without Edge Sealing or Simple Edge Sealing

To simplify the sample holder operation and cost, in certain embodiments, there is no sealing between the two plates that confine a sample; namely, the sample sandwiched between the plates can evaporate from the sample edge into environment. However, in our experiments, we found that in our sample card configuration, such evaporation is negligible relative to total sample volume, due to a large ratio of the lateral sample area to the sample edge area; the plates have prevented most of the evaporation.

In some embodiments, an enclosure ring spacer or some discontinuous spacer walls can be put on one or both of the plates to reduce or eliminate a sample evaporation.

P-2 Forced Air Cool

In certain embodiments, there is a forced air cooling/circulating system near the RHC card to speed up the cooling process. The example of forced air cooling system includes but not limit to a fan circulating the cool air near the card, several fans circulating the cool air near the card, a cooling source cool the air near the card, a cooling pad direct touch the card or their combinations.

In certain embodiments, there is a forced air cooling/circulating system cooling the air on the top surface of the card.

In certain embodiments, there is a forced air cooling/circulating system cooling the air on the bottom surface of the card.

In certain embodiments, there is a forced air cooling/circulating system cooling the air surrounding all the surface of the card.

2. Mechanical Structure Designs

N. Movable Plates and Compressed Open Flow, Hinges, Opening Notches, Recessed Edge and Sliders To load a sample simply, in certain embodiments in the present invention, the two plates of a RHC card are movable relative to each other into different configurations. A sample is deposited at an open configuration of the plates, and then the plates are pressed into a closed configuration. During the pressing, the sample will flow between the plates into a thin layer, and the flow is termed "compressed open flow", since there are plenty room between the plates that allow the sample to flow.

In certain embodiments, spaces for regulating the sample thickness are added on one or both of the plates, hence a device for rapidly changing the temperature of a fluidic sample, comprising:

a first plate (10), a second plate (20), a heating layer (112-1), and a cooling layer (112-2), wherein:
the first and second plates are movable relative to each other into different configurations;
each of the first plate and the second plate has, on its respective inner surface, a sample contact area for contacting a fluidic sample; wherein the sample contact areas face each other, are separated by an average separation distance of 200 um or less, and are capable of sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates;
configured to cool the relevant sample volume; and
comprises a layer of material that that has a thermal conductivity to thermal capacity ratio of 0.6 $cm^2$/sec or larger;
wherein one of the configurations is an open configuration, in which: the two plates are partially or completely separated apart and the average spacing between the plates is at least 300 um;
wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less; and
wherein, in some embodiments, the heating layer and cooling layer are the same material layer that has a heating zone and a cooling zone, and wherein the heating zone and cooling zone can have the same area or different areas.

In some embodiments, the sample holder (also termed "RHC card" or "Q-card") with movable plates further comprises hinges, notches, recesses, which help to facilitate the manipulation of the sample holder and the measurement of the samples. Furthermore, the sample holders can slide into sliders. The structure, material, function, variation and dimension of the hinges, notches, recesses, sliders and compress open flow are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Spacers (13)

In certain embodiments, the spacers as described in embodiment SH-5 will be used to regulate the sample thickness and make the thickness uniform. The spacers also allow to achieve uniform sample thickness, even when both plates are very thin (e.g. 25 um thick or less).

In certain embodiments, the spacers are fixed on one or both of the plates. In certain embodiments, the spacers are mixed with the sample. In some embodiments, the spacers have a uniform height and the spacers, together with the first plate and the second plate, regulate the sample layer. In some embodiments, the thickness of the sample layer is substantially equal to the height of the spacers.

In some embodiments, the plates are flat (e.g. as shown in FIG. 3). In some embodiments, either one or both of the plates include wells (e.g. as shown in FIG. 4). For example, in certain embodiments the width of the wells can be less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In certain embodiments, the depth of the wells can be less than 500 um, 200 um, 100 um, 50 um, 25 um, 10 um, 5 um, 2.5 um, 1 um, 500 nm, 400 nm, 300 nm, 200 nm, 100 nm, 50 nm, 20 nm, 10 nm, 5 nm, 2 nm, or 1 nm, or in a range between any of the two values In some embodiments, one or both of the plates have wells and most or entire of the samples are only inside the well of one plate and is covered by other plate (not shown in the figures).

P. Sample Cartridge and Thermal Conduction Isolation

In certain embodiments, the RHC card (sample holder) can be further mounted on a sample cartridge. The cartridge can be configured to slide in or out a base (also termed "adaptor"). A base houses the power source, temperature sensors and controllers, signal measurement devices, and a slot for the sample holder with or without a cartridge to slide in or out of the base.

In some embodiments, the sample holder, the cartridge (i.e. the sample holder support) or both are "thermal conduction isolated", namely, they do not have or almost do not have, during a thermal cycling, a thermal conduction to the environment. In this case, the cooling in the thermal cycling is essentially by thermal radiation (this is termed "no conductive heat transfer"). In some embodiment, the "thermal conduction isolation" is achieved in the sample holder, the cartridge, or both by configuration their materials, the geometry (including of thickness reduction), or both.

Q. Combination of Above

An embodiment of a RHC card can be any combination of the specification described in SH-1, SH-2, SH-3 and in subsections of A to P.

R. Heating Sources

The heating layer or the heating/cooling layer in a RHC card is configured to be heated by a heating source, wherein the heating source delivers heat energy to the heating/cooling layer optically, electrically, by radio frequency (RF) radiation, or a combination thereof.

S. Base (i.e. Adaptor)

In some embodiments, the apparatus further comprises a base (an adaptor) that is configured to house the sample card, the heating source, temperature sensors, a part of an entire of temperature controlled (include a smartphone in some embodiments), extra-heat sink (optionally), a fan (optionally) or a combination of thereof. In some embodiments, the adaptor comprises a card slot, into which the sample card or a sample cartridge can be inserted. In some embodiments, the sample card or the sample cartridge, after being fully inserted into the slot, or after reaching a pre-defined position in the slot, is stabilized and stays in place without any movement.

T. Smartphone

In some embodiments, a smartphone is used to mage the sample card, controlling the heating and/cooling, sensing a signal, monitor operation use camera, provide light/energy with a flash, communicate to a local or a remote device, integrated through a base (adaptor) in a system, of a combination thereof.

U. Applications for Isothermal Nucleic Acid Amplification

The present invention with a slight modification also provides useful devices and methods for isothermal nucleic acid amplification, where a sample temperature needs to be raised from environment to an elevated temperature (i.e. 65° C.) and keep at the temperature for a period of time (i.e. 5-10 min). In some embodiments, one of the modifications needed for isothermal nucleic acid amplification test, is to reduce or eliminate the cooling zone/layer, so that loss of thermal energy from the sample and/or the sample holder to the environment is reduced.

The present invention with a slight modification provides useful devices and methods for reverse transcription polymerase chain reaction, which contains an isothermal process before the regular PCR, where a sample temperature needs to be raised from environment to an elevated temperature (i.e. 50° C.) and keep at the temperature for a period of time (i.e. 5-10 min). The present invention with a slight modification provides useful devices and methods for minimize PCR cross-contamination as method to use dUTP and uracil-DNA N-glycosylase, where a sample temperature needs to be raised from environment to an elevated temperature (i.e. 50° C.) and keep at the temperature for a period of time (i.e., 1-20 min).

Sample Wells

In certain embodiments, one or both of the plates have sample wells, wherein the well regulates the maximum volume of the sample in the well and prevents the sample to flow into other location of the plates.

Plate Thickness

To reduce the thermal mass of the first and second plates as well as reduce the lateral thermal conduction loss in the plates, the thickness of the first plate and the second plate is preferred to be thin.

In certain embodiments, the first plate or the second plate has a thickness of 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

In some embodiments, the first plate or the second plate has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

The first plate and the second plate can have the same thickness or a different thickness, and can be made of the same materials or different materials.

In some preferred embodiments, the first plate or the second plate has a thickness in a range of between 10 nm and 500 nm, 500 nm and 1 um, 1 um and 2.5 um, 2.5 um and 5 um, 5 um and 10 um, 10 um and 25 um, 25 um and 50 um, 50 um and 100 um, 100 um and 200 um, or 200 um and 500 um, or 500 um and 1000 um.

A preferred thickness of the first plate or the second plate is 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, or in a range between any two of the values. In some preferred embodiments, the thickness of the plate that has the heating/cooling layer is thinner than the other plate that does not have a heater.

In some preferred embodiments, the first plate has a thickness of 100 nm, 200 nm, 500 nm, 1 μm (micron), 2 μm, 5 μm, 10 μm, 25 μm, 50 μm, 100 μm, 125 μm, 150 μm, 175 μm, 200 μm, 250 μm, or in a range between any two of the values; while the second plate has a thickness of 25 μm, 50 μm, 100 μm, 125 μm, 150 μm, 175 μm, 200 μm, 250 μm, 500 μm, 1 mm, 1.5 mm, 2 mm, or in a range between any two of the values, In some embodiments, the average thickness for at least one of the plates is in the range of 1 to 1000 µm, 10 to 900 µm, 20 to 800 µm, 25 to 700 µm, 25 to 800 µm, 25 to 600 µm, 25 to 500 µm, 25 to 400 µm, 25 to 300 µm, 25 to 200 µm, 30 to 200 µm, 35 to 200 µm, 40 to 200 µm, 45 to 200 µm, or 50 to 200 µm.

In some embodiments, the average thickness for at least one of the plates is in the range of 50 to 75 µm, 75 to 100 µm, 100 to 125 µm, 125 to 150 µm, 150 to 175 µm, or 175 to 200 µm.

In some embodiments, the average thickness for at least one of the plates is about 50 µm, about 75 µm, about 100 µm, about 125 µm, about 150 µm, about 175 µm, or about 200 µm.

Plate Area. In some embodiments, the first plate and/or the second plate has a lateral area of 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 20 cm$^2$ or less, 30 cm$^2$ or less, 50 cm$^2$ or less, 100 cm$^2$ or less, 500 cm$^2$ or less, 1,000 cm$^2$ or less, 5,000 cm$^2$ or less, 10,000 cm$^2$ or less, or in a range between any two of these values.

In preferred embodiments, the first plate and/or the second plate has a lateral area in a range of 1 mm$^2$ (square millimeter) to 10 mm$^2$, 10 mm$^2$ to 50 mm$^2$, 50 mm$^2$ to 100 mm$^2$, 1 cm$^2$ to 5 cm$^2$, 5 cm$^2$ to 20 cm$^2$, 20 cm$^2$ to 50 cm$^2$, 50 cm$^2$ to 100 cm$^2$, 100 cm$^2$ to 500 cm$^2$, 500 cm$^2$ to 1000 cm$^2$, or 1000 cm$^2$ to 10,000 cm$^2$.

In some embodiments, the first plate and the second plate have the same lateral dimension. In some embodiments, one of the plates has an area that is different from the other plates by 10% or less, 30% or less, 50% or less, 80% or less, 90% or less, 95% or less, 99% or less, or in a range between any two of these values (take the largest plate is the base in calculation the different percentage).

In some embodiment, the first plate and/or the second plate has a width or a length of 5 mm, 10 mm, 20 mm, 25 mm, 30 mm, 40 mm, 50 mm, 75 mm, 100 mm, or in a range between any two of these values.

In preferred embodiments, the first plate and/or the second plate has a width or a length in a range of 5 mm to 10 mm, 20 mm to 30 mm, 30 mm to 50 mm, 50 mm to 75 mm, or 75 mm to 100 mm.

In one preferred embodiment, the plate has a width or length in a range of 5 mm to, 50 mm. In another preferred embodiment, the plate has a width in a range of 5 mm to 50 mm and a length in a range of 6 mm to 70 mm.

Materials for Plates

In some embodiments, the materials for the first plate and the second plates, contain but are not limit to polymers (e.g. plastics) or amorphous organic materials. The polymer materials include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the materials for the first plate and the second plate contain but are not limit to inorganic materials including dielectric materials of silicon oxide, porcelain, orcelain (ceramic), mica, glass, oxides of various metals, etc.

In some embodiments, the materials for the first plate and the second plate contain but are not limit to inorganic materials including aluminum oxide, aluminum chloride, cadmium sulfide, gallium nitride, gold chloride, indium arsenide, lithium borohydride, silver bromide, sodium chloride, graphite, carbon nanotubes, carbon fibers, etc.

In some embodiments, the materials for the first plate and the second plate contain but are not limit to metals (e.g. gold, copper, aluminum, etc.) and alloys.

In some embodiments, the materials for the first plate and the second plate are made of multi-layers and/or mixture of the materials listed above.

Heating Layer and Cooling Layer

In certain embodiments, a heating layer (112-1) and a cooling layer (112-2) comprises high K material and/or a high KC ratio material. The high K and/or high KC ratio material comprises materials/structures, such as, but not limited to, metallic film, semiconductors, semimetals, plasmonic surface, metamaterials (e.g. nanostructures), black silicon, graphite, carbon nanotube, silicon sandwich, graphene, superlattice, plasmonic materials, any material/structure that is capable of efficiently absorbing the electromagnetic wave and converting the absorbed energy into thermal energy, and any combination thereof. For a heating layer that is heated by an optical heating source, a heating layer comprises a material layer that significantly absorb the radiated energy from the optical heating source. The significant absorption means that the heating/cooling layer absorbs the radiated energy from the optical heating source more significantly than the sample and the plates.

In certain embodiments, the heating/cooling layer has thickness in the range of 50 nm to 15 um. In certain embodiments, the heating/cooling layer comprise a high K layer that has thickness in the range of 100 nm to 1 um.

In some embodiments, the dimension of the light heating area is about 1 um, 2 um, 5 um, 10 um, 20 um, 50 um, 100 um, 200 um, 500 um, 1 mm, 2 mm, 5 mm, 10 mm, 20 mm, 50 mm, or 100 mm, or in a range between any of the two values. In various embodiments, the size and shape of the light heating areas can vary.

In some embodiments, the heating/cooling layer comprise a dot-coupled-dots-on-pillar antenna (D2PA) array, such as, but not limited to the D2PA array described in U.S. Provisional Patent Application No. 61/347,178, which was filed on May 21, 2010, U.S. Provisional Patent Application 61/622,226, which was filed on Apr. 10, 2012, U.S. PCT Application No. PCT/US2011/037455, which was filed on May 20, 2011, PCT Application No. PCT/US2013/032347, which was filed on Mar. 15, 2013, and U.S. patent application Ser. No. 13/699,270, which was filed on Jun. 13, 2013, the complete disclosures of which are hereby incorporated by reference for all purposes.

In some embodiments, there can be more than one heating/cooling layer. For examples, at least two surfaces of any of the first or second plates have a heating/cooling layer.

In some embodiments, the heating/cooling layer can be two-layer materials: one layer for heating and one for cooling, and the two-layer materials can be on the same surface of any of the first or second plate. For sample, the heating layer can be on the outer surface of the second plate, while the cooling layer is on the outer surface or the inner surface of the first plate. Even the cooling layer is on the outer surface of the first plate, which should be efficient in cooling the sample as long as the first plate has thin thickness (e.g., 25 um or less).

Spacers

In some embodiments of the present invention there are spacers between the two plates. In some embodiments, at least one of the spacers is in the sample contact area. In some embodiments, the spacers have uniform height. In some embodiments, the thickness of the sample is the sample as the height of the spacers. In some embodiments, the spacers are fixed on one of the plates.

Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

Spacer architectures and shapes. To achieve desired sample thickness reduction and control, in certain embodiments, the spacers are fixed on its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Some embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer.), and the enclosed spacer is the spacer that stop the sample flow (i.e. the sample cannot flow beyond the spacer. For example, a ring shape spacer and the sample is inside the ring.). Both types of spacers use their height to regular the final sample thickness at a closed configuration.

In some embodiments, the spacers are open-spacers only. In some embodiments, the spacers are enclosed-spacers only. In some embodiments, the spacers are a combination of open-spacers and enclosed-spacers.

The term "pillar spacer" means that the spacer has a pillar shape and the pillar shape refers to an object that has height and a lateral shape that allow a sample to flow around it during a compressed open flow. In some embodiments, the spacers have a flat top (e.g. pillars with a flat top to contact a plate).

In some embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In some embodiments, the spacers can be and/or can include posts, columns, beads, spheres, and/or other suitable geometries. The lateral shape and dimension (i.e., transverse to the respective plate surface) of the spacers can be anything, except, in some embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in some embodiments, they require some spacers to be closed spacers to restrict the sample flow.

In some embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In some embodiments, the spacers are pillars of various lateral shapes, sidewalls, and pillar-height to pillar lateral area ratio.

In a preferred embodiment, the spacers have shapes of pillars for allowing open flow. Spacers' materials. In the present invention, the spacers are generally made of any material that is capable of being used to regulate, together with the two plates, the thickness of a relevant volume of the sample. In some embodiments, the materials for the spacers are different from that for the plates. In some embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

Spacer's mechanical strength and flexibility. In some embodiments, the mechanical strength of the spacers are strong enough, so that during the compression and at the closed configuration of the plates, the height of the spacers is the same or significantly same as that when the plates are in an open configuration. In some embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

Spacer inside Sample. To achieve desired sample thickness reduction and control, particularly to achieve a good sample thickness uniformity, in certain embodiments, the spacers are placed inside the sample, or the relevant volume of the sample. In some embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

Spacer height. In some embodiments, all spacers have the same pre-determined height. In some embodiments, spacers have different pre-determined height. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height. In some embodiments, on the same plate, the spacer height in one ration is different from the spacer height in another region. In some cases, the plate with different spacer height in different regions have advantages of assaying.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1,000 nm in a separate preferred embodiment, 1 um (i.e., 1,000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In some embodiments, the spacer height and/or sample thickness is (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. Too many overlaps between the RBC's can cause serious errors in counting.

In the present invention, in some embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (i.e. less surface concentration).

Spacer lateral dimension. For an open-spacer, the lateral dimensions can be characterized by its lateral dimension (sometimes being called width) in the x and y-two orthogonal directions. The lateral dimension of a spacer in each direction is the same or different.

In some embodiments, the ratio of the lateral dimensions of x to y direction is 1, 1.5, 2, 5, 10, 100, 500, 1,000, 10,000, or a range between any two of the value. In some embodiments, a different ratio is used to regulate the sample flow direction; the larger the ratio, the flow is along one direction (larger size direction).

In some embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In some embodiments, all spacers have the same shape and dimensions. In some embodiments, each spacer has different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

Aspect ratio of height to the average lateral dimension of pillar spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

Spacer height precisions. The spacer height should be controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers has a lattice of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

The distance between neighboring spacers (i.e. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or in a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a10 mm or less, 20 mm or less, 30 mm or less, 50 mm or less, 70 mm or less, 100 mm or less, or any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

Spacer density. The spacers are arranged on the respective plates at a surface density of greater than one per $um^2$, greater than one per 10 $um^2$, greater than one per 100 $um^2$, greater than one per 500 $um^2$, greater than one per 1,000 $um^2$, greater than one per 5,000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

The spacers are configured to not take significant surface area (volume) in a given sample area (volume);

Ratio of spacer volume to sample volume. In many embodiments, the ratio of the spacer volume (i.e., the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e., flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

Spacers fixed to plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

Some embodiments of the present invention is that the spacers are fixed on one of the plates before the plates are brought to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In some embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In some embodiments, a spacer is fixed to a plate monolithically.

In some embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In some embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In some embodiments, at least a distance between two spacers is predetermined ("predetermined inter-spacer distance" means that the distance is known when a user uses the plates.).

In some embodiments of all methods and devices described herein, there are additional spacers besides to the fixed spacers.

In one preferred embodiment, the spacers are monolithically made on the Plate by embossing (e.g. nanoimprinting) a thin plastic film using a mold, and are made of the same materials, and the thickness of the Plate is from 50 um to 500 um.

In one preferred embodiment, the spacers are monolithically made on the Plate by embossing (e.g. nanoimprinting) a thin plastic film using a mold, and are made of the same materials, and the thickness of the Plate is from 50 um to 250 um.

In one preferred embodiment, the spacers are monolithically made on the Plate and are made of the same materials, and the thickness of the Plate is from 50 um to 500 um.

In one preferred embodiment, the spacers are monolithically made on the Plate a thin plastic film using a mold, and are made of the same materials, and the thickness of the Plate is from 50 um to 250 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene).

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene) and the thickness of the Plate is from 50 um to 500 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene) and the thickness of the Plate is from 50 um to 250 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene), and the spacers have either a square or rectangle shape, and have the same spacer height.

In one preferred embodiment, the spacers have a square or rectangle shape (with or without round corners).

In one preferred embodiment, the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-100 um. In one preferred embodiment, the spacers made of PMMA or PS have square or rectangle pillars with the pillar width (spacer width in each lateral direction) between 1 um to 200 um; pillar period (i.e. spacer period) from 2 um-2000 um, and pillar height (i.e. spacer height) from 1 um-100 um.

In one preferred embodiment, the spacers are monolithically made on the Plate and are made of plastic materials, and the spacers have square or rectangle pillars with the pillar width (spacer width in each lateral direction) between 1 um to 200 um; pillar period (i.e. spacer period) from 2 um-2,000 um, and pillar height (i.e. spacer height) from 1 um-100 um. In one preferred embodiment, the spacers are monolithically made on the Plate and are made of the same materials, and the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-10 um.

In one preferred embodiment, the spacers are monolithically made on the Plate and are made of the same materials selected from PS or PMMA or other plastics, and the spacers have square or rectangle pillars with the pillar width (spacer width in each lateral direction) between 1 um to 200 um; pillar period (i.e. spacer period) from 2 um-2,000 um, and pillar height (i.e. spacer height) from 10 um-50 um.

Specific sample thickness. In present invention, it was observed that a larger plate holding force (i.e. the force that holds the two plates together) can be achieved by using a smaller plate spacing (for a given sample area), or a larger sample area (for a given plate-spacing), or both.

In some embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

Final Sample Thickness and Uniformity. In some embodiments, significantly flat is determined relative to the final sample thickness, and has, depending upon on embodiments and applications, a ratio of to the sample thickness of less than 0.1%, less than 0.5%, less than 1%, less than 2%, less than 5%, or less than 10%, or a range between any two of these values.

In some embodiments, flatness relative to the sample thickness can be less than 0.1%, less than 0.5%, less than 1%, less than 2%, less than 5%, less than 10%, less than 20%, less than 50%, or less than 100%, or a range between any two of these values. In some embodiments, significantly flat can mean that the surface flatness variation itself (measured from an average thickness) is less than 0.1%, less than 0.5%, less than 1%, less than 2%, less than 5%, or less than 10%, or a range between any two of these values. Generally, flatness relative to the plate thickness can be less than 0.1%, less than 0.5%, less than 1%, less than 2%, less than 5%, less than 10%, less than 20%, less than 50%, or less than 100%, or in a range between any two of these values.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1,000 nm in a separate preferred embodiment, 1 µm (i.e., 1,000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the spacers can be in spherical beads and randomly distrusted in a sample.

In some embodiments, the QMAX device is fully transparent or partially transparent to reduce the heat absorption by card self, wherein the transparence is above 30%, 40%, 50%, 60%, 70%, 80%, 90%, 100%, or a range between any two of the values.

In some embodiments, the QMAX device is partially reflective to reduce the heat absorption by card self, wherein the reflectance of the surface is above 30%, 40%, 50%, 60%, 70%, 80%, 90%, 100%, or in a range between any two of the values.

In some embodiments, the QMAX device and clamp is coated with a heat insulator layer to reduce the heat absorption by card self. Wherein the heat insulator layer contains materials including the low thermal conductivity material above.

In some embodiments, the clamp covers and seals all the QMAX card in close configuration.

In some embodiments, the clamp covers and seal only the perimeter of the QMAX card in close configuration.

In some embodiments, the clamp covers and seal only the perimeter of the QMAX card in close configuration, and not the heating and cooling zone area.

In some embodiments, the clamp covers some of the surface of QMAX card in close configuration.

In some embodiments, the clamp has a window which is transparent to allow the light go inside the QMAX card and out from the QMAX card.

In some embodiments, the clamp is fully transparent to allow the light go inside the QMAX card and out from the QMAX card.

wherein the transparence of the clamp is above 30%, 40%, 50%, 60%, 70%, 80%, 90%, 100%, or a range between any two of the values.

In some embodiments, there is air or liquid between the clamp and QMAX device in close configuration. In certain embodiments, the liquid includes but not limit to water, ethane, methane, oil, benzene, Hexane, heptane, silicone oil, polychlorinated biphenyls, liquid air, liquid oxygen, liquid nitrogen etc. In certain embodiments, the gas includes but not limit to air, argon, helium, nitrogen, oxygen, carbon dioxide, etc.

In some embodiments, after close the clamp, the pressure on QMAX card surface applied by the clamp is 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, 500 kg/cm$^2$, or a range between any two of the values; and a preferred range of 0.1 kg/cm$^2$ to 0.5 kg/cm$^2$, 0.5 kg/cm$^2$ to 1 kg/cm$^2$, 1 kg/cm$^2$ to 5 kg/cm$^2$, 5 kg/cm$^2$ to 10 kg/cm$^2$ (Pressure).

In some embodiments, after close the clamp, the pressure on QMAX card surface applied by the clamp is at least 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, or 500 kg/cm$^2$, As shown in the cross-sectional views of the device in FIG. 7A and FIG. 7B, the heating/cooling layer 112 spans across the sample contact area. It should be noted, however, it is also possible that the lateral area of the heating/cooling layer occupy only a portion of the sample contact area at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less. In some embodiments, in order to facilitate the temperature change of the sample, in some embodiments the lateral area of the heating/cooling layer is configured so that the sample 90 receive the thermal radiation from the heating/cooling layer 112 substantially uniformly across the lateral dimension of the sample 90 over the sample contact area.

In some embodiments, the radiation absorbing area is 10%, 30%, 40%, 50%, 60%, 70%, 80%, 90%, 100% the total plate area, or a range between any two of the values. In some embodiments, the heating/cooling layer 112 have a thickness of 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 75 um or less, 40 um or less, 15 um or less, 7.5 um or less, 4 um or less, 1.5 um or less, 750 nm or less, 400 nm or less, 150 nm or less, 75 nm or less, 40 nm or less, or 15 nm or less, or in a range between any of the two values. In certain embodiments, the heating/cooling layer 112 have thickness of 100 nm or less.

In some embodiments, the area of the sample layer and the heating/cooling layer 112 is substantially larger than the uniform thickness. Here, the term "substantially larger" means that the general diameter or diagonal distance of the sample layer and/or the heating/cooling layer is at least 10 time, 15 times, 20 time, 25 times, 30 time, 35 times, 40 time, 45 times, 50 time, 55 time, 60 time, 65 times, 70 time, 75 times, 80 time, 85 time, 90 time, 95 times, 100 time, 150 times, 200 time, 250 time, 300 time, 350 time, 400 time, 450 times, 500 time, 550 time, 600 time, 650 time, 700 time, 750 times, 800 time, 850 time, 900 time, 950 times, 1u000 time, 1,500 time, 2,000 time, 2,500 time, 3,000 time, 3,500 times, 4,000 time, 4,500 times, or 5000 time, or in a range between any of the two values. In some embodiments, the heating/cooling layer has an area that is less than 1000 mm$^2$, 900 mm$^2$, 800 mm$^2$, 700 mm$^2$, 600 mm$^2$, 500 mm$^2$, 400 mm$^2$, 300 mm$^2$, 200 mm$^2$, 100 mm$^2$, 90 mm$^2$, 80 mm$^2$, 75 mm$^2$, 70 mm$^2$, 60 mm$^2$, 50 mm$^2$, 40 mm$^2$, 30 mm$^2$, 25 mm$^2$, 20 mm$^2$, 10 mm$^2$, 5 mm$^2$, 2 mm$^2$, 1 mm$^2$, 0.5 mm$^2$, 0.2 mm$^2$, 0.1 mm$^2$, or 0.01 mm$^2$, or in a range between any of the two values. In some embodiments, the heating/cooling layer has an area that is substantially smaller than the area of the first plate (and/or the second plate). For example, in certain embodiments, area of the heating/cooling layer occupy only a portion of the area of the first plate (or the second plate; or the sample contact area of the first plate or the second plate) at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less.

In some embodiments, the heating/cooling layer has a substantially uniform thickness. In some embodiments, the heating/cooling layer has a thickness of less than 10 nm, 20 nm, 50 nm, 100 nm, 200 nm, 500 nm, 1 um, 2 um, 5 um, 10 um, 20 um, 50 um, 100 um, 200 um, 300 um, 400 um, 500 um, 600 um, 700 um, 800 um, 900 um, 1 mm, 1.5 mm, 2 mm, 2.5 mm, 3 mm, 3.5 mm, 4 mm, 4.5 mm, 5 mm, or 10 mm, or in a range between any of the two values.

The heating/cooling layer can take any shape. For example, from a top view the heating/cooling layer can be square, circle, ellipse, triangle, rectangle, parallelogram, trapezoid, pentagon, hexagon, octagon, polygon, or various other shapes.

In some embodiments, the first plate or the second plate has a thickness of 2 nm or less, 10 nm or less, 100 nm or less, 200 nm or less, 500 nm or less, 1,000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values.

In some embodiments, the first plate and the second plate has a lateral area of 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1,000 cm$^2$ or less, 5,000 cm$^2$ or less, 10,000 cm$^2$ or less, 10,000 cm$^2$ or less, or in a range between any two of these values. In certain embodiments, a fourth power of the inter-spacer-distance (ISD) of the spacers divided by the thickness (h) and the Young's modulus (E) of the plate (ISD4/(hE)) is 5×10$^6$ um$^3$/GPa or less;

In certain embodiments, a product of the pillar contact filling factor and the Young's modulus of the spacers is 2 MPa or larger, wherein the pillar contact filling factor is the ratio of pillar contact area (that contact the plate at a closed configuration) inside a relavent sample volume to the total plate area in the relevant sample volume . . .

In certain embodiments, the spacers have a predetermined substantially uniform height and a predetermined constant inter-spacer distance that is at least about 2 times larger than the size of the analyte, up to 200 um, and wherein at least one of the spacers is inside the sample contact area.

In some embodiments, the plate (either the first plate, the second plate, or both plates) that has the heating/cooling layer is thin so that the temperature of the sample can be rapidly changed. For example, in certain embodiments the plate that is in contact with the heating/cooling layer has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In some embodiments, if only one plate is on contact with the heating/cooling layer, the plate in contact with the heating/cooling layer is substantially thinner than the plate that is not in contact with the heating/cooling layer. For example, in some embodiments, the thickness of the plate that is in contact with the heating/cooling layer is less than 1/1,000,000, 1/500,000, 1/100,000, 1/50,000, 1/10,000, 1/5,000, 1/1,000, 1/500, 1/100, 1/50, 1/10, 1/5, or 1/2 of the thickness of the plate that is in contact with the heating/cooling layer, or in a range between any of the two values.

In some embodiments, the sample layer is thin so that the temperature of the sample layer can be rapidly changed. In certain embodiments, the sample layer has a thickness equal to or less than 100 um, 50 um, 25 um, 10 um, 5 um, 2.5 um, 1 um, 500 nm, 400 nm, 300 nm, 200 nm, or 100 nm, or in a range between any of the two values.

In various embodiments, the positioning of the heating/cooling layer can also vary.

As herein shown and described, in some embodiments, the sample holder is configured to compress the fluidic sample into a thin layer, thus reducing the thermal mass of the sample. But reducing the thermal mass, a small amount energy can be able to change the temperature of the sample quickly. In addition, by limiting the sample thickness, the thermal conduction is also limited.

In some embodiments, there is a sample contact area on the respective surfaces of the first plate 10 and the second plate 20. The sample contact area can be any portion of the surface of the first plate 10 and/or the second plate 20. In some embodiments, the heating/cooling layer at least partly overlaps with the sample contact area. In the overlapping part, the sample is heated quickly due to close proximity and small thermal mass.

In some embodiments, the sample holder 100 is a compressed regulated open flow (CROF, also known as QMAX) device, such as but not limited to the CROF device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/046437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

Edge Sealing for Reducing Sample Evaporation

When the two plates sandwich a sample into a shape with a large lateral to vertical ratio (e.g., 15 mm vs 30 um=500), the evaporation of the sample during a thermal cycling is greatly reduced, since the sample surfaces covered by the two plate is 500 times larger. Experimentally, we found that in 30 temperature cycling (about 60 secs), there was no visible changes in the sample volume.

On the other hand, in some embodiments, it has a seal element that is in contact with the two plates to form an enclosed chamber which prevents sample vapor going out. Such seal element can reduce sample contamination, in addition to reduce or eliminate sample evaporation. The sealing element can be a tape, plastic seal, oil seal, or a combination of thereof.

In some embodiments, the sealing element does not reach the sample, but the sealing element is in contact with the two plates to form an enclosed chamber which prevents sample vapor going out. In some embodiments, the sealing element can be used as spacers to regulate the relevant sample's thickness.

Figure 10:
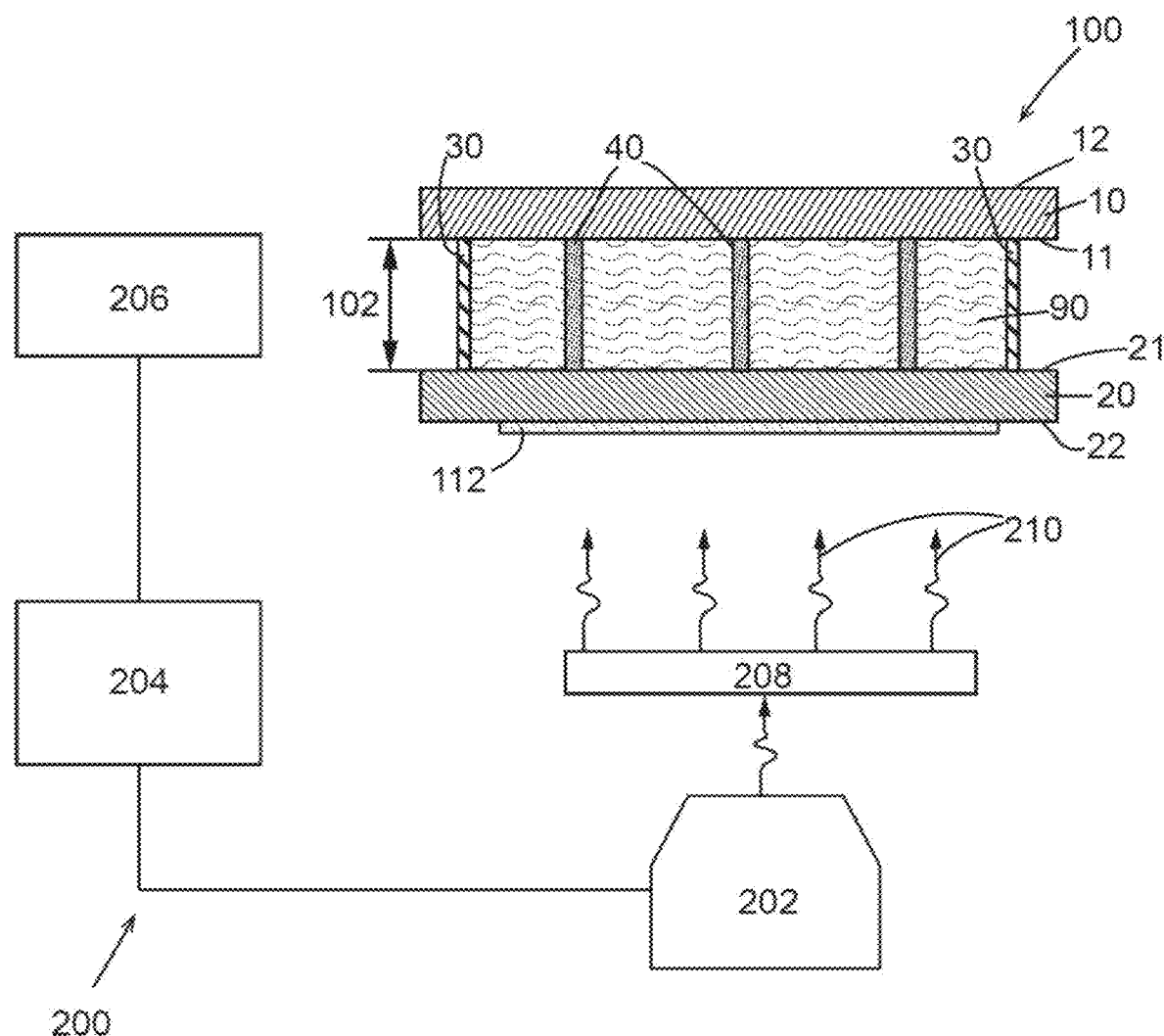
FIG. 10 shows a sectional view of a system showing additional elements that facilitate temperature change and control, according to some embodiments.

In some embodiments, as shown in FIG. 10, the sample holder 100 comprises a sealing element 30 that is configured to seal the spacing 102 between the first plate 10 and second plate 20 outside the medium contact area at the closed configuration. In certain embodiments, the sealing element 30 encloses the sample 90 within a certain area (e.g. the sample receiving area) so that the overall lateral area of the sample 90 is well defined and measurable. In certain embodiments, the sealing element 30 improves the uniformity of the sample 90, especially the thickness of the sample layer.

In some embodiments, as shown in FIG. 10, the sealing element 30 comprises an adhesive applied between the first plate 10 and second plate 20 at the closed configuration. The adhesive is selective from materials such as but not limited to: starch, dextrin, gelatin, asphalt, bitumen, polyisoprene natural rubber, resin, shellac, cellulose and its derivatives, vinyl derivatives, acrylic derivatives, reactive acrylic bases, polychloroprene, styrene-butadiene, styrene-diene-styrene, polyisobutylene, acrylonitrile-butadiene, polyurethane, polysulfide, silicone, aldehyde condensation resins, epoxide resins, amine base resins, polyester resins, polyolefin polymers, soluble silicates, phosphate cements, or any other adhesive material, or any combination thereof. In some embodiments, the adhesive is drying adhesive, pressure-sensitive adhesive, contact adhesive, hot adhesive, or one-part or multi-part reactive adhesive, or any combination thereof. In some embodiments, the glue is natural adhesive or synthetic adhesive, or from any other origin, or any combination thereof. In some embodiments, the adhesive is spontaneous-cured, heat-cured, UV-cured, or cured by any other treatment, or any combination thereof.

In some embodiments, as shown in FIG. 10, the sealing element 30 comprises an enclosed spacer (well). For example, the enclosed spacer has a circular shape (or any other enclosed shape) from a top view and encircle the sample 90, essentially restricting the sample 90 together with the first plate 10 and the second plate 20. In certain embodiments, the enclosed spacer (well) also function as the spacing mechanism 40. In such embodiments, the enclosed spacer seals the lateral boundary of the sample 90 as well as regulate the thickness of the sample layer.

In some embodiments, there is an "evaporation-prevention ring" outside of the liquid area (e.g. sample area) that prevents or reduces the vapor of the liquid escape the card, during a heating.

In some embodiments, there is a clamp outside of the QMAX-card to fix the QMAX card in its closed configuration during a heating.

In some embodiments, the two plates are compressed by an imprecise pressing force, which is neither set to a precise level nor substantially uniform. In certain embodiments, the two plates are pressed directly by a human hand.

In some embodiments, the QMAX card/RHC card, including the plates and spacer, is made of the material with low thermal conductivity to reduce the heat absorption by card self.

In some embodiments, there is clamp outside of the QMAX-card to fix the QMAX card in its closed configuration during a heating (namely, the clamp clamps only round the edge of the plates, not the center of the plate pair). In some embodiments, the clamp is made of the material with low thermal conductivity to reduce the heat absorption by card self.

Heating Source, Extra Heat Sink, Temperature Sensor, and Temperature Control

The heating layer or the heating/cooling layer in a RHC card is configured to be heated by a heating source, wherein the heating source delivers heat energy to the heating/cooling layer optically, electrically, by radio frequency (RF) radiation, or a combination thereof.

Optical Heating Source. In some embodiments, when a heating layer is heated by a heating source optically, the heating source comprises a light source, that include, but not limited to, LED (light emitting diode), lasers, lamps, or a combination of thereof.

To get more light from a light source in an optical heating source to a heating layer, some embodiments of the heating sources uses an optical lens, an optical pipe, or a combination thereof.

In some embodiments, the wavelength of the electromagnetic waves is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values. In some embodiments, the wavelength of the electromagnetic waves is 100 nm to 300 nm, 400 nm to 700 nm (visible range), 700 nm to 1000 nm (IR range), 1 um to 10 um, 10 um to 100 um, or in a range between any of the two values.

The lens has an NA (numerical aperture) of 0.001, 0,01, 0.05, 0.1, 0.2, 0.3, 04, 0.5, 0.6, 0.7, 0.8, 0.9, 1.0, 1.1, 1.5, or in a range between any of the two values.

In preferred embodiments, the lens has an NA in a range of 0.01 to 0.1, 0.1 to 0.4, 0.4 to 0.7, 0.7 to 1.0, or 1.0 to 1.5.

Electrical Heating Source. In some embodiments, when the heating layer or the heating/cooling layer is heated by a heating source electrically, the electric heating source comprises an electrical power supply that sends an electrical power, though electrical wiring, to the heating/cooling layer.

Extra Heat Sink. In some embodiments, the heat is removed from the sample and the sample holder to the environment, but in some embodiments, extra heat sink will be used to accelerate the heat removal. The extra heat sink can be a Peltier cooler, passive heat radiator, or both. In some embodiments, fan will be used to create air convention (directly to the sample and the sample holder, directly to extra heat sink, or both) which accelerate a cooling of the sample.

Temperature sensors. The temperature of the sample can be controlled by delivering pre-calibrated energy to the heating zone/layer with a real time temperature sensor, by using a real time temperature sensor, or both.

A real time temperature sensor can be thermometer, thermal couple, radiation temperature sensor, temperature sensitive dye (which change either light intensity or color or both with temperature), or a combination thereof.

As shown in FIG. 10, in some embodiments the thermal control unit 200 comprises a thermometer 206. In some embodiments, the thermometer 206 provides a monitoring and/or feedback mechanism to control/monitor/adjust the temperature of the sample 90. For example, in some embodiments the thermometer 206 is configured to measure the temperature at or in proximity of the sample contact area. In certain embodiments, the thermometer 206 is configured to directly measure the temperature of the sample 90. In some embodiments, the thermometer 206 is selected from the group consisting of: fiber optical thermometer, infrared thermometer, fluidic crystal thermometer, pyrometer, quartz thermometer, silicon bandgap temperature sensor, temperature strip, thermistor, and thermocouple. In certain embodiments, the thermometer 206 is an infrared thermometer.

In some embodiments, the thermometer 206 is configured to send signals to the controller 204. Such signals comprise information related to the temperature of the sample 90 so that the controller 204 makes corresponding changes. For example, during a PCR, for the denaturation step the target temperature is set for 95° C.; after measurement, the thermometer sends a signal to the controller 204, indicating that the measured temperature of the sample 90 is actually 94.8°

C.; the controller 204 thus alters the output the heating source 202, which projects an electromagnetic wave or adjust particular parameters (e.g., intensity or frequency) of an existing electromagnetic wave so that the temperature of the sample 90 is increased to 95° C. Such measurement-signaling-adjustment loop is applied to any step in any reaction/assay.

Controllers. Referring to panels (A) and (B) of FIG. 9, the controller 204 is configured to control the electromagnetic wave 210 projected from the heating source 202 for the temperature change of the sample. The parameters of the electromagnetic wave 210 that the controller 204 controls include, but are not limited to, the presence, intensity, wavelength, incident angle, and any combination thereof. In some embodiments, the controller is operated manually, for instance, it is as simple as a manual switch that controls the on and off of the heating source, and therefore the presence of the electromagnetic wave projected from the heating source. In other embodiments, the controller includes hardware and software that are configured to control the electromagnetic wave automatically according to one or a plurality of pre-determined programs.

In some embodiments, the pre-determined program refers to a schedule in which the parameter(s) (e.g., presence, intensity, and/or wavelength) of the electromagnetic wave 210 is/are set to pre-determined levels for respective pre-determined periods of time. In other embodiments, the pre-determined program refers to a schedule in which the temperature of the sample 90 is set to pre-determined levels for respective pre-determined periods of time and the time periods for the change of the sample temperature from one pre-determined level to another pre-determined level are also set respectively. In some embodiments, the controller 204 is configured to be programmable, which means the controller 204 comprises hardware and software that are configured to receive and carry out pre-determined programs for the system that are delivered by the operator of the system.

FIG. 10 shows a sectional view of an embodiment of the present invention, demonstrating the thermal cycler system and showing additional elements that facilitates temperature change and control. As shown in FIG. 10, the thermal cycler system comprises a sample holder 100 and a thermal control unit 200. The sample holder 100 comprises a first plate 10, a second plate 20, a spacing mechanism 40, and a sealing element 30; the thermal control unit 200 comprises a heating source 202, a controller 204, a thermometer 206, and an expander 208.

FIG. 10 shows the sample holder 100 in a closed configuration, in which the inner surfaces 11 and 21 of the first and second plates 10 and 20 face each other and the spacing 102 between the two plates are regulated by a spacing mechanism 40. If a sample 90 has been deposited on one or both of the plates in the open configuration, when switching to the closed configuration, the first plate 10 and the second plate 20 are pressed by a human hand or other mechanisms, the sample 90 is thus compressed by the two plates into a thin layer. In some embodiments, the thickness of the layer is uniform and the same as the spacing 102 between the two plates. In certain embodiments, the spacing 102 (and thus the thickness of the sample layer) is regulated by the spacing mechanism 40. In some embodiments, the spacing mechanism comprises an enclosed spacer that is fixed to one of the plates. In some embodiments, the spacing mechanism 40 comprises a plurality of pillar shaped spacers that are fixed to one or both of the plates. Here the term "fixed" means that the spacer(s) is attached to a plate and the attachment is maintained during at least a use of the plate.

In some embodiments, the controller 204 is configured to adjust the temperature of the sample to facilitate an assay and/or reaction involving the sample 90 according to a pre-determined program. In some embodiments, the assay and/or reaction is a PCR. In certain embodiments, the controller 204 is configured to control the presence, intensity, and/or frequency of the electromagnetic wave from the heating source 206.

Sample Signal Monitoring

Figure 11A:
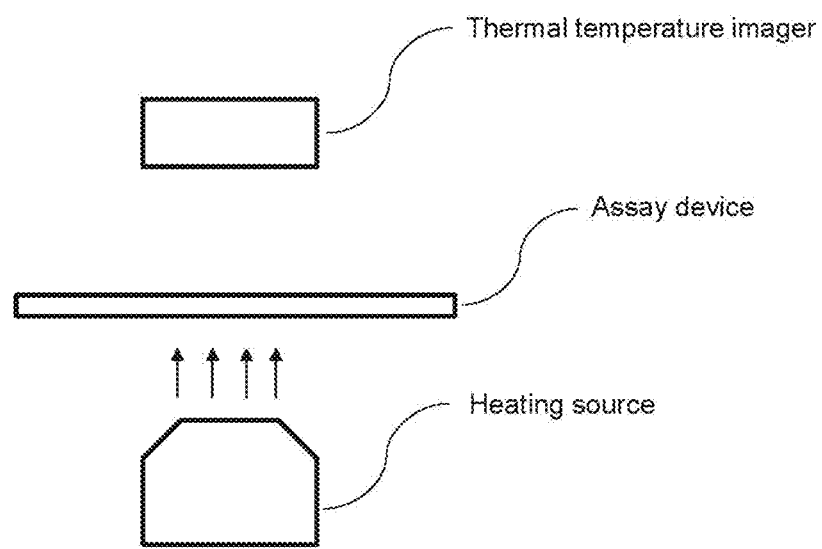
FIG. 11A schematically illustrates a system of heating and temperature monitoring device for the assay device, according to some embodiments.
Figure 11B:
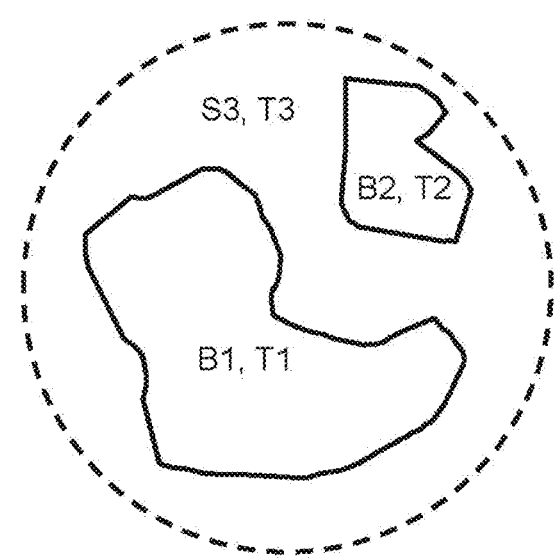
FIG. 11B schematically illustrates a field of view of the thermal imager in the system described in FIG. 11A when heating up the assay device, according to some embodiments.
Figure 12:
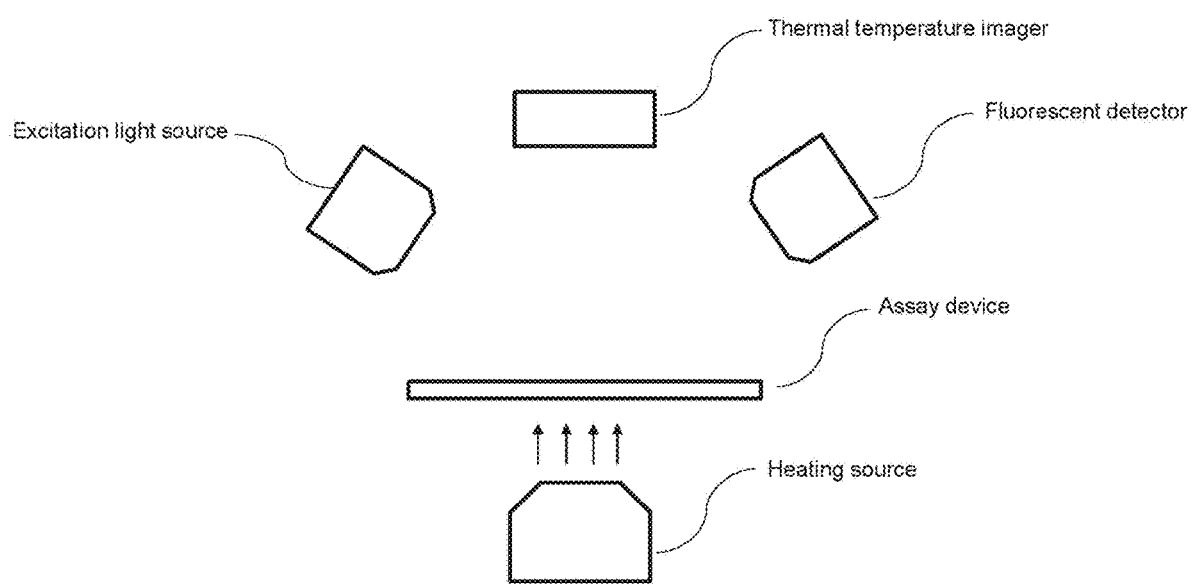
FIG. 12 schematically illustrates a real-time PCR system comprising a heating source and temperature monitoring system as described FIG. 11A and FIG. 11B and a pair of fluorescent excitation light source and detector, according to some embodiments.

As shown in FIGS. 11 and 12, a signal sensor can be used to detect the signal from the sample (and the products from a reaction during a temperature change) in the sample holder.

In some embodiments, the signal sensor is an optical sensor that is configured to image the fluidic sample. For example, optical sensor is a photodetector, camera, or a device capable of capturing images of the fluidic sample. In some embodiments, the optical sensor can be a camera. In some embodiments, the camera is a camera integrated into a mobile device (e.g. a smartphone or tablet computer). In some embodiments, the camera is separated from other parts of the system. In some embodiments, a light source or multi light sources are used to excite the sample (and the products from a reaction during a temperature change) for generating a signal In some embodiments, the signal sensor is an electrical sensor that is configured to detect electrical signals from the device. In some embodiments, the signal sensor is a mechanical sensor that is configured to detect mechanical signals from the device.

In some embodiments, the signal sensor is configured to monitor the amount of an analyte in the sample. In some embodiments, the signal sensor is outside the chamber and receive optical signals from the sample through an optical aperture on the chamber.

Base and Systems

In some embodiments, the apparatus further comprises a base (an adaptor) that is configured to house the sample card, the heating source, temperature sensors, a part of an entire of temperature controlled (include a smartphone in some embodiments), extra-heat sink (optionally), a fan (optionally) or a combination of thereof. In some embodiments, the adaptor comprises a card slot, into which the sample card can be inserted. In some embodiments, the sample card, after being fully inserted into the slot, or after reaching a pre-defined position in the slot, is stabilized and stays in place without any movement.

In some embodiments, the base (adaptor) is configured to position the sample card, and the sample within the sample card, in the field of view of an optical sensor (e.g. a camera) so that the sample can be imaged. In certain embodiments, the camera is part of a mobile device (e.g. a smartphone). In some embodiments, the adaptor comprises a slider in the slot. In certain embodiments, the sample card can be put onto the slider, which can slide into or out of the slot in the adaptor. In some embodiments, the adaptor comprises a card support. In certain embodiments, the sample card can be put on the card support, which does not need to be moved before imaging.

In some embodiments, the adaptor is configured to be connectable to an optical sensor so that the relative position of the optical sensor (e.g., mobile device; e.g., smartphone) and the sample card is fixed. In certain embodiments, the adaptor can include a connecting member that is replaceable and directly attach to the mobile device (as an example). The connecting member can be slid onto the mobile device and firmly attach the adaptor to the mobile device, optimally positioning the sample card to be imaged or for the detection and/or measurement of the analyte. In certain embodiments, the connecting member is replaceable so that different connecting members can be used for different mobile devices.

In some embodiments, the adaptor comprises a radiation aperture that allows the passage of the electromagnetic waves that heat or cool the sample. In some embodiments, the adaptor comprises an optical aperture that allows imaging of the sample. In some embodiments, the adaptor serves as a heating sink for the sample card As shown in FIG. 10, the thermal control unit 200 comprises a beam expander 208, which is configured to expand the electromagnetic wave from the heating source 202 from a smaller diameter to a larger diameter. In some embodiments, the electromagnetic wave projected from the heating source 202 is sufficient to cover the entire sample contact area; in some embodiments however, it is necessary to expand the covered area of the electromagnetic wave projected directed from the heating source 202 to produce an expanded electromagnetic wave 210, providing a heat source for all the sample contact area(s). The beam expander 208 employs any known technology, including but not limited to the beam expanders described in U.S. Pat. Nos. 4,545,677, 4,214,813, 4,127,828, and 4,016,504, and U.S. Pat. Pub. No. 2008/0297912 and 2010/0214659, which are incorporated by reference in their entireties for all purposes.

Smartphone

In some embodiments, the sample card is imaged by a mobile device. In certain embodiments, the mobile device is a smartphone, which can serve as an example.

In some embodiments, the smartphone comprises a camera that can be used to image the sample in the sample card. In some embodiments, an adaptor is used to accommodate the sample card and the adaptor is configured to attach to the smartphone so that the sample card (and the sample therein) can be placed in the field of view of the camera.

In some embodiments, the smartphone can also serve as the control unit, which is configured to control the apparatus. For example, the smartphone can be used control the heating and/or cooling of the sample card. In certain embodiments, the smartphone is connected to the heating source and controls the electromagnetic waves from the heating source. In some embodiments, the smartphone controls the presence, intensity, wavelength, frequency, and/or angle of the electromagnetic waves. In certain embodiments, the smartphone receives the temperature data from a thermometer that measures the temperature of the sample. In certain embodiments, the smartphone controls the electromagnetic waves based on the temperature data.

In some embodiments, the smartphone can also serve as a data processing and communication device. For example, after the sample has been imaged, the images can be saved in the smart phone. In certain embodiments, the save images can be processed by software or applications in the smartphone. For example, the presence and/or amount of the analyte can be deduced from the images by software or applications in the smartphone. In certain embodiments, the processed results can be displayed on the screen of the smart phone. In certain embodiments, the processed results can be sent to the user, e.g. with email or other messaging software. In certain embodiments, the processed results can be sent to a third party, e.g., a healthcare professional, who can make further diagnostics and/or process the data in additional steps. In some embodiments, the images, without process- ing, can be displayed and/or transmitted. In certain embodiments, the images are displayed on the screen of the smartphone. In certain embodiments, the images are sent to the user, e.g. by email or other messaging software. In certain embodiments, the images can be sent to a third party, e.g. a remote server, which can process the images further. In some embodiments, the results and/or images are compressed and/or encrypted before being sent.

Use of RHC Card

The RHC card in the description can be used as one step of multiple steps in test a sample, or as one step that perform entire test.

In some embodiments, a RHC card is used in a so-called "one-step assay", wherein all reagents and a sample for an analysis are loaded on a RHC card and a thermal cycling or temperature change is performed and the signal is being observed during the thermal cycling or temperature change.

OTHER EMBODIMENTS

Embodiment 1

One embodiment comprises a device of the embodiment SH-1 to SH-6, wherein the first plate and the second plate are flexible plastic film and/or thin glass film, that each has a substantially uniform thickness of a value selected from a range between 1 um to 25 um.

Each plate has an area in a range of 1 cm$^2$ to 16 cm$^2$.

The sample sandwiched between the two plate has a thickness of 40 um or less.

The relevant sample to the entire sample ratio (RE ratio) is 12% or less.

The cooling zone is at least 9 times larger than the heating zone.

The sample to non-sample thermal mass ratio is 2.2 or lager.

The RHC have no spacer in some embodiments, but do have spacers in other embodiments.

STC ratio is and the cooling zone comprises a layer of the material that has a thermal conductivity of 70 W/m-K or higher and a thermal conductivity times its thickness.

Embodiment 2

For the embodiments of SH-1 to SH-x, they have the following parameter arrange for fast thermal cycling.

The first plate and second plates are plastic or a thin glass. The first plate and second plate have a thickness of 100 nm, 500 nm, 1 um, 5 um, 10 um, in a range between any of the two values.

The sample between the two plates has a thickness of 5 um, 10 um, 30 um, 50 um, 100 um, or in a range between any of the two values.

The distance from the H/C layer to the sample is 10 nm, 100 nm, 500 nm, 1 um, 5 um, 10 um, or in a range between any of the two values.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

Embodiment 3

For the embodiments of SH-1 to SH-x, they have the following parameter arrange for fast thermal cycling.

The first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values.

The sample between the two plates has a thickness of 5 um, 10 um, 30 um, 50 um, 100 um, or in a range between any of the two values.

The distance between the H/C layer and the sample is 10 nm, 100 nm, 500 nm, 1 um, 5 um, 10 um, or in a range between any of the two values.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

Embodiment 4

For the embodiments of SH-1 to SH-x, they have the following parameter arrange for fast thermal cycling.

The first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values.

The sample between the two plates has a thickness of 100 nm, 500 nm, 1 um, 5 um, 10 um, 25 um, 50 um, 100 um, 250 um, or in a range between any of the two values.

The distance between the H/C layer and the sample is 100 nm, 500 nm, 1 um, 5 um, 10 um, 25 um, 50 um, 100 um, 175 um, 250 um, or in a range between any of the two values.

The ratio of the cooling zone area to the relevant sample area is 100, 64, 16, 9, 4, 2, 1, 0.5, 0.1, or in a range between any of the two values.

The ratio of the cooling zone area to the heating zone is 100, 64, 16, 9, 4, 2, 1, 0.5, 0.1, or in a range between any of the two values.

The distance between the H/C layer and the heating source (e.g. LED) is 500 um, 1 mm, 3 mm, 5 mm, 10 mm, 20 mm, 30 mm, or in a range between any of the two values.

Embodiment 5

For the embodiments of SH-1 to SH-5, they have the following parameter arrange for fast thermal cycling.

A light pipe collimates the light from a light source (e.g. LED) into the heating zone. The light pile comprises a structure with a hollow hole (e.g. a tube or a structure milled a hole) with a reflective wall. The light pile has a lateral dimension for 1 mm to 8 mm and length of 2 mm to 50 mm.

Embodiment 6

For the embodiments of SH-1 to SH-5, they have the following parameter arrange for fast thermal cycling.

The first plate and second plates are plastic or a thin glass. The first plate and second plate have a thickness of 100 nm, 500 nm, 1 um, 5 um, 10 um, in a range between any of the two values.

The sample between the two plates has a thickness in a range of 1 to 5 um, 5 um to 10 um, 10 to 30 um, or 30 um to 50 um.

The distance from the H/C layer to the sample is in a range of 10 nm to 100 nm, 100 nm to 500 nm, 500 nm to 1 um, 1 um to 5 um, 5 um to 10 um, or 10 um to 25 um.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

The KC ratio for the cooling layer is in a range of between 0.5 $cm^2$/sec and 0.7 $cm^2$/sec, 0.7 $cm^2$/sec and 0.9 $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and 2 $cm^2$/sec, or 2 $cm^2$/sec and $cm^2$/sec.

The sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100.

Embodiment 7

For the embodiments of SH-1 to SH-5, as well as Embodiments 1 to Embodiments 6, they have the following parameter arrange for fast thermal cycling:

The first plate and/or the second plate has a lateral area in a range of 1 $mm^2$ (square millimeter) to 10 $mm^2$, 10 $mm^2$ to 50 $mm^2$, 50 $mm^2$ to 100 $mm^2$, 1 $cm^2$ to 5 $cm^2$, 5 $cm^2$ to 20 $cm^2$, or 20 $cm^2$ to 50 $cm^2$.

The scaled thermal conduction ratio (STM ratio) is in a range of between 10 to 20, 30 to 50, 50 to 70, 70 to 100, 100 to 1,000, 1,000 to 10,000, or 10,000 to 1,000,000; and the cooling zone (layer) has thermal conductivity times its thickness of $6 \times 10^{-5}$ W/K, $9 \times 10^{-5}$ W/K, $1.2 \times 10^{-4}$ W/K, $1.5 \times 10^{-4}$ W/K, $1.8 \times 10^{-4}$ W/K, $2.1 \times 10^{-4}$ W/K, $2.7 \times 10^{-4}$ W/K, $3 \times 10^{-4}$ W/K, $1.5 \times 10^{-4}$ W/K, or in a range between any of the two values.

The sample holder (RHC card) has not significant thermal conduction to the environment during a thermal cycling.

Sample Types

The devices, systems, and methods herein disclosed can be used for samples such as but not limited to diagnostic sample, clinical sample, environmental sample and foodstuff sample. The types of sample include but are not limited to the samples listed, described and summarized in PCT Application (designating U.S.) Nos. PCT/US2016/046437 and PCT/US2016/051775, which were respectively filed on Aug. 10, 2016 and Sep. 14, 2016, and are hereby incorporated by reference by their entireties.

For example, in some embodiments, the devices, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, systems, and methods are applied.

In some embodiments, the devices, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, pre-processed food as well as partially or fully processed food, etc. In certain embodiments, samples that are not in liquid form are converted to liquid form before the subject devices, systems, and methods are applied.

The subject devices, systems, and methods can be used to analyze any volume of the sample. Examples of the volumes include, but are not limited to, about 10 mL or less, 5 mL or less, 3 mL or less, 1 microliter (uL, also "uL" herein) or less, 500 uL or less, 300 uL or less, 250 uL or less, 200 uL or less, 170 uL or less, 150 uL or less, 125 uL or less, 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 uL or less, 1 uL or less, or a range between any two of the values.

In some embodiments, the volume of the sample includes, but is not limited to, about 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 uL or less, 1 uL or less, or a range between any two of the values. In some embodiments, the volume of the sample includes, but is not limited to, about 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 uL or less, 1 uL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

D. Imager Based Rapid Temperature Assaying And Real Time PCR

Imaging Based Temperature Sensor

In certain embodiments, during a thermal cycling process, one or more temperature sensing images are used to monitoring the temperature of a sample. The temperature sensing image can sense a local temperature at different locations of a sample. One can determine a suitable heating temperature to the sample (e.g. control the heating power), based on the temperature map of a sample, rather than just a single lump-sum temperature.

When heating up the assay device, some air bubbles and other defects will form and be trapped in the heating area of the assay device. And the temperature of sample liquid and air are different. If using a lump-sum temperature sensor to measure the average temperature in the heating area to be used as the temperature of sample liquid, it is not accurate. In order to accurately measure the temperature of the sample liquid in the heating area, an image-based temperature sensor should be used in the system to distinguish the temperature between air bubble and sample liquid.

Some enbedments have a system of heating and temperature monitoring device for the assay device. A heating source is put under the assay device to heat up the assay device. And on top of the thermal imager, there is a thermal temperature sensor to monitor the temperature of the heating area on the assay device. The temperature sensor is a thermal imager whose field of view is aligned with the heating area.

Some enbedments have a thermal imager in the system described above when heating up the assay device. For example, B1 and B2 are two air bubbles and/or defects which are generated and trapped in the assay device during heating up. And S3 is the sample liquid region. Using the image based thermal sensor, we can tell the difference between the temperature of the sample liquid T3 and the air bubble region temperatures T1 and T2. So that we can get more accurate temperature of the sample liquid in the heating area.

In this experiment, the assay device has a top (first) PMMA plate with 50 um thickness, pillar array with 30 um pillar height, 30 um by 40 um pillar size, and 80 um inter pillar distance; a bottom (second) PET plate with 50 um thickness. A heating/cooling layer is on the outer surface of the second plate, and covers the entire second plate outer surface. The heating/cooling layer comprises an Au (gold) film and a black paint layer. The gold film has one surface in contact with the second plate outer surface, and another surface being painted with a black paint. The black paint is a commercial product of a film composited of black carbon nanoparticle and polymer mixture. The black paint had an average thickness of ~9 um (~2 um thickness variation). The black paint layer may be directly facing incoming LED light. Between the Au film and the second plate outer surface, there is a 5 nm adhesion layer of Ti, which improves the adhesion between Au and the second plate. The heating source is a blue light emitting diode (LED) with a central wavelength of 450 nm and power consumption around 500 mW.

1. In certain embodiments, a system, comprising:
 (i) a device, comprising:
  a first plate comprising a polymer material and having a thickness less than or equal to 100 μm,
  a second plate comprising a polymer material and having a thickness less than or equal to 100 μm, wherein the second plate is separated from the first plate in a parallel arrangement by a distance less than or equal to the thickness of the second plate,
  a heating/cooling layer disposed on either the first plate or the second plate, the heating/cooling layer having a thickness and a thermal conductivity between 6×10⁻⁵ W/K multiplied by the thickness of the heating/cooling layer and 1.5×10⁻⁴ W/K multiplied by the thickness of the heating/cooling layer, and
a support frame configured to support at least one of the first plate and the second plate;
an optical source configured to direct electromagnetic radiation towards the heating/cooling layer,
a temperature sensor to monitor the temperature of the heating area in the device;
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source, and
wherein the system consumes less than 500 mW of power.

2. The system of any prior embodiment, wherein the temperature sensor is an image-based temperature sensor.

3. The system of any prior embodiment, wherein the temperature sensor's field of view is 1 mm², 10 mm², 100 mm², 1000 mm², or in a range between any of the two values.

4. The system of any prior embodiment, wherein the temperature sensor's resolution is 1 um, 10 um, 100 um, 1 mm, or in a range between any of the two values.

5. The system of any prior embodiment, wherein the working thermal radiation wavelength of the temperature sensor's falls in the range of 1 um to 10 um or 10 um to 100 um.

6. The system of any prior embodiment, wherein the thermal sensor has a least a lens.

7. The system of any prior embodiment, wherein the thermal sensor is an imager that can image at least a part of the sample.

8. A method for measuring temperature of sample liquid in assay device, comprising: imaging the heating area in the assay device under thermal imager;
segmenting air bubble area or defect area and sample liquid area in the image; measuring the temperature of sample liquid area.

E. Real Time Detection (qPCR) Setup

In certain embodiments, a system comprise a assay device, the heater, and an optical monitor to monitor an optical signal from a sample in the card, wherein the optical signal give an indication of a nucleic acid amplification inside the Q-card and the optical signal is monitored during a PCR process (that is a real time PCR).

In certain embodiments, the optical monitor is a photodetector. In certain embodiments, the optical monitor is one or more imagers that image an area or a volume of the sample. Hence the image gives an optical signal in each location of the sample being imaged. An analysis of the optical signal image can give more accurate analysis on the nucleic acid amplification than a lump-sum optical signal detection.

In certain embodiments, the nucleic amplification during a PCR process is monitored by an imager or more imagers, where the imagers image an area or a volume of a sample and the signal of the imager represents the nucleic acid amplification by the PCR. In certain embodiments, signal is fluorescence signal. In certain embodiments, signal is a color signal.

The terms "assay device" and "sample holder" are interchangeable.

In the optical signal image analysis, in certain embodiments, artificial intelligence is used. In the optical signal image analysis, in certain embodiments, machine learning is used.

In certain embodiments, the system does real-time PCR by adding one or multi fluorescent excitation light sources and detectors into the heating and temperature monitoring system.

In certain embodiments, a system has imagers for sample temperature imaging and for nucleic acid amplification signals monitoring imaging. In certain embodiments, the sample temperature imaging and the nucleic acid amplification signal monitoring imaging uses a single optical monitor.

Some embodiments have a real-time PCR system comprising a heating source and temperature monitoring system as described FIG. 11 and a pair of fluorescent excitation light source and detector. In this case, the excitation light source and fluorescence detector are on top of the assay device and aligned to the same excitation and detection area on the assay device.

Some enbedments have a real-time PCR system comprising a heating source, a fan and temperature detector as a temperature control system and a pair of fluorescent excitation light source (with filter) and detector (with lens and filter) as the real time detection system; both temperature control system and real time detection system are controlled by Programmable logic controller (PLC). The PLC is further controlled by an interface installed on a smartphone.

1. A system, comprising:
a device, comprising:
a first plate comprising a polymer material and having a thickness less than or equal to 100 μm, a second plate comprising a polymer material and having a thickness less than or equal to 100 μm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between 6×10.5 W/K multiplied by the thickness of the heating/cooling layer and 1.5×10⁻⁴ W/K multiplied by the thickness of the heating/cooling layer, and
a support frame configured to support at least one of the first plate and the second plate;
an optical source configured to direct electromagnetic radiation towards the heating/cooling layer,
a temperature sensor to monitor the temperature of the heating area in the device;
a fluorescent excitation light source;
a fluorescent detector;
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source.

The system of any prior embodiment, wherein the excitation light source can be but not limited to be a laser. The system of any prior embodiment, wherein the excitation light source can be but not limited to be a LED. The system of any prior embodiment, wherein the fluorescent detector is a photodetector. The system of any prior embodiment, wherein the fluorescent detector is mounted on an optical tube. The system of any prior embodiment, wherein the fluorescent detector is an image-based sensor.

A method for measuring fluorescence signal of sample liquid in assay device, comprising:
  imaging the heating area in the assay device under thermal imager;
  segmenting air bubble area or defect area and sample liquid area in the image;
  measuring the signal of sample liquid area.

A method for measuring fluorescence signal of sample liquid in assay device,
  the time of measuring fluorescence signal is at the primer annealing and extension of each cycle.

A method for measuring fluorescence signal of sample liquid in assay device, the time of measuring fluorescence signal is at the end of primer annealing and extension of each cycle.

A method for measuring fluorescence signal of sample liquid in assay device, the time of measuring fluorescence signal is at the time of heating source is off in each cycle.

In certain embodiments, an imager (either for temperature sensing or for nucleic acid amplification monitoring) in the present invention, is connected to a computer, where various signal processing techniques, including machine learning is used. In certain embodiments, the signal processing results will be used to control the heating to the sample.

F. Heating Optical Pipe Structure

In certain embodiments, an optical pipe (also termed optical collimator), that collimates the light of a light source into the heating zone/plate, comprises a hollow tube with a reflective wall.

One embodiment of an optical pipe comprises a hollow structure (e.g., hollow tube) of round circle, rectangle, hexagonal, polygon, elliptic or combination thereof.

One preferred embodiment of an optical pipe comprises a hexagonal hollow structure.

One embodiment of an optical pipe comprises a hollow tube with a reflective wall (i.e., its inner wall, outer wall, or both reflective). The reflective wall can be a thin light reflective coating on a wall of the hollow tube. The reflective coating can be a thin metal film, such as gold, aluminum, silver, copper, or any mixture or combination thereof.

In certain embodiments, the hollow structure is made of a dielectric material of glasses, plastics, or a combination. In certain embodiments, the hollow structure is made of a metallic material.

Some embodiments have a round heating tube and a hexagonal heating tube with a diameter of 6 mm and a point LED light source at the center of one tube end. (b) shows the optical beam intensity measured at the other end of tube. Clearly the hexagonal heating tube provides a more uniform distribution of heating light intensity in the central 6 mm area.

In some embodiments, the hollow pipe has a length in the range of 1 mm to 70 mm, an inner dimension (diameter or width) in the range of 1 mm to 40 mm, and a wall thickness in the range of 0.01 mm to 10 mm.

In some preferred embodiments, the hollow pipe for the light pipe has an inner diameter (or an average width) in a range of 1 mm to 5 mm, 5 mm to 10 mm, 10 mm to 15 mm, 15 mm to 20 mm, 20 mm to 30 mm, or 30 mm to 50 mm.

In some preferred embodiments, the hollow pipe for the light pipe has a wall thickness (or an average width) in a range of 0.001 mm to 0.01 mm, 0.01 mm to 0.1 mm, 0.1 mm to 0.5 mm, 0.5 mm to 1 mm, 1 mm to 2 mm, or 2 mm to 50 mm.

Example. Fast SNAP PCR Amplification of PUC57 plasmid DNA

The present technology uses the disclosed system for the PCR amplification of PUC57 plasmid DNA. The PCR reaction mixture was prepared by mixing 10 uM PUC57 Forward primer, 10 uM PUC57 Reverse primer and Cy5 labeled DNA probe with DNA buffer, 2.5 U/uL Aptataq Polymerase, 25 mM MgCl2, dNTP, additives as Betaine, bovine serum albumin (BSA), template DNA and ddH2O. 5 uL to 10 µl of the reaction was added onto the SNAP card and sealed for amplification.

In certain case, the whole card is incubated with 1% NaOH for 2 hours under 37° C., then washed with deionized water, then incubated with 4% bovine serum albumin (BSA) overnight under 4° C., washed with deionized water and dried at room temperature.

After amplification, the card is open and the production liquid is sucked out for Gel electrophoresis analyze.

Our experiments have achieved a working SNAP PCR amplification of nucleic acid (E-*coli* plasmid DNA) with assay device demonstrating (a) 4.5 sec thermal cycling time (1 sec heating time from 60° C. to 95° C., 0.5 sec staying at 95° C., 2.5 sec cooling time from 95° C. to 60° C., and 0.5 sec staying at 60° C.); (b) Gel electrophoresis results of SNAP PCR products ran in 3 minutes (40 cycles) and conventional PCR products (40 cycles) ran in 40 minutes shows 3 min SNAP PCR has a comparable amplification performance as 40 min conventional PCR. The M line in the figure is a Gel electrophoresis marker with 100 bp line marked. Both SNAP PCR and conventional PCR have clear 100 bp production line and similar intensity. Negative sample without template does not show bar in gel analyze.

Applications

The devices, systems, and methods herein disclosed can be used in various types of biological/chemical sampling, sensing, assays and applications, which include the applications listed, described and summarized in PCT Application (designating U.S.) No. PCT/US2016/046437, which was filed on Aug. 10, 2016, and is hereby incorporated by reference by its entirety.

In some embodiments, the devices, systems, and methods herein disclosed are used in a variety of different application in various field, wherein determination of the presence or absence, quantification, and/or amplification of one or more analytes in a sample are desired. For example, in certain embodiments the subject devices, systems, and methods are used in the detection of proteins, peptides, nucleic acids, synthetic compounds, inorganic compounds, and other molecules, compounds, mixtures and substances. The various fields in which the subject devices, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, systems, and methods are used in the detection of nucleic acids, proteins, or other molecules or compounds in a sample. In certain embodiments, the devices, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, systems, and methods are used in the detection and/or quantification of one or more, two or more, or three or more foodstuff marks from a food sample obtained from tap water, drinking water, prepared food, processed food or raw food.

In some embodiments, the devices, systems and methods of the invention can be used to detect an analyte. In some embodiments, the analyte is a pathogen. Exemplary pathogens that can be detected include, but are not limited to: Varicella zoster; *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*; gonorrhea(*Neisseria gorrhoeae*), syphilis(*Treponena pallidum*), chlamydia (*Chlamydia tracomitis*), nongonococcal urethritis(*Ureaplasm urealyticum*), chancroid(*Haemophilus ducreyi*), trichomoniasis(*Trichomonas vaginalis*); *Pseudomonas aeruginosa*, methicillin-resistant *Staphlococcccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae, Legionella pneumophila, Mycoplasma pneumoniae*, and *Mycobacterium tuberculosis*, etc.

In some embodiments, the devices, systems and methods of the invention can be used to detect an analyte that is a diagnostic marker.

In some embodiments, the invention is directed to a kit containing a device of the invention. In some embodiments, the kit includes a device configured to specifically bind an analyte described herein. In some embodiments, the kit includes instructions for practicing the subject methods using a hand held device, e.g., a mobile phone. In some embodiments, the instructions can be present in the kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In some embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the device, or can be provided in the device.

In some embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

In some embodiments, the devices, systems and methods of the invention can be used for simple, rapid blood cell counting using a smartphone. In some embodiments, the first plate and the second plate are selected from a thin glass slide (e.g., 0.2 mm thick) or a thin plastic film (e.g., 15 mm thick) of a relative flat surface, and each have an areas with a length and width in about 0.5 cm to 10 cm. In some embodiments, the spacers are made of glass, plastics, or other materials that would not deform significantly under a pressing. In some embodiments, before the sample deposition, the spacers are placed on the first plate, the second plate or both; and the first plate, the second plate or both are optionally coated with reagent that facilitate the blood counting (staining dyes and/or anticoagulant). In some embodiments, the first plate and the second plate can be sealed in a bag for easy transport and longer shelf life-time.

In some embodiments of blood cell count testing, only about 1 uL (microliter) (or about 0.1 uL to 3 uL) of blood is needed for the sample, which can be taken, for example, from a finger or other human body location. In some embodiments, the blood sample can be directly deposited from human body (e.g., finger) onto the first plate and the second plate, without any dilution. In such embodiments, the first plate and the second plate can face each other, so that blood sample is between the inner surfaces of the first plate and the second plate. In some embodiments, reagents are pre-deposited (staining dyes or anticoagulant), they are deposited on the inner surface for mixing with the sample. The first plate and the second plate can then be pressed by fingers or a simple mechanical device (e.g. a clip that presses using a spring). Under the press, the inner spacing is reduced, the reduction will be eventually stopped at the value set by the spacers' height and the final sample thickness is reached, which generally is equal to the final inner spacing. Since the final inner spacing is known, the final sample thickness become known, namely being quantified (measured) by this method.

In some embodiments, if the blood sample is not diluted, after pressing (sample deformation) the spacers and hence the final sample thickness can be thin, e.g., less than 1 um, less than 2 um, less than 3 um, less than 4 um, less than 5 um, less than 7 um, less than 10 um, less than 15 um, less than 20 um, less than 30 um, less than 40 um, less than 50 um, less than 60 um, less than 80 um, less than 100 um, less than 150 um, or any ranges between any of the two numbers. A thin final sample can be useful because if the final sample thickness is thick, then many red cells can overlap during the imaging, which can make the cell counting inaccurate. For example, about 4 um thick of whole blood without dilution will give about one layer of blood red cells.

After the pressing, the sample can be imaged by a smartphone either directly or through an additional optical elements (e.g. lenses, filters, or light sources as needed). The image of the sample can be processed to identify the types of the cells as well as the cell number. The image processing can be done locally at the same smartphone that takes the image or remotely but the final result transmitted back to the smartphone (where the image is transmitted to a remote location and is processed there.) The smart phone will display the cell number for a particular cell. In some cases, certain advices will be displayed. The advices can stored on the smartphone before the test or come from a remote machines or professionals.

In certain embodiments, reagents are placed on the inner surfaces of the first plate and/or the second plate using the methods and devices described herein.

In some embodiments, a device or a method for the blood testing comprises (a) a device or a method described herein and (b) a plate spacing (i.e. the distance between the inner surfaces of the two plates) at the closed configuration or a use of such spacing, wherein a undiluted whole blood in the plate-spacing has an average inter-cell distance in the lateral direction for the red blood cells (RBC) larger than the average diameter of the disk shape of the RBC.

In some embodiments, a device or a method to arrange the orientation of a non-spherical cell comprises (a) a device or a method in as described herein and (b) a plate spacing (i.e. the distance between the inner surfaces of the two plates) at the closed configuration or a use of such spacing, wherein the spacing less than the average size of the cell in its long direction (the long direction is the maximum dimension direction of a cell). Such arrangement can improve the measurements of the sample volume (e.g. red blood cell volume).

In some embodiments, the analytes in the blood tests include protein markers, a list of which can be found at the website of the American Association for Clinical Chemistry).

In some embodiments, the devices, systems and methods of the invention can be used to detect or diagnose a health condition. In some embodiments, the health condition includes, but is not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause.

In some embodiments, relative levels of nucleic acids in two or more different nucleic acid samples can be obtained using such methods, and compared. In these embodiments, the results obtained from the methods described herein are usually normalized to the total amount of nucleic acids in the sample (e.g., constitutive RNAs), and compared. This can be done by comparing ratios, or by any other means. In particular embodiments, the nucleic acid profiles of two or more different samples can be compared to identify nucleic acids that are associated with a particular disease or condition.

In some embodiments, the devices, systems and methods in the present invention can include a) obtaining a sample, b) applying the sample to device containing a capture agent that binds to an analyte of interest, under conditions suitable for binding of the analyte in a sample to the capture agent, c) washing the device, and d) reading the device, thereby obtaining a measurement of the amount of the analyte in the sample. In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food. In some embodiments, the device can be placed in a microfluidic device and the applying step b) can include applying a sample to a microfluidic device comprising the device. In some embodiments, the reading step d) can include detecting a fluorescence or luminescence signal from the device. In some embodiments, the reading step d) can include reading the device with a handheld device configured to read the device. The handheld device can be a mobile phone, e.g., a smart phone. In some embodiments, the device can include a labeling agent that can bind to an analyte-capture agent complex on the device. In some embodiments, the devices, systems and methods in the present invention can further include, between steps c) and d), the steps of applying to the device a labeling agent that binds to an analyte-capture agent complex on the device, and washing the device. In any embodiment, the reading step d) can include reading an identifier for the device. The identifier can be an optical barcode, a radio frequency ID tag, or combinations thereof. In some embodiments, the devices, systems and methods in the present invention can further include applying a control sample to a control device containing a capture agent that binds to the analyte, wherein the control sample includes a known detectable amount of the analyte, and reading the control device, thereby obtaining a control measurement for the known detectable amount of the analyte in a sample. In some embodiments, the sample can be a diagnostic sample obtained from a subject, the analyte can be a biomarker, and the measured amount of the analyte in the sample can be diagnostic of a disease or a condition.

In some embodiments, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition. In some embodiments, the devices, systems and methods in the present invention can further include diagnosing the subject based on information including the measured amount of the biomarker in the sample. In some embodiments, the diagnosing step includes sending data containing the measured amount of the biomarker to a remote location and receiving a diagnosis based on information including the measurement from the remote location. In some embodiments, the biomarker can be selected from those listed in the Tables. In some embodiments, the device can contain a plurality of capture agents that each binds to a biomarker described herein, wherein the reading step d) includes obtaining a measure of the amount of the plurality of biomarkers in the sample, and wherein the amount of the plurality of biomarkers in the sample is diagnostic of a disease or condition. In some embodiments, the capture agent can be an antibody epitope and the biomarker can be an antibody that binds to the antibody epitope. In some embodiments, the antibody epitope includes a biomolecule, or a fragment thereof, selected from the Tables. In some embodiments, the antibody epitope includes an allergen, or a fragment thereof, selected from the Tables. In some embodiments, the antibody epitope includes an infectious agent-derived biomolecule, or a fragment thereof, selected from Tables. In some embodiments, the device can contain a plurality of antibody epitopes selected from the Tables, wherein the reading step d) includes obtaining a measure of the amount of a plurality of epitope-binding antibodies in the sample, and wherein the amount of the plurality of epitope-binding antibodies in the sample is diagnostic of a disease or condition.

In some embodiments, the sample can be an environmental sample, and wherein the analyte can be an environmental marker. In some embodiments, the environmental marker described herein. In some embodiments, the method can include receiving or providing a report that indicates the safety or harmfulness for a subject to be exposed to the environment from which the sample was obtained. In some embodiments, the method can include sending data containing the measured amount of the environmental marker to a remote location and receiving a report that indicates the safety or harmfulness for a subject to be exposed to the environment from which the sample was obtained. In any embodiment, the device can include a plurality of capture agents that each binds to an environmental marker described herein, and wherein the reading step d) can include obtaining a measure of the amount of the plurality of environmental markers in the sample.

In some embodiments, the sample can be a foodstuff sample, wherein the analyte can be a foodstuff marker, and wherein the amount of the foodstuff marker in the sample can correlate with safety of the foodstuff for consumption. In some embodiments, the foodstuff marker is an example described herein. In any embodiment, the method can include receiving or providing a report that indicates the safety or harmfulness for a subject to consume the foodstuff from which the sample is obtained. In any embodiment, the method can include sending data containing the measured amount of the foodstuff marker to a remote location and receiving a report that indicates the safety or harmfulness for a subject to consume the foodstuff from which the sample is obtained. In any embodiment, the device array can include a plurality of capture agents that each binds to a foodstuff marker described herein, wherein the obtaining can include obtaining a measure of the amount of the plurality of foodstuff markers in the sample, and wherein the amount of the plurality of foodstuff marker in the sample can correlate with safety of the foodstuff for consumption.

In some embodiments, the subject device is part of a microfluidic device. In some embodiments, the subject devices, systems, and methods are used to detect a fluorescence or luminescence signal. In some embodiments, the subject devices, systems, and methods include, or are used together with, a communication device, such as but not limited to: mobile phones, tablet computers and laptop computers. In some embodiments, the subject devices, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

Various samples can be used in the assays conducted with the devices, apparatus, and systems herein described. In some embodiments, the sample comprises nucleic acids. In some embodiments, the sample comprises proteins. In some embodiments, the sample carbohydrates. The current devices, apparatus, and systems can be used to rapidly change the temperature of the sample and steadily maintain the temperature of the sample, providing a fast and cost-effective approach to process samples. In addition, various applications (e.g. assays) can be conducted with the devices, apparatus, and systems herein described. Such applications include but are not limited to diagnostic testing, health monitoring, environmental testing, and/or forensic testing. Such applications also include but are not limited to various biological, chemical, and biochemical assays (e.g. DNA amplification, DNA quantification, selective DNA isolation, genetic analysis, tissue typing, oncogene identification, infectious disease testing, genetic fingerprinting, and/or paternity testing).

In some embodiments, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

As used herein, "necessary reagents" or "reagents" include but are not limited to, primers, deoxynucleotides (dNTPs), bivalent cations (e.g. $Mg^{2+}$), monovalent cation (e.g. $K^+$), buffer solutions, enzymes, additives, and reporters. "Necessary reagents for nucleic acid amplification" or "reagents for nucleic acid amplification" can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase. Examples of suitable DNA-dependent polymerases include but not limited to AptaTaq polymerase, Kapa2G Fast polymerase, Kapa2G Robust, Z-Taq polyermase, Terra PCR Direct Polymerase, SpeedStar HS DNA polymerase, Phusion DNA polymerase, and High-Fidelity DNA polymerase.

As used herein, "additives", in some embodiments, include but not limited to, 7-deaza-2'-deoxyguanosine 7-deaza dGTP, BSA, gelatin, betaine, DMSO, formamide, Tween 20, NP-40, Triton X-100, tetramethylammonium chloride.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some other embodiments, as used herein, "necessary reagents" or "reagents" (e.g., for nucleic acid amplification reactions) can also include cell lysing reagent, which facilitates to break down cellular structures. Cell lysing reagents include but not limited to salts, detergents, enzymes, and other additives. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions. In some embodiments, for example when conducting isothermal amplification via LAMP, the sample is heated to 60-65° C. for about 1-70 min.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

As used herein, "cell lysing reagents", intend to include but not limited to salts, detergents, enzymes, and other additives, which facilitates to disrupt cellular structures. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

As used herein, "necessary reagent 2" include but not limited to, primers, deoxynucleotides (dNTPs), bivalent cations (e.g. $Mg^{2+}$), monovalent cation (e.g. $K^+$), buffer solutions, enzymes, and reporters. Necessary reagent 2 for nucleic acid amplification can be either in the dry form on the inner surface of the first or the second plate or both, or in a liquid form encased in, embedded in, or surrounded by, a material that melts with increasing temperatures, such as, for example, paraffin.

A Rapid Heating and Cooling Apparatus where a Separate Heating Element Outside QMAX-Card In some embodiments, the apparatus further comprises a separate heating element that is outside of RHC card and is configured to heat the RHC card when being placed near or in contact with the RHC card. The separate heating element is capable of attaching or detaching a RHC card, and gain energy from a heating source, in a similar fashion as the heating/cooling layer. The separate heating element allow a RHC card without a heating/cooling layer.

The terms "CROF Card (or card)", "COF Card", "QMAX-Card", "Q-Card", "CROF device", "COF device", "QMAX-device", "CROF plates", "COF plates", and "QMAX-plates" are interchangeable and may be used to identify embodiments of the devices described herein. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017, which is incorporated herein in its entirety for all purposes.

A RHC card is a QMAX-care with or without spacer plus a heating/cooling layer on or inside of one of the plate.

FIGS. 4A and 4B show perspective and sectional views of an embodiment of the device of the present invention. FIG. 9A illustrates the device (also termed "sample holder" of the system) 100 in an open configuration. As shown in FIG. 4A, the sample holder 100 comprises a first plate 10, a second plate 20, and a spacing mechanism (not shown). The first plate 10 and second plate 20 respectively comprise an inner surface (11 and 21, respectively) and an outer surface (12 and 22, respectively). Each inner surface has a sample contact area (not indicated) for contacting a fluidic sample to be processed and/or analyzed by the device.

The first plate 10 and the second plate 20 are movable relative to each other into different configurations. One of the configurations is the open configuration, in which, as shown in FIG. 9A, the first plate 10 and the second plate 20 are partially or entirely separated apart, and the spacing between the first plate 10 and the second plate 20 (i.e. the distance between the first plate inner surface 11 and the second plate inner surface 21) is not regulated by the spacing mechanism. The open configuration allows a sample to be deposited on the first plate, the second plate, or both, in the sample contact area.

As shown in FIG. 9A, the second plate 20 further comprises a heating/cooling layer 112 in the sample contact area. It is also possible that the first plate 10 alternatively or additionally comprise the heating/cooling layer 112. In some embodiments, the heating/cooling layer 112 is configured to efficiently absorb radiation (e.g. electromagnetic waves) shed on it. The absorption percentage is 50% or more, 60% or more, 70% or more, 80% or more, 90% or more, 95% or more, 99% or more, 100% or less, 85% or less, 75% or less, 65% or less, or 55% or less, or in a range between any of the two values. The heating/cooling layer 112 is further configured to convert at least a substantial portion of the absorbed radiation energy into heat (thermal energy). For example, the heating/cooling layer 112 is configured to emit radiation in the form of heat after absorbing the energy from electromagnetic waves. The term "substantial portion" or "substantially" as used herein refers to a percentage that is 50% or more, 60% or more, 70% or more, 80% or more, 90% or more, 95% or more, 99% or more, 99% or more, or 99.9% or more.

FIGS. 8A and 3B illustrate the sample card in a closed configuration, where the heating/cooling layer comprises a heating zone that is directly being/to be heated by a heating source; FIG. 3A shows a prospective view and FIG. 3B shows a sectional view. In some embodiments, the heating/cooling layer comprises a heating zone that is being/to be directly heated by a heating source. In some embodiments, the heating sources emits electromagnetic radiation (waves) that, with or without modulation by lenses or other modulators, reaches the heating/cooling layer. The area that directly receives such radiation (waves) is referred to as the heating zone.

In some embodiments, the heating zone is smaller than the entire area of the heating/cooling layer. In some embodiments, the heating zone is about 1/1000, 1/500, 1/200, 1/100, 1/50, 1/20, 1/10, 1/5, 1/2, or 2/3 of the area of the heating/cooling layer, or in a range between any of the two values. In some embodiments, when the sample is loaded and compressed, by the two plates, into a thin layer, the volume of the sample directly in the path of the electromagnetic waves, or directly in contact with the area of the heating zone, is referred to as the heated volume. In some embodiments, since the sample layer is thin and/or due to the superior absorption properties of the heating/cooling layer, the sample in the heated volume can be rapidly heated to a desired temperature. In some embodiments, the sample in the heated volume can also be rapidly cooled to a desired temperature.

Biochemistry and Assays

The thermal cycler system and associated methods of the present invention can be used to facilitate a chemical, biological or medical assay or reaction. In some embodiments, the reaction requires temperature changes. In some embodiments, the reaction requires or prefers rapid temperature change in order to avoid non-specific reaction and/or reduce wait time. In certain embodiments, the system and methods of the present invention is used to facilitate a reaction that requires cyclical temperature changes for amplification of a nucleotide in a fluidic sample; such reactions include but are not limited to polymerase chain reaction (PCR). The descriptions below use PCR as an example to illustrate the capability and utilization of the thermal cycler system and method of the present invention. It is should be noted, however, some embodiments of the device, systems and method herein described also apply to other assays and/or reactions that require temperature control and change.

In some embodiments, the assays (e.g. PCR) can be conducted with a non-processed sample. For example, the template of a PCR reaction can be provided by a sample directed obtained from a subject without additional processing. In some embodiments, the sample can be whole blood from an individual. In some embodiments, such a "one-step" approach would allow for more convenient use of the devices herein described.

In some embodiments, the sample 90 is a pre-mixed reaction medium for polymerase chain reaction (PCR). For example, in certain embodiments, the reaction medium includes components such as but not limited to: DNA template, two primers, DNA polymerase (e.g. Taq polymerase), deoxynucleoside triphosphates (dNTPs), bivalent cations (e.g. $Mg^{2+}$), monovalent cation (e.g. $K^+$), and buffer solution. The specific components, the concentrations of each component, and the overall volume varies according to rational design of the reaction. In some embodiments, the PCR assay requires a number of changes/alterations in sample temperature between the following steps: (i) the optional initialization step, which requires heating the sample to 92-98° C.; (2) the denaturation step, which requires heating the sample to 92-98° C.; (3) the annealing step, which requires lowering the sample temperature to 50-65° C.; (4) extension (or elongation) step, which requires heating the sample to 75-80° C.; (5) repeating steps (2)-(4) for about 20-40 times; and (6) completion of the assay and lowering the temperature of the sample to ambient temperature (e.g. room temperature) or cooling to about 4° C. The specific temperature and the specific time period for each step varies and depends on a number of factors, including but not limited to length of the target sequence, length of the primers, the cation concentrations, and/or the GC percentage.

The thermal cycler system of the present invention provides rapid temperature change for the PCR assay. For example, referring to panels (A) and (B) of FIG. 3 and panel (B) of FIG. 9, in some embodiments, the sample 90 (e.g. pre-mixed reaction medium) is added to one or both of the plates 10 and 20 in the open configuration and the plates is switched to the closed configuration to compress the sample 90 into a thin layer which has a thickness 102 that is regulated by a spacing mechanism (not shown); the heating source 202 projects an electromagnetic wave 210 to the first plate 10 (e.g. specifically to the heating/cooling layer 112); the heating/cooling layer 112 is configured to absorb the electromagnetic wave 210 and convert at least a substantial portion of said electromagnetic wave 210 into heat, which increases the temperature of the sample; the removal of the electromagnetic wave 210 results in a temperature decrease in the sample 90.

In some embodiments, by projecting an electromagnetic wave 210 to the heating/cooling layer 112 or increasing the intensity of the electromagnetic wave, the thermal cycler systems provide rapid heating (increase temperature) for any or all of the initialization step, the denaturation step and/or the extension/elongation step; in some embodiments, with the removal of the electromagnetic wave projected from the heating source 202 or the decrease of the intensity of the electromagnetic wave, the cooling to the annealing step and/or the final cooling step is achieved with rapid speed. In some embodiments, the electromagnetic wave 210 or an increase of the intensity of the electromagnetic wave 210 creates an ascending temperature ramp rate of at least 80° C./s, 70° C./s, 60° C./s, 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average ascending temperature ramp rate in a PCR assay is 10° C./s or more. In some embodiments, the removal of the electromagnetic wave 210 or a reduction of the intensity of the electromagnetic wave 210 results in a descending temperature ramp rate of at least 80° C./s, 70° C./s, 60° C./s, 50° C./s, 45° C./s, 40° C./s, 35° C./s, 30° C./s, 25° C./s, 20° C./s, 18° C./s, 16° C./s, 1° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average descending temperature ramp rate in a PCR assay is 5° C./s or more. As used here, the term "ramp rate" refers to the speed of temperature change between two pre-set temperatures. In some embodiments, the average ascending or descending temperature to each step is different.

During a PCR, within any step after the target temperature has been reached, the sample needs to be maintained at the target temperature for a certain period of time. The thermal cycler system of the present invention provides the temperature maintenance function by (1) adjusting the intensity of the electromagnetic wave 210, lowering it if the temperature has been raised to the target or increasing it if the temperature has been decreased to the target, and/or (2) keep the target temperature by balancing the heat provided to the sample and the heat removed from the sample.

Additional Exemplary Embodiments

AAA-1.1 A device for rapidly changing the temperature of a fluidic sample, comprising:
a first plate (10), a second plate (20), a heating layer (112-1), and a cooling layer (112-2), wherein:
each of the first plate and the second plate has, on its respective inner surface, a sample contact area for contacting a fluidic sample; wherein the sample contact areas face each other, are separated by an average separation distance of 200 um or less between them, and are capable of contacting the sample and sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 $cm^2$/sec or larger;
wherein the distance between the cooling layer and a surface of the relevant sample volume is zero or less than a distance that is configured to make the thermal conductance per unit area between the cooling layer and the surface of the relevant sample volume equal to 70 W/($m^2$·K) or larger; and
wherein, in some embodiments, the heating layer and cooling layer are the same material layer that has a heating zone and a cooling zone, and wherein the heating zone and cooling zone can have the same area or different areas.

AAA-1.2 A device for rapidly changing the temperature of a fluidic sample, comprising:
A first plate (10), a second plate (20), a heating layer (112-1), and a cooling layer (112-2), wherein:
each of the first plate and the second plate has, on its respective inner surface, a sample contact area for contacting a fluidic sample; wherein the sample contact areas face each other, are separated by an average separation distance of 200 um or less from each other, and are capable of contacting the sample and sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger; and
wherein, in some embodiments, the heating layer and cooling layer are the same material layer that has a heating zone and a cooling zone, and wherein the heating zone and cooling zone can have the same area or different areas.

AAA-1.3 A device for rapidly changing the temperature of a fluidic sample, comprising:
a first plate (10), a second plate (20), a heating layer (112-1), and a cooling layer (112-2), wherein:
the first and second plates are movable relative to each other into different configurations;
each of the first plate and the second plate has, on its respective inner surface, a sample contact area for contacting a fluidic sample; wherein the sample contact areas face each other, are separated by an average separation distance of 200 um or less, and are capable of sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger;
wherein one of the configurations is an open configuration, in which: the two plates are partially or completely separated apart and the average spacing between the plates is at least 300 um;
wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less; and
wherein, in some embodiments, the heating layer and cooling layer are the same material layer that has a heating zone and a cooling zone, and wherein the heating zone and cooling zone can have the same area or different areas.

AAA-1.4 A device for rapidly changing the temperature of a fluidic sample, comprising:
a first plate (10), a second plate (20), spacers, a heating layer (112-1), and a cooling layer (112-2), wherein:
the first and second plates are movable relative to each other into different configurations;
each of the first plate and the second plate has, on its respective inner surface, a sample contact area for contacting a fluidic sample; wherein the sample contact areas face each other, are separated by an average separation distance of 200 um or less between them, and are capable of contacting the sample and sandwiching the sample between them; one or both of the plates comprise the spacers and the spacers are fixed on the inner surface of a respective plate;
the spacers have a predetermined substantially uniform height that is equal to or less than 200 microns, and the inter-spacer-distance is predetermined;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger;
wherein one of the configurations is an open configuration, in which: the two plates are partially or completely separated apart, the spacing between the plates is not regulated by the spacers, and the sample is deposited on one or both of the plates; and
wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers; and wherein, in some embodiments, the heating layer and cooling layer are the same material layer that has a heating zone and cooling zone, and wherein the heating zone and cooling zone can have the same area or different areas.

AAA-1.5 A device for rapidly changing the temperature of a fluidic sample, comprising:

a first plate (10), a second plate (20), and a heating/cooling layer (112), wherein:

the first plate (10) and the second plate (20) face each other, and are separated by a distance from each other;

each of the plates has, on its respective inner surface (11, 21), a sample contact area for contacting a fluidic sample; wherein the sample contact areas are facing each other, are in contact with the sample, sandwich a sample between them, and have an average separation distance (102) from each other, the heating/cooling layer (112) is on the outer surface (22) of the second plate (20); and the heating/cooling layer is configured to comprise a heating zone and a cooling zone; wherein the heat zone is configured to heat the fluidic sample, the cooling zone is configured to cool the sample significantly by thermal radiative cooling;

wherein the heating zone is configured to receive a heating energy from a heating source and to have an area smaller than the total area of the heating/cooling layer; and wherein at least a part of a heating zone of the heating layer overlaps with the sample area.

AAA-1.6 A device for rapidly changing the temperature of a fluidic sample, comprising:

a first plate (10), a second plate (20), and a heating/cooling layer (112), wherein:

each of the first plate (10) and the second plate (20) has, on its respective inner surface (11, 21), a sample contact area for contacting a fluidic sample; wherein the sample contact areas are facing each other, are separated by an average separation distance (102) from each other, and are capable of contacting the sample and sandwiching the sample between them;

the heating/cooling layer (112) has a thermal conductivity of 50 W/(m·K) or larger and is on the outer surface (22), on the inner surface, or inside of the second plate (20); and the heating/cooling layer is configured to comprise a heating zone and a cooling zone; wherein the heating zone is configured to heat a portion of the sample and have an area smaller than the total area of the heating/cooling layer, and wherein the cooling zone is configured to cool the sample;

wherein the heating zone, the second plate, and the portion of the sample are configured to have a scaled thermal conduction ratio (STC ratio) of 2 or larger;

wherein the heating zone is configured to receive a heating energy from a heating source; and wherein at least a part of the heating zone of the heating layer overlaps with the sample area.

AAA-1.7 A device for rapidly changing the temperature of a fluidic sample, comprising:

a first plate (10), a second plate (20), and a heating/cooling layer (112), wherein: each of the plates has, on its respective inner surface (11, 21), a sample contact area for contacting a fluidic sample; wherein the sample contact areas are facing each other, are in contact with the sample, sandwich the sample between them, and have an average separation distance (102) from each other;

the heating/cooling layer (112) has a thermal conductivity of 50 W/(m·K) or larger and is on the outer surface (22), on the inner surface, or inside of the second plate (20); and the heating/cooling layer is configured to comprise a heating zone and a cooling zone; wherein the heating zone is configured to heat a portion of the sample and have an area smaller than the total area of the heating/cooling layer, and wherein the cooling zone is configured to cool the sample;

wherein the heating zone, the second plate, and the portion of the sample are configured to have a scaled thermal conduction ratio (STC ratio) of 2 or larger;

wherein the heating/cooling layer has a thermal conductivity multiplying its thickness in the range of $6 \times 10^{-5}$ W/K to $3 \times 10^{-4}$ W/K.

wherein the heating zone is configured to receive a heating energy from a heating source; and wherein at least a part of the heating zone of the heating layer overlaps with the sample area.

AAA-2.1. The device of any prior embodiments, wherein the heating layer is configured to be heated by a heating source.

AAA-2.2. The device of any prior embodiments, wherein the heating layer is the same layer as the cooling layer, and the same layer comprises a heating zone area and a cooling zone area.

AAA-2.3. The device of any prior embodiments, wherein the heating layer (i.e. the heating zone) has an area smaller than the cooling layer (i.e. cooling zone).

AAA-2.4. The device of any prior embodiments, wherein the heating layer (i.e., the heating zone) has an area that is about 1/100, 1/50, 1/20, 1/10, 1/8, 1/6, 1/5, 1/4, 1/3, 1/2, 2/3, 3/4 or 5/6 of the cooling layer (i.e. cooling zone) area, or in a range between any of the two values.

AAA-2.5. The device of any prior embodiments, wherein the distance between the cooling layer and a surface of the relevant sample volume is zero or less than a distance that is configured to make the thermal conductance per unit area between the cooling layer and the surface of the relevant sample volume equal to 150 W/(m²·K) or larger.

AAA-2.6. The device of any prior embodiments, wherein the heating layer comprises metallic plasmonic materials, metamaterials, black silicon, graphite, carbon nanotube, silicon sandwich, graphene, or superlattice, or a combination thereof.

AAA-2.7. The device of any prior embodiments, wherein the heating layer comprises Al, Ag, or Au, with or without a paint layer.

AAA-2.8. The device of any prior embodiments, wherein the heating layer has a thermal conductance per unit area that is equal to or larger than 1000 W/(m²·K), 2000 W/(m²·K), 3000 W/(m²·K), 4000 W/(m²·K), 5000 W/(m²·K), 7000 W/(m²·K), 10000 W/(m²·K), 20000 W/(m²·K), 50000 W/(m²·K), 50000 W/(m²·K), 100000 W/(m²·K), or in range between any of the two values.

AAA-2.9. The device of any prior embodiments, wherein the heating layer has a thermal conductance per unit area that is in a range of 1000 W/(m²·K) to 2000 W/(m²·K), 2000

W/(m²·K) to 4000 W/(m²·K), 4000 W/(m²·K) to 10,000 W/(m²·K), or 10000 W/(m²·K) to 100000 W/(m²·K).

AAA3.1 The device of any prior embodiments, wherein the cooling layer has a thermal conductance per unit area that is equal to or larger than 1000 W/(m²·K), 2000 W/(m²·K), 3000 W/(m²·K), 4000 W/(m²·K), 5000 W/(m²·K), 7000 W/(m²·K), 10000 W/(m²·K), 20000 W/(m²·K), 50000 W/(m²·K), 50000 W/(m²·K), 100000 W/(m²·K), or in range between any of the two values.

AAA-3.2. The device of any prior embodiments, wherein the cooling layer has a thermal conductance per unit area that is in a range of 1000 W/(m²·K) to 2000 W/(m²·K), 2,000 W/(m²·K) to 4,000 W/(m²·K), 4,000 W/(m²·K) to 10,000 W/(m²·K), or 10,000 W/(m²·K) to 100,000 W/(m²·K).

AAA-3.3 The device of any prior embodiments, wherein the cooling layer cools the relevant sample primarily by thermal radiative cooling.

AAA-3.4 The device of any prior embodiments, wherein the cooling of the relevant sample through thermal radiative cooling is larger than the cooling through thermal conduction cooling in the direction lateral to the plates.

AAA-3.5 The device of any prior embodiments, wherein the cooling of the sample through thermal radiative cooling is at least 1.2 times, 1.5 times, 2 times, 5 times, 10 times, 20 times, 50 times, 100 times, 200 times, 500 times, or 1000 times larger than the cooling through thermal conduction cooling, or in a range between any of the two values.

AAA4.1 The device of any prior embodiments, wherein the heating layer or the cooling layer has a thickness that is about 0.1 um, 0.2 um, 0.5 um, 1 um, 2 um, 5 um, 10 um, 20 um, 30 um, 40 um, 50 um, 100 um, 200 um, 500 um, 1 mm, 2 mm, 5 mm, 10 mm, 20 mm, or 50 mm, or in a range between any of the two values.

AAA4.2 The device of any prior embodiments, wherein the heating layer or the cooling layer has an area that is less than 0.01 mm², 0.02 mm², 0.05 mm², 0.1 mm², 0.2 mm², 0.5 mm², 1 mm², 2 mm², 5 mm², 10 mm², 20 mm², 50 mm², 100 mm², 200 mm², 500 mm², or 1000 mm², or in a range between any of the two values.

AAA4.3 The device of any prior embodiments, wherein the heating layer or the cooling layer has an area dimension that is about 1 mm, 2 mm, 3 mm, 5 mm, 6 mm, 7 mm, 8 mm, 9 mm 10 mm, 12 mm, or 15 mm, or in a range between any two values.

AAA4.4 The device of any prior embodiments, wherein the heating layer or the cooling layer comprises metallic plasmonic materials, metamaterials, black silicon, graphite, carbon nanotube, silicon sandwich, graphene, or superlattice, or a combination thereof.

AAA5.1 The device of any prior embodiments, wherein the heating layer and the cooling layer are structurally separate layers, the heating layer has a heating zone, and the cooling layer has a cooling zone.

AAA6.1 The device of any prior embodiments, wherein the ratio of the cooling zone area to the heating zone area is larger than 1, 1.5, 2, 2.5, 3, 5, 10, 15, 20, 25, 50, 75, 100, 200, 500, or 1000, or in a range between any of the two values.

AAA6.2 The device of any prior embodiments, wherein the cooling zone area is larger than the lateral area of the relevant sample volume by a factor that is equal to or large than 1.2 times, 1.5 times, 2 times, 5 times, 10 times, 20 times, 50 times, 100 times, 200 times, 500 times, or 1000 times larger than the cooling through thermal conduction cooling, or in a range between any of the two values.

AAA6.3 The device of any prior embodiments, wherein the cooling of the device has a thermal radiation cooling that, during a thermal cycling, is equal to or larger than 50%, 55%, 60%, 65%, 70%, 75%, 80%, 85%, 90%, 95%, or 99% of the total cooling or in a range between any of the two values, wherein the total cooling is the sum of radiative cooling and conductive cooling.

AAA6.4 The device of any prior embodiments, wherein the cooling of the device by thermal radiation through a high K cooling layer, during a thermal cycling, is equal to or larger than. 60%, 65%, 70%, 75%, 80%, 85%, 90%, 95%, or 99% of the total cooling or in a range between any of the two values, wherein the total cooling is the sum of radiative cooling and conductive cooling.

AAA7.1 The device of any prior embodiments, wherein at least one of the plates is flexible.

AAA8.1 The device of any prior embodiments, wherein the device comprises spacers that regulate the thickness of the sample when the sample is confined by the two plates into a thin layer.

AAA8.2 The device of any prior embodiments, wherein the spacers has an inter-spacer-distance (ISD), and wherein the fourth power of the inter-spacer-distance (ISD) divided by the thickness (h) and the Young's modulus (E) of the flexible plate (ISD4/(hE)) is $5 \times 10^6$ um³/GPa or less.

AAA8.3. The device of any prior embodiments, wherein the spacers has a contact filling factor, wherein the product of the contact filling factor and the Young's modulus of the spacers is 2 MPa or larger, and wherein the contact filling factor is, in the sample contact area, the ratio of the contact area between spacer and the plate to the total plate area.

AAA8.4. The device of any prior embodiments, wherein the spacers are in the sample contact area.

AAA8.5. The device of any prior embodiments, wherein the spacers have a shape of the pillars with substantially flat top.

AAA8.6. The device of any prior embodiments, wherein the spacers are fixed on either one or both of the plates.

AAA8.7. The device of any prior embodiments, wherein the spacers have a uniform height.

AAA8.8. The device of any prior embodiments, wherein the thickness of the sample is the same as the height of the spacers.

AAA9.1 The device of any prior embodiments, wherein the heating layer and/or the cooling layer is on the inner surface of one of the plates.

AAA9.2 The device of any prior embodiments, wherein the heating layer and/or the cooling layer is on the outer surface of one of the plates.

AAA9.3 The device of any prior embodiments, wherein the heating layer and the cooling layer are separate, the heating layer is on the outer surface of one of the plates, and the cooling layer is on the outer surface of the other plate.

AAA9.4 The device of any prior embodiments, wherein the heating layer and the cooling layer are separate, the heating layer is on the inner surface of one of the plates, and the cooling layer is on the inner surface of the other plate.

AAA9.5 The device of any prior embodiments, wherein the heating layer and the cooling layer are separate, the heating layer is on the inner or outer surface of one of the plates, and the cooling layer is on the inner or outer surface of the other plate.

AAA9.6 The device of any prior embodiments, wherein the heating layer and the cooling layer are inside one or both of the plates.

AAA9.7 The device of any prior embodiments, wherein the heating zone and the cooling zone are partly overlapping on the heating and/or cooling layer.

AAA10.1 The device of any prior embodiments, wherein the first plate or the second plate has a thickness that is less than 10 nm, 100 nm, 200 nm, 500 nm, 1000 nm, 2 μm (micron), 5 μm, 10 μm, 20 μm, 50 μm, 100 μm, 150 μm, 200 μm, 300 μm, 500 μm, 800 μm, 1 mm (millimeter), 2 mm, 3 mm, 5 mm, 10 mm, 20 mm, 50 mm, 100 mm, 500 mm, or in a range between any two of these values.

AAA10.2 The device of any prior embodiments, wherein the first plate or the second plate has an lateral area that is less than 1 mm$^2$ (square millimeter), 10 mm$^2$, 25 mm$^2$, 50 mm$^2$, 75 mm$^2$, 1 cm$^2$ (square centimeter), 2 cm$^2$, 3 cm$^2$, 4 cm$^2$, 5 cm$^2$, 10 cm$^2$, 100 cm$^2$, 500 cm$^2$, 1000 cm$^2$, 5000 cm$^2$, 10,000 cm$^2$, 10,000 cm$^2$, or in a range between any two of these values.

AAA10.3.1 The device of any prior embodiments, wherein the first plate or the second plate comprises PMMA.

AAA10.4 The device of any prior embodiments, wherein the plates are thermal-isolated from a structure that accommodate the plates.

AAA11.1 The device of any prior embodiments, wherein the relevant sample has a volume that is about 0.01 ul, 0.02 ul, 0.05 ul, 0.1 ul, 0.2 ul, 0.5 ul, 1 ul, 2 ul, 5 ul, 10 ul, 20 ul, 50 ul, 100 ul, 200 ul, 500 ul, 1 ml, 2 ml, 5 ml, 10 ml, 20 ml, or 50 ml, or in a range between any of the two values.

AAA11.2 The device of any prior embodiments, wherein ratio of the lateral average dimension of the relevant sample area to the sample thickness is greater than 1, 2, 3, 4, 5, 6, 7, 8, 9, 10, 20, 30, 40, 50, 60, 70, 80, 90,100,200, 500, 1000, 2000, 5000, 100,000, or in a range between any of the two values.

AAA12.1 The device of any prior embodiments, wherein the plates are configured to be operable directly by human hands.

AAA12.2 The device of any prior embodiments, wherein the plates are configured to be compressed directly by human hands with imprecise force, which is neither set to a precise level nor substantially uniform.

AAA12.3 The device of any prior embodiments, further comprising a hinge, which connects the first plate and the second plate and allows the two plates to pivot against each other into different configurations.

AAA12.4 The device of any prior embodiments, wherein at least one of the plates comprises one or more open notches on an edge or corners of the plate, and the notch(es) facilitates changing the plates between different configurations.

AAA12.5 The device of any prior embodiments, wherein at least one of the plates comprises one or more open notches on an edge or corners of the plate, and the notch(es) facilitates changing the plates from a configuration that is near or at closed configuration to an open configuration.

AAA13.1. A sample cartridge, comprising the device of any prior embodiments, and a sample support that is configured to support the device.

AAA13.2. The sample cartridge of any prior embodiments, wherein the sample support comprises one or more apertures that allow energy to reach the heating layer.

AAA14.1 An apparatus for rapidly changing temperature of a fluidic sample, comprising:
 the device of any prior embodiments;
 a heating source that is configured to supply energy to the device.

AAA14.2 The apparatus of any prior embodiments, wherein the heating source is configured to radiate electromagnetic waves in a range of wavelength that the heating/cooling layer has an absorption coefficient of 50% or higher.

AAA14.3. The apparatus of any prior embodiments, wherein the heating source comprises one or an array of light-emitting diodes (LEDs), one or an array of lasers, one or an array of lamps, or a combination of thereof.

AAA14.4. The apparatus of any prior embodiments, wherein the heating source comprises halogen lamp, halogen lamp with reflector, LED with focusing lens, laser with focusing lens, halogen lamp with coupling optical fiber, LED with coupling optical fiber, laser with coupling optical fiber.

AAA14.5 The apparatus of any prior embodiments, further comprising an optical pipe between the heating source and the device, wherein the optical pipe is configured to guide the energy from the heating source to the heating layer.

AAA15.1 An apparatus for rapidly changing temperature of a fluidic sample, comprising:
 the device of any prior embodiments; and
 an adaptor that is configured to accommodate the device.

AAA15.2 The apparatus of any prior embodiments, wherein the adaptor comprises a sample slot that is configured to accommodate the device and position the device to receive the electromagnetic waves from the heating source.

AAA15.3 The apparatus of any prior embodiments, wherein adaptor comprises a slider that is configured to allow the device to slide into the sample slot.

AAA16.1 An apparatus for rapidly changing temperature of a fluidic sample, comprising:
 the device of any prior embodiments;
 a heating source that is configured to supply energy the device; and
 a control unit that is configured to control the heating unit.

AAA16.2 The apparatus of any prior embodiments, wherein the control unit is configured to control electromagnetic waves from the heating source.

AAA16.3 The apparatus of any prior embodiments, wherein the control unit is configured to control the presence, intensity, wavelength, frequency, and/or angle of the electromagnetic waves.

AAA16.2 The apparatus of any prior embodiments, wherein the control unit comprises a temperature sensor that is configured to detect the temperature of the sample.

A16.2.1 The apparatus of any prior embodiments, wherein the control unit controls the energy supplied by the heating source based on the temperature detected by the temperature sensor.

AAA17.1. A system for rapidly changing temperature of a fluidic sample, comprising: a device of any prior embodiments;
 a heating source that is configured to emit electromagnetic waves that can be received by the device; and
 a control unit, which is configured to control heating and cooling of the sample, at least in part by changing the electromagnetic waves from the heating source.

AAA17.2 The system of any prior embodiments, further comprising an adaptor that is configured to accommodate the device.

AAA17.3 The system of any prior embodiments, further comprising an optical pipe that is configured to guide the electromagnetic waves from the heating source to the device.

AAA17.4 The system of any prior embodiments, further comprising a signal sensor that is configured to detect a signal from the sample.

AAA17.4.1. The system of any prior embodiments, wherein the signal sensor is an optical sensor that is configured to image the fluidic sample.

AAA18.1 A kit for rapidly changing temperature of a fluidic sample, comprising: a device of any prior embodiments; and reagents that configured to facilitate a chemical/biological reaction.

AAA18.2 The kit of any prior embodiments, wherein the reagents are configured for nucleic acid amplification:

AAA18.3 The kit of any prior embodiments, wherein the reagents comprises a pre-mixed polymerase chain reaction (PCR) medium:

AAA18.4 The kit of any prior embodiments, wherein the reagents are configured to detect nucleic acids by amplifying (generating numerous copies of) the target molecules in samples, wherein target molecule refers to a sequence, or partial sequence, of nucleic acid of interest.

AAA18.5 The kit of any prior embodiments, wherein the reagents comprise: primers, deoxynucleotides (dNTPs), bivalent cations (e.g. $Mg^{2+}$), monovalent cation (e.g. $K^+$), buffer solutions, enzymes, or reporters, or any combination or mixture thereof.

AAA18.6 The kit of any prior embodiments, wherein the reagents are either in the dry form on the inner surface of the first or the second plate or both, or in a liquid form encased in, embedded in, or surrounded by, a material that melts with increasing temperatures, such as, for example, paraffin.

AAA18.7 The kit of any prior embodiments, wherein the reagents comprise DNA-dependent polymerase, or RNA-dependent DNA polymerase, or DNA-dependent RNA polymerase.

AAA18.8 The kit of any prior embodiments, wherein the reagents comprise "reporters" that refer to any tag, label, or dye that can bind to, or intercalate within, the nucleic acid molecule or be activated by byproducts of the amplification process to enable visualization of the nucleic acid molecule or the amplification process.

AAA18.9 The kit of any prior embodiments, wherein the reagents comprise cell lysing reagent, which is configured to facilitate breaking down cellular structures.

AAA19.1 The device, apparatus, system, and/or kit of any prior embodiments, wherein the heating layer and/or the cooling layer are attached to the first plate and/or the second plate by e-beam evaporation.

AAA19.2. The device, apparatus, system, and/or kit of any prior embodiments, wherein the heating layer and/or the cooling layer comprise gold and the gold is attached to the first plate and/or the second plate by e-beam evaporation.

AA1. A device for rapidly changing a fluidic sample temperature, comprising:
a first plate, a second plate, and a heating/cooling layer, wherein:
the plates are movable relative to each other into different configurations;
each of the plates has, on its respective inner surface, a sample contact area for contacting a fluidic sample, and the heating/cooling layer is configured to heat the fluidic sample;
wherein the heating/cooling layer is (a) on (either the inner or outer surface) or inside one of the plates, and (b) capable of being heated by a heating source, wherein the heating source delivers heat energy to the heating/cooling layer optically, electrically, by radio frequency (RF) radiation, or a combination thereof;
wherein at least a part of a heating area of the heating/cooling layer overlaps with the sample area,
wherein one of the configurations is an open configuration, in which: the two plates are partially or completely separated apart and the average spacing between the plates is at least 300 um; and
wherein another of the configurations is a closed configuration which is configured after the fluidic sample is deposited on one or both of the sample contact areas in the open configuration; and in the closed configuration:
at least part of the sample is compressed by the two plates into a layer, wherein the average sample thickness is 200 um or less.

AA2.1 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;
the first plate and the second plate are configured to confine the fluidic sample into a layer of highly uniform thickness of 0.1-200 um and substantially stagnant relative to the plates; and
the heating/cooling layer: (1) has a thickness of less than 1 mm, (2) has an area that is substantially less than the area of either the first or the second plate, and (3) is configured to convert energy from electromagnetic waves into heat to raise the temperature of at least part of the fluidic sample in the layer of uniform thickness.

AA2.2 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;
the first plate and the second plate are configured to confine at least part of the sample into a layer of highly uniform thickness of 0.1-200 um and substantially stagnant relative to the plates,
the first plate has a thickness of 500 um or less, and the second plate has a thickness of 5 mm or less; and the heating/cooling layer has a thickness of less than 1 mm and an area of less than 100 $mm^2$ and is configured to convert energy from electromagnetic waves into heat to raise the temperature of the at least part of the fluidic sample in the layer of uniform thickness.

AA2.3 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;
the first plate and the second plate are configured to confine at least part of the sample into a layer of highly uniform thickness of 0.1-200 um and substantially stagnant relative to the plates,
the first plate has a thickness of 500 um or less, and the second plate has a thickness of 5 mm or less; and
the heating/cooling layer: (1) has a thickness of less than 1 mm, (2) has an area of less than 100 $mm^2$ that is substantially less than the area of either the first or the second plate, and (3) is configured to convert energy from electromagnetic waves into heat to raise the temperature of at least part of the fluidic sample in the layer of uniform thickness.

AA3 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;
the first plate and the second plate are configured to confine at least part of the sample into a layer of highly uniform thickness of 500 um or less and substantially stagnant relative to the plates,
the first plate is in contact with the heating/cooling layer and has a thickness of 1 um or less, and the second plate is not in contact with the heating/cooling layer and has a thickness of 5 mm or less; and
the heating/cooling layer is configured to convert energy from electromagnetic waves into heat to raise the temperature of the at least part of the fluidic sample in the layer of uniform thickness, has an absorption coefficient of 50% or higher, and has a thickness of less than 3 mm.

AA4 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;
the first plate and the second plate are configured to confine at least part of the sample into a layer of highly uniform thickness of 500 um or less and substantially stagnant relative to the plates,
the first plate is in contact with the heating/cooling layer and has a thickness of 1 um or less, and the second plate is not in contact with the heating/cooling layer and has a thickness of 0.1-2 mm; and
the heating/cooling layer is configured to convert energy from electromagnetic waves into heat to raise the temperature of the at least part of the fluidic sample in the layer of uniform thickness, has an absorption coefficient of 60% or higher, and has a thickness of less than 2 mm.

AA6.1 The device of any prior embodiments, wherein the heating/cooling layer is on the inner surface of one of the plates.

AA6.2 The device of any prior embodiments, wherein the heating/cooling layer is on the outer surface of one of the plates.

AA6.3 The device of any prior embodiments, wherein the heating/cooling layer inside one of plates.

AA6.4 The device of any prior embodiments, wherein the heating/cooling layer is in contact with at least one of the plates.

AA6.5 The device of any prior embodiments, wherein the heating/cooling layer is not in contact with any of the plates.

AA6.6 The device of any prior embodiments, wherein the heating/cooling layer is in contact with the sample when the plates are in the closed configuration.

AA7. The device of any prior embodiments, wherein the heating/cooling layer is made from a single material or compound materials.

AA7.1 The device of any prior embodiments, wherein the heating/cooling layer comprises semiconductors or metallic materials with high absorbing surfaces.

AA7.2 The device of any prior embodiments, wherein the heating/cooling layer comprises Silicon, Ge, InP, GaAs, CdTe, CdS, aSi, metal including Au, Al, Ag, Ti, carbon coated Al, black painted Al, carbon (graphene, nanotube, nanowire) or a combination thereof.

AA7.3 The device of any prior embodiments, wherein the heating/cooling layer is acting as the fast heating conductive layer comprises Silicon, Ge, InP, GaAs, CdTe, CdS, aSi, metal including Au, Al, Ag, Ti, carbon coated Al, black painted Al, carbon (graphene, nanotube, nanowire) or a combination thereof.

AA8 The device of any prior embodiments, wherein the part of the heating area that overlaps the sample area is less than 1%, 5%, 10%, 20%, 30%, 40%, 50%, 60%, 70%, 80%, 90%, 95%, or 99% of the sample area, or in a range between any of the two values.

AA8.1 The device of any prior embodiments, wherein the part of the heating area that overlaps the sample area is less than $0.1 \text{ mm}^2$, $0.5 \text{ mm}^2$, $1 \text{ mm}^2$, $5 \text{ mm}^2$, $10 \text{ mm}^2$, $25 \text{ mm}^2$, $50 \text{ mm}^2$, $75 \text{ mm}^2$, $1 \text{ cm}^2$ (square centimeter), $2 \text{ cm}^2$, $3 \text{ cm}^2$, $4 \text{ cm}^2$, $5 \text{ cm}^2$, $10 \text{ cm}^2$, or in a range between any of the two values.

AA9. The device of any prior embodiments, wherein the absorption coefficient of the heating/cooling layer is more than 30%, 40%, 50%, 60%, 70%, 80%, 90%, or in a range between any of the two values.

AA9.1. The device of any prior embodiments, wherein the absorption coefficient of the heating/cooling layer is more than 60%, 70%, 80%, 90%, or in a range between any of the two values.

AA9.2. The device of any prior embodiments, wherein the absorption coefficient of the heating/cooling layer is more than 60%.

AA10. The device of any prior embodiments, wherein the heating/cooling layer has an absorption wavelength range that is 100 nm to 300 nm, 400 nm to 700 nm (visible range), 700 nm to 1000 nm (IR range), 1 um to 10 um, 10 um to 100 um, or in a range between any of the two values.

AA11. The device of any prior embodiments, wherein the heating/cooling layer has a thickness equal to or less than 3 mm, 2 mm, 1 mm, 750 um, 500 um, 250 um, 100 um, 50 um, 25 um, 10 um, 500 nm, 200 nm, 100 nm, or 50 nm, or in a range between any of the two values.

AA12. The device of any prior embodiments, wherein the heating/cooling layer has an area of $0.1 \text{ mm}^2$ or less, $1 \text{ mm}^2$ or less, $10 \text{ mm}^2$ or less, $25 \text{ mm}^2$ or less, $50 \text{ mm}^2$ or less, $75 \text{ mm}^2$ or less, $1 \text{ cm}^2$ (square centimeter) or less, $2 \text{ cm}^2$ or less, $3 \text{ cm}^2$ or less, $4 \text{ cm}^2$ or less, $5 \text{ cm}^2$ or less, $10 \text{ cm}^2$ or less, or in a range between any of the two values.

AA13. The device of any prior embodiments, wherein the first plate has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. AA13.1. The device of any prior embodiments, wherein the first plate has a thickness equal of 10-200 um.

AA14. The device of any prior embodiments, wherein the second plate has a thickness equal to or less than 5 mm, 4 mm, 3 mm, 2 mm, 1 mm, 750 um, 500 um, 250 um, 100 um, 75 um, 50 um, or 25 um, or in a range between any of the two values.

AA14.1. The device of any prior embodiments, wherein the second plate has a thickness equal of 10-1000 um.

AA15. The device of any prior embodiments, wherein the sample layer has a highly uniform thickness.

AA15.1 The device of any prior embodiments, wherein the sample layer has a thickness of equal to or less than 100 um, 50 um, 20 um, 10 um, 5 um, 1 um, 500 nm, 400 nm, 300 nm, 200 nm, or 100 nm, or in a range between any of the two values.

AA15.2. The device of any prior embodiments, wherein the sample layer has a thickness of 1-100 um.

AA16. The device of any prior embodiments, wherein the area of at least one of the plate is 1 mm$^2$ or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values.

AA17.1 The device of any prior embodiments, wherein the area of at least one of the plates is in the range of 500 to 1,000 mm$^2$; or around 750 mm$^2$.

AA18. The device of any prior embodiments, further comprising spacers that are configured to regulate the thickness of the sample layer.

AA18.1 The device of any prior embodiments, wherein the spacers are fixed on either one or both of the plates.

AA18.2 The device of any prior embodiments, wherein the spacers are fixed on the inner surface of either one or both of the plates.

AA18.3 The device of any prior embodiments, wherein the spacers have a uniform height.

AA18.4 The device of any prior embodiments, wherein at least one of the spacers is inside the sample contact area.

AA18.5 The device of any prior embodiments, wherein the thickness of the sample layer is the same as the height of the spacers.

AA19 The device any prior embodiments, wherein one or both plates are flexible.

AA20. The device of any prior embodiments, further comprising sealing structures that are attached to either one or both of the contact and second plates, wherein the sealing structures are configured to limit the evaporation of liquid inside the device.

AA21. The device of any prior embodiments, further comprising a clamping structure that is attached to either one or both of the first and second plates, wherein the clamp structure is configured to hold the device and regulate the thickness of the sample layer during the heating of the device.

AA22. The device of any prior embodiments, wherein the second plate is transparent for an electromagnetic wave from the sample.

AA23. The device of any prior embodiments, wherein the sample holder and the heating/cooling layer are connected by a thermal coupler.

AA24. The device of any prior embodiments, wherein the areas of the at least part of the sample and the heating/cooling layer are substantially larger than the uniform thickness.

AA25. The device of any prior embodiments, wherein the heating/cooling layer is configured to absorb electromagnetic waves selected from the group consisting of: radio waves, microwaves, infrared waves, visible light, ultraviolet waves, X-rays, gamma rays, and thermal radiation.

AA26. The device of any prior embodiments, wherein the sample is a pre-mixed polymerase chain reaction (PCR) medium.

AA27. The device of any prior embodiments, wherein the sample layer is laterally sealed to reduce sample evaporation.

AA28. The device of any prior embodiments, wherein the area of the radiation is smaller than the area of radiation absorption pad; The area of the radiation absorption pad is less than the area of sample liquid area; The area of sample liquid area is less than the first and second plate size.

AA29. The device of any prior embodiments, wherein the fluidic sample comprises a processed or unprocessed bodily fluid.

AA30. The device of any prior embodiments, wherein the fluidic sample comprises amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled condensate, or a mixture thereof.

AA31. The device of any prior embodiments, wherein the fluidic sample comprises nucleic acids or proteins, or a mixture thereof.

AA32. The device of any prior embodiments, wherein the fluidic sample comprises DNA or RNA, or a mixture thereof.

Apparatus with Heating Source

BB1. An apparatus for rapidly changing temperature of a fluidic sample, comprising:
- a holder that can hold a device of any AA embodiments; and
- a heating source that is configured to supply energy to the heating/cooling layer; and
- a controller that is configured to control the heating source.

BB1.1 The apparatus of any prior BB embodiments, wherein the heating source is configured to radiate electromagnetic waves in a range of wavelength that the heating/cooling layer has an absorption coefficient of 50% or higher.

BB2. The apparatus of any prior BB embodiments, wherein the heating source comprises one or an array of light-emitting diodes (LEDs), one or an array of lasers, one or an array of lamps, or a combination of thereof.

BB2.1. The apparatus of any prior BB embodiments, wherein the heating source comprises halogen lamp, halogen lamp with reflector, LED with focusing lens, laser with focusing lens, halogen lamp with coupling optical fiber, LED with coupling optical fiber, laser with coupling optical fiber.

BB3. The apparatus of any prior BB embodiments, wherein the wavelength is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values.

BB3.1 The apparatus of any prior BB embodiments, wherein the wavelength of the electromagnetic waves is 100 nm to 300 nm, 400 nm to 700 nm (visible range), 700 nm to 1,000 nm (IR range), 1 um to 10 um, 10 um to 100 um, or in a range between any of the two values.

BB4. The apparatus of any prior BB embodiments, further comprising a heat sink that is configured to absorb at least part of the heat radiated from the sample holder and/or the heating source.

BB4.1. The apparatus of any prior BB embodiments, wherein the heat sink is chamber that at least partially encloses the device.

BB4.2. The apparatus of any prior BB embodiments, wherein the chamber comprises a lower aperture configured to allow passage of electromagnetic waves from the heating source to the heating/cooling layer, and an upper aperture configured to allow imaging of the sample.

BB5. The apparatus of any prior BB embodiments, wherein the sample holder is heated optically, electrically, by RF, or a combination of thereof.

BB6. An apparatus for rapidly changing temperature of a fluidic sample, comprising: a device of any AA embodiments; and a heat sink that is configured to absorb at least part of the heat radiated from the sample holder and/or the heating source.

BB7. The apparatus of any prior BB embodiments, wherein the heat sink is a chamber that at least partially encloses the device, wherein the chamber comprises a radiation aperture configured to allow passage of electromagnetic waves from a heating source to the heating/cooling layer, and an optical aperture configured to allow imaging of the sample.

BB8. The apparatus of any prior BB embodiments, further comprising a cooling member attached to the chamber, wherein the cooling member is configured to reduce temperature in the chamber.

BB9. The apparatus of embodiment BB7, wherein the cooling member is a fan.

BB10. The apparatus of embodiment BB7, wherein the cooling member is a Peltier cooler.

BB11. The apparatus of any BB embodiments, wherein the chamber has a non-reflective inner surface.

BB11.1 The apparatus of any BB embodiments, wherein the chamber has an inner surface made of black metal.

BB12. The apparatus of any BB embodiments, wherein the device is suspended (i.e. has minimum) thermal conduction contact with the chamber wall.

BB13. The apparatus of any BB embodiments, wherein the heat sink is configured to connect the sample holder to a mobile device.

BB13.1 The apparatus of embodiment B13, wherein the mobile device is a smartphone comprising a camera.

BB14. The apparatus of any BB embodiments, wherein the heat sink comprises optical elements that optimizes capturing images of the sample in the sample card.

CC1. A system for rapidly changing temperature of a fluidic sample, comprising: a device of any AA embodiments or an apparatus of any BB embodiments; and a signal sensor that is configured to senses a signal from the sample on the device.

CC2. The system of any prior CC embodiments, wherein the signal sensor is an optical sensor that is configured to image the fluidic sample.

CC2.1 The system of any prior CC embodiments, wherein the optical sensor is a photodetector, camera, or a device capable of capturing images of the fluidic sample.

CC3. The system of any prior CC embodiments, wherein the signal sensor is an electrical sensor that is configured to detect electrical signals from the device.

CC4. The system of any prior CC embodiments, wherein the signal sensor is a mechanical sensor that is configured to detect mechanical signals from the device.

CC5. The system of any prior CC embodiments, wherein the signal sensor is configured to monitor the amount of an analyte in the sample.

CC6. The system of any prior CC embodiments, wherein signal sensor is outside the chamber and receive optical signals from the sample through an optical aperture on the chamber.

CC7. The system of any CC embodiment, further comprising a thermal coupler bound to the heating/cooling layer.

CC8. The system of any prior CC embodiments, further comprising a thermostat that monitor the temperature of the heating/cooling layer.

CC9. The system of any prior CC embodiments, further comprising a temperature monitoring dye that is configured to facilitate monitoring the temperature of the sample in the device.

CC9.1. The system of any prior CC embodiments, wherein the temperature monitoring dye is in liquid form.

CC9.2. The system of any prior CC embodiments, wherein the temperature monitoring dye comprises LDS 688, LDS 698, LDS 950, LD 390, LD 423, LD 425, or IR 144, or a combination thereof.

DD1. The device, apparatus, or system of any prior embodiments, wherein:
  there are spacers that are fixed on one of both of the plates, wherein at least one of the spacers is in the sample contact area;
  the sample layer has a thickness of 0.1-200 um;
  the first plate is in contact with the heating/cooling layer and has a thickness of 500 um or less, and the second pate is not in contact with the heating/cooling layer and has a thickness of 5 mm or less; and
  the heating/cooling layer: (1) has a thickness of less than 1 mm, (2) has an area of less than 100 $mm^2$ that is substantially less than the area of either the first or the second plate, and (3) is configured to convert energy from electromagnetic waves into heat to raise the temperature of at least part of the fluidic sample in the layer of uniform thickness.

DD2. The device, apparatus, or system of any prior embodiments, wherein:
  the heating/cooling layer is on the inner surface of the first plate and in contact with the sample when the plates are in the closed configuration;
  the heating/cooling layer is made from silicon; and
  there is a chamber that encloses the sample holder and the chamber has a non-reflective inner surface.

DD3. The device, apparatus, or system of any prior embodiments, wherein:
  there is a heating source that is configured to radiate electromagnetic waves in a range of wavelength that the heating/cooling layer has an absorption coefficient of 50% or higher;
  there is a chamber that comprises a lower aperture configured to allow passage of electromagnetic waves from the heating source to the heating/cooling layer, and an upper aperture configured to allow imaging of the sample; and
  there is an optical sensor that is configured to capture images of the fluidic sample in the sample holder.

EE1.1. A method for rapidly changing temperature of a fluidic sample, comprising:
  providing a device that comprises a first plate, a second plate, a heating layer, and a cooling layer, wherein:
  each of the plates comprises, on its respective inner surface, a sample contact area;
  the heating layer is positioned on the inner surface, the outer surface, or inside of one of the plates; and is configured to heat a relevant volume of the sample, wherein the relevant volume of the sample is a portion or an entirety of the sample that is being heated to a desired temperature; and the cooling layer is positioned on the inner surface, the outer surface, or inside of one of the plates; is configured to cool the relevant sample volume; and comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;

wherein the distance between the cooling layer and a surface of the relevant sample volume is zero or less than a distance that is configured to make the thermal conductance per unit area between the cooling layer and the surface of the relevant sample volume equal to 150 W/(m$^2$·K) or larger.

depositing a fluidic sample on one or both of the sample contact areas of the respective plates;

pressing the plates, by hand, to make the sample contact areas face each other, wherein the plates are separated by an average separation distance of 200 um or less, sandwiching the sample between them and pressing at least part of the sample into a thin layer:

changing and/or maintaining the temperature of the relevant volume in the device.

EE1.2. A method for rapidly changing temperature of a fluidic sample, comprising:

providing the device of the SC-A embodiments:

depositing a fluidic sample on one or both of the sample contact areas of the respective plates;

pressing the plates, by hand, to sandwich the sample between them and pressing at least part of the sample into a thin layer:

changing and/or maintaining the temperature of the relevant volume in the device.

EE1.3. A method for rapidly changing temperature of a fluidic sample, comprising:

obtaining the system of the CC embodiments;

depositing the fluidic sample in the sample holder;

pressing the first plate and the second plate to compress at least part of the sample into a layer of uniform thickness; and changing and maintaining the temperature of the sample layer by changing the presence, intensity, wavelength, frequency, and/or angle of the electromagnetic waves from the heating source.

EE2. The method of any prior EE embodiments, wherein changing the temperature of the sample layer comprises raising the temperature or lowering the temperature.

EE3. The method of any prior EE embodiments, further comprising imaging the sample layer with the optical sensor.

EE4. The method of any prior EE embodiments, further comprising monitoring the temperature of the sample layer and adjusting the step of changing and maintaining the temperature of the sample layer.

EE5. The method of any prior EE embodiments, wherein the step of changing and maintaining the temperature of the sample layer is conducted according to a pre-determined program.

EE6. The method of any prior EE embodiments, wherein the method is customized to facilitate polymerase chain reaction (PCR) assays for changing temperature of the sample according to a predetermined program EE7. The method of any prior EE embodiments, further comprising monitoring the amount of an analyte in the sample in real time.

FF1. The device, apparatus, system or method of any prior embodiments, wherein the sample comprises nucleic acids.

FF1.1 The device, apparatus, system or method of any prior embodiments, wherein the sample comprises DNA.

FF1.2 The device, apparatus, system or method of any prior embodiments, wherein the sample comprises RNA.

FF1.3 The device, apparatus, system or method of any prior embodiments, wherein the sample comprises DNA or RNA molecule, or a DNA/RNA hybrid, or mixtures of DNA and/or RNA.

FF1.4 The device, apparatus, system or method of any prior embodiments, wherein the sample comprises genomic or chromosomal DNA, plasmid DNA, amplified DNA, cDNA, total RNA, mRNA and small RNA.

FF1.5 The device, apparatus, system or method of any prior embodiments, wherein the sample comprises natural DNA and/or RNA molecule, or synthetic DNA and/or RNA molecule.

FF1.6 The device, apparatus, system or method of any prior embodiments, wherein the sample comprises cell-free nucleic acids, wherein "cell-free" refers to nucleic acids are not contained in any cellular structures.

FF1.7 The device, apparatus, system or method of any prior embodiments, wherein the sample comprises nucleic acids are contained within cellular structures, which include but not limited to human cells, animal cells, plant cells, bacterial cells, fungi cells, and/or viral particles.

FF1.8 The device, apparatus, system or method of any prior embodiments, wherein the sample comprises purified nucleic acids.

FF2. The device, apparatus, system or method of any prior embodiments, wherein the sample comprises proteins and/or lipids.

FF3. The device, apparatus, system or method of any prior embodiments, wherein the sample comprises reagents configured for nucleic acid amplification.

FF3.1. The device, apparatus, system or method of any prior embodiments, wherein the sample comprises a premixed polymerase chain reaction (PCR) medium.

FF3.2. The device, apparatus, system or method of any prior embodiments, wherein the sample comprises reagents configured to detect nucleic acids by amplifying (generating numerous copies of) the target molecules in samples, wherein target molecule refers to a sequence, or partial sequence, of nucleic acid of interest.

FF3.3. The device, apparatus, system or method of any prior embodiments, wherein the nucleic acid amplification refers to nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

FF3.4. The device, apparatus, system or method of any prior embodiments, wherein the reagents comprise primers, deoxynucleotides (dNTPs), bivalent cations (e.g. Mg$^{2+}$), monovalent cation (e.g. K$^+$), buffer solutions, enzymes, or reporters, or any combination or mixture thereof.

FF3.5. The device, apparatus, system or method of any prior embodiments, wherein the reagents are either in the dry form on the inner surface of the first or the second plate or both, or in a liquid form encased in, embedded in, or surrounded by, a material that melts with increasing temperatures, such as, for example, paraffin.

FF3.6. The device, apparatus, system or method of any prior embodiments, wherein primers comprise one or more pairs of forward and reverse primers.

FF3.7. The device, apparatus, system or method of any prior embodiments, wherein the reagents comprise DNA-dependent polymerase, or RNA-dependent DNA polymerase, or DNA-dependent RNA polymerase.

FF3.8. The device, apparatus, system or method of any prior embodiments, wherein the reagents comprise "reporters" that refer to any tag, label, or dye that can bind to, or intercalate within, the nucleic acid molecule or be activated by byproducts of the amplification process to enable visualization of the nucleic acid molecule or the amplification process.

FF3.8.1 The device, apparatus, system or method of any prior embodiments, wherein the reports include but are not limited to fluorescent labels or tags or dyes, intercalating agents, molecular beacon labels, or bioluminescent molecules, or a combination thereof.

FF3.9. The device, apparatus, system or method of any prior embodiments, wherein the reagents comprise cell lysing reagent, which is configured to facilitate breaking down cellular structures.

FF3.9.1. The device, apparatus, system or method of any prior embodiments, wherein the cell lysing reagent includes but not limited to salts, detergents, enzymes, and other additives.

FF3.9.2. The device, apparatus, system or method of any prior embodiments, wherein the salt includes but not limited to lithium salt (e.g. lithium chloride), sodium salt (e.g. sodium chloride), potassium (e.g. potassium chloride).

FF3.9.2. The device, apparatus, system or method of any prior embodiments, wherein the detergents are ionic, including anionic and cationic, non-ionic or zwitterionic. FF3.9.3. The device, apparatus, system or method of any prior embodiments, wherein the ionic detergent includes any detergent which is partly or wholly in ionic form when dissolved in water.

FF3.9.4. The device, apparatus, system or method of any prior embodiments, wherein anionic detergents include but not limited to sodium dodecyl sulphate (SDS) or other alkali metal alkylsulphate salts or similar detergents, sarkosyl, or combinations thereof. FF3.10. The device, apparatus, system or method of any prior embodiments, wherein enzymes includes but not limited to lysozyme, cellulose, and proteinase.

FF3.11. The device, apparatus, system or method of any prior embodiments, wherein chelating agents include but not limited to EDTA, EGTA and other polyamino carboxylic acids, and some reducing agents, such as dithiotreitol (dTT).

FF4. The device, apparatus, system or method of any prior embodiments, wherein the sample comprises an analyte the amount of which is changed with the temperature changes.

FF5. The device, apparatus, system or method of any prior embodiments, wherein the sample comprises human bodily fluids, such as but not limited to whole blood, plasma, serum, urine, saliva, and sweat, and cell cultures (mammalian, plant, bacteria, fungi), and a combination or mixture thereof.

FF6. The device, apparatus, system or method of any prior embodiments, wherein the sample is freshly obtained, stored or treated in any desired or convenient way, for example by dilution or adding buffers, or other solutions or solvents.

FF7. The device, apparatus, system or method of any prior embodiments, wherein the sample comprises cellular structures such as but not limited to human cells, animal cells, plant cells, bacteria cells, fungus cells, and virus particles, and a combination or mixture thereof.

GG1. The device, apparatus, system or method of any prior embodiments, wherein an analyte in the sample is stained.

GG2. The device, apparatus, system or method of any prior GG embodiments, wherein the amount of the analyte is measured by fluorescence intensity.

GG3. The device, apparatus, system or method of any prior GG embodiments, wherein the amount of the analyte is measured by colorimetric intensity.

GG4. The device, apparatus, system or method of any prior embodiments, wherein the analyte is nucleic acid, which is stained with ethidium bromide (EB), methylene blue, SYBR green I, SYBR green II, pyronin Y, DAPI, acridine orange, or Nancy-520, or a combination thereof.

GG5. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with fluorescence intensity.

GG6. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with colorimetric intensity.

GG7. The device, apparatus, system or method of any prior embodiments, wherein the analyte is RNA, which is stained with ethidium bromide (EB), methylene blue, SYBR green II, pyronin Y, or acridine orange, or a combination thereof, and measured with fluorescence intensity.

GG8. The device, apparatus, system or method of any prior embodiments, wherein the analyte is RNA, which is stained with ethidium bromide (EB), methylene blue, SYBR green II, pyronin Y, or acridine orange, or a combination thereof, and measured with colorimetric intensity.

GG9. The device, apparatus, system or method of any prior embodiments, wherein the analyte is nucleic acid to be detected by reporters.

GG9.1. The device, apparatus, system or method of any prior embodiments, wherein the reporters include but not limited to tag, label, or dye that can bind to, or intercalate within, the nucleic acid molecule or be activated by byproducts of the amplification process to enable visualization of the nucleic acid molecule or the amplification process.

GG9.2. The device, apparatus, system or method of any prior embodiments, wherein the reporters include but are not limited to fluorescent labels or tags or dyes, intercalating agents, molecular beacon labels, or bioluminescent molecules, or a combination thereof.

GG9.3. The device, apparatus, system or method of any prior embodiments, wherein the amount of reporter is measured by colorimetric intensity and/or by fluorescence intensity.

HH1. The device, apparatus, system or method of any prior embodiments, wherein the device, apparatus, system or method is configured to facilitate PCR assays for changing temperature of the sample according to a predetermined program.

HH2. The device, apparatus, system or method of any prior embodiments, wherein the device, apparatus, system or method is configured to conduct diagnostic testing, health monitoring, environmental testing, and/or forensic testing.

HH3. The device, apparatus, system or method of any prior embodiments, wherein the device, apparatus, system or method is configured to conduct DNA amplification, DNA quantification, selective DNA isolation, genetic analysis, tissue typing, oncogene identification, infectious disease testing, genetic fingerprinting, and/or paternity testing.

HH4. The device, apparatus, system or method of any prior embodiments, wherein the device, apparatus, system or method is configured to conduct real time PCR.

HH5. The device, apparatus, system or method of any prior embodiments, wherein the device, apparatus, system or method is configured to conduct nucleic acid amplification.

HH5.1 The device, apparatus, system or method of any prior embodiments, wherein nucleic acid amplification includes any techniques used to detect nucleic acids by amplifying (generating numerous copies of) the target molecules in samples, wherein target molecule refers to a sequence, or partial sequence, of nucleic acid of interest.

HH6 The device, apparatus, system or method of any prior embodiments, wherein the device, apparatus, system or method is configured to conduct nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

A1. A device for rapidly changing temperature of a thin fluidic sample layer, comprising:
 a first plate, a second plate, and a heating/cooling layer, wherein:
 the heating/cooling layer is on one of the plates,
 each of the plates comprises, on its respective surface, a sample contact area for contacting a fluidic sample; and
 the plates have a configuration for rapidly changing temperature of the sample, in which:
 the sample contact areas face each other and are significant parallel,
 the average spacing between the contact areas is equal to or less than 200 microns,
 the two plates regulate (or confine) at least part of the sample into a layer of highly uniform thickness and substantially stagnant relative to the plates,
 the heating/cooling layer is near the at least part of the sample of uniform thickness,
 the area of the at least part of the sample and the heating/cooling layer are substantially larger than the uniform thickness.

A2. The device of embodiment A1, wherein the heating/cooling layer comprises a disk-coupled dots-on-pillar antenna (D2PA) array, silicon sandwich, graphene, back materials, superlattice or other plasmonic materials, other a combination thereof.

A3. The device of embodiment A1, wherein the heating/cooling layer comprises carbon or black nanostructures or a combination thereof.

A4. The device of any of embodiments A1-A3, wherein the heating/cooling layer is configured to absorb radiation energy.

A5. The device of any of embodiments A1-A4, wherein the heating/cooling layer is configured to radiate energy in the form of heat after absorbing radiation energy.

A6. The device of any of embodiments A1-A5, wherein the heating/cooling layer is positioned underneath the sample layer and in direct contact with the sample layer.

A7. The device of any of embodiments A1-A6, wherein the heating/cooling layer is configured to absorbing electromagnetic waves selected from the group consisting of: radio waves, microwaves, infrared waves, visible light, ultraviolet waves, X-rays, gamma rays, and thermal radiation.

A8. The device of any of embodiments A1-A7, wherein at least one of the plates does not block the radiation that the heating/cooling layer absorbs.

A9. The device of any of embodiments A1-A8, wherein one or both of the plates have low thermal conductivity.

A10. The device of any of embodiments A1-A9, wherein the uniform thickness of the sample layer is regulated by one or more spacers that are fixed to one or both of the plates.

A11. The device of any of embodiments A1-A10, wherein the sample is a pre-mixed polymerase chain reaction (PCR) medium.

A12. The device of embodiment A11, wherein the device is configured to facilitate PCR assays for changing temperature of the sample according to a predetermined program.

A13. The device of any of embodiments A1-A12, wherein the device is configured to conduct diagnostic testing, health monitoring, environmental testing, and/or forensic testing.

A14. The device of any of embodiments A1-A13, wherein the device is configured to conduct DNA amplification, DNA quantification, selective DNA isolation, genetic analysis, tissue typing, oncogene identification, infectious disease testing, genetic fingerprinting, and/or paternity testing.

A15. The device of any of embodiment A1-A14, wherein the sample layer is laterally sealed to reduce sample evaporation.

B1. A system for rapidly changing temperature of a thin fluidic sample layer, comprising:
 a first plate, a second plate, a heating/cooling layer, and a heating source, wherein:
 the heating/cooling layer is on one of the plates;
 the heating source is configured to radiate electromagnetic waves that the heating/cooling layer absorbs significantly;
 each of the plates comprises, on its respective surface, a sample contact area for contacting a fluidic sample; and
 the plates have a configuration for rapidly changing temperature of the sample, in which:
 the sample contact areas face each other and are significant parallel,
 the average spacing between the contact areas is equal to or less than 200 um,
 the two plates confine at least part of the sample into a layer of highly uniform thickness and substantially stagnant relative to the plates,
 the heating/cooling layer is near the at least part of the sample of uniform thickness,
 the area of the at least part of the sample and the heating/cooling layer are substantially larger than the uniform thickness.

B2. The system of embodiment B1, wherein the heating/cooling layer comprises a disk-coupled dots-on-pillar antenna (D2PA) array, silicon sandwich, graphene, superlattice or other plasmonic materials, other a combination thereof.

B3. The system of embodiment B1, wherein the heating/cooling layer comprises carbon or black nanostructures or a combination thereof.

B4. The system of any of embodiments B1-B3, wherein the heating/cooling layer is configured to absorb at least 80% of the radiation energy from the electromagnetic waves from the heating source.

B5. The system of any of embodiments B1-B4, wherein the heating/cooling layer is configured to radiate energy in the form of heat after absorbing radiation energy.

B6. The system of any of embodiments B1-B5, wherein the heating/cooling layer is positioned underneath the sample layer and in direct contact with the sample layer.

B7. The system of any of embodiments B1-B6, wherein the heating/cooling layer is configured to absorbing electromagnetic waves selected from the group consisting of: radio waves, microwaves, infrared waves, visible light, ultraviolet waves, X-rays, gamma rays, and thermal radiation.

B8. The system of any of embodiments B1-B7, wherein at least one of the plates does not block the radiation from the heating source.

B9. The system of any of embodiments B1-B8, wherein one or both of the plates have low thermal conductivity.

B10. The system of any of embodiments B1-B9, wherein the uniform thickness of the sample layer is regulated by one or more spacers that are fixed to one or both of the plates.

B11. The system of any of embodiments B1-B10, wherein the sample is a pre-mixed polymerase chain reaction (PCR) medium.

B12. The system of embodiment B11, wherein the system is configured to facilitate PCR assays for changing temperature of the sample according to a predetermined program.

B13. The system of any of embodiments B1-B12, wherein the system is configured to conduct diagnostic testing, health monitoring, environmental testing, and/or forensic testing.

B14. The system of any of embodiments B1-B15, wherein the system is configured to conduct DNB amplification, DNB quantification, selective DNB isolation, genetic analysis, tissue typing, oncogene identification, infectious disease testing, genetic fingerprinting, and/or paternity testing.

B15. The system of any of embodiments B1-B14, wherein the sample layer is laterally sealed to reduce sample evaporation.

B16. The system of any of embodiments B1-B15, further comprising a controller, which is configured to control the presence, intensity, wavelength, frequency, and/or angle of the electromagnetic waves.

B17. The system of any of embodiments B1-B16, further comprising a thermometer, which is configured to measure the temperature at or in proximity of the sample contact area and send a signal to the controller based on the measured temperature.

B18. The system of embodiment B17, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

C1. A system for facilitating a polymerase chain reaction (PCR) by rapidly changing temperature of a thin fluidic PCR sample layer, comprising:
   a first plate, a second plate, a heating/cooling layer, a heating source, and a controller wherein:
   the heating/cooling layer is on one of the plates;
   the heating source is configured to radiate electromagnetic waves that the heating/cooling layer absorbs significantly;
   each of the plates comprises, on its respective surface, a sample contact area for contacting a fluid PCR sample, which is a pre-mixed PCR medium;
   the controller is configured to control the heating source and rapidly change the temperature of the sample according to a predetermined program; and
   the plates have a configuration for rapidly changing temperature of the sample, in which:
   the sample contact areas face each other and are significant parallel,
   the average spacing between the contact areas is equal to or less than 200 µm,
   the two plates confine at least part of the sample into a layer of highly uniform thickness and substantially stagnant relative to the plates,
   the heating/cooling layer is near the at least part of the sample of uniform thickness, and
   the area of the at least part of the sample and the heating/cooling layer are substantially larger than the uniform thickness.

C2. The system of embodiment C1, wherein the controller is configured to control the present, intensity, wavelength, frequency, and/or angle of the electromagnetic waves from the heating source.

C3. The system of embodiment C1 or C2, wherein the heating source and the heating/cooling layer are configured that the electromagnetic waves cause an average ascending temperature rate ramp of at least 10° C./s; and the removal of the electromagnetic waves results in an average descending temperature rate ramp of at least 5° C./s.

C4. The system of any of embodiments C1-C2, wherein the heating source and the heating/cooling layer are configured to create an average ascending temperature rate ramp of at least 10° C./s and an average descending temperature rate ramp of at least 5° C./s.

C5. The system of any of embodiments C1-C2, wherein the heating source and the heating/cooling layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

C6. The system of any of embodiments C1-C5, wherein the PCR sample comprises: template DNA, primer DNA, cations, polymerase, and buffer.

D1. A method for rapidly changing temperature of a thin fluidic sample layer, comprising:
   providing a first plate a second plate, each of the plates comprising, on its respective inner surface, a sample contact area;
   providing a heating/cooling layer and a heating source, wherein the heating/cooling layer is on one of the plates, and the heating source is configured to radiate electromagnetic waves that the heating/cooling layer absorbs significantly;
   depositing a fludic sample on one or both of the plates;
   pressing the plates into a closed configuration, in which:
   the sample contact areas face each other and are significant parallel,
   the average spacing between the contact areas is equal to or less than 200 µm,
   the two plates confine at least part of the sample into a layer of highly uniform thickness and substantially stagnant relative to the plates;
   the heating/cooling layer is near the at least part of the sample of uniform thickness,
   the area of the at least part of the sample and the heating/cooling layer are substantially larger than the uniform thickness; and changing and maintaining the temperature of the sample layer by changing the presence, intensity, wavelength, frequency, and/or angle of the electromagnetic waves from the heating source.

D2. The method of embodiment D1, wherein the step of pressing the plates into a closed figuration comprises pressing the plates with an imprecise pressing force.

D3. The method of embodiment D1 or D2, wherein the step of pressing the plates into a closed figuration comprises pressing the plates directedly with human hands.

D4. The method of any of embodiments D1-D3, wherein the layer of highly uniform thickness has a thickness variation of less than 10%.

D5. The method of any of embodiments D1-D4, wherein the heating/cooling layer comprises a disk-coupled dots-on-pillar antenna (D2PA) array, silicon sandwich, graphene, superlattice or other plasmonic materials, other a combination thereof.

D6. The method of any of embodiments D1-D5, wherein the heating/cooling layer comprises carbon or black nanostructures or a combination thereof.

D7. The method of any of embodiments D1-D6, wherein the heating/cooling layer is configured to absorb at least 80% of the radiation energy from the electromagnetic waves from the heating source.

D8. The method of any of embodiments D1-D7, wherein the heating/cooling layer is configured to radiate energy in the form of heat after absorbing radiation energy.

D9. The method of any of embodiments D1-D8, wherein the heating/cooling layer is positioned underneath the sample layer and in direct contact with the sample layer.

D10. The method of any of embodiments D1-D9, wherein the heating/cooling layer is configured to absorbing electromagnetic waves selected from the group consisting of: radio waves, microwaves, infrared waves, visible light, ultraviolet waves, X-rays, gamma rays, and thermal radiation.

D11. The method of any of embodiments D1-D10, wherein at least one of the plates does not block the radiation from the heating source.

D12. The method of any of embodiments D1-D11, wherein one or both of the plates have low thermal conductivity.

D13. The method of any of embodiments D1-D12, wherein the uniform thickness of the sample layer is regulated by one or more spacers that are fixed to one or both of the plates.

D14. The method of any of embodiments D1-D13, wherein the sample is a pre-mixed polymerase chain reaction (PCR) medium.

D15. The method of embodiment D14, wherein the method is used to facilitate PCR assays for changing temperature of the sample according to a predetermined program.

D16. The method of any of embodiments D1-D15, wherein the method is used to conduct diagnostic testing, health monitoring, environmental testing, and/or forensic testing.

D17. The method of any of embodiments D1-D16, wherein the method is used to conduct DNB amplification, DNB quantification, selective DNB isolation, genetic analysis, tissue typing, oncogene identification, infectious disease testing, genetic fingerprinting, and/or paternity testing.

D18. The method of any of embodiments D1-D17, wherein the sample layer is laterally sealed to reduce sample evaporation.

D19. The method of any of embodiments D1-D18, wherein the heating source is controlled by a controller, which is configured to control the presence, intensity, wavelength, frequency, and/or angle of the electromagnetic waves.

D20. The method of any of embodiments D1-D19, wherein the controller is configured to receive signals from a thermometer, which is configured to measure the temperature at or in proximity of the sample contact area and send a signal to the controller based on the measured temperature.

D21. The method of embodiment D20, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

E1. A method for facilitating a polymerase chain reaction (PCR) by rapidly changing temperatures in a fluidic PCR sample, comprising:
  providing a first plate a second plate, each of the plates comprising, on its respective inner surface, a sample contact area;
  providing a heating/cooling layer, a heating source and a controller, wherein the heating/cooling layer is on one of the plates, and the heating source is configured to radiate electromagnetic waves that the heating/cooling layer absorbs significantly; depositing a fluidic PCR sample on one or both of the plates;
  pressing the plates into a closed configuration, in which:
  the sample contact areas face each other and are significant parallel,
  the average spacing between the contact areas is equal to or less than 200 μm,
  the two plates confine at least part of the PCR sample into a layer of highly uniform thickness and substantially stagnant relative to the plates;
  the heating/cooling layer is near the at least part of the PCR sample of uniform thickness,
  the area of the at least part of the sample and the heating/cooling layer are substantially larger than the uniform thickness; and
  using the controller to control the heating source to conduct a PCR by changing and maintaining the temperature of the PCR sample layer according to a predetermined program, wherein when the temperatures are changed, the heating source creates an average ascending temperature rate ramp of at least 10° C./s and an average descending temperature rate ramp of at least 5° C./s during the PCR.

E2. The method of embodiment E1, wherein changing and maintaining the temperature of the PCR sample layer is achieved by adjusting the intensity, wavelength, frequency, and/or angle of the electromagnetic waves from the heating source.

E3. The system of any of embodiments E1-E2, wherein the heating source and the heating/cooling layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

E4. The method of any of embodiments E1-E3, wherein the PCR sample comprises: template DNA, primer DNA, cations, polymerase, and buffer.

NN1 A device for rapidly changing temperature of a thin fluidic sample layer, comprising:
a first plate, and a second plate, wherein:
each of the plates comprises, on its respective surface, a sample contact area for contacting a fluidic sample; and
the plates have a configuration for rapidly changing temperature of the sample, in which:
the sample contact areas face each other and are significant parallel,
the average spacing between the contact areas is equal to or less than 200 microns,
the two plates regulate (or confine) at least part of the sample into a layer of highly uniform thickness and substantially stagnant relative to the plates,
the heating/cooling layer is near the at least part of the sample of uniform thickness,
the area of the at least part of the sample and the heating/cooling layer are substantially larger than the uniform thickness.

JJ1. The device of any prior embodiments, further comprising a hinge that connects the first plate and the second plate, and is configured to allow the two plates to rotate around the hinge into different configurations.

JJ2. The device of any prior embodiments, wherein after relative position of the plates are adjusted by an external force, the hinge maintains an angle between the two plates that is within 5 degrees from the angle just before the external force is removed.

JJ3. The device of any prior embodiments, wherein the wherein after relative position of the plates are adjusted by an external force, the hinge maintains an angle between the two plates that is within 10 degrees from the angle just before the external force is removed.

JJ4. The device of any prior embodiments, wherein the hinge is made of a piece of a piece of hinge material of a substantially uniform thickness, wherein the hinge material is attached to a part of the inner surface of the first plate and a part of the outer surface of the second plate, and the attachments do not completely separate using operation.

JJ5. The device of any prior embodiments, wherein the hinge is made of a piece of hinge material of a substantially uniform thickness, wherein the hinge material is attached a part of the outer surfaces of the first plate and the second plate, and the attachments do not completely separate using operation.

JJ6. The device of any prior embodiments, wherein the hinge material is a metal.

JJ7. The device of any prior embodiments, wherein the hinge materials is selected from a group consisting of: gold, silver, copper, aluminum, iron, tin, platinum, nickel, cobalt, and alloys thereof.

JJ8. The device of any prior embodiments, wherein the hinge comprises a first leaf, a second leaf, and a joint that connects the leaves and is configured for the leaves to rotate around the joint,
wherein the first leaf is attached to the first plate inner surface without wrapping around any edge of the first plate, the second leaf is attached to the second plate outer surface, and the joint is positioned longitudinally parallel to the hinge edge of the second plate, allowing the two plates to rotate around the joint KK1. The device of any prior embodiments, wherein:
one of the plate comprises one or more open notches on an edge or corners of the plate, and
at or near the closed configuration, an edge of the other plate is configured to overlap with the open notch KK2. The device of any prior embodiments, wherein the notch facilitates changing the plates from a configuration that is near or at closed configuration to an open configuration for sample deposition.

KK3. The device of any prior embodiments, wherein the the width of at least one notch is in the range of 1/6 to 2/3 of the width of the notched edge.

KK4. The device of any prior embodiments, wherein the opening edge of the plate without the notch is inside the notched edge except for the part over the notch.

KK5. The device of any prior embodiments, wherein the first plate comprises one or more notched edges, each of which has at least one notch; and the second plate comprises one or more corresponding opening edges juxtaposed over the notches, allowing a user to push against one of the opening edges over the notch to switch the two plates between the closed configuration and the open configuration or to change the angle formed by the first plate and the second plate KK6. The device of any prior embodiments, wherein the notch is positioned at an intersection of two neighboring notched edges.

LL1. The device of any prior embodiments, wherein any prior device embodiment, wherein each of the plate further comprises, on its respective outer surface, a force area for applying a pressing force that forces the plates together, and wherein the force is an imprecise force that has a magnitude which is, at the time that the force is applied, either (a) unknown and unpredictable, or (b) cannot be known and cannot be predicted within an accuracy equal or better than 30% of the force applied.

LL2. The device of any prior embodiments, wherein each of the plate further comprises, on its respective outer surface, a force area for applying a pressing force that forces the plates together, and wherein the force is an imprecise force that has a magnitude which cannot, at the time that the force is applied, be determined within an accuracy equal or better than 30%, 40%, 50%, 70%, 100%, 200%, 300%, 500%, 1000%, 2000%, or any range between the two values.

LL3. The device of any prior embodiments, wherein the imprecise force is provided by human hand.

MM1. The device, apparatus, system, or method of any prior embodiments, wherein the first plate and the second plate are flexible plastic film and/or thin glass film, that each has a substantially uniform thickness of a value selected from a range between 1 um to 25 um.

MM2. The device, apparatus, system, or method of any prior embodiments, wherein each plate has an area in a range of 1 cm^2 to 16 cm^2.

MM3. The device, apparatus, system, or method of any prior embodiments, wherein the sample sandwiched between the two plate has a thickness of 40 um or less.

MM4. The device, apparatus, system, or method of any prior embodiments, wherein the relevant sample to the entire sample ratio (RE ratio) is 12% or less.

MM5. The device, apparatus, system, or method of any prior embodiments, wherein the cooling zone is at least 9 times larger than the heating zone.

MM6. The device, apparatus, system, or method of any prior embodiments, wherein the sample to non-sample thermal mass ratio is 2.2 or lager.

MM7. The device, apparatus, system, or method of any prior embodiments, wherein the RHC card does not comprise spacer.

MM8. The device, apparatus, system, or method of any prior embodiments, wherein the RHC card comprises spacers that are fixed on one or both of the plates.

MM9. The device, apparatus, system, or method of any prior embodiments, wherein: the first plate and second plates are plastic or a thin glass. The first plate and second plate have a thickness of 100 nm, 500 nm, 1 um, 5 um, 10 um, in a range between any of the two values;
- the sample between the two plates has a thickness of 5 um, 10 um, 30 um, 50 um, 100 um, or in a range between any of the two values;
- the distance from the H/C layer to the sample is 10 nm, 100 nm, 500 nm, 1 um, 5 um, 10 um, or in a range between any of the two values;
- the ratio of the cooling zone area to the relevant sample area is 16, 9, 4, 2, or in a range between any of the two values;
- the ratio of the cooling zone area to the heating area is 16, 9, 4, 2, or in a range between any of the two values; AND
- the distance between the H/C layer and the heating source (e.g. LED) is 5 mm, 10 mm, 20 mm, 30 mm, or in a range between any of the two values.

MM10. The device, apparatus, system, or method of any prior embodiments, wherein:
- the first plate and second plates are plastic or a thin glass. The first plate and second plate have a thickness of 100 nm, 500 nm, 1 um, 5 um, 10 um, in a range between any of the two values;
- the sample between the two plates has a thickness of 5 um, 10 um, 30 um, 50 um, 100 um, or in a range between any of the two values;
- the distance from the H/C layer to the sample is 10 nm, 100 nm, 500 nm, 1 um, 5 um, 10 um, or in a range between any of the two values;
- the ratio of the cooling zone area to the relevant sample area is 16, 9, 4, 2, or in a range between any of the two values;
- the ratio of the cooling zone area to the heating area is 16, 9, 4, 2, or in a range between any of the two values; OR the distance between the H/C layer and the heating source (e.g. LED) is 5 mm, 10 mm, 20 mm, 30 mm, or in a range between any of the two values.

MM11. The device, apparatus, system, or method of any prior embodiments, wherein:
- the first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values;
- the sample between the two plates has a thickness of 5 um, 10 um, 30 um, 50 um, 100 um, or in a range between any of the two values;
- the distance between the H/C layer and the sample is 10 nm, 100 nm, 500 nm, 1 um, 5 um, 10 um, or in a range between any of the two values;
- the ratio of the cooling zone area to the relevant sample area is 16, 9, 4, 2, or in a range between any of the two values;
- the ratio of the cooling zone area to the heating area is 16, 9, 4, 2, or in a range between any of the two values; AND the distance between the H/C layer and the heating source (e.g. LED) is 5 mm, 10 mm, 20 mm, 30 mm, or in a range between any of the two values.

MM12. The device, apparatus, system, or method of any prior embodiments, wherein:
- the first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values;
- the sample between the two plates has a thickness of 5 um, 10 um, 30 um, 50 um, 100 um, or in a range between any of the two values;
- the distance between the H/C layer and the sample is 10 nm, 100 nm, 500 nm, 1 um, 5 um, 10 um, or in a range between any of the two values;
- the ratio of the cooling zone area to the relevant sample area is 16, 9, 4, 2, or in a range between any of the two values;
- the ratio of the cooling zone area to the heating area is 16, 9, 4, 2, or in a range between any of the two values; OR the distance between the H/C layer and the heating source (e.g. LED) is 5 mm, 10 mm, 20 mm, 30 mm, or in a range between any of the two values.

MM13. The device, apparatus, system, or method of any prior embodiments, wherein:
- the first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values;
- the sample between the two plates has a thickness of 100 nm, 500 nm, 1 um, 5 um, 10 um, 25 um, 50 um, 100 um, 250 um, or in a range between any of the two values;
- the distance between the H/C layer and the sample is 100 nm, 500 nm, 1 um, 5 um, 10 um, 25 um, 50 um, 100 um, 175 um, 250 um, or in a range between any of the two values;
- the ratio of the cooling zone area to the relevant sample area is 100, 64, 16, 9, 4, 2, 1, 0.5, 0.1, or in a range between any of the two values;
- the ratio of the cooling zone area to the heating zone is 100, 64, 16, 9, 4, 2, 1, 0.5, 0.1, or in a range between any of the two values; AND the distance between the H/C layer and the heating source (e.g. LED) is 500 um, 1 mm, 3 mm, 5 mm, 10 mm, 20 mm, 30 mm, or in a range between any of the two values.

MM14. The device, apparatus, system, or method of any prior embodiments, wherein:
- the first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values;
- the sample between the two plates has a thickness of 100 nm, 500 nm, 1 um, 5 um, 10 um, 25 um, 50 um, 100 um, 250 um, or in a range between any of the two values;
- the distance between the H/C layer and the sample is 100 nm, 500 nm, 1 um, 5 um, 10 um, 25 um, 50 um, 100 um, 175 um, 250 um, or in a range between any of the two values;
- the ratio of the cooling zone area to the relevant sample area is 100, 64, 16, 9, 4, 2, 1, 0.5, 0.1, or in a range between any of the two values;
- the ratio of the cooling zone area to the heating zone is 100, 64, 16, 9, 4, 2, 1, 0.5, 0.1, or in a range between any of the two values; OR
- the distance between the H/C layer and the heating source (e.g. LED) is 500 um, 1 mm, 3 mm, 5 mm, 10 mm, 20 mm, 30 mm, or in a range between any of the two values.

MM15. The device, apparatus, system, or method of any prior embodiments, wherein a light pipe collimates the light from a light source (e.g. LED) into the heating zone; the light pipe comprises a structure with a hollow hole (e.g. a tube or a structure milled a hole) with a reflective wall; and the light pipe has a lateral dimension for 1 mm to 8 mm and length of 2 mm to 50 mm.

MM16. The device, apparatus, system, or method of any prior embodiments, wherein:
the first plate and second plates are plastic or a thin glass;
the first plate and second plate have a thickness of 100 nm, 500 nm, 1 um, 5 um, 10 um, in a range between any of the two values;
the sample between the two plates has a thickness in a range of 1 to 5 um, 5 um to 10 um, 10 to 30 um, or 30 um to 50 um;
the distance from the H/C layer to the sample is in a range of 10 nm to 100 nm, 100 nm to 500 nm, 500 nm to 1 um, 1 um to 5 um, 5 um to 10 um, or 10 um to 25 um;
the ratio of the cooling zone area to the relevant sample area is 16, 9, 4, 2, or in a range between any of the two values;
the ratio of the cooling zone area to the heating area is 16, 9, 4, 2, or in a range between any of the two values;
the distance between the H/C layer and the heating source (e.g. LED) is 5 mm, 10 mm, 20 mm, 30 mm, or in a range between any of the two values;
the KC ratio for the cooling layer is in a range of between 0.5 $cm^2$/sec and 0.7 $cm^2$/sec, 0.7 $cm^2$/sec and 0.9 $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and $cm^2$/sec, or 2 $cm^2$/sec and $cm^2$/sec; and the sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100. MM17. The device, apparatus, system, or method of any prior embodiments, wherein:
the first plate and second plates are plastic or a thin glass;
the first plate and second plate have a thickness of 100 nm, 500 nm, 1 um, 5 um, 10 um, in a range between any of the two values;
the sample between the two plates has a thickness in a range of 1 to 5 um, 5 um to 10 um, 10 to 30 um, or 30 um to 50 um;
the distance from the H/C layer to the sample is in a range of 10 nm to 100 nm, 100 nm to 500 nm, 500 nm to 1 um, 1 um to 5 um, 5 um to 10 um, or 10 um to 25 um;
the ratio of the cooling zone area to the relevant sample area is 16, 9, 4, 2, or in a range between any of the two values;
the ratio of the cooling zone area to the heating area is 16, 9, 4, 2, or in a range between any of the two values;
the distance between the H/C layer and the heating source (e.g. LED) is 5 mm, 10 mm, 20 mm, 30 mm, or in a range between any of the two values;
the KC ratio for the cooling layer is in a range of between 0.5 $cm^2$/sec and 0.7 $cm^2$/sec, 0.7 $cm^2$/sec and $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and 2 $cm^2$/sec, or 2 $cm^2$/sec and 3 $cm^2$/sec; OR
the sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100.

NN1. The device, apparatus, system or method of any prior embodiments, wherein the device comprises a heating layer and a cooling layer, where the cooling layer has an area larger than that heating zone.

NN2. The device, apparatus, system or method of any prior embodiments, wherein the device comprises one heating/cooling layer, where the cooling zone has an area larger than that heating zone.

NN3. The device, apparatus, system or method of any prior embodiments, wherein the device comprises a cooling layer that has a high thermal conductivity (50 $W/(m^2 \cdot K)$) and an area larger than lateral area of a relevant sample.

NN4. The device, apparatus, system or method of any prior embodiments, wherein the device comprises a cooling layer that has a high thermal conductivity (greater than 50 $W/(m^2 \cdot K)$ $(m \cdot K)$) and an area larger than lateral area of a relevant sample by a factor of 2 to 40.

NN5. The device, apparatus, system or method of any prior embodiments, wherein the device comprises a cooling layer that has (i) a high thermal conductivity (greater than 50 $W/(m \cdot K)$), and (ii) thermal radiation enhancement layer (specify the thermal radiation).

NN6. The device, apparatus, system or method of any prior embodiments, wherein the device comprises a cooling layer that has (i) a high thermal conductivity (greater than 50 $W/(m \cdot K)$), and (ii) thermal radiation enhancement layer, and (iii) an area larger than lateral area of a relevant sample.

NN7. The device, apparatus, system or method of any prior embodiments, wherein the device comprises a cooling layer that has (i) a high thermal conductivity (greater than 50 $W/(m \cdot K)$), and (ii) thermal radiation enhancement layer, and (iii) an area larger than lateral area of a relevant sample by a factor of 1.5 to 100.

NN8. The device, apparatus, system or method of any prior embodiments, wherein the device comprises a cooling zone has a thermal radiation enhancement layer that has an average light absorption coefficient of 70% over the wavelength range.

NN9. The device, apparatus, system or method of any prior embodiments, wherein the device comprises a cooling zone has a thermal conductivity multiplying its thickness in the range of $6 \times 10^{-5}$ W/K to $3 \times 10^{-4}$ W/K.

NN10. The device, apparatus, system or method of any prior embodiments, wherein the device comprises a cooling zone comprises a gold layer of a thickness in the range of 200 nm to 800 nm.

NN11. The device, apparatus, system or method of any prior embodiments, wherein the device comprises a thermal conductivity multiplying its thickness in the range of $6 \times 10^{-5}$ W/K to $3 \times 10^{-4}$ W/K.

NN12. The device, apparatus, system or method of any prior embodiments, wherein the device comprises a cooling layer that:
has a high thermal conductivity (greater than 50 $W/(m \cdot K)$), comprises thermal radiation enhancement layer that has an average light absorption coefficient of 70% over the wavelength range;
has an area larger than lateral area of a relevant sample by a factor of 1.5 to 100; and
has a thermal conductivity multiplying its thickness in the range of $6 \times 10^{-5}$ W/K to $3 \times 10^{-4}$ W/K.

NN13. The device, apparatus, system or method of any prior embodiments, wherein the device comprises a cooling zone (layer) has thermal conductivity times its thickness of $6 \times 10^{-5}$ W/K, $9 \times 10^{-5}$ W/K, $1.2 \times 10^{-4}$ W/K, $1.5 \times 10^{-4}$ W/K, $1.8 \times 10^{-4}$ W/K, $2.1 \times 10^{-4}$ W/K, $2.7 \times 10^{-4}$ W/K, $3 \times 10^{-4}$ W/K, $1.5 \times 10^{-4}$ W/K, or in a range between any of the two values.

NN14. The device, apparatus, system or method of any prior embodiments, wherein the device comprises a cooling zone (layer) has thermal conductivity times its thickness in a range of $6 \times 10^{-5}$ W/K to $9 \times 10^{-5}$ W/K, $9 \times 10^{-5}$ W/K to $1.5 \times 10^{-4}$ W/K, $1.5 \times 10^{-4}$ W/K to $2.1 \times 10^{-4}$ W/K, $2.1 \times 10^{-4}$ W/K to $2.7 \times 10^{-4}$ W/K, $2.7 \times 10^{-4}$ W/K to $3 \times 10^{-4}$ W/K, or $3 \times 10^{-4}$ W/K to $1.5 \times 10^{-4}$ W/K.

NN15. The device, apparatus, system or method of any prior embodiments, wherein the device comprises cooling zone (layer) has thermal conductivity times its thickness in a range of $9 \times 10^{-5}$ W/K to $2.7 \times 10^{-4}$ W/K, $9 \times 10^{-5}$ W/K to $2.4 \times 10^{-4}$ W/K, $9 \times 10^{-5}$ W/K to $2.1 \times 10^{-4}$ W/K, or $9 \times 10^{-5}$ W/K to $1.8 \times 10^{-4}$ W/K.

NN16. The device, apparatus, system or method of any prior embodiments, wherein the device comprises cooling zone comprises a gold layer of a thickness in the range of 200 nm to 800 nm. In another embodiment, a cooling zone comprises a gold layer of a thickness in the range of 300 nm to 700 nm.

NN17. The device, apparatus, system or method of any prior embodiments, wherein in the device the materials between the heating zone and the relevant sample has a thermal conductivity and a thickness configured to have a conductance per unit area that is equal to or larger than 1,000 W/(m²·K), 2000 W/(m²·K), 3,000 W/(m²·K), 4000 W/(m²·K), 5000 W/(m²·K), 7,000 W/(m²·K), 10,000 W/(m²·K), 20,000 W/(m²·K), 50,000 W/(m²·K), 50,000 W/(m²·K), 100,000 W/(m²·K), or in a range of any the values.

NN18. The device, apparatus, system or method of any prior embodiments, wherein a preferred conductance per unit area of the material between the heating zone and the relevant sample is in a range of 1,000 W/(m²·K) to 2,000 W/(m²·K), 2,000 W/(m²·K) to 4000 W/(m²·K), 4,000 W/(m²·K) to 10,000 W/(m²·K), or 10,000 W/(m²·K) to 100,000 W/(m²·K).

NN19. The device, apparatus, system or method of any prior embodiments, wherein there is zero distance between the heating zone and the relevant sample, and hence an infinity for the conductance per unit area of the material between the heating zone and the relevant sample.

NN20. The device, apparatus, system or method of any prior embodiments, wherein the heating layer or the cooling layer is separated from a relevant sample by a thin plastics plate (or film) which has a thermal conductivity in the range of 0.1 to 0.3 W/(m·K), and the thin plastic layer has a thickness of 0 nm, 10 nm, 50 nm, 100 nm, 200 nm, 300 nm, 400 nm, 500 nm, 1 um, 2.5 um, 5 um, 10 um, 25 um, 50 um, 75 nm 100 um, 150 um, or in a range between any of the two values NN21. The device, apparatus, system or method of any prior embodiments, wherein the thin plastic plate (or film) that separate the relevant sample from the heating layer or the cooling layer has thickness in a range between 0 nm and 100 nm, 100 nm and 500 nm, 500 nm and 1 um, 1 um and 5 um, 5 um and 10 um, 10 um and 25 um, 25 um and 50 um, 50 um and 75 um, 75 um and 100 um, or 100 um and 150 um.

NN22. The device, apparatus, system or method of any prior embodiments, wherein the thin plastic plate (or film) that separates the relevant sample from the heating layer or the cooling layer has thickness of 0.1 um, 0.5 um, 1 um, 5 um, 10 um, 20 um, 25 um, or a range between any two values.

NN23. The device, apparatus, system or method of any prior embodiments, wherein the area of the heating zone is only a fraction of the area of the cooling zone or area, and the area of the cooling zone (layer) is larger than the area of the heating zone by a factor of 1.1, 1.5, 2, 3, 4, 5, 10, 20, 30, 40, 50, 70,100,200, 300, 400, 500, 600, 700, 800, 800, 1,000, 5000, 10,000, 100,000, or in a range between any of the two values.

NN24. The device, apparatus, system or method of any prior embodiments, wherein the cooling zone (layer) has an area that is larger than the lateral area of the hearing zone (layer) by a factor in a range of 1.1 to 1.5, 1.5 to 5, 5 to 10, 10 to 50, 50 to 100, 100 to 500, 500 to 1,000, 1000, to 10,000, or 10,000 to 100,000.

NN25. The device, apparatus, system or method of any prior embodiments, wherein the cooling zone (layer) has an area that is larger than the lateral area of the relevant sample by a factor of 1.5, 2, 3, 4, 5, 10, 20, 50, 70,100,200, 300, 400, 500, 600, 700, 800, 800, 1,000, 2000, 5000, 10,000, 100, 000, or in a range between any of the two values.

NN26. The device, apparatus, system or method of any prior embodiments, wherein the cooling zone (layer) has an area that is larger than the lateral area of the relevant sample by a factor in a range of 1.5 to 5, 5 to 10, 10 to 50, 50 to 100, 100 to 500, 500 to 1,000, 1000, to 10,000, or 10,000 to 100,000.

NN27. The device, apparatus, system or method of any prior embodiments, wherein the first plate or the second plate has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

NN28. The device, apparatus, system or method of any prior embodiments, wherein the first plate and the second plate can have the same thickness or a different thickness, and can be made of the same materials or different materials.

NN29. The device, apparatus, system or method of any prior embodiments, wherein the first plate or the second plate has a thickness in a range of between 10 nm and 500 nm, 500 nm and 1 um, 1 um and 2.5 um, 2.5 um and 5 um, 5 um and 10 um, 10 um and 25 um, 25 um and 50 um, 50 um and 100 um, 100 um and 200 um, or 200 um and 500 um, or 500 um and 1000 um.

NN30. The device, apparatus, system or method of any prior embodiments, wherein the first plate and second plates are plastic, a thin glass, or a material with similar physical properties. The first plate or second plate have a thickness of 100 nm, 500 nm, 1 um, 5 um, 10 um, 25 um, 50 um, 100 um, 175 um, 250 um, or in a range between any of the two values.

NN31. The device, apparatus, system or method of any prior embodiments, wherein the ratio of the average lateral size of the relevant sample volume to the diffusion length of the reagent during the time for thermal cycling or a reaction is equal to or larger than 5, 6, 7, 10, 15, 20, 25, 30, 40, 50, 60, 70, 80, 90, 100, 150, 200, 500, 1,000, 5,000, 10,000, 100,000, or in a range between any two values.

NN32. The device, apparatus, system or method of any prior embodiments, wherein the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1,000, 1,000 to 5000, 5,000 to 10,000, or 10,000 to 100,000.

NN33. The device, apparatus, system or method of any prior embodiments, wherein the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1,000, 1,000 to 5,000, 5,000 to 10,000, or 10,000 to 100,000.

NN34. The device, apparatus, system or method of any prior embodiments, wherein the average lateral dimension of the relevant volume is 1 mm, 2 mm, 3 mm, 5 mm, 6 mm, 7 mm, 8 mm, 9 mm 10 mm, 12 mm, 15 mm, 20 mm, 30 mm, 40 mm, 50 mm, 70 mm, 100 mm, 200 mm, or in a range between any two values.

NN35. The device, apparatus, system or method of any prior embodiments, wherein the average lateral dimension of the relevant volume is in a range of 1 mm to 5 mm, 5 mm to 10 mm, 10 mm to 20 mm, 20 mm to 40 mm, 40 mm to 70 mm, 70 mm to 100 mm, or 100 mm to 200 mm.

NN36. The device, apparatus, system or method of any prior embodiments, wherein the average lateral dimension of the relevant volume is in a range of 1 mm to 5 mm, 1 mm to 10 mm, or 5 mm to 20 mm.

NN37. The device, apparatus, system or method of any prior embodiments, wherein the thermal radiation enhancement surface has a high average light absorptance (e.g. the black paint used in our experiments). In certain embodiments, the cooling zone has a surface that has an average light absorptance of 30%, 40%, 50%, 60%, 70%, 80%, 90%, 95%, 100%, or in a range between any of the two values.

NN38. The device, apparatus, system or method of any prior embodiments, wherein the cooling zone has a surface that has an average light absorptance in a range of 30% to 40%, 40% to 60%, 60% to 80% to 90%, or 90% to 100%.

NN39. The device, apparatus, system or method of any prior embodiments, wherein the cooling zone has a surface that has an average light absorptance in a range of 30% to 100%, 50% to 100%, 70% to 100%, or 80% to 100%.

NN40. The device, apparatus, system or method of any prior embodiments, wherein the cooling zone has a surface that has an average light absorptance of a value given above by averaging over a wavelength range 400 nm to 800 nm, 700 nm to 1500 nm, 900 nm to 2,000 nm, or 2,000 nm to 20,000 nm.

NN41. The device, apparatus, system or method of any prior embodiments, wherein the black paints are polymer mixtures that look black by human eyes. A black paint include, but not limited to, a mixture of polymers and nanoparticles. One example of the nanoparticles is black carbon nanoparticle, carbon, nanotubes, graphite particles, graphene, metal nanoparticles, semiconductor nanoparticles, or a combination thereof.

NN42. The device, apparatus, system or method of any prior embodiments, wherein the plasmonic structures include nanostructured plasmonic structures.

NN43. The device, apparatus, system or method of any prior embodiments, wherein a cooling plate comprise a layer of high thermal conductivity metal (50 W/(m·K) or higher) with a surface thermal radiation enhancement layer. In some embodiments, the surface thermal radiation enhancement layer has a low lateral thermal conductance, which is due to either ultrathin layer, low thermal conductivity, or both.

NN44. The device, apparatus, system or method of any prior embodiments, wherein thermal radiative cooling is achieved by increasing the area of radiative cooling layer (i.e. a high-K material, unless stated otherwise), and the radiative cooling layer area is larger than the lateral area of the relevant sample by a factor of 1.2, 1.5, 2, 3, 4, 5, 10, 20, 30, 40, 50, 60, 70, 80 100, 200, 300, 400, 500, 600, 700, 800, 800, 1,000, 2,000, 5,000, 10,000, 100,000, or in a range between any of the two values.

NN45. The device, apparatus, system or method of any prior embodiments, wherein the radiative cooling zone (layer) has an area that is larger than the lateral area of the relevant sample by a factor in a range of 1.2 to 3, 3 to 5, 5 to 10, 10 to 50, 50 to 100, 100 to 500, 500 to 1,000, 1000, to 10,000, or 10,000 to 100,000.

NN46. The device, apparatus, system or method of any prior embodiments, wherein the ratio of the thermal radiation cooling by the cooling zone (layer) to the total cooling of the sample and sample holder during a thermal cycling is 10%, 20%, 30%, 40%, 50%, 60%, 70%, 80%, 90%, 99%, or in a range between any of the two values.

NN47. The device, apparatus, system or method of any prior embodiments, wherein the ratio of the thermal radiation cooling by the cooling zone (layer) to the total cooling of the sample and sample holder during a thermal cycling is in a range of between 10% and 20%, 20% and 30%, 30% and 40%, 40% and50%, 50% and 60%, 60% and 70%, 70% and 80%, 80% and 90%, or 90% and 99%.

NN48. The device, apparatus, system or method of any prior embodiments, wherein the KC ratio materials for the heating layer is equal to or higher than 0.1 $cm^2$/sec, 0.2 $cm^2$/sec, 0.3 $cm^2$/sec, 0.4 $cm^2$/sec, 0.5 $cm^2$/sec, 0.6 $cm^2$/sec, 0.7 $cm^2$/sec, 0.8 $cm^2$/sec, 0.9 $cm^2$/sec, 1 $cm^2$/sec, 1.1 $cm^2$/sec, 1.2 $cm^2$/sec, 1.3 $cm^2$/sec, 1.4 $cm^2$/sec, 1.5 $cm^2$/sec, 1.6 $cm^2$/sec, 2 $cm^2$/sec, 3 $cm^2$/sec, or in a range between any of the two values.

NN49. The device, apparatus, system or method of any prior embodiments, wherein the KC ratio for the heating layer is in a range of between 0.5 $cm^2$/sec and 0. $cm^2$/sec, 0.7 $cm^2$/sec and 0.9 $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and 2 $cm^2$/sec, or 2 $cm^2$/sec and 3 $cm^2$/sec.

NN50. The device, apparatus, system or method of any prior embodiments, wherein a thermal radiation enhancement surface(s) will be used (on one side or both side of the heating zone). A thermal radiation absorption enhancement surface can be achieved by directly modify the structures of the surface (e.g. patterning nanostructures), coating a high thermal radiation materials (e.g. coating a black paint), or both.

NN51. The device, apparatus, system or method of any prior embodiments, wherein the thermal radiation enhancement surface has a high average light absorptance (e.g. the black paint used in our experiments). In certain embodiments, the heating zone has a surface that has an average light absorptance of 30%, 40%, 50%, 60%, 70%, 80%, 90%, 95%, 100%, or in a range between any of the two values.

NN52. The device, apparatus, system or method of any prior embodiments, wherein the heating zone has a surface that has an average light absorptance in a range of 30% to 40%, 40% to 60%, 60% to 80% to 90%, or 90% to 100%.

NN53. The device, apparatus, system or method of any prior embodiments, wherein the heating zone has a surface that has an average light absorptance in a range of 30% to 100%, 50% to 100%, 70% to 100%, or 80% to 100%.

NN54. The device, apparatus, system or method of any prior embodiments, wherein the heating zone has a surface that has an average light absorptance of a value given above by averaging over a wavelength range 400 nm to 800 nm, 700 nm to 1,500 nm, 900 nm to 2,000 nm, or 2,000 nm to 20,000 nm.

NN55. The device, apparatus, system or method of any prior embodiments, wherein the LVS ratio for sample is 5, 10, 20, 50, 70,100,200, 300, 400, 500, 600, 700, 800, 800, 1,000, 2,000, 5,000, 10,000, 100,000, or in a range between any of the two values.

NN56. The device, apparatus, system or method of any prior embodiments, wherein the LVS ratio for sample is in a range of 5 to 10, 10 to 50, 50 to 100, 100 to 500, 500 to 1,000, 1,000, to 10,000, or 10,000 to 100,000, NN57. The device, apparatus, system or method of any prior embodiments, wherein the sample has a lateral dimension of 15 mm and a thickness of 30 um, hence an LVS for the sample of 500.

NN58. The device, apparatus, system or method of any prior embodiments, wherein the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

NN59. The device, apparatus, system or method of any prior embodiments, wherein the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

NN60. The device, apparatus, system or method of any prior embodiments, wherein the KC ratio materials for the cooling layer is equal to or higher than 0.1 cm$^2$/sec, 0.2 cm$^2$/sec, 0.3 cm$^2$/sec, 0.4 cm$^2$/sec, 0.5 cm$^2$/sec, 0.6 cm$^2$/sec, 0.7 cm$^2$/sec, 0.8 cm$^2$/sec, 0.9 cm$^2$/sec, 1 cm$^2$/sec, 1.1 cm$^2$/sec, 1.2 cm$^2$/sec, 1.3 cm$^2$/sec, 1.4 cm$^2$/sec, 1.5 cm$^2$/sec, 1.6 cm$^2$/sec, 2 cm$^2$/sec, 3 cm$^2$/sec, or in a range between any of the two values. NN61. The device, apparatus, system or method of any prior embodiments, wherein the KC ratio for the cooling layer is in a range of between 0.5 cm$^2$/sec and 0.7 cm$^2$/sec, 0.7 cm$^2$/sec and 0.9 cm$^2$/sec, 0.9 cm$^2$/sec and 1 cm$^2$/sec, 1 cm$^2$/sec and 1.1 cm$^2$/sec, 1.1 cm$^2$/sec and 1.3 cm$^2$/sec, 1.3 cm$^2$/sec and 1.6 cm$^2$/sec.

NN62. The device, apparatus, system or method of any prior embodiments, wherein a high thermal conductivity (i.e. high-K) material is used for the cooling layer, and the high-K material has a thermal conductivity of equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), or in a range between any of the two values.

NN63. The device, apparatus, system or method of any prior embodiments, wherein the sample to non-sample thermal mass ratio (NSTM ratio) is 0.1, 0.2, 0.3, 0.4, 0.5, 0.6, 0.7, 1, 1.5, 2, 3, 4, 5, 10, 20, 30, 40, 50, 60, 70,100,200, 300, 1,000, 4,000, or in a range between any of the two values.

NN64. The device, apparatus, system or method of any prior embodiments, wherein the sample to non-sample thermal mass ratio (NSTM ratio) is in a range of between 0.1 to 0.2, 0.2 to 0.5, 0.5 to 0.7, 0.7 to 1, 1 to 1.5, 1.5 to 5, 5 to 10, 10 to 30, 30 to 50, 50 to 100, 100 to 300, 300 to 1,000, or 1,000 to 4,000.

NN65. The device, apparatus, system or method of any prior embodiments, wherein the device is configured to make the sample to non-sample thermal mass ratio high, one need to keep the area thermal mass of the non-sample low, which in turn, needs to make the plates and the heating/cooling layer thin, and/or the volume specific heat low.

NN66. The device, apparatus, system or method of any prior embodiments, wherein the device comprises a thin material that has multi-layers or mixed materials. For examples, a carbon fiber layer(s) with plastic sheets or carbon mixed with plastics, which can have a thickness of 0.1 um, 0.2 um, 0.5 um, 1 um, 2 um, 5 um, 10 um, 25 um, 50 um, or in a range between any of the two values.

NN67. The device, apparatus, system or method of any prior embodiments, wherein the relevant volume of the sample is 0.001 ul, 0.005 ul, 0.01 ul, 0.02 ul, 0.05 ul, 0.1 ul, 0.2 ul, 0.5 ul, 1 ul, 2 ul, 5 ul, 10 ul, 20 ul, 30 uL, 50 ul, 100 ul, 200 ul, 500 ul, 1 ml, 2 ml, 5 ml, or in a range between any of the two values.

NN68. The device, apparatus, system or method of any prior embodiments, wherein the relevant sample volume is in a range of 0.001 uL to 0.1 uL, 0.1 um to 2 uL, 2 uL to 10 uL, 10 uL to 30 uL, 30 uL to 100 uL, 100 uL to 200 uL, or 200 uL to 1 mL.

NN69. The device, apparatus, system or method of any prior embodiments, wherein the relevant sample volume is in a range of 0.001 uL to 0.1 uL, 0.1 um to 1 uL, 0.1 uL to 5 uL, or 0.1 uL to 10 uL.

NN70. The device, apparatus, system or method of any prior embodiments, wherein the ratio of the relevant sample to entire sample volume (RE ratio) is 0.01%, 0.05%, 0.1%, 0.5%, 0.1%, 0.5%, 1%, 5%, 10%, 20%, 30%, 40%, 50%, 60%, 70%, 80%, 90%, 100%, or in a range between any of the two values.

NN71. The device, apparatus, system or method of any prior embodiments, wherein the RE ratio is in a range of between 0.01% and 0.1%, 0.1% and 1%, 1% and 10%, 10% and 30%, 30% and 60%, 60% and 90%, or 90% and 100%.

NN72. The device, apparatus, system or method of any prior embodiments, wherein the area of the heating zone is only a fraction of the sample lateral area, and the fraction (i.e. the ratio of the heating zone to the sample lateral area) is 0.01%, 0.05%, 0.1%, 0.5%, 0.1%, 0.5%, 1%, 5%, 10%, 20%, 30%, 40%, 50%, 60%, 70%, 80%, 90%, 99%, or in a range between any of the two values.

NN73. The device, apparatus, system or method of any prior embodiments, wherein the ratio of the heating zone area to the sample lateral area is in a range of between 0.01% and 0.1%, 0.1% and 1%, 1% and 10%, 10% and 30%, 30% and 60%, 60% and 90%, or 90% and 99%.

NN74. The device, apparatus, system or method of any prior embodiments, wherein the scaled thermal conduction ratio (STM ratio) is 2 or larger, 5 or larger, 10 or larger, 20 or larger, 30 or larger, 40 or larger, 50 or larger, 100 or larger, 1,000 or larger, 10,000 or larger, 10,000 or larger, or in a range between any of the two values.

NN75.1 The device, apparatus, system or method of any prior embodiments, wherein the scaled thermal conduction ratio (STM ratio) is in a range of between 10 to 20, 30 to 50, 50 to 70, 70 to 100, 100 to 1,000, 1,000 to 10,000, or 10,000 to 1,000,000.

NN75.2 The device, apparatus, system or method of any prior embodiments, wherein the scaled thermal conduction ratio (STM ratio) is in a range of between 10 to 20, 30 to 50, 50 to 70, 70 to 100, 100 to 1,000, 1,000 to 10,000, or 10,000 to 1,000,000; and the cooling zone (layer) has thermal conductivity times its thickness of $6\times10^{-5}$ W/K, $9\times10^{-5}$ W/K, $1.2\times10^{-4}$ W/K, $1.5\times10^{-4}$ W/K, $1.8\times10^{-4}$ W/K, $2.1\times10^{-4}$ W/K, $2.7\times10^{-4}$ W/K, $3\times10^{-4}$ W/K, $1.5\times10^{-4}$ W/K, or in a range between any of the two values.

NN75.3 The device, apparatus, system or method of any prior embodiments, wherein the scaled thermal conduction ratio (STM ratio) is in a range of between 20 to 80.

NN76. The device, apparatus, system or method of any prior embodiments, wherein the lateral to vertical size (LVS) ratio for relevant sample is 5, 10, 20, 50, 70, 100, 200, 300, 400, 500, 600, 700, 800, 800, 1,000, 2000, 5000, 10,000, 100,000, or in a range between any of the two values.

NN77. The device, apparatus, system or method of any prior embodiments, wherein the LVS ratio for relevant sample is in a range of 5 to 10, 10 to 50, 50 to 100, 100 to 500, 500 to 1,000, 1,000, to 10,000, or 10,000 to 100,000.

NN78. The device, apparatus, system or method of any prior embodiments, wherein the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

NN78. The device, apparatus, system or method of any prior embodiments, wherein the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

OO1. A device, comprising:
a first plate comprising a polymer material and having a thickness less than or equal to 100 um;
a second plate comprising a polymer material and having a thickness less than or equal to 100 μm; and
a heating/cooling layer disposed on either the first plate or the second plate, the heating/cooling layer having a thermal conductivity between $6 \times 10^{-5}$ W/K multiplied by the thickness of the heating/cooling layer and $1.5 \times 10^{-4}$ W/K multiplied by the thickness of the heating/cooling layer,
wherein the first plate and the second plate face each other in a parallel arrangement, and are separated from each other by a distance, and wherein the first plate and the second plate are configured to receive a fluid sample sandwiched between the first plate and the second plate.

OO2. A device, comprising:
a first plate;
a second plate having a thickness less than or equal to 100 μm, wherein the second plate is separated from the first plate in a parallel arrangement by a distance less than or equal to the thickness of the second plate; and
a heating/cooling layer disposed on either the first plate or the second plate,
wherein the heating/cooling layer is configured to receive electromagnetic radiation such that at least a portion of a liquid sample sandwiched between the first plate and the second plate is heated at a rate of at least 30° C./sec.

OO3. A device, comprising:
a first plate;
a second plate having a thickness less than or equal to 100 μm, wherein the second plate is separated from the first plate in a parallel arrangement by a distance less than or equal to the thickness of the second plate; and
a heating/cooling layer disposed on either the first plate or the second plate,
wherein at least a portion of a liquid sample sandwiched between the first plate and the second plate is cooled at a rate of at least 30° C./sec when the heating/cooling layer is not receiving electromagnetic radiation generated by an optical source.

OO4. A device, comprising:
a first plate;
a second plate having a thickness less than or equal to 100 μm, wherein an inner surface of the second plate is separated from an inner surface of the first plate in a parallel arrangement by a distance less than or equal to the thickness of the second plate;
a heating/cooling layer disposed on the inner surface or on an outer surface of the second plate; and
a layer of reagents dried on the inner surface of the first plate.

OO5. The device of any of OO1-OO4 embodiments, further comprising a light absorbing layer disposed on the heating/cooling layer, wherein the light absorbing layer has an average light absorptance of at least 30%.

OO6. The device of OO5, wherein the light absorbing layer comprises black paint.

OO7. The device of any of OO1-OO6 embodiments, wherein the first plate is movable relative to the second plate.

OO8. The device of any of OO1-OO7 embodiments, wherein a thickness of the heating/cooling layer is less than or equal to 3 μm.

OO9. The device of any of OO1-OO8 embodiments, wherein at least one of the first plate and the second plate has an area across its major surface of about 400 mm².

OO10. The device of any of OO1-OO9 embodiments, further comprising a plurality of spherical spacers disposed between the first plate and the second plate.

OO11. The device of any of OO1-OO9 embodiments, further comprising a plurality of spacers having a height of about 10 um, wherein the plurality of spacers are disposed between the first plate and the second plate.

OO12. The device of any of OO1-OO11 embodiments, wherein the distance between the first plate and the second plate is less than or equal to 100 μm.

OO13. The device of any of OO1-OO12 embodiments, further comprising a hinge configured to connect the first plate with the second plate, and coupled to an edge of the first plate or the second plate.

OO14. The device of any of OO1-OO13 embodiments, wherein the at least a portion of the liquid sample comprises a volume of the sample along a path of the electromagnetic radiation.

OO15. The device of any of OO1-OO14 embodiments, wherein the at least a portion of the liquid sample comprises a volume of the sample that is adjacent to the heating/cooling layer.

OO16. The device of OO4, wherein the layer of dried reagents comprises reagents used for nucleic acid amplification.

PP1. A system, comprising:
a device, comprising:
a first plate comprising a polymer material and having a thickness less than or equal to 100 μm,
a second plate comprising a polymer material and having a thickness less than or equal to 100 μm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between $6 \times 10^{-5}$ W/K multiplied by the thickness of the heating/cooling layer and $1.5 \times 10^{-4}$ W/K multiplied by the thickness of the heating/cooling layer, and
a support frame configured to support at least one of the first plate and the second plate;
a housing having a first opening configured to receive the device and at least one other opening;
an optical source configured to direct electromagnetic radiation towards the heating/cooling layer,
wherein the heating/cooling layer is configured to absorb at least a portion of the electromagnetic radiation such that at least a portion of a liquid sample sandwiched between the first plate and the second plate is heated at a rate of at least 30° C./sec, and wherein at least the portion of the liquid sample sandwiched between the first plate and the second plate is cooled at a rate of at least 30° C./sec when the heating/cooling layer is not receiving the electromagnetic radiation generated by the optical source, and wherein the system consumes less than 500 mW of power.

PP2. A system, comprising:
a device, comprising:
a first plate,
a second plate having a thickness less than or equal to 100 µm, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate; and
an optical source configured to direct electromagnetic radiation towards the heating/cooling layer,
wherein at least a portion of a liquid sample sandwiched between the first plate and the second plate is cooled at a rate of at least 30° C./sec when the heating/cooling layer is not receiving the electromagnetic radiation generated by the optical source.

PP3. A system, comprising:
a device, comprising:
a first plate,
a second plate having a thickness less than or equal to 100 µm, wherein the second plate is separated from the first plate in a parallel arrangement by a distance less than or equal to the thickness of the second plate,
a heating/cooling layer disposed on either the first plate or the second plate; and
an optical source configured to direct electromagnetic radiation towards the heating/cooling layer, wherein the system consumes less than 500 mW of power.

PP4. A system, comprising:
a device, comprising:
a first plate,
a second plate having a thickness less than or equal to 100 µm, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate;
a housing having a first opening configured to receive the device and at least one other opening; and
an optical source configured to direct electromagnetic radiation through the at least one other opening of the housing and towards the heating/cooling layer,
wherein a liquid sample sandwiched between the first plate and the second plate is cooled at a rate of at least 30° C./sec when the heating/cooling layer is not receiving the electromagnetic radiation generated by the optical source.

PP5. The system of any one of PP1-PP4 embodiments, wherein the device further comprises a light absorbing layer disposed on the heating/cooling layer, wherein the light absorbing layer has an average light absorptance of at least 30%.

PP6. The system of PP5, wherein the light absorbing layer comprises black paint.

PP7. The system of any one of PP1-PP6 embodiments, wherein the first plate is movable relative to the second plate.

PP8. The system of any one of PP1-PP7 embodiments, wherein a thickness of the heating/cooling layer is less than or equal to 3 µm.

PP9. The system of any one of PP1-PP8 embodiments, wherein at least one of the first plate and the second plate has an area across its major surface of about 400 mm².

PP10. The system of any one of PP1-PP9 embodiments, wherein the optical source comprises a light emitting diode (LED.)

PP11. The system of PP10, wherein the LED comprises a blue LED.

PP12. The system of any one of PP1-PP11 embodiments, further comprising an optical pipe configured to guide the electromagnetic radiation from the optical source to the heating/cooling layer.

PP13. The system of PP1 or PP4, wherein the at least one other opening of the housing is configured to be aligned over at least the portion of the liquid sample sandwiched between the first plate and the second plate when the device is placed within the housing via the first opening.

PP14. The system of any one of PP1-PP13 embodiments, wherein the support frame is configured to support at least the first plate or the second plate along a perimeter of the first plate or second plate.

QQ1. A method of using a device, comprising:
placing a second plate over a first plate such that a fluidic sample is sandwiched between the first plate and the second plate at a thickness determined by one or more spacers located on at least one of the first plate and the second plate;
activating a heat source configured to radiate electromagnetic radiation towards a heating layer located on either the first plate or the second plate; and
heating, using at least the heating layer, at least a portion of the fluidic sample at a rate of at least 30° C./sec.

QQ2. A method of using a device, comprising:
placing a second plate over the first plate such that a fluidic sample is sandwiched between the first plate and the second plate at a thickness determined by one or more spacers located on at least one of the first plate and the second plate;
activating, for a given time period, a heat source configured to radiate electromagnetic radiation towards a heating/cooling layer located on either the first plate or the second plate;
deactivating the heat source after the given time period, wherein at least a portion of the fluidic sample cools at a rate of at least 30° C./sec after the deactivating.

QQ3. A method of using a device, comprising:
placing a second plate over the first plate such that a fluidic sample is sandwiched between the first plate and the second plate at a thickness determined by one or more spacers located on at least one of the first plate and the second plate;
activating a heat source configured to radiate electromagnetic radiation towards a heating layer located on either the first plate or the second plate, wherein the heat source consumes less than 500 mW of power; and
heating, using at least the heating layer, at least a portion of the fluidic sample.

QQ4. The method of any one of QQ1-QQ3 embodiments, wherein the first plate or the second plate further comprises a light absorbing layer disposed on the heating layer, wherein the light absorbing layer has an average light absorptance of at least 30%.

QQ5. The method of QQ4, wherein the light absorbing layer comprises black paint.

QQ6. The method of any one of QQ1-QQ5 embodiments, further comprising closing the second plate over the first plate using a hinge connected between the first plate and the second plate.

QQ7. The method of any one of QQ1-QQ6 embodiments, wherein a thickness of the heating layer is less than or equal to 3 μm.

QQ8. The method of any one of QQ1-QQ7 embodiments, wherein at least one of the first plate and the second plate has an area across its major surface of about 400 mm².

QQ9. The method of any one of QQ1-QQ8 embodiments, wherein activating a heat source comprises activating an LED to radiate light towards the heating layer.

QQ10. The method of QQ9, further comprising controlling an output of the LED based on a measured or estimated temperature of the portion of the fluidic sample.

QQ11. The method of any one of QQ1-QQ10 embodiments, further comprising expanding the electromagnetic radiation using a beam expander before the electromagnetic radiation reaches the heating layer.

QQ12. The method of any one of QQ1-QQ11 embodiments, further comprising supporting a perimeter of either the first plate or the second plate on a support frame.

RR1. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec; and
accumulating nucleic acid amplification products in at least the portion of the fluidic sample sandwiched between the first plate and the second plate.

RR2. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
amplifying nucleic acids in the sample by conducting one or more PCR cycles, wherein each PCR cycle comprises a denaturing step, an annealing step, and an elongation step;
wherein one or more of the denaturing step, the annealing step, and/or the elongation step comprises:
activating a heat source configured to radiate electromagnetic radiation towards a heating layer located on either the first plate or the second plate; and
heating, using at least the heating layer, at least a portion of the fluidic sample at a rate of at least 30° C./sec.

RR3. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
accumulating nucleic acid amplification products in at least the portion of the fluidic sample sandwiched between the first plate and the second plate.

RR4. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
amplifying nucleic acids in the sample by conducting one or more PCR cycles, wherein each PCR cycle comprises a denaturing step, an annealing step, and an elongation step;
wherein one or more of the denaturing steps, the annealing step, and/or the elongation step comprises: activating a heat source configured to radiate electromagnetic radiation towards a heating layer located on either the first plate or the second plate; and deactivating the heat source after the given time period, wherein at least a portion of the fluidic sample adjacent to the heating/cooling layer cools at a rate of at least 30° C./sec after the deactivating; and accumulating nucleic acid amplification products in at least the portion of the fluidic sample sandwiched between the first plate and the second plate.

RR5. A method of amplifying nucleic acids, comprising:
depositing a fluidic sample containing nucleic acids on a first plate of a fluidic device;
placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
accumulating nucleic acid amplification products in at least the portion of the fluidic sample sandwiched between the first plate and the second plate.

RR6. A method of amplifying nucleic acids, comprising:
depositing a fluidic sample containing nucleic acids on a first plate of a fluidic device;
placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;

amplifying nucleic acids in the sample by conducting one or more PCR cycles, wherein each PCR cycle comprises a denaturing step, an annealing step, and an elongation step;

wherein one or more of the denaturing step, the annealing step, and/or the elongation step comprises:

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and accumulating nucleic acid amplification products in at least the portion of the fluidic sample sandwiched between the first plate and the second plate.

RR7. The method of any one of RR1-RR6 embodiments, wherein the first plate or the second plate further comprises a light absorbing layer disposed on the heating/cooling layer, wherein the light absorbing layer has an average light absorptance of at least 30%.

RR8. The method of RR7, wherein the light absorbing layer comprises black paint.

RR9. The method of any one of RR1-RR8 embodiments, further comprising closing the second plate over the first plate using a hinge connected between the first plate and the second plate.

RR10. The method of any one of RR1-RR9 embodiments, wherein a thickness of the heating/cooling layer is less than or equal to 3 μm.

RR11. The method of any one of RR1-RR10 embodiments, wherein at least one of the first plate and the second plate has an area across its major surface of about 400 mm$^2$.

RR12. The method of any one of RR1-RR11 embodiments, wherein activating a heat source comprises activating an LED to radiate light towards the heating/cooling layer.

RR13. The method of RR12, further comprising controlling an output of the LED based on a measured or estimated temperature of the portion of the fluidic sample.

RR14. The method of any one of RR1-RR13 embodiments, further comprising expanding the electromagnetic radiation using a beam expander before the electromagnetic radiation reaches the heating layer.

RR15. The method of any one of RR1-RR14 embodiments, further comprising supporting a perimeter of either the first plate or the second plate on a support frame.

SS1. A method for detecting whether a target nucleic acid sequence is present or absent in a sample, comprising:

depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;

activating a heat source configured to radiate electromagnetic radiation towards a heating layer located on either the first plate or the second plate;

heating, using at least the heating layer, at least a portion of the fluidic sample at a rate of at least 30° C./sec; and detecting whether the fluidic sample contains amplified product of the target nucleic acid sequence.

SS2. A method for detecting whether a target nucleic acid sequence is present or absent in a sample, comprising:

depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;

activating, for a given time period, a heat source configured to radiate electromagnetic radiation towards a heating/cooling layer located on either the first plate or the second plate;

deactivating the heat source after the given time period, wherein at least a portion of the fluidic sample adjacent to the heating/cooling layer cools at a rate of at least 30° C./sec after the deactivating; and detecting whether the fluidic sample contains amplified product of the target nucleic acid sequence.

SS3. A method for detecting whether a target nucleic acid sequence is present or absent in a sample, comprising:

depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and detecting whether the fluidic sample contains amplified product of the target nucleic acid sequence.

SS4. The method of any one of SS1-SS3 embodiments, wherein the first plate or the second plate further comprises a light absorbing layer disposed on the heating/cooling layer, wherein the light absorbing layer has an average light absorptance of at least 30%. SS5. The method of SS4, wherein the light absorbing layer comprises black paint.

SS6. The method of any one of SS1-SS5 embodiments, further comprising closing the second plate over the first plate using a hinge connected between the first plate and the second plate.

SS7. The method of any one of SS1-SS6 embodiments, wherein a thickness of the heating/cooling layer is less than or equal to 3 μm.

SS8. The method of any one of SS1-SS7 embodiments, wherein at least one of the first plate and the second plate has an area across its major surface of about 400 mm$^2$.

SS9. The method of any one of SS1-SS8 embodiments, wherein activating a heat source comprises activating an LED to radiate light towards the heating/cooling layer.

SS10. The method of SS9, further comprising controlling an output of the LED based on a measured or estimated temperature of the portion of the fluidic sample.

SS11. The method of any one of SS1-SS10 embodiments, further comprising expanding the electromagnetic radiation using a beam expander before the electromagnetic radiation reaches the heating layer.

SS12. The method of any one of SS1-SS11 embodiments, further comprising supporting a perimeter of either the first plate or the second plate on a support frame.

TT1. A method for detecting the presence or absence of an analyte in a sample, comprising:
- depositing a fluidic sample on a first plate of a fluidic device;
- placing a second plate over the first plate such that the fluidic sample is sandwiched between the first plate and the second plate, wherein reagents for detection of the analyte are present on the inner surface of the second plate;
- activating a heat source configured to radiate electromagnetic radiation towards a heating layer located on either the first plate or the second plate;
- heating, using at least the heating layer, at least a portion of the fluidic sample at a rate of at least 30° C./sec; and
- detecting whether the fluidic sample contains the analyte.

TT2. A method for detecting the presence or absence of an analyte in a sample, comprising:
- depositing a fluidic sample containing on a first plate of a fluidic device;
- placing a second plate over the first plate such that the fluidic sample is sandwiched between the first plate and the second plate, wherein reagents for detection of the analyte are present on the inner surface of the second plate;
- activating, for a given time period, a heat source configured to radiate electromagnetic radiation towards a heating/cooling layer located on either the first plate or the second plate;
- deactivating the heat source after the given time period, wherein at least a portion of the fluidic sample adjacent to the heating/cooling layer cools at a rate of at least 30° C./sec after the deactivating; and
- detecting whether the fluidic sample contains the analyte.

TT3. A method for detecting the presence or absence of an analyte in a sample, comprising:
- depositing a fluidic sample on a first plate of a fluidic device;
- placing a second plate over the first plate such that the fluidic sample is sandwiched between the first plate and the second plate, wherein reagents for detection of the analyte are present on the inner surface of the second plate;
- activating a heat source configured to radiate electromagnetic radiation towards a heating layer located on either the first plate or the second plate, wherein the heat source consumes less than 500 mW of power;
- heating, using at least the heating layer, at least a portion of the fluidic sample; and
- detecting whether the fluidic sample contains the analyte.

UU1. A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of an analyte are present on the inner surface of the second plate;
- activating a heat source configured to radiate electromagnetic radiation towards a heating layer located on either the first plate or the second plate;
- heating, using at least the heating layer, at least a portion of the fluidic sample at a rate of at least 30° C./sec; and
- detecting whether the fluidic sample contains the analyte; wherein presence or absence of the analyte indicates that the subject has the condition.

UU2. A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of the analyte are present on the inner surface of the second plate;
- activating, for a given time period, a heat source configured to radiate electromagnetic radiation towards a heating/cooling layer located on either the first plate or the second plate;
- deactivating the heat source after the given time period, wherein at least a portion of the fluidic sample adjacent to the heating/cooling layer cools at a rate of at least 30° C./sec after the deactivating; and
- detecting whether the fluidic sample contains the analyte; wherein presence or absence of the analyte indicates that the subject has the condition.

UU3. A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of an analyte are present on the inner surface of the second plate;
- activating a heat source configured to radiate electromagnetic radiation towards a heating layer located on either the first plate or the second plate, wherein the heat source consumes less than 500 mW of power;
- heating, using at least the heating layer, at least a portion of the fluidic sample; and
- detecting whether the fluidic sample contains the analyte; wherein presence or absence of the analyte indicates that the subject has the condition.

UU4. A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of an analyte are present on the inner surface of the second plate;
- activating a heat source configured to radiate electromagnetic radiation towards a heating layer located on either the first plate or the second plate;
- heating, using at least the heating layer, at least a portion of the fluidic sample at a rate of at least 30° C./sec;
- quantifying the amount of the analyte in the fluidic sample; and
- comparing the amount to a control or reference amount of the analyte;
- wherein a greater or reduced amount of the analyte in the sample compared to the control or reference amount indicates that the subject has the condition.

UU5. A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of an analyte are present on the inner surface of the second plate;

activating, for a given time period, a heat source configured to radiate electromagnetic radiation towards a heating/cooling layer located on either the first plate or the second plate;

deactivating the heat source after the given time period, wherein at least a portion of the fluidic sample adjacent to the heating/cooling layer cools at a rate of at least 30° C./sec after the deactivating;

quantifying the amount of the analyte in the fluidic sample; and comparing the amount to a control or reference amount of the analyte;

wherein a greater or reduced amount of the analyte in the sample compared to the control or reference amount indicates that the subject has the condition.

UU6. A method for diagnosing a condition in a subject, comprising:

depositing a fluidic sample from the subject on a first plate of a fluidic device;

placing a second plate over the first plate such that the fluidic sample is sandwiched between the first plate and the second plate, wherein reagents for detection of an analyte are present on the inner surface of the second plate;

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and quantifying the amount of the analyte in the fluidic sample; and comparing the amount to a control or reference amount of the analyte;

wherein a greater or reduced amount of the analyte in the sample compared to the control or reference amount indicates that the subject has the condition.

VV1. A kit, comprising:

a device of any one of OO embodiments; and a pre-mixed polymerase chain reaction medium.

VV2. The kit of VV1, wherein the pre-mixed polymerase chain reaction medium comprises: a DNA template, two primers, a DNA polymerase, deoxynucleoside triphosphates (dNTPs), a bivalent cation, a monovalent cation, and a buffer solution.

PCR and Molecule Amplification

In some embodiments, the device, apparatus, system, and/or method herein described can be used for rapid molecule (e.g. nucleic acid) amplification. In certain embodiments, the device, apparatus, system, and method can be used for isothermal nucleic acid amplification. In certain embodiments, the device, apparatus, and system can be used for non-isothermal nucleic acid amplification.

Non-isothermal nucleic acid amplification generally requires the cycled addition and removal of thermal energy. Many non-isothermal strategies that can be used for nucleic acid amplification involve the heating and cooling, to precise temperatures at precise times, of a reaction mixture that includes one or several nucleic acids of interest (that can or cannot be chemically modified with additional agents) and reagents necessary to complete an amplification reaction. Non-limiting examples of such nucleic acid amplification reactions include PCR; variants of PCR (e.g., reverse transcriptase PCR (RT-PCR), quantitative PCR (Q-PCR), or realtime quantitative PCR (RTQ-PCR)); ligase-chain reaction (LCR); variants of LCR (e.g., reverse transcriptase LCR (RTLCR), quantitative LCR (Q-LCR), real-time quantitative LCR (RTQ-LCR)); and digital nucleic amplification reactions (e.g., digital PCR (dPCR), digital RT-PCR (dRT-PCR), digital Q-PCR (dQ-PCR), digital RTQ-PCR (dRTQ-PCR), digital LCR (dLCR), digital RT-LCR (dRT-LCR), digital Q-LCR (dQ-LCR), digital RTQ-LCR (dRTQ-LCR). These nucleic acid amplification reactions, and others, are described in more detail below.

PCR Reactions

The device, apparatus, system, and method of the current disclosure can include the completion of a PCR amplification reaction, or any step comprising a PCR amplification (e.g., denaturation, annealing, elongation, etc). In some embodiments, a sample can comprise reagents necessary to complete a PCR reaction. Nonlimiting examples of reagents for a PCR reaction include a template nucleic acid (e.g., DNA) molecule to be amplified, a set of two primers that can hybridize with a target sequence on the template nucleic acid, a polymerase (e.g., DNA polymerase), deoxynucleotide triphosphates (dNTPs), a buffer at a pH and concentration suitable for a desired PCR reaction, a monovalent cation, and a divalent cation. Generally, the ratio of each reagent in the sample can vary and depend upon, for example, the amount of nucleic acid to be amplified and/or the desired amount of amplification products. Methods to determine the ratio of each reagent necessary for a PCR amplification reaction are found in, for example, U.S. Pat. Nos. 4,683,202 and 4,683,195, which are entirely incorporated herein by reference for all purposes.

PCR generally involves the heating and cooling of a reaction mixture that includes several key reagents and a nucleic acid (e.g., DNA) template. Non-limiting examples of reagents that, in addition to a nucleic acid template, can be used for PCR include primers, a polymerase, deoxynucleoside triphosphates (dNTPs), buffer solution, divalent cations, and monovalent cations. In general, at least two different primers per nucleic acid template can be included in the reaction mixture, wherein each primer is complementary to a portion of (e.g., the 3' ends of) the nucleic acid template. The nucleic acid template is replicated by a Non-limiting examples of DNA polymerases that can be useful in PCR include Taq polymerase, Pfu polymerase, Pwo polymerase, Tfl polymerase, Tli polymerase, Tma polymerase, and VentR polymerase, Kapa2g polymerase, KOD polymerase, HaqZ05 polymerase, Haqz05 polymerase, or combinations thereof.

dNTPs are nucleotides that include triphosphate groups and are generally the building-blocks from which amplified DNA is synthesized. Non-limiting examples of dNTPs useful in PCR include deoxyadenosine triphosphate (dATP), deoxyguanosine triphosphate (dGTP), deoxycytidine triphosphate (dCTP), and deoxythymidine triphosphate (dTTP).

A buffer solution can be generally used to provide a suitable chemical environment (e.g., pH, ionic strength, etc.) for optimum activity and stability of the DNA polymerase and/or other dependent components in the reaction mixture. For example, buffers of Tris-hydrochloride can be useful in PCR methods.

Divalent cations can also be required for DNA polymerase functionality, with non-limiting examples including magnesium ions ($Mg^{2+}$) and manganese ($Mn^{2+}$) ions. Monovalent cations, such as, for example, potassium ions ($K^+$) can be included and can be useful in minimizing the production of unwanted, non-specific amplification products.

In some embodiments, the reagents for a PCR reaction can be a component of an assay designed to test a blood or other liquid sample for the presence of an analyte. For example, chloride ions can be measured by any of the following protocols, and components of these assays can be present in a storage site: Colorimetric methods: chloride ions displace thiocyanate from mercuric thiocyanate. Free thiocyanate reacts with ferric ions to form a colored complex-ferric thiocyanate, which is measured photometrically. Coulometric methods: passage of a constant direct current between silver electrodes produces silver ions, which react with chloride, forming silver chloride. After all the chloride combines with silver ions, free silver ions accumulate, causing an increase in current across the electrodes and indicating the end point to the reaction. Mercurimetric methods: chloride is titrated with a standard solution of mercuric ions and forms $HgCl_2$ soluble complex. The end point for the reaction is detected colorimetrically when excess mercury ions combine with an indicator dye, diphenylcarbazon, to form a blue color. Likewise, magnesium can be measured colorimetrically using calmagite, which turns a red-violet color upon reaction with magnesium; by a formazan dye test; emits at 600 nm upon reaction with magnesium or using methylthymol blue, which binds with magnesium to form a blue colored complex. Likewise, calcium can be detected by a colorimetric technique using O-Cresolphtalein, which turns a violet color upon reaction of O-Cresolphtalein complexone with calcium. Likewise, Bicarbonate can be tested bichromatically because bicarbonate ($HCO3^-$) and phosphoenolpyruvate (PEP) are converted to oxaloacetate and phosphate in the reaction catalyzed by phosphoenolpyruvate carboxylase (PEPC). Malate dehydrogenase (MD) catalyzes the reduction of oxaloacetate to malate with the concomitant oxidation of reduced nicotinamide adenine dinucleotide (NADH). This oxidation of NADH results in a decrease in absorbance of the reaction mixture measured bichromatically at 380/410 nm proportional to the Bicarbonate content of the sample. Blood urea nitrogen can be detected in a colorimetric test in which diacetyl, or fearon develops a yellow chromogen with urea and can be quantified by photometry, or multiusing the enzyme urease, which converts urea to ammonia and carbonic acid, which can be assayed by, e.g., i) decrease in absorbance at 340 nm when the ammonia reacts with alpha-ketoglutaric acid, ii) measuring the rate of increase in conductivity of the solution in which urea is hydrolyzed. Likewise, creatinine can be measured colorimetrically, by treated the sample with alkaline picrate solution to yield a red complex. In addition, creatine can be measured using a non-Jaffe reaction that measures ammonia generated when creatinine is hydrolyzed by creatinine iminohydrolase. Glucose can be measured in an assay in which blood is exposed to a fixed quantity of glucose oxidase for a finite period of time to estimate concentration. After the specified time, excess blood is removed and the color is allowed to develop, which is used to estimate glucose concentration. For example, glucose oxidase reaction with glucose forms nascent oxygen, which converts potassium iodide (in the filter paper) to iodine, forming a brown color. The concentration of glycosylated hemoglobin as an indirect read of the level of glucose in the blood. When hemolysates of red cells are chromatographed, three or more small peaks named hemoglobin A1a, A1b, and A1c are eluted before the main hemoglobin A peak. These "fast" hemoglobins are formed by the irreversible attachment of glucose to the hemoglobin in a two-step reaction. Hexokinase can be measured in an assay in which glucose is phosphorylated by hexokinase (HK) in the presence of adenosine triphosphate (ATP) and magnesium ions to produce glucose-6-phosphate and adenosine diphosphate (ADP). Glucose-6-phosphate dehydrogenase (G6P-DH) specifically oxidises glucose-6-phosphate to gluconate-6-phosphate with the concurrent reduction of NAD+ to NADH. The increase in absorbance at 340 nm is proportional to the glucose concentration in the sample. HDL, LDL, triglycerides can be measured using the Abell-Kendall protocol that involves color development with Liebermann-Burchard reagent (mixed reagent of acetic anhydride, glacial acetic acid, and concentrated sulfuric acid) at 620 nm after hydrolysis and extraction of cholesterol. A fluorometric analysis can be used utilized to determine triglyceride reference values. Plasma high-density lipoprotein cholesterol (HDL-C) determination is measured by the same procedures used for plasma total cholesterol, after precipitation of apoprotein B-containing lipoproteins in whole plasma (LDL and VLDL) by heparin-manganese chloride. These compounds can also be detected colorimetrically in an assay that is based on the enzyme driven reaction that quantifies both cholesterol esters and free cholesterol. Cholesterol esters are hydrolyzed via cholesterol esterase into cholesterol, which is then oxidized by cholesterol oxidase into the ketone cholest-4-en-3-one plus hydrogen peroxide. The hydrogen peroxide is then detected with a highly specific colorimetric probe. Horseradish peroxidase catalyzes the reaction between the probe and hydrogen peroxide, which bind in a 1:1 ratio. Samples can be compared to a known concentration of cholesterol standard.

A single cycle of PCR typically comprises a series of steps that include a denaturation step, an annealing step, and an elongation step. During denaturation, a double-stranded DNA template can be melted into its individual strands, such that the hydrogen bonds formed between bases in each base-pair of the double-stranded DNA are broken. After denaturation, an annealing step is completed, wherein the reaction mixture is incubated under conditions at which the primers hybridize with complementary sequences present on each of the original individual strands. After annealing, the elongation step commences, wherein the primers are extended by a DNA polymerase, using dNTPs present in the reaction mixture. At the conclusion of elongation, two new double-stranded DNA molecules result, each comprising one of the original individual strands of the DNA template. Each step of PCR is generally initiated by a change in the temperature of the reaction mixture that results from the heating or cooling of the reaction mixture. At the completion of a single round of amplification, the thermal cycle can be repeated for further rounds of amplification. The generation of replicate amplification products is theoretically exponential with each subsequent thermal cycle. For example, for a single DNA template, each step n, can result in a total of r replicates.

Successful PCR amplification requires high yield, high selectivity, and a controlled reaction rate at each step. Yield, selectivity, and reaction rate also generally depend on temperature, and optimal temperatures depend on the composition and length of the polynucleotide, enzymes, and other components in the reaction mixture. In addition, different temperatures can be optimal for different steps or different nucleic acids to be amplified. Moreover, optimal reaction conditions can vary, depending on the sequence of the template DNA, sequence of a designed primer, and composition of the reaction mixture. Thermal cyders that can be used to perform a PCR reaction can be programmed by selecting temperatures to be maintained, time durations for each portion of a cycle, number of cycles, rate of temperature change, and the like.

Primers for PCR can be designed according to known algorithms. For example, algorithms implemented in commercially available or custom software can be used to design primers. In some examples, primers can consist of at least about 12 bases. In other examples, a primer can consist of at least about 15, 18, or 20 bases in length. In still other examples, a primer can be up to 50+ bases in length. Primers can be designed such that all of the primers participating in a particular reaction have melting temperatures that are within at least about 5° C., and more typically within about 2° C. of each other. Primers can be further designed to avoid selfhybridization or hybridization with other desired primers. Those of skill in the art will recognize that the amount or concentration of primer in a reaction mixture will vary, for example, according to the binding affinity of the primers for a given template DNA and/or the quantity of available template DNA. Typical primer concentrations, for example, can range from 0.01 uM to 0.5 uM.

In an example PCR reaction, a reaction mixture, including a double-stranded DNA template and additional reagents necessary for PCR, is heated to about 80-98° C. and held at that temperature for about 10-90 seconds, in order to denature the DNA template into its individual strands. Each individual strand, during the annealing step, is then hybridized to its respective primer included in the reaction mixture by cooling the reaction mixture to a temperature of about 30-65° C. and holding it at that temperature for about 1-2 minutes. The elongation step then commences, wherein elongation of the respective primers hybridized to each individual strand occurs by the action of a DNA polymerase adding dNTPs to the primers. Elongation is initiated by heating the reaction mixture to a temperature of about 70-75° C. and holding at that temperature for 30 seconds to 5 minutes. The reaction can be repeated for any desired number of cycles depending on, for example, the initial amount of DNA template, the length of the desired amplification product, the amount of dNTPs, the amount of primer, and/or primer stringency.

While general PCR methods can be useful for nucleic acid amplification, other more specialized forms of PCR can be even more useful for a given application. Nonlimiting examples of commonly used, more-specialized forms of PCR include reverse transcription PCR (RT-PCR) (e.g., U.S. Pat. No. 7,883,871), quantitative PCR (qPCR) (e.g., U.S. Pat. No. 6,180,349), real-time quantitative PCR (RTQ-PCR) (e.g., U.S. Pat. No. 8,058,054), allele-specific PCR (e.g., U.S. Pat. No. 5,595,890), assembly PCR (e.g. U.S. Patent Publication No. 20120178129), asymmetric PCR (e.g., European Patent Publication No. EP23 73 807), dial-out PCR (e.g., Schwartz J, NATURE METHODS, September 2012; 9 (9): 913-915), helicase-dependent PCR (e.g., Vincent M, EMBO REPORTS 5, 2004, 5 (8): 795-800), hot start PCR (e.g., European Patent Publication No. EP1419275), inverse PCR (e.g., U.S. Pat. No. 6,607,899), methylation-specific PCR (e.g., European Patent Publication No. EP1690948), miniprimer PCR (U.S. Patent Publication No. 20120264132), multiplex PCR (U.S. Patent Publication No. 20120264132), nested PCR (U.S. Patent Publication No. 20120264132), overlap-extension PCR (U.S. Patent Publication No. 20120264132), thermal asymmetric interlaced PCR (U.S. Patent Publication No. 20120264132), and touchdown PCR (U.S. Patent Publication No. 20120264132). The device, apparatus, system, and/or method herein disclosed can be utilized to conduct such more-specialized forms of PCR.

RT-PCR Reactions

The device, apparatus, system, and method of the current disclosure can include the completion of an RT-PCR amplification reaction, and, thus, a sample can comprise reagents necessary to complete a RT-PCR reaction. Non-limiting examples of such reagents include the reagents necessary to complete a PCR reaction, a reverse transcriptase, and a RNA template that can be used to synthesize a complementary DNA (cDNA) complement. In cases where reverse transcriptase must be removed prior to cDNA amplification, a sample supplied to a thermal cycler cannot contain reagents necessary to complete a PCR reaction and can require a separate amplification reaction. Generally, the ratio of each reagent in the sample can vary and depend upon, for example, the amount of nucleic acid to be amplified and/or the desired amount of amplification products. Methods to determine the ratio of each reagent necessary for an RT-PCR amplification reaction are generally known by those skilled in the art.

Reverse transcription refers to a process by which ribonucleic acid (RNA) is replicated to its single-stranded complementary DNA (cDNA) by a reverse transcriptase enzyme. Non-limiting examples of reverse transcriptase enzymes include Moloney murine leukemia virus (MMLV) transcriptase, avian myeloblastosis virus (AMY) transcriptase, variants of AMV-transcriptase, or reverse transcriptases that have endo H activity. In reverse transcription PCR (RT-PCR), a reverse transcriptase, generally with endo H3 activity, is added to a reaction mixture that includes an RNA template and necessary reagents for PCR. The reverse transcriptase can complete RNA template replication to cDNA, by hybridizing dNTPs to the RNA template at proper conditions.

At the conclusion of replication, the reverse transcriptase can remove the single-stranded, cDNA replicated from the RNA template to permit additional replication of the cDNA with PCR methods described above. The cDNA and its amplification products that are produced from PCR can be used indirectly to garner information about the RNA, such as, for example, the sequence of the RNA. The cDNA product that is synthesized from an RNA by a reverse transcriptase can be removed from the reaction mixture to be used as a DNA template in a separate, subsequent set of PCR reactions or amplification via PCR can occur in situ where reverse transcriptase is included in the reaction mixture with reagents necessary for PCR.

Q-PCR or RTQ-PCR Reactions

The device, apparatus, system, and method of the current disclosure can include the completion of a Q-PCR or RTQ-PCR amplification reaction, and, thus a sample can comprise reagents necessary to complete a Q-PCR or RTQ-PCR amplification reaction. Non-limiting examples of such reagents include the reagents necessary to complete a PCR reaction and a reporter used to detect amplification products. Generally, the ratio of each reagent in the sample can vary and depend upon, for example, the amount of nucleic acid to be amplified and/or the desired amount of amplification products. Methods to determine the ratio of each reagent necessary for a Q-PCR or RTQ-PCR amplification reaction are generally known by those skilled in the art.

Quantitative PCR (Q-PCR) is a variation of PCR in which the amount of template DNA in a sample is quantified. Generally, amplification products produced by PCR methods are linked to a reporter, such as, for example, a fluorescent dye. At the end of a reaction, the reporter can be detected and the results back-calculated (based on the association ratio of reporter to DNA and the known number of thermal cycles) to determine the amount of original DNA template present. In some examples, the fluorescent dye can be detected in real time as amplification progresses. Such a variation of Q-PCR can be appropriately called real-time quantitative PCR (RTQ-PCR), real-time PCR, or kinetic PCR. Both Q-PCR and RTQ-PCR can be used to determine whether or not a specific DNA template is present in a sample. In general, due to the possible changes to reaction efficiency as the number of PCR cycles increases, however, RTQ-PCR methods can be generally more sensitive, more reliable, and thus, more frequently employed by those skilled in the art as measurements are made on amplification products as they are synthesized rather than on the aggregate of amplification products obtained at the completion of the desired number of thermal cycles. Q-PCR and RTQ-PCR can also be combined with other PCR methods, such as, for example, RT-PCR. As an example, utility of combining Q-PCR or RTQ-PCR with other PCR methods, reporters can be included in an RT-PCR reaction mixture to detect and/or quantify low levels of messenger RNA (mRNA) via replication of its associated cDNA, which can enable the quantification of relative gene expression in a particular cell or tissue.

One or more reporters can be used to quantify DNA amplified as part of Q-PCR and RTQ-PCR methods. Reporters can be associated with DNA both by covalent and/or non-covalent linkages (e.g., ionic interactions, Van der Waals forces, hydrophobic interactions, hydrogen bonding, etc.). For example, a fluorescent dye that non-covalently intercalates with double-stranded DNA can be used as a reporter. In another example, a DNA oligonucleotide probe that fluoresces when hybridized with a complementary DNA can be used as a reporter. In some examples, reporters can bind to initial reactants and changes in reporter levels can be used to detect amplified DNA. In other examples, reporters can only be detectable or non-detectable as DNA amplification progresses. Detection of reporters can be accomplished with one of many detection systems that are suitable in the art. Optical detectors (e.g., fluorimeters, ultra-violet/visible light absorbance spectrophotometers) or spectroscopic detectors (e.g., nuclear magnetic resonance (NMR), infrared spectroscopy) can be, for example, useful modalities of reporter detection. Gel based techniques, such as, for example, gel electrophoresis can also be used for detection.

A reporter used in a Q-PCR or RTQ-PCR reaction can be an intercalator that can be detected. An intercalator generally binds to DNA by disrupting hydrogen bonds between complementary bases, and, instead fits itself between the disrupted bases. An intercalator can form its own hydrogen bonds with one or more of the disrupted bases. Non-limiting examples of intercalators include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA.

A reporter used in a Q-PCR or RTQ-PCR reaction can be a minor groove binder that can be detected. Nonlimiting examples of minor grove binders include indoles and imidazoles (e.g., Hoechst 33258, Hoechst 33342, Hoechst 34580 and DAPI).

A reporter used in a Q-PCR or RTQ-PCR reaction can be a nucleic acid stain that can be detected. Non-limiting examples of nucleic acid stains include acridine orange (also capable of intercalating), 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

A reporter used in a Q-PCR or RTQ-PCR reaction can be a fluorescent dye that can be detected. Non-limiting examples of fluorescent dyes include fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5-(or 6-) iodoacetamidofluorescein, 5-{[2 (and 3)-5-(Acetylmercapto)-succinyl] amino}fluorescein (SAMSA-fluorescein), lissamine rhodamine B sulfonyl chloride, 5 and/or 6 carboxy rhodamine (ROX), 7-aminomethyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-aminonaphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores known to those of skill in the art. For detailed listing of fluorophores that can be useful in Q-PCR and RTQ-PCR methods, see also Hermanson, G. T., BIOCONJUGATE TECHNIQUES (Academic Press, San Diego, 1996) and Lakowicz, J. R., PRINCIPLES OF FLUORESCENCE SPECTROSCOPY, (Plenum Pub Corp, 2nd edition (July 1999)), which are incorporated herein by reference.

A reporter used in a Q-PCR or RTQ-PCR reaction can be a radioactive species that can be detected. Nonlimiting examples of radioactive species that can be useful in Q-PCR and RTQ-PCR methods include 14C 1231 1241 1251 131 I, Tc99m, 35S, or 3H.

A reporter used in a Q-PCR or RTQ-PCR reaction can be an enzyme that can produce a detectable signal. Such signal can be produced by action of the enzyme on its given substrate. Non-limiting examples of enzymes that can be useful in Q-PCR or RTQ-PCR methods include alkaline phosphatase, horseradish peroxidase, 12-galactosidase, alkaline phosphatase, galactosidase, acetylcholinesterase, and luciferase.

A reporter used in a Q-PCR or RTQ-PCR reaction can be an affinity ligand-label that can be detected. A particular ligand can include a label, such as for example, a fluorescent dye, and binding of the labeled ligand to its substrate can produce a useful signal. Non-limiting examples of binding pairs that can be useful in Q-PCR or RTQ-PCR methods include streptavidin/biotin, avidin/biotin or an antigen/antibody complex, such as, for example, rabbit IgG and anti-rabbit IgG;

A reporter used in a Q-PCR or RTQ-PCR reaction can be a nanoparticle that can be detected via light scattering or surface plasmon resonance (SPR). Non-limiting examples of materials useful for SPR-based detection include gold and silver materials. Other nanoparticles that can be useful in Q-PCR or RTQ-PCR reactions can be quantum dots (Qdots). Qdots are generally constructed of semiconductor nanocrystals, described, for example in U.S. Pat. No. 6,207,392. Nonlimiting examples of semiconductor materials that can be used to produce a Qdot include MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe, GaAs, InGaAs, InP, InAs, or mixed compositions thereof.

A reporter used in a Q-PCR or RTQ-PCR reaction can be a labeled oligonucleotide probe. Probe based quantitative methods rely on the sequence-specific detection of amplification products of a desired DNA template, using a labeled oligonucleotide. The oligonucleotide can be a primer or a longer, different type of oligonucleotide. The oligonucleotide can be DNA or RNA. As a result, unlike non-sequence specific reporters, a labeled, sequence-specific probe hybridizes with several bases in an amplification product, and, thus, results in increased specificity and sensitivity of detection. A label linked to a probe can be any of the various reporters mentioned above and can also include a quencher (a molecule used, for example, to inhibit fluorescence). Methods for performing probe-based quantitative amplification are described in U.S. Pat. No. 5,210,015, which is entirely incorporated herein by reference. Non-limiting examples of probes that can be useful in Q-PCR or RTQ-PCR reactions include TaqMan probes, TaqMan Tamara probes, TaqMan MGB probes, or Lion probes.

A variety of arrangements of quencher and fluorescent dye can be used when both are used. In the case of a molecular beacon, for example, a quencher is linked to one end of an oligonucleotide capable of forming a hairpin structure. At the other end of the oligonucleotide is a fluorescent dye. Unbound to a complementary sequence on an amplification product, the oligonucleotide inter-hybridizes with itself and assumes a hairpin configuration. In the hairpin configuration, the fluorescent dye and quencher are brought in close proximity which effectively prevents fluorescence of the dye. Upon hybridizing with an amplification product of a desired template DNA, however, the oligonucleotide hybridizes in a linear fashion, the fluorescence and quencher separate, and fluorescence from the dye can be achieved and subsequently detected. In other example, a linear, RNA based probe that includes a fluorescent dye and a quencher held in adjacent positions can be used for detection. The close proximity of the dye to the quencher prevents its fluorescence. Upon the breakdown of the probe with the exonuclease activity of a DNA polymerase, however, the quencher and dye are separated, and the free dye can fluoresce and be detected. As different probes can be designed for different sequences, multiplexing is possible. In a multiplexed detection, assaying for several DNA templates in the same reaction mixture can be possible by using different probes, each labeled with a different reporter, for each desired DNA template.

A Q-PCR or RTQ-PCR reaction can include a single reporter or can include multiple reporters. One or more detection methodologies can be used for quantification. Moreover, as Q-PCR and RT-PCR generally adds just a quantification step, it can be generally linked to any type of PCR reaction.

LCR Reactions

The device, apparatus, system, and method of the current disclosure can include the completion of a LCR amplification reaction (or any step of a LCR reaction-as described elsewhere herein), and, thus, a sample can comprise reagents necessary to complete a LCR amplification reaction. Non-limiting examples of such reagents include a template DNA molecule to be amplified, a set of oligonucleotide probes that can each hybridize with a different, but adjacent to the other, portion of a target sequence on the template DNA, a DNA ligase, a buffer at a pH and concentration suitable for a desired LCR reaction, a monovalent cation, and a divalent cation. Generally, the ratio of each reagent in the sample can vary and depend upon, for example, the amount of nucleic acid to be amplified and/or the desired amount of amplification products. Methods to determine the ratio of each reagent necessary for a LCR amplification reaction are generally known by those skilled in the art.

LCR is generally a method similar to PCR, with some important key distinctions. A key distinction of general LCR over PCR, is that LCR amplifies an oligonucleotide probe using a DNA ligase enzyme to produce amplification products instead of through polymerization of nucleotides with a DNA polymerase. In LCR, two complementary oligonucleotide probe pairs that are specific to a DNA template can be used. After denaturation of a to-be-replicated template DNA into its individual strands, each probe pair can hybridize to adjacent positions on its respective individual strand of the template. Primers are generally not used in LCR. Any gap and/or nick created by the joining of two probes can be sealed by the enzyme DNA ligase, in order to produce a continuous strand of DNA complementary to the template DNA. Similar to PCR, though, LCR generally requires thermal cycling, with each part of the thermal cycle driving a particular step of the reaction. Repeated temperature changes can result in the denaturation of the DNA template, annealing of the oligonucleotide probes, ligation of the oligonucleotide probes, and separation of the ligated unit from the original DNA template. Moreover, a ligated unit synthesized in one thermal cycle can be replicated in the next thermal cycle. Each thermal cycle can result in a doubling of the DNA template, resulting in exponential amplification of the template DNA in a fashion analogous to PCR.

Gap LCR Reactions

The device, apparatus, system, and method of the current disclosure can include the completion of a gap LCR amplification reaction, and, thus, a sample can comprise reagents necessary to complete a gap LCR amplification reaction. Non-limiting examples of such reagents include the reagents necessary to complete a LCR reaction, wherein the set of oligonucleotide probes can each hybridize with a different, non-adjacent portion of a target sequence on the template DNA, dNTPs, and a DNA polymerase. Generally, the ratio of each reagent in the sample can vary and depend upon, for example, the amount of nucleic acid to be amplified and/or the desired amount of amplification products. Methods to determine the ratio of each reagent necessary for a gap LCR amplification reaction are generally known by those skilled in the art.

Gap LCR is a specialized type of LCR that utilizes modified oligonucleotide probes that cannot be ligated if a specific sequence is not present on a DNA template. The probes can be designed in a way that when they hybridize to an individual strand of a DNA template, they do so discontinuously and are generally separated by a gap of one to several base pairs. The gap can be filled by with dNTPs using a DNA polymerase, which can result in adjacency of the two original probes. As in general LCR, DNA ligase can join the two resulting, adjacent probes in order to produce a continuous strand of DNA complementary to the original template. The newly synthesized strand can then be used for further thermal cycles of template amplification. Gap LCR generally has higher sensitivity than LCR as it minimizes ligation where a desired sequence is not present on a template DNA. Moreover, the combined use of both DNA ligase and DNA polymerase can also result in a more accurate identification of a sequence of interest, even in cases where low levels of DNA template are available.

Additionally, since LCR is a DNA replication method, analogous methods to RT-PCR, Q-PCR, and RTQPCR are possible. For example, any of the reporters specified above can be considered for use in a quantitative (Q-LCR) or real-time quantitative LCR (RTQ-LCR) reaction. Moreover, LCR methods can be combined with PCR or other nucleic amplification techniques.

Q-LCR and LTQ-LCR Reactions

The device, apparatus, system, and method of the current disclosure can include the completion of a Q-LCR or LTQ-PCR reaction, and, thus, a sample can comprise reagents necessary to complete a Q-LCR or RTQ-LCR reaction. Non-limiting examples of such reagents include the reagents necessary to complete a LCR reaction and a reporter used to detect amplification products. Generally, the ratio of each reagent in the sample can vary and depend upon, for example, the amount of nucleic acid to be amplified and/or the desired amount of amplification products. Methods to determine the ratio of each reagent necessary for a Q-LCR and RTQ-LCR amplification reaction are generally known by those skilled in the art.

Since LCR is a DNA replication method, analogous methods to RT-PCR, Q-PCR, and RTQPCR are possible. For example, any of the reporters specified above can be considered for use in a quantitative (Q-LCR) or real-time quantitative LCR (RTQ-LCR) reaction. Moreover, LCR methods can be combined with PCR or other nucleic amplification techniques.

Digital Nucleic Acid Amplification Reactions

The device, apparatus, system, and method of the current disclosure can include the completion of a digital nucleic acid amplification reaction, and, thus, a sample can comprise reagents necessary to complete a digital nucleic acid amplification reaction. In general, any of the example nucleic acid amplification reactions discussed herein can be conducted in digital form, upon proper separation of a sample and/or reagents necessary for nucleic acid amplification into smaller partitions. In some embodiments, such partitions can be droplets or can be larger aliquots of the original sample. Generally, the ratio of each reagent in partitions can vary and depend upon, for example, the amount of nucleic acid to be amplified in each droplet and/or the desired amount of amplification products. Methods to determine the ratio of each reagent necessary for a particular digital nucleic acid amplification reaction are generally known by those skilled in the art.

Digital nucleic acid amplification is a technique that allows amplification of a subset of nucleic acid templates fractioned into partitions obtained from a larger sample. In some cases, a partition can comprise a single nucleic acid template, such that amplification products generated from amplification of the template are exclusively derived from the template. Amplification products can be detected using a reporter, including any of those example reporters described herein. The amplification of a single nucleic acid template can be useful in discriminating genetic variations that include, for example, wild-type alleles, mutant alleles, maternal alleles, or paternal alleles of a gene. More comprehensive discussions of this technology, with respect to PCR, can be found elsewhere-see Pohl et al., Expert Rev. Mo!. Diagn., 4 (1): 41-7 (2004), and Vogelstein and Kinzler, Proc. Natl. Acad. Sci. USA 96:9236-9241 (1999), which are both incorporated herein in entirety by reference. So long as the proper thermal cycling of a partition comprising a complete reaction mixture (e.g., a reaction mixture comprising both the nucleic acid template to be amplified and the required reagents for the desired nucleic acid amplification reaction) is achieved, any of the example nucleic acid amplification reactions discussed herein can be conducted digitally. Indeed, digital nucleic acid amplification methods still require thermal cycling and accurate temperature control, as do their non-digital analogues.

In a digital nucleic acid amplification reaction, a large sample is fractioned into a number of smaller partitions, whereby the partitions can contain on average a single copy of a nucleic acid template or multiple copies of a template. Individual nucleic acid molecules can be partitioned with the aid of a number of devices and strategies with non-limiting examples that include micro-well plates, capillaries, dispersions that comprise emulsions, arrays of miniaturized chambers, nucleic acid binding surfaces, flow cells, droplet partitioning, or combinations thereof. Each partition can be thermal cycled to generate amplification products of its component template nucleic acid, using a nucleic acid amplification reaction of choice with non-limiting examples of such reactions that include a digital PCR (dPCR) nucleic acid amplification reaction, a digital LCR (dLCR) nucleic acid amplification reaction, a digital RT-PCR (dRT-PCR) nucleic acid amplification reaction, a digital (dRT-LCR) nucleic acid amplification reaction, a digital Q-PCR (dQ-PCR) nucleic acid amplification reaction, a digital Q-LCR (dQ-LCR) nucleic acid amplification reaction, a digital RTQ-PCR (dRTQ-PCR) nucleic acid amplification reaction, a digital LTQ-LCR (dLTQ-LCR) nucleic acid amplification reaction, or combinations thereof.

In cases where reporters are used, each partition can be considered "positive" or "negative" for a particular nucleic acid template of interest. The number of positives can be counted and, thus, one can deduce the starting amount of the template in the pre-partitioned sample based upon the count. In some examples, counting can be achieved by assuming that the partitioning of the nucleic acid template population in the original sample follows a Poisson distribution. Based on such an analysis, each partition is labeled as either containing a nucleic acid template of interest (e.g., labeled "positive") or not containing the nucleic acid template of interest (e.g., labeled "negative"). After nucleic acid amplification, templates can be quantified by counting the number of partitions that comprise "positive" reactions. Moreover, digital nucleic acid amplification is not dependent on the number of amplification cycles to determine the initial amount of nucleic acid template present in the original sample. This lack of dependency eliminates relying on assumptions with respect to uncertain exponential amplification, and, therefore, provides a method of direct, absolute quantification.

Most commonly, multiple serial dilutions of a starting sample are used to arrive at the proper concentration of nucleic acid templates in the partitions. The volume of each partition can depend on a host of factors that include, for example, the volume capacity of a thermal cycler used to generate amplification products. Furthermore, quantitative analyses conducted by digital nucleic acid amplification can generally require reliable amplification of single copies of nucleic acid template with low false positive rates. Such capability can require careful optimization in microliter-scale vessels. Moreover, the analytical precision of a nucleic acid amplification reaction can be dependent on the number of reactions.

In some embodiments, digital nucleic acid amplification reactions can be droplet digital nucleic acid amplification reactions. Non-limiting examples of such nucleic acid amplification reactions include droplet digital PCR (ddPCR), droplet digital RT-PCR (ddRT-PCR), droplet digital Q-PCR (ddQ-PCR), droplet digital RTQ-PCR (ddRTQ-PCR), droplet digital LCR (ddLCR), droplet digital RT-LCR (ddRT-LCR), droplet digital Q-LCR (ddQ-LCR), or droplet digital RTQ-LCR (ddRTQ-PCR), or combinations thereof.

In some cases, a digital nucleic acid amplification reaction can be a droplet digital nucleic acid amplification reaction. For example, such a nucleic acid amplification reaction can be a droplet digital PCR (ddPCR) nucleic acid amplification reaction. A ddPCR nucleic acid amplification reaction can be completed by first partitioning a larger sample comprising nucleic acids into a plurality of droplets. Each droplet comprises a random partition of nucleic acids in the original sample. The droplets can then be combined with different droplets that comprise the reagents necessary for a PCR reaction (e.g., a set of two primers that can hybridize with a target sequence on the template DNA, a DNA polymerase, deoxynucleotide triphosphates (dNTPs), a buffer at a pH and concentration suitable for a desired PCR reaction, a monovalent cation, and a divalent cation). The new combined droplet is then properly thermal cycled in a thermal cycler and PCR commences. Alternatively, a sample can already comprise reagents necessary for PCR prior to partitioning into droplets—droplet combination with other droplets would, thus, not be required.

Analogous procedures can be followed to complete a droplet digital RT-PCR (ddRT-PCR) nucleic acid amplification reaction, a droplet digital LCR (ddLCR) nucleic acid amplification reaction, a droplet digital RT-PCR (ddRT-LCR) nucleic acid amplification reaction, a droplet digital Q-PCR (ddQ-PCR) nucleic acid amplification reaction, a droplet digital RTQ-PCR (ddRTQ-PCR) nucleic acid amplification reaction, a droplet digital Q-LCR (ddQ-LCR) nucleic acid amplification reaction, or a droplet digital RTQ-LCR (ddRTQ-LCR) reaction.

In the case of a quantitative droplet digital nucleic acid amplification reaction (e.g., ddQ-PCR, ddRTQ-PCR, ddQ-LCR, or ddRTQ-LCR), droplets can also comprise a reporter used to detect amplification products. Such reporters can be contacted with nucleic acids by combining droplets or can already be included in a partition comprising nucleic acid templates to be amplified.

Droplet nucleic acid amplification can be completed using a variety of sample holders. In some examples, droplets can be applied to one or more wells of a sample holder and then thermal cycled. In other examples, a device comprising fluidic channels, such as, for example, a flow cell or microfluidic device can be used. Fluidic channels can be used to transport droplets through a sample holder (or other component of a thermal cycler) such that droplet thermal contact with different temperature regions of the sample holder (or other component of a thermal cycler) results in proper thermal cycling of the droplets.

Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Labels The devices, systems, and methods herein disclosed can employ various types of labels that are used for analytes detection. The labels are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, labeling an analyte includes using, for example, a labeling agent, such as an analyte specific binding member that includes a detectable label. Detectable labels include, but are not limited to, fluorescent labels, colorimetric labels, chemiluminescent labels, enzyme-linked reagents, multicolor reagents, avidin-streptavidin associated detection reagents, and the like. In some embodiments, the detectable label is a fluorescent label. Fluorescent labels are labeling moieties that are detectable by a fluorescence detector. For example, binding of a fluorescent label to an analyte of interest allows the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

In some embodiments, suitable fluorescent molecules (fluorophores) for labeling include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl) maleimide; anthranilamide; 4,4-difluoro-5-(2-thienyl)-4-bora-3a,4a diaza-5-indacene-3-propionic acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallolsulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino] naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, 5 pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas 10 Red); N,N,N',N'-tetramethyl-6-carboxyrhodamine (TAMRA); tetramethyl rhodamine; tetramethyl rhodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In some embodiments, dyes that can be used to stain blood cells comprise Wright's stain (Eosin, methylene blue), Giemsa stain (Eosin, methylene blue, and Azure B), Can-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride).

Cloud. The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/046437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.II. RAPID SAMPLE TEMPERATURE CHANGING FOR ASSAYING (VI)

The following disclosure is not intended to include all features and aspects of the present invention.

The present invention provides, among other things, the devices and methods that can rapidly change or cycle (i.e. heating and cooling) a sample temperature with high speed, less heating energy, high energy efficiency, a compact and simplified apparatus (e.g. handheld), easy and fast operation, and/or low cost.

The present invention has experimentally achieved a cycling of a sample temperature between 95° C. and 55° C.) in a second or less.

The invention has six novel aspects (1) the devices and methods that allow fast thermal cycling, (2) the devices and methods that allow the sample thickness uniform and sample holder mechanically stable for handling, (3) simple operation, (3) devices and methods for doing real time PCR (4) biochemistry, and (5) smartphone based systems.

To rapid thermal cycle the temperature of a sample or a portion of it, one must reduce the thermal mass and lateral heat.

Radiative heating and cooling are preferred.

A. Imager Based Rapid Temperature Assaying and Real Time PCR

1. Imaging based temperature sensor

In certain embodiments, during a thermal cycling process, one or more temperature sensing images are used to monitoring the temperature of a sample. The temperature sensing image can sense a local temperature at different locations of a sample. One can determine a suitable heating temperature to the sample (e.g. control the heating power), based on the temperature map of a sample, rather than just a single lump-sum temperature.

When heating up the assay device, some air bubbles and other defects will form and be trapped in the heating area of the assay device. And the temperature of sample liquid and air are different. If using a lump-sum temperature sensor to measure the average temperature in the heating area to be used as the temperature of sample liquid, it is not accurate. In order to accurately measure the temperature of the sample liquid in the heating area, an image-based temperature sensor should be used in the system to distinguish the temperature between air bubble and sample liquid.

FIG. 11A is the schematic of the system of heating and temperature monitoring device for the assay device. A heating source is put under the assay device to heat up the assay device. And on top of the thermal imager, there is a thermal temperature sensor to monitor the temperature of the heating area on the assay device. The temperature sensor is a thermal imager whose field of view is aligned with the heating area.

FIG. 11B is the schematic of the field of view of the thermal imager in the system described in FIG. 11A when heating up the assay device. For example, B1 and B2 are two air bubbles and/or defects which are generated and trapped in the assay device during heating up. And S3 is the sample liquid region. Using the image based thermal sensor, we can tell the difference between the temperature of the sample liquid T3 and the air bubble region temperatures T1 and T2. So that we can get more accurate temperature of the sample liquid in the heating area.

In this experiment, the assay device has a top (first) PMMA plate with 50 um thickness, pillar array with 30 um pillar height, 30 um by 40 um pillar size, and 80 um inter pillar distance; a bottom (second) PET plate with 50 um thickness. A heating/cooling layer is on the outer surface of the second plate, and covers the entire second plate outer surface. The heating/cooling layer comprises an Au (gold) film and a black paint layer. The gold film has one surface in contact with the second plate outer surface, and another surface being painted with a black paint. The black paint is a commercial product of a film composited of black carbon nanoparticle and polymer mixture. The black paint had an average thickness of ~9 um (~2 um thickness variation). The black paint layer may be directly facing incoming LED light. Between the Au film and the second plate outer surface, there is a 5 nm adhesion layer of Ti, which improves the adhesion between Au and the second plate. The heating source is a blue light emitting diode (LED) with a central wavelength of 450 nm and power consumption around 500 mW.

9. In certain embodiments, a system, comprising:
(i) a device, comprising:
a first plate comprising a polymer material and having a thickness less than or equal to 100 μm,
a second plate comprising a polymer material and having a thickness less than or equal to 100 μm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between $6\times10^{-5}$ W/K multiplied by the thickness of the heating/cooling layer and $1.5\times10^{-4}$ W/K multiplied by the thickness of the heating/cooling layer, and
a support frame configured to support at least one of the first plate and the second plate;
an optical source configured to direct electromagnetic radiation towards the heating/cooling layer,
a temperature sensor to monitor the temperature of the heating area in the device;
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source, and
wherein the system consumes less than 500 mW of power.

10. The system of any prior embodiment, wherein the temperature sensor is an image-based temperature sensor.

11. The system of any prior embodiment, wherein the temperature sensor's field of view is 1 mm$^2$, 10 mm$^2$, 100 mm$^2$, 1000 mm$^2$, or in a range between any of the two values.

12. The system of any prior embodiment, wherein the temperature sensor's resolution is 1 um, 10 um, 100 um, 1 mm, or in a range between any of the two values.

13. The system of any prior embodiment, wherein the working thermal radiation wavelength of the temperature sensor's falls in the range of 1 um to 10 um or 10 um to 100 um.

14. The system of any prior embodiment, wherein the thermal sensor has a least a lens.

15. The system of any prior embodiment, wherein the thermal sensor is an imager that can image at least a part of the sample.

16. A method for measuring temperature of sample liquid in assay device, comprising:

imaging the heating area in the assay device under thermal imager;
segmenting air bubble area or defect area and sample liquid area in the image;
measuring the temperature of sample liquid area.

2. Real Time Detection (qPCR) Setup

In certain embodiments, a system comprise a assay device, the heater, and an optical monitor to monitor an optical signal from a sample in the card, wherein the optical signal give an indication of a nucleic acid amplification inside the Q-card and the optical signal is monitored during a PCR process (that is a real time PCR).

In certain embodiments, the optical monitor is a photodetector. In certain embodiments, the optical monitor is one or more imagers that image an area or a volume of the sample. Hence the image gives an optical signal in each location of the sample being imaged. An analysis of the optical signal image can give more accurate analysis on the nucleic acid amplification than a lump-sum optical signal detection.

In certain embodiments, the nucleic amplification during a PCR process is monitored by an imager or more imagers, where the imagers image an area or a volume of a sample and the signal of the imager represents the nucleic acid amplification by the PCR. In certain embodiments, signal is fluorescence signal. In certain embodiments, signal is a color signal.

The terms "assay device" and "sample holder" are interchangeable.

In the optical signal image analysis, in certain embodiments, artificial intelligence is used. In the optical signal image analysis, in certain embodiments, machine learning is used.

In certain embodiments, the system does real-time PCR by adding one or multi fluorescent excitation light sources and detectors into the heating and temperature monitoring system.

In certain embodiments, a system has imagers for sample temperature imaging and for nucleic acid amplification signals monitoring imaging. In certain embodiments, the sample temperature imaging and the nucleic acid amplification signal monitoring imaging uses a single optical monitor.

FIG. 12 is a schematic of the real-time PCR system comprising a heating source and temperature monitoring system as described FIG. 11 and a pair of fluorescent excitation light source and detector. In this case, the excitation light source and fluorescence detector are on top of the assay device and aligned to the same excitation and detection area on the assay device.

Figure 13:
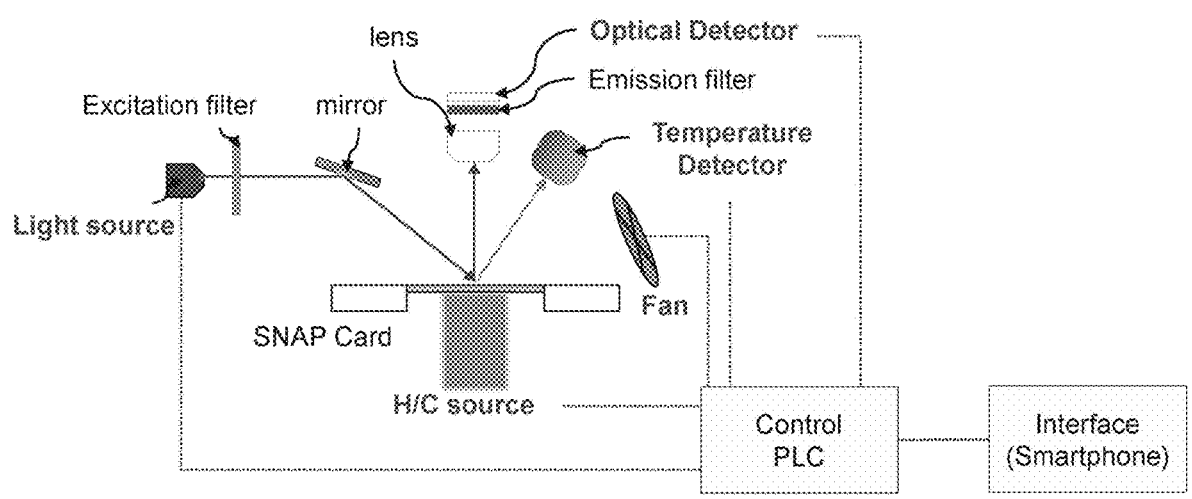
FIG. 13 schematically illustrates an embodiment of a real-time PCR system comprising a heating source, a fan and temperature detector as a temperature control system and a pair of fluorescent excitation light source (with filter) and detector (with lens and filter) as the real time detection system.

FIG. 13 is an example schematic of the real-time PCR system comprising a heating source, a fan and temperature detector as a temperature control system and a pair of fluorescent excitation light source (with filter) and detector (with lens and filter) as the real time detection system; both temperature control system and real time detection system are controlled by Programmable logic controller (PLC). The PLC is further controlled by an interface installed on a smartphone.

2. A system, comprising:
a device, comprising:
a first plate comprising a polymer material and having a thickness less than or equal to 100 µm,
a second plate comprising a polymer material and having a thickness less than or equal to 100 µm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between $6 \times 10^{-5}$ W/K multiplied by the thickness of the heating/cooling layer and $1.5 \times 10^{-4}$ W/K multiplied by the thickness of the heating/cooling layer, and
a support frame configured to support at least one of the first plate and the second plate;
an optical source configured to direct electromagnetic radiation towards the heating/cooling layer,
a temperature sensor to monitor the temperature of the heating area in the device;
a fluorescent excitation light source;
a fluorescent detector;
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source.

3. The system of any prior embodiment, wherein the excitation light source can be but not limited to be a laser.

4. The system of any prior embodiment, wherein the excitation light source can be but not limited to be a LED.

5. The system of any prior embodiment, wherein the fluorescent detector is a photodetector.

6. The system of any prior embodiment, wherein the fluorescent detector is mounted on an optical tube.

7. The system of any prior embodiment, wherein the fluorescent detector is an image-based sensor.

8. A method for measuring fluorescence signal of sample liquid in assay device, comprising:
imaging the heating area in the assay device under thermal imager;
segmenting air bubble area or defect area and sample liquid area in the image;
measuring the signal of sample liquid area.

9. A method for measuring fluorescence signal of sample liquid in assay device, the time of measuring fluorescence signal is at the primer annealing and extension of each cycle.

10. A method for measuring fluorescence signal of sample liquid in assay device, the time of measuring fluorescence signal is at the end of primer annealing and extension of each cycle.

11. A method for measuring fluorescence signal of sample liquid in assay device, the time of measuring fluorescence signal is at the time of heating source is off in each cycle.

In certain embodiments, an imager (either for temperature sensing or for nucleic acid amplification monitoring) in the present invention, is connected to a computer, where various signal processing techniques, including machine learning is used. In certain embodiments, the signal processing results will be used to control the heating to the sample.

3. Heating Optical Pipe Structure

In certain embodiments, an optical pipe (also termed optical collimator), that collimates the light of a light source into the heating zone/plate, comprises a hollow tube with a reflective wall.

One embodiment of an optical pipe comprises a hollow structure (e.g. hollow tube) of round circle, rectangle, hexagonal, polygon, elliptic or combination thereof.

One preferred embodiment of an optical pipe comprises a hexagonal hollow structure.

One embodiment of an optical pipe comprises a hollow tube with a reflective wall (i.e. its inner wall, outer wall, or both reflective). The reflective wall can be a thin light reflective coating on a wall of the hollow tube. The reflective coating can be a thin metal film, such as gold, aluminum, silver, copper, or any mixture or combination thereof.

In certain embodiments, the hollow structure is made of a dielectric material of glasses, plastics, or a combination. In certain embodiments, the hollow structure is made of a metallic material.

Figure 14:
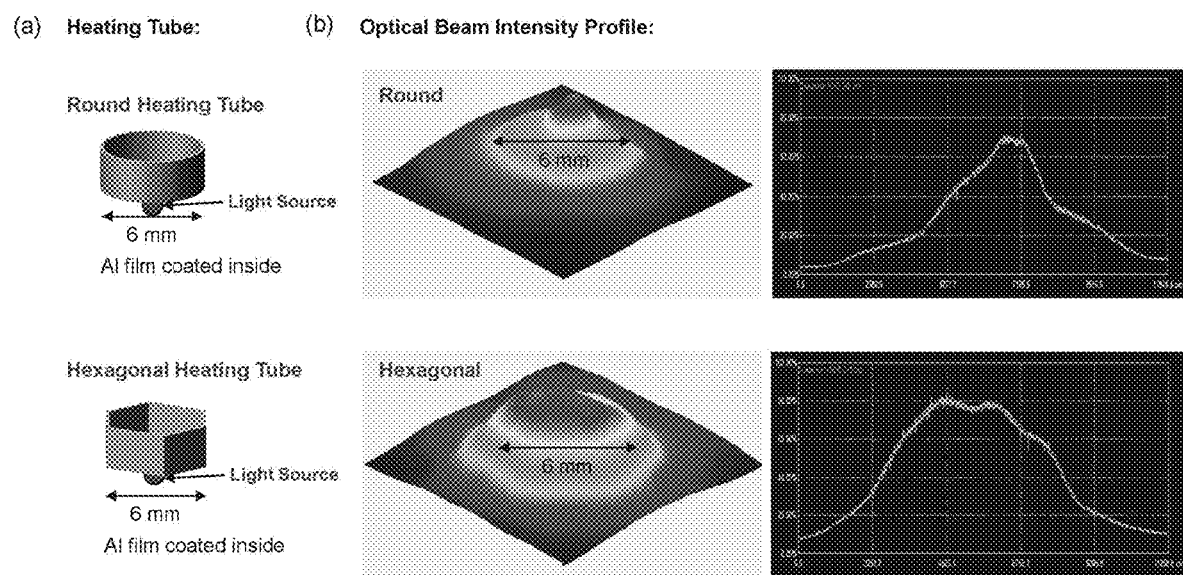
FIG. 14(a) shows a perspective view of a round heating tube and a hexagonal heating tube with a diameter of 6 mm and a point LED light source at the center of one tube end, according to some embodiments.
FIG. 14(b) shows the optical beam intensity measured at the other end of tube, according to some embodiments.

FIG. 14(a) shows a perspective view of a round heating tube and a hexagonal heating tube with a diameter of 6 mm and a point LED light source at the center of one tube end. (b) shows the optical beam intensity measured at the other end of tube. Clearly the hexagonal heating tube provides a more uniform distribution of heating light intensity in the central 6 mm area.

In some embodiments, the hollow pipe has a length in the range of 1 mm to 70 mm, an inner dimension (diameter or width) in the range of 1 mm to 40 mm, and a wall thickness in the range of 0.01 mm to 10 mm.

In some preferred embodiments, the hollow pipe for the light pipe has an inner diameter (or an average width) in a range of 1 mm to 5 mm, 5 mm to 10 mm, 10 mm to 15 mm, 15 mm to 20 mm, 20 mm to 30 mm, or 30 mm to 50 mm.

In some preferred embodiments, the hollow pipe for the light pipe has a wall thickness (or an average width) in a range of 0.001 mm to 0.01 mm, 0.01 mm to 0.1 mm, 0.1 mm to 0.5 mm, 0.5 mm to 1 mm, 1 mm to 2 mm, or 2 mm to 50 mm.

Example. Fast SNAP PCR Amplification of PUC57 plasmid DNA

The present technology uses the disclosed system for the PCR amplification of PUC57 plasmid DNA. The PCR reaction mixture was prepared by mixing 10 uM PUC57 Forward primer, 10 uM PUC57 Reverse primer and Cy5 labeled DNA probe with DNA buffer, 2.5 U/uL Aptataq Polymerase, 25 mM MgCl2, dNTP, additives as Betaine, bovine serum albumin (BSA), template DNA and ddH2O. 5 uL to 10 µl of the reaction was added onto the SNAP card and sealed for amplification.

In certain case, the whole card is incubated with 1% NaOH for 2 hours under 37° C., then washed with deionized water, then incubated with 4% bovine serum albumin (BSA) overnight under 4° C., washed with deionized water and dried at room temperature.

After amplification, the card is open and the production liquid is sucked out for Gel electrophoresis analyze.

Figure 15:
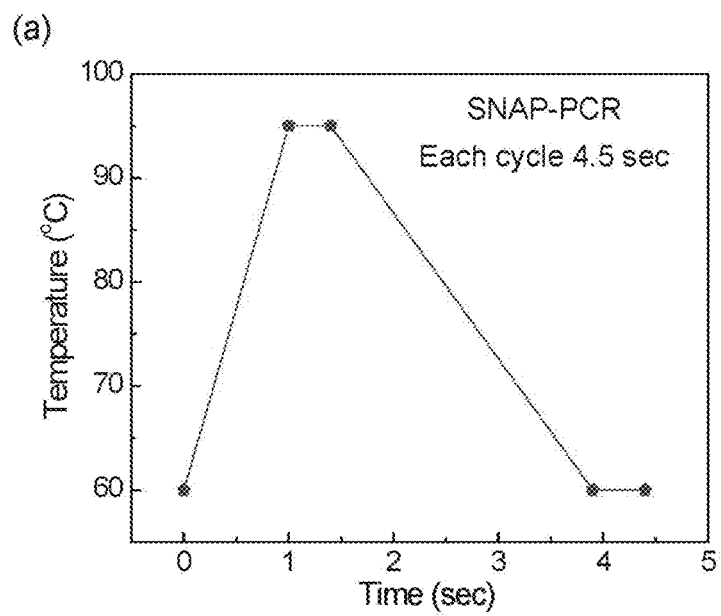
FIG. 15 shows a working SNAP PCR amplification of nucleic acid(*E-coli* plasmid DNA) with assay device demonstrating (a) 4.5 sec thermal cycling time (1 sec heating time from 60° C. to 95° C., 0.5 sec staying at 95° C., 2.5 sec cooling time from 95° C. to 60° C., and 0.5 sec staying at 60° C.); (b) Gel electrophoresis results of SNAP PCR products ran in 3 minutes (40 cycles) and conventional PCR products (40 cycles) ran in 40 minutes shows 3 min SNAP PCR has a comparable amplification performance as 40 min conventional PCR. The M line in the figure is a Gel electrophoresis marker with 100 bp line marked. Both SNAP PCR and conventional PCR have clear 100 bp production line and similar intensity. Negative sample without template does not show bar in gel analyze
Figure 15:
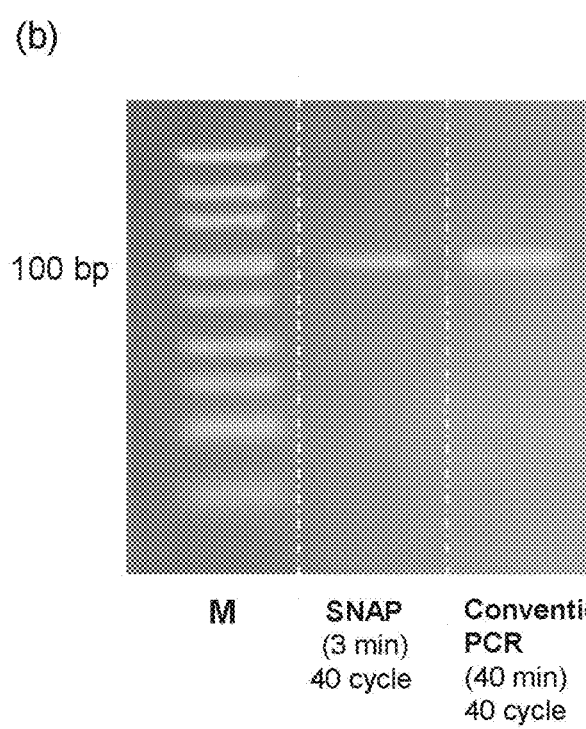

FIG. 15 shows a working SNAP PCR amplification of nucleic acid (E-*coli* plasmid DNA) with assay device demonstrating (a) 4.5 sec thermal cycling time (1 sec heating time from 60° C. to 95° C., 0.5 sec staying at 95° C., 2.5 sec cooling time from 95° C. to 60° C., and 0.5 sec staying at 60° C.); (b) Gel electrophoresis results of SNAP PCR products ran in 3 minutes (40 cycles) and conventional PCR products (40 cycles) ran in 40 minutes shows 3 min SNAP PCR has a comparable amplification performance as 40 min conventional PCR. The M line in the figure is a Gel electrophoresis marker with 100 bp line marked. Both SNAP PCR and conventional PCR have clear 100 bp production line and similar intensity. Negative sample without template does not show bar in gel analyze.

B. Clamping for Fast Thermal Change and/or Thermal Cycling

The present invention provides, among other things, devices and methods to improve the time and energy needed in thermal cycling of a liquid sample by reducing the flow of the liquid sample from the inside to the outside of a thermal cycling sample area.

In certain chemical, biological, or medical assays, a rapid change or a rapid thermal cycling of a sample temperature is needed (e.g. Polymerase chain reaction (PCR) for amplifying nucleic acids).

During thermal cycling, a liquid sample will change in its volume with temperature, and this can cause liquid sample flow. Liquid sample flow can change the sample temperature and increase the time and energy needed to do thermal cycling. Therefore, there is a need to reduce the liquid sample flow during thermal cycling.

One objective of the present invention is to address the need to reduce the liquid sample flow during thermal cycling. The present invention additionally provides devices and methods for isothermal nucleic acid amplification.

According to the present invention, a sample holder comprised a first plate and a second plate, where a liquid sample is sandwiched between the plates. In some embodiments, the two plate are fixed to each other. In some embodiments, the two plates are movable relative to each other. In some embodiments, there are spacers between the two plates to regulate the spacing between the two plates.

According to the present invention, a clamp structure comprises two rings, wherein the clamp has different configuration: inactive configuration and active configuration. In an inactive configuration, the two rings of the claim are open and the two rings do not insert any compression force on the sample plates. And in an activation configuration, the rings are being pushed towards to each other and insert a compressing force on the areas of a sample holder that are under the rings, and the comprising pinch force pinches the sample holder area under the ring together. In some embodiments, the pinching of the sample holder can reduce the sample in the inside of the clamp ring to flow to the outside of the clamp.

According to the present invention, during a thermal cycling, a clamp is used and active, and the use of the clamp reduces the flow of the liquid sample in the inside of the ring to the outside of the ring. The use of the claim reduces the liquid sample flow and hence the energy exchange between the sample in the inside of the ring to the outside of the ring, and reduce the heating energy for heating up the sample inside of the clamp, and increase the thermal cycling time.

According the present invention, during a thermal cycling, the use of a clamp can reduce air bubbles during thermal cycling, which in turn improve thermal cycling quality.

Figure 16:
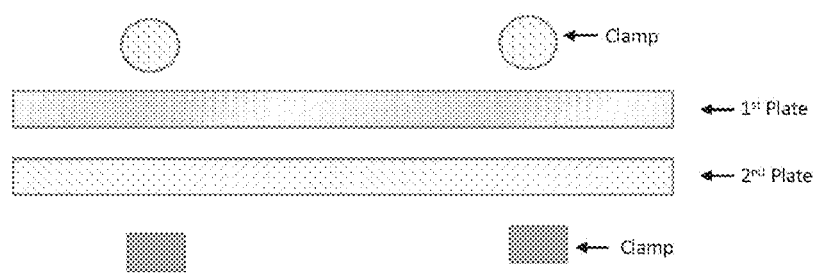
FIG. 16 shows a sectional view of an embodiment of the system of the present invention, comprising a sample holder and a clamping structure.
Figure 16:
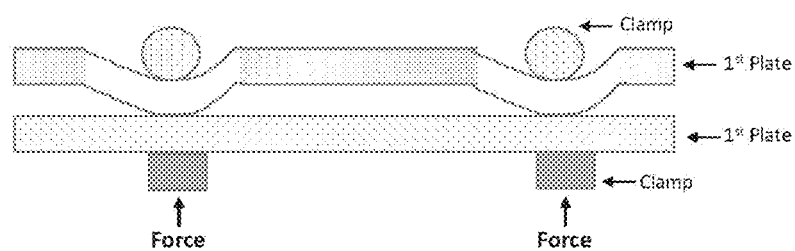

FIG. 16 shows a sectional view of an embodiment of the system of the present invention, comprising a sample holder and a clamping structure. The active clamp. Panel (A) illustrates the system before the clamping structure is activated, where the two rings of the clamp are open and hence does not assert a force to push the two plate together. Panel (B) illustrates that the clamp is activated, where a force is applied by the clamping structure to pinch the sample holder area that is pressed by the claim. The activation of the clamping structure, which clamps the area of the sample holder under the claim, will prevent a fluid sample from flowing outside the chamber as heat is delivered the heating/cooling layer. In some embodiments, the first plate and the second plate are fixed relative to each other. In some embodiments, the first plate and the second plate are movable relative to each other.

Figure 17:
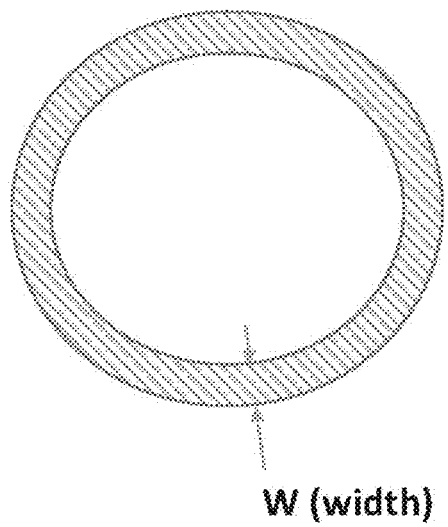
FIG. 17 shows a top view of an embodiment of one side of a ring clamp.
Figure 17:
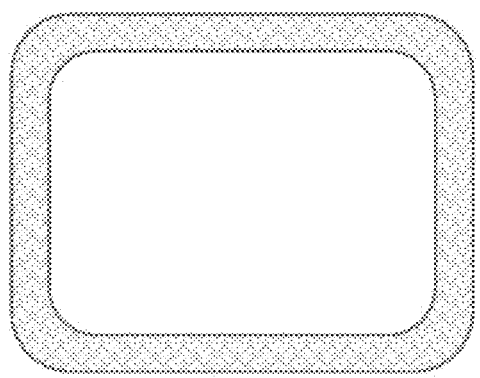

FIG. 17 shows a top view of an embodiment of one side of a ring clamp. Each ring has a width and a circumference. It shows a circular shaped ring clamp and a rectangle shaped ring clamp. In some embodiments, the ring clamp has other shapes including, but not limited to, round circle, rectangle, hexagonal, polygon, elliptic or combination thereof.

Figure 18:
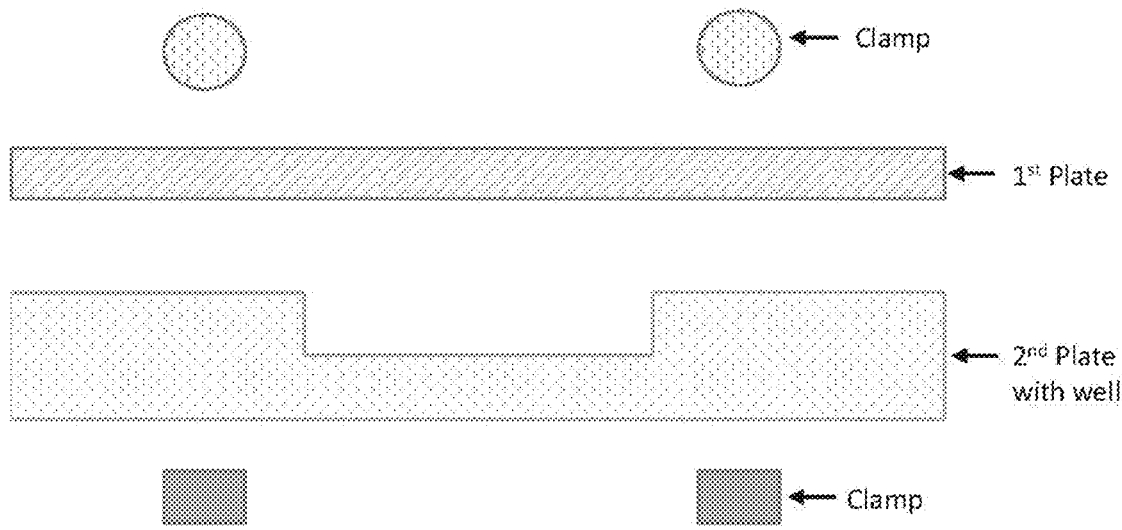
FIG. 18 shows a sectional view of an embodiment of the system of the present invention, comprising a sample holder, and a clamping structure. The sample holder comprises a first plate and a second plate that are movable to each other, wherein the second plate a well.
Figure 18:
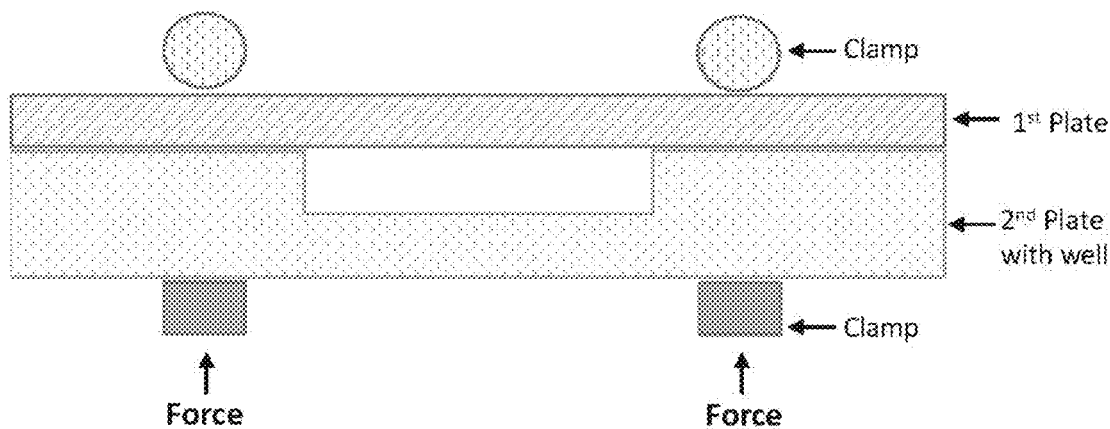

FIG. 18 shows a sectional view of an embodiment of the system of the present invention, comprising a sample holder, and a clamping structure. The sample holder comprises a first plate and a second plate that are movable to each other, where in the second plate a well. Panel (A) illustrates the system before the ring clamping structure is activated, where the two rings of the clamp does not assert a force to push the two plate together. Panel (B) illustrates the system after a force is applied by the clamping structure. The activation of the clamping structure will prevent a fluid sample from flowing outside the chamber as heat is delivered the heating/cooling layer.

Figure 19:
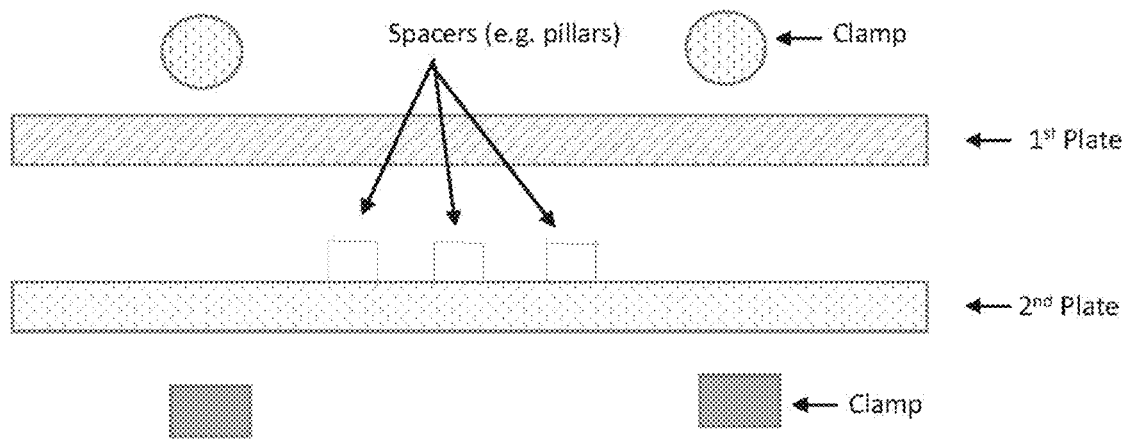
FIG. 19. shows a sectional view of an embodiment of the system of the present invention, comprising a sample holder and a clamping structure. The sample holder comprises a first plate, a second plate with spacers that are fixed on the inner surface.
Figure 19:
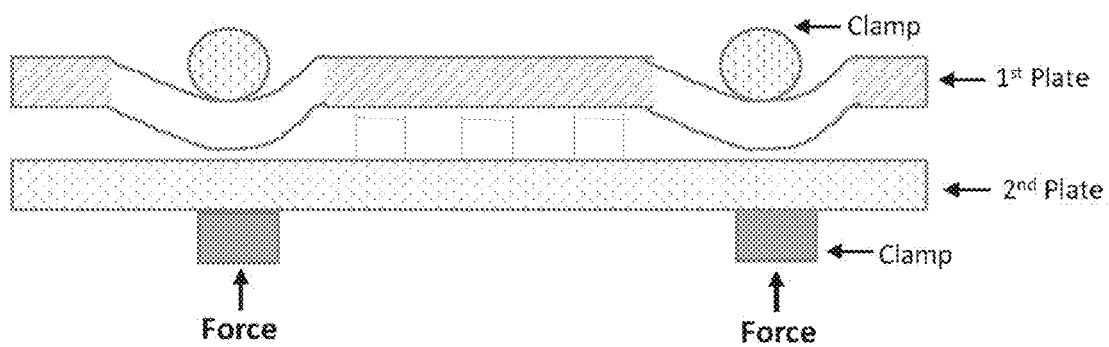

FIG. 19. shows a sectional view of an embodiment of the system of the present invention, comprising a sample holder and a clamping structure. The sample holder comprises a first plate, a second plate with spacers that are fixed on the inner surface. Panel (A) illustrates the system before the clamping structure is activated. Panel (B) illustrates the system after a force is applied by the clamping structure. The activation of the clamping structure will prevent a fluid sample from flowing outside the chamber as heat is delivered the heating/cooling layer.

Figure 20:
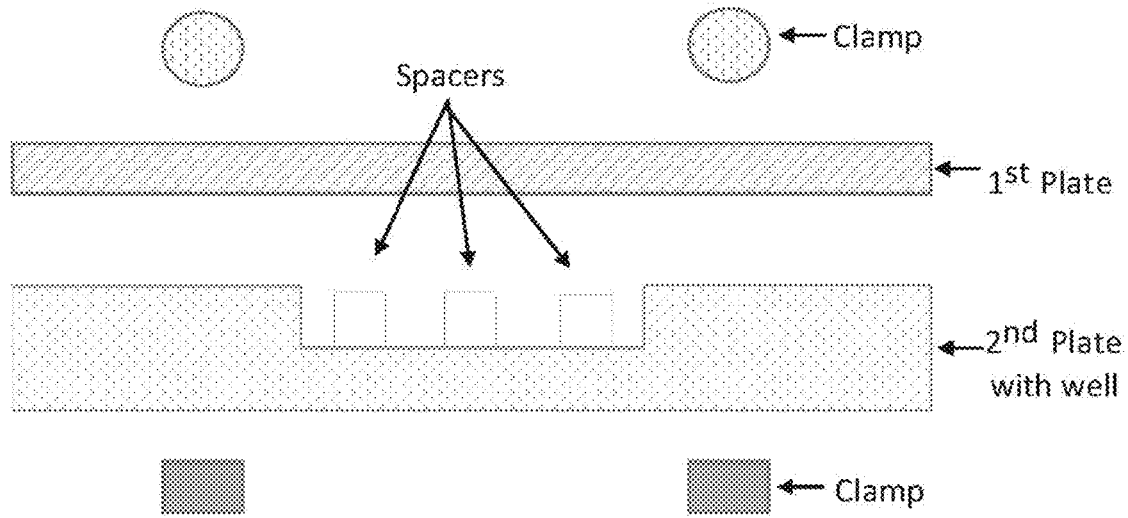
FIG. 20. shows a sectional view of an embodiment of the system of the present invention, comprising a first plate, a second plate with a well and spacers that are fixed on the inner surface, and a clamping structure.
Figure 20:
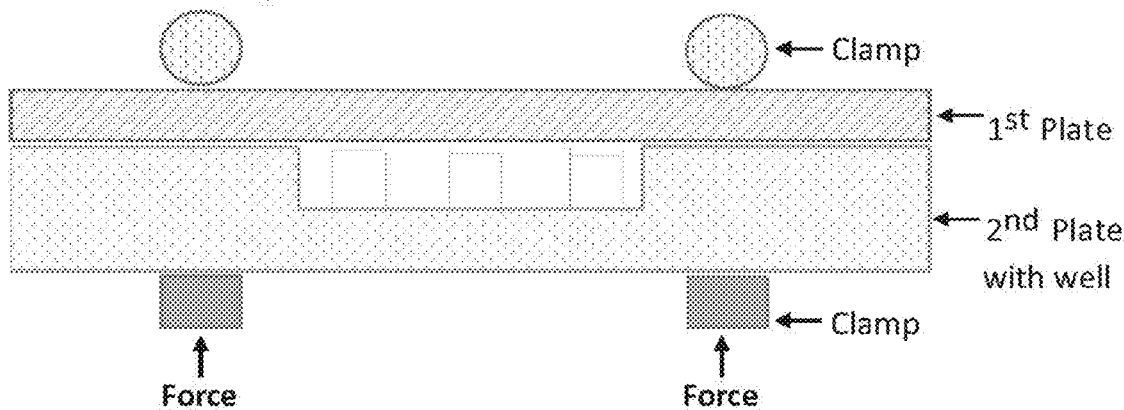

FIG. 20. shows a sectional view of an embodiment of the system of the present invention, comprising a first plate, a second plate with a well and spacers that are fixed on the inner surface, and a clamping structure. Panel (A) illustrates the system before the clamping structure is activated. Panel (B) illustrates the system after a force is applied by the clamping structure. The activation of the clamping structure will prevent a fluid sample from flowing outside the chamber as heat is delivered the heating/cooling layer.

Figure 21:
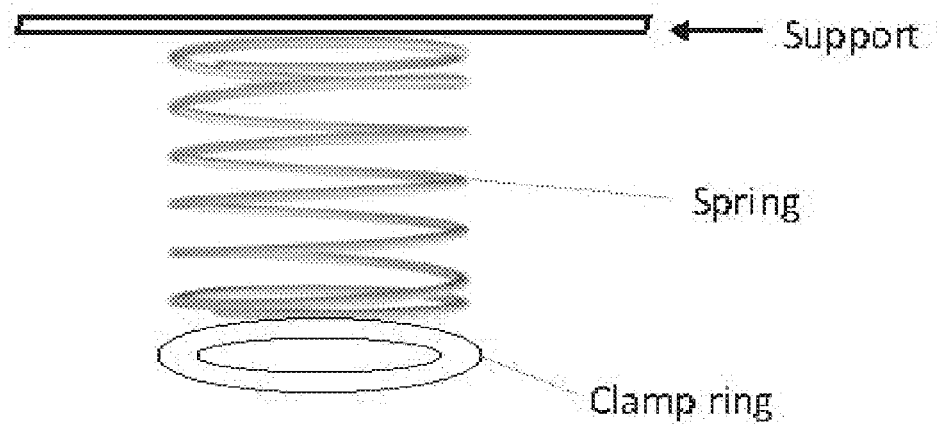
FIG. 21 schematically illustrates two types of clamping structures.
Figure 21:
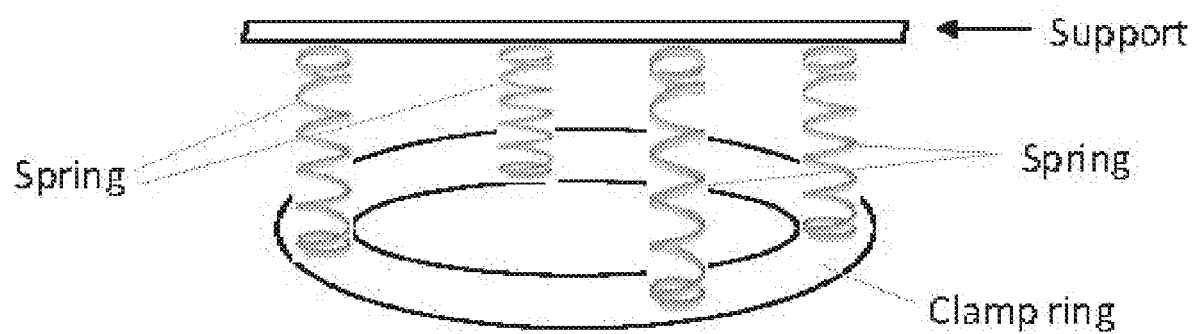

FIG. 21. shows exemplary embodiments of two types of clamping structures. Panel (A) comprises a support with a one-spring ring structure. Panel (B) comprises a support with a four-spring ring structure.

In one aspect, the present invention provides a device for rapidly changing the temperature of a fluidic sample, comprising: a first plate, a second plate, and a clamping structure, wherein:
  iii. the first plate and the second plate have on their inner surface a sample contact area for contacting a fluidic sample; wherein the sample contact area of the first plate and the second plate face each other, are separated by a distance of 200 um or less, and are capable of sandwiching the sample between them;
  iv. the clamping structure comprises a top ring and a bottom ring that are movable to each other and comprise:
    a. an open configuration, wherein the top ring and the bottom ring do not push the first plate and second plate together; and
    b. a closed configuration, wherein the top ring and the bottom ring assert a force again each other to push the first plate and the second plate in the closed configuration, so the flow of a sample from the inside to the outside of a ring area during thermal cycling is reduced compared to without using a clamping structure.

In one aspect, the present invention provides a device for rapidly changing the temperature of a fluidic sample, comprises: a first plate, a second plate with a well, and a clamping structure, wherein:
  iii. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;
  iv. the clamping structure comprises a top ring and a bottom ring that are movable to each other and comprise:
    c. an open configuration, wherein the top ring and the bottom ring do not push the first plate and the second plate with a well together; and
    d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

As illustrated in FIG. 17 (Panel A and Panel B) and FIG. 18 (Panel A and Panel B), the sectional views of certain embodiments show an open configuration (before clamp activation) and a closed configuration (after the clamp is activated).

In certain embodiments, the first plate and second plate are flat. FIG. 17 illustrates an exemplary flat plate.

In certain embodiments, the second plate further comprises a wall. FIG. 18 illustrates an exemplary well in the second plate.

In one aspect, the present invention provides a device for rapidly changing the temperature of a fluidic sample, comprises: a first plate, a second plate, spacers, and a clamping structure, wherein:
  iv. the first plate and/or second plate comprise spacers fixed to the inner surface of the first plate and/or second plate,
  v. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them,
  vi. the clamping structure comprises a top ring and a bottom ring that are movable to each other and comprise:
    c. an open configuration, wherein the top ring and the bottom ring do not push the first plate and the second plate with a well together; and
    d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a device for rapidly changing the temperature of a fluidic sample, comprises: a first plate, a second plate with a well, spacers, and a clamping structure, wherein:
  iv. the first plate and/or second plate with a well comprise spacers fixed to the inner surface of the first plate and/or second plate, v. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them, vi. the clamping structure comprises a top ring and a bottom ring that are movable to each other and comprise:

c. an open configuration, wherein the top ring and the bottom ring do not push the first plate and the second plate with a well together; and d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

As illustrated in FIG. 19 (Panel A and Panel B) and FIG. 20 (Panel A and Panel B), the sectional views of the embodiments show an open configuration (before clamp activation) and a closed configuration (after the clamp is activated) wherein spacers are positioned between the first plate and the second plate to regulate the distance between the two plates (i.e., the spacing of the first plate and the second plate), to regulate the sample thickness. The spacers allow the thickness of the sample between the first plate and the second plate to be uniform over a large area, even when the first plate and second plate are thin and flexible.

FIG. 19 illustrates certain embodiments where the first plate and the second plate are flat.

FIG. 20 illustrates certain embodiments where the second plate further comprises a well.

In one aspect, the present invention provides a device for rapidly changing the temperature of a fluidic sample, comprising: a first plate, a second plate, and a clamping structure, wherein:

iii. the first plate and the second plate have on their inner surface a sample contact area for contacting a fluidic sample; wherein the sample contact area of the first plate and the second plate face each other, are separated by a distance of 200 um or less, and are capable of sandwiching the sample between them;

iv. the clamping structure comprises a top ring and a bottom ring that are movable to each other and comprise:

a. an open configuration, wherein the top ring and the bottom ring do not push the first plate and second plate together; and b. a closed configuration, wherein the top ring and the bottom ring assert a force again each other to push the first plate and the second plate in the closed configuration, so the flow of a sample from the inside to the outside of a ring area during thermal cycling is reduced compared to without using a clamping structure.

In one aspect, the present invention provides a device for rapidly changing the temperature of a fluidic sample, comprising: a first plate, a second plate with a well, and a clamping structure, wherein:

v. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;

vi. the clamping structure comprises a top ring and a bottom ring that are movable to each other and comprise:

d. an open configuration, wherein the top ring and the bottom ring do not push the first plate and the second plate with a well together; and e. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a device for rapidly changing the temperature of a fluidic sample, comprising: a first plate, a second plate, spacers, and a clamping structure, wherein:

iv. the first plate and/or second plate comprise spacers fixed to the inner surface of the first plate and/or second plate, v. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them, vi. the clamping structure comprises a top ring and a bottom ring that are movable to each other and comprise:

c. an open configuration, wherein the top ring and the bottom ring do not push the first plate and the second plate with a well together; and d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a device for rapidly changing the temperature of a fluidic sample, comprising: a first plate, a second plate with a well, spacers, and a clamping structure, wherein:

iv. the first plate and/or second plate with a well comprise spacers fixed to the inner surface of the first plate and/or second plate, v. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them, vi. the clamping structure comprises a top ring and a bottom ring that are movable to each other and comprise:

c. an open configuration, wherein the top ring and the bottom ring do not push the first plate and the second plate with a well together; and d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a method for rapidly changing the temperature of a fluidic sample, comprising: a first plate, a second plate, and a clamping structure, wherein:
  iii. the first plate and the second plate have on their inner surface a sample contact area for contacting a fluidic sample; wherein the sample contact area of the first plate and the second plate face each other, are separated by a distance of 200 um or less, and are capable of sandwiching the sample between them;
  iv. the clamping structure comprises a top ring and a bottom ring that are movable to each other and comprise:
    a. an open configuration, wherein the top ring and the bottom ring do not push the first plate and second plate together; and
    b. a closed configuration, wherein the top ring and the bottom ring assert a force again each other to push the first plate and the second plate in the closed configuration, so the flow of a sample from the inside to the outside of a ring area during thermal cycling is reduced compared to without using a clamping structure.

In one aspect, the present invention provides a method for rapidly changing the temperature of a fluidic sample, comprising: a first plate, a second plate with a well, and a clamping structure, wherein:
  i. the first plate and the second plate with a well have on their inner surface a sample contact area for contacting a fluidic sample; wherein the sample contact area of the first plate and the second plate face each other, are separated by a distance of 200 um or less, and are capable of sandwiching the sample between them;
  ii. the clamping structure comprises a top ring and a bottom ring that are movable to each other and comprise:
    a) an open configuration, wherein the top ring and the bottom ring do not push the first plate and the second plate with a well together; and
    b) a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a method for rapidly changing the temperature of a fluidic sample, comprising: a first plate, a second plate, spacers, and a clamping structure, wherein:
  iv. the first plate and/or second plate comprise spacers fixed to the inner surface of the first plate and/or second plate,
  v. the first plate and the second plate comprise on their inner surface a sample contact area for contacting a fluidic sample; wherein the sample contact area of the first plate and the second plate face each other, are separated by a distance of 200 um or less, and are capable of sandwiching the sample between them,
  vi. the clamping structure comprises a top ring and a bottom ring that are movable to each other and comprise:
    c. an open configuration, wherein the top ring and the bottom ring do not push the first plate and the second plate with a well together; and
    d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In one aspect, the present invention provides a method for rapidly changing the temperature of a fluidic sample, comprising: a first plate, a second plate with a well, spacers, and a clamping structure, wherein:
  iv. the first plate and/or second plate with a well comprise spacers fixed to the inner surface of the first plate and/or second plate,
  v. the first plate and the second plate with a well comprise on their inner surface a sample contact area for contacting a fluidic sample; wherein the sample contact area of the first plate and the second plate face each other, are separated by a distance of 200 um or less, and are capable of sandwiching the sample between them,
  vi. the clamping structure comprises a top ring and a bottom ring that are movable to each other and comprise:
    c. an open configuration, wherein the top ring and the bottom ring do not push the first plate and the second plate with a well together; and
    d. a closed configuration, wherein the top ring and the bottom ring assert a force again each other to push the first plate and the second plate with a well in the closed configuration, so the flow of a sample from the inside to the outside of a ring area during thermal cycling is reduced compared to without using a clamping structure.

In certain embodiments, the device further comprises a heating layer.

In certain embodiments, the heating layer is positioned on the inner surface, the outer surface, or on the inside of one of the plates.

In certain embodiments, the heating layer is configured to heat a relevant volume of the sample, wherein the relevant volume of the sample is a portion or an entirety of the sample that is being heated to a desired temperature.

In certain embodiments, the device further comprising a cooling layer.

In certain embodiments, the cooling layer is positioned on the inner surface, the outer surface, or inside one of the plates.

In certain embodiments, the cooling layer is configured to cool the relevant sample volume.

In certain embodiments, the cooling layer comprises a layer of material that has a thermal conductivity to thermal capacity ratio of 0.6 $cm^2$/sec or larger.

In certain embodiments, the clamping structure is attached to either one or both of the first and second plates, and wherein the clamping structure is configured to hold the device and regulate the thickness of the sample layer during the heating of the device.

In certain embodiments, the clamp is in a shape such as, but not limited to, circle, triangle, round, elliptical, polygon, or any superposition of these shapes.

In certain preferred embodiments, the shape of the clamp is circle and elliptical.

In certain embodiments, the width of the clamp is 100 um, 300 um, 500 um, 1 mm, 2 mm, 3 mm, 4 mm, 5 mm, 10 mm, or in a range between any of the two values.

In certain preferred embodiments, the width of the clamp is 1 mm, 2 mm, and 3 mm. In certain embodiments, the thickness of the clamp is 100 um, 300 um, 500 um, 1 mm, 2 mm, 3 mm, 4 mm, 5 mm, 10 mm, 15 mm, 20 mm, 30 mm or in a range between any of the two values.

In certain preferred embodiments, the thickness of the clamp is 1 mm, 2 mm, 10 mm, and 15 mm.

In certain embodiments, the circumference of the clamp is 5 mm, 10 mm, 20 mm, 30 mm, 38 mm, 50 mm, 62 mm, 100 mm or in a range between any of the two values. In certain preferred embodiments, the circumference of the clamp is 38 mm and 62 mm.

In certain preferred embodiments, the pressure provided by clamp on the card is 5 PSI, 10 PSI, 30 PSI, 60 PSI, 90 PSI, 100 PSI, 150 PSI, 200 PSI, 500 PSI or in a range between any of the two values.

In certain preferred embodiments, the pressure provided by clamp on the card is less than 30 PSI, less than 60 PSI, and less than 90 PSI.

In certain embodiments, the material of clamp includes, but not limited to, glass, quartz, oxides, silicon-dioxide, silicon-nitride, hafnium oxide (HfO), aluminum oxide (AlO), semiconductors: (silicon, GaAs, GaN, etc.).

In certain preferred embodiments, the material of clamp includes, but not limited to metals (e.g. gold, silver, coper, aluminum, Ti, Ni, etc.), ceramics, or any combinations of thereof.

In certain preferred embodiments, the material of clamp includes, but not limited to, polymers (e.g. plastics) or amorphous organic materials. The polymer materials include, but not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain preferred embodiments, the material of clamp includes, but not limited to glass, quartz, oxides, silicon-dioxide, silicon-nitride, hafnium oxide (HfO), aluminum oxide (AlO), semiconductors: (silicon, GaAs, GaN, etc.), plastics, metals (e.g. gold, silver, coper, aluminum, Ti, Ni, etc.), ceramics, or any combinations of thereof.

C. Fast Temperature Changes

Working Principle

One aspect of the present invention is to reduce thermal cycling time, to reduce the heating energy used for such cycling, to increase energy efficiency, and to reduce total power consumption.

The thermal cycling time (speed), heating energy, energy efficiency, and power consumption are related. When more heating energy is needed in raising the temperature of a given sample, the more energy must be removed in cooling the sample, which, in turn, needs more time and/or more energy to perform the cooling.

Many thermal cyclers in prior art require a use of a significant amount of heating energy to the sample holder (e.g. plastic chamber walls) rather than to the sample; a use of lateral thermal conduction through large thermal mass and poor-thermal conduction materials of the sample holder as the major cooling channel to cool the sample (note that a material needs to absorb and release energy to perform a thermal conduction); a use of conductive cooling as major cooling method, and/or a use of an extra cooling gas or a moving cooling block. These approaches lead to issues of long thermal cycling time, high heating energy, low energy efficiency, bulky apparatus, and/or high cost.

Based on theoretical and experimental investigations, the present invention provides solutions to certain drawbacks in a sample thermal cycling in the prior arts.

To illustrate the working principle of the present invention, let us look at the energy components in heating and cooling a sample by a thermal cycler. The heating and cooling share three energy components: (i) one related to thermal mass (i.e. a material's ability to absorb and store energy; larger the thermal mass, more energy needed to be added for heating up and more energy needed to be removed in cooling), (ii) heat loss by thermal radiation, and (iii) heat loss by thermal conduction/convection. To heat fast, all three energy components need to be small. But to cool fast, the first energy component needs to be small, but at least one of the last two energy components needs to be large.

Through theoretical and experimental investigation, the present invention balances and/or optimizes the three energy components for achieving rapid heating and cooling. Particularly, in certain embodiments, the present invention reduces the thermal mass that must be heated in a thermal cycle, limits lateral thermal conduction, and uses radiative heat loss as a primary way to remove energy from the heated sample.

According to the present invention, the cooling of a sample is significantly by thermal radiative cooling, not by thermal conduction cooling. Therefore, in a thermal cycling, most or a significant part of the non-sample materials on a sample holder do not absorb and release as much energy as that in a thermal conduction dominated system.

One aspect of the present invention provides devices and methods that reduce the heating to non-sample materials on the sample holder.

Another aspect of the present invention provides devices and methods that reduce lateral thermal conduction through large thermal mass and poor-thermal conduction materials on the sample holder.

Another aspect of the present invention provides devices and methods that use thermal radiative cooling as the major cooling channel to cool the sample.

Another aspect of the present invention provides devices and methods that place spacers between to plates (i.e. walls) that sandwich a sample. The spacers provides good sample uniformity over a large area, even when the plates are thin (e.g. 25 um thick) and flexible. Without spacers, it can be difficult to achieve a uniform sample thickness, when the two plates that confine the sample become very thin.

Another aspect of the present invention provides devices and methods that make the device operation easier.

According to the present invention, the thermal radiative cooling uses a material layer are configured (in terms of materials and shape) that has good thermal radiative cool properties during the cooling, and a low thermal mass (hence a low heating energy) during heating.

According to the present invention, the sample holder is configured to limit/minimize the thermal conduction cooling.

According to the present invention, the sample thickness, the first plate and the second plate (which are facing each other) of the sample chamber wall thickness are configured to reduce the lateral thermal conduction (i.e. in the direction of the plate).

According to the present invention, in some embodiments, the thermal radiative cooling layer is the same heating/cooling layer of the heating layer, but the ratio of the cooling zone to the heating zone, the material properties, and the material thickness and geometry are configured to make the heating/cooling layer has a low thermal mass in heating and high rate of thermal radiative cooling.

Another objective of the present invention is to make one cycle of a sample temperature change (e.g. from 95° C. to 55° C.) in a few seconds or even sub-second (e.g., 0.7 second).

Another aspect of the present invention is that it provides useful devices and methods for isothermal nucleic acid amplification, where a sample temperature needs to be raised from environment to an elevated temperature (i.e. 65° C.) and keep there for a period of time (i.e., 5-10 min). One aspect of the present invention is to raise the temperature fast, to use less energy, and to make the apparatus compact, lightweight, and portable.

One aspect of the present invention is that the thermal masses of the card as well as the sample are minimized to reduce the energy needed for heating and the energy to be removed for cooling.

Another aspect of the present invention is that in certain embodiments, only a small portion of the sample is heated and/or cooled.

Another aspect of the present invention is that it uses a thin high thermal conductivity layer that has an area size larger than that of the relevant sample area.

Another aspect of the present invention is that it uses a thin high thermal conductivity layer that has an area size larger than the heating zone area.

Another aspect of the present invention provides devices and methods that reduce the heating to non-sample materials on the sample holder.

Another aspect of the present invention provides devices and methods that reduce lateral thermal conduction in large thermal mass and poor-thermal conduction materials on the sample holder.

Another aspect of the present invention provides devices and methods that use thermal radiative cooling as the major cooling channel to cool the sample.

Another aspect of the present invention is that it can achieve fast thermal cycling without using a cooling gas.

Another aspect of the present invention is that the thermal masses of the card as well as the sample are minimized to reduce the energy needed for heating and the energy to be removed for cooling.

Another aspect of the present invention is that the radiative cooling and convention cooling are adjusted for rapid cooling.

Another aspect of the present invention is that heat sink for radiative cooling and/or convention cooling is used for rapid cooling.

Figure 22:
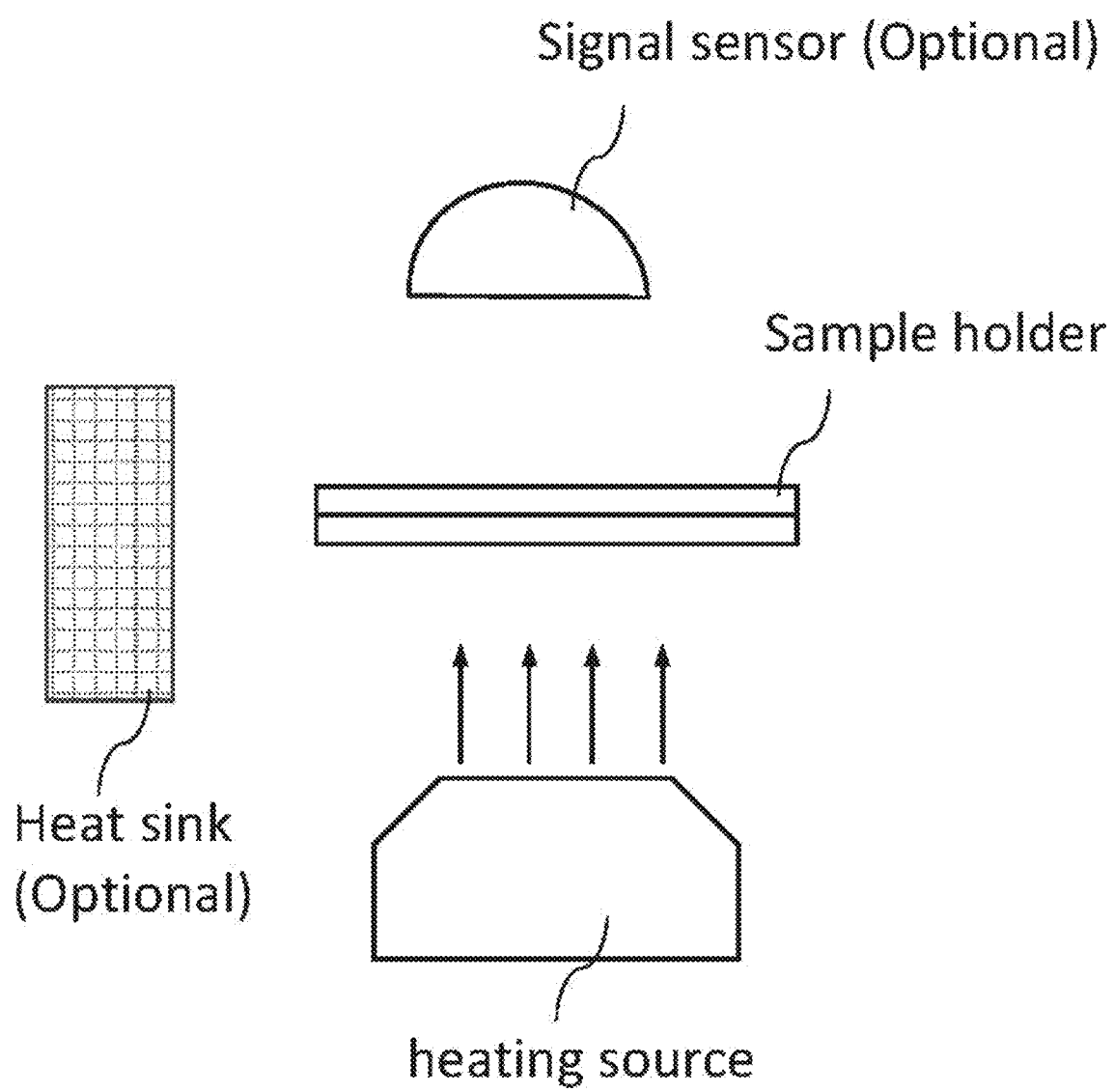
FIG. 22 schematically illustrates certain components of a system for changing the temperature of a sample and for monitoring a signal from the sample, according to some embodiments.

One embodiment of a sample thermal cycling apparatus in the present invention (as illustrated in FIG. 22) comprises: (i) a sample holder, termed "RHC (rapid heating and cooling) Card" or "sample card", that allows a rapid heating and cooling of a sample on the card; (ii) a heating source, (iii) an extra heat sink (optional), (iv) a temperature control system, and (v) a signal monitoring system (optional). The temperature control system and signal monitoring system are not explicitly illustrated in FIG. 22, but may be used to control the output of the heating source. In some embodiments, a signal sensor is included to detect optical signals from samples on the sample holder. Note that certain embodiments of the present invention can have just one or several components illustrated in FIG. 22.

Figure 23A:
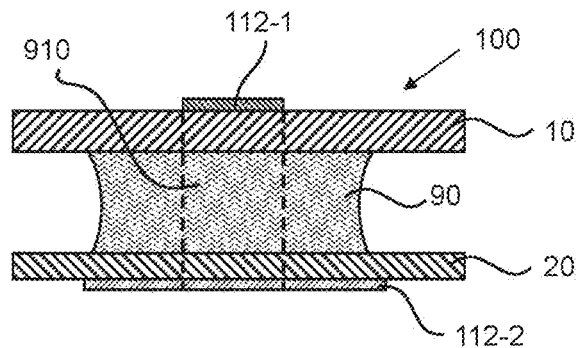
FIG. 23A schematically illustrates a device with a heating layer separated from a cooling layer, in accordance with one or more embodiments.
Figure 23B:
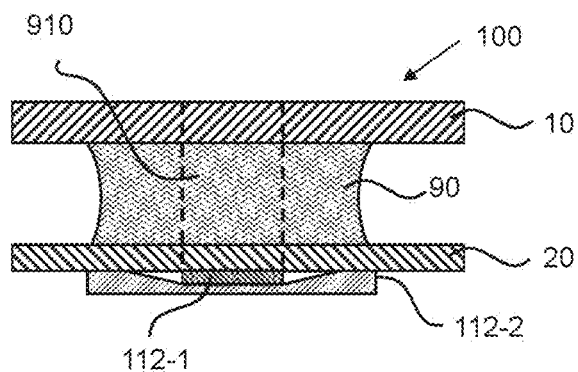
FIG. 23B schematically illustrates an embodiment having a heating layer contacting a cooling layer.

FIGS. 23A and 23B show sectional views of two embodiments of the device of the present invention. FIG. 23A shows an embodiment comprising a separate heating layer (112-1) and a separate cooling layer (112-2), wherein the heating layer (112-1) is on the outer surface of one of the plates and the cooling layer (112-2) is on the outer surface of the other plate. FIG. 23B shows an embodiment comprising a heating layer (112-1) and a cooling layer (112-2), wherein the heating layer (112-1) and the cooling layer (112-2) are structurally distinct but in contact with each other, and the two layers are both on the outer surface of one of the plates.

SH-1 One detailed description of one embodiment of a RHC card in the present invention is that a device for rapidly changing the temperature of a fluidic sample, comprising:

a first plate (10), a second plate (20), a heating layer (112-1), and a cooling layer (112-2), wherein:

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates, and configured to cool the relevant sample volume; and comprises a layer of material that that has a thermal conductivity to thermal capacity ratio of 0.6 $cm^2$/sec or larger;

wherein the distance between the cooling layer and a surface of the relevant sample volume is zero or less than a distance that is configured to make the thermal conductance per unit area between the cooling layer and the surface of the relevant sample volume equal to 70 W/($m^2$·K) or larger; and wherein, in some embodiments, the heating layer and cooling layer are the same material layer that have a heating zone and cooling zone, and wherein the heating zone and cooling zone can have the same area or different areas.

SH-2 Another detailed description of one embodiment of a RHC card (sample holder) in the present invention is that a device for rapidly changing the temperature of a fluidic sample, comprising:

A first plate (10), a second plate (20), a heating layer (112-1), and a cooling layer (112-2), wherein:

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates; and configured to cool the relevant sample volume; and comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;

wherein the distance between the cooling layer and a surface of the relevant sample volume is zero or less than a distance that is configured to make the thermal conductance per unit area between the cooling layer and the surface of the relevant sample volume equal to 150 W/(m$^2$·K) or larger; and wherein, in some embodiments, the heating layer and cooling layer are the same material layer that have a heating zone and cooling zone, and wherein the heating zone and cooling can have the same area or different areas.

Figure 24A:
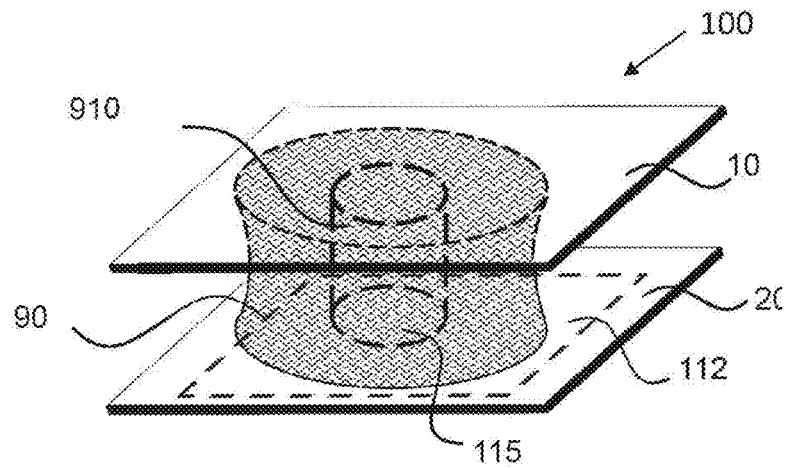
FIGS. 24A and 24B schematically illustrate a prospective view and a sectional view, respectively, of a combination heating/cooling layer on an outer surface of a plate, in accordance with one or more embodiments.
Figure 24B:
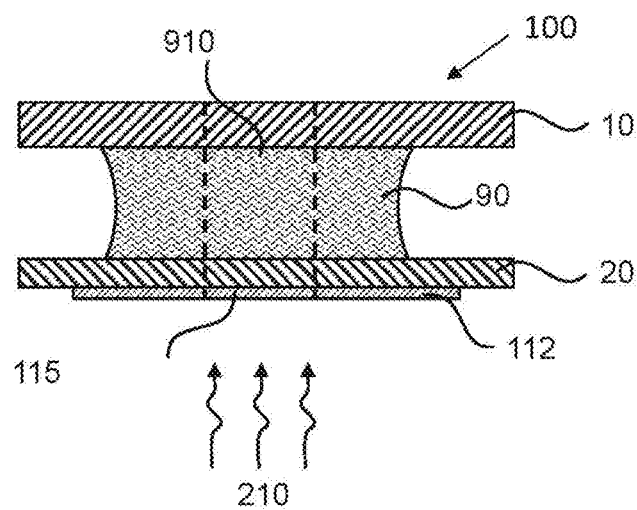

As illustrated in FIGS. 24A and 24B, in some embodiments of the present invention, the heating layer and the cooling layer are combined into one layer (heating/cooling layer) creating a heating zone and cooling zone, where the cooling zone is larger than the heating zone. A sample card 100 (also termed "RHC card") may include two thin plates (10, 20) that sandwich a fluidic sample (90) between them and a heating/cooling layer (112) is under the sample, and the heating/cooling layer (112) is heated by a heat source positioned away from the card. According to an embodiment, at the edge of the sample, there are no walls to contain the sample, but the edge of the sample will not flow due to capillary forces that keep the shape of the fluidic sample edges.

Figure 25A:
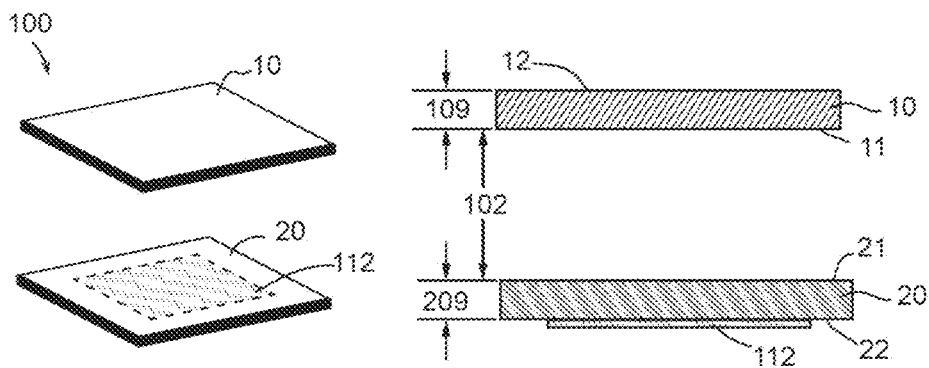
FIG. 25A schematically illustrates perspective and sectional views of the device in an open configuration, in accordance with one or more embodiments.
Figure 25B:
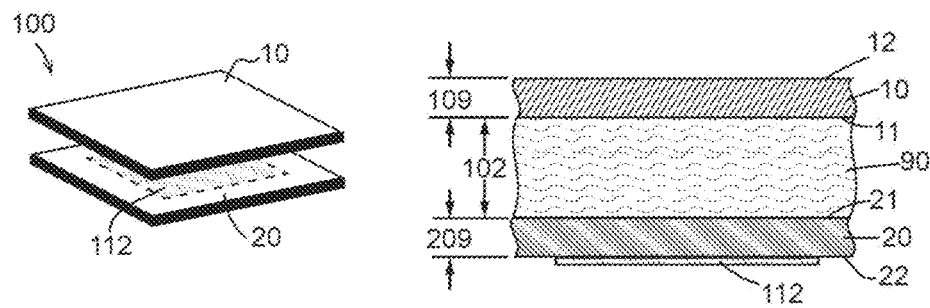
FIG. 25B schematically illustrates perspective and sectional views of the device when the sample holder is in a closed configuration, in accordance with one or more embodiments.

As illustrated in FIG. 25A, plates 10 and 20 may have inner surfaces 11 and 21 that are separated by a spacing 102, according to an embodiment. Spacing 102 may be large when the device is ready to receive a sample (e.g., in an open position). FIG. 25B illustrates a closed configuration of device 100 where spacing 102 is made small (e.g., less than about 200 μm) to sandwich a sample 90 between plates 10 and 20. In this embodiment, heating/cooling layer 112 is positioned on an outer surface 22 of plate 20.

SH-3 Another detailed description of one embodiment of a RHC card in the present invention is that a device for rapidly changing the temperature of a fluidic sample, comprising:

a first plate (10), a second plate (20), and a heating/cooling layer (112), wherein:

the first plate (10) and the second plate (20) face each other, and are separated by a distance from each other;

each of the plates has, on its respective inner surface (11, 21), a sample contact area for contacting a fluidic sample; wherein the sample contact areas are facing each other, are in contact with the sample, confines a sample between them, and have an average separation distance (102) from each other, and the sample;

the heating/cooling layer (112) is on the outer surface (22) of the second plate (20); and the heating/cooling layer is configured to comprise a heating zone and a cooling zone; wherein the heat zone is configured to heat the fluidic sample, the cooling zone is configured to cool the sample by thermal radiative cooling;

wherein the heating zone is configured to receive heating energy from a heating source and configured to have an area smaller than the total area of the heating/cooling layer; and wherein at least a part of a heating zone of the heating layer overlaps with the sample area.

SH-4 A device for rapidly changing the temperature of a fluidic sample, comprising: a first plate (10), a second plate (20), a heating layer (112-1), and a cooling layer (112-2), wherein:

the first and second plates are movable relative to each other into different configurations;

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer:

is positioned on the inner surface, the outer surface, or inside of one of the plates, is configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates; and configured to cool the relevant sample volume; and comprises a layer of material that that has a thermal conductivity to thermal capacity ratio of 0.6 cm$^2$/sec or larger;

wherein one of the configurations is an open configuration, in which: the two plates are partially or completely separated apart and the average spacing between the plates is at least 300 um;

wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less.

SH-5 A device for rapidly changing the temperature of a fluidic sample, comprising:

a first plate (10), a second plate (20), spacers, a heating layer (112-1), and a cooling layer (112-2), wherein:

the first and second plates are movable relative to each other into different configurations;

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

one or both of the plates comprise the spacers and the spacers are fixed on the inner surface of a respective plate;

the spacers have a predetermined substantially uniform height that is equal to or less than 200 microns, and the inter-spacer-distance is predetermined;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates; and configured to cool the relevant sample volume; and comprises a layer of material that that has a thermal conductivity to thermal capacity ratio of 0.6 cm²/sec or larger;

wherein one of the configurations is an open configuration, in which: the two plates are partially or completely separated apart, the spacing between the plates is not regulated by the spacers, and the sample is deposited on one or both of the plates; and wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In some embodiments, the heating/cooling layer (112) can be on the inner surface (21) or inside the second plate (20), rather than on the outer surface (22) of the second plate (20).

In some embodiments of all embodiments of devices, the RHC card further comprises spacers that are positioned between the first and second plate to regulate the distance between the two plates (i.e. the spacing of the plates), and hence to regulate the sample thickness. The spacers can allow the thickness of the sample between the two plates uniform over a large area, even when the plates are thin and flexible.

In some embodiments, there are more than one heating/cooling layer.

A. Small Relevant Sample Volume (RE Ratio)

Reduction of the sample volume that should be heated or cooled to a desirable temperature can shorten the heating time and cooling time in a thermal cycle as well as heating power. A reduction of the sample volume that will be thermal cycled can be achieved by (a) reducing the entire sample volume or (b) heating just a portion of the sample on the sample holder. The term "relevant sample" or "relevant sample volume" refers to the volume of the sample that is being heated and/or cooled to desired temperatures during a thermal cycling, and the relevant sample can be a portion or an entire volume of a sample on a sample holder, and there is no fluidic separation between the portion of the sample to the rest of the sample.

In some embodiments, the relevant volume of the sample is 0.001 ul, 0.005 ul, 0.01 ul, 0.02 ul, 0.05 ul, 0.1 ul, 0.2 ul, 0.5 ul, 1 ul, 2 ul, 5 ul, 10 ul, 20 ul, 30 uL, 50 ul, 100 ul, 200 ul, 500 ul, 1 ml, 2 ml, 5 ml, or in a range between any of the two values.

In some preferred embodiments, the relevant sample volume is in a range of 0.001 uL to 0.1 uL, 0.1 um to 2 uL, 2 uL to 10 uL, 10 uL to 30 uL, 30 uL to 100 uL, 100 uL to 200 uL, or 200 uL to 1 mL.

In some preferred embodiments, the relevant sample volume is in a range of 0.001 uL to 0.1 uL, 0.1 um to 1 uL, 0.1 uL to 5 uL, or 0.1 uL to 10 uL.

In certain embodiments, the ratio of the relevant sample to entire sample volume (RE ratio) is 0.01%, 0.05%, 0.1%, 0.5%, 0.1%, 0.5%, 1%, 5%, 10%, 20%, 30%, 40%, 50%, 60%, 70%, 80%, 90%, 100%, or in a range between any of the two values.

In some preferred embodiments, the RE ratio is in a range of between 0.01% and 0.1%, 0.1% and 1%, 1% and 10%, 10% and 30%, 30% and 60%, 60% and 90%, or 90% and 100%.

To heat only a portion of the sample, in some embodiments, the area of the heating zone is only a fraction of the sample lateral area, and the fraction (i.e. the ratio of the heating zone to the sample lateral area) is 0.01%, 0.05%, 0.1%, 0.5%, 0.1%, 0.5%, 1%, 5%, 10%, 20%, 30%, 40%, 50%, 60%, 70%, 80%, 90%, 99%, or in a range between any of the two values.

In some preferred embodiments, the ratio of the heating zone area to the sample lateral area is in a range of between 0.01% and 0.1%, 0.1% and 1%, 1% and 10%, 10% and 30%, 30% and 60%, 60% and 90%, or 90% and 99%.

B. Local Heating, High Vertical to Lateral Heat Transfer

When a high-K (high thermal conductivity) layer is (e.g. a metal layer) on the inner surface, the outer surface, or inside of one of the plates of a sample holder (RHC card), to make only a part of the high-K layer and a part of sample volume above the part of the high-K layer to be heated to desired temperatures, while keeping the rest of the high-K layer and the rest of the sample volume at much lower temperatures during a thermal cycling, several conditions must be met. The key conditions are (1) the heat source must directly heat a portion of the high-K layer (the portion is termed "heat zone" e.g., only the portion is directly heated by a LED light or has a local electric heater, while the rest is not), (2) the vertical heating transfer between the heat zone and a portion of the sample should be much larger than the lateral heat transfer within the high-K material (i.e. in the lateral direction of the high-K material), (3) the relevant sample should have a large lateral to vertical size ratio, and (4) the heating power of the heat zone must sufficient to heat up the relevant sample volume in a time frame that lateral heat transfer (i.e., heat conduction) is relatively negligible.

To satisfy the condition (2) above, the scaled thermal conduction ratio (STC ratio) of the vertical heat transfer from the high-K heating zone to the sample through the middle layer that is between the high-K and the sample to the lateral heat transfer inside the high-K layer is defined as:

$$STC\ ratio = \eta = 0.025 \cdot K_m K_s D^2 / K_k (K_m t_s + K_s t_m) t_k$$

wherein $K_k$, $K_s$, and $K_m$ is, respectively, the thermal conductivity of the high-K layer, the relevant sample, and the middle layer (i.e. the layer between the high-K and the sample), $t_k$, $t_s$, and $t_m$ is, respectively, the thickness of the high-K layer, the sample, and the middle layer; D is the average lateral dimension of the relevant sample, and 0.025 is a scaling factor.

To locally heat a part of the high-K layer and a part of sample volume above the part of the high-K layer to desired temperatures, while keeping the rest of the high-K layer and the rest of the sample volume at much lower temperatures during a thermal cycling. In some embodiments, the scaled thermal conduction ratio (STM ratio) is 2 or larger, 5 or larger, 10 or larger, 20 or larger, 30 or larger, 40 or larger, 50 or larger, 100 or larger, 1000 or larger, 10000 or larger, 10000 or larger, or in a range between any of the two values.

In some preferred embodiments, the scaled thermal conduction ratio (STM ratio) is in a range of between 10 to 20, 30 to 50, 100 to 1,000, 1,000 to 10,000, or 10,000 to 1,000,000.

To satisfying the condition (2) and (3) above, in some embodiments, the lateral to vertical size (LVS) ratio for relevant sample is 5, 10, 20, 50, 70,100,200, 300, 400, 500, 600, 700, 800, 800, 1,000, 2,000, 5,000, 10,000, 100,000, or in a range between any of the two values.

In some preferred embodiments, the LVS ratio for relevant sample is in a range of 5 to 10, 10 to 50, 50 to 100, 100 to 500, 500 to 1,000, 1,000, to 10,000, or 10,000 to 100,000, In certain embodiments, the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

In some preferred embodiments, the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

c. Large sample to non-sample thermal mass ratio (NSTM ratio)

An increase of the sample-to-non-sample thermal mass ratio can shorten heating time, reduce heating energy, and increase energy efficiency. In an embodiment where a sample is sandwiched between the two plates, a thermal mass ratio can be estimated by only considering the relevant sample volume and the portions of the two plates that sandwich the relevant sample, assuming there are no thermal losses in these volumes. Therefore, one parameter to measure a thermal mass ratio is the ratio of "specific area thermal mass" of the relevant sample to the non-sample (the portions of the plates that sandwich the relevant sample as well as the part heating/cooling layer on the plate portion). The term "specific area thermal mass" of a material refers to as the volume specific heat of the material multiplying its thickness.

The sample to non-sample thermal mass ratio is a ratio of the useful heat energy (which directly heat the relevant sample) to the "wasted heat energy (that heats non-sample materials), assuming that the heat losses by thermal conduction and radiation are negligible.

For examples, water has a volume specific heat of 4.2 J/(cm$^3 \cdot °$C.), thus the area specific heat for a 30 um thick water layer is $1.26 \times 10^{-2}$ J/(cm$^3 \cdot °$C.). A PMMA has a volume specific heat of 1.77 J/(cm$^3 \cdot °$C.), thus the area specific heat for a 25 um thick PMMA layer is $4.43 \times 10^{-3}$ J/(cm$^3 \cdot °$C.), which is ~2.8 times less than that of 30 um water layer. Gold has a volume specific heat of 2.5 J/(cm^3-C), thus the area specific heat for a 0.5 um thick gold layer is $1.25 \times 10^{-4}$ J/(cm^2-C), which is ~100 times less than that of 30 um water layer, and is negligible. The negligible area specific heat of the Au is due to its thin thickness.

If, in a RHC card embodiment, the relevant sample is sandwiched between two plates of 25 um thick each and the heating/cooling layer is 0.5 um thick, then the sample to non-sample thermal mass ratio for this case is ~1.4. Namely, when the heat losses by thermal conduction and radiation are neglected, the useful energy to the wasted energy ratio is ~1.4, and the useful energy to the total heating energy ratio is 58%.

In some embodiments, the sample to non-sample thermal mass ratio (NSTM ratio) is 0.1, 0.2, 0.3, 0.4, 0.5, 0.6, 0.7, 1, 1.5, 2, 3, 4, 5, 10, 20, 30, 40, 50, 60, 70,100,200, 300, 1000, 4000, or in a range between any of the two values.

In preferred embodiments, the sample to non-sample thermal mass ratio (NSTM ratio) is in a range of between 0.1 to 0.2, 0.2 to 0.5, 0.5 to 0.7, 0.7 to 1, 1 to 1.5, 1.5 to 5, 5 to 10, 10 to 30, 30 to 50, 50 to 100, 100 to 300, 300 to 1,000, or 1,000 to 4,000.

To make the sample to non-sample thermal mass ratio high, one needs to keep the area thermal mass of the non-sample low, which in turn, needs to make the plates and the heating/cooling layer thin, and/or the volume specific heat low.

To make the thermal mass ratio large, one embodiment uses a thin material that has multi-layers or mixed materials. For examples, a carbon fiber layer(s) with plastic sheets or carbon mixed with plastics, which can have a thickness of 0.1 um, 0.2 um, 0.5 um, 1 um, 2 um, 5 um, 10 um, 25 um, 50 um, or in a range between any of the two values.

D. Thin Thickness and Large Lateral to Vertical Size Ratio (LVS Ratio) for Relevant Sample The term of "lateral to vertical size ratio for sample" or "LVS ratio for sample" refers to the ratio of the average lateral size of the relevant sample volume to its average vertical size. A larger LVS ratio for sample can reduce the wasted heating energy and increase heating speed and/or cooling speed in the embodiments that the heating and/or cooling is primarily from the vertical direction, and can reduce the lateral thermal conduction loss at the edge of the relevant sample relative to the total thermal energy. All of these can increase and/or can increase cooling time.

In some embodiments, the LVS ratio for relevant sample is 5, 10, 20, 50, 70, 100, 200, 300, 400, 500, 600, 700, 800, 800, 1,000, 2,000, 5000, 10,000, 100,000, or in a range between any of the two values.

In some preferred embodiments, the LVS ratio for relevant sample is in a range of 5 to 10, 10 to 50, 50 to 100, 100 to 500, 500 to 1,000, 1000, to 10,000, or 10,000 to 100,000, For example, a sample has a lateral dimension of 15 mm and a thickness of 30 um, hence an LVS for the sample of 500.

In certain embodiments, the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

In some preferred embodiments, the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

E. Thin Thickness and Large Lateral to Vertical Size Ratio (LVS Ratio) for Non-Samples The term of "lateral to vertical size ratio for non-sample" or "LVS ratio for non-sample" refers to the ratio of the average lateral size of the portions of the two plates that sandwich the relevant sample (which is the same as the average lateral size of the relevant sample volume) to its thickness. A large LVS ratio for non-sample can reduce the lateral thermal conduction loss at the edge of the non-sample relative to the total thermal energy.

In some embodiments, the LVS ratio for non-sample is 5, 10, 20, 50, 70,100,200, 300, 400, 500, 600, 700, 800, 800, 1,000, 2000, 5000, 10,000, 100,000, or in a range between any of the two values.

In preferred embodiments, the LVS ratio for non-sample is in a range of 5 to 10, 10 to 50, 50 to 100, 100 to 500, 500 to 1,000, 1000, to 10,000, or 10,000 to 100,000, For example, two 25 um thick plates sandwich a sample of 5 mm or larger lateral dimension of the relevant sample, hence an LVS for the non-sample of 200 or higher for each plate.

To shorten heating time, reduce heating energy, and increase energy efficiency, the lateral thermal conduction through a non-sample material (on the sample holder) should be reduced.

In particularly, when the first and the second plates are made of the materials that are not good thermal materials, the thickness of the plates should be minimized.

In some embodiments, the first plate or the second plate or each of both plates has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

In some preferred embodiments, the first plate or the second plate or each of both plates has a thickness of 10 nm, 100 nm, 200 nm, 300 nm, 400 nm, 500 nm, 1 um, 2.5 um, 5 um, 10 um, 25 um, 50 um, 75 um, or in a range between any of the two values.

The first plate and the second plate can have the same thickness or a different thickness, and can be made of the same materials or different materials.

In some preferred embodiments, the first plate or the second plate or each of both plates has a thickness in a range of between 10 nm and 500 nm, 500 nm and 1 um, 1 um and 2.5 um, 2.5 um and 5 um, 5 um and 10 um, 10 um and 25 um, 25 um and 50 um, 50 um and 100 um, 100 um and 200 um, or 200 um and 500 um, or 500 um and 1,000 um.

In some preferred embodiments, the first plate and second plates are plastic, a thin glass, or a material with similar physical properties. The first plate or second plate has a thickness of 100 nm, 500 nm, 1 um, 5 um, 10 um, 25 um, 50 um, 100 um, 175 um, 250 um, or in a range between any of the two values.

In some preferred embodiments, the first plate and second plates are plastic, a thin glass, or a material with similar physical properties. The first plate has a thickness of 5 um, 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values.

F. Cooling layer of high K and/or high thermal conductivity-to-capacity ratio (KC Ratio)

Since any thermal conduction through a non-sample material will waste energy and since lateral thermal conduction has much longer thermal path than vertical thermal conduction, the energy wasted in lateral thermal conduction in non-sample materials should be minimized. One way to minimize this type of wasted energy is to use a high thermal conduction (high-K) or more precisely a high thermal conductivity-to-capacity ratio (KC ratio) materials for the cooling layer. For a given thermal conductivity, a given temperature change, and a given geometry, a high K and/or a high KC ratio material would need much less energy to be heated up than a low K and/or low KC ratio material.

In some embodiments, the KC ratio materials for the cooling layer is equal to or higher than 0.1 $cm^2/sec$, 0.2 $cm^2/sec$, 0.3 $cm^2/sec$, 0.4 $cm^2/sec$, 0.5 $cm^2/sec$, 0.6 $cm^2/sec$, 0.7 $cm^2/sec$, 0.8 $cm^2/sec$, 0.9 $cm^2/sec$, 1 $cm^2/sec$, 1.1 $cm^2/sec$, 1.2 $cm^2/sec$, 1.3 $cm^2/sec$, 1.4 $cm^2/sec$, 1.5 $cm^2/sec$, 1.6 $cm^2/sec$, 2 $cm^2/sec$, 3 $cm^2/sec$, or in a range between any of the two values.

In some preferred embodiments, the KC ratio for the cooling layer is in a range of between 0.5 $cm^2/sec$ and 0.7 $cm^2/sec$, 0.7 $cm^2/sec$ and 0.9 $cm^2/sec$, 0.9 $cm^2/sec$ and 1 $cm^2/sec$, 1 $cm^2/sec$ and 1.1 $cm^2/sec$, 1.1 $cm^2/sec$ and 1.3 $cm^2/sec$, 1.3 $cm^2/sec$ and 1.6 $cm^2/sec$.

In some embodiments, a high thermal conductivity (i.e. high-K) material is used for the cooling layer, and the high-K material has a thermal conductivity that is equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), 600 W/(m·K), 1000 W/(m·K), 5000 W/(m·K), or in a range between any of the two values.

In some preferred embodiments, a high thermal conductivity (i.e. high-K) material is used for the cooling layer, and the high-K material has a thermal conductivity that is in the range of 50 W/(m·K) to 100 W/(m·K), 110 W/(m·K) to 200 W/(m·K), 200 W/(m·K) to 400 W/(m·K), 400 W/(m·K) to 600 W/(m·K), or 400 W/(m·K) to 5000 W/(m·K).

In some embodiments, the high-K material is selected from metals, semiconductors, and allows of thermal conductivity higher than 50 W/(m·K), and any combinations (including any mixtures). In some embodiments, the high-K material is selected from gold, copper, silver, and aluminum, and any combinations (including any mixtures). In some embodiments, the high-K material is selected from carbon particles, carbon tubes, graphite, silicon, and any combinations (including any mixtures).

G-1. Cooling Zone Area Larger than lateral relevant sample area and Heating Zone Area To effectively cool a sample while reducing the wasted energy in non-sample materials, in some embodiments, a high K and/or a high KC ratio material (termed "high K material") is used as the major channel for removing the heat from the sample. The area of high-K cooling zone (layer) should be larger than the relevant sample lateral size.

In certain embodiments, the cooling zone (layer) has an area that is larger than the lateral area of the relevant sample by a factor of 1.5, 2, 3, 4, 5, 10, 20, 50, 70, 100, 200, 300, 400, 500, 600, 700, 800, 800, 1,000, 2,000, 5,000, 10,000, 100,000, or in a range between any of the two values.

In preferred embodiments, the cooling zone (layer) has an area that is larger than the lateral area of the relevant sample by a factor in a range of 1.5 to 5, 5 to 10, 10 to 50, 50 to 100, 100 to 500, 500 to 1,000, 1000, to 10,000, or 10,000 to 100,000.

To increase the cooling speed and thermal cycling efficiency, in certain embodiments, the high-K cooling layer (zone) should an area to large than the heating zone area.

In some embodiments, the area of the cooling zone (layer) is larger than the area of the heating zone (layer) by a factor (i.e. the ratio of the cooling zone area to the heating zone area, "CH ratio") of 1.1, 1.5, 2, 3, 4, 5, 10, 20, 30, 40, 50, 70, 100, 200, 300, 400, 500, 600, 700, 800, 800, 1,000, 5000, 10,000, 100,000, or in a range between any of the two values.

In preferred embodiments, the cooling zone (layer) has an area that is larger than the lateral area of the hearing zone (layer) by a factor in a range of 1.1 to 1.5, 1.5 to 5, 5 to 10, 10 to 50, 50 to 100, 100 to 500, 500 to 1,000, 1,000, to 10,000, or 10,000 to 100,000.

G-2. Cooling Zone Area and Heating Zone Area are the Same as Lateral Relevant Sample Area In certain embodiments, cooling zone area and heating zone area are the same as lateral relevant sample area, which is much smaller than the total sample area on the plat, and is smaller than the area of the plate. The cooling zone has an area of 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, 1 $mm^2$, The cooling zone can have different shape. In certain embodiments, there are more than one cooling zones on one plate, and the cooling zones are separated from each other by a low thermal conductive material such as air or plastic.

H. Heating Zone of High K and/or High Thermal Conductivity-to-Capacity Ratio (KC Ratio)

Since any thermal conduction through a non-sample material that will waste energy and lateral thermal conduction has much longer thermal path than vertical thermal conduction, the energy wasted in lateral thermal conduction in non-sample materials should be minimized. One way to minimize this type of wasted energy is to use high thermal conductivity-to-capacity (KC) ratio materials for the materials in heating zone, which would need much less energy of heating up for a given thermal conductivity, a given temperature change, and a given geometry.

In some embodiments, the KC ratio materials for the heating layer is equal to or higher than 0.1 cm$^2$/sec, 0.2 cm$^2$/sec, 0.3 cm$^2$/sec, 0.4 cm$^2$/sec, 0.5 cm$^2$/sec, 0.6 cm$^2$/sec, 0.7 cm$^2$/sec, 0.8 cm$^2$/sec, 0.9 cm$^2$/sec, 1 cm$^2$/sec, 1.1 cm$^2$/sec, 1.2 cm$^2$/sec, 1.3 cm$^2$/sec, 1.4 cm$^2$/sec, 1.5 cm$^2$/sec, 1.6 cm$^2$/sec, 2 cm$^2$/sec, 3 cm$^2$/sec, or in a range between any of the two values.

In some preferred embodiments, the KC ratio for the heating layer is in a range of between 0.5 cm$^2$/sec and 0.7 cm$^2$/sec, 0.7 cm$^2$/sec and 0.9 cm$^2$/sec, 0.9 cm$^2$/sec and 1 cm$^2$/sec, 1 cm$^2$/sec and 1.1 cm$^2$/sec, 1.1 cm$^2$/sec and 1.3 cm$^2$/sec, 1.3 cm$^2$/sec and 1.6 cm$^2$/sec, 1.6 cm$^2$/sec and 2 cm$^2$/sec, or 2 cm$^2$/sec and 3 cm$^2$/sec.

In some embodiments, a high thermal conductivity (i.e. high-K) material is used for the heating layer, and the high-K material has a thermal conductivity that is equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), 600 W/(m·K), 1000 W/(m·K), 5000 W/(m·K), or in a range between any of the two values.

In some preferred embodiments, a high thermal conductivity (i.e. high-K) material is used for the heating layer, and the high-K material has a thermal conductivity that is in the range of 50 W/(m·K) to 100 W/(m·K), 110 W/(m·K) to 200 W/(m·K), 200 W/(m·K) to 400 W/(m·K), 400 W/(m·K) to 600 W/(m·K), or 400 W/(m·K) to 5000 W/(m·K).

In some embodiments, the high-K material is selected from metals, semiconductors, and allows of thermal conductivity higher than 50 W/(m·K), and any combinations (including any mixtures). In some embodiments, the high-K material is selected from gold, copper, silver, and aluminum, and any combinations (including any mixtures). In some embodiments, the high-K material is selected from carbon particles, carbon tubes, graphite, silicon, and any combinations (including any mixtures).

To receive light energy by a heating zone (layer), a thermal radiation enhancement surface(s) will be used (on one side or both side of the heating zone). A thermal radiation absorption enhancement surface can be achieved by directly modify the structures of the surface (e.g. patterning nanostructures), coating a high thermal radiation materials (e.g. coating a black paint), or both.

The thermal radiation enhancement surface has a high average light absorptance (e.g. the black paint used in our experiments). In certain embodiments, the heating zone has a surface that has an average light absorptance of 30%, 40%, 50%, 60%, 70%, 80%, 90%, 95%, 100%, or in a range between any of the two values.

In certain preferred embodiments, the heating zone has a surface that has an average light absorptance in a range of 30% to 40%, 40% to 60%, 60% to 80% to 90%, or 90% to 100%.

In some preferred embodiments, the heating zone has a surface that has an average light absorptance in a range of 30% to 100%, 50% to 100%, 70% to 100%, or 80% to 100%.

In certain embodiments, the heating zone has a surface that has an average light absorptance of a value given above by averaging over a wavelength range 400 nm to 800 nm, 700 nm to 1500 nm, 900 nm to 2000 nm, or 2000 nm to 20000 nm.

Increasing Thermal Radiative Cooling

In certain embodiments, a fast temperature cycling is achieved by increasing thermal radiative cooling percentage in the total cooling of the sample and the sample holder (i.e. removing heat to the environment) during a thermal cycling, preferably through using high thermal conductivity material as the material for thermal radiative cooling. One reason is that cooling through lateral thermal conduction needs to heat up many non-sample materials, wasting energy. Another reason is that thermal radiation cooling is proportional to the fourth power of the temperature and can be more effective than thermal conduction in a thin film.

To enhancing thermal radiative cooling, in certain embodiments, the thermal radiative cooling uses a cooling layer (cooling zone) that is enhanced for thermal radiative cooling. The enhancement includes (i) increase thermal conductivity of the cooling zone (layer), (ii) enlarging the area of the cooling zone (layer), (iii) enhance the surface thermal radiation of the cooling zone, and (iv) a combination thereof.

Examples of a high thermal conductivity materials are metals (such as gold, silver, coper, aluminum), semimetals, semiconductors (e.g. silicon) or a combination thereof.

To further enhance thermal radiation of a cooling zone (layer), a thermal radiation enhancement surface(s) will be used (on one side or both side of the cooling zone). A thermal radiation enhancement surface can be achieved by directly modify the structures of the surface (e.g. patterning nanostructures), coating a high thermal radiation material (e.g. coating a black paint), or both.

The thermal radiation enhancement surface has a high average light absorptance (e.g. the black paint used in our experiments). In certain embodiments, the cooling zone has a surface that has an average light absorptance of 30%, 40%, 50%, 60%, 70%, 80%, 90%, 95%, 100%, or in a range between any of the two values.

In certain preferred embodiments, the cooling zone has a surface that has an average light absorptance in a range of 30% to 40%, 40% to 60%, 60% to 80% to 90%, or 90% to 100%.

In some preferred embodiments, the cooling zone has a surface that has an average light absorptance in a range of 30% to 100%, 50% to 100%, 70% to 100%, or 80% to 100%.

In certain embodiments, the cooling zone has a surface that has an average light absorptance of a value given above by averaging over a wavelength range 400 nm to 800 nm, 700 nm to 1,500 nm, 900 nm to 2,000 nm, or 2,000 nm to 20,000 nm.

In certain embodiments, the surface thermal radiation enhancement layer is black paint, plasmonic structures, nanostructures, or any combination thereof.

The high thermal radiation materials are polymer mixtures that look black by human eyes (often termed "black paints"). A high thermal radiation material include, but not limited to, a mixture of polymers and nanoparticles. One example of the nanoparticles is black carbon nanoparticle, carbon, nanotubes, graphite particles, graphene, metal nanoparticles, semiconductor nanoparticles, or a combination thereof.

The high thermal radiation material further comprises a material that is deposited or made on the layer surface and look blacks by human eyes. The materials include, but not limited to, black carbon nanoparticle, carbon, nanotubes, graphite particles, graphene, metal nanoparticles, semiconductor nanoparticles, or a combination thereof.

The plasmonic structures include nanostructured plasmonic structures.

In some embodiments, a cooling layer comprise a layer of high thermal conductivity metal (50 W/(m·K) or higher) with a surface thermal radiation enhancement layer. In some embodiments, the surface thermal radiation enhancement layer has a low lateral thermal conductance, which is due to either ultrathin layer, low thermal conductivity, or both.
Percentage of Thermal Radiative Cooling.

In certain embodiments, thermal radiative cooling is achieved by increasing the area of radiative cooling layer (i.e. a high-K material, unless stated otherwise), and the radiative cooling layer area is larger than the lateral area of the relevant sample by a factor of 1.2, 1.5, 2, 3, 4, 5, 10, 20, 30, 40, 50, 60, 70, 80 100, 200, 300, 400, 500, 600, 700, 800, 800, 1,000, 2,000, 5,000, 10,000, 100,000, or in a range between any of the two values.

In preferred embodiments, the radiative cooling zone (layer) has an area that is larger than the lateral area of the relevant sample by a factor in a range of 1.2 to 3, 3 to 5, 5 to 10, 10 to 50, 50 to 100, 100 to 500, 500 to 1,000, 1,000, to 10,000, or 10,000 to 100,000.

In some embodiments, the ratio of the thermal radiation cooling by the cooling zone (layer) to the total cooling of the sample and sample holder during a thermal cycling is 10%, 20%, 30%, 40%, 50%, 60%, 70%, 80%, 90%, 99%, or in a range between any of the two values.

In some preferred embodiments, the ratio of the thermal radiation cooling by the cooling zone (layer) to the total cooling of the sample and sample holder during a thermal cycling is in a range of between 10% and 20%, 20% and 30%, 30% and 40%, 40% and 50%, 50% and 60%, 60% and 70%, 70% and 80%, 80% and 90%, or 90% and 99%.
J. Control of Cooling Layer Thickness In certain embodiments, the thickness of the cooling layer thickness is configured to facilitate to optimize heating locally and/or energy efficiency. If the cooling zone (layer) is too thick, a significant percentage of the heating energy will be wasted by the cooling layer, lengthening heating time (for a given heating power). On the other hand, if the cooling zone is too thin, the cooling time will be significantly longer. Hence, the cooling layer thickness should be optimized for both fast heating and cooling.

Through our experiments, we found that the thickness of the high-K cooling layer can regulate the cooling rate. By selecting a proper high-K cooling layer thickness and a proper LED power density, a fast heating and cooling can be achieved.

Since a thermal conductance of a layer proportional to a material's thermal conductivity times the layer thickness, so it is this product should be optimized.

In some embodiments, a cooling zone (layer) has thermal conductivity times its thickness of $6\times10^{-5}$ W/K, $9\times10^{-5}$ W/K, $1.2\times10^{-4}$ W/K, $1.5\times10^{-4}$ W/K, $1.8\times10^{-4}$ W/K, $2.1\times10^{-4}$ W/K, $2.7\times10^{-4}$ W/K, $3\times10^{-4}$ W/K, $1.5\times10^{-4}$ W/K, or in a range between any of the two values. In some preferred embodiments, a cooling zone (layer) has thermal conductivity times its thickness in a range of $6\times10^{-5}$ W/K to $9\times10^{-5}$ W/K, $9\times10^{-5}$ W/K to $1.5\times10^{-4}$ W/K, $1.5\times10^{-4}$ W/K to $2.1\times10^{-4}$ W/K, $2.1\times10^{-4}$ W/K to $2.7\times10^{-4}$ W/K, $2.7\times10^{-4}$ W/K to $3\times10^{-4}$ W/K, or $3\times10^{-4}$ W/K to $1.5\times10^{-4}$ W/K.

In certain preferred embodiments, a cooling zone (layer) has thermal conductivity times its thickness in a range of $9\times10^{-5}$ W/K to $2.7\times10^{-4}$ W/K, $9\times10^{-5}$ W/K to $2.4\times10^{-4}$ W/K, $9\times10^{-5}$ W/K to $2.1\times10^{-4}$ W/K, or $9\times10^{-5}$ W/K to $1.8\times10^{-4}$ W/K.

In one embodiment, a cooling zone comprises a gold layer of a thickness in the range of 200 nm to 800 nm. In another embodiment, a cooling zone comprises a gold layer of a thickness in the range of 300 nm to 700 nm.
K. Large Conductance Between Sample and Heating Zone or Cooling Zone For a fast heating and cooling a sample, the thermal conduction per unit area between a relevant sample and a heating layer and/or the cooling layer should be large. The thermal conduction per area is equal to the conductivity (unit volume) divided by the material thickness for the materials that are between the HC layer and the sample. For example, for 100 nm thick of PS as the second plate which has the HC layer on one surface and the sample on the other surface, the conductance between the HC layer and the sample is ~1000 W/(m²·K)

Based on experiments, in some embodiments of a RHC card, the materials between the heating zone and the relevant sample has a thermal conductivity and a thickness configured to be about 1000 W/(m²·K) or higher.

In some embodiments of a RHC card, the materials between the heating zone and the relevant sample has a thermal conductivity and a thickness configured to have a conductance per unit area that is equal to or larger than 1000 W/(m²·K), 2000 W/(m²·Km²·K), 3000 W/(m²·Km²·K), 4000 W/(m²·Km²·K), 5000 W/(m²·Km²·K), 7000 W/(m²·Km²·K), 10000 W/(m²·K), 20000 W/(m²·K), 50000 W/(m²·K), 50000 W/(m²·K), 100000 W/(m²·K), or in a range of any the values.

A preferred conductance per unit area of the material between the heating zone and the relevant sample is in a range of 1000 W/(m²·K) to 2000 W/(m²·K), 2000 W/(m²·K) to 4000 W/(m²·K), 4000 W/(m²·K) to 10,000 W/(m²·K), or 10000 W/(m²·K) to 100000 W/(m²·K).

In another preferred embodiment, it has zero distance between the heating zone and the relevant sample, and hence an infinity for the conductance per unit area of the material between the heating zone and the relevant sample.

In certain embodiments, the heating layer or the cooling layer is separated from a relevant sample by a thin plastics plate (or film) which has a thermal conductivity in the range of 0.1 to 0.3 W/(m·K), and the thin plastic layer has a thickness of 0 nm, 10 nm, 50 nm, 100 nm, 200 nm, 300 nm, 400 nm, 500 nm, 1 um, 2.5 um, 5 um, 10 um, 25 um, 50 um, 75 nm 100 um, 150 um, or in a range between any of the two values In some preferred embodiments, the thin plastic plate (or film) that separate the relevant sample from the heating layer or the cooling layer has thickness in a range between 0 nm and 100 nm, 100 nm and 500 nm, 500 nm and 1 um, 1 um and 5 um, 5 um and 10 um, 10 um and 25 um, 25 um and 50 um, 50 um and 75 um, 75 um and 100 um, or 100 um and 150 um.

In one preferred embodiment of the RHC card, the thin plastic plate (or film) that separate the relevant sample from the heating layer or the cooling layer has thickness of 1 nm, 10 nm, 0.1 um, 0.5 um, 1 um, 5 um, 10 um, 20 um, 25 um, or a range between any two values.

L. Small Relative Reagent Lateral Diffusion

In order to make a biochemical reaction substantially uniform in the relevant sample volume during a temperature change or a thermal cycling, the average lateral area of the relevant sample should be significantly larger than the lateral diffusion of the nucleic acids and/or other regents used for a molecular amplification and/or reaction. In this way, during the time of temperature change or a thermal cycling, most of the molecules inside the relevant sample volume do not have enough time to diffuse out of the relevant sample volume, while most of the molecules outside the relevant sample volume do not have enough time to diffuse into the relevant sample volume.

Considering a thermal cycling time duration of 3 min and a diffusion constant of $\sim 1 \times 10^{\wedge} -6$ cm$^2$/s for a molecule about 600 Da molecular weight, the diffusion length is ~130 um.

In certain embodiments, the ratio of the average lateral size of the relevant sample volume to the diffusion length of the reagent during the time for thermal cycling or a reaction is equal to or larger than 5, 6, 7, 10, 15, 20, 25, 30, 40, 50, 60, 70, 80, 90,100,150, 200, 500, 1000, 5000, 10000, 100000, or in a range between any two values.

In some preferred embodiments, the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1000, 1000 to 5000, 5000 to 10,000, or 10,000 to 100,000.

In some preferred embodiments, the ratio of the average lateral size of the relevant sample volume to the diffusion length of the reagent during the time for thermal cycling or a reaction is in a range of 5 to 10, 10 to 30, 30 to 60, 6 to 100, 100 to 200, 200 to 500, 500 to 1,000, 1,000 to 5,000, 5,000 to 10,000, or 10,000 to 100,000.

In certain preferred embodiments, the average lateral dimension of the relevant volume is 1 mm, 2 mm, 3 mm, 5 mm, 6 mm, 7 mm, 8 mm, 9 mm 10 mm, 12 mm, 15 mm, 20 mm, 30 mm, 40 mm, 50 mm, 70 mm, 100 mm, 200 mm, or in a range between any two values.

In some preferred embodiments, the average lateral dimension of the relevant volume is in a range of 1 mm to 5 mm, 5 mm to 10 mm, 10 mm to 20 mm, 20 mm to 40 mm, 40 mm to 70 mm, 70 mm to 100 mm, or 100 mm to 200 mm.

In another preferred embodiments, the average lateral dimension of the relevant volume is in a range of 1 mm to 5 mm, 1 mm to 10 mm, or 5 mm to 20 mm.

M. Without Edge Sealing or Simple Edge Sealing

To simplify the sample holder operation and cost, in certain embodiments, there is no sealing between the two plates that confine a sample; namely, the sample sandwiched between the plates can evaporate from the sample edge into environment. However, in our experiments, we found that in our sample card configuration, such evaporation is negligible relative to total sample volume, due to a large ratio of the lateral sample area to the sample edge area; the plates have prevented most of the evaporation.

In some embodiments, an enclosure ring spacer or some discontinuous spacer walls can be put on one or both of the plates to reduce or eliminate a sample evaporation.

P-2 Forced Air Cool

In certain embodiments, there is a forced air cooling/circulating system near the RHC card to speed up the cooling process. The example of forced air cooling system includes but not limit to a fan circulating the cool air near the card, several fans circulating the cool air near the card, a cooling source cool the air near the card, a cooling pad direct touch the card or their combinations.

In certain embodiments, there is a forced air cooling/circulating system cooling the air on the top surface of the card.

In certain embodiments, there is a forced air cooling/circulating system cooling the air on the bottom surface of the card.

In certain embodiments, there is a forced air cooling/circulating system cooling the air surrounding all the surface of the card.

2. Mechanical Structure Designs

N. Movable Plates and Compressed Open Flow, Hinges, Opening Notches, Recessed Edge and Sliders To load a sample simply, in certain embodiments in the present invention, the two plates of a RHC card are movable relative to each other into different configurations. A sample is deposited at an open configuration of the plates, and then the plates are pressed into a closed configuration. During the pressing, the sample will flow between the plates into a thin layer, and the flow is termed "compressed open flow", since there are plenty room between the plates that allow the sample to flow.

In certain embodiments, spaces for regulating the sample thickness are added on one or both of the plates, hence a device for rapidly changing the temperature of a fluidic sample, comprising:

a first plate (10), a second plate (20), a heating layer (112-1), and a cooling layer (112-2), wherein:

the first and second plates are movable relative to each other into different configurations;

each of the first plate and the second plate has, on its respective inner surface, a sample contact area for contacting a fluidic sample; wherein the sample contact areas face each other, are separated by an average separation distance of 200 um or less, and are capable of sandwiching the sample between them;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates;

configured to cool the relevant sample volume; and comprises a layer of material that that has a thermal conductivity to thermal capacity ratio of 0.6 cm$^2$/sec or larger;

wherein one of the configurations is an open configuration, in which: the two plates are partially or completely separated apart and the average spacing between the plates is at least 300 um;

wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less; and wherein, in some embodiments, the heating layer and cooling layer are the same material layer that has a heating zone and a cooling zone, and wherein the heating zone and cooling zone can have the same area or different areas.

In some embodiments, the sample holder (also termed "RHC card" or "Q-card") with movable plates further comprises hinges, notches, recesses, which help to facilitate the manipulation of the sample holder and the measurement of the samples. Furthermore, the sample holders can slide into sliders. The structure, material, function, variation and dimension of the hinges, notches, recesses, sliders and compress open flow are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Spacers (13)

In certain embodiments, the spacers as described in embodiment SH-5 will be used to regulate the sample thickness and make the thickness uniform. The spacers also allow to achieve uniform sample thickness, even when both plates are very thin (e.g. 25 um thick or less).

In certain embodiments, the spacers are fixed on one or both of the plates. In certain embodiments, the spacers are mixed with the sample. In some embodiments, the spacers have a uniform height and the spacers, together with the first plate and the second plate, regulate the sample layer. In some embodiments, the thickness of the sample layer is substantially equal to the height of the spacers.

Figure 33A:
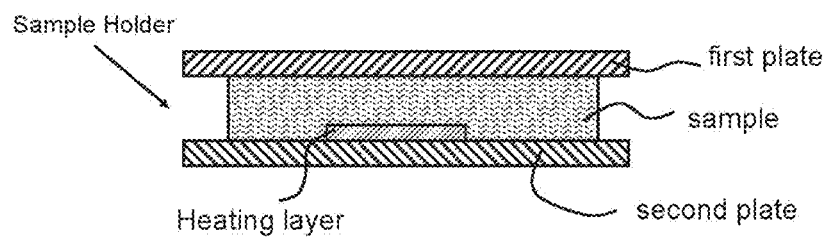
FIGS. 33A and 33B schematically illustrates sectional views of a device having a first plate, a second plate, and a heating/cooling layer, in accordance with some embodiments.
Figure 33B:
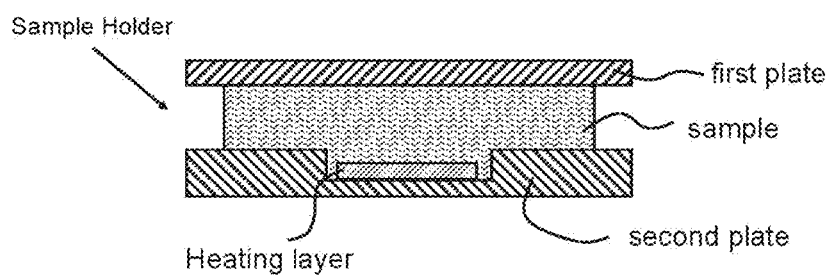

In some embodiments, the plates are flat (e.g. as shown in FIG. 33A). In some embodiments, either one or both of the plates include wells (e.g. as shown in FIG. 33B). For example, in certain embodiments the width of the wells can be less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In certain embodiments, the depth of the wells can be less than 500 um, 200 um, 100 um, 50 um, 25 um, 10 um, 5 um, 2.5 um, 1 um, 500 nm, 400 nm, 300 nm, 200 nm, 100 nm, 50 nm, 20 nm, 10 nm, 5 nm, 2 nm, or 1 nm, or in a range between any of the two values In some embodiments, one or both of the plates have wells and most or entire of the samples are only inside the well of one plate and is covered by other plate (not shown in the figures).

P. Sample Cartridge and Thermal Conduction Isolation

In certain embodiments, the RHC card (sample holder) can be further mounted on a sample cartridge. The cartridge can be configured to slide in or out a base (also termed "adaptor"). A base houses the power source, temperature sensors and controllers, signal measurement devices, and a slot for the sample holder with or without a cartridge to slide in or out of the base.

In some embodiments, the sample holder, the cartridge (i.e. the sample holder support) or both are "thermal conduction isolated", namely, they do not have or almost do not have, during a thermal cycling, a thermal conduction to the environment. In this case, the cooling in the thermal cycling is essentially by thermal radiation (this is termed "no conductive heat transfer"). In some embodiment, the "thermal conduction isolation" is achieved in the sample holder, the cartridge, or both by configuration their materials, the geometry (including of thickness reduction), or both.

Q. Combination of Above

An embodiment of a RHC card can be any combination of the specification described in SH-1, SH-2, SH-3 and in subsections of A to P.

R. Heating Sources

The heating layer or the heating/cooling layer in a RHC card is configured to be heated by a heating source, wherein the heating source delivers heat energy to the heating/cooling layer optically, electrically, by radio frequency (RF) radiation, or a combination thereof.

S. Base (i.e. Adaptor)

In some embodiments, the apparatus further comprises a base (an adaptor) that is configured to house the sample card, the heating source, temperature sensors, a part of an entire of temperature controlled (include a smartphone in some embodiments), extra-heat sink (optionally), a fan (optionally) or a combination of thereof. In some embodiments, the adaptor comprises a card slot, into which the sample card or a sample cartridge can be inserted. In some embodiments, the sample card or the sample cartridge, after being fully inserted into the slot, or after reaching a pre-defined position in the slot, is stabilized and stays in place without any movement.

T. Smartphone

In some embodiments, a smartphone is used to mage the sample card, controlling the heating and/cooling, sensing a signal, monitor operation use camera, provide light/energy with a flash, communicate to a local or a remote device, integrated through a base (adaptor) in a system, of a combination thereof.

U. Applications for Isothermal Nucleic Acid Amplification

The present invention with a slight modification also provides useful devices and methods for isothermal nucleic acid amplification, where a sample temperature needs to be raised from environment to an elevated temperature (i.e. 65° C.) and keep at the temperature for a period of time (i.e. 5-10 min). In some embodiments, one of the modifications needed for isothermal nucleic acid amplification test, is to reduce or eliminate the cooling zone/layer, so that loss of thermal energy from the sample and/or the sample holder to the environment is reduced.

The present invention with a slight modification provides useful devices and methods for reverse transcription polymerase chain reaction, which contains an isothermal process before the regular PCR, where a sample temperature needs to be raised from environment to an elevated temperature (i.e. 50° C.) and keep at the temperature for a period of time (i.e. 5–10 min). The present invention with a slight modification provides useful devices and methods for minimize PCR cross-contamination as method to use dUTP and uracil-DNA N-glycosylase, where a sample temperature needs to be raised from environment to an elevated temperature (i.e. 50° C.) and keep at the temperature for a period of time (i.e., 1-20 min).

Experimentations of Certain Embodiments

Certain embodiments of the present invention have been tested experimentally. Some of experimental results are illustrated here.

Figure 39A:
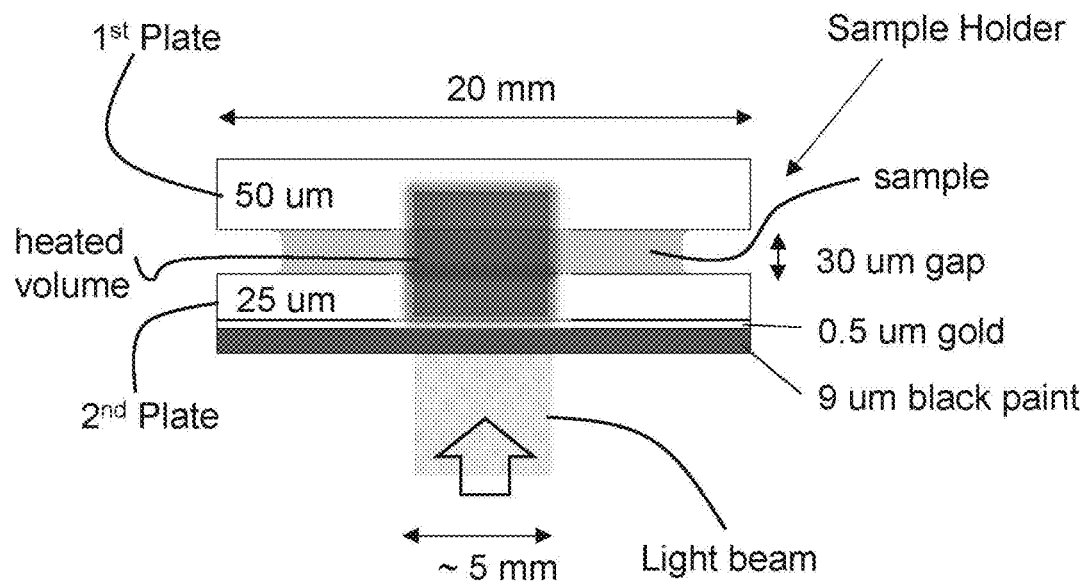
FIGS. 39A and 39B schematically illustrate a side view and a top view, respectively, a sample device that is heated with a heat source, in accordance with one or more embodiments.

In some of our experiments, the apparatus, illustrated in FIG. 39A, comprises a sample holder (e.g. an RHC card), a LED light source (i.e. energy source) that was focused by a lens onto an area of (~5 mm by 5 mm) of the sample holder, and a sample holder support (not shown in FIG. 39A) made of a thermal conduction insulating material. The sample holder support supports a ~2 mm rim at the two opposite edges of the second plate (e.g., around a perimeter of the second plate.) There was no extra heat sink, and the heat was mainly radiated into an open environment (e.g., the room).

In the experiments described in this section, the sample holder comprises a first plate, a second plate, and a heating/cooling layer. One of the plates has spacers. The first plate and second plates are movable relative to each other into different configurations. One of the configurations is an open configuration, wherein the two plate are separated an average distance at least 300 um. In an open configuration, a sample deposited on one of the plates. Then the other card was placed on top of the sample, and a hand pressing of the two plates into a close configuration. In the close configuration, the spacers regulate the distance between the two plates, and therefore the sample thickness is regulated by the two plates and the spacers. By using proper spacers and plates (see other part of the description), the sample thickness at a closed configuration can be uniform over large area and is close to the spacer height. Experimentally, we found that the sample thickness was uniform even different hand pressing forces, pressures and sequence (pressing one area first and then rub into other area of the RHC card).

The first plate is made of a poly(methyl methacrylate) (PMMA) film of ~50 um thickness, 20 mm wide and 20 mm long.

The second plate is a polyethylene terephthalate (PET) film of 20 mm wide square and 25 um thickness. The second plate has, on its inner surface, a periodic array of pillar spacers of 30 um height, 30 um×40 um size and 80 um inter spacer distance. The spacer has a uniform height and a flat top surface (Note other types of spacers can be used and will be described later). The spacers, that are fixed on the plate, were fabricated by a direct imprint of the flat PMMA plate (other fabrication methods are also possible).

Figure 40:
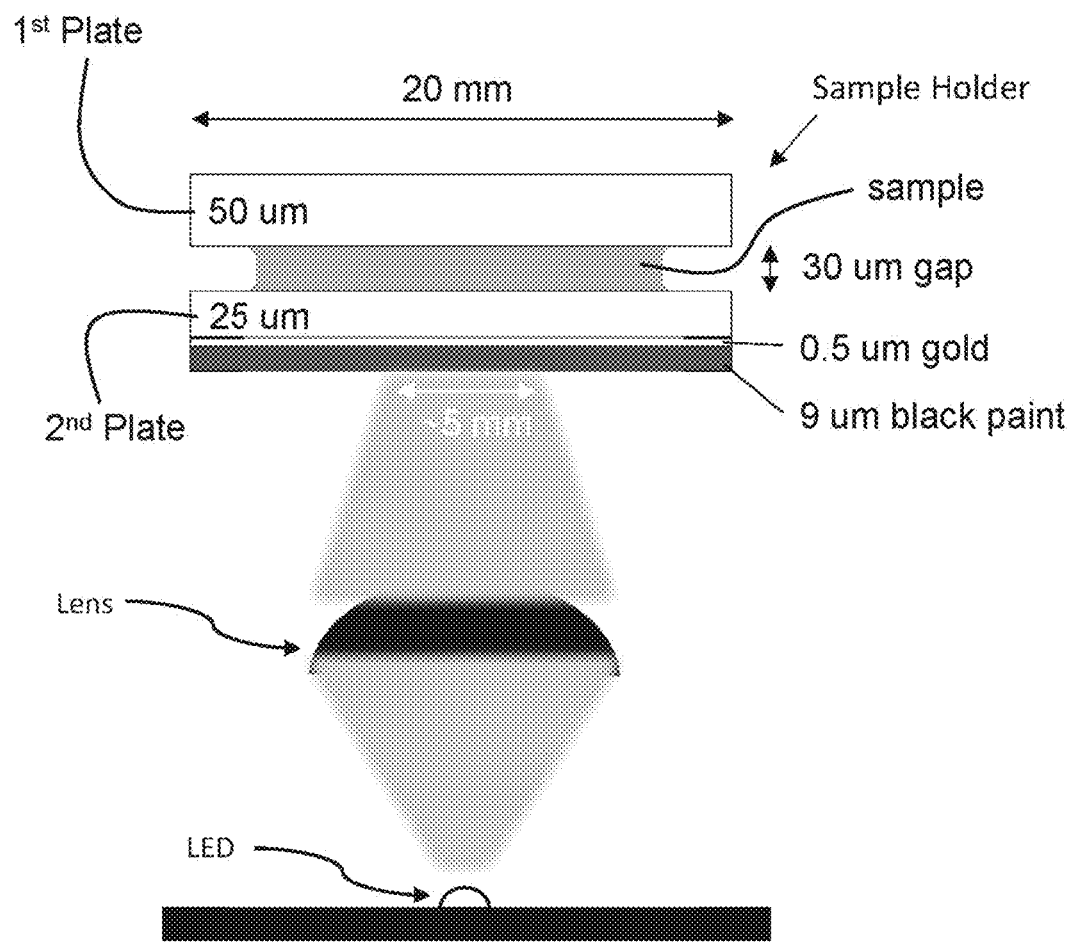
FIG. 40 schematically illustrates a schematic side view of the device, having a lens that focuses light from a heat source, in accordance with one or more embodiments.

Various heating/cooling layer of different materials and geometries on either outer or inner surface of the second plate were experimentally tested. One example (shown in FIG. 39A) is that the heating/cooling layer is on the outer surface of the second plate, and covers the entire second plate outer surface. The heating/cooling layer comprises an Au (gold) film and a black paint layer. The gold film has one surface in contact with the second plate outer surface, and another surface being painted with a black paint. The black paint is a commercial product of a film composited of black carbon nanoparticle and polymer mixture. The black paint had an average thickness of ~9 um (~2 um thickness variation). The black paint layer may be directly facing incoming LED light as illustrated in FIG. 40. Between the Au film and the second plate outer surface, there is a 5 nm adhesion layer of Ti, which improves the adhesion between Au and the second plate. But the adhesion layer is optional and should have minor or no effects on thermal properties of the sample holder, because of the thin thickness of the adhesion layer.

The heating source may be a blue light emitting diode (LED) with a central wavelength of 450 nm. As illustrated in FIG. 40, light from the LED was projected, using a lens, to the heating/cooling layer, but only on the central area of the heating/cooling layer, and typically the LED spot of size (i.e. area) on the heating/cooling layer is about 5 mm×5 mm, according to some embodiments. As shown later, for the given sample card and the sample thickness, only the sample over the LED heating spot can change and/or reach the designed temperature. Hence the heating zone area is about 5 mm×5 mm. In some embodiments, compared with the cooling zone area which is the entire area of the first plate, the cooling zone area may be about 16 times larger than that of the heating zone area (i.e. high-K C/H ratio=16).

The LED heating source is powered by a power supply that can change the LED current with a time less than 100 ms. In some embodiments, an aspherical condenser lens is used to focus the LED light and the lens has a diameter of 12 mm, focal length of 10.5 mm and numerical aperture (N.A.) of 0.54.

A temperature sensitive dye (LDS698) monitors the temperature of the sample in the heating zone (i.e. the area directly radiated by LED). The photodetector was used to monitor the temperature sensitive dye and feedback to control the LED current and hence the LED heating source and the heating zone temperature.

In the experiments described below (Experiment 1 to Experiment 12), unless stated otherwise, the sample holder supports the sample holder by supporting a ~2 mm rim at the two opposite edges of the second plate, therefore the sample holder is thermal conduction isolated from the outside, the cooling of sample holder is primarily by thermal radiative cooling. The thermal radiative cooling is primarily provided by the H/C layer, since the sample and the plates are poor thermal radiator and have much lower thermal conduction than the H/C layer. The thermal radiative cooling radiates thermal energy into an open environment (i.e. the room).

In our experiments, ~5 uL liquid sample with thermal properties close to water was deposited between the two plates and approximately in the center area of the plate surface. The sample was dropped on one of the plates of a RHC card first, then the other card was placed on top of the sample, and a hand press of the two plates into a closed configuration. Due to the spacers on the plate, when the two plates are in a closed configuration, the spacing between the two plates are regulated by the 30 um height spacer array to a separation of 30 um, and the sample thickness was found uniform even with different hand pressing forces, pressures and sequence (pressing one area first and then rub into other area of the RHC card). To achieve a good sample thickness by human hand pressing offers several advantages in practical use of the present invention.

Figure 39B:
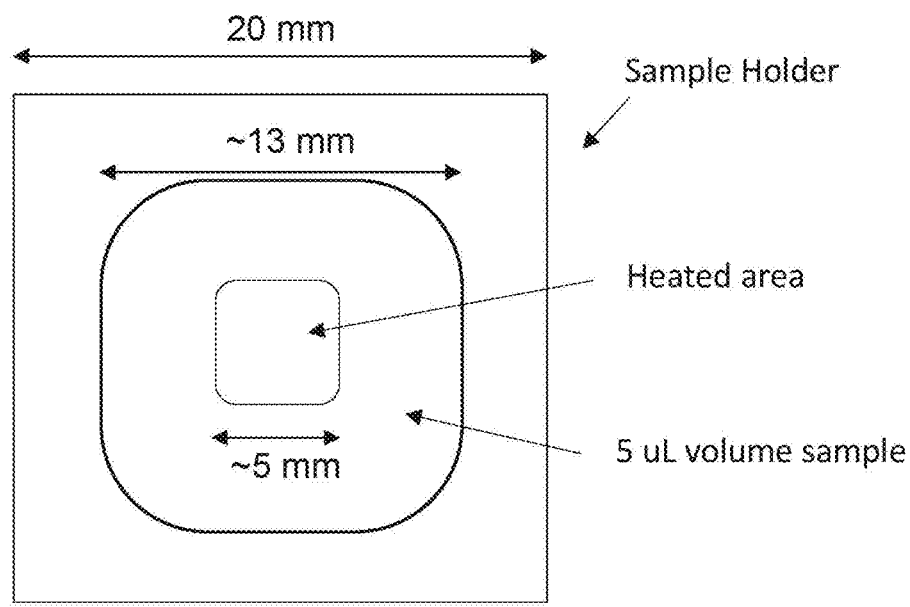

For a ~5 uL sample between the two plates, the sample has a thickness of 30 um and an area of ~166 mm$^2$ (approximately ~13 mm by ~13 mm square—the sample lateral shape is influenced by the spacers on the plate as illustrated in the top-down view of FIG. 39B). In some embodiments, the total sample area is over ~6.6 times larger than the heating zone area (~5 mm by 5 mm). Experimentally, we found that with this setup, only the potation of the sample above the heating zone got heated to the desired temperature. Namely, the area (volume) of the portion of the sample being heated is about ⅙th of the total sample area (volume).

In this setup, there was no physical wall at the edge of the sample disk, but only air. However, as described later, we found that the sample disk diameter before and after a 30 cycle PCR does not change much (i.e. hardly seen the difference by a naked eye), this means that even without a physical wall (except an air-liquid interface) to enclose liquid sample, the sample evaporation is nearly negligible.

All spacers used in this experimental section are the pillars fixed on one plate and having a flat top that can contact the other plate.

In our experiments, the liquid sample was deposited on one of the plate and then the second plate was put on top of the sample. The plates were pressed together by human hands. During the hand pressing, the sample spreads to form a film between the plates. Due to the spacers (of uniform height) on the plate, even with a hand-pressing, the final sample thickness is uniform and regulated by the two plate surfaces and the spacer height.

Furthermore, after the sample reaches the final thickness and the hand pressing force was removed, the two plates of the sample holder "self"-hold to each other by the capillary force of the liquid sample to "self"-maintain the constant sample thickness. Moreover, even during a thermal cycling of 65-95 C, the capillary force still held the sample thickness constant. Such self-sample holding without using any clamps can greatly simplify the device operation and cost.

Experiment 1

Light Absorption of Different H/C Layer Materials

In this experiment, the effects of the materials for H/C layer on absorption of the LED light were studied.

Figure 41:
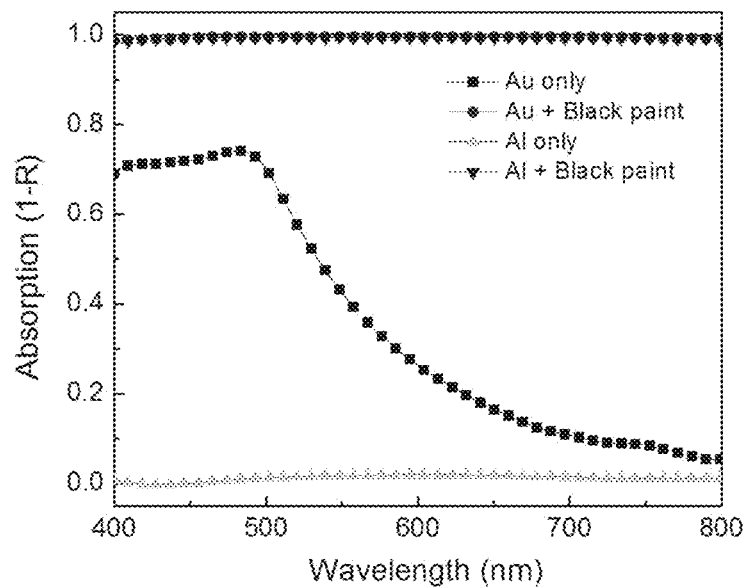
FIG. 41 shows experimental absorption spectra of different materials, in accordance with an embodiment.

Optical absorption spectrum of different materials for heating/cooling (H/C) layer. Experimentally, we tested the optical absorption spectrum (i.e. 1-R (the light reflection)) of four different H/C layer materials for the 450 nm LED irradiation: Au (gold) only (i.e. without a black paint) of 500 nm thick, Al (aluminum) only of 400 nm thick, Au (500 nm thick) with a black paint (9 um thick), and Al (400 nm thick) with a black paint (9 um thick). We found that as shown FIG. 41, the optical absorption is ~99% for the black paint coated Au and Al for the entire wavelength range of 400 to 800 nm, a maximum 73% (at ~490 nm wavelength) and much smaller after 490 nm wavelength for the Au only; and 0.1% over 400 nm to 800 nm bandwidth for Al only. This means that the 9 um thick black paint used in our experiments has greatly enhanced the light absorption and radiation of the H/C layer.

Experiment 2

Heating Zone Area Size Measurements

In this experiment, the area of heating zone on the HC layer was measured. We found experimentally that due to the fact that vertical heat transfer from the HC layer to the plates and sample are several orders of the magnitude better than the lateral thermal conduction in the plates, sample even with HC layer. The area of heating zone in the sample is about the same area as the LED irradiation area on the HC layer.

Experimentally, the sample holder card (as shown in FIG. 39A) has a first plate of 50 um thick PMMA plate, a second plate of 25 um thick PET, 30 um thick sample gap controlled by spacers, and a H/C layer of gold is on the outer surface of the second plate. The first plate, the second plate, and the gold/black-paint HC layer have the same area of 20 mm×20 mm. The HC layer comprises an Au (gold) film of 500 nm thick and a black paint layer. The gold film has one surface in contact with the second plate outer surface, and another surface being painted with a black paint. The black paint is a commercial product of a film composited of black carbon nanoparticle and polymer mixture. The black paint had an average thickness of ~9 um (~2 um thickness variation). The LED heating power projected on ~5 mm×5 mm heating zone of the H/C layer is 300 mW. The sample liquid is 5 uL temperature sensitive dye LDS698 2 mg/mL in 60% water and 40% DMSO. The temperature sensitive dye allows us to measure the sample temperature optically. The 5 uL sample on the RHC card has 30 um thickness and ~167 mm² area, which is much larger than the heating zone area. The thermal cycling is between 65° C. and 95° C.

We have observed experimentally that for the given condition, in thermal cycling (65-95° C.), based on measuring temperature sensitive dye, for the 167 mm² of sample area, only the sample area on top of the LED direct irradiation (~5 mm×5 mm) has a thermal cycling (65-95° C.), while the rest of the sample area stays nearly a constant temperature close to the room temperature (i.e. the environment temperature (e.g. ~20° C.)). The thermal cycling zone in the sample is approximately about ⅙th of the total sample area. The transition distance from the thermal cycling zone of the sample to the sample area with the environment temperature is, measured from the temperature sensitive dye, approximately 2-3 mm. This experiment also indicates that for the gold/black-paint HC layer of 20 mm×20 mm area, only the area of sample that is directly irradiated by the LED (~5 mm×5 mm) is heated. Namely, the heating zone is only ¹/₁₆th of the total HC layer (i.e. high-K C/H ratio=16). The reason is, as stated before, that in the given RHC card, the vertical heat transfer from the HC layer to the plates and sample are several orders of the magnitude better than a lateral thermal conduction in the plates and sample with HC layer.

Experiment 3

HC Layer Area Effects on Heating and Cooling Time

In this experiment, the effects of H/C zone area on heating and cooling time were studied. Two types of RHC cards were investigated.

Type-1 RHC card uses round disk-shaped HC layer. Type-1 RHC cards may include a first plate of 100 um thick PMMA poly(methyl methacrylate) plate, a second plate of 50 um thick PET (polyethylene terephthalate), 30 um thick sample gap controlled by spacers, and a H/C layer is 700 nm thick gold film on the outer surface of the second plate. The first plate and the second plate have a square shape and the same area of 20 mm×20 mm. The second plate has, on its inner surface, a periodic array of pillar spacers of flat top, uniform 30 um height, 30 um×40 um size and 80 um inter spacer distance. The HC layer positioned at center of the outer surface of the second plate is an Au layer of 700 nm thickness and a round disk shape with different disk diameters for different RHC cards.

Type-2 RHC card uses a square shaped HC layer. Type-2 RHC cards may include a first plate of 50 um thick PMMA plate, a second plate of 50 um thick PET, 30 um height spacers to control a sample thickness to 30 um, and a H/C layer is a 500 nm thick gold film on the outer surface of the second plate. The first plate has a square shape, an area of 20 mm×20 mm, and, on its inner surface, a periodic array of pillar spacers of flat top, uniform 30 um height, 30 um×40 um size and 80 um inter spacer distance. The second plate has a square shape, and four different area for four different HC layers. Two of the second plates have area of 20 mm×20 mm for the HC layer area of 10 mm×10 mm and 20 mm×20 mm, respectively; but the other two have area same as the HC layer for the HC layer area of 30 mm×30 mm and 40 mm×40 mm, respectively.

In testing two types of RHC cards, the LED heating power projected on ~5 mm×5 mm area of the H/C layer to form a heating zone and has a power of 300 mW. The sample liquid is 5 uL temperature sensitive dye LDS698 2 mg/ml in 60% water and 40% DMSO. The temperature sensitive dye allows us to measure the sample local temperature optically. The 5 uL sample on the RHC card has 30 um thickness (regulated by the spacer) and ~167 mm^2 area, which is much larger than the heating zone area. The thermal cycling is between 65° C. and 95° C.

Figure 43:
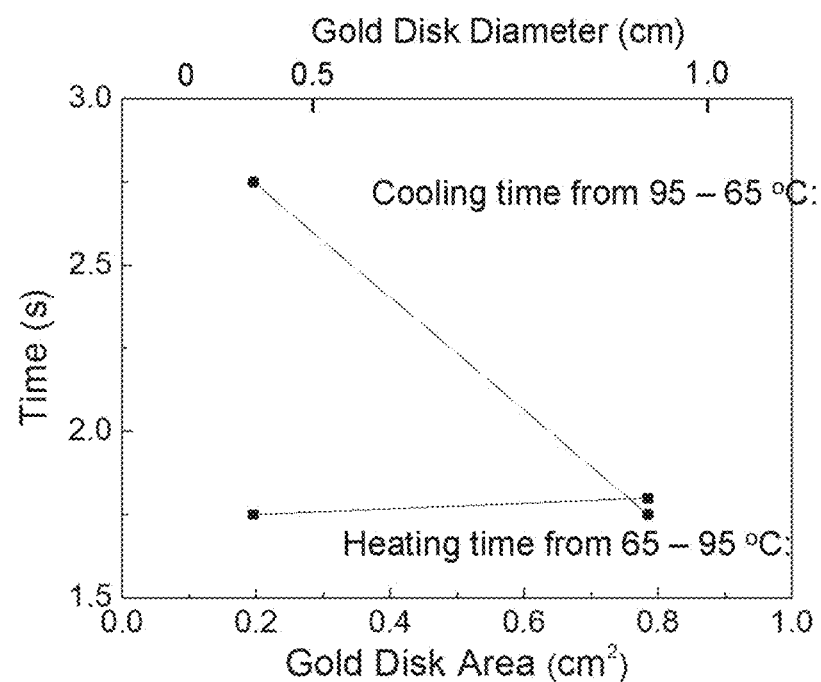
FIG. 43 shows experimental data of the effects of the area of the heating/cooling layer on heating and cooling time, in accordance with an embodiment.
Figure 44:
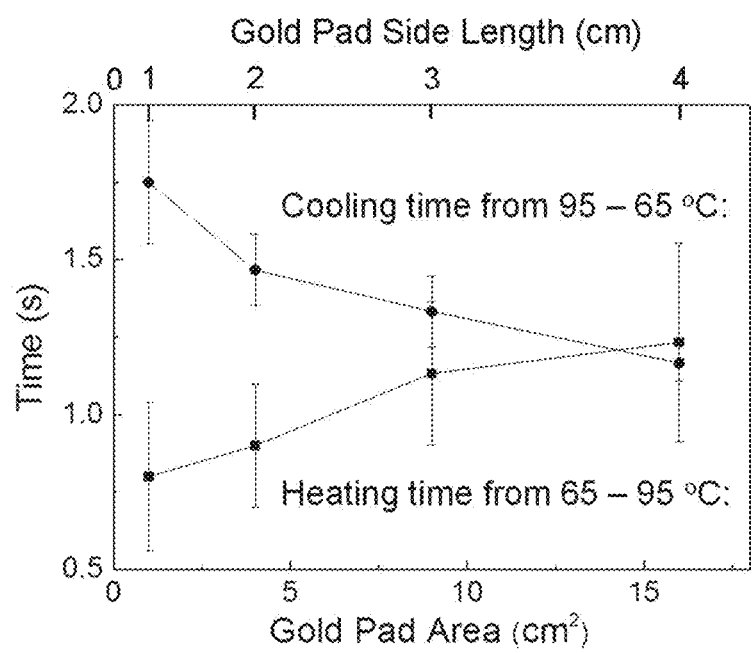
FIG. 44 shows experimental data of the heating and cooling time vs. the area size of the heating/cooling layer, in accordance with an embodiment.

The experimental data (shown in FIG. 43 and FIG. 44) show that as the H/C layer area becomes larger, the heating time increases, but the cooling time decreases. For Type-1 RHC card, the HC layer has no direct physical contact with the mechanical support to the card (e.g., sample holder), hence the decrease in cooling cycle time is primarily due to the increase of the thermal radiation cooling of the HC layer caused by the increase of the HC layer's radiative cooling area.

Experiment 4

Figure 42:
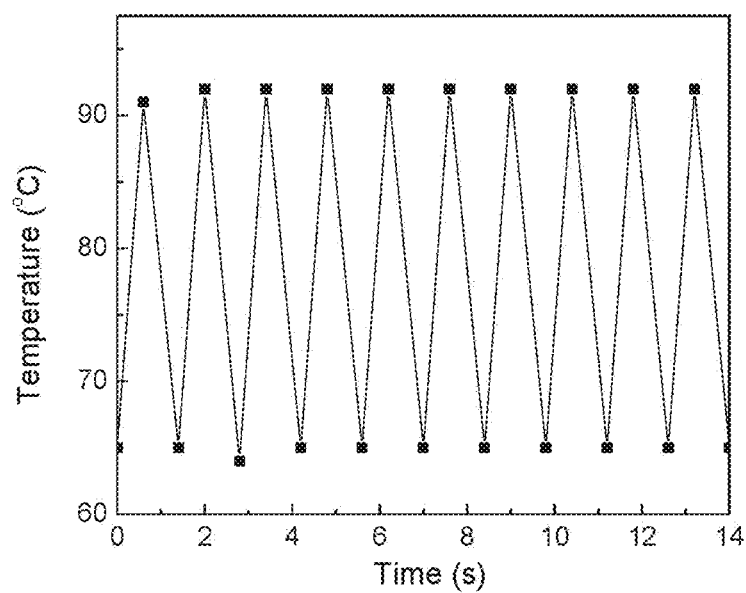
FIG. 42 shows experimental thermal cycling data, in accordance with an embodiment.

0.6 s Heating, 0.75 s Cooling Achieved with 500 nm Au H/C Layer and 500 mW Heating In this experiment, the heating and cooling cycle of a RHC card (the same as the one shown in FIG. 39A) with a water-like sample of 30 um thickness and 5 uL and a 500 mW LED power were studied. The experimental data shown in FIG. 42 shows 10 times cycling between 65° C. to 93° C. with heating time of ~0.65 second (an average temperature raising ramping 43° C./sec); and a cooling time of ~0.75 sec (an average temperature dropping ramping 37° C./sec).

Experiment 5

H/C Layer Thickness Effects on Heating and Cooling Time

In one experiment, the effects of H/C gold layer thickness on heating and cooling time were studied.

The example RHC card has a first plate of 100 um thick PMMA plate, a second plate of 50 um thick PET, 30 um thick spacers array to control sample thickness, and an H/C layer of gold is on the outer surface of the second plate. The first plate, the second plate, and the gold HC layer have the same area of 20 mm×20 mm. The LED heating power projected on a ~5 mm×5 mm heating zone of the H/C layer is 300 mW. 5 μl water-like sample on the RHC card has 30 um thickness and ~167 mm^2 area, which is much larger than the heating zone area. The thermal cycling is between 65° C. and 95° C.

Figure 45A:
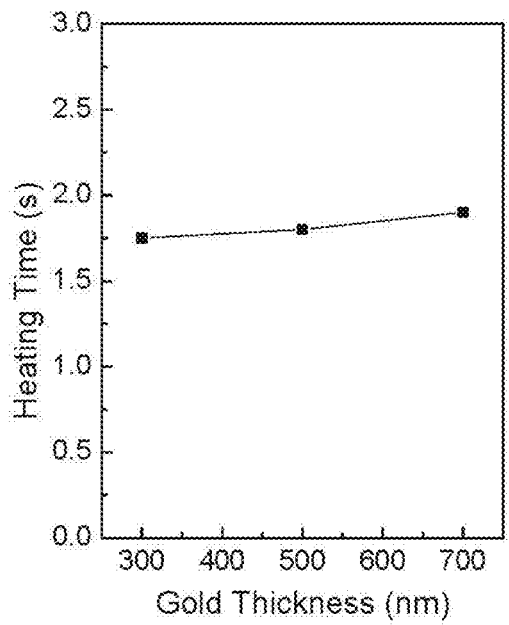
FIG. 45A shows experimental data of the relationship between the heating time and the heating/cooling layer thickness, in accordance with an embodiment.
Figure 45B:
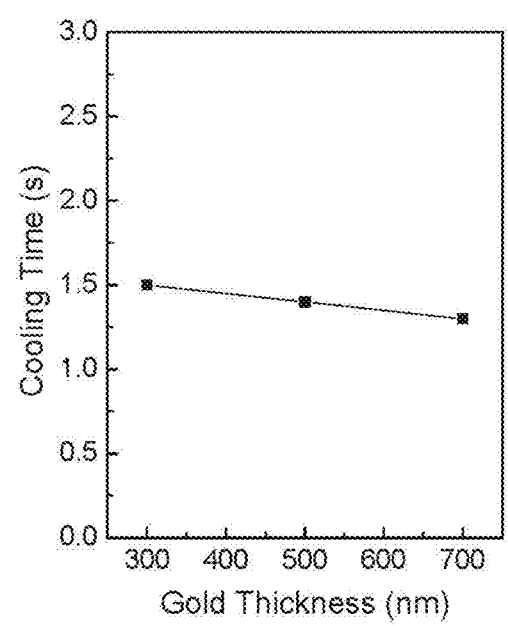
FIG. 45B shows experimental data of the relationship between the cooling time and the heating/cooling layer thickness, in accordance with an embodiment.

The experimental data shown in FIGS. 45A and 45B show that as the gold thickness of the HC layer changes from 300 nm to 700 nm, the heating time in a thermal cycle increases slightly (from 1.75 sec to 1.90 sec), but the cooling time in a thermal cycle decrease with the gold thickness (from 1.5 sec to 1.3 sec).

The cooling cycle time is shorter with the gold thickness. It suggests that (a) the gold HC layer thermal radiative cooling is important in the cooling of the sample and (b) the thermal radiative cooling involves a thermal conduction of the heat from the sample through the gold to the gold surface for radiation. A thicker gold, a better thermal conduction of the heat from the sample to the gold HC layer edge.

The heating cycle time gets longer with an increase of the gold thickness. Clearly, a thicker gold will increase the total heating energy. But in this experiment, the LED heats only ~5 mm×5 mm relevant sample area and the gold HC layer area to the maximum cycling temperature, and the gold thermal mass is small (due to the thin thickness), hence the increase in the total heating energy is small, leading to a weak increase of the heating cycle with the increase of gold thickness.

Experiment 6

Effects of Heating/Cooling Layer to Sample Distance on Heating and Cooling Time

In this experiment, the effects of the distance between the HC layer and sample on heating and cooling time were studied.

The example RHC card has a first plate of 100 um thick PMMA plate, a second plate of PET film that has different thickness for a different RHC card, 30 um thick sample thickness controlled by spacers, and a HC layer is made of a bare 0.5 um thick gold and is on the outer surface of the second plate. The first plate, the second plate, and the gold HC layer have the same area of 20 mm×20 mm. The LED heating power projected on ~5 mm×5 mm heating zone of the H/C layer is 300 mW. 5 uL water-like sample on the RHC card has 30 um thickness and ~167 mm$^2$ area, which is much larger than the heating zone area. The thermal cycling is between 65° C. and 95° C.

The distance between the HC layer and sample is the distance between the gold surface that is in contact with a second plate surface and the sample surface that is in contact with another second plate surface (i.e., the gold to the sample distance).

Figure 46A:
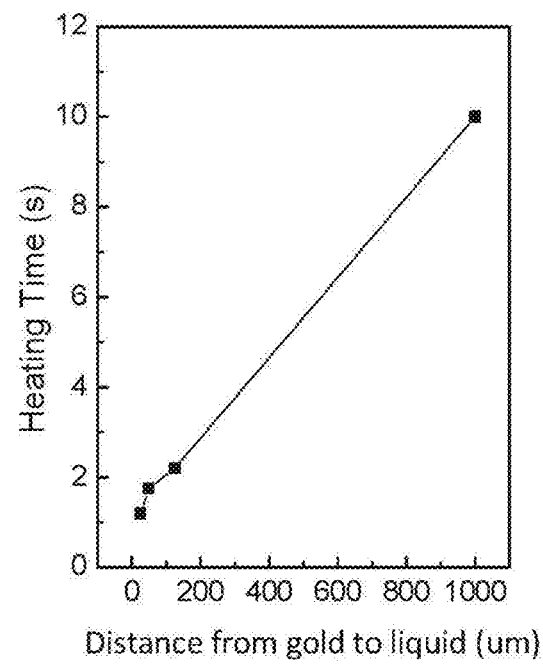
FIG. 46A shows experimental data of the relationship between the heating time and the distance between the heating/cooling layer and the sample, in accordance with an embodiment.
Figure 46B:
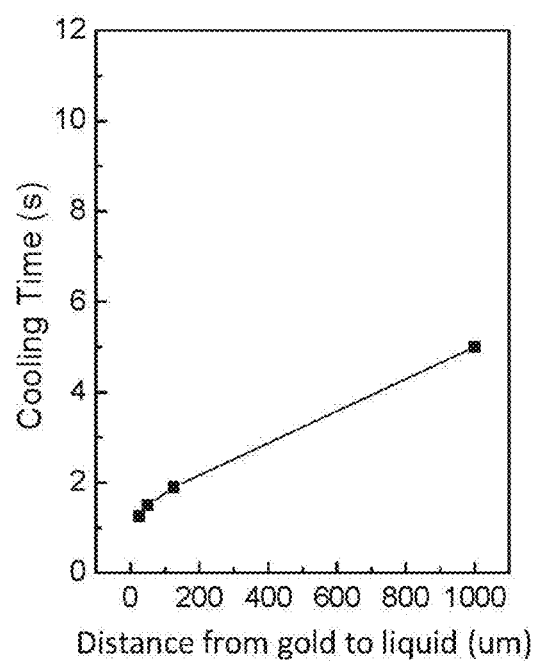
FIG. 46B shows experimental data of the relationship between the cooling time and the distance between the heating/cooling layer and the sample, in accordance with an embodiment.
Figure 47A:
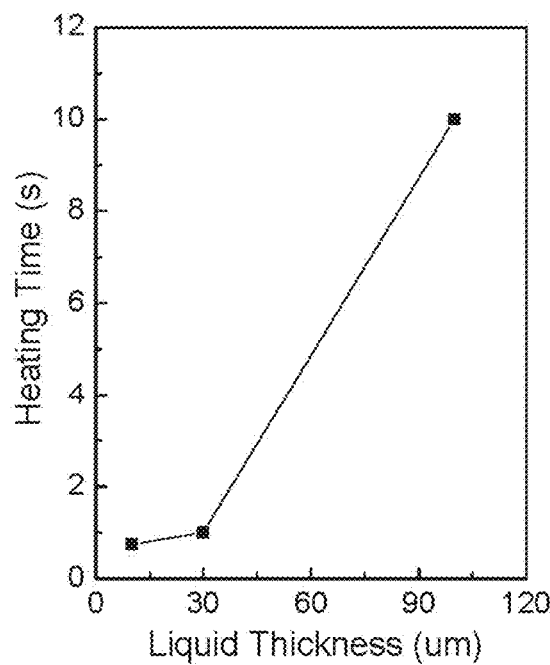
FIG. 47A shows experimental data of the relationship between the heating time and the sample layer thickness, in accordance with an embodiment.
Figure 47B:
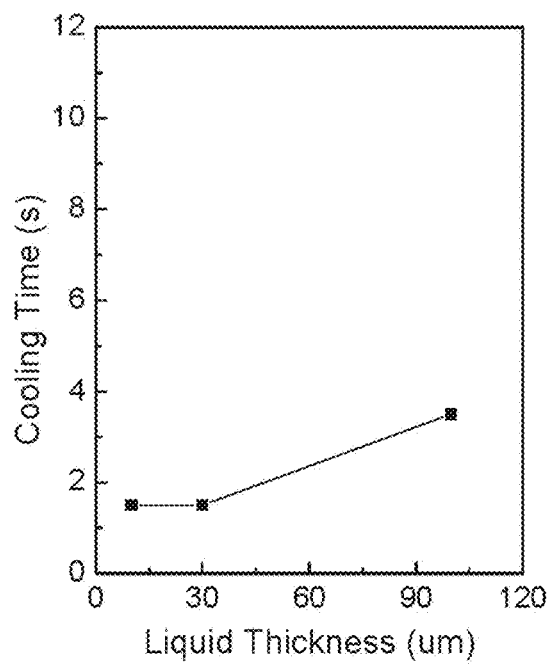
FIG. 47B shows experimental data of the relationship between the cooling time and the sample layer thickness, in accordance with an embodiment.

The experimental data shown in FIGS. 46B and 46C show that as the thickness of the second plate changes (hence the gold to the sample distance) from 25 um to 1000 um, both the heating cycle time and the cooling cycle time increase; however, the heating cycle time increases with the second plate thickness far more significantly than the cooling cycle time.

The data suggests that as the increase in the second plate thickness would cause significant increase in the energy required for heating and cooling the second plate, and significant reduction of thermal conduction between the sample and the HC layer.

For fast heating and cooling, one should reduce the thickness of the second plate (which is physically sandwiched by the sample and the HC layer), which should be as thin as possible. A preferred thickness of the second plate is 25 nm or less. Another preferred thickness of the second plate is 10 nm or less.

Experiment 7

Sample Thickness Effects on Heating and Cooling Time

In this experiment, the effects of the thickness of the sample sandwiched between two plates on heating and cooling time were studied.

The example RHC card has a first plate of 100 um thick PMMA plate, a second plate of 25 um thick PET film, a periodic array of spacers to control the sample thickness, and a HC layer is made of a bare 0.5 um thick gold and is on the outer surface of the second plate. A water-like sample has a different gap (i.e. thickness) for each different RHC card. The first plate, the second plate, and the gold HC layer have the same area of 20 mm×20 mm. The LED heating power projected on ~5 mm×5 mm heating zone of the H/C layer is 300 mW. Water-like sample on the RHC card has ~167 mm$^2$ area, which is much larger than the heating zone area. The thermal cycling is between 65° C. and 95° C.

Figure 48A:
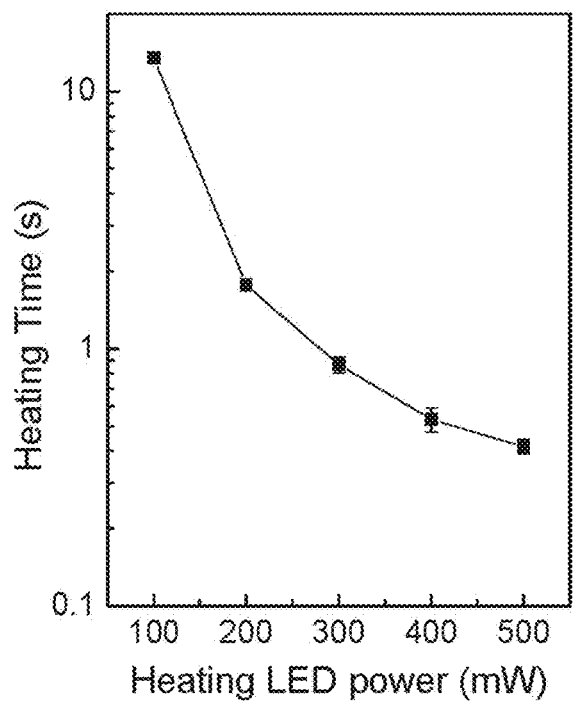
FIG. 48A shows experimental data of the relationship between the heating time and the heating source power, in accordance with an embodiment.
Figure 48B:
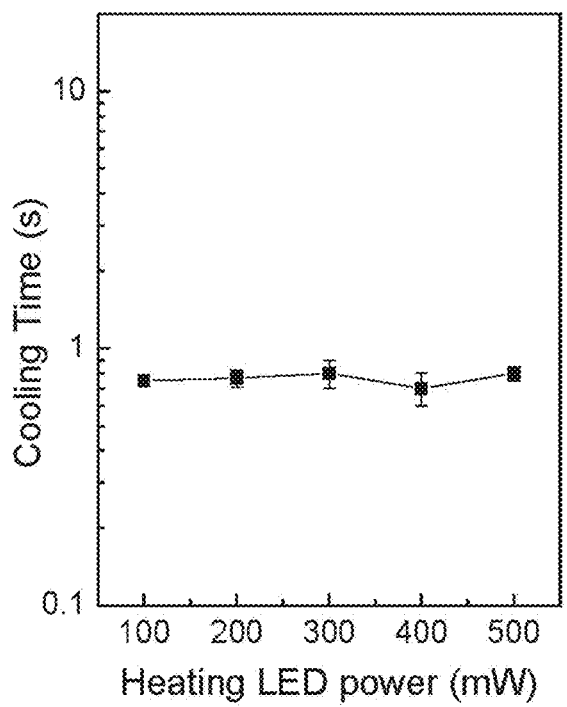
FIG. 48B shows experimental data of the relationship between the cooling time and the heating source power on the sample, according to some embodiments.

The experimental data shown in FIGS. 48A and 48B show that as the sample thickness changes from 10 um to 100 um, both the heating cycle time and the cooling cycle time increase, however the heating cycle time increases with the second plate thickness far more significantly than the cooling cycle time.

The data suggests that the increase in the sample thickness would cause significant increase in the energy required for heating and cooling the sample.

For fast heating and cooling, one should reduce the sample thickness should be as thin as possible. A preferred thickness of the sample is 30 um or less. Another preferred thickness of the sample is 10 um or less. Another preferred thickness of the sample is 5 um or less.

Experiment 8

LED Power Effects on Heating and Cooling Time

In this experiment, the effects of LED power on heating and cooling time were studied. The example RHC card has a first plate of 50 um thick PMMA plate, a second plate of 25 um thick PET, a HC layer is on the outer surface of the second plate. The first plate, the second plate, and the gold/black-paint HC layer have the same area of 20 mm×20 mm. The first plate has, on its inner surface, a periodic array of spacers that has a 30 um height, a 30 um×40 um lateral sectional size and an 80 um inter spacer distance. The HC layer comprise an Au (gold) film of 500 nm thick and a black paint layer. The gold film has one surface in contact with the second plate outer surface, and another surface being painted with a black paint. The black paint is a commercial product of a film composited of black carbon nanoparticle and polymer mixture. The black paint had an average thickness of ~9 um (~2 um thickness variation).

The heating power, provided by a blue (450 nm peak wavelength) LED, was projected on ~5 mm×5 mm heating zone of the H/C layer, and the power was varied from 100 mw to 500 mW. The sample liquid is 5 uL temperature sensitive dye LDS698 2 mg/ml in 60% water and 40% DMSO. The temperature sensitive dye allows us to measure the sample temperature optically. The 5 uL sample on the RHC card has 30 um thickness and ~167 mm² area, which is much larger than the heating zone area.

Experimental data shown in FIG. 48A shows the relationship between the heating time and the heating source power, illustrating experimental data of the time needed for heating from 65° C. to 93° C. with heating LED power strength from 100 mW to 500 mW on the RHC card.

Experimental data shown in FIG. 48B shows the relationship between the cooling time and the heating source power, illustrating the time needed for cooling from 93° C. to 65° C. The heating/cooling time results are also shown in Table 1.

The experimental data show that for the given sample holder (i.e. RHC card) as the LED power was increased from 100 mW to 500 mW, the heat cycle time drops from 14 sec to 0.4 sec, while the cooling cycle time is nearly constant.

The experimental data suggest that for a low heating power (i.e. low heating power density), it would take a longer time to deliver a fixed amount of energy, and the longer time will increase the energy loss in thermal conduction and radiation loss, and hence increase wasted energy. For cooling, since the amount of the thermal energy stored in a fixed volume sample at a given temperature is fixed, regardless how long to reach that temperature, the cooling time is almost independent of the heating cycle time.

The experiment showed that in order to reduce the total thermal cycle time, one should increase the heating power.

TABLE 1

LED power effects on RHC heating and cooling time

| Heating LED power | 100 mW | 200 mW | 300 mW | 400 mW | 500 mW |
| --- | --- | --- | --- | --- | --- |
| Heating time (65-93° C.) (second) | 14 | 1.76 | 0.87 | 0.53 | 0.4 |

TABLE 1-continued

LED power effects on RHC heating and cooling time

| Heating LED power | 100 mW | 200 mW | 300 mW | 400 mW | 500 mW |
| --- | --- | --- | --- | --- | --- |
| Cooling time (65-93° C.) (second) | 0.75 | 0.77 | 0.8 | 0.7 | 0.8 |
| Heating time + Cooling time (second) | 14.75 | 2.53 | 1.67 | 1.23 | 1.2 |

Experiment 9

H/C Layer Materials Effects on Heating and Cooling Time

In this experiment, the effects of H/C layer materials on heating and cooling time were studied. The example RHC card has a first plate of 50 um thick PMMA plate, a second plate of 25 um thick PET film, a periodic array of spacers to regulate a water-like sample to a thickness to 30 um thickness, and a HC layer is on the outer surface of the second plate. The HC layer has a different material for each different RHC card. The first plate, the second plate, and the HC layer have the same area of 20 mm×20 mm. The LED heating power projected on ~5 mm×5 mm heating zone of the H/C layer is 300 mW. 5 uL water-like sample on the RHC card has 30 um thickness and ~167 mm² area, which is much larger than the heating zone area. The thermal cycling is between 65° C. and 93° C.

Figure 49A:
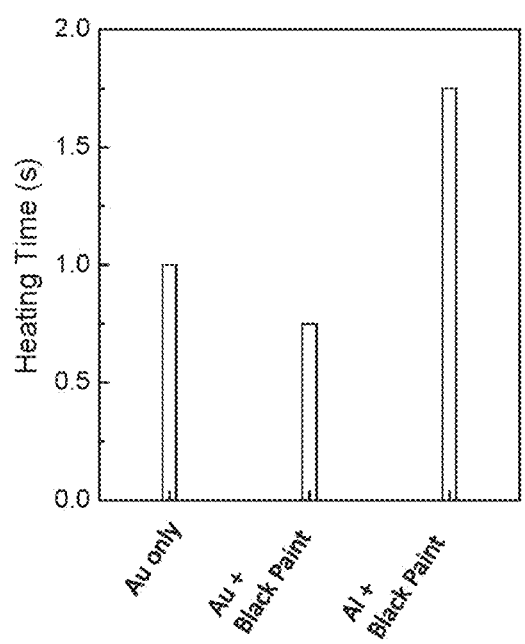
FIG. 49A shows experimental data of the relationship between the heating time and different heating/cooling layer materials, according to some embodiments.
Figure 49B:
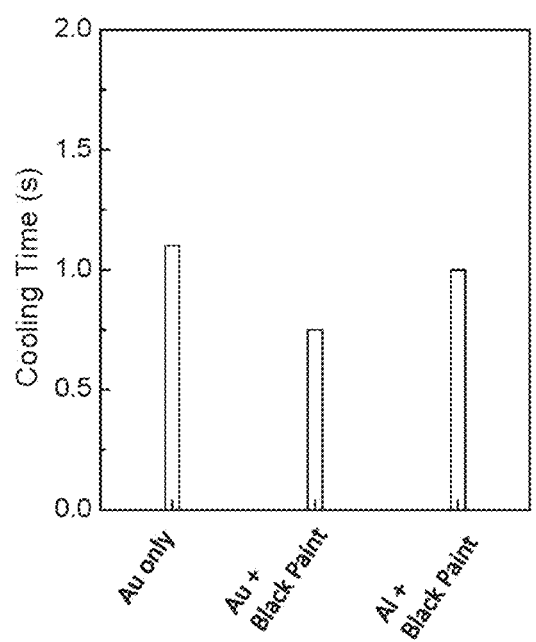
FIG. 49B shows experimental data of the relationship between the cooling time and different heating/cooling layer materials, according to some embodiments.

The experimental data shown in FIGS. 49A and 49B show that for the three different HC layer materials tested, the heating cycle time and cooling cycle time is 0.75 sec and 0.75 sec, respectively for sample holder with the HC layer of Au (500 nm thick) plus 9 um black paint, 1 sec and 1.1 sec for the sample holder with the HC layer of Au (500 nm thick) only, and 1.75 sec and 1 sec for the sample holder with the HC layer of Al (500 nm thick) plus 9 um black paint.

This experiment indicates the significance of a good lateral thermal conductance in thermal radiation cooling. Compared with the gold with a black paint, the aluminum plus black paint has nearly the sample light absorption (hence radiation), but much poorer lateral thermal conduction, which makes the effect thermal radiation area much less, because the heat cannot spread laterally as much.

The experiments show that a preferred embodiment for the material for HC layer is a thin gold film plus a black paint.

Experiment 10

Demonstration of 0.73 Sec Thermal Cycling Time 0.23 Sec Heating Time and 0.5 Sec Cooling Time Sec In this experiment, for a thermal cycling between 65 C to 93 C, a RHC card (Card-B) experimentally demonstrated 0.73 sec thermal cycling time (0.23 sec heating time and 0.5 sec cooling time) and another RHC card (Card-A) experimentally demonstrated 0.9 sec thermal cycling time (0.3 sec heating time and 0.6 sec cooling time)

Figure 50A:
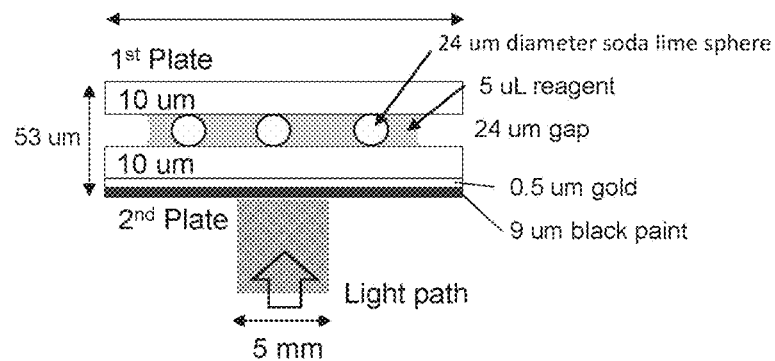
FIG. 50A shows a schematic of a device having sphere-shaped spacers, according to some embodiments.

FIG. 50A illustrates a sample holder having two plates, each of them being a high-density polyethylene (HDPE) film that has about a 10 um thickness, about 20 mm wide and about 20 mm long, according to some embodiments. The spacers that control the sample thickness were about 24 um diameter soda lime spheres with concentration of approximately 60 mg/mL. The sphere spacers were mixed with the sample.

Figure 50B:
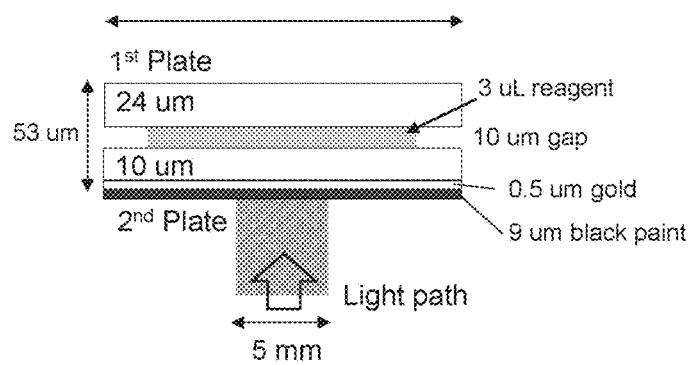
FIG. 50B shows a schematic of a device having pillar-like spacers, according to some embodiments.

FIG. 50B illustrates a sample holder having a first plate of poly(methyl methacrylate) (PMMA) film of 25 um thickness, and a second plate of high-density polyethylene (HDPE) film of 10 um thickness. Both plates have the same area of 20 mm×20 mm. The first plate has, on its inner surface, a periodic array of spacers of 10 um height, 30 um×40 um size and 80 um inter spacer distance.

Both sample holder embodiments illustrated in FIGS. 50A and 50B have a H/C layer on the entire outer surface of the second plate. The H/C layer comprises an Au film with 500 nm thickness, that has one surface in contact with the second plate outer surface, and another surface being painted with a black paint. The black paint is a commercial product of a film composed a black carbon nanoparticle and polymer mixture, and the film painted has average thickness of 9 um and 2 um thickness variation.

The sample is a liquid temperature sensitive dye LDS698 with 2 mg/mL concentration in 60% water and 40% DMSO. The volume of the sample is 5 uL for the sample holder in FIG. 50A and 3 uL for the sample holder in FIG. 50B.

The heating source, which is a blue light emitting diode (LED) with a central wavelength of 450 nm, projected 500 mW energy on the black paint layer of the HC layer, forming a heating zone of an ~5 mm×5 mm area in the center of the second plate.

The experimental data (Table 2) show that for a thermal cycling of 65° C. to 93° C., the sample holder of FIG. 50A (has 0.3s heating cycle time and 0.60s cooling time, hence 0.90 sec total thermal cycle time; and the sample holder of FIG. 50B has 0.23s heating cycle time and 0.50s cooling time, hence 0.73 sec total thermal cycle time.

TABLE 2.1

RHC parameters

| Card | 1st Plate | 2nd Plate | Spacer |
|---|---|---|---|
| FIG. 50A | 10 um HDPE | 10 um HDPE | 24 um diameter beads |
| FIG. 50B | 24 um PMMA | 10 um HDPE | 10 um height pillar |

TABLE 2.2

Heating/Cooling performance

| Card | Heating time (s) 65° C. to 93° C. | Cooling time (s) 93° C. to 65° C. | Cycling time (s) |
|---|---|---|---|
| FIG. 50A | 0.30 s | 0.60 s | 0.90 s |
| FIG. 50B | 0.23 s | 0.50 s | 0.73 s |

Experiment 11

Effects of Using Sample Support and Sample Adaptor on Heating and Cooling Time

In this experiment, the effects of using sample holder support and sample adaptor on heating and cooling time were studied.

In the experiment, a RHC card was put on a mechanical sample card support (termed "card support"), and then the card support was slide into an adaptor. The thermal cycling time was measured for the cases of (a) the RHC card only, (b) the RHC card on the card support, and (c) the RHC card on the card support and the card support is slid into the adaptor.

In some embodiments, a sample holder (illustrated in FIGS. 51A and 51B) comprises a first plate is a poly(methyl methacrylate) (PMMA) film that has a 10 um to 50 um thickness, a 22 mm width and a 27 mm length. The first plate has, on its inner surface, a periodic array of spacers having a 30 um height, a 30 um×40 um sectional size and 80 um inter spacer distance.

In some embodiments, the second plate is a polyethylene terephthalate (PET) film or high-density polyethylene film that has a 10 um to 50 um thickness, a 20 mm width and a 27 mm length. The heating/cooling layer covers the entire outer surface of the second plate. The heating/cooling layer comprises an Au film with 100 nm to 500 nm thickness that has one surface in contact with the second plate outer surface, and another surface being painted with a black paint. The black paint has an average thickness of 9 um.

Figure 51A:
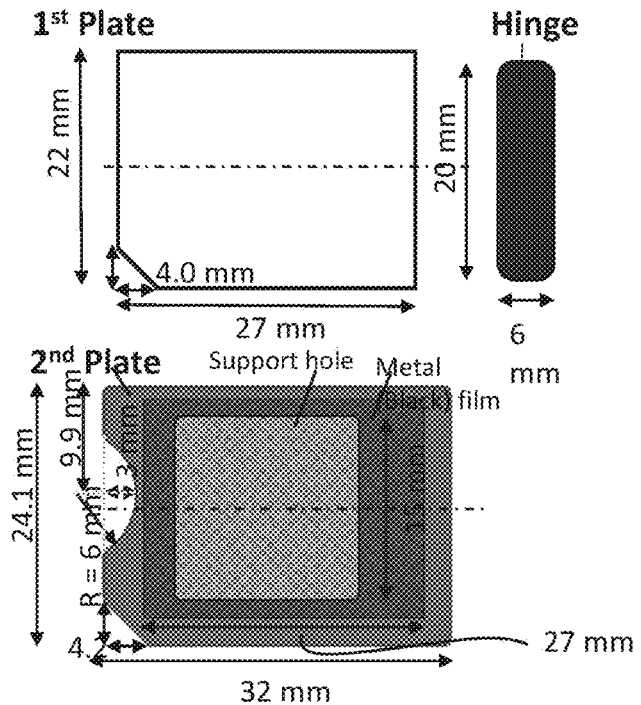
FIGS. 51A and 51B show a top view and a side view, respectively, of a device on a support, according to some embodiments.
Figure 51B:
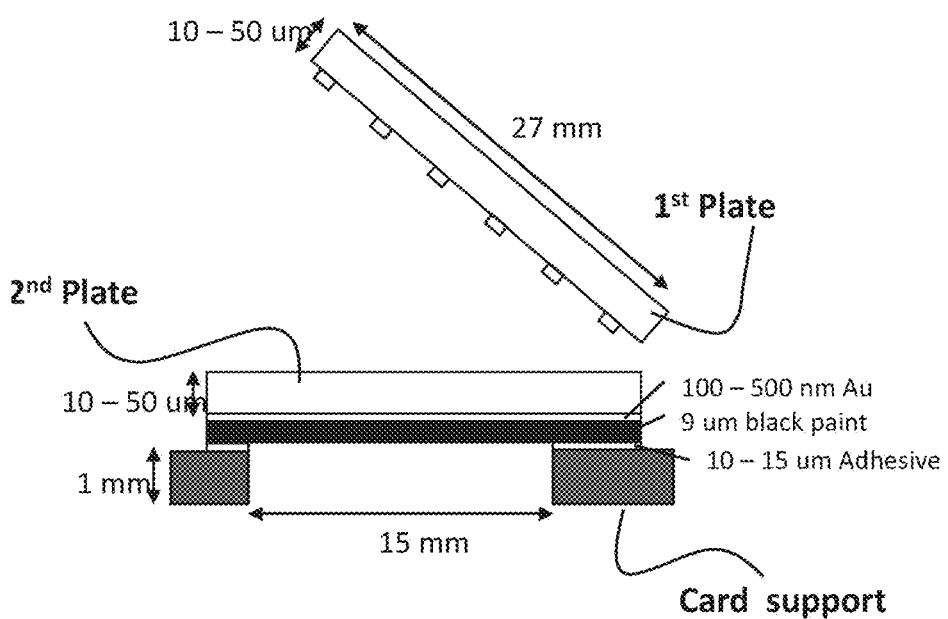

According to some embodiments, a card support (as illustrated in FIGS. 51A and 51B) comprises 1 mm thick PMMA plate of 24 mm width and 32 mm length that has a 15 mm×15 mm square hole in the center. The RHC card and the card support were glued together using 10-15 um thick adhesive between the black paint of the RHC card and a surface of the card support as illustrated in FIG. 51B.

According to some embodiments, the card adapter comprises an assembly of two U shaped frames that a sample card can slide in or out of the U. One of U shape frame is made of a plastic and the other piece is made of an aluminum, where the two U shape frame are assembled in parallel with a gap between them, and the gap is the slot for the sample card to slide. An example of the card adaptor is to cut a conventional SD card connecter into U shape (cut from the back end).

In testing the thermal cycling time of a RHC card of 50 nm thick first card and 25 nm thick PET second card (both has 20 mm×20 mm area), the sample liquid was 5 uL temperature sensitive dye LDS698 2 mg/mL in 60% water and 40% DMSO, and a blue 450 nm LED) was projected on the black paint with 5 mm×5 mm area (forming the heating zone) and 300 mW power.

Figure 52:
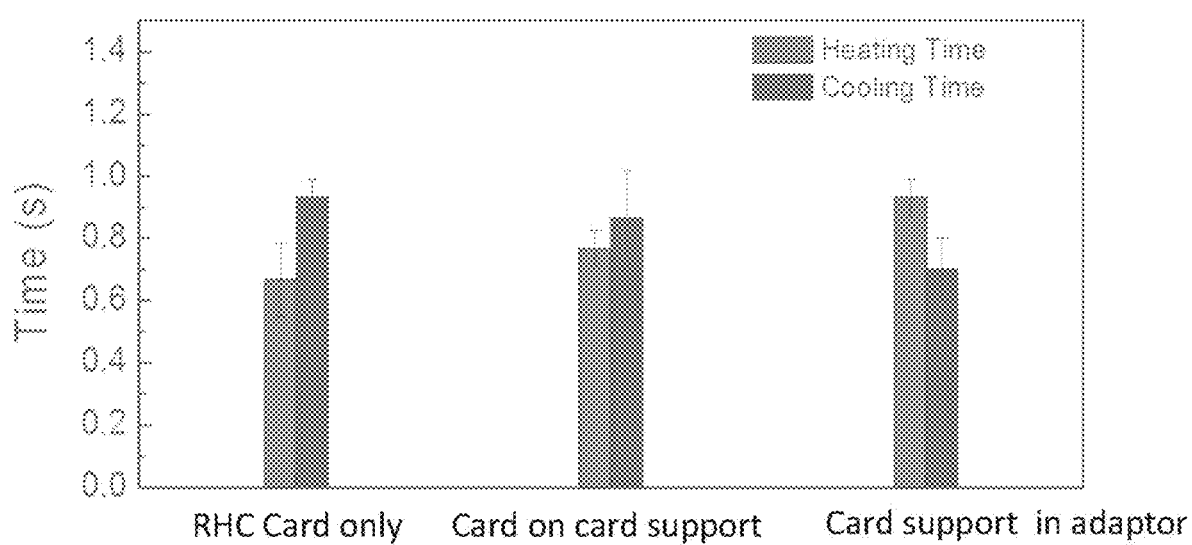
FIG. 52 shows experimental data of the effects of putting a device on a device support and/or a device adaptor on heating and cooling time, according to some embodiments.

The experimental data shown in FIG. 52 demonstrates that for a thermal cycling between 65° C. and 93° C., (a) for just the RHC card only, the heating cycle time was 0.67 sec, the cooling cycle was 0.9 sec, and total thermal cycle time was 1.57 sec; (b) for the RHC card on the card support, the heating cycle time was 0.77 sec, the cooling cycle was 0.87 sec, and total thermal cycle time was 1.64 sec; and (c) for the RHC card on the card support and the card support is slide into the adaptor, the heating cycle time was 0.93 sec, the cooling cycle was 0.7 sec, and total thermal cycle time was 1.63 sec.

The experimental data suggest that by making a RHC card cooling primarily based on thermal radiative cooling, the RHC card can be supported by a card support and the card support can be inserted into an adaptor while increasing the thermal cycle time less than 4%.

Experiment 12

Effects of Using Extra Heat Sink

In this experiment, the effects of adding an external heat sink on heating and cooling time were studied. In this experiment, rather than let heat from the RHC card radiate into the environment, a Peltier cool was put in touch with an edge of the HC layer of a RHC card.

The RHC card has a first plate of 50 um thick PMMA plate, a second plate of 50 um thick PET film, a periodic array of spacers to control the sample thickness to 30 um, and a HC layer is made of a bare 0.3 um thick gold and is on the outer surface of the second plate. The first plate has an area of 20 mm×20 mm. The second plate and the gold HC layer have the same area of 30 mm×30 mm.

The LED heating power projected on ~5 mm×5 mm heating zone of the H/C layer is 500 mW. 5 uL water-like sample on the RHC card has 30 um thickness and ~167 mm² area, which is much larger than the heating zone area. The thermal cycling is between 65° C. and 93° C.

In some setups, a Peltier cooler, providing 0 C heat sink, is either in contact with or nearby the HC layer by overlapping 3 mm edge with the second plate. In a reference setup, there was no Peltier cooler. Sample liquid is 5 uL temperature sensitive dye LDS698 with 2 mg/mL concentration in 60% water and 40% DMSO.

The experimental data (Table 3) show that without the Peltier cooler, the liquid inside RHC card's heating time from 65° C. to 93° C. is 0.63s, while the cooling time from 93° C. to 65° C. is 1.2s, and that with Peltier cooler in contact with the Au film, the liquid inside RHC card's heating time from 65° C. to 93° C. is increased to 0.73s, while the cooling time from 93° C. to 65° C. is shorten to 0.93s. Using the Peltier cooler, the total thermal cycle time is reduced from 1.83 to 1.66. This was achieved by a slightly increase of the heating cycle time, but a significantly reduce of the cooling cycle time.

TABLE 3

Effects of Using Extra Heat Sink with RHC card

| Setup | No Peltier | Peltier on RHC edge; touching Au |
|---|---|---|
| Heating Time (65-93° C.) (seconds) | 0.63 | 0.73 |
| Cooling Time (93-65° C.) (seconds) | 1.2 | 0.93 |
| Heating Time + Cooling Time (seconds) | 1.83 | 1.66 |

Sample Card (i.e. RHC Card)

Certain exemplary embodiments of the key components of a sample card (i.e. RHC card) are given below.

Sample Thickness

To reduce the thermal mass of the sample as well as reduce the thermal convention loss in the sample, in some embodiments, the average sample thickness at the region being heated by the heating/cooling layer is 500 um or less, 200 um or less, 100 um or less, 50 um or less, 20 um or less, 10 um or less, 5 um or less, 2 um or less, 1 um or less, 500 nm or less, 300 nm or less, 100 nm or less, 50 nm or less, or a range between any two of the values.

One preferred average sample thickness at the region being heated by the heating/cooling layer is from 0.1 um to 0.5 um, 0.5 um to 10 um, 10 um to 20 um, 20 um to 30 um, 30 um to 50 um, from 50 um to 80 um, 80 um to 100 um, or 100 um to 150 um.

Experiment 13

Example of Real Time PCR Amplification with RHC Card and System

The RHC card in this experiment has a first plate of 50 um thick PMMA plate, a second plate of 25 um thick PET, a H/C layer is on the outer surface of the second plate. The gold/black-paint HC layer have an area of 10 mm in diameter. The first plate has, on its inner surface, a periodic array of spacers. The HC layer comprise a thin Au (gold) film and a black paint layer. The gold film has one surface in contact with the second plate outer surface, and another surface in contact with a black paint. The black paint is a commercial product of a film composited of black carbon nanoparticle and polymer mixture. The black paint had an average thickness of ~9 um (~2 um thickness variation).

PCR (real-time PCR) reagents for amplification of *Staphylococcus aureus* genomic DNA with a total volume of 20 uL comprise MSSA Forward primer, MSSA Reverse primer and Cy5 labeled DNA probe with AptaTaq DNA buffer, Aptataq Polymerase, MgCl2, dNTP, bovine serum albumin (BSA), template DNA and ddH2O.

In a real time PCR experiments, two positive RHC cards have shown clear increase in fluorescence signal vs. cycle number, especially after 20 cycles' amplification. While one negative RHC card does not have obvious increased fluorescence signal vs. cycle number. After 40 cycles of amplification in RHC system, the PCR products in RHC cards are extracted and a nucleic acid gel run is performed to confirm that only two positive RHC cards have successful amplification band.

Sample Wells

In certain embodiments, one or both of the plates have sample wells, wherein the well regulates the maximum volume of the sample in the well and prevents the sample to flow into other location of the plates.

Plate Thickness

To reduce the thermal mass of the first and second plates as well as reduce the lateral thermal conduction loss in the plates, the thickness of the first plate and the second plate is preferred to be thin.

In certain embodiments, the first plate or the second plate has a thickness of 2 nm or less, 10 nm or less, 100 nm or less, 200 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, 5 mm or less, 10 mm or less, or in a range between any two of these values.

In some embodiments, the first plate or the second plate has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

The first plate and the second plate can have the same thickness or a different thickness, and can be made of the same materials or different materials.

In some preferred embodiments, the first plate or the second plate has a thickness in a range of between 10 nm and 500 nm, 500 nm and 1 um, 1 um and 2.5 um, 2.5 um and 5 um, 5 um and 10 um, 10 um and 25 um, 25 um and 50 um, 50 um and 100 um, 100 um and 200 um, or 200 um and 500 um, or 500 um and 1000 um.

A preferred thickness of the first plate or the second plate is 10 nm or less, 100 nm or less, 200 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, or in a range between any two of the values.

In some preferred embodiments, the thickness of the plate that has the heating/cooling layer is thinner than the other plate that does not have a heater.

In some preferred embodiments, the first plate has a thickness of 100 nm, 200 nm, 500 nm, 1 um (micron), 2 um, 5 um, 10 um, 25 um, 50 um, 100 um, 125 um, 150 um, 175 um, 200 um, 250 um, or in a range between any two of the values; while the second plate has a thickness of 25 um, 50 um, 100 um, 125 um, 150 um, 175 um, 200 um, 250 um, 500 um, 1 mm, 1.5 mm, 2 mm, or in a range between any two of the values, In some embodiments, the average thickness for at least one of the plates is in the range of 1 to 1000 um, 10 to 900 um, 20 to 800 um, 25 to 700 um, 25 to 800 um, 25 to 600 um, 25 to 500 um, 25 to 400 um, 25 to 300 um, 25 to 200 um, 30 to 200 um, 35 to 200 um, 40 to 200 um, 45 to 200 um, or 50 to 200 um.

In some embodiments, the average thickness for at least one of the plates is in the range of 50 to 75 um, 75 to 100 um, 100 to 125 um, 125 to 150 um, 150 to 175 um, or 175 to 200 um.

In some embodiments, the average thickness for at least one of the plates is about 50 um, about 75 um, about 100 um, about 125 um, about 150 um, about 175 um, or about 200 um.

Plate Area. In some embodiments, the first plate and/or the second plate has a lateral area of 1 $mm^2$ (square millimeter) or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 20 $cm^2$ or less, 30 $cm^2$ or less, 50 $cm^2$ or less, 100 $cm^2$ or less, 500 $cm^2$ or less, 1,000 $cm^2$ or less, 5,000 $cm^2$ or less, 10,000 $cm^2$ or less, or in a range between any two of these values.

In preferred embodiments, the first plate and/or the second plate has a lateral area in a range of 1 $mm^2$ (square millimeter) to 10 $mm^2$, 10 $mm^2$ to 50 $mm^2$, 50 $mm^2$ to 100 $mm^2$, 1 $cm^2$ to 5 $cm^2$, 5 $cm^2$ to 20 $cm^2$, 20 $cm^2$ to 50 $cm^2$, 50 $cm^2$ to 100 $cm^2$, 100 $cm^2$ to 500 $cm^2$, 500 $cm^2$ to 1000 $cm^2$, or 1000 $cm^2$ to 10,000 $cm^2$.

In some embodiments, the first plate and the second plate have the same lateral dimension. In some embodiments, one of the plates has an area that is different from the other plates by 10% or less, 30% or less, 50% or less, 80% or less, 90% or less, 95% or less, 99% or less, or in a range between any two of these values (take the largest plate is the base in calculation the different percentage).

In some embodiment, the first plate and/or the second plate has a width or a length of 5 mm, 10 mm, 20 mm, 25 mm, 30 mm, 40 mm, 50 mm, 75 mm, 100 mm, or in a range between any two of these values.

In preferred embodiments, the first plate and/or the second plate has a width or a length in a range of 5 mm to 10 mm, 20 mm to 30 mm, 30 mm to 50 mm, 50 mm to 75 mm, or 75 mm to 100 mm.

In one preferred embodiment, the plate has a width or length in a range of 5 mm to, 50 mm. In another preferred embodiment, the plate has a width in a range of 5 mm to 50 mm and a length in a range of 6 mm to 70 mm.

Materials for Plates

In some embodiments, the materials for the first plate and the second plates, contain but are not limit to polymers (e.g. plastics) or amorphous organic materials. The polymer materials include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the materials for the first plate and the second plate contain but are not limit to inorganic materials including dielectric materials of silicon oxide, porcelain, orcelain (ceramic), mica, glass, oxides of various metals, etc.

In some embodiments, the materials for the first plate and the second plate contain but are not limit to inorganic materials including aluminum oxide, aluminum chloride, cadmium sulfide, gallium nitride, gold chloride, indium arsenide, lithium borohydride, silver bromide, sodium chloride, graphite, carbon nanotubes, carbon fibers, etc.

In some embodiments, the materials for the first plate and the second plate contain but are not limit to metals (e.g. gold, copper, aluminum, etc.) and alloys.

In some embodiments, the materials for the first plate and the second plate are made of multi-layers and/or mixture of the materials listed above.

Heating Layer and Cooling Layer

In certain embodiments, a heating layer (112-1) and a cooling layer (112-2) comprises high K material and/or a high KC ratio material. The high K and/or high KC ratio material comprises materials/structures, such as, but not limited to, metallic film, semiconductors, semimetals, plasmonic surface, metamaterials (e.g. nanostructures), black silicon, graphite, carbon nanotube, silicon sandwich, graphene, superlattice, plasmonic materials, any material/structure that is capable of efficiently absorbing the electromagnetic wave and converting the absorbed energy into thermal energy, and any combination thereof.

For a heating layer that is heated by an optical heating source, a heating layer comprises a material layer that significantly absorb the radiated energy from the optical heating source. The significant absorption means that the heating/cooling layer absorbs the radiated energy from the optical heating source more significantly than the sample and the plates.

In certain embodiments, the heating/cooling layer has thickness in the range of 50 nm to 15 um. In certain embodiments, the heating/cooling layer comprise a high K layer that has thickness in the range of 100 nm to 1 um.

In some embodiments, the dimension of the light heating area is about 1 um, 2 um, 5 um, 10 um, 20 um, 50 um, 100 um, 200 um, 500 um, 1 mm, 2 mm, 5 mm, 10 mm, 20 mm, 50 mm, or 100 mm, or in a range between any of the two values. In various embodiments, the size and shape of the light heating areas can vary.

In some embodiments, the heating/cooling layer comprise a dot-coupled-dots-on-pillar antenna (D2PA) array, such as, but not limited to the D2PA array described in U.S. Provisional Patent Application No. 61/347,178, which was filed on May 21, 2010, U.S. Provisional Patent Application 61/622,226, which was filed on Apr. 10, 2012, U.S. PCT Application No. PCT/US2011/037455, which was filed on May 20, 2011, PCT Application No. PCT/US2013/032347, which was filed on Mar. 15, 2013, and U.S. patent application Ser. No. 13/699,270, which was filed on Jun. 13, 2013, the complete disclosures of which are hereby incorporated by reference for all purposes.

In some embodiments, there can be more than one heating/cooling layer. For examples, at least two surfaces of any of the first or second plates have a heating/cooling layer.

In some embodiments, the heating/cooling layer can be two-layer materials: one layer for heating and one for cooling, and the two-layer materials can be on the same surface of any of the first or second plate. For sample, the heating layer can be on the outer surface of the second plate, while the cooling layer is on the outer surface or the inner surface of the first plate. Even the cooling layer is on the outer surface of the first plate, which should be efficient in cooling the sample as long as the first plate has thin thickness (e.g., 25 um or less).

Spacers

In some embodiments of the present invention there are spacers between the two plates. In some embodiments, at least one of the spacers is in the sample contact area. In some embodiments, the spacers have uniform height. In some embodiments, the thickness of the sample is the sample as the height of the spacers. In some embodiments, the spacers are fixed on one of the plates.

Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

Spacer architectures and shapes. To achieve desired sample thickness reduction and control, in certain embodiments, the spacers are fixed on its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Some embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer.), and the enclosed spacer is the spacer that stop the sample flow (i.e. the sample cannot flow beyond the spacer. For example, a ring shape spacer and the sample is inside the ring.). Both types of spacers use their height to regular the final sample thickness at a closed configuration.

In some embodiments, the spacers are open-spacers only. In some embodiments, the spacers are enclosed-spacers only. In some embodiments, the spacers are a combination of open-spacers and enclosed-spacers.

The term "pillar spacer" means that the spacer has a pillar shape and the pillar shape refers to an object that has height and a lateral shape that allow a sample to flow around it during a compressed open flow. In some embodiments, the spacers have a flat top (e.g. pillars with a flat top to contact a plate).

In some embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In some embodiments, the spacers can be and/or can include posts, columns, beads, spheres, and/or other suitable geometries. The lateral shape and dimension (i.e., transverse to the respective plate surface) of the spacers can be anything, except, in some embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in some embodiments, they require some spacers to be closed spacers to restrict the sample flow.

In some embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In some embodiments, the spacers are pillars of various lateral shapes, sidewalls, and pillar-height to pillar lateral area ratio.

In a preferred embodiment, the spacers have shapes of pillars for allowing open flow. Spacers' materials. In the present invention, the spacers are generally made of any material that is capable of being used to regulate, together with the two plates, the thickness of a relevant volume of the sample. In some embodiments, the materials for the spacers are different from that for the plates. In some embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

Spacer's mechanical strength and flexibility. In some embodiments, the mechanical strength of the spacers are strong enough, so that during the compression and at the closed configuration of the plates, the height of the spacers is the same or significantly same as that when the plates are in an open configuration. In some embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

Spacer inside Sample. To achieve desired sample thickness reduction and control, particularly to achieve a good sample thickness uniformity, in certain embodiments, the spacers are placed inside the sample, or the relevant volume of the sample. In some embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

Spacer height. In some embodiments, all spacers have the same pre-determined height. In some embodiments, spacers have different pre-determined height. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height. In some embodiments, on the same plate, the spacer height in one ration is different from the spacer height in another region. In some cases, the plate with different spacer height in different regions have advantages of assaying.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1,000 nm in a separate preferred embodiment, 1 um (i.e., 1,000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In some embodiments, the spacer height and/or sample thickness is (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. Too many overlaps between the RBC's can cause serious errors in counting.

In the present invention, in some embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (i.e. less surface concentration).

Spacer lateral dimension. For an open-spacer, the lateral dimensions can be characterized by its lateral dimension (sometimes being called width) in the x and y-two orthogonal directions. The lateral dimension of a spacer in each direction is the same or different.

In some embodiments, the ratio of the lateral dimensions of x to y direction is 1, 1.5, 2, 5, 10,100,500, 1,000, 10,000, or a range between any two of the value. In some embodiments, a different ratio is used to regulate the sample flow direction; the larger the ratio, the flow is along one direction (larger size direction).

In some embodiments, the different lateral dimensions of the spacers in x and y direction are used as (a) using the spacers as scale-markers to indicate the orientation of the plates, (b) using the spacers to create more sample flow in a preferred direction, or both. In a preferred embodiment, the period, width, and height.

In some embodiments, all spacers have the same shape and dimensions. In some embodiments, each spacer has different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

Aspect ratio of height to the average lateral dimension of pillar spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

Spacer height precisions. The spacer height should be controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers has a lattice of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

The distance between neighboring spacers (i.e. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or in a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a10 mm or less, 20 mm or less, 30 mm or less, 50 mm or less, 70 mm or less, 100 mm or less, or any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

Spacer density. The spacers are arranged on the respective plates at a surface density of greater than one per $um^2$, greater than one per 10 $um^2$, greater than one per 100 $um^2$, greater than one per 500 $um^2$, greater than one per 1,000 $um^2$, greater than one per 5,000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

The spacers are configured to not take significant surface area (volume) in a given sample area (volume);

Ratio of spacer volume to sample volume. In many embodiments, the ratio of the spacer volume (i.e., the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e., flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

Spacers fixed to plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

Some embodiments of the present invention is that the spacers are fixed on one of the plates before the plates are brought to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In some embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In some embodiments, a spacer is fixed to a plate monolithically.

In some embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together. In some embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In some embodiments, at least a distance between two spacers is predetermined ("predetermined inter-spacer distance" means that the distance is known when a user uses the plates.).

In some embodiments of all methods and devices described herein, there are additional spacers besides to the fixed spacers.

In one preferred embodiment, the spacers are monolithically made on the Plate by embossing (e.g. nanoimprinting) a thin plastic film using a mold, and are made of the same materials, and the thickness of the Plate is from 50 um to 500 um.

In one preferred embodiment, the spacers are monolithically made on the Plate by embossing (e.g. nanoimprinting) a thin plastic film using a mold, and are made of the same materials, and the thickness of the Plate is from 50 um to 250 um.

In one preferred embodiment, the spacers are monolithically made on the Plate and are made of the same materials, and the thickness of the Plate is from 50 um to 500 um.

In one preferred embodiment, the spacers are monolithically made on the Plate a thin plastic film using a mold, and are made of the same materials, and the thickness of the Plate is from 50 um to 250 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene).

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene) and the thickness of the Plate is from 50 um to 500 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene) and the thickness of the Plate is from 50 um to 250 um.

In one preferred embodiment, the spacers are monolithically made on the Plate by embossing (e.g. nanoimprinting) a thin plastic film using a mold, and are made of the same materials, where the plastic film are either PMMA (polymethyl methacrylate) of PS (polystyrene), and the spacers have either a square or rectangle shape, and have the same spacer height.

In one preferred embodiment, the spacers have a square or rectangle shape (with or without round corners).

In one preferred embodiment, the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-100 um. In one preferred embodiment, the spacers made of PMMA or PS have square or rectangle pillars with the pillar width (spacer width in each lateral direction) between 1 um to 200 um; pillar period (i.e. spacer period) from 2 um-2000 um, and pillar height (i.e. spacer height) from 1 um-100 um.

In one preferred embodiment, the spacers are monolithically made on the Plate and are made of plastic materials, and the spacers have square or rectangle pillars with the pillar width (spacer width in each lateral direction) between 1 um to 200 um; pillar period (i.e. spacer period) from 2 um-2,000 um, and pillar height (i.e. spacer height) from 1 um-100 um. In one preferred embodiment, the spacers are monolithically made on the Plate and are made of the same materials, and the spacers have square or rectangle pillars with the pillar width (spacer width in each lateral direction) between 1 um to 200 um; pillar period (i.e. spacer period) from 2 um-2000 um, and pillar height (i.e. spacer height) from 1 um-10 um.

In one preferred embodiment, the spacers are monolithically made on the Plate and are made of the same materials selected from PS or PMMA or other plastics, and the spacers have square or rectangle pillars with the pillar width (spacer width in each lateral direction) between 1 um to 200 um; pillar period (i.e. spacer period) from 2 um-2,000 um, and pillar height (i.e. spacer height) from 10 um-50 um.

Specific sample thickness. In present invention, it was observed that a larger plate holding force (i.e. the force that holds the two plates together) can be achieved by using a smaller plate spacing (for a given sample area), or a larger sample area (for a given plate-spacing), or both.

In some embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

Final Sample Thickness and Uniformity. In some embodiments, significantly flat is determined relative to the final sample thickness, and has, depending upon on embodiments and applications, a ratio of to the sample thickness of less than 0.1%, less than 0.5%, less than 1%, less than 2%, less than 5%, or less than 10%, or a range between any two of these values.

In some embodiments, flatness relative to the sample thickness can be less than 0.1%, less than 0.5%, less than 1%, less than 2%, less than 5%, less than 10%, less than 20%, less than 50%, or less than 100%, or a range between any two of these values. In some embodiments, significantly flat can mean that the surface flatness variation itself (measured from an average thickness) is less than 0.1%, less than 0.5%, less than 1%, less than 2%, less than 5%, or less than 10%, or a range between any two of these values. Generally, flatness relative to the plate thickness can be less than 0.1%, less than 0.5%, less than 1%, less than 2%, less than 5%, less than 10%, less than 20%, less than 50%, or less than 100%, or in a range between any two of these values.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or in a range between any two of the values. The spacer height, the spacing between the plates, and/or sample thickness is between 1 nm to 100 nm in one preferred embodiment, 100 nm to 500 nm in another preferred embodiment, 500 nm to 1,000 nm in a separate preferred embodiment, 1 um (i.e., 1,000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In some embodiments, the spacers can be in spherical beads and randomly distrusted in a sample.

In some embodiments, the QMAX device is fully transparent or partially transparent to reduce the heat absorption by card self, wherein the transparence is above 30%, 40%, 50%, 60%, 70%, 80%, 90%, 100%, or a range between any two of the values.

In some embodiments, the QMAX device is partially reflective to reduce the heat absorption by card self, wherein the reflectance of the surface is above 30%, 40%, 50%, 60%, 70%, 80%, 90%, 100%, or in a range between any two of the values.

In some embodiments, the QMAX device and clamp is coated with a heat insulator layer to reduce the heat absorption by card self. Wherein the heat insulator layer contains materials including the low thermal conductivity material above.

In some embodiments, the clamp covers and seals all the QMAX card in close configuration.

In some embodiments, the clamp covers and seal only the perimeter of the QMAX card in close configuration.

In some embodiments, the clamp covers and seal only the perimeter of the QMAX card in close configuration, and not the heating and cooling zone area.

In some embodiments, the clamp covers some of the surface of QMAX card in close configuration.

In some embodiments, the clamp has a window which is transparent to allow the light go inside the QMAX card and out from the QMAX card.

In some embodiments, the clamp is fully transparent to allow the light go inside the QMAX card and out from the QMAX card.

wherein the transparence of the clamp is above 30%, 40%, 50%, 60%, 70%, 80%, 90%, 100%, or a range between any two of the values.

In some embodiments, there is air or liquid between the clamp and QMAX device in close configuration. In certain embodiments, the liquid includes but not limit to water, ethane, methane, oil, benzene, Hexane, heptane, silicone oil, polychlorinated biphenyls, liquid air, liquid oxygen, liquid nitrogen etc. In certain embodiments, the gas includes but not limit to air, argon, helium, nitrogen, oxygen, carbon dioxide, etc.

In some embodiments, after close the clamp, the pressure on QMAX card surface applied by the clamp is 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, 500 kg/cm$^2$, or a range between any two of the values; and a preferred range of 0.1 kg/cm$^2$ to 0.5 kg/cm$^2$, 0.5 kg/cm$^2$ to 1 kg/cm$^2$, 1 kg/cm$^2$ to 5 kg/cm$^2$, 5 kg/cm$^2$ to 10 kg/cm$^2$ (Pressure).

In some embodiments, after close the clamp, the pressure on QMAX card surface applied by the clamp is at least 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, or 500 kg/cm$^2$, As shown in the cross-sectional views of the device in FIG. 23A and FIG. 23B, the heating/cooling layer 112 spans across the sample contact area. It should be noted, however, it is also possible that the lateral area of the heating/cooling layer occupy only a portion of the sample contact area at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less. In some embodiments, in order to facilitate the temperature change of the sample, in some embodiments the lateral area of the heating/cooling layer is configured so that the sample 90 receive the thermal radiation from the heating/cooling layer 112 substantially uniformly across the lateral dimension of the sample 90 over the sample contact area.

In some embodiments, the radiation absorbing area is 10%, 30%, 40%, 50%, 60%, 70%, 80%, 90%, 100% the total plate area, or a range between any two of the values.

In some embodiments, the heating/cooling layer 112 have a thickness of 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 75 um or less, 40 um or less, 15 um or less, 7.5 um or less, 4 um or less, 1.5 um or less, 750 nm or less, 400 nm or less, 150 nm or less, 75 nm or less, 40 nm or less, or 15 nm or less, or in a range between any of the two values. In certain embodiments, the heating/cooling layer 112 have thickness of 100 nm or less.

In some embodiments, the area of the sample layer and the heating/cooling layer 112 is substantially larger than the uniform thickness. Here, the term "substantially larger" means that the general diameter or diagonal distance of the sample layer and/or the heating/cooling layer is at least 10 time, 15 times, 20 time, 25 time, 30 time, 35 time, 40 time, 45 times, 50 time, 55 time, 60 time, 65 times, 70 time, 75 times, 80 time, 85 time, 90 time, 95 times, 100 time, 150 times, 200 time, 250 times, 300 time, 350 times, 400 time, 450 times, 500 time, 550 times, 600 time, 650 times, 700 time, 750 times, 800 time, 850 time, 900 time, 950 times, 1u000 time, 1,500 time, 2,000 time, 2,500 time, 3,000 time, 3,500 times, 4,000 time, 4,500 times, or 5000 time, or in a range between any of the two values.

Figure 32A:
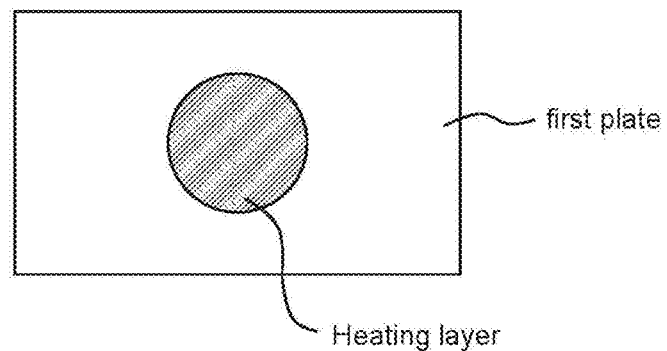
FIGS. 32A and 32B schematically illustrates a top view and a sectional view, respectively, of a heating layer on a plate of the device, in accordance with one or more embodiments.
Figure 32B:
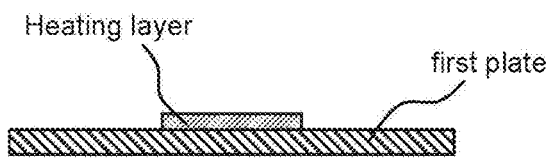

FIGS. 32A and 32B show exemplary embodiments of the first plate and the heating/cooling layer of the present invention. FIG. 32A is a top view and FIG. 32B is a sectional view. FIGS. 33A and 33B show sectional views of two exemplary embodiments of the present invention, demonstrating the first plate, the second plate, and the heating/cooling layer. As a whole, the first plate and the second plate, and optionally the heating/cooling layer, can be viewed as a sample holder, which refers to not only the embodiments herein shown and/or described, but also other embodiments that are capable of compressing at least part of a liquid sample into a layer of uniform thickness.

As shown in FIGS. 32A and 32B, in some embodiments, the heating/cooling layer is in contact with the first plate. It should be noted, however, that in some embodiments the heating/cooling layer can be in contact with the second plate 20. In addition, in some embodiments the heating/cooling layer is not in contact with any of the plates. In some embodiments, there is no separate structure of the heating/cooling layer; the first plate and/or the second plate 20 and/or the sample itself can absorb the electromagnetic radiation some that the sample's temperature can be raised.

In some embodiments, the heating/cooling layer has an area that is less than 1000 mm², 900 mm², 800 mm², 700 mm², 600 mm², 500 mm², 400 mm², 300 mm², 200 mm², 100 mm², 90 mm², 80 mm², 75 mm², 70 mm², 60 mm², 50 mm², 40 mm², 30 mm², 25 mm², 20 mm², 10 mm², 5 mm², 2 mm², 1 mm², 0.5 mm², 0.2 mm², 0.1 mm², or 0.01 mm², or in a range between any of the two values. In some embodiments, the heating/cooling layer has an area that is substantially smaller than the area of the first plate (and/or the second plate). For example, in certain embodiments, area of the heating/cooling layer occupy only a portion of the area of the first plate (or the second plate; or the sample contact area of the first plate or the second plate) at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less.

In some embodiments, the heating/cooling layer has a substantially uniform thickness. In some embodiments, the heating/cooling layer has a thickness of less than 10 nm, 20 nm, 50 nm, 100 nm, 200 nm, 500 nm, 1 um, 2 um, 5 um, 10 um, 20 um, 50 um, 100 um, 200 um, 300 um, 400 um, 500 um, 600 um, 700 um, 800 um, 900 um, 1 mm, 1.5 mm, 2 mm, 2.5 mm, 3 mm, 3.5 mm, 4 mm, 4.5 mm, 5 mm, or 10 mm, or in a range between any of the two values.

The heating/cooling layer can take any shape. For example, from a top view the heating/cooling layer can be square, circle, ellipse, triangle, rectangle, parallelogram, trapezoid, pentagon, hexagon, octagon, polygon, or various other shapes.

In some embodiments, the first plate or the second plate has a thickness of 2 nm or less, 10 nm or less, 100 nm or less, 200 nm or less, 500 nm or less, 1,000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values.

In some embodiments, the first plate and the second plate has a lateral area of 1 mm² (square millimeter) or less, 10 mm² or less, 25 mm² or less, 50 mm² or less, 75 mm² or less, 1 cm² (square centimeter) or less, 2 cm² or less, 3 cm² or less, 4 cm² or less, 5 cm² or less, 10 cm² or less, 100 cm² or less, 500 cm² or less, 1,000 cm² or less, 5,000 cm² or less, 10,000 cm² or less, 10,000 cm² or less, or in a range between any two of these values.

In certain embodiments, a fourth power of the inter-spacer-distance (ISD) of the spacers divided by the thickness (h) and the Young's modulus (E) of the plate (ISD4/(hE)) is $5 \times 10^6$ um³/GPa or less;

In certain embodiments, a product of the pillar contact filling factor and the Young's modulus of the spacers is 2 MPa or larger, wherein the pillar contact filling factor is the ratio of the area of the plate being contacted by the pillars to the entire plate area (in the pillar region).

In certain embodiments, the spacers have a predetermined substantially uniform height and a predetermined constant inter-spacer distance that is at least about 2 times larger than the size of the analyte, up to 200 um, and wherein at least one of the spacers is inside the sample contact area.

In some embodiments, the plate (either the first plate, the second plate, or both plates) that has the heating/cooling layer is thin so that the temperature of the sample can be rapidly changed. For example, in certain embodiments the plate that is in contact with the heating/cooling layer has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In some embodiments, if only one plate is on contact with the heating/cooling layer, the plate in contact with the heating/cooling layer is substantially thinner than the plate that is not in contact with the heating/cooling layer. For example, in some embodiments, the thickness of the plate that is in contact with the heating/cooling layer is less than 1/1,000,000, 1/500,000, 1/100,000, 1/50,000, 1/10,000, 1/5,000, 1/1,000, 1/500, 1/100, 1/50, 1/10, 1/5, or 1/2 of the thickness of the plate that is in contact with the heating/cooling layer, or in a range between any of the two values.

In some embodiments, the sample layer is thin so that the temperature of the sample layer can be rapidly changed. In certain embodiments, the sample layer has a thickness equal to or less than 100 um, 50 um, 25 um, 10 um, 5 um, 2.5 um, 1 um, 500 nm, 400 nm, 300 nm, 200 nm, or 100 nm, or in a range between any of the two values.

In various embodiments, the positioning of the heating/cooling layer can also vary. In some embodiments, as shown in FIG. 33A or 33B, the heating/cooling layer is positioned at the inner surface of the first plate. Here the inner surface is defined as the surface that is in contact with the sample when the sample is compressed into a layer. The other surface is the outer surface. In some embodiments, the heating/cooling layer is at the inner surface of the first plate. In some embodiments, the heating/cooling layer is at the inner surface of the second plate. In some embodiments, the heating/cooling layer is at the outer surface of the first plate. In some embodiments, the heating/cooling layer is inside one or both of the plates. In some embodiments, the heating/cooling layer is at the outer surface the second plate. In some embodiments, there are at least two heating/cooling layers at the inner surfaces and/or outer surfaces of the first plate and/or the second plate.

As herein shown and described, in some embodiments, the sample holder is configured to compress the fluidic sample into a thin layer, thus reducing the thermal mass of the sample. But reducing the thermal mass, a small amount energy can be able to change the temperature of the sample quickly. In addition, by limiting the sample thickness, the thermal conduction is also limited.

In some embodiments, there is a sample contact area on the respective surfaces of the first plate 10 and the second plate 20. The sample contact area can be any portion of the surface of the first plate 10 and/or the second plate 20. In some embodiments, the heating/cooling layer at least partly overlaps with the sample contact area. In the overlapping part, the sample is heated quickly due to close proximity and small thermal mass.

In some embodiments, the sample holder 100 is a compressed regulated open flow (CROF, also known as QMAX) device, such as but not limited to the CROF device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

Edge Sealing for Reducing Sample Evaporation

When the two plates sandwich a sample into a shape with a large lateral to vertical ratio (e.g., 15 mm vs 30 um=500), the evaporation of the sample during a thermal cycling is greatly reduced, since the sample surfaces covered by the two plate is 500 times larger. Experimentally, we found that in 30 temperature cycling (about 60 secs), there was no visible changes in the sample volume.

On the other hand, in some embodiments, it has a seal element that is in contact with the two plates to form an enclosed chamber which prevents sample vapor going out. Such seal element can reduce sample contamination, in addition to reduce or eliminate sample evaporation. The sealing element can be a tape, plastic seal, oil seal, or a combination of thereof.

In some embodiments, the sealing element does not reach the sample, but the sealing element is in contact with the two plates to form an enclosed chamber which prevents sample vapor going out. In some embodiments, the sealing element can be used as spacers to regulate the relevant sample's thickness.

Figure 28:
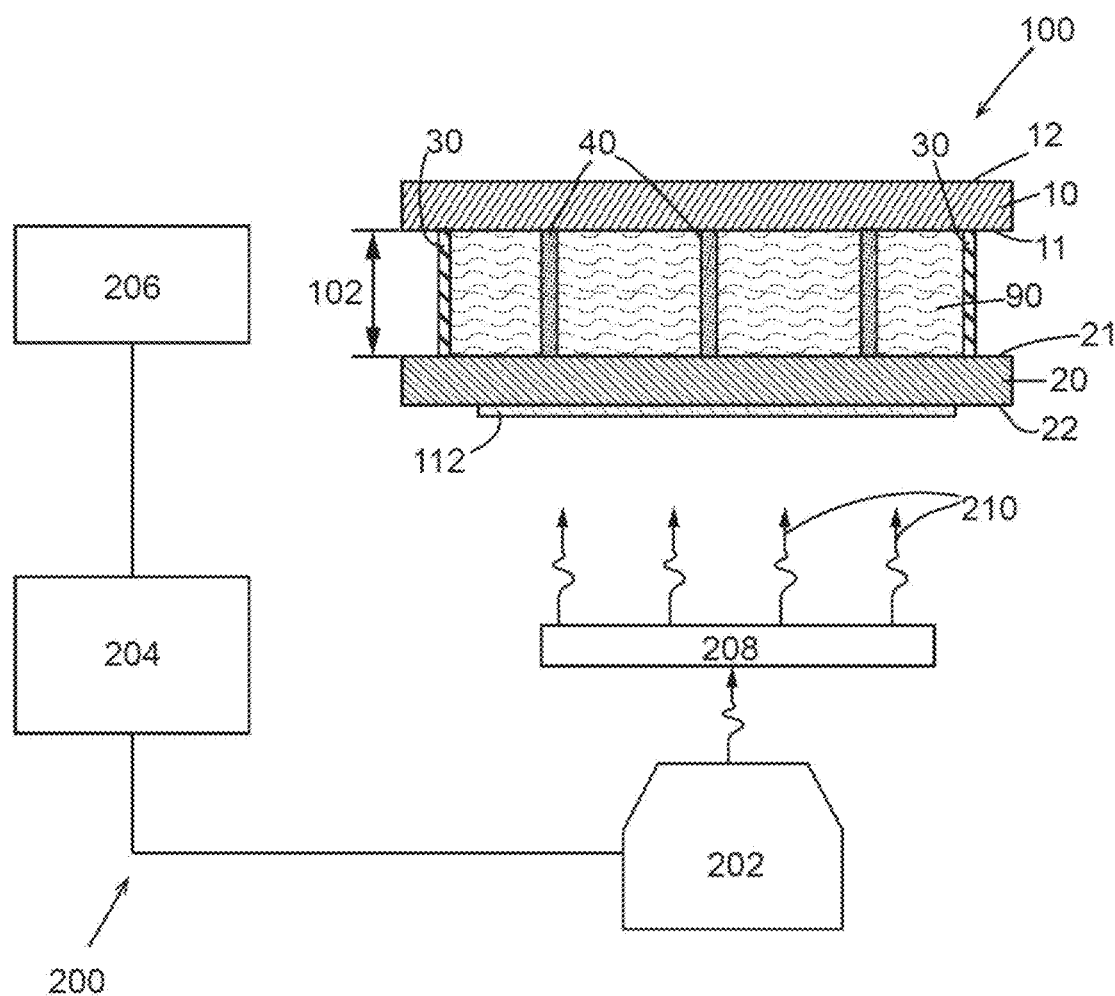
FIG. 28 schematically illustrates a sectional view of a system showing additional elements that facilitate temperature change and control, according to some embodiments.

In some embodiments, as shown in FIG. 28, the sample holder 100 comprises a sealing element 30 that is configured to seal the spacing 102 between the first plate 10 and second plate 20 outside the medium contact area at the closed configuration. In certain embodiments, the sealing element 30 encloses the sample 90 within a certain area (e.g. the sample receiving area) so that the overall lateral area of the sample 90 is well defined and measurable. In certain embodiments, the sealing element 30 improves the uniformity of the sample 90, especially the thickness of the sample layer.

In some embodiments, as shown in FIG. 28, the sealing element 30 comprises an adhesive applied between the first plate 10 and second plate 20 at the closed configuration. The adhesive is selective from materials such as but not limited to: starch, dextrin, gelatin, asphalt, bitumen, polyisoprene natural rubber, resin, shellac, cellulose and its derivatives, vinyl derivatives, acrylic derivatives, reactive acrylic bases, polychloroprene, styrene-butadiene, styrene-diene-styrene, polyisobutylene, acrylonitrile-butadiene, polyurethane, polysulfide, silicone, aldehyde condensation resins, epoxide resins, amine base resins, polyester resins, polyolefin polymers, soluble silicates, phosphate cements, or any other adhesive material, or any combination thereof. In some embodiments, the adhesive is drying adhesive, pressure-sensitive adhesive, contact adhesive, hot adhesive, or one-part or multi-part reactive adhesive, or any combination thereof. In some embodiments, the glue is natural adhesive or synthetic adhesive, or from any other origin, or any combination thereof. In some embodiments, the adhesive is spontaneous-cured, heat-cured, UV-cured, or cured by any other treatment, or any combination thereof.

In some embodiments, as shown in FIG. 28, the sealing element 30 comprises an enclosed spacer (well). For example, the enclosed spacer has a circular shape (or any other enclosed shape) from a top view and encircle the sample 90, essentially restricting the sample 90 together with the first plate 10 and the second plate 20. In certain embodiments, the enclosed spacer (well) also function as the spacing mechanism 40. In such embodiments, the enclosed spacer seals the lateral boundary of the sample 90 as well as regulate the thickness of the sample layer.

In some embodiments, there is an "evaporation-prevention ring" outside of the liquid area (e.g. sample area) that prevents or reduces the vapor of the liquid escape the card, during a heating.

In some embodiments, there is a clamp outside of the QMAX-card to fix the QMAX card in its closed configuration during a heating.

In some embodiments, the two plates are compressed by an imprecise pressing force, which is neither set to a precise level nor substantially uniform. In certain embodiments, the two plates are pressed directly by a human hand.

In some embodiments, the QMAX card/RHC card, including the plates and spacer, is made of the material with low thermal conductivity to reduce the heat absorption by card self. In some embodiments, there is clamp outside of the QMAX-card to fix the QMAX card in its closed configuration during a heating (namely, the clamp clamps only round the edge of the plates, not the center of the plate pair). In some embodiments, the clamp is made of the material with low thermal conductivity to reduce the heat absorption by card self.

Heating Source, Extra Heat Sink, Temperature Sensor, and Temperature Control

The heating layer or the heating/cooling layer in a RHC card is configured to be heated by a heating source, wherein the heating source delivers heat energy to the heating/cooling layer optically, electrically, by radio frequency (RF) radiation, or a combination thereof.

Optical Heating Source. In some embodiments, when a heating layer is heated by a heating source optically, the heating source comprises a light source, that include, but not limited to, LED (light emitting diode), lasers, lamps, or a combination of thereof.

To get more light from a light source in an optical heating source to a heating layer, some embodiments of the heating sources uses an optical lens, an optical pipe, or a combination thereof.

In some embodiments, the wavelength of the electromagnetic waves is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values. In some embodiments, the wavelength of the electromagnetic waves is 100 nm to 300 nm, 400 nm to 700 nm (visible range), 700 nm to 1000 nm (IR range), 1 um to 10 um, 10 um to 100 um, or in a range between any of the two values.

The lens has an NA (numerical aperture) of 0.001, 0,01, 0.05, 0.1, 0.2, 0.3, 04, 0.5, 0.6, 0.7, 0.8, 0.9, 1.0, 1.1, 1.5, or in a range between any of the two values.

In preferred embodiments, the lens has an NA in a range of 0.01 to 0.1, 0.1 to 0.4, 0.4 to 0.7, 0.7 to 1.0, or 1.0 to 1.5.

FIGS. 35A and 35B show a perspective view and a sectional view, respectively, of an embodiment of the present invention, in which an optical pipe is used to guide the electromagnetic waves (e.g. light) from the heating source (e.g. LED light) to the heating zone or plate.

In certain embodiments, an optical pipe (also termed optical collimator), that collimates the light of a light source into the heating zone/plate, comprises a hollow tube with a reflective wall.

Figure 38:
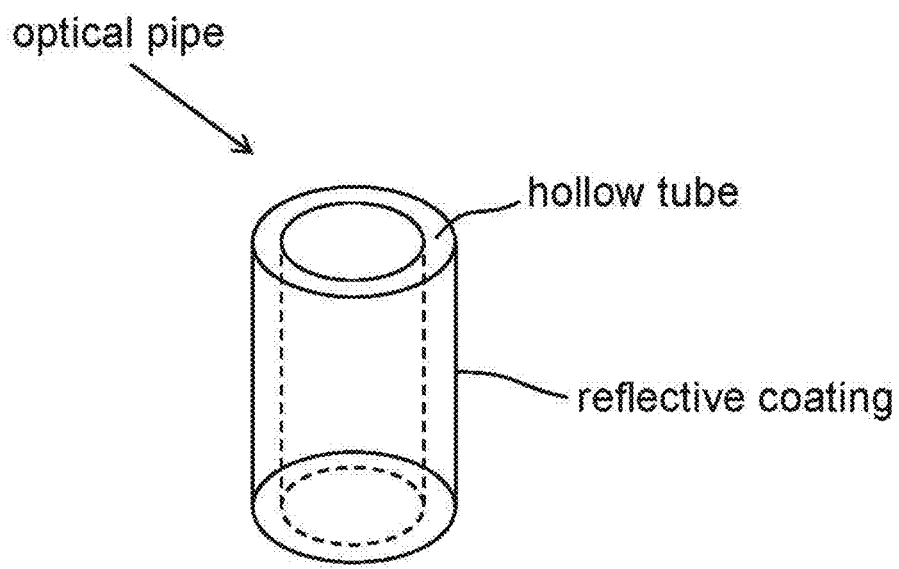
FIG. 38 schematically illustrates a perspective view of an optical pipe, in accordance with one or more embodiments.

One embodiment of an optical pipe comprises a hollow dielectric tube with a reflective wall (i.e. its inner wall, outer wall, or both reflective). The hollow dielectric tube can be made of the materials of glasses, plastics, or a combination. The reflective wall can be a thin light reflective coating on a wall of the hollow tube. The reflective coating can be a thin metal film, such as gold, aluminum, silver, copper, or any mixture or combination thereof. FIG. 38 shows a perspective view of an embodiment of an optical pipe, comprising a hollow tube and a reflective material coating on the outer wall of the tube. A reflective coating also can be in the inside wall. The reflective wall also can be made of multi-layer interference materials that reflect the light of interests. The light pipe can be a material block with a hollow pipe that has a reflective wall.

In some embodiments, the hollow pipe has a length in the range of 1 mm to 70 mm, an inner dimension (diameter or width) in the range of 1 mm to 40 mm, and a wall thickness in the range of 0.01 mm to 10 mm.

In some preferred embodiments, the hollow pipe for the light pipe has an inner diameter (or an average width) in a range of 1 mm to 5 mm, 5 mm to 10 mm, 10 mm to 15 mm, 15 mm to 20 mm, 20 mm to 30 mm, or 30 mm to 50 mm.

In some preferred embodiments, the hollow pipe for the light pipe has a wall thickness (or an average width) in a range of 0.001 mm to 0.01 mm, 0.01 mm to 0.1 mm, 0.1 mm to 0.5 mm, 0.5 mm to 1 mm, 1 mm to 2 mm, or 2 mm to 50 mm.

Electrical Heating Source. In some embodiments, when the heating layer or the heating/cooling layer is heated by a heating source electrically, the electric heating source comprises an electrical power supply that sends an electrical power, though electrical wiring, to the heating/cooling layer.

Extra Heat Sink. In some embodiments, the heat is removed from the sample and the sample holder to the environment, but in some embodiments, extra heat sink will be used to accelerate the heat removal. The extra heat sink can be a Peltier cooler, passive heat radiator, or both. In some embodiments, fan will be used to create air convention (directly to the sample and the sample holder, directly to extra heat sink, or both) which accelerate a cooling of the sample.

Figure 27A:
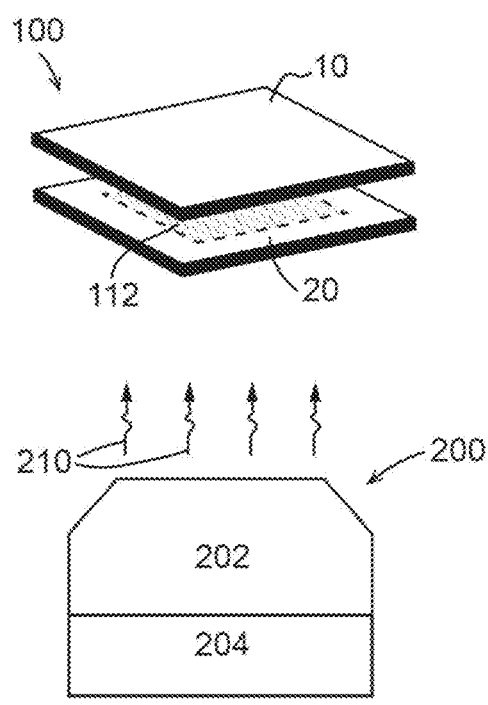
FIG. 27A schematically illustrates the perspective view of the system when the device (sample holder of the system) is in an open configuration, in accordance with one or more embodiments.
Figure 27B:
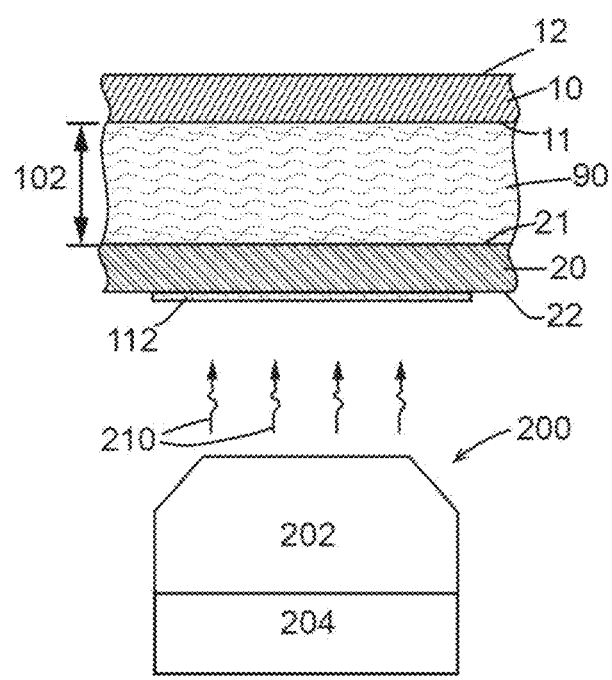
FIG. 27B schematically illustrates a sectional view of the system when the sample holder is in a closed configuration, in accordance with one or more embodiments.

FIGS. 27A and 27B further show a perspective view and a sectional view, respectively, of some embodiments of the thermal cycling system that comprises a sample holder 100 in a closed position and a thermal control unit 200. Sample holder 100 may include a first plate 10, a second plate 20, and a spacing mechanism (not shown). The thermal control unit 200 may include a heating source 202 and a controller 204.

As shown in FIG. 27B, the thermal control unit 200 may include a heating source 202 and controller 204. In some embodiments, the thermal control unit 200 provide the energy in the form of electromagnetic waves for temperature change of the sample.

Referring to both FIGS. 27A and 27B, the heating source 202 is configured to project an electromagnetic wave 210 to the heating/cooling layer 112 of the sample holder 100, which is configured to absorb the electromagnetic wave 210 and convert a substantial portion of the electromagnetic wave 210 into heat, resulting in thermal radiation that elevate the temperature of a portion of the sample 90 that is in proximity of the heating/cooling layer 112. In other words, the coupling of the heating source 202 and the heating/cooling layer 112 is configured to generate the thermal energy that is needed to facilitate the temperature change of the sample 90.

In some embodiments, the radiation from the heating source 202 comprise radio waves, microwaves, infrared waves, visible light, ultraviolet waves, X-rays, gamma rays, or thermal radiation, or any combination thereof. In some embodiments, the heating/cooling layer 112 has a preferred range of light wavelength at which the heating/cooling layer 112 has a high absorption efficiency. In some embodiments, the heating source 202 is configured to project the electromagnetic wave at a wavelength range within, overlapping with, or enclosing the preferred wavelength range of the heating/cooling layer 112. In other embodiments, in order to facilitate the temperature change, the wavelength is rationally designed away from the preferred wavelength of the heating/cooling layer.

In some embodiments, the heating source 202 comprise a laser source providing a laser light within a narrow wavelength range. In other embodiments, the heating source 202 comprises a LED (light-emitting diode) of a plurality thereof.

Temperature sensors. The temperature of the sample can be controlled by delivering pre-calibrated energy to the heating zone/layer with a real time temperature sensor, by using a real time temperature sensor, or both.

A real time temperature sensor can be thermometer, thermal couple, radiation temperature sensor, temperature sensitive dye (which change either light intensity or color or both with temperature), or a combination thereof.

As shown in FIG. 28, in some embodiments the thermal control unit 200 comprises a thermometer 206. In some embodiments, the thermometer 206 provides a monitoring and/or feedback mechanism to control/monitor/adjust the temperature of the sample 90. For example, in some embodiments the thermometer 206 is configured to measure the temperature at or in proximity of the sample contact area. In certain embodiments, the thermometer 206 is configured to directly measure the temperature of the sample 90. In some embodiments, the thermometer 206 is selected from the group consisting of: fiber optical thermometer, infrared thermometer, fluidic crystal thermometer, pyrometer, quartz thermometer, silicon bandgap temperature sensor, temperature strip, thermistor, and thermocouple. In certain embodiments, the thermometer 206 is an infrared thermometer.

In some embodiments, the thermometer 206 is configured to send signals to the controller 204. Such signals comprise information related to the temperature of the sample 90 so that the controller 204 makes corresponding changes. For example, during a PCR, for the denaturation step the target temperature is set for 95° C.; after measurement, the thermometer sends a signal to the controller 204, indicating that the measured temperature of the sample 90 is actually 94.8° C.; the controller 204 thus alters the output the heating source 202, which projects an electromagnetic wave or adjust particular parameters (e.g., intensity or frequency) of an existing electromagnetic wave so that the temperature of the sample 90 is increased to 95° C. Such measurement-signaling-adjustment loop is applied to any step in any reaction/assay.

Controllers. Referring to panels (A) and (B) of FIG. 25, the controller 204 is configured to control the electromagnetic wave 210 projected from the heating source 202 for the temperature change of the sample. The parameters of the electromagnetic wave 210 that the controller 204 controls include, but are not limited to, the presence, intensity, wavelength, incident angle, and any combination thereof. In some embodiments, the controller is operated manually, for instance, it is as simple as a manual switch that controls the on and off of the heating source, and therefore the presence of the electromagnetic wave projected from the heating source. In other embodiments, the controller includes hardware and software that are configured to control the electromagnetic wave automatically according to one or a plurality of pre-determined programs.

In some embodiments, the pre-determined program refers to a schedule in which the parameter(s) (e.g., presence, intensity, and/or wavelength) of the electromagnetic wave 210 is/are set to pre-determined levels for respective pre-determined periods of time. In other embodiments, the pre-determined program refers to a schedule in which the temperature of the sample 90 is set to pre-determined levels for respective pre-determined periods of time and the time periods for the change of the sample temperature from one pre-determined level to another pre-determined level are also set respectively. In some embodiments, the controller 204 is configured to be programmable, which means the controller 204 comprises hardware and software that are configured to receive and carry out pre-determined programs for the system that are delivered by the operator of the system.

FIG. 28 shows a sectional view of an embodiment of the present invention, demonstrating the thermal cycler system and showing additional elements that facilitates temperature change and control. As shown in FIG. 28, the thermal cycler system comprises a sample holder 100 and a thermal control unit 200. The sample holder 100 comprises a first plate 10, a second plate 20, a spacing mechanism 40, and a sealing element 30; the thermal control unit 200 comprises a heating source 202, a controller 204, a thermometer 206, and an expander 208.

FIG. 28 shows the sample holder 100 in a closed configuration, in which the inner surfaces 11 and 21 of the first and second plates 10 and 20 face each other and the spacing 102 between the two plates are regulated by a spacing mechanism 40. If a sample 90 has been deposited on one or both of the plates in the open configuration, when switching to the closed configuration, the first plate 10 and the second plate 20 are pressed by a human hand or other mechanisms, the sample 90 is thus compressed by the two plates into a thin layer. In some embodiments, the thickness of the layer is uniform and the same as the spacing 102 between the two plates. In certain embodiments, the spacing 102 (and thus the thickness of the sample layer) is regulated by the spacing mechanism 40. In some embodiments, the spacing mechanism comprises an enclosed spacer that is fixed to one of the plates. In some embodiments, the spacing mechanism 40 comprises a plurality of pillar shaped spacers that are fixed to one or both of the plates. Here the term "fixed" means that the spacer(s) is attached to a plate and the attachment is maintained during at least a use of the plate.

In some embodiments, the controller 204 is configured to adjust the temperature of the sample to facilitate an assay and/or reaction involving the sample 90 according to a pre-determined program. In some embodiments, the assay and/or reaction is a PCR. In certain embodiments, the controller 204 is configured to control the presence, intensity, and/or frequency of the electromagnetic wave from the heating source 206.

Sample Signal Monitoring

As shown in FIGS. 32 and 33, a signal sensor can be used to detect the signal from the sample (and the products from a reaction during a temperature change) in the sample holder.

In some embodiments, the signal sensor is an optical sensor that is configured to image the fluidic sample. For example, optical sensor is a photodetector, camera, or a device capable of capturing images of the fluidic sample. In some embodiments, the optical sensor can be a camera. In some embodiments, the camera is a camera integrated into a mobile device (e.g. a smartphone or tablet computer). In some embodiments, the camera is separated from other parts of the system. In some embodiments, a light source or multi light sources are used to excite the sample (and the products from a reaction during a temperature change) for generating a signal In some embodiments, the signal sensor is an electrical sensor that is configured to detect electrical signals from the device. In some embodiments, the signal sensor is a mechanical sensor that is configured to detect mechanical signals from the device.

In some embodiments, the signal sensor is configured to monitor the amount of an analyte in the sample. In some embodiments, the signal sensor is outside the chamber and receive optical signals from the sample through an optical aperture on the chamber.

Base and Systems

In some embodiments, the apparatus further comprises a base (an adaptor) that is configured to house the sample card, the heating source, temperature sensors, a part of an entire of temperature controlled (include a smartphone in some embodiments), extra-heat sink (optionally), a fan (optionally) or a combination of thereof. In some embodiments, the adaptor comprises a card slot, into which the sample card can be inserted. In some embodiments, the sample card, after being fully inserted into the slot, or after reaching a pre-defined position in the slot, is stabilized and stays in place without any movement.

In some embodiments, the base (adaptor) is configured to position the sample card, and the sample within the sample card, in the field of view of an optical sensor (e.g. a camera) so that the sample can be imaged. In certain embodiments, the camera is part of a mobile device (e.g. a smartphone). In some embodiments, the adaptor comprises a slider in the slot. In certain embodiments, the sample card can be put onto the slider, which can slide into or out of the slot in the adaptor. In some embodiments, the adaptor comprises a card support. In certain embodiments, the sample card can be put on the card support, which does not need to be moved before imaging.

In some embodiments, the adaptor is configured to be connectable to an optical sensor so that the relative position of the optical sensor (e.g., mobile device; e.g., smartphone) and the sample card is fixed. In certain embodiments, the adaptor can include a connecting member that is replaceable and directly attach to the mobile device (as an example). The connecting member can be slid onto the mobile device and firmly attach the adaptor to the mobile device, optimally positioning the sample card to be imaged or for the detection and/or measurement of the analyte. In certain embodiments, the connecting member is replaceable so that different connecting members can be used for different mobile devices.

Figure 34:
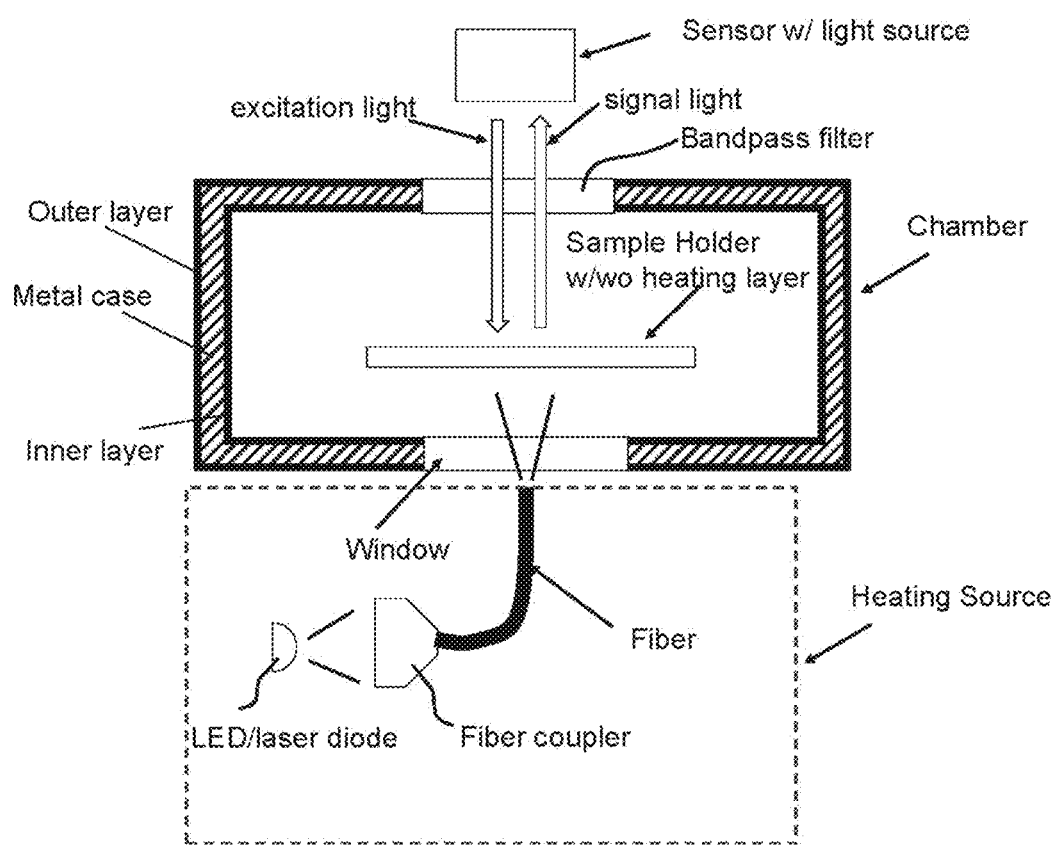
FIG. 34 schematically illustrates a sectional view of a system to rapidly change the temperature of a sample, including a heating source using a fiber, in accordance with one or more embodiments.
Figure 35:
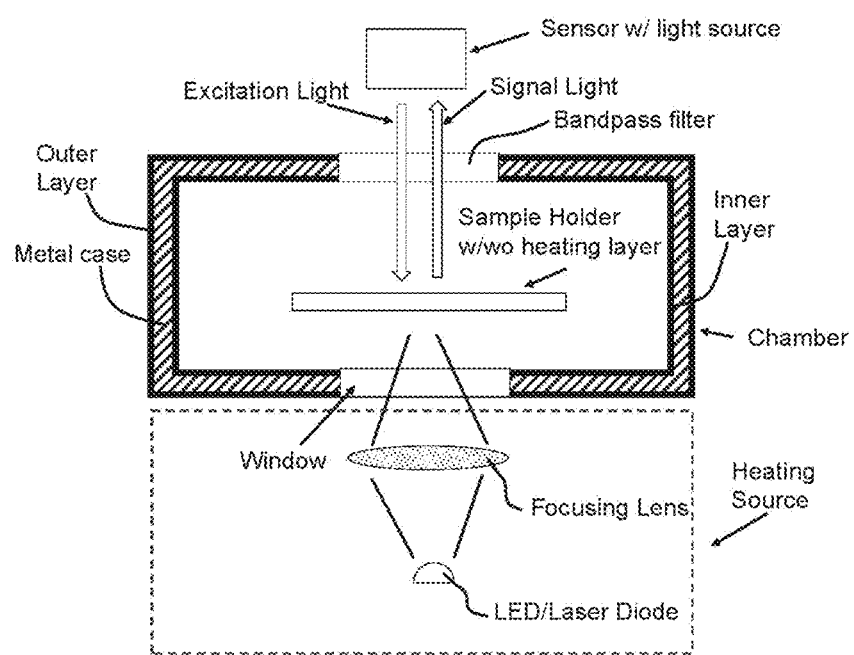
FIG. 35 schematically illustrates a sectional view of a system to rapidly change the temperature of a sample, including a heating source using a lens, in accordance with one or more embodiments.

In some embodiments, the adaptor comprises a radiation aperture that allows the passage of the electromagnetic waves that heat or cool the sample. In some embodiments, the adaptor comprises an optical aperture that allows imaging of the sample. In some embodiments, the adaptor serves as a heating sink for the sample card. FIGS. 34 and 35 provide additional embodiments of the system. FIG. 34 shows a sectional view of an exemplary embodiment of the present invention, demonstrating the system to rapidly change the temperature of a sample. FIG. 34 shows the detailed elements of a heating source according to one embodiment.

As shown in FIG. 34 and FIG. 35, in some embodiments, the system comprises a sample holder and a heating source. In some embodiments, the sample holder comprises the first plate, the second plate, and/or the heating/cooling layer, as herein described. The heating source emits electromagnetic waves that reach the sample and can be converted to heat that raises the temperature of the sample. In some embodiments, the conversion is conducted by the heating/cooling layer. When there is no specific heating/cooling layer, the conversion is conducted by other parts of the sample holder.

As shown in FIG. 34 and FIG. 35, in some embodiments, the system comprises a chamber that encages the sample holder. In some embodiments, the chamber is an example of the extra heat sink in FIG. 22. In some embodiments, the chamber comprises an optical aperture that is configured to allow imaging of the sample. In some embodiments, the chamber comprises a radiation aperture configured to allow passage of electromagnetic waves from a heating source to the heating/cooling layer. In certain embodiments, a window is positioned at the radiation aperture to allow the passage of the electromagnetic waves. In certain embodiments, a filter (e.g. bandpass filter) is positioned at the optical aperture to allow the imaging of the sample in the sample holder.

In some embodiments, the chamber is used to absorb the heat from the sample and/or the heating source. In some embodiments, the chamber comprises a metal case. In some embodiments, the chamber comprises an outer layer. In certain embodiments, the outer layer is black. In some embodiments, the outer layer is made from black metal. In some embodiments, the chamber comprises an inner layer. In some embodiments, the inner layer is made from non-reflective material. In certain embodiments, the inner layer is black. In some embodiments, the inner layer is made from black metal.

As shown in FIG. 34 and FIG. 35, in some embodiments, the system comprises an optical sensor, which is configured to capture images of the fluidic sample in the sample holder. In some embodiments, the system further comprises a light source, which in some cases can be integrated with the optical sensor and in some cases can be separate. In some embodiments, the light source is configured to provide excitation light that can reach the sample. In some embodiments, the sample can provide signal light that can be captured by the optical sensor so that images are taken.

As shown in FIG. 34, in some embodiments, the heating source comprises an LED or laser diode. In certain embodiments, the heating source further comprises a fiber coupler and a fiber that direct the light from the LED/Laser diode to the sample holder.

FIG. 35 shows a sectional view of an exemplary embodiment of the present invention, demonstrating the system to rapidly change the temperature of a sample. FIG. 35 shows the detailed elements of a heating source according to one embodiment. As shown in FIG. 35, in some embodiments, the heating source comprises an LED or laser diode. In certain embodiments, the heating source further comprises one or more focusing lenses that focuses the electromagnetic waves from the heating source to the sample in the sample holder.

As shown in FIG. 28, the thermal control unit 200 comprises a beam expander 208, which is configured to expand the electromagnetic wave from the heating source 202 from a smaller diameter to a larger diameter. In some embodiments, the electromagnetic wave projected from the heating source 202 is sufficient to cover the entire sample contact area; in some embodiments however, it is necessary to expand the covered area of the electromagnetic wave projected directed from the heating source 202 to produce an expanded electromagnetic wave 210, providing a heat source for all the sample contact area(s). The beam expander 208 employs any known technology, including but not limited to the beam expanders described in U.S. Pat. Nos. 4,545,677, 4,214,813, 4,127,828, and 4,016,504, and U.S. Pat. Pub. No. 2008/0297912 and 2010/0214659, which are incorporated by reference in their entireties for all purposes.

Smartphone

In some embodiments, the sample card is imaged by a mobile device. In certain embodiments, the mobile device is a smartphone, which can serve as an example.

In some embodiments, the smartphone comprises a camera that can be used to image the sample in the sample card. In some embodiments, an adaptor is used to accommodate the sample card and the adaptor is configured to attach to the smartphone so that the sample card (and the sample therein) can be placed in the field of view of the camera.

In some embodiments, the smartphone can also serve as the control unit, which is configured to control the apparatus. For example, the smartphone can be used control the heating and/or cooling of the sample card. In certain embodiments, the smartphone is connected to the heating source and controls the electromagnetic waves from the heating source. In some embodiments, the smartphone controls the presence, intensity, wavelength, frequency, and/or angle of the electromagnetic waves. In certain embodiments, the smartphone receives the temperature data from a thermometer that measures the temperature of the sample. In certain embodiments, the smartphone controls the electromagnetic waves based on the temperature data.

In some embodiments, the smartphone can also serve as a data processing and communication device. For example, after the sample has been imaged, the images can be saved in the smart phone. In certain embodiments, the save images can be processed by software or applications in the smartphone. For example, the presence and/or amount of the analyte can be deduced from the images by software or applications in the smartphone. In certain embodiments, the processed results can be displayed on the screen of the smart phone. In certain embodiments, the processed results can be sent to the user, e.g. with email or other messaging software. In certain embodiments, the processed results can be sent to a third party, e.g., a healthcare professional, who can make further diagnostics and/or process the data in additional steps. In some embodiments, the images, without processing, can be displayed and/or transmitted. In certain embodiments, the images are displayed on the screen of the smartphone. In certain embodiments, the images are sent to the user, e.g. by email or other messaging software. In certain embodiments, the images can be sent to a third party, e.g. a remote server, which can process the images further. In some embodiments, the results and/or images are compressed and/or encrypted before being sent.

Use of RHC Card

The RHC card in the description can be used as one step of multiple steps in test a sample, or as one step that perform entire test.

In some embodiments, a RHC card is used in a so-called "one-step assay", wherein all reagents and a sample for an analysis are loaded on a RHC card and a thermal cycling or temperature change is performed and the signal is being observed during the thermal cycling or temperature change.

OTHER EMBODIMENTS

Embodiment 1

One embodiment comprises a device of the embodiment SH-1 to SH-6, wherein the first plate and the second plate are flexible plastic film and/or thin glass film, that each has a substantially uniform thickness of a value selected from a range between 1 um to 25 um.

Each plate has an area in a range of 1 $cm^2$ to 16 $cm^2$.

The sample sandwiched between the two plate has a thickness of 40 um or less.

The relevant sample to the entire sample ratio (RE ratio) is 12% or less.

The cooling zone is at least 9 times larger than the heating zone.

The sample to non-sample thermal mass ratio is 2.2 or lager.

The RHC have no spacer in some embodiments, but do have spacers in other embodiments.

STC ratio is and the cooling zone comprises a layer of the material that has a thermal conductivity of 70 W/m-K or higher and a thermal conductivity times its thickness.

Embodiment 2

For the embodiments of SH-1 to SH-x, they have the following parameter arrange for fast thermal cycling.

The first plate and second plates are plastic or a thin glass. The first plate and second plate have a thickness of 100 nm, 500 nm, 1 um, 5 um, 10 um, in a range between any of the two values.

The sample between the two plates has a thickness of 5 um, 10 um, 30 um, 50 um, 100 um, or in a range between any of the two values.

The distance from the H/C layer to the sample is 10 nm, 100 nm, 500 nm, 1 um, 5 um, 10 um, or in a range between any of the two values.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

Embodiment 3

For the embodiments of SH-1 to SH-x, they have the following parameter arrange for fast thermal cycling.

The first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values.

The sample between the two plates has a thickness of 5 um, 10 um, 30 um, 50 um, 100 um, or in a range between any of the two values.

The distance between the H/C layer and the sample is 10 nm, 100 nm, 500 nm, 1 um, 5 um, 10 um, or in a range between any of the two values.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

Embodiment 4

For the embodiments of SH-1 to SH-x, they have the following parameter arrange for fast thermal cycling.

The first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values.

The sample between the two plates has a thickness of 100 nm, 500 nm, 1 um, 5 um, 10 um, 25 um, 50 um, 100 um, 250 um, or in a range between any of the two values.

The distance between the H/C layer and the sample is 100 nm, 500 nm, 1 um, 5 um, 10 um, 25 um, 50 um, 100 um, 175 um, 250 um, or in a range between any of the two values.

The ratio of the cooling zone area to the relevant sample area is 100, 64, 16, 9, 4, 2, 1, 0.5, 0.1, or in a range between any of the two values.

The ratio of the cooling zone area to the heating zone is 100, 64, 16, 9, 4, 2, 1, 0.5, 0.1, or in a range between any of the two values.

The distance between the H/C layer and the heating source (e.g. LED) is 500 um, 1 mm, 3 mm, 5 mm, 10 mm, 20 mm, 30 mm, or in a range between any of the two values.

Embodiment 5

For the embodiments of SH-1 to SH-5, they have the following parameter arrange for fast thermal cycling.

A light pipe collimates the light from a light source (e.g. LED) into the heating zone. The light pile comprises a structure with a hollow hole (e.g. a tube or a structure milled a hole) with a reflective wall. The light pile has a lateral dimension for 1 mm to 8 mm and length of 2 mm to 50 mm.

Embodiment 6

For the embodiments of SH-1 to SH-5, they have the following parameter arrange for fast thermal cycling.

The first plate and second plates are plastic or a thin glass. The first plate and second plate have a thickness of 100 nm, 500 nm, 1 um, 5 um, 10 um, in a range between any of the two values.

The sample between the two plates has a thickness in a range of 1 to 5 um, 5 um to 10 um, 10 to 30 um, or 30 um to 50 um.

The distance from the H/C layer to the sample is in a range of 10 nm to 100 nm, 100 nm to 500 nm, 500 nm to 1 um, 1 um to 5 um, 5 um to 10 um, or 10 um to 25 um.

The ratio of the cooling zone area to the relevant sample area is 16, 9, 4, 2, or in a range between any of the two values.

The ratio of the cooling zone area to the heating area is 16, 9, 4, 2, or in a range between any of the two values.

The distance between the H/C layer and the heating source (e.g. LED) is 5 mm, 10 mm, 20 mm, 30 mm, or in a range between any of the two values.

The KC ratio for the cooling layer is in a range of between 0.5 cm$^2$/sec and 0.7 cm$^2$/sec, 0.7 cm$^2$/sec and 0.9 cm$^2$/sec, 0.9 cm$^2$/sec and 1 cm$^2$/sec, 1 cm$^2$/sec and 1.1 cm$^2$/sec, 1.1 cm$^2$/sec and 1.3 cm$^2$/sec, 1.3 cm$^2$/sec and 1.6 cm$^2$/sec, 1.6 cm$^2$/sec and 2 cm$^2$/sec, or 2 cm$^2$/sec and cm$^2$/sec.

The sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100.

Embodiment 7

For the embodiments of SH-1 to SH-5, as well as Embodiments 1 to Embodiments 6, they have the following parameter arrange for fast thermal cycling:

The first plate and/or the second plate has a lateral area in a range of 1 mm$^2$ (square millimeter) to 10 mm$^2$, 10 mm$^2$ to 50 mm$^2$, 50 mm$^2$ to 100 mm$^2$, 1 cm$^2$ to 5 cm$^2$, 5 cm$^2$ to 20 cm$^2$, or 20 cm$^2$ to 50 cm$^2$.

The scaled thermal conduction ratio (STM ratio) is in a range of between 10 to 20, 30 to 50, 50 to 70, 70 to 100, 100 to 1,000, 1,000 to 10,000, or 10,000 to 1,000,000; and the cooling zone (layer) has thermal conductivity times its thickness of $6\times10^{-5}$ W/K, $9\times10^{-5}$ W/K, $1.2\times10^{-4}$ W/K, $1.5\times10^{-4}$ W/K, $1.8\times10^{-4}$ W/K, $2.1\times10^{-4}$ W/K, $2.7\times10^{-4}$ W/K, $3\times10^{-4}$ W/K, $1.5\times10^{-4}$ W/K, or in a range between any of the two values.

The sample holder (RHC card) has not significant thermal conduction to the environment during a thermal cycling.

Sample Types

The devices, systems, and methods herein disclosed can be used for samples such as but not limited to diagnostic sample, clinical sample, environmental sample and foodstuff sample. The types of sample include but are not limited to the samples listed, described and summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, systems, and methods are applied.

In some embodiments, the devices, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, pre-processed food as well as partially or fully processed food, etc. In certain embodiments, samples that are not in liquid form are converted to liquid form before the subject devices, systems, and methods are applied.

The subject devices, systems, and methods can be used to analyze any volume of the sample. Examples of the volumes include, but are not limited to, about 10 mL or less, 5 mL or less, 3 mL or less, 1 microliter (μL, also "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 uL or less, 10 uL or less, 1 uL or less, or a range between any two of the values.

In some embodiments, the volume of the sample includes, but is not limited to, about 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values. In some embodiments, the volume of the sample includes, but is not limited to, about 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

Applications

The devices, systems, and methods herein disclosed can be used in various types of biological/chemical sampling, sensing, assays and applications, which include the applications listed, described and summarized in PCT Application (designating U.S.) No. PCT/US2016/045437, which was filed on Aug. 10, 2016, and is hereby incorporated by reference by its entirety.

In some embodiments, the devices, systems, and methods herein disclosed are used in a variety of different application in various field, wherein determination of the presence or absence, quantification, and/or amplification of one or more analytes in a sample are desired. For example, in certain embodiments the subject devices, systems, and methods are used in the detection of proteins, peptides, nucleic acids, synthetic compounds, inorganic compounds, and other molecules, compounds, mixtures and substances. The various fields in which the subject devices, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, systems, and methods are used in the detection of nucleic acids, proteins, or other molecules or compounds in a sample. In certain embodiments, the devices, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, systems, and methods are used in the detection and/or quantification of one or more, two or more, or three or more foodstuff marks from a food sample obtained from tap water, drinking water, prepared food, processed food or raw food.

In some embodiments, the devices, systems and methods of the invention can be used to detect an analyte. In some embodiments, the analyte is a pathogen. Exemplary pathogens that can be detected include, but are not limited to: Varicella zoster; *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*; gonorrhea(*Neisseria gorrhoeae*), syphilis(*Treponema pallidum*), chlamydia (*Chlamydia tracomitis*), nongonococcal urethritis(*Ureaplasm urealyticum*), chancroid(*Haemophilus ducreyi*), trichomoniasis(*Trichomonas vaginalis*); *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae, Legionella pneumophila, Mycoplasma pneumoniae*, and *Mycobacterium tuberculosis*, etc.

In some embodiments, the devices, systems and methods of the invention can be used to detect an analyte that is a diagnostic marker. In some embodiments, the diagnostic marker is selected from any of the following Tables.

TABLE 4.1

Diagnostic markers

| Marker(s) (source of sample) | Disease(s), Disorder(s), or Condition(s) |
|---|---|
| Aβ42, amyloid beta-protein (cerebrospinal fluid, CSF) | Alzheimer's disease (AD) |
| Fetuin-A (CSF) | Multiple sclerosis (MS) |
| Tau (CSF) | Niemann-pick type C, parkinsonian disorders (neurodegenerative disorders) |
| Secretogranin II (CSF) | Bipolar disorder |
| Prion protein (CSF) | AD, prion disease |
| Cytokines (CSF) | HIV-associated neurocognitive disorders |
| Alpha-synuclein (CSF) | Parkinsonian disorders (neurodegenerative disorders) |
| Neurofilament light chain (CSF) | Axonal degeneration |
| Parkin (CSF) | Neurodegenerative disorders |
| PTEN induced putative kinase 1 (CSF) | Neurodegenerative disorders |
| DJ-1 (CSF) | Neurodegenerative disorders |
| Leucine-rich repeat kinase (CSF) | Neurodegenerative disorders |
| Mutated ATP12A2 (CSF) | Kufor-Rakeb disease |

TABLE 4.1-continued

| Diagnostic markers | |
|---|---|
| Marker(s) (source of sample) | Disease(s), Disorder(s), or Condition(s) |
| Apo H (CSF) | Parkinson's disease (PD) |
| Ceruloplasmin (CSF) | PD |
| Peroxisome proliferator-activated receptor gamma coactivator-1-alpha (PGC-1α)(CSF) | PD |
| Transthyretin (CSF) | CSF rhinorrhea (nasal surgery samples) |
| Vitamin-D binding protein (CSF) | MS progression |
| Proapoptotic kinase R (PKR) and its phosphorylated PKR (pPKR)(CSF) | AD |
| CXCL13 (CSF) | MS |
| IL-12p40, CXCL13 and IL-8 (CSF) | Intrathecal inflammation |
| Dkk-3 (semen) | Prostate cancer |
| p14 endocan fragment (blood) | Sepsis, lung inflammatory reaction |
| Serum (blood) | Neuromyelitis optica |
| ACE2 (blood) | Cardiovascular disease |
| Autoantibody to CD25 (blood) | Early diagnosis of esophageal squamous cell carcinoma |
| hTERT (blood) | Lung cancer |
| CAI25 (MUC 16)(blood) | Lung cancer |
| VEGF (blood) | Lung cancer |
| sIL-2 (blood) | Lung cancer |
| Osteopontin (blood) | Lung cancer |
| Human epididymis protein 4 (HE4)(blood) | Ovarian cancer |
| Alpha-fetal protein (blood) | Pregnancy |
| Albumin (urine) | Diabetes |
| Albumin (urine) uria | Albuminuria |
| Microalbuminuria (urine) | Kidney leaks |
| AFP (urine) | Mirror fetal AFP levels |
| Neutrophil gelatinase-associated lipocalin (NGAL)(urine) | Acute kidney injury |
| Interleukin-18 (IL-18)(urine) | Acute kidney injury |
| Kidney injury molecule-1 (KIM-1)(urine) | Acute kidney injury |
| Liver fatty acid binding protein (L-FABP)(urine) | Acute kidney injury |
| LMP1 (saliva) | Epstein-Barr virus oncoprotein (nasopharyngeal carcinomas) |
| BARF1 (saliva) | Epstein-Barr virus oncoprotein (nasopharyngeal carcinomas) |
| Interleukin-8 (IL-8)(saliva) | Oral cancer, spinalcellular carcinoma |
| Carcinoembryonic antigen (CEA)(saliva) | Oral or salivary malignant tumors |
| BRAF, CCNI, EGRF, FGF19, FRS2, GREB1, and LZTS1 (saliva) | Lung cancer |
| CA 125 (saliva) | Ovarian cancer |
| Thioredoxin (saliva) | Spinalcellular carcinoma |
| Beta-2 microglobulin (saliva) | HIV |
| Tumor necrosis factor-alpha receptors (saliva) | HIV |
| CA15-3 (saliva) | Breast cancer |

TABLE 4.2

Diagnostic markers

HPA axis activity (Cushing's disease, Adrenal cortex diseases, etc.): Cortisol
Pregnancy/fetal development: Progesterone, human chorionic gonadotropin,
Levonorgestrel, alpha-fetoprotein, early conception factor, Unconjugated Estriol, Estradiol,
interleukin-6, Inhibin-A
Infant development: NGAL, KIM-1, Cys-C, and B2mG, AFP, S100B, MBP
Menopause: Follicle stimulating hormone (FSH), Estrogen and progesterone,
testosterone, free testosterone, and dehydroepiandrosterone sulfate (DHEAS), cortisol
and dehydroepiandrosterone (DHEA)
Polycystic ovary syndrome: testosterone
Andropause: testosterone; testosterone precursors such as pregnenolone, progesterone,
17-hydroxypregnenolone, 17-hydroxyprogesterone, dehydroepiandrosterone (DHEA) and
delta-4-androstene-3,17-dione; testosterone and dihydrotestosterone metabolites such as
the 17-ketosteroids androsterone and etiocholanolone, polar metabolites in the form of
diols, triols, and conjugates, as well as estradiol, estrogens, androsteindione, cortisol, FSH TABLE 4.2-continued Diagnostic markers (follicle stimulating hormone), LH (luteinizing hormone), and GnRH (gonadotropin-releasing hormone)
Coagulation status/disorders: b-Thromboglobulin, Platelet factor 4, Von Willebrand factor, Factor I: Fibrinogen, Factor II: Prothrombin, Factor III: Tissue factor, Factor IV: Calcium, Factor V: Proaccelerin, Factor VI, Factor VII: Proconvertin, Factor VIII:, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1)
Autism: miR-484, miR-21, miR-212, miR-23a, miR-598, miR-95, miR-129, miR-431, miR-7, miR-15a, miR-27a, miR-15b, miR-148b, miR-132, or miR-128; miR-93, miR-106a, miR-539, miR-652, miR-550, miR-432, miR-193b, miR-181d, miR-146b, miR-140, miR-381, miR-320a, or miR-106b; GM1, GD1a, GD1b, or GT1b; Ceruloplasmin, Metalothioneine, Zinc, Copper, B6, B12, Glutathione, Alkaline phosphatase, and Activation of apo-alkaline phosphatases
Alzheimer's Disease: miR-107, miR-29a, miR-29b-1, or miR-9; miR-128; HIF-1α, BACE1, Reelin, CHRNA7, or 3Rtau/4Rtau, Reelin, Cystatin C, Truncated Cystatin C, C3a, t-Tau, Complement factor H, or alpha-2-macroglobulin; β-amyloid(1-42), β-amyloid(1-40), tau, phosphor-tau-181, acetylcholinesterase enzyme (AChE), GSK-3, PKC, VCAM-1 and ICAM-1, macrophage inflammatory proteins-1δ and -4 (MIPδ and MIP4), regulated upon activation normal T-cell (RANTES), tumor necrosis factor-alpha (TNFα), midregional pro-atrial natriuretic peptide (MR-proANP), AD-associated neuronal thread protein (AD7c-NTP)
Parkinson's Disease: miR-133b; Nurr1, BDNF, TrkB, gstm1, or S100 beta; apo-H, Ceruloplasmin, BDNF, Beta2-microglobulin, apoAII, tau, ABeta1-42, DJ-1, cTnI, myoglobin, MMP-9, MMP-8, MMP-2, sICAM-1, myeloperoxidase [MPO], IL-4, and/or IL-5; B-type natiuretic peptide [BNP], IL-1α, IL-11, IL-10, TNFα, IFN-γ, VEGF, insulin, GLP-1 (active), GLP-1 (total), TREM1, Leukotriene E4, Akt1, Aβ-40, Aβ-42, Fas ligand, PSA, G-CSF, MIP-1α, IL-22, IL-8, IL-21, IL-15, IL-6, IL-7, GM-CSF, IL-2, IL-12, IL-17α, IL-1β, MCP, IL-32 or RANTES, apolipoproteins A1, D and E, ischemia-modified albumin (IMA), fibronectin, s. alpha-amylase, aspartate aminotransferase, lactate dehydrogenase, tissue factor activity, MCP-1, sVCAM-1, sCD-40, insulin-like growth factor I (IGF-I), IGF-II
Schizophrenia: miR-181b; miR-7, miR-24, miR-26b, miR-29b, miR-30b, miR-30e, miR-92, or miR-195; IFITM3, SERPINA3, GLS, or ALDH7A1BASP1; TP5B, ATP5H, ATP6V1B, DNM1, NDUFV2, NSF, PDHB
Bipolar disease: FGF2, ALDH7A1, AGXT2L1, AQP4, or PCNT2
Mood disorder: Mbp, Edg2, Fgfr1, Fzd3, Mag, Pmp22, Ugt8, Erbb3, Igfbp4, Igfbp6, Pde6d, Ptprm, Nefh, Atp2c1, Atxn1, Btg1, C6orf182, Dicer1, Dnajc6, and Ednrb
Major Depressive Disorder: FGFR1, FGFR2, FGFR3, or AQP4, Secretogranin, VGF, Cortisol, EGF, GCS, PPY, ACTH, AVP, CRH, A1AT, A2M, ApoC3, CD40L, IL-6, IL-13, IL-18, IL-1ra, MPO, PAI-1, TNFA, ACRP30, ASP, FABP, INS, LEP, PRL, RETN, Testosterone, TSH, BDNF, S100B, NTF3, GDNF, ARTN
Prion disease: Amyloid B4, App, IL-1R1, or SOD1; PrP(c), 14-3-3, NSE, S-100, Tau, AQP-4
Inflammation: TNF-α, IL-6, IL1β, Rheumatoid factor (RF), Antinuclear Antibody (ANA), acute phase markers including C-reactive protein (CRP), Clara Cell Protein (Uteroglobin); 14-3-3 protein epsilon; Isoform Long of Protocadherin alpha C2 precursor; Insulin-like growth factor IA precursor; Isoform 1 of Protocadherin-8 precursor; Isoform 1 of Sodium/potassium/calcium exchanger 2 precursor; Complement factor H-related 5; Di-N-acetylchitobiase precursor; Isoform 1 of Protein NDRG2; N-acetylglucosamine-6-sulfatase precursor; Isoform 1 of Semaphorin-3B precursor; Cadherin-5 precursor; UPF0454 protein C12orf49 precursor; Dihydrolipoyl dehydrogenase, mitochondrial precursor;
Metallothionein-3; Fas apoptotic inhibitory molecule 2; Coactosin-like protein; Isoform Long of Platelet-derived growth factor A chain Precursor; Isoform Long of Endothelin-3 precursor; HLA class I histocompatibility antigen, A-1 alpha chain Precursor; Neuronal pentraxin-2 precursor; retbindin isoform 2; Neuroendocrine convertase 2 precursor; 15 kDa selenoprotein isoform 1 precursor; Phospholipase D4; Isoform 1 of CD109 antigen precursor; Ectonucleotide pyrophosphatase/phosphodiesterase family; member 6 precursor; Fascin; Golgi phosphoprotein 2; Isoform Delta 6 of Calcium/calmodulin-dependent protein kinase type II delta chain; Isoform 1 of FRAS1-related extracellular matrix protein 2 Precursor; Putative uncharacterized protein LOC130576; Isoform 1 of L-lactate dehydrogenase A chain; Isoform 1 of Polypeptide N-acetylgalactosaminyltransferase 13; Papilin; Protein DJ-1; Beta-mannosidase precursor; Protein YIPF3; Isoform 1 of Receptor-type tyrosine-protein phosphatase N2 Precursor;
Cell growth regulator with EF hand domain protein 1; Sulfhydryl oxidase 2 precursor; Ig lambda chain V-II region TRO; Ig lambda chain V-VI region AR; Ig heavy chain V-III region WEA; Ig heavy chain V-III region CAM; Ig heavy chain V-III region BUR; Myosin-reactive immunoglobulin kappa chain variable region (Fragment); Microfibrillar protein 2 (Fragment); Ig kappa chain V-III region IARC/BL41 precursor; Ig kappa chain V-I region Kue; Ig kappa chain V-I region Scw; Ig kappa chain V-III region B6; IGLV6-57 protein; hypothetical protein LOC402665; Isoform 1 of Proline-rich acidic protein 1 precursor; Rheumatoid factor RF-ET13; Rheumatoid factor D5 heavy chain (Fragment); Uncharacterized protein ENSP00000375027; Uncharacterized protein ENSP00000375043; Uncharacterized protein ENSP00000375019; Isoform 1 of Protocadherin-1 precursor; Isoform 1 of Epithelial discoidin domain-containing receptor 1 precursor; Serine protease HTRA1 precursor; Isoform Delta of Poliovirus receptor-related protein 1 Precursor; chemokine (C—X—C motif) ligand 16; Plastin-2; 14-3-3 protein TABLE 4.2-continued Diagnostic markers zeta/delta; Apolipoprotein C-II precursor; Brain-specific angiogenesis inhibitor 1 precursor; Semaphorin-3G precursor; Follistatin-related protein 3 precursor; Hepatocyte growth factor activator precursor; Isoform 1 of Contactin-associated protein-like 2 precursor; Phosphoglycerate kinase 1; Gamma-enolase; Phosphoglycerate mutase 2; Low affinity immunoglobulin gamma Fc region receptor III-A precursor; Isoform Beta of Poliovirus receptor precursor; Serine protease inhibitor Kazal-type 6 precursor; Isoform 1 of Chordin precursor; Out at first protein homolog precursor; Isoform 1 of Carboxypeptidase B2 precursor; ROBO2 isoform a Ig kappa chain V-III region POM; Isoform 1 of Protein-L-isoaspartate(D-aspartate) O-Methyltransferase CDNA FLJ45296 fis, clone BRHIP3003340, moderately similar to Actin, alpha skeletal muscle 2; Isoform 1 of RGM domain family member B precursor; Carboxypeptidase N subunit 2 precursor; Hypothetical LOC284297; L-6, IL-17, PAR-3, IL-17, T1/ST2, JunD, 5-LO, LTA4H, MBP, PLP, or alpha-beta crystalline; antithrombin III; α-2 glycoprotein 1, zinc; transthyretin (prealbumin); NADH dehydrogenase (ubiquinone) 1 beta subcomplex, 2; neurotrimin; orosomucoid 1 precursor (α-1-acid glycoprotein-1); leucine-rich α-2-glycoprotein; leucine-rich repeat protein; α-1-antitrypsin Chronique fatigue syndrome: Cortisol; Ig alpha-1 chain C region; Polymeric immunoglobulin receptor; Protein S100-A7; Cystatin-C; Cystatin-B; 14-3-3 protein zeta/delta; Zinc-alpha-2-glycoprotein (ZAG)

Sjögren's syndrome: IgA, IgG, IgM autoantibodies; IgA, lactoferrin and beta2-microglobulin; lysozyme C, and cystatin C, amylase and carbonic anhydrase; Autoantibodies (SSA/Ro; LA/SS-B)

Systemic lupus erythematosus (SLE): Autoantibodies (CDC25B, APOBEC3G, ARAF, BCL2A1, CLK1, CREB1, CSNK1G1, CSNK2A1, CWC27, DLX4, DPPA2, EFHD2, EGR2, ERCC2, EWSR1, EZH2, FES, FOS, FTHL17, GEM, GNA15, GNG4, HMGB2, HNRNPUL1, HOXB6, ID2, IFI35, IGF2BP3, IGHG1, JUNB, KLF6, LGALS7, LIN28A, MLLT3, NFIL3, NRBF2, PABPC1, PATZ1, PCGF2, PPP2CB, PPP3CC, PRM1, PTK2, PTPN4, PYGB, RET, RPL18A, RPS7, RRAS, SCEL, SH2B1, SMAD2, STAM, TAF9, TIE1, UBA3, VAV1, WT1, ZAP70, ZNRD1, KIT, C6orf93, RPL34, DOM3Z, COPG2, DNCL12, RRP41, FBXO9, RALBP1, PIAS2, EEF1D, CONI, KATNB1, POLR2E, CCT3, KIAA0643, RPL37A, GTF2H2, MAP2K5, CDK3, RPS6KA1, MARK4, MTO1, MGC42105, NFE2L2, WDR45L, STK4, PFKFB3, NTRK3, MLF1, TRIM37, ACTL7B, RPL18A, CKS1B, TUBA1, NME6, SUCLA2, IGHG1, PRKCBP1, BAG3, TCEB3, RPL15, SSX4, MAP2K7, EEF1G, RNF38, PHLDA2, KCMF1, NUBP2, VPS45A, SSA/Ro, dsDNA, Smith, histones, thrombin)

CREST syndrome: Autoantibodies (centromere)

Systemic sclerosis: Autoantibodies (Type I topoisomerase)

Primary biliary cirrhosis: Autoantibodies (nucleoporin 62, Sp100 nuclear antigen, nucleoporin 210 kDa, mitochondria)

Cirrhosis: NLT; NLT, HBsAG, AST, YKL-40, Hyaluronic acid, TIMP-1, alpha 2 macroglobulin, a-1-antitrypsin P1Z allele, haptoglobin, or acid phosphatase ACP AC Autoimmune hepatitis: Autoantibodies (Liver kidney microsomal type 1, smooth muscle)

Celiac disease: Autoantibodies (tTG, actin)

Celiac disease Irritable Bowel Syndrome (IBS): Anti-IgA gliadin, REG1A, MMP3

Inflammatory bowel disease (IBD): Trypsinogen IV, SERT; Il-16, Il-1beta, Il-12, TNF-alpha, interferon gamma, 11-6, Rantes, MCP-1, Resistin, or 5-HT Ulcerative colitis: IFITM1, IFITM3, STAT1, STAT3, TAP1, PSME2, PSMB8, HNF4G, KLF5, AQP8, APT2B1, SLC16A, MFAP4, CCNG2, SLC44A4, DDAH1, TOB1, 231152_at, MKNK1, CEACAM7*, 1562836_at, CDC42SE2, PSD3, 231169_at, IGL@*, GSN, GPM6B, CDV3*, PDPK1, ANP32E, ADAM9, CDH1, NLRP2, 215777_at, OSBPL1, VNN1, RABGAP1L, PHACTR2, ASH1L, 213710_s_at, CDH1, NLRP2, 215777_at, OSBPL1, VNN1, RABGAP1L, PHACTR2, ASH1, 213710_s_at, ZNF3, FUT2, IGHA1, EDEM1, GPR171, 229713_at, LOC643187, FLVCR1, SNAP23*, ETNK1, LOC728411, POSTN, MUC12, HOXA5, SIGLEC1, LARP5, PIGR, SPTBN1, UFM1, C6orf62, WDR90, ALDH1A3, F2RL1, IGHV1-69, DUOX2, RAB5A, or CP; (P)ASCA Hyperplastic Polyp: SLC6A14, ARHGEF10, ALS2, IL1RN, SPRy4, PTGER3, TRIM29, SERPINB5, 1560327 at, ZAK, BAG4, TRIB3, TTL, FOXQ1

Psoriasis: miR-146b, miR-20a, miR-146a, miR-31, miR-200a, miR-17-5p, miR-30e-5p, miR-141, miR-203, miR-142-3p, miR-21, or miR-106a; miR-125b, miR-99b, miR-122a, miR-197, miR-100, miR-381, miR-518b, miR-524, let-7e, miR-30c, miR-365, miR-133b, miR-10a, miR-133a, miR-22, miR-326, or miR-215; IL-20, VEGFR-1, VEGFR-2, VEGFR-3, or EGR1;

Dermatitis herpetiformis: Autoantibodies (eTG)

Miller-Fisher Syndrome: Autoantibodies (ganglioside GQ1B)

Wegener's granulomatosis: Autoantibodies (c-ANCA)

Neuropathies: Autoantibodies (ganglioside GD3, ganglioside GM1)

Microscopic polyangiitis: Autoantibodies (p-ANCA)

Polymyositis: Autoantibodies (Signal recognition particles)

Scleromyositis: Autoantibodies (exosome complex Signal recognition particles)

Myasthenia gravis: Autoantibodies (nicotinic acetylcholine receptor Signal recognition particles, muscle-specific kinase (MUSK) Signal recognition particles)

Lambert-Eaton myasthenic syndrome: Autoantibodies (voltage-gated calcium channel (P/Q-type))

Hashimoto's thyroiditis: Autoantibodies (thyroid peroxidase)

Graves' disease: Autoantibodies (TSH receptor)

Paraneoplastic cerebellar syndrome: Autoantibodies (Hu, Yo (cerebellar Purkinje Cells), amphiphysin)

TABLE 4.2-continued

Diagnostic markers

Encephalitis: Autoantibodies (voltage-gated potassium channel (VGKC), N-methyl-D-aspartate receptor (NMDA))
Sydenham's chorea: Autoantibodies (basal ganglia neurons)
Neuromyelitis: Autoantibodies (aquaporin-4)
Allergies: Allergen-specific IgAs
Rheumatic disease: miR-146a, miR-155, miR-132, miR-16, or miR-181; HOXD10, HOXD11, HOXD13, CCL8, LIM homeobox2, or CENP-E; TNFα
Rheumatoid arthritis: Autoantibodies (Rheumatoid factor, cyclic citrullinated protein), ATP-binding cassette, sub-family A, member 12 isoform b; ATP-binding cassette A12; apolipoprotein; B-100 precursor - human; complement component 3 precursor; alpha-2-glycoprotein 1, zinc; Alpha-2-glycoprotein, zinc; serine (or cysteine) proteinase inhibitor, clade A (alpha-1 antiproteinase, antitrypsin), member 2; Protease inhibitor 1-like; protease inhibitor 1 (alpha-1-antitrypsin)-like; group-specific component (vitamin D binding protein); hDBP; serine (or cysteine) proteinase inhibitor, clade A (alpha-1 antiproteinase, antitrypsin), member 1; Protease inhibitor (alpha-1-antitrypsin); protease inhibitor 1 (anti-elastase), alpha-1-antitrypsin; Vitronectin precursor V65 subunit; A kinase anchor protein 9 isoform 2; retrovirus-related hypothetical protein II -human retrotransposon LINE-1; nuclear receptor coactivator RAP250; peroxisome proliferator-act; nuclear receptor coactivator RAP2; Ig kappa chain NIG26 precursor - human; Vitamin D-binding protein precursor (DBF) (Group-specific component) (GC-globulin) (VDB) complement C4A precursor [validated] Human; guanine nucleotide binding protein (G protein), gamma transducing activity polypeptide 1; nucleoporin 98 kD isoform 4; nucleoporin 98 kD; Nup98-Nup96 precursor; GLFG-repeat containing; nucleoporin; vitronectin precursor; serum spreading factor; somatomedin B; complement S-protein; Alpha-1-antitrypsin precursor; HMG-BOX transcription; factor BBX; x 001; protein; hect domain and RLD 2; calcium channel, voltage-dependent, L type, alpha 1C subunit; Alpha-2-antiplasmin precursor (Alpha-2-plasmin inhibitor) (Alpha-2-PI) (Alpha-2-AP); Neuronal PAS domain protein 2 (Neuronal PAS2) (Member of PAS protein 4) (MOP4); Retinoic acid receptor gamma-2 (RAR-gamma-2) alpha-1-B-glycoprotein - human; Heparin cofactor II precursor (HC-II) (Protease inhibitor leuserpin 2) (HLS2); Ig gamma-1 chain C region; isocitrate dehydrogenase 3 (NAD+) alpha precursor; H-IDH alpha; isocitric dehydrogenase; isocitrate dehydrogenase [NAD] sub- unit alpha, mitochondrial; NAD+-specific ICDH; NAD(H)-specific isocitrate dehydrogenase alpha subunit precursor; isocitrate dehydrogenase (NAD+) alpha chain precursor; ferroxidase (EC 1.16.3.1) precursor [validated] - human; similar to zona pellucida binding protein; N-acetylneuraminic acid phosphate synthase; sialic acid synthase; sialic acid phosphate synthase; triple functional domain (PTPRF interacting); deleted in bladder cancer chromosome region candidate 1; ceruloplasmin (ferroxidase); Ceruloplasmin; RAB3A interacting protein (rabin3)-like 1; talin 2; similar to Ceruloplasmin precursor (Ferroxidase); orosomucoid 1 precursor; Orosomucoid-1 (alpha-1-acid glycoprotein-1); Ig lambda chain precursor - human; cold autoinflammatory syndrome 1; chromosome 1 open reading frame 7; angio-tensin/vasopressin receptor; similar to KIAA0913 protein; sodium channel, voltage-gated, type V, alpha polypeptide; hypothetical protein FLJ10379; orosomucoid 2; alpha-1-acid glycoprotein, type 2; Ig alpha-1 chain C region; corticosteroid binding globulin precursor; corticosteroid binding globulin; alpha-1 anti-proteinase, antitrypsin; KV3M_HUMAN IG KAPPA CHAIN V-III REGION HIC PRECURSOR; MUC_HUMAN Ig mu chain C region; similar to Ig gamma-2 chain C region; alpha-1-antichymotrypsin, precursor; alpha-1-antichymotrypsin; Antichymotrypsin; thyroid hormone receptor-associated protein, 240 kDa subunit; Ig heavy chain - human; Alpha-1-antichymotrypsin precursor (ACT) hypothetical protein XP_173158; hypothetical protein DKFZp434G2226; haptoglobin; Plasma protease C1 inhibitor precursor (C1 Inh) (C1Inh) Haptoglobin-1 precursor; leucine-rich alpha-2-glycoprotein; S-arrestin; S-antigen; NAD(P)H dehydrogenase, quinone 2; NAD(P)H menadione oxidoreductase-1, di-oxin-inducible-2; NAD(P)H menadione oxi-doreductase 2, dioxin-inducible; angiotensin precursor [validated] - human; similar to KIAA1902 protein; similar to KIAA1728 protein; calpain 3 isoform d; calpain, large polypep- tide L3; calpain p94, large [catalytic] subunit; muscle-specific calcium-activated neutral protease 3 large subunit; asp (abnormal spindle)-like, microcephaly associated; haptoglobin-related protein; Haptoglobin-related locus; Ig alpha-2 chain C region; hypothetical protein DKFZp434P1818.1 - human (fragment); GC3_HUMAN Ig gamma-3 chain C region (Heavy chain disease protein) (HDC)
Organ Rejection: miR-658, miR-125a, miR-320, miR-381, miR-628, miR-602, miR-629, or miR-125a; miR-324-3p, miR-611, miR-654, miR-330_MM1, miR-524, miR-17-3p_MM1, miR-483, miR-663, miR-5,6-5p, miR-326, miR-197_MM2, or miR-346; matix metalloprotein-9, proteinase 3, or HNP
Bone turnover/ Osteoporosis: Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b, deoxypyridinium (D-PYR) and osteocalcin (OC), hepatocyte growth factor and interleukin-1 beta, Osteocalcin, alkaline phosphatase, bone-specific alkaline phosphatase, serum type 1 procollagen (C1NP, P1NP)
Jaw osteonecrosis: PTH, insulin, TNF-α, leptin, OPN, OC, OPG and IL6
Gaucher's disease: lyso-Gbl, Chitotriosidase and CCL18
Traumatic brain injury: apoA-1, S-100B, isoprostane, GFAP, NGAL, neuron-specific enolase (NSE)
Septic shock: 15-Hydroxy-PG dehydrogenase (up), LAIR1 (up), NFKB1A (up), TLR2, PGLYPR1, TLR4, MD2, TLR5, IFNAR2, IRAK2, IRAK3, IRAK4, PI3K, PI3KCB, MAP2K6, MAPK14, NFKB1A, NFKB1, IL1R1, MAP2K1IP1, MKNK1, FAS, CASP4, GADD45B, SOCS3, TNFSF10, TNFSF13B, OSM, HGF, IL18R1, IL-6, Protein-C, IL-1beta TABLE 4.2-continued Diagnostic markers Cancer: FEN-1; CEA, NSE, CA 19-9, CA 125, PSA, proGRP, SCC, NNMT, anti-p53 autoantibodies, Separase and DPPFV/Separase, SERPINA3; ACTB; AFM; AGT; AMBP; APOF; APOA2; APOC1; APOE; APOH; SERPINC1; C1QB; C3; C4BPA; C8G; C9; SERPINA6; CD14; CP; CRP; CSK; F9; FGA; FGG; FLNA; FN1; GC; HRG; IF; IGFALS; ITGA1; ITIH1; ITIH2; ITIH4; KLKB1; LPA; MLL; MRC1; MYL2; MYO6; ORM1; SERPINF1;
SERPINA1; SERPINA4; PROS1; QSCN6; RGS4; SAA4; SERPINA7; TF; TFRC; TTN; UBC; ALMS1; ATRN; PDCD11; KIAA0433; SERPINA10; BCOR; C10orf18; YY1AP1; FLJ10006; BDP1; SMARCAD1; MKL2; CHST8; MCPH1; MYO18B; MICAL-L1; PGLYRP2; KCTD7; MGC27165; A1BG; A2M; ABLIM1; ACTA1; AHSG; ANK3; APCS; APOA1; APOA4; APOB; APOC3; APOL1; AZGP1; B2M; BF; C1R; C1S; C2; C4B; C5; C6; C7; C8A; C8B; CDK5RAP2/CDK5RA2; CHGB; CLU; COMP; CORO1A; CPN1; CUL1; DET1; DSC1; F13A1; F2; F5; FGB; GOLGA1; GSN; HBA1; HBB; HP; HPX; HSPA5; HUNK; IGFBP5; IGHG1; IGLV4-3; KIF5C; KNG1; KRT1; KRT10; KRT9; LBP; LGALS3BP; LRG1; LUM; MMP14; MYH4; NEB; NUCB2; ORM2; PF4V1; PIGR; PLG; PON1; PPBP; RBP4; RIMS1; RNF6; SAA1; SEMA3D; SERPIND1; SERPINF2; SERPING1; SF3B1; SPINK1; SPP1; SPTB; SYNE1; TAF4B; TBC1D1; TLN1; TMSB4X; TRIP11; TTR; UROC1; VTN; VWF; ZFHX2; ZYX; PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine; Zinc α2-glycoprotein (ZAG)
Adenoma: SI, DMBT1, CFI*, AQP1, APOD, TNFRSF17, CXCL10, CTSE, IGHA1, SLC9A3, SLC7A1, BATF2, SOCS1, DOCK2, NOS2A, HK2, CXCL2, IL15RA, POU2AF1, CLEC3B, ANI3BP, MGC13057, LCK*, C4BPA, HOXC6, GOLT1A, C2orf32, IL10RA, 240856_at, SOCS3, MEIS3P1, HIPK1, GLS, CPLX1, 236045_x_at, GALC, AMN, CCDC69, CCL28, CPA3, TRIB2, HMGA2, PLCL2, NR3C1, EIF5A, LARP4, RP5-1022P6.2, PHLDB2, FKBP1B, INDO, CLDN8, CNTN3, PBEF1, SLC16A9, CDC25B, TPSB2, PBEF1, ID4, GJB5, CHN2, LIMCH1, or CXCL9; ABCA8, KIAA1199, GCG, MAMDC2, C2orf32, 229670_at, IGF1, PCDH7, PRDX6, PCNA, COX2, or MUC6
Head and Neck cancer: IL-1, IL-6, IL-8, VEGF, MMP-9, TGF-β, TNF-α, MMP-7, plasminogen activated (PA), uPA, IGF, or INF-2
Barrett's esophagus: miR-21, miR-143, miR-145, miR-194, or miR-215; S100A2, S100A4; p53, MUC1, MUC2
Lung cancer: miR-21, miR-205, miR-221 (protective), let-7a (protective), miR-137 (risky), miR-372 (risky), or miR-122a (risky); miR-17-92, miR-19a, miR-92, miR-155, miR-191, or miR-210; EGFR, PTEN, RRM1, RRM2, ABCB1, ABCG2, LRP, VEGFR2, VEGFR3, class III b-tubulin; KRAS, hENT1; RLF-MYCL1, TGF-ALK, or CD74-ROS1, CCNI, EGFR, FGF19, FRS2, and GREB1 LZTS, BRAF, FRS2, ANXA1, Haptoglobin Hp2, Zinc Alpha2-Glycoprotein, Calprotectin, Porphyromonas catoniae 16S rRNA, Campylobacter showae 16S rRNA, Streptococcus salivaris 16S rRNA, Campylobacter rectus 16S rRNA, Veillonella parvula 16S rRNA, Kigella oralis 16S rRNA, and Granulicatella adiacens 16S rRNA
Pancreatic cancer: miR-221, miR-181a, miR-155, miR-210, miR-213, miR-181b, miR-222, miR-181b-2, miR-21, miR-181b-1, miR-220, miR-181d, miR-223, miR-100-1/2, miR-125a, miR-143, miR-10a, miR-146, miR-99, miR-100, miR-199a-1, miR-10b, miR-199a-2, miR-221, miR-181a, miR-155, miR-210, miR-213, miR-181b, miR-222, miR-181b-2, miR-21, miR-181b-1, miR-181c, miR-220, miR-181d, miR-223, miR-100-1/2, miR-125a, miR-143, miR-10a, miR-146, miR-99, miR-100, miR-199a-1, miR-10b, miR-199a-2, miR-107, miR-103, miR-103-2, miR-125b-1, miR-205, miR-23a, miR-221, miR-424, miR-301, miR-100, miR-376a, miR-125b-1, miR-21, miR-16-1, miR-181a, miR-181c, miR-92, miR-15, miR-155, let-7f-1, miR-212, miR-107, miR-024-1/2, miR-18a, miR-31, miR-93, miR-224, or let-7d; miR-148a, miR-148b, miR-375, miR-345, miR-142, miR-133a, miR-216, miR-217 or miR-139; KRAS, CTNNLB1, AKT, NCOA3, or B-RAF; BRCA2, PALB2, or p16, MBD3L2, KRAS, STIM2, DMXL2, ACRV1, DMD and CABLES1, TK2, GLTSCR2, CDKL3, TPT1 and DPM1
Breast cancer: miR-21, miR-155, miR-206, miR-122a, miR-210, miR-155, miR-206, miR-210, or miR-21; let-7, miR-10b, miR-125a, miR-125b, miR-145, miR-143, miR-16, miR-10b, miR-125a; hsp70, MART-1, TRP, HER2, hsp70, MART-1, TRP, HER2, ER, PR, Class III b-tubulin, or VEGFA; GAS5; ETV6-NTRK3; CAH6 (Carbonic anhydrase VI), K2C4 (Cytokeratin 4), CYTA (Cystatin A), FABP4 (Epid. Fatty acid binding prot.), IGHG1 (Ig gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1 ra (Interleukin-1 receptor anatagonist protein precursor), S10A7 (S100 calcium-binding protein A7), and SPLC2 (Short palate, lung and nasel epith Carc. assoc. protein 2)
Ovarian cancer: c-erbB-2, cancer antigen 15-3, p53, HER2/neu (c-erbB-2), 47D10 antigen, PTCD2, SLC25A20, NFKB2, RASGRP2, PDE7A, MLL, PRKCE, GPATC3, PRIC285 and GSTA4, MIPEP, PLCB2, SLC25A19, DEF6, ZNF236, C18orf22, COX7A2, DDX11, TOP3A, C9orf6, UFC1, PFDN2, KLRD1, LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, LOC284184, FLJ23235, GPATC3, CPSF4, CREM, HIST1H1D, HPS4, TABLE 4.2-continued Diagnostic markers FN3KRP, ANKRD16, C8 orf16, ATF71P2, PRIC285, miR-200a, miR-141, miR-200c, miR-200b, miR-21, miR-200a, miR-200b, miR-200c, miR-203, miR-205, miR-214, miR-199", or miR-215; miR-199a, miR-140, miR-145, miR-100, miR-let-7 cluster, or miR-125b-1; ERCC1, ER, TOPO1, TOP2A, AR, PTEN, CD24 or EGFR; VEGFA, VEGFR2, CA 125
Prostate cancer: AGPAT1, B2M, BASP2, IER3, IL1B, miR-9, miR-21, miR-141, miR-370, miR-200b, miR-210, miR-155, or miR-196a; miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-71, miR-188, miR-25, miR-106b, miR-449, miR-99b, miR-93, miR-92-1/2, miR-125a, or miR-141; let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b; miR-15a, miR-16-1, miR-143 or miR-145; AR, PCA3; FASLG or TNFSF10; U50; ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5, KLK2-ETV4, kallikrein-2 (KLK2), C reactive protein (CRP), cysteine-rich secretory protein 3 (CRISP3) and chromogranin A (CHGA), comprises prostatic acid phosphatase (PAP), lactate dehydrogenase (LDH), alkaline phosphatase (ALP), PSA
Esophageal Cancer: PCA3, GOLPH2, SPINK1, TMPRSS2:ERG, miR-192, miR-194, miR-21, miR-200c, miR-93, miR-342, miR-152, miR-93, miR-25, miR-424, or miR-151; miR-27b, miR-205, miR-203, miR-342, let-7c, miR-125b, miR-100, miR-152, miR-192, miR-194, miR-27b, miR-205, miR-203, miR-200c, miR-99a, miR-29c, miR-140, miR-103, miR-107
Gastric cancer: miR-106a, miR-21, miR-191, miR-223, miR-24-1, miR-24-2, miR-107, miR-92-2, miR-214, miR-25, or miR-221; let-7a; RRM2, or surviving; EphA4
Gastrointestinal Stromal Tumor (GIST): DOG-1, PKC-theta, KIT, GPR20, PRKCQ, KCNK3, KCNH2, SCG2, TNFRSF6B, or CD34; PDGFRA, c-kit
Colorectal carcinoma: miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p; miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, or miR-148b; EFNB1, ERCC1, HER2, VEGF, or EGFR; AFRs, Rabs, ADAM10, CD44, NG2, ephrin-B1, MIF, b-catenin, Junction, plakoglobin, glialectin-4, RACK1, tetrspanin-8, FasL, TRAIL, A33, CEA, EGFR, dipeptidase 1, hsc-70, tetraspanins, ESCRT, TS, PTEN, or TOPO1; GREM1, DDR2, GUCY1A3, TNS1, ADAMTS1, FBLN1, FLJ38028, RDX, FAM129A, ASPN, FRMD6, MCC, RBMS1, SNA12, MEIS1, DOCK10, PLEKHC1, FAM126A, TBC1D9, VWF, DCN, ROBO1, MSRB3, LATS2, MEF2C, IGFBP3, GNB4, RCN3, AKAP12, RFTN1, 226834_at, COL5A1, GNG2, NR3C1*, SPARCL1, MAB21L2, AXIN2, 236894_at, AEBP1, AP1S2, C10orf56, LPHN2, AKT3, FRMD6, COL15A1, CRYAB, COL14A1, LOC286167, QKI, WWTR1, GNG11, PAPPA, or ELDT1; 227458_at, INDO, CXCL9, CCR2, CD38, RARRES3, CXCL10, FAM26F, TNIP3, NOS2A, CCRL1, TLR8, IL18BP, FCRL5, SAMD9L, ECGF1, TNFSF13B, GBPS, or GBP1; TMEM37*, IL33, CA4, CCDC58, CLIC6, VERSUSNL1, ESPN, APCDD1, C13orf18, CYP4X1, ATP2A3, LOC646627, MUPCDH, ANPEP, C1orf115, HSD3B2, GBA3, GABRB2, GYLTL1B, LYZ, SPC25, CDKN2B, FAM89A, MOGAT2, SEMA6D, 229376_at, TSPAN5, IL6R, or SLC26A2
Melanoma: miR-19a, miR-144, miR-200c, miR-211, miR-324-5p, miR-331, or miR-374; miR-9, miR-15a, miR-17-3p, miR-23b, miR-27a, miR-28, miR-29b, miR-30b, miR-31, miR-34b, miR-34c, miR-95, miR-96, miR-100, miR-104, miR-105, miR-106a, miR-107, miR-122a, miR-124a, miR-125b, miR-127, miR-128a, miR-128b, miR-129, miR-135a, miR-135b, miR-137, miR-138, miR-139, miR-140, miR-141, miR-149, miR-154, miR-154#3, miR-181a, miR-182, miR-183, miR-184, miR-185, miR-189, miR-190, miR-199, miR-199b, miR-200a, miR-200b, miR-204, miR-213, miR-215, miR-216, miR-219, miR-222, miR-224, miR-299, miR-302a, miR-302b, miR-302c, miR-302d, miR-323, miR-325, let-7a, let-7b, let-7d, let-7e, or let-7g; MUM-1, beta-catenin, or Nop/5/Sik; DUSP-1, Alix, hsp70, Gib2, Gia, moesin, GAPDH, malate dehydrogenase, p120 catenin, PGRL, syntaxin-binding protein 1 & 2, septin-2, or WD-repeat containing protein 1; H/ACA (U1071), SNORA11D
Head and neck cancer: miR-21, let-7, miR-18, miR-29c, miR-142-3p, miR-155, miR-146b, miR-205, or miR-21; miR-494; HPV E6, HPV E7, p53, IL-8, SAT, H3FA3; EGFR, EphB4, or EphB2; CHCHD7-PLAG1, CTNNB1-PLAG1, FHIT-HMGA2, HMGA2-NFIB, LIFR-PLAG1, or TCEA1-PLAG1
Oral squamous cell carcinoma: p53 autoantibodies, defensing-1, lncRNAs (MEG-3, MALAT-1, HOTAIR, NEAT-1, UCA) Cortisol, lactate dehydrogenase, Transferrin, cyclin D1, Maspin, alpha-amylase, IL-8, TNF-α, IL-1, IL-6, Basic fibroblast growth factor, Statherin, Cyfra 21.1, TPA, CA125, Endothelin-1, IL-1β, CD44, IGF-1, MMP-2, MMP-9, CD59, Catalase, Profilin, S100A9/MRP14, M2BP, CEA, Carcinoma associated antigen CA-50, Salivary carbonyls, Maspin, 8-oxoguanine DNA glycosylase, OGG1, Phosphorylated-Src, Ki-67, Zinc finger protein 501 peptide, Hemopexin, Haptoglobin,

TABLE 4.2-continued

Diagnostic markers

Complement C3, Transthyretin, a1-antitrypsin, Peroxidase, GST, SOD, 8-OHdG, Glutathione, MDA, miR-125a, miR-200a, miR-31

Salivary gland tumors: Fibroblast growth factor 2 (FGF2) and fibroblast growth factor receptor 1 (FGFR1)

Hepatocellular carcinoma: miR-221; et-7a-1, let-7a-2, let-7a-3, let-7b, let-7c, let-7d, let-7e, let-7f-2, let-fg, miR-122a, miR-124a-2, miR-130a, miR-132, miR-136, miR-141, miR-142, miR-143, miR-145, miR-146, miR-150, miR-155(BIC), miR-181a-1, miR-181a-2, miR-181c, miR-195, miR-199a-1-5p, miR-199a-2-5p, miR-199b, miR-200b, miR-214, miR-223, or pre-miR-594; miR-122, miR-100, or miR-10a; miR-198 or miR-145

Renal cell carcinoma: miR-141, miR-200; miR-28, miR-185, miR-27, miR-let-7f-2; laminin receptor 1, betaig-h3, Galectin-1, a-2 Macroglobulin, Adipophilin, Angiopoietin 2, Caldesmon 1, Class II MHC-associated invariant chain (CD74), Collagen IV-al, Complement component, Complement component 3, Cytochrome P450, subfamily IIJ polypeptide 2, Delta sleep-inducing peptide, Fc g receptor 111a (CD16), HLA-B, HLA-DRa, HLA-DRb, HLA-SB, IFN-induced transmembrane protein 3, IFN-induced transmembrane protein 1, or Lysyl Oxidase; IF1 alpha, VEGF, PDGFRA; ALPHA-TFEB, NONO-TFE3, PRCC-TFE3, SFPQ-TFE3, CLTC-TFE3, or MALAT1-TFEBf Renal cell carcinoma: Akt, total Erk1/2, total Met, total GSK3b, total Hif1a, total p21, total AMPKa1, total VEGF, total PIGF, total VEGFR-1/Flt-1, phosphorylated Akt, phosphorylated Erk1/2, phosphorylated. Met, phosphorylated STAT3, phosphorylated GSK3b, and phosphorylated AMPKa1

Cervical cancer: HPV E6, HPV E7, or p53

Thyroid cancer: AKAP-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET; PAX8-PPARy Neuroblastoma: Neuron-specific enolase (NSE)

Glioblastoma: GFAP

Brain cancer: miR-21, miR-10b, miR-130a, miR-221, miR-125b-1, miR-125b-2, miR-9-2, miR-21, miR-25, or miR-123; miR-128a, miR-181c, miR-181a, or miR-181b; GOPC-ROS1; MGMT; EGFR Blood Cancers: HOX11, TAL1, LY1, LMO1, or LMO2; TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, for acute lymphocytic leukemia (ALL); BCL11B-TLX3, IL2-TNFRFS17, NUP214-ABL1, NUP98-CCDC28A, TAL1-STIL, or ETV6-ABL2, for T-cell acute lymphocytic leukemia (T-ALL); ATIC-ALK, KIAA1618-ALK, MSN-ALK, MYH9-ALK, NPM1-ALK, TGF-ALK or TPM3-ALK, for anaplastic large cell lymphoma (ALCL); BCR-ABL1, BCR-JAK2, ETV6-EVI1, ETV6-MN1 or ETV6-TCBA1, for chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVl1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, for AML; CCND1-FSTL3, for chronic lymphocytic leukemia (CLL); and FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, for hyper eosinophilia/chronic eosinophilia; miR-23b, miR-24-1, miR-146, miR-155, miR-195, miR-221, miR-331, miR-29a, miR-195, miR-34a, or miR-29c; miR-15a, miR-16-1, miR-29 or miR-223; miR-128b, miR-204, miR-218, miR-331, miR-181b-1, miR-17-92

B-Cell Chronic Lymphocytic Leukemia: miR-183-prec, miR-190, miR-24-1-prec, miR-33, miR-19a, miR-140, miR-123, miR-10b, miR-15b-prec, miR-92-1, miR-188, miR-154, miR-217, miR-101, miR-141-prec, miR-153-prec, miR-196-2, miR-134, miR-141, miR-132, miR-192, or miR-181b-prec; miR-213, miR-220; ZAP70, AdipoR1; BCL3-MYC, MYC-BTG1, BCL7A-MYC, BRWD3-ARHGAP20 or BTG1-MYC B-cell lymphoma: miR-17-92 polycistron, miR-155, miR-210, or miR-21, miR-19a, miR-92, miR-142 miR-155, miR-221 miR-17-92, miR-21, miR-191, miR-205, U50; miR-17-92, miR-155, miR-210, or miR-21; A-myb, LMO2, JNK3, CD10, bcl-6, Cyclin D2, IRF4, Flip, or CD44; CITTA-BCL6, CLTC-ALK, IL21R-BCL6, PIM1-BCL6, TFCR-BCL6, IKZF1-BCL6 or SEC31A-ALK Burkitt's lymphoma: pri-miR-155; MYC, TERT, NS, NP, MAZ, RCF3, BYSL, IDE3, CDC7, TCL1A, AUTS2, MYBL1, BMP7, ITPR3, CDC2, BACK2, TTK, MME, ALOX5, or TOP1; BCL6, Kl-67; IGH-MYC, LCP1-BCL6

Endometrial cancer: miR-185, miR-106a, miR-181a, miR-210, miR-423, miR-103, miR-107, or let-7c; miR-71, miR-221, miR-193, miR-152, or miR-30c; NLRP7, AlphaV Beta6 integrin Uterine leiomyomas: let-7 family member, miR-21, miR-23b, miR-29b, or miR-197

Myelofibrosis: miR-190; miR-31, miR-150 and miR-95; miR-34a, miR-342, miR-326, miR-105, miR-149, miR-147

Pheochromocytoma: Catecholamines (epinephrine, norepinephrine, adrenaline)

Kidney disease/injury: ADBP-26, NHE3, KIM-1, glutamyltransferase, N-acetyl-beta-D-glucosaminidase, lysozyme, NGAL, L-FABP, bikunin, urea, prostaglandins, creatinine, alpha-1-microglobulin, retinol binding protein, glutathione-S-transferases, adiponectin, beta-2-macroglobuin, calbindin-D, cysteine-rich angiogenic inducer 61, endothelial/epithial growth factors, alpha-1-acid glycoprotein (orosomucoid), prealbumin, modified albumin, albumin, transferrin, alpha-1-lipoprotein, alpha-1-antitrypsin matrix metalloproteinases TABLE 4.2-continued Diagnostic markers (MMPs), alpha-1-fetoprotein, Tamm Horsfall protein, homoarginine, interleukin 18, monocyte chemotactic protein-1 (MCP-1), Lipocalin, VCAN, NRP1, CCL2, CCL19, COL3A1, GZMM, alpha-galactosidase, casein kinase 2, IP-10, Mig, I-TAC, MIP-1α, MIP-3α, and MIP-β, alpha-2-glycoprotein-Zinc, leucine-rich alpha-2-glycoprotein, uromodulin, Pacsin 2, hepcidin-20, hepcidin-25, AIF-2, urinary type-IV collagen, lipocalin-type prostaglandin D synthase (L-PGDS), urinary neutrophil gelatinase-associated lipocalin (uNGAL), Annexin A1, Rab23, Shh, Ihh, Dhh, PTCH1, PTCH2, SMO, Gli1, Gli2, Gli3, TLR4, cystatin C, AQPI, AQP2, AQP3, NKCC2, NaPill, DAHKSEVAHRFKD; [RNA:] SLC12A1, UMOD, VWF, MMPI, MMP3, SLC22A6, SLC22A 8, SLC22A 12, podocin, cubulin, LRP2, AQP9, and albumin, carcinoembryonic antigen (CEA), mucin, alpha-fetoprotein, tyrosinase, melanoma associated antigen, mutated tumor protein 53, p21, PUMA, prostate-specific antigen (PSA) or thyroglobulin, von Willebrand factor (VWF), thrombin, factor VIII, plasmin, fibrin, osteopontin (SPP1), Rab23, Shh, Ihh, Dhh, PTCH1, PTCH2, SMO, Gli1, Gli2, Gli3

Liver failure/disease: Lactoferrin, uric acid, cortisol, alpha-amylase, Carnitine; Cholic Acid; Chenodeoxycholic, Deoxycholic, Lithocholic, Glycocholic; Prostaglandin $E_2$; 13,14-dihydro-15-keto Prostaglandin A2; Prostaglandin B2; Prostaglandin F2a; 15-keto-Prostaglandin F2α; 6-keto-Prostaglandin F1α; Thromboxane B2; 11-dehydro-Thromboxane B2; Prostaglandin D2; Prostaglandin J2; 15-deoxy-Δ12,14-Prostaglandin J2; 11β-Prostaglandin F2α; 5(S)-Hydroxyeicosatetraenoic acid; 5(S)-Hydroxyeicosapentaenoic acid; Leukotriene B4; Leukotriene B5; Leukotriene C4; Leukotriene D4; Leukotriene E4; Leukotriene F4; 12(S)-Hydroxyeicosatetraenoic acid; 12(S)-Hydroxyeicosapentaenoic acid; 15(S)-Hydroxyeicosatetraenoic acid; 15(S)-Hydroxyeicosapentaenoic acid; Lipoxin A4; 8(S)-Hydroxyeicosatetraenoic acid; 9-Hydroxyeicosatetraenoic acid; 11-Hydroxyeicosatetraenoic acid; 8-iso-Prostaglandin F2α; 9-Hydroxyoctadecadienoic acid; 13-Hydroxyoctadecadienoic acid; 20(S)-Hydroxyeicosatetraenoic acid; 9,10-Epoxyoctadecenoic acid; 12,13-Epoxyoctadecenoic acid; 12,13-Dihydroxyoctadecenoic acid; 5,6-Epoxyeicosatrienoic acid; 11,12-Epoxyeicosatrienoic acid; 14,15-Epoxyeicosatrienoic acid; 5,6-Dihydroxyeicosatrienoic acid; 8,9-Dihydroxyeicosatrienoic acid; 11,12-Dihydroxyeicosatrienoic acid; 14,15-Dihydroxyeicosatrienoic acid; 14,15-Epoxyeicosatetraenoic acid; 17,18-Epoxyeicosatetraenoic acid; 14,15-Dihydroxyeicosatetraenoic acid; 17,18-Dihydroxyeicosatetraenoic acid; 19,20-Dihydroxydocosapentaenoic acid; diacetylspermine, hemopexin, TLR4

Stroke: MMP9, S100-P, S100A12, SI00A9, coag factor V, Arginasel, CA-IV, monocarboxylic acid transporter, ets-2, EIF2alpha, cytoskeleton associated protein 4, N-formylpeptide receptor, Ribonuclease2, N-acetylneuraminate pyruvate lyase, BCL-6, or Glycogen phosphorylase Heart failure/Cardiovascular health: 8-iso-prostaglandin F2α (8-iso-PGF2α), miR-195, miR-208, miR-214, let-7b, let-7c, let-7e, miR-15b, miR-23a, miR-24, miR-27a, miR-27b, miR-93, miR-99b, miR-100, miR-103, miR-125b, miR-140, miR-145, miR-181a, miR-191, miR-195, miR-199a, miR-320, miR-342, miR-451, or miR-499; miR-1, miR-10a, miR-17-5p, miR-19a, miR-19b, miR-20a, miR-20b, miR-26b, miR-28, miR-30e-5p, miR-101, miR-106a, miR-126, miR-222, miR-374, miR-422b, or miR-423; MRP14, CD69; CK-MB, cTnI (cardiac troponin), CRP, BPN, IL-6, MCSF, CD40, CD40L, SFRP-3, NT-proBNP, troponin T, SKITHRIHWESASLL, AHKSEVAHRFK, uroguanylin, BNP, miR-378, miR-497, miR-21, miR-99a, miR 29a, miR-30b, miR-29c, miR-331.3p, miR-19a, miR-22, miR-502.3, and miR-652; IL-16, sFas, Fas ligand, MCP-3, HGF, CTACK, EOTAXIN, adiponectin, IL-18, TIMP.4, TIMP.1, CRP, VEGF, and EGF, C-reactive protein (CRP); myoglobin (MYO), creatinine kinase myocardial band (CK-MB), cardiac troponins (cTn), and myeloperoxidase; TNF-α, and MMP-9; CD40

Vulnerable plaque: Amylase, L-6, MMP-9, PAPP-A, D-dimer, fibrinogen, Lp-PLA2, SCD40L, II-18, oxLDL, GPx-1, MCP-1, P1GF, or CRP High blood pressure: lysozyme Fibromyalgia: NR2D Neuropathic Pain: CCR2/4, CNP; ICAM-1, CGRP, TIMP-1, CLR-1, HSP-27, FABP, or apolipoprotein D; OX42, ED9

Tiredness/fatigue: PPGKPQGPPPQGGNQPQGPPPPPGKPQ (SEQ ID NO: //); GNPQGPSPQGGNKPQGPPPPPGKPQ (SEQ ID NO: //); SPPGKPQGPPQQEGNKPQGPPPPPGKPQ (SEQ ID NO: //); GGHPPPP (SEQ ID NO: //), ESPSLIA (SEQ ID NO: //); endorepellin; human herpesvirus 6, human herpesvirus 7, human cytomegalovirus, and Epstein-Barr virus (EBV)

Stress: Cortisol, chromogranin A, alpha-amylase, secretary IgA, lysozyme, dehydro-androsteronesulfate; 17-ketosteroidsulfate; dehydro-epiandrostronesulfate; corticosteroid, 17-hydroxycorticosteroid, growth hormone, oxytocin, aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide Malnutrition: sIgA TABLE 4.2-continued Diagnostic markers Nutritional status: Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor)

Energy balance (protein excretion)/energy status/metabolic state: AMPK, pre-albumin, retinol binding protein, urea, cholesterol, lipoproteins, insulin, insulin C peptide, IGF binding proteins, e.g. IGF-BPI, liver enzymes Diabetes: 11-8, CTSS, ITGB2, HLA-DRA, CD53, PLAG27, or MMP9; RBP4; 8-iso-prostaglandin F2α (8-iso-PGF2α), 11-dehydro-thromboxane $B_2$ (TXM), C-peptide, Advanced glycosylation end products (AGEs), 1,5-anhydroglucitol, NGPTL3 and 4, autoantibodies (Zn transporter 8, glutamic acid decarboxylase (GAD)), ATP-binding cassette, sub-family C (CFTR/MRP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth

TABLE 4.2-continued

Diagnostic markers factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta- melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin;
interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline
Metabolic syndrome/prediabetes: GFAP autoantibodies
Alcohol abuse/dependence: aminotransferases, gamma-glutamyltransferase, ethanol, ethyl glucuronide, sialic acid, β-hexosaminidase A, oral peroxidase, methanol, diethylene/ethylene glycol, α-amylase, clusterin, haptoglobin, heavy/light chains of immunoglobulins and transferrin; α-fucosidase (FUC), α-mannosidase (MAN), β-galactosidase (GAL), and β-glucuronidase (GLU)
Non-alcoholic fatty liver disease: cytokeratin CK-18 (M65 antigen), caspase-cleaved CK-18 (M30-antigen), resistin, adiponectin, visfatin, insulin, tumor necrosis factor-alpha (TNF-α), interleukin 6 (IL-6), or interleukin 8 (IL-8), aspartate aminotransferase (AST) and alanine aminotransferase (ALT); gamma-glutamyltransferase (GGT), immunoglobulin A, carbohydrate-deficient transferrin (CDT), glutamic oxaloacetic transaminase (GOT), glutamic pyruvic transaminase (GPT), bilirubin
Cystic fibrosis: amylase, cathepsin-D, lactate dehydrogenase
Ectodermal dysplasia: alpha-amylase
Sarcoidosis: IL-6, TNF-α, IFN-α, IL-17, IP-10, MIG, HGF, VEGF, TNF-RII, G-CSF, IFN-γ, MCP-1, RANTES and IL-5

TABLE 4.2-continued

Diagnostic markers

Asthma: eotaxin-1/CCL11, RANTES/CCL5, and IL-5; IL-1β, IL-6, MCP-1/CCL2, and IL-8/CXCL8; IP-10/CXCL10
Periodontitis/dental caries: aspartate aminotransferase (AST) and alkaline phosphatase (ALP), uric acid and albumin; 12-HETE; MMP-8, TIMP-1, and ICTP
Muscle damage: Myoglobin, creatine kinase (CK), lactate dehydrogenase (LDH), aldolase, troponin, carbonic anhydrase type 3 and fatty acid-binding protein (FABP), transaminases
Infection (Mycobacterium tuberculosis): IL-32, NXNL1, PSMA7, C6orf61, EMP1, CLIC1, LACTB and DUSP3, LOC389541, MIDI IP 1, KLRC3, KLF9, FBXQ32, C50RF29, CHUK , LOC652062, C6ORF60, MTMR I I, sCD170; IFN-gamma; IL-Iβ, IL-6, IL-8, IL-10, IL-12p70, sCD4, SCD25, SCD26, sCD32b/c, SCD50, SCD56, sCD66a, SCD83, sCD85j, SCD95, SCD106, sCD120b, sCD121b, SCD127, SCD154, SCD222, SCD226, sCDw329 and TNF alpha; VEGF, AAT, CRP, IL-IRA, TIMP-1, IL- 18, A2Macro, Haptoglobin ICAM-1, VCAM- 1, SCF, IL-17, Fibrinogen, beta-2-macroglobulin, TNF-alpha, C3 and TNFR2, GPR117, TAZ, HSDL I, HIP 1 (host)
Infection (*Helicobacter pylori*): MUC-5B and MUC 7
Infection (*Candida* species): Hsp70, calprotectin, histatins, mucins, basic proline rich proteins and peroxidases (host);
Infection (influenza): Hemagglutinin (H1), neuraminidase (N1); C-reactive protein, [RNA:] DNA cross-link repair 1A, PSO2 homolog, synaptonemal complex protein 3, v-maf musculoaponeurotic fibrosarcoma oncogene family, chitinase 3-like 3, matrix metalloproteinase 12, ATP-binding cassette, sub-family E (OABP), member 1, ATP-binding cassette, sub-family F (GCN20), member 1, feminization 1 homolog a (*C. elegans*), general transcription factor II H. polypeptide 2, forkhead box P1, zinc finger protein 282, arginyl-tRNA synthetase-like, Mitochondrial ribosomal protein L48, ribosomal protein S4, X-linked, eukaryotic translation elongation factor 1 alpha 1, proteaseome (prosome, macropain) 28 subunit 3, GLE1 RNA export mediator-like (yeast), small nuclear ribonucleoprotein polypeptide A', cleavage and polyadenylation specific factor 2, ribosomal protein L27a, , thioredoxin domain containing 4 (endoplasmic reticulum), flap structure specific endonuclease 1, ADP-ribosylation factor-like 6 interacting protein 2, cytidine 5'-triphosphate synthase 2, glutathione S-transferase, mu 5, phospholipase D1, aspartate-beta-hydroxylase, leukotriene A4 hydrolase, cytochrome P450 family 17, subfamily a, polypeptide 1, thioredoxin interacting protein, carbonyl reductase 2, alpha globin regulatory element containing gene, male-specific lethal-2 homolog (Drosophila), RAB1, member RAS oncogene family, protein tyrosine phosphatase, non-receptor type 21, potassium voltage-gated channel, Isk-related subfamily, gene 3, Bcl2-associated athanogene 3, lymphocyte cytosolic protein 2, pore forming protein-like, tumor necrosis factor receptor superfamily, member 19, filamin beta, microtubule-actin crosslinking factor 1, keratin complex 1, acidic, gene 18, keratin complex 1, acidic, gene 19, mesoderm development candiate 2, tubulin, alpha 4, , glutathione peroxidase 1, integrin linked kinase, guanine nucleotide binding protein, alpha inhibiting 2, cyclin L2, tubulin, alpha 2, DEAD (Asp-Glu-Ala-Asp) box polypeptide 5, programmed cell death 4, proteasome (prosome, macropain) 26S subunit, non-ATPase 8, signal sequence receptor, beta, RAD23b homolog (host)*****
Infection (HIV-1): p24, gp41, gp120
Infection (Hepatitis B virus): Core, Envelope, Surface (Ay)
Infection (Hepatitis C virus): Core, NS3, NS4, NS5
Infection (Hepatitis E virus): orf2 3 KD, orf2 6 KD, orf3 3 KD
Infection (*Vibrio cholerae*): Cholera Toxin
Infection (*Corynebacterium diphtheria*): Diphtheria toxin
Infection (Epstein-Barr virus): EA, VCA, NA
Infection (Herpes simplex virus HSV-1): gD
Infection (Herpes simplex virus HSV-2): gG
Infection (*Clostridium tetani*): Tetanus toxin
Infection (*Treponema pallidum*): 15 kd, p47
Infection (*Entamoeba histolytica*): M17
Infection (*Toxoplasma gondii*): a2-HS glycoprotein and apB glycoprotein (host); TGME49 052280, TGME49_021500, TGME49J) 19630, TGME49_061720 and TGME49_076220
Infection (Dengue virus): IL-10, fibrinogen, C4A, immunoglobulin, tropomyosin, albumin, SCSb-9 complement complex (host); NS-1
Infection (*Streptococcus pneumonia*): stratifin, cullin 1, selenoprotein K, metal response element binding transcription factor 2, prostaglandin E synthase 2, HLA-B associated transcript 4, zinc finger protein (C2H2 type) 276, GCIP-interacting protein p29, mitochondrial ribosomal protein L20, aryl hydrocarbon receptor nuclear translocator-like, secretory carrier membrane protein 1, nuclear receptor subfamily 5, group A, member 2, NIMA (never in mitosis gene a)-related expressed, kinase 7, ribosomal protein L28, ribosomal protein S25, lysosomal-associated protein transmembrane 5, neural precursor cell expressed, developmentally, down-regulted gene 4, alpha glucosidase 2, alpha neutral subunit, coatomer protein complex, subunit beta 2 (beta prime), ribosomal protein L3, NADH dehydrogenase (ubiquinone) 1 alpha, subcomplex, assembly factor 1, isoprenylcysteine carboxyl methyltransferase, , cytoplasmic polyadenylation element binding protein 3, mannoside acetylglucosaminyltransferase 1, RNA-binding region (RNP1, RRM) containing 1, , folate receptor 4 (delta), ATPase, H+ transporting, lysosomal 50/57 kDa, V1, subunit H, zinc finger, DHHC domain containing 6, phosphoribosyl pyrophosphate synthetase-associated, protein 2, choline/ethanolaminephosphotransferase 1, , solute carrier family 38, member 1, ATP synthase, H+ transporting, mitochondrial F0, complex, subunit f, isoform 2, glucose

TABLE 4.2-continued

Diagnostic markers phosphate isomerase 1, 2'-5' oligoadenylate synthetase 1A, tyrosine hydroxylase, hemoglobin alpha, adult chain 1, selenoprotein P, plasma, 1, acetyl-Coenzyme A dehydrogenase, long-chain, mannosidase, beta A, lysosomal, , deltex 3 homolog (Drosophila), ras homolog gene family, member AB, estrogen receptor 1 (alpha), phosphoglycerate kinase 1, , keratin complex 2, basic, gene 8, emerin, nucleoporin 153, formin 2, prothymosin alpha, synapsin I, ,cullin 4B, regulator of chromosome condensation (RCC1) and, BTB (POZ) domain containing protein 1, , immediate early response 5, SAM domain and HD domain, 1, tumor rejection antigen gp96, lymphocyte antigen 6 complex, locus E, , DAZ associated protein 2, general transcription factor II I, RNA polymerase II transcriptional coactivator, SWI/SNF-related, matrix-associated actin-dependent, regulator of chromatin, subfamily a, containing DEAD/H, box 1, structure specific recognition protein 1, ankyrin repeat and FYVE domain containing 1, SET translocation, myocyte enhancer factor 2A, homeo box D9, H2A histone family, member Z, cellular nucleic acid binding protein, , golgi reassembly stacking protein 2, cathepsin L, eukaryotic translation initiation factor 5, ubiquitin specific protease 9, X chromosome, proteasome (prosome, macropain) subunit, alpha type 7, pescadillo homolog 1, containing BRCT domain, (zebrafish), heterogeneous nuclear ribonucleoprotein K, DEAD (Asp-Glu-Ala-Asp) box polypeptide 52, sorting nexin 5, cathepsin B, DnaJ (Hsp40) homolog, subfamily B, member 9, ribosomal protein S3a, , cytoplasmic polyadenylation element binding protein 3, 5'-3' exoribonuclease 2, small nuclear ribonucleoprotein polypeptide F, , arachidonate 5-lipoxygenase activating protein, cytochrome c oxidase, subunit VIc, RIKubiquinol cytochrome c reductase core protein 2, lactate dehydrogenase 2, B chain, ubiquinol-cytochrome c reductase core protein 1, ATP synthase, H+ transporting, mitochondrial F0, complex, subunit b, isoform 1, microsomal glutathione S-transferase 1, ras homolog gene family, member A, RAB7, member RAS oncogene family, EGF-like module containing, mucin-like, hormone, receptor-like sequence 1, annexin A6, mitogen activated protein kinase 3, tyrosine kinase, non-receptor, 2, villin 2, tubulin, beta 5, catenin src (host); Pneumolysin, pneumococcal histidine triad D (PhtD), pneumococcal histidine triad E (PhtE), LytB, and pneumococcal choline-binding protein A (PcpA)
Infection (*Mycoplasma pneumonia*): Dnak, L7/L12, P1, exotoxin
Infection (*Campylobacter jejuni*): gyrA, 16S rDNA, or flaA/flaB
Infection (*Bacillus anthracis*): Lethal factor, HtrA (BA3660), NlpC/P60-domain endopeptidase (BA1952), BA0796 locus (BA0796), SAP
Infection (West Nile virus):
Infection (Human papilloma virus): E6, E7
Infection: RNase 7 (host)

In some embodiments, the devices, systems and methods of the invention can be used to inform a subject from whom a sample is derived about a health condition. Health conditions that may be diagnosed or measured by the present methods, devices and systems include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. Table 4.3 provides exemplary diagnostic markers that can be detected using the present invention, and their associated health conditions.

TABLE 4.3

Diagnostic markers

| Health Condition | Sample Source | Marker(s) |
| --- | --- | --- |
| Diabetes | Saliva | pIgR, Arp 3, CA VI, and IL-1Ra; PLS-2, LEI, and IGJ chain, resistin |
| Diabetes | Miscellaneous | ATP-binding cassette, sub-family C (CFTR/MRP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; |

TABLE 4.3-continued

Diagnostic markers

| Health Condition | Sample Source | Marker(s) |
|---|---|---|
| | | apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; f orkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; |

TABLE 4.3-continued

Diagnostic markers

| Health Condition | Sample Source | Marker(s) |
|---|---|---|
| | | glucagonlike peptide 1 receptor; guanine nucleotide binding protein (G protein), beta polypeptide 3; glutamicpyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor corepressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulindependent Diabetes Mellitus (common, type 2) 2; Noninsulindependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, Gprotein coupled, 10; purinergic receptor P2Y, Gprotein coupled, 12; purinergic receptor P2Y, Gprotein coupled, 2; progestagen-associated endometrial; protein (placental protein 14, pregnancy-associated endometrial alpha-2- |

TABLE 4.3-continued

Diagnostic markers

| Health Condition | Sample Source | Marker(s) |
|---|---|---|
| | | globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatinlike phospholipase domain containing 2; proopiomelanocortin (adrenocorticotropin/betalipotropin/alpha-melanocyte stimulating hormone/beta-melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B☐(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandinendoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Rasrelated associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMGbox); transforming growth factor, beta 1 (Camurati-Engelmann disease); transglutaminase 2 (C polypeptide, protein-glutamine-gammaglutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); |

TABLE 4.3-continued

Diagnostic markers

| Health Condition | Sample Source | Marker(s) |
|---|---|---|
| | | upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |
| Metabolic syndrome/ prediabetes | Serum | GFAP autoantibodies |
| Kidney failure/disease | Saliva | Lactoferrin, uric acid, cortisol, alpha-amylase |
| Kidney failure/disease | Miscellaneous | ADBP-26, NHE3, KIM-1, glutamyltransferase, Nacetyl-beta-D-glucosaminidase, lysozyme, NGAL, L-FABP, bikunin, urea, prostaglandins, creatinine, alpha-1-microglobulin, retinol binding protein, glutathione-S-transferases, adiponectin, beta-2-macroglobuin, calbindin-D, cysteine-rich angiogenic inducer 61, endothelial/epithial growth factors, alpha-1-acid glycoprotein (orosomucoid), prealbumin, modified albumin, albumin, transferrin, alpha-1-lipoprotein, alpha-1-antitrypsin matrix metalloproteinases (MMPs), alpha-1-fetoprotein, Tamm Horsfall protein, homoarginine, interleukin 18, monocyte chemotactic protein-1 (MCP-1), Lipocalin, VCAN, NRP1, CCL2, CCL19, COL3A1, GZMM, alpha-galactosidase, casein kinase 2, IP-10, Mig, I-TAC, MIP-1α, MIP-3α, MIP-1β, alpha-2-glycoprotein-Zinc, leucine-rich alpha-2-glycoprotein, uromodulin, Pacsin 2, hepcidin-20, hepcidin-25, AIF-2, urinary type-IV collagen, lipocalin-type prostaglandin D synthase (L-PGDS), urinary neutrophil gelatinase-associated lipocalin (uNGAL), Annexin A1, Rab23, Shh, Ihh, Dhh, PTCH1, PTCH2, SMO, Gli1, Gli2, Gli3, TLR4, cystatin C, AQPI, AQP2, AQP3, NKCC2, NaPill, DAHKSEVAHRFKD RNA:] SLC12A1, UMOD, vWF, MMPI, MMP3, SLC22A6, SLC22A 8, SLC22A 12, podocin, cubulin, LRP2, AQP9, and albumin, carcinoembryonic antigen (CEA), mucin, alphafetoprotein, tyrosinase, melanoma associated antigen, mutated tumor protein 53, p21, PUMA, prostate-specific antigen (PSA) or thyroglobulin, von Willebrand factor (VWF), thrombin, factor VIII, plasmin, fibrin, osteopontin (SPP1), Rab23, Shh, Ihh, Dhh, PTCH1, PTCH2, SMO, Gli1, Gli2, Gli3 |

TABLE 4.3-continued

Diagnostic markers

| Health Condition | Sample Source | Marker(s) |
|---|---|---|
| Liver failure/disease | Miscellaneous | Carnitine; Cholic Acid; Chenodeoxycholic, Deoxycholic, Lithocholic, Glycocholic; Prostaglandin E2; 13,14-dihydro-15-keto Prostaglandin A2; Prostaglandin B2; Prostaglandin F2a; 15-keto-prostaglandin F2α; 6-keto-prostaglandin F1α, Thromboxane B2; Prostaglandin D2; Prostaglandin J2; 15-deoxy-Δ12,14-prostaglandin J2; 11β-prostaglandin F2α; 5(S)-Hydroxyeicosatetraenoic acid; 5(S)-Hydroxyeicosapentaenoic acid; Leukotriene B4; Leukotriene B5; Leukotriene C4; Leukotriene D4; Leukotriene E4; Leukotriene F4; 12(S)-Hydroxyeicosatetraenoic acid; 12(S)-Hydroxyeicosapentaenoic acid; 15(S)-Hydroxyeicosatetraenoic acid; 15(S)-Hydroxyeicosapentaenoic acid; Lipoxin A4; 8(S)-Hydroxyeicosatetraenoic acid; 9-Hydroxyeicosatetraenoic acid; 11-Hydroxyeicosatetraenoic acid; 8-iso-Prostaglandin F2α; 9-Hydroxyoctadecadienoic acid; 13-Hydroxyoctadecadienoic acid; 20(S)-Hydroxyeicosatetraenoic acid; 9,10-Epoxyoctadecenoic acid; 12,13-Epoxyoctadecenoic acid; 12,13-Dihydroxyoctadecenoic acid; 5,6-Epoxyeicosatrienoic acid; 11,12-Epoxyeicosatrienoic acid; 14,15-Epoxyeicosatrienoic acid; 5,6-Dihydroxyeicosatrienoic acid; 8,9-Dihydroxyeicosatrienoic acid; 11,12-Dihydroxyeicosatrienoic acid; 14,15-Dihydroxyeicosatrienoic acid; 14,15-Epoxyeicosatetraenoic acid; 17,18-Epoxyeicosatetraenoic acid; 14,15-Dihydroxyeicosatetraenoic acid; 17,18-Dihydroxyeicosatetraenoic acid; 19,20-Dihydroxydocosapentaenoic acid; diacetylspermine, hemopexin, TLR4 |
| Heart Failure | Miscellaneous | SFRP-3, NT-proBNP, troponin T, SKITHRIHWESASLL, AHKSEVAHRFK, uroguanylin, BNP |
| Cardiovascular health | Miscellaneous | miR-378, miR-497, miR-21, miR-15b, miR-99a, miR 29a, miR-24, miR-30b, miR-29c, miR-331.3p, miR-19a, miR-22, miR-126, let-7b, miR-502.3, and miR-652, IL-16, sFas, Fas ligand, MCP-3, HGF, CTACK, EOTAXIN, adiponectin, IL-18, TIMP.4, TIMP.1, CRP, VEGF, and EGF |
| Cardiovascular health | Saliva | C-reactive protein (CRP); myoglobin (MYO), creatinine kinase myocardial band (CK-MB), cardiac troponins (cTn), and myeloperoxidase; TNF-α, MMP-9; CD40 |
| High blood pressure | Saliva | lysozyme |
| Tiredness/fatigue | Urine | Endorepellin, human herpesvirus 6, human herpesvirus 7, human cytomegalovirus, and Epstein-Barr virus (EBV) |
| Tiredness/fatigue | Saliva | PPGKPQGPPPQGGNQPQGPPPPPGKPQ; GNPQGPSPQGGNKPQGPPPPPGKPQ; SPPGKPQGPPQQEGNKPQGPPPPGKPQ |
| Tiredness/fatigue | Miscellaneous | GGHPPPP, ESPSLIA |
| Malnutrition | Saliva | sIgA |
| Depressive disorder | Miscellaneous | Secretogranin, VGF |
| Alzheimer's disease | CSF, serum, saliva | β-amyloid(1-42), β-amyloid(1-40), tau, phosphortau-181 |
| Stress | Saliva | Cortisol, dehydro-androsteronesulfate; 17-ketosteroidsulfate; dehydro-epiandrostronesulfate; corticosteroid, 17-hydroxycorticosteroid, chromogranin A, alpha-amylase, secretary IgA, lysozyme, growth hormone, oxytocin |
| Stress | Miscellaneous | aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, |

TABLE 4.3-continued

Diagnostic markers

| Health Condition | Sample Source | Marker(s) |
|---|---|---|
| | | c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor ß, tumor suppressor p53, vasoactive intestinal peptide |
| Circadianrhythm | Saliva | melatonin |
| Bone turnover/ osteoporosis | Urine | Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b |
| Bone turnover/ osteoporosis | Saliva | deoxypyridinium (D-PYR) and osteocalcin (OC), hepatocyte growth factor and interleukin-1 beta |
| Muscle damage | Serum, urine | Myoglobin, creatine kinase (CK), lactate dehydrogenase (LDH), aldolase, troponin, carbonic anhydrase type 3 and fatty acid-binding protein (FABP), transaminases |
| Exercise/athletic activity | Sweat | Urea |
| Exercise/athletic activity | Serum | Myostatin, follistatin-like related gene |
| Exercise/athletic activity | Saliva | Testosterone |
| Performance enhancement | Miscellaneous | interleukin-6, interleukin-1 beta, G-CSF, interferongamma, interleukin-8, interleukin-9, MCP-1, MIPbeta, and/or TNF alpha |
| Energy balance (protein excretion)/ Energy status/ metabolic state | Serum | AMPK |
| Energy balance (protein excretion)/ Energy status/ metabolic state | Urine, sweat, feces | pre-albumin, retinol binding protein, urea |
| Energy balance (protein excretion)/ Energy status/ metabolic state | Miscellaneous | cholesterol, lipoproteins, insulin, insulin C peptide, IGF binding proteins, e.g. IGF-BPI, liver enzymes |
| Growth | Saliva | IGF-1 |
| Andropause | Saliva | testosterone; testosterone precursors such aspregnenolone, progesterone, 17-hydroxypregnenolone, 17-hydroxyprogesterone, dehydroepiandrosterone (DHEA) and delta-4-androstene-3,17-dione; testosterone and dihydrotestosterone metabolites such as the 17-ketosteroids androsterone and etiocholanolone, polar metabolites in the form of diols, triols, and conjugates, as well estradiol, estrogens, androsteindione, cortisol, DHEA, FSH (follicle stimulating hormone), LH (luteinizing hormone), and GnRH (gonadotropin-releasing hormone) |
| Menopause | Saliva | Follicle stimulating hormone (FSH) Estrogen and progesterone, testosterone, free testosterone, and dehydroepiandrosterone sulfate (DHEAS), cortisol and dehydroepiandrosterone (DHEA) |
| Pregnancy/fetal development | Saliva | Progesterone |
| Pregnancy/fetal development | Urine | human chorionic gonadotropin, Levonorgestrel, alpha-fetoprotein |
| Pregnancy/fetal development | Serum | Estradiol |
| Breast cancer | Urine | 47D10 antigen, PTCD2, SLC25A20, NFKB2, RASGRP2, PDE7A, MLL, PRKCE, GPATC3, PRIC285 and GSTA4, MIPEP, PLCB2, SLC25A19, DEF6, ZNF236, C18orf22, COX7A2, DDX11, TOP3A, C9orf6, UFC1, PFDN2, KLRD1, |

TABLE 4.3-continued

Diagnostic markers

| Health Condition | Sample Source | Marker(s) |
|---|---|---|
| | | LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, LOC284184, FLJ23235, GPATC3, CPSF4, CREM, HIST1H1D, HPS4, FN3KRP, ANKRD16, C8orf16, ATF71P2, PRIC285 |
| Prostate cancer | Serum, saliva Urine | Prostate specific antigen (PSA) PCA3, GOLPH2, SPINK1, TMPRSS2:ERG |
| Infections | | See Table 4.2 |
| Dental caries/ periodontal disease | Saliva | aspartate aminotransferase (AST) and alkaline phosphatase (ALP), uric acid and albumin; 12-HETE; MMP-8, TIMP-1, and ICTP |
| Heavy metal poisoning | Saliva | Lead, cadmium |
| Drugs/drug metabolites | Saliva | Marijuana, cocaine (crystalline tropane alkaloid), methamphetamine, amphetamine, heroin, methyltestosterone, mesterolone, morphine, cyclophosphamide metabolites, haloperidol, barbiturates; antipyrine, caffeine, cisplatin, cyclosporine, diazepam, digoxin, methadone, phenytoin, theophylline, tolbutamide. nicotine/cotinine, cannabis |
| Drugs/drug metabolites | Urine | trichloroethanol glucuronide, anabolic steroids, androstenedione, benzodiazepines, chlordiazepoxide, lorazepam, zidovudine |
| Allergies | Saliva | Allergen-specific IgAs |

In other embodiments, the diagnostic marker that can be detected by the present method is an antibody in a sample, e.g., a diagnostic sample, that is probative for diagnosing a disease or health condition of the subject from which the sample is derived. Table 4.4 provides a list of 5 autoantibody targets, which can be used, in whole or as an epitope fragment, as a capture agent in the present method to measure the amount of the epitope-binding antibody analyte in a sample and thereby diagnose the associated disease or health condition, e.g., an autoimmune disease. In some cases, the disease or health condition is related to an immune response to an allergen. Table 4.5 provides a list of allergens, which 10 can be used, in whole or as an epitope fragment, as a capture agent in the present method to measure the amount of the epitope-binding antibody analyte in a sample and thereby diagnose the associated disease or health condition, e.g., an allergy. In certain instances, the disease or health condition is related to an infectious disease, where the infectious agent may be diagnosed based on information including the measured amount of antibodies against one or more epitopes derived from the infectious agent (e.g., lipopolysaccharides, toxins, proteins, etc). Table 4.6 provides a list of infectious-agent derived epitopes which can be used, in whole or as an epitope fragment, as a capture agent in the present method to measure the amount of the epitope-binding antibody analyte in a sample and thereby diagnose the associated disease or health condition, e.g., an infection. Other epitopes or antigens that may be suitable for use in the present diagnostic method are described in, e.g., PCT App. Pub. No. WO 2013164476, which is incorporated herein by reference.

TABLE 4.4

Diagnostic autoantibody epitopes

| Disease/condition | Autoantibody Targets |
|---|---|
| Cancer | ACAA2; ANXA13; AQP2; ASPA; BCL2; BCL2L1; BIK; CD160; CD37; CDK4; CDK6; CHEK2; CITED2; CNN2; CTSC; CTSZ; CycE2; ELK1; FGF10; FN1; GATA3; GJA1; GNRH1; GRB2, HBB; HBE1; HIST2H2AA; HPRT1; ID2; IER2; IFI27; IFITM1; IFITM2; IL15; IL18; IL8; IL9; KRT16; LALBA; LDHA; LDHB; LECT1; MAFK; Mage3; MAGEA3; MMP2; NPPB; OAS1, p21; p53; PCNA; PENK; PEX3; PHB; PHYH; PI3; PKBa; PLN; S100A7; SCAMP1; SCGB1A1; SLC38A5; SNRP2; SNX9; SST; SSTR2; TACSTD1; TNNC2; TOB1; TSG101; VDRIP; WNT2, p62 and Koc; ZFP161, Ubiquilin-1, HOX-B6, YB-1, Osteonectin, ILF3 |
| Squamous cell lung carcinoma | protein kinase C and p53-binding protein (TP53 BP), lymphoid blast crisis oncogene (LBC), |
| Small cell lung cancer | SOX families B1 and B2, MUC-1, |
| Lung cancer | MUC-1, p53, surviving, LAMR1, annexin I, 14-3-3-theta; AKR1B10; GOT2; HNRPR; PDIA3; NME2; RTN4; HI1FX; G3BP; HSPCA; ACTN4; PGP9.5; |
| Colorectal cancer | MUC-1, surviving, p-53; translationally controlled tumor protein; HSPC218; Ribosomal protein S18; v-Fte-1; v-Fos transformation effector protein; MAGEA3, SSX2, NY-ESO-1, HDAC5, MBD2, TRIP4, NY-CO-45, KNSL6, HIP1R, Seb4D, KIAA1416, and LMNA; UCHL3 |

TABLE 4.4-continued

Diagnostic autoantibody epitopes

| Disease/condition | Autoantibody Targets |
|---|---|
| Hepatocellular carcinoma | fibrillarin and p330d/CENP-F, insulin-like growth factor II mRNA-binding proteins (IMP) 1, IMP3 and p53, NOR-90, nucleophosmin/protein B23, cyclin B1, DNA topoisomerase II (topo II), p62, HCC1, SG2NA, MAGE-C2, AF146731; AF219119; AF146019; Ligatin; AF220416; AF218421; AF257175; AF244135; AF243495; AF287265; AF258340; AF270491; AF286340; small nuclear RNA-associated sm-like protein; Dna J protein; CENP-F; translationally controlled tumor protein; LDH-A; Albumin; Hsp89αΔN; SEC63; AF100141; 14,5 kDa protein; GCF2; Metallopanstimulin 1; SMP-30 D31815; Cg1 protein,; C3VS protein; F1-ATPase, β subunit; Human ribosomal protein L10; Pre-apolipoprotein CIII; Galactose-1-phosphate-uridyl- transferase (GALT); DNA polymerase Δ, small subunit; Mitochondrial DNA |
| Renal cancer | AF257175; small nuclear RNA-associated sm-like protein; Dna J protein; smooth muscle protein 22-alpha (SM22-alpha); carbonic anhydrase I (CAI) |
| Acute leukemia | Rho GDP dissociation inhibitor 2, γ-actin, F-actin capping protein (CAPZA1), heterogeneous nuclear ribonucleoprotein L (hnRNP L), tubulin-α 6, PCNA |
| Chronic lymphocytic leukemia | KIAA1641; PIPMT; FosB; ZNF268; SEBD4; Ikaros; p75/LDEGF; CHIP; PYGB; ZNF148; KIAA0336; RPL11; FMNL; HGRG8 |
| non-Hodgkin's lymphoma | CENP-F, |
| Multiple myeloma | NY-ESO-1 |
| melanoma | NY-ESO-1, MAGE-1, BAGE, GAGE, MART-1/melan A, gp100, and tyrosinase |
| Pancreatic cancer | Calreticulin, DEAD-box protein 48 (DDX48) |
| Ovarian cancer | ACSBG1 , AFP, CSNK1A1 L, DHFR, MBNL1 , TP53, PRL, PSMC1, PTGFR, PTPRA, RAB7L1 , and SCYL3, her2/neu, MUC1, c-myc, ECPKA, and NY-ESO-1, p53, UBQLN1, HOXB6, TOP2A, putative helicase-RUVBL (RUVBL), HMBA-inducible (HEXIM1), DDX5 and HDCMA |
| Prostate cancer | BcI2, NY-ESO-1, survival protein lens epithelium-derived growth factor p75 (LEDGF/p75), PRDX6/AOP2, clusterin, DJ-1, superoxide dismutase, alcohol dehydrogenase, HSP70, HSP27/HSPB1, lactoylglutathione lyase, glucose-regulated protein-78 kDa (GRP78), p62, Koc, and IMP1, α-Methylacyl-coenzyme A racemase and 5-α-reductase, AKRIA1; Brd2; C17orf25; CAPZA1; c-MYC; Cyclin A; Cyclin B1; Cyclin D1; Drebrin; eIF4G1; HIP1; HSPA8; Lactoylglutathione lyase; MAD-CT-1; MAD-CT-2; No55; P53; P62; P90; PP4R; PIP; PSA; RPL13a; RPL22; Survivin; Syntenin 1; TDP-43; VCP; vWF; Lage-1, and Xage-1; bromo domain-containing protein 2 (BRD2), ribosomal proteins L22 and L13a, XP_373908 |
| Breast cancer | p53, c-myc, NY-ESO-1, BRCA1, BRCA2, HER2, MUC1, IGFBP-2, TOPO2α, ribosomal protein S6, eukaryotic elongation factor 2, eukaryotic elongation factor 2 kinase, and heat shock protein 90 (HSP90), Ku protein, topoisomerase I, and the 32-kDa subunit of replication protein A; CENP-F; AF146731; int-2, pentraxin I, integrin beta5, cathepsin L2 and S3 ribosomal protein; RNA-binding protein regulatory subunit (RS), DJ-1 oncogene, glucose-6-phosphate dehydrogenase, heat shock 70-kDa protein 1 (HS71), and dihydrolipoamide dehydrogenase |
| Nasopharyngeal carcinoma | MAGE, HSP70, Fibronectin, CD44, EBV antigens |
| Oral cancer | Cyclin B1, p53 |
| Oral squamous cell carcinoma | p53 |
| Head and neck squamous cell carcinoma | CASP-8, SART-1, TREX1, 3' repair exonuclease; BRAP (BRCA1 associated): Nuclear localization protein; Trim 26 zinc finger domains; GTF21 transcription factor. Murine homolog TF11-1; NSEP1 (YB-1) transcription factor; MAZ transcription factor associated with c-myc; SON (DBP-5; KIAA1019; NREBP DNA binding protein); NACA nascent polypeptide-associated complex; NUBP2 nucleotide binding protein; EEF2 Translation elongation factor 2; GU2 Putative RNA helicase; RPLI3A ribosomal protein; SFRS21P (CASP11; SIP1; SRRP1290 splicing factor); RPS12 ribosomal protein; MGC2835 RNA helicase; TMF1, TATA modulatory factor; PRC1 regulator of cytokinesis; KRT14 keratin 14; Viniculin; H2AFY histone family member; SLK (KIAA02304) Ste related kinase; NOL3 (ARC) nuclear protein 3, apoptosis repressor; DNAJA2 member of Hsp40 family; DNAJA1 member of HSP40 family; LINE-1 retrotransposon; MOG (HSPC 165) Homolog of yeast protein; LIMS1 (PINCH): LIM and senescent antigen-like domain; COPB2 coatomer protein complex subunit protein; FLJ22548 hypothetical protein; C21orf97; FLJ21324; MGC15873; SSNA1 Sjogrens syndrome nuclear autoantigen 1; KIAA0530, zinc finger domain; rat stannin; hypothetical protein DKFZp4340032; human FLJ23089; PC326 |
| Esophageal cancer | NY-ESO-1; SURF1, HOOK2, CENP-F, ZIC2, hCLA-iso, Ki-1/57, enigma, HCA25a, SPK, LOC146223 and AGENCOURT_7565913 |
| Metabolic syndrome/ prediabetes | GFAP |
| Diabetes | Zn transporter 8, glutamic acid decarboxylase (GAD), CD38, gad65, IA2, insulin, MRPS31, ICA1, L-type voltage gated calcium channel; SNRPB2; DDX42; C11orf63; TCOF1; TSSK2; KDM4B; PDGFB; LTK; RPL14; VIM; |

TABLE 4.4-continued

Diagnostic autoantibody epitopes

| Disease/condition | Autoantibody Targets |
|---|---|
| | GTF21; BCL2L13; LARP6; DKFZP434K028; USP39; SERBP1; CCL19; GAD2; MCM10; ZNF688; PTEN; RP6-166C19.11; GIPC1; TIGD1; CCDC131; HTF9C; SOX5; MCF2L; TRAF3IP1; 6CKINE; ACY3; AMMECR1L; ARHGAP9; ASNS; BATF2; BMX; C9ORF25; CDC2; CHGB; CXORF38; CXORF56; DMD; ECHDC1; EIF3F; EPHA2; ERMN; FAM136A; (includes; EG: 84908); FILIP1; FLT1; GART; GIMAP6; GNG7; GTF2F1; HGS; IFI6; KDM4B; LACE1; LGALS1; LGALS7; LIMS2; LTK; LUC7L; NCAPG; (includes; EG: 64151); NME6; NUPL1; PAK4; PDE4DIP; PSIP1; RAB20; RNGTT; RPS3; SPG20; TALDO1; TBRG1; THAP1; TRAF3IP2; UBL4A; ZC3HC1; ZNF131; RAD51AP1; HADH; (HADH); C11orf16; (C11orf16); TAC3; ABR; ECE1; PPP1R2; GRINL1A; ABR; C19orf44; MUSTN1; ETHE1; BMI1; BAZ2B; ; TBC1D22A; CAMK2N2; ASS1; CCNY; MARK2; RAD51AP1; RAB38; RIOK1; HSP90AA1; C11orf74; ARID3A; LMOD1; CAPRIN1; ITGB3BP; MND1; SGK; NADK; MED9; LDHA; ARHGAP26; ANKRA2; CRY2; IL23A; DUSP14; ZBTB44; SIRT1; SLC2A3; GPR172B; CCDC89; BATF; HMOX1; ARRDC1; USF2; GBGT1; EDC3; SGIP1; GCGR; ZRANB2; NLGN4Y; GJB6; CDK10; PSG1; CCDC74A; DENND1C; MAP2K6 |
| Autoimmune heart disease | cardiac troponin I (cTnI) |
| Immunoglobulin A nephropathy | PRKD1, MATN2, DDX17, UBE2W, CDKN1 B, SOD2, FLOT2, IQCK, BLZF1, BRD9, CDS2, EFNA3, EIF4A2, FLU, LIMCH1, MAGEA4, MEF2D, MLLT6, MRPL28, MUTED, NKAIN4, PCTK1, PLXNA1, PODN, POLH, PRKD2, RNF113A, SEPT5, TNS1, TOM1, TRPV4, USP12, ZMYM3, CIAPIN1, GDI2, HSPA8, SERPINA5 and TGM1 |
| End stage renal disease | IGLC1; IGHG1; EDC3; IGHG1; APEX2; CD3D; TRIM21; IGKV1-5; IGHG3; CTLA-FC; CD7; CLIP4; MAPRE1; SNRPB2; IGHG1; ZBTB44; CD3D; IGHG1; TRAM1; ERR beta-; LBD; CNBP; OLFM1; IGHM; SIRT5; CEP290; PHLDA1 |
| Glomerular nephritis | |
| Addison's disease | 21-hydroxylase, P450-17a-hydroxylase (17OH) and P450-side chain cleavage (SCC) |
| Primary ovarian insufficiency | Jo-1, proteinase 3 (PR3) |
| Sjögren's syndrome | IgA, IgG, IgM autoantibodies; IgA, lactoferrin and beta2-microglobulin; lysozyme C, and cystatin C, amylase and carbonic anhydrase SSA/Ro; LA/SS-B |
| Systemic lupus erythematosus (SLE) | CDC25B, APOBEC3G, ARAF, BCL2A1, CLK1, CREB1, CSNK1G1, CSNK2A1, CWC27, DLX4, DPPA2, EFHD2, EGR2, ERCC2, EWSR1, EZH2, FES, FOS, FTHL17, GEM, GNA15, GNG4, HMGB2, HNRNPUL1, HOXB6, ID2, IFI35, IGF2BP3, IGHG1, JUNB, KLF6, LGALS7, LIN28A, MLLT3, NFIL3, NRBF2, PABPC1, PATZ1, PCGF2, PPP2CB, PPP3CC, PRM1, PTK2, PTPN4, PYGB, RET, RPL18A, RPS7, RRAS, SCEL, SH2B1, SMAD2, STAM, TAF9, TIE1, UBA3, VAV1, WT1, ZAP70, or ZNRD1 KIT, C6orf93, RPL34, DOM3Z, COPG2, DNCL12, RRP41; FBXO9; RALBP1, PIAS2; EEF1D; CONI; KATNB1; POLR2E; CCT3; KIAA0643; RPL37A, GTF2H2; MAP2K5; CDK3; RPS6KA1; MARK4; MTO1; MGC42105; NFE2L2; WDR45L, STK4, PFKFB3; NTRK3; MLF1; TRIM37, ACTL7B, RPL18A, CKS1B; TUBA1, NME6, SUCLA2, IGHG1, PRKCBP1; BAG3; TCEB3; RPL15, SSX4; MAP2K7; EEF1G; RNF38, PHLDA2, KCMF1; NUBP2, VPS45A SSA/Ro; dsDNA; Smith; histones; thrombin; v-Fos transformation effector protein, tryptase, Sm antigen, beta 2; cardiolipin; glycoprotein I β2; Endothelial PC/activated PC receptor; human gamma enolase |
| CREST syndrome | centromere |
| Systemic sclerosis | Type I topoisomerase |
| Primary biliary cirrhosis | nucleoporin 62, Sp100 nuclear antigen, nucleoporin 210 kDa, mitochondria, mitochondrial pyruvate dehydrogenase (PDH) or E3 binding protein |
| Dermatitis herpetiformis | eTG |
| Miller-Fisher Syndrome | ganglioside GQ1B |
| Wegener's granulomatosis | c-ANCA |
| Neuropathies microscopic polyangiitis | ganglioside GD3, ganglioside GM1, GA1, GM2, MAG p-ANCA |
| Polymyositis | Signal recognition particles |
| scleromyositis | exosome complex Signal recognition particles |
| myasthenia gravis | nicotinic acetylcholine receptor Signal recognition particles, muscle-specific kinase (MUSK) Signal recognition particles |
| Lambert-Eaton myasthenic syndrome | voltage-gated calcium channel (P/Q-type) |
| Hashimoto's thyroiditis | thyroid peroxidase |
| Graves' disease | TSH receptor |
| paraneoplastic cerebellar syndrome | Hu, Yo (cerebellar Purkinje Cells), amphiphysin |
| encephalitis | voltage-gated potassium channel (VGKC), N-methyl-D-aspartate receptor (NMDA) |

TABLE 4.4-continued

Diagnostic autoantibody epitopes

| Disease/condition | Autoantibody Targets |
| --- | --- |
| Sydenham's chorea | basal ganglia neurons |
| antiphospholipid syndrome | glycoprotein 1 (2GPI), Endothelial PC/activated PC receptor |
| Systemic vasculitis | proteinase 3 (PR3) and myeloperoxidase (MPO) |
| Neuromyelitis | aquaporin-4 |
| Allergies | Allergen-specific IgAs |
| Rheumatoid arthritis | Rheumatoid factor, cyclic citrullinated protein; human cartilage gp39 peptides and type II collagen; citrullinated fibrinogen, citrullinated vimentin, citrulline-substituted filaggrin peptides, hnRNP-A2/B1, BiP, tryptase |
| Asthma | tryptase |
| Multiple sclerosis | myelin basic protein, spectrin, fodrin, myelin oligodentrocyte glycoprotein, proteolipid protein (PLP), 2',3'-cyclic nucleotide-phosphodiesterase (CNP), Glc($\alpha$1,4)Glc($\alpha$) (GAGA4), Glc($\alpha$1,6)Glc($\alpha$) (GAGA6) |
| amyotrophic lateral sclerosis (ALS) | HMGB1 |
| Idiopathic thrombo-cytopenia purpura | platelet glycoprotein (GP) IIb/IIIa, GPIb/IX, GPIa/IIa |
| Thrombosis | thrombomodulin |
| Cardiovascular disease | Endothelial PC/activated PC receptor; IL-1 alpha, alpha-actinin-2 (aActn2); alpha-Myosin Heavy Chain (alpha-MHC-S1); SI fragment of alpha-Myosin Heavy Chain 6 (alpha-MHC6-SI); alpha-Myosin Heavy Chain 7 (MyHC7) |
| post-streptococcal disease such as PANDAS, post-GABHS glomerulonephritis, rheumatic fever, autism and Syndenham's chorea | ELAVL2, ELAVL3, ELAVL4, Nova-1, Nova-2, Cdr1, Cdr2; and Cdr3 |
| Parkinson's Disease | alpha-synuclein; myelin basic protein (MBP), proteolipid protein (PLP), myelin oligodendrocyte glycoprotein (MOG), myelin associated glycoprotein (MAG), oligodendrocytes specific protein (OSP) |
| pernicious anemia | Vitamin B$_{12}$ |

TABLE 45

Allergen epitopes

| Source | Allergen |
| --- | --- |
| mites | Acas13, Blot1, Blot3, Blot4, Blot5, Blot6, Blot10, Blot11, Blot12, Blot13, Blot19; American house dust mite (Derf1, Derf2, Derf3, Derf7, Derf10, Derf11, Derf14, Derf15, Derf16, Derf17, Derf18w); house dust mite (Derm1); European house dust mite (Derp1, Derp2, Derp3, Derp4, Derp5, Derp6, Derp7, Derp8, Derp9, Derp10, Derp11, Derp14, Derp20, Derp21); mite (Eurm2; Eurm14); storage mite (Glyd2, Lepd2, Lepd5, Lepd7, Lepd10, Lepd13, Tyrp2, Tyrp13); *Dermatophagoides farinae* (Derf1.0101, Derf1.0102, Derf1.0103, Derf1.0104, Derf1.0105, Derf2.0101, Derf2.0102, Derf2.0103, Derf2.0104, Derf2.0105, Derf2.0106, Derf2.0107, Derf2.0108, Derf2.0109, Derf2.0110, Derf2.0111, Derf2.0112, Derf2.0113, Derf2.0114, Derf2.0115, Derf2.0116, Derf2.0117); *Dermatophagoides pteronyssinus* (Derp1.0101, Derp1.0102, Derp1.0103, Derp1.0104, Derp1.0105, Derp1.0106, Derp1.0107, Derp1.0108, Derp1.0109, Derp1.0110, Derp1.0111, Derp1.0112, Derp1.0113, Derp1.0114, Derp1.0115, Derp1.0116, Derp1.0117, Derp1.0118, Derp1.0119, Derp1.0120, Derp1.0121, Derp1.0122, Derp1.0123, Derp2.0101, Derp2.0102, Derp2.0103, Derp2.0104, Derp2.0105, Derp2.0106, Derp2.0107, Derp2.0108, Derp2.0109, Derp2.0110, Derp2.0111, Derp2.0112, Derp2.0113); *Euroglyphus maynei* (Eurm2.0101, Eurm2.0102); *Glycyphagus domesticus* (Glyd2.0101, Glyd2.0201); and *Lepidoglyphus destructor* (Lepd2.0101, Lepd2.0101, Lepd2.0101, Lepd2.0102, Lepd2.0201, Lepd2.0202) |
| Pollen | Short Ragweed (*Ambrosia artemisiifolia*) allergen, Amb a 1, Amba2, Amba3, Amba5, Amba6, Amba7, Amba8, Amba9, Amba10; *Betula verrucosa* allergen, Bet v 1, *Phleum pratense* allergen, Phl p 5), giant ragweed (Ambt5); mugwort (Artv1, Artv2, Artv3, Artv4, Artv5, Artv6); sunflower (Hela1, Hela2, Hela3); *Mercurialis annua* (Mera1); lamb's-quarters, pigweed (Chea1); white goosefoot (Chea2, Chea3); Russian-thistle (Salk1); Rosy periwinkle (Catr1); English plantain (Plal1); Japanese hop (Humj1); *Parietaria judaica* (Parj1, Parj2, Parj3); *Parietaria officinalis* (Paro1); *Ambrosia artemisiifolia* (Amba8.0101, Amba8.0102, Amba9.0101, Amba9.0102); *Plantago lanceolata* (Plal1.0101, Plal1.0102, Plal1.0103); and *Parietaria judaica* (Parj1.0101, Parj1.0102, Parj1.0201, Par2.0101, Parj2.0102, Parj3.0101, Parj3.0102), Bermuda grass (Cynd1, Cynd7, Cynd12, Cynd15, Cynd22w, Cynd23, Cynd24); orchard grass (Dacg1, Dacg2, Dacg3, Dacg5); meadow fescue (Fesp4w); velvet grass (Holl1); rye grass (Lolp1, Lolp2, Lolp3, Lolp5, Lolp11); canary grass (Phaa1); Timothy (Phlp1, Phlp2, Phlp4, Phlp5, Phlp6, Phlp11, Phlp12, Phlp13); Kentucky blue grass (Poap1, Poap5); Johnson grass (Sorh1); *Cynodon dactylon* (Cynd1.0101, Cynd1.0102, Cynd1.0103, Cynd1.0104, Cynd1.0105, Cynd1.0106, Cynd1.0107, Cynd1.0201, Cynd1.0202, Cynd1.0203, Cynd1.0204); *Holcus lanatus* (Holl1.0101, Holl1.0102); *Lolium perenne* (Lolp1.0101, Lolp1.0102, Lolp1.0103, Lolp5.0101, |

TABLE 45-continued

Allergen epitopes

| Source | Allergen |
|---|---|
| | Lolp5.0102); *Phleum pretense* (Phlp1.0101, Phlp1.0102, Phlp4.0101, Phlp4.0201, Phlp5.0101, Php5.0102, Phlp5.0103, Phlp5.0104, Phlp5.0105, Phlp5.0106, Phlp5.0107, Phlp5.0108, Phlp5.0201, Phlp5.0202); and *Secale cereale* (Secc20.0101, Secc20.0201), Alder (Alng1); Birch (Betv1, Betv2, Betv3, Betv4, Betv6, Betv7); hornbeam (Carb1); chestnut (Cass1, Cass5, Cass8); hazel (Cora1, Cora2, Cora8, Cora9, Cora10, Cora11); White oak (Quea1); Ash (Frae1); privet (Ligv1); olive (Olee1, Olee2, Olee3, Olee4, Olee5, Olee6, Olee7, Olee8, Olee9, Olee10); Lilac (Syrv1); Sugi (Cryj1, Cryj2); cypress (Cupa1); common cypress (Cups1, Cups3w); mountain cedar (Juna1, Juna2, Juna3); prickly juniper (Juno4); mountain cedar (Juns1); eastern red cedar (Junv1); London plane tree (Plaa1, Plaa2, Plaa3); date palm (Phod2); *Betula verrucosa* (Betv1.0101, Betv1.0102, Betv1.0103, Betv1.0201, Betv1.0301, Betv1.0401, Betv1.0402, Betv1.0501, Betv1.0601, Betv1.0602, Betv1.0701, Betv1.0801, Betv1.0901, Betv1.1001, Betv1.1101, Betv1.1201, Betv1.1301, Betv1.1401, Betv1.1402, Betv1.1501, Betv1.1502, Betv1.1601, Betv1.1701, Betv1.1801, Betv1.1901, Betv1.2001, Betv1.2101, Betv1.2201, Betv1.2301, Betv1.2401, Betv1.2501, Betv1.2601, Betv1.2701, Betv1.2801, Betv1.2901, Betv1.3001, Betv1.3101, Betv6.0101, Betv6.0102); *Carpinus betulus* (Carb1.0101, Carb1.0102, Carb1.0103, Carb1.0104, Carb1.0105, Carb1.0106, Carb1.0106, Carb1.0106, Carb1.0106, Carb1.0107, Carb1.0107, Carb1.0108, Carb1.0201, Carb1.0301, Carb1.0302); *Corylus avellana* (Cora1.0101, Cora1.0102, Cora1.0103, Cora1.0104, Cora1.0201, Cora1.0301, Cora1.0401, Cora1.0402, Cora1.0403, Cora1.0404); *Ligustrum vulgare* (Ligv1.0101, Ligv1.01.02); *Olea europea* (Olee1.0101, Olee1.0102, Olee1.0103, Olee1.0104, Olee1.0105, Olee1.0106, Olee1.0107); *Syringa vulgaris* (Syrv1.0101, Syrv1.0102, Syrv1.0103); *Cryptomeria japonica* (Cryj2.0101, Cryj2.0102); and *Cupressus sempervirens* (Cups1.0101, Cups1.0102, Cups1.0103, Cups1.0104, Cups1.0105) |
| mold | *Alternaria alternata* allergen, Alt a 1, Alta3, Alta4, Alta5, Alta6, Alta7, Alta8, Alta10, Alta12, Alta13, *Aspergillus fumigatus* allergen, Asp f 1, Aspf2, Aspf3, Aspf4, Aspf5, Aspf6, Aspf7, Aspf8, Aspf9, Aspf10, Aspf11, Aspf12, Aspf13, Aspf15, Aspf16, Aspf17, Aspf18, Aspf22w, Aspf23, Aspf27, Aspf28, Aspf29); *Aspergillus niger* (Aspn14, Aspn18, Aspn25); *Aspergillus oryzae* (Aspo13, Aspo21); *Penicillium brevicompactum* (Penb13, Penb26); *Penicillium chrysogenum* (Pench13, Pench18, Pench20); *Penicillium citrinum* (Penc3, Penc13, Penc19, Penc22w, Penc24); *Penicillium oxalicum* (Peno18); *Fusarium culmorum* (Fusc1, Fusc2); *Trichophyton rubrum* (Trir2, Trir4); *Trichophyton tonsurans* (Trit1, Trit4); *Candida albicans* (Canda1, Canda3); *Candida boidinii* (Candb2); *Psilocybe cubensis* (Psic1, Psic2); shaggy cap (Copc1, Copc2, Copc3, Copc5, Copc7); *Rhodotorula mucilaginosa* (Rhom1, Rhom2); *Malassezia furfur* (Malaf2, Malaf3, Malaf4); *Malassezia sympodialis* (Malas1, Malas5, Malas6, Malas7, Malas8, Malas9, Malas10, Malas11, Malas12, Malas13); *Epicoccum purpurascens* (Epip1); and *Alternaria alternate* (Alta1.0101, Alta1.0102), *Aspergillus versicolor* antigen, *S. chartarum* antigen), *Cladosporium herbarum* (Clah2, Clah5, Clah6, Clah7, Clah8, Clah9, Clah10, Clah12); *Aspergillus flavus* (Aspf113); |
| mammals | *Bos domesticus* dander allergen, Bos d 2, Bosd3, Bosd4, Bosd5, Bosd6, Bosd7, Bosd8, Bosd2.0101, Bosd2.0102, Bosd2.0103, *Canis familiaris* allergen, Can f 1, Canf2, Canf3, Canf4, *Equus caballus* allergen, Equc1, Equc2, Equc3, Equc4, Equc5, *Felis domesticus* allergen, Fel d 1, Feld2, Feld3, Feld4, Feld5w, Feld6w, Feld7w, guinea pig (Cavp1, Cavp2); Mouse Urinary Protein (MUP, Musm1) allergen, Mus m 1, Rat Urinary Protein (RUP, Ratn1) allergen, Rat n 1., *Equus caballus* (Equc2.0101, Equc2.0102)) |
| Insects | Mosquito (Aeda1, Aeda2); honey bee (Apim1, Apim2, Apim4, Apim6, Apim7); bumble bee (Bomp1, Bomp4); German cockroach (Blag1, Blag2, Blag4, Blag5, Blag6, Blag7, Blag8); American cockroach (Pera1, Pera3, Pera6, Pera7); midge (Chit1-9, Chit1.01, Chit1.02, Chit2.0101, Chit2.0102, Chit3, Chit4, Chit5, Chit6.01, Chit6.02, Chit7, Chit8, Chit9); cat flea (Ctef1, Ctef2, Ctef3); pine processionary moth (Thap1); silverfish (Leps1); white face hornet (Dolm1, Dolm2, Dolm5); yellow hornet (Dola5); wasp (Pola1, Pola2, Pola5, Pole1, Pole5, Polf5, Polg5, Polm5, Vesvi5); Mediterranean paper wasp (Pold1, Pold4, Pold5); European hornet (Vespc1, Vespc5); giant asian hornet (Vespm1, Vespm5); yellowjacket (Vesf5, Vesg5, Vesm1, Vesm2, Vesm5, Vesp5, Vess5, Vesv1, Vesv2, Vesv5); Australian jumper ant (Myrp1, Myrp2); tropical fire ant (Solg2, Solg4); fire ant (Soli2, Soli3, Soli4); Brazilian fire ant (Sols2); California kissing bug (Triap1); *Blattella germanica* (Blag1.0101, Blag1.0102, Blag1.0103, Blag1.02, Blag6.0101, Blag6.0201, Blag6.0301); *Periplaneta Americana* (Pera1.0101, Pera1.0102, Pera1.0103, Pera1.0104, Pera1.02, Pera3.01, Pera3.0201, Pera3.0202, Pera3.0203, Pera7.0101, Pera7.0102); *Vespa crabo* (Vespc5.0101, Vespc5.0101); and *Vespa mandarina* (Vesp m 1.01, Vesp m 1.02) |
| Rubber | rubber (latex) (Hevb1, Hevb2, Hevb3, Hevb4, Hevb5, Hevb6.01, Hevb6.02, Hevb6.03, Hevb7.01, Hevb7.02, Hevb8, Hevb9, Hevb10, Hevb11, Hevb12, Hevb13); *Hevea brasiliensis* (Hevb6.01, Hevb6.0201, Hevb6.0202, Hevb6.03, Hevb8.0101, Hevb8.0102, Hevb8.0201, Hevb8.0202, Hevb8.0203, Hevb8.0204, Hevb10.0101, Hevb10.0102, Hevb10.0103, Hevb11.0101, Hevb11.0102) |
| Others | Nematode (Anis1, Anis2, Anis3, Anis4); pigeon tick (Argr1); worm (Ascs1); papaya (Carp1); soft coral (Denn1); human autoallergens (Homs1, Homs2, Homs3, Homs4, Homs5); obeche (Trips1) |

TABLE 4.6

| Infectious agent-derived epitopes | |
| --- | --- |
| Infectious Agent | Epitope |
| *Mycobacterium tuberculosis* | isocitrate dehydrogenase (ICDs) |
| Influenza virus | Hemagglutinin (H1), neuraminidase (N1) |
| Dengue virus | envelope (E) |
| *Toxoplasma gondii* | microneme proteins, SAG1, SAG2, GRA1, GRA2, GRA4, GRA6, GRA7, GRA3, ROP1, ROP2, p30, MIC3, MIC2, M2AP, p29, p35, p66 |
| *Entamoeba histolytica* | M17, neutral thiol proteinase |
| *Streptococcus pneumonia* | Pneumolysin, pneumococcal histidine triad D (PhtD), pneumococcal choline-binding protein A (PcpA), pneumococcal histidine triad E (PhtE), LytB |
| *Mycoplasma pneumonia* | exotoxin |
| Epstein-Barr virus | VCA |
| *Helicobacter pylori* | CagA, Vacuolating protein, ureB, hsp60, ureH, urea, ferritin like protein |
| *Campylobacter jejuni* | PEB1, PEB3 |
| *Bacillus anthracis* | SAP |
| SARS virus | RNA-dependent replicases Ia and Ib, spike (S) protein, small envelope (E) protein, membrane (M) protein, and nucleocapsid (N) protein |
| Ebola virus | Nucleoprotein N |
| Schmallenberg virus | N nucleoprotein |
| enterovirus 71 | VPI protein |
| Japanese Encephalitis virus | soluble E protein, envelope E protein |
| Ross River virus | soluble E2 protein |
| Mayaro virus | soluble E2 protein |
| Equine Encephalitis viruses | soluble E2 protein |
| Akabane virus | N nucleoprotein |
| human betacoronavirus | Nucleoprotein N, protein S |
| Hepatitis C virus | protein C, core antigen |
| Hepatitis E virus | protein C |
| *Plasmodium falciparum* | MSP-1 + AMA-1 protein |
| *Leptospira interrogans* | HbpA, LruA, LruB, or LipL32 |

In some embodiments, the devices, systems and methods of the invention can be used to detect a diagnostic marker that is a microRNA (miRNA) biomarker associated with a disease or a health condition. Table 4.7 provides an exemplary list of miRNA biomarkers that can be used and their associated diseases/health conditions.

TABLE 4.7

| Diagnostic miRNA markers | |
| --- | --- |
| Disease/Condition | Marker* |
| Breast cancer | miR-10b, miR-21, miR-125b, miR-145, miR-155, miR-191, miR-382, MiR-1, miR-133a, miR-133b, miR-202, miR-1255a, miR-671-3p, miR-1827, miR-222, miR-744, miR-4306, miR-151-3p, miR-130, miR-149, miR-652, miR-320d, miR-18a, miR-181a, miR-3136, miR-629, miR-195, miR-122, miR-375, miR-184, miR-1299, miR381, miR-1246, miR-410, miR-196a, miR-429, miR-141, miR-376a, miR-370, miR-200b, miR-125a-5p, miR-205, miR-200a, miR-224, miR-494, miR-216a, miR-654-5p, miR-217, miR-99b, miR-885-3p, miR-1228, miR-483-5p, miR-200c, miR-3065-5p, miR-203, miR-1308, let-7a, miR-17-92, miR-34a, miR-223, miR-150, miR-15b, miR-199a-5p, miR-33a, miR-423-5p, miR-424, let-7d, miR-103, miR-23b, miR-30d, miR-425, miR-23a, miR-26a, miR-339-3p, miR-127-3p, miR-148b, miR-376a, miR-376c, miR-409-3p, miR-652, miR-801 (miR-92a, miR-548d-5p, miR-760, miR-1234, miR-18b, miR-605, miR-193b, miR-29) |
| Leukemia | miR-98, miR-155, miR-21, let-7, miR-126, miR-196b, miR-128, miR-195, miR-29a, miR-222, miR-20a, miR-150, miR-451, miR-135a, miR-486-5p, miR-92, miR-148a, miR-181a, miR-20a, miR-221, miR-625, miR-99b (miR-92a, miR-15, miR-16, miR-15a, miR-16-1, miR-29) |
| Multiple myeloma | miR-15a, miR-16, miR-193b-365, miR-720, miR-1308, miR-1246, miR-1, miR-133a, miR-221, miR-99b, Let-7e, miR-125a-5p, miR-21, miR-181a/b, miR-106b-25, miR-32, miR-19a/b, miR-17-92, miR-17, miR-20, miR-92, miR-20a, miR-148a, miR-153, miR-490, miR-455, miR-642, miR-500, miR-296, miR-548d, miR-373, miR-554, miR-888, miR-203, miR-342, miR-631, miR-200a, miR-34c, miR-361, miR-9*, miR-200b, miR-9, miR-151, miR-218, miR-28-3p, miR-200c, miR-378, miR-548d-5p, miR-621, miR-140-5p, miR-634, miR-616, miR-130a, miR-593, miR-708, miR-200a*, miR-340, miR-760, miR-188-5p, miR-760, miR-885-3p, miR-590-3p, miR-885-5p, miR-7, miR-338, miR-222, miR-99a, miR- |

TABLE 4.7-continued

Diagnostic miRNA markers

| Disease/Condition | Marker* |
|---|---|
| | 891a, miR-452, miR-98, miR-629, miR-515-3p, miR-192, miR-454, miR-151-3p, miR-141, miR-128b, miR-1227, miR-128a, miR-205, miR-27b, miR-608, miR-432, miR-220, miR-135a, miR-34a, miR-28, miR-412, miR-877, miR-628-5p, miR-532-3p, miR-625, miR-34b, miR-31, miR-106b, miR-146a, miR-210, miR-499-5p, miR-140, miR-188, miR-610, miR-27a, miR-142-5p, miR-603, miR-660, miR-649, miR-140-3p, miR-300, miR-335, miR-206, miR-20b, miR-130b, miR-183, miR-652, miR-133b, miR-191, miR-212, miR-194, miR-100m miR-1234m miR-182m miR-888, miR-30e-5p, miR-574, miR-135b, miR-125b, miR-502m miR-320, miR548-421, miR-129-3p, miR-190b, miR-18a, miR-549, 338-5p, miR-756-3p, miR-133a, miR-521, miR-486-3p, miR-553, miR-452*, miR-628-3p, miR-620, miR-566, miR-892a, miR- miR-339-5p, miR-628, miR-520d-5p, miR-297, miR-213, miR-519e*, miR-422a, miR-198, miR-122a, miR-1236, miR-548c-5p, miR-191*, miR-583, miR-376c, miR-34c-3p, miR-453, miR-509, miR-124a, miR-505, miR-208, miR-659, miR-146b, miR-518c, miR-665, miR-324-5p, miR-152, miR-548d, miR-455-3p<br>(miR-15a, miR-373*, miR-378*, miR-143, miR-337, miR-223, miR-369-3p, miR-520g, miR-485-5p, miR-524, miR-520h, miR-516-3p, miR-519d, miR-371-3p, miR-455, miR-520b, miR-518d, miR-624, miR-296, miR-16) |
| monoclonal gammopathy of undetermined significance | miR-21, miR-210, miR-9*, miR-200b, miR-222, miR-376<br>(miR-339, miR-328) |
| Myelodysplastic syndrome | (Let-7a, miR-16) |
| Lymphoma | miR-155, miR-210, miR-21, miR-17-92, miR-18a, miR-181a, miR-222, miR-20a/b, miR-194, miR-29, miR-150, miR-155, miR-223, miR-221, let-7f, miR-146a, miR-15, miR-16-1, miR-34b/c, miR-17-5p<br>(miR-20b, miR-184, miR-200a/b/c, miR-205, miR-34a, miR-29a, miR-29b-1, miR-139, miR-345, miR-125a, miR-126, miR-26a/b, miR-92a, miR-20a, miR-16, miR-101, miR-29c miR-138, miR-181b) |
| Lung cancer | let-7c, miR-100, miR-10a, miR-10b, miR-122a, miR-125b, miR-129, miR-148a, miR-150, miR-17-5p, miR-183, miR-18a*, miR-18b, miR-190, miR-192, miR-193a, miR-196b, miR-197, miR-19a, miR-19b, miR-200c, miR-203, miR-206, miR-20b, miR-210, miR-214, miR-218, miR-296, miR-30a-3p, miR-31, miR-346, miR-34c, miR-375, miR-383, miR-422a, miR-429, miR-448, miR-449, miR-452, miR-483, miR-486, miR-489, miR-497, miR-500, miR-501, miR-507, miR-511, miR-514, miR-516-3p, miR-520d, miR-527, miR-7, miR-92, miR-93, miR-99a, miR-25, miR-223, miR-21, miR-155, miR-556, miR-550, miR-939, miR-616*, miR-146b-3p and miR-30c-1*, miR-142-5p, miR-328, miR-127, miR-151, miR-451, miR-126, miR-425-5p, miR-222, miR-769-5p, miR-642, miR-202, miR-34a<br>(let-7a, let-7d, let-7e, let-7g, let-7i, miR-1, miR-103, miR-106a, miR-125a, miR-130a, miR-130b, miR-133a, miR-145, miR-148b, miR-15a, miR-15b, miR-17-3p, miR-181d, miR-18a, miR-196a, miR-198, miR-199a, miR-199a*, miR-212, miR-22, miR-221, miR-23a, miR-23b, miR-26a, miR-27a, miR-27b, miR-29b, miR-30b, miR-30d, miR-30e-3p, miR-320, miR-323, miR-326, miR-331, miR-335, miR-339, miR-374, miR-377, miR-379, miR-410, miR-423, miR-433, miR-485-3p, miR-485-5p, miR-487b, miR-490, miR-491, miR-493, miR-493-3p, miR-494, miR-496, miR-502, miR-505, miR-519d, miR-539, miR-542-3p, miR-98) |
| Colorectal cancer | miR-29a, miR-17-3p, miR-92, miR-21, miR-31, miR-155, miR-92a, miR-141, mir-202, mir-497, mir-3065, mir-450a-2, mir-3154, mir-585, mir-3175, mir-1224, mir-3117, mir-1286<br>(miR-34) |
| Prostate cancer | miR-141, miR-375, miR-16, miR-92a, miR-103, miR-107, miR-197, miR-485-3p, miR-486-5p, miR-26a, miR-92b, miR-574-3p, miR-636, miR-640, miR-766, miR-885-5p, miR-141, miR-195, miR-375, miR-298, miR-346, miR-1-1, miR-1181, miR-1291, miR-133a-I, miR-133b, miR-1469, miR-148*, miR-153, miR-182, miR-182*, miR-183, miR- 183*, miR-185, miR-191, miR-192, miR-1973, miR-200b, miR-205, miR-210, miR-33b*, miR-3607-5p, miR-3621, miR-378a, miR-429, miR-494, miR-582, miR-602, miR-665, miR-96 , miR-99b*, miR-100, miR-125b, miR-143, miR-200a, miR-200c, miR-222, miR-296, and miR-425-5p |
| Ovarian cancer | miR-21, miR-92, miR-93, miR-126, miR-29a, miR-141, miR-200a/b/c, miR-203, miR-205, miR-214, miR-221, miR-222, miR- 146a, miR-150, miR-193a-5p, miR-31, miR-370, let-7d, miR-508-5p, miR-152, miR-509-3-5p, miR-508-3p, miR-708, miR-431, miR-185, miR-124, miR-886-3p, hsa-miR-449, hsa-miR-135a, hsa-miR-429, miR-205, miR-20b, hsa-miR-142-5p, miR-29c, miR-182<br>(miR-155, miR-127, miR-99b) |

TABLE 4.7-continued

Diagnostic miRNA markers

| Disease/Condition | Marker* |
|---|---|
| Cervical cancer | miR-21, miR-9, miR-200a, miR-497<br>(miR-143, miR-203, miR-218) |
| Esophageal carcinoma | miR-21, hsa-miR-200a, hsa-miR-345, hsa-miR-373*, hsa-miR-630, hsa-miR-663, hsa-miR-765, hsa-miR-625, hsa-miR-93, hsa-miR-106b, hsa-miR-155, hsa-miR-130b, hsa-miR-30a, hsa-miR-301a, hsa-miR-15b<br>(miR-375) |
| Gastric cancer | miR-17-5p, miR-21, miR-106a, miR-106b, miR-187, miR-371-5p, miR-378<br>(let-7a, miR-31, miR-192, miR-215, miR-200/141) |
| Pancreatic cancer, ductal adenocarcinoma | miR-210, miR-21, miR-155, miR-196a, miR-1290, miR-20a, miR-24, miR-25, miR-99a, miR-185, miR-191, miR-18a, miR-642b-3p, miR-885-5p, miR-22-3p, miR-675, miR-212, miR-148a*, miR-148, miR-187, let-7g*, miR-205, miR-944, miR-431, miR-194*, miR-769-5p, miR-450b-5p, miR-222, miR-222*, miR-146, miR-23a*, miR-143*, miR-216a, miR-891a, miR-409-5p, miR-449b, miR-330-5p, miR-29a*, miR-625 |
| Hepatocellular carcinoma | miR-500, miR-15b, miR-21, miR-130b, miR-183, miR-122, miR-34a, miR-16, miR-221, miR-222 |
| Melanoma | miR-150, miR-15b, miR-199a-5p, miR-33a, miR-423-5p, miR-424, miR-let-7d, miR-103, miR-23b, miR-30d, miR-425, miR-222, miR-23a, miR-26a, miR-339-3p |
| Squamous cell carcinoma | miR-184a |
| Bladder cancer | miR-126, miR-182 (urine), miR-16, miR-320<br>(miR-143, miR-145, miR-200/141) |
| Renal cancer | miR-1233, miR-199b-5p, miR-130b<br>(miR-10b, miR-139-5p) |
| Oral cancer | miR-31, miR-24, miR-184; miR-34c; miR-137; miR-372; miR-124a; miR-21; miR-124b; miR-31; miR-128a; miR-34b; miR-154; miR-197; miR-132; miR-147; miR-325; miR-181c; miR-198; miR-155; miR-30a-3p; miR-338; miR-17-5p; miR-104; miR-134; miR-213<br>(miR-200a, miR-125a, miR-133a; miR-99a; miR-194; miR-133; miR-219; miR-100; miR-125; miR-26b; miR-138; miR-149; miR-195; miR-107; and miR-139 (saliva)) |
| Head and neck cancer | miR-455-3p, miR-455-5p, miR-130b, miR-130b*, miR-801, miR-196a, miR-21, miR-31 |
| Endometrial cancer | miR-503, miR-424, miR-29b, miR-146a, miR-31 |
| Testicular cancer | miR-372, miR-373 |
| Glioblastoma | miR-21, miR-221, miR-222 |
| Thyroid cancer | miR-187, miR-221, miR-222, miR-146b, miR-155, miR-224, miR-197, miR-192, miR-328, miR-346, miR-512-3p, miR-886-5p, miR-450a, miR-301 b, miR-429, miR-542-3p, miR-130a, miR-146b-5p, miR-199a-5p, miR-193a-3p, miR-152, miR-199a-3p/miR-199b-3p, miR-424, miR-22, miR-146a, miR-339-3p, miR-365, let-7i*, miR-363*, miR-148a, miR-299-3p, let-7a*, miR-200b, miR-200c, miR-375, miR-451, miR-144, let-7i, miR-1826, miR-1201 , miR-140-5p, miR-126, miR-126*, let-7f-2*, miR-148b, miR-21*, miR-342-3p, miR-27a, miR-145*, miR-513b, miR-101, miR-26a, miR-24, miR-30a*, miR-377, miR-518e7, miR-519a7, miR-519b-5p, miR-519c-5p, miR-5227, miR-523*, miR-222*, miR-452, miR-665, miR-584, miR-492, miR-744, miR-662, miR-219-2-3p, miR-631 and miR-637, miRPlus-E1078, miR-19a, miR-501-3p, miR-17, miR-335, miR-106b, miR-15a, miR-16, miR-374a, miR-542-5p, miR-503, miR-320a, miR-326, miR-330-3p,<br>miR-1, miR-7b, miR-26b, miR-106a, miR-139, miR-141, miR-143, miR-149, miR-182, miR-190b, miR-193a, miR-193b, miR-211, miR-214, miR-218, miR-302c*, miR-320, miR-324, miR-338, miR-342, miR-367, miR-378, miR-409, miR-432, miR-483, miR-486, miR-497, miR-518f, miR-574, miR-616, miR-628, miR-663b, miR-888, miR-1247, miR-1248, miR-1262, and miR-1305<br>miR-21, miR-25, miR-32, miR-99b*, miR-125a, miR-125b, miR-138, miR-140, miR-181a, miR-213, miR-221, miR-222, and miR-345 |
| Ischemic heart disease/Myocardial infarction | miR-1, miR-30c, miR-133, miR-145, miR-208a/b, miR-499, miR-663b, miR-1291<br>(miR-126, miR-197, miR-223) |
| Heart failure | miR-29b, miR-122, miR-142-3p, miR-423-5p, miR-152, miR-155, miR-497<br>(miR-107, miR-125b, miR-126, miR-139, miR-142-5p, miR-497) |
| Stroke | miR-124, miR-145<br>(miR-210) |
| Coronary artery disease | miR-21, miR-27b, miR-130a, miR-134, miR-135a, miR-198, miR-210, miR-370<br>(miR-17, miR-92a, miR-126, miR-145m miR-155m miR-181a, miR-221, miR-222) |
| Diabetes | miR-9, miR-28-3p, miR-29a, miR-30d, miR-34a, miR-124a, miR-146a, miR-375, miR-503, 144<br>(miR-15a, miR-20b, miR-21, miR-24, miR-126, miR-191, miR-197, 223, miR-320, miR-486) |

TABLE 4.7-continued

Diagnostic miRNA markers

| Disease/Condition | Marker* |
|---|---|
| Hypertension | Hcmv-miR-UL112, Let-7e<br>(miR-296-5p) |
| Chronic HCV infection | miR-155, miR-122, miR-125b, miR-146a, miR-21 |
| Liver injury | miR-122, miR-192 |
| Sepsis | miR-146a, miR223 |
| Arthritis | miR-125a-5p, miR-24, miR-26a, miR-9, miR-25, miR-98, miR-146a, miR-124a, miR-346, miR-223, miR-155<br>(miR-132, miR-146) |
| Systemic lupus erythematosus | (miR-200a/b/c, miR-205, miR-429, miR-192, miR-141, miR-429, miR-192 (urine or serum)) |
| Chron disease | miR-199a-5p, miR-362-3p, miR-532-3p, miR-plus-E1271, miR-340*<br>(miR-149*, miR-plus-F1065) |
| Ulcerative colitis | miR-28-5p, miR-151-5p, miR-199-5p, miR-340*, miR-plus-E1271, miR-103-2*, miR-362-3p, miR-532-3p<br>(miR-505) |
| Asthma | miR-705, miR-575, let-7d, miR-173p, miR-423-5p, miR-611, miR-674, let-7f-1, miR-23b, miR-223, miR-142-3p, let-7c, miR-25, miR-15b, let-7g, and miR-542-5p, miR-370<br>(miR-325, miR-134, miR-198, miR-721, miR-515-3p, miR-680, miR-601, miR-206, miR-202, miR-671, miR-381, miR-630, miR-759, miR-564, miR-709, miR-513, miR-298) |
| Chronic pulmonary disease | miR-148a, miR-148b, miR-152 |
| Idiopathic pulmonary fibrosis | miR-199a-5p |
| Alzheimer's disease | (miR-137, miR-181c, miR-9, miR-29a/b) |
| Duchenne muscular dystrophy | miR-1, miR-133a, miR-206 |
| Multiple sclerosis | miR-633, miR-181c-5p (CSF), miR-17-5p, miR-193a, miR-326, miR-650, miR-155, miR-142-3p, miR-146a, miR-146b, miR-34a, miR-21, miR-23a, miR-199a, miR-27a, miR-142-5p, miR-193a, miR-15a, miR-200c, miR-130a, miR-223, miR-22, miR-320, miR-214, miR-629, miR-148a, miR-28, miR-195, miR-135a, miR-204, miR-660, miR-152, miR-30a-5p, miR-30a-3p, miR-365, miR-532, let-7c, miR-20b, miR-30d, miR-9, hsa-mir-18b, hsa-mir-493, hsa-mir-599, hsa-mir-96, hsa-mir-193, hsa-mir-328, hsa-mir-409-5p, hsa-mir-449b, hsa-mir-485-3p, hsa-mir-554<br>(miR-922 (CSF), miR-497, miR-1 and miR-126, miR-656, miR-184, miR-139, miR-23b, miR-487b, miR-181c, miR-340, miR-219, miR-338, miR-642, miR-181b, miR-18a, miR-190, miR-213, miR-330, miR-181d, miR-151, miR-140) |
| Preeclampsia | miR-210<br>(miR-152) |
| Gestational diabetes | (miR-29a, miR-132) |
| Platelet activity | miR-126, miR-197, miR-223, miR-24, miR-21 |
| Pregnancy/placenta-derived | miR-526a, miR-527, miR-520d-5p, miR-141, miR-149, miR-299-5p, miR-517a |
| Drug treatment for immunomodulation | miR-130a, miR-146b, miR-143, miR-145, miR-99b, miR-125a, miR-204, miR-424, miR-503 |
| Aging | (miR-151a-3p, miR-181a-5p, miR-1248) |

*miRNA markers in parentheses are downregulated

In some embodiments, the devices, systems and methods of the invention can be used to detect or analyze an environmental sample. An environmental sample can be obtained from any suitable source, such as a river, ocean, lake, rain, snow, sewage, sewage processing runoff, agricultural runoff, industrial runoff, water, tap water or drinking water, etc.).

In some embodiments, an analyte that can be detected or analyzed using the devices, systems and methods of the invention is an environmental marker. An environmental marker can be any suitable marker that can be captured by a capturing agent that specifically binds the environmental marker in a device configured with the capturing agent. In some embodiments, the devices, systems and methods of the present invention detect the concentration of lead or toxins in water. In some embodiments, the presence, absence, or quantitative level of an environmental marker in a sample can be indicative of the state of the environment from which the sample was obtained. In some embodiments, the environmental marker can be a substance that is toxic or harmful to an organism, e.g., human, companion animal, plant, etc., that is exposed to the environment. In some embodiments, the environmental marker can be an allergen that can cause allergic reactions in some individuals who are exposed to the environment. In some embodiments, the presence, absence or quantitative level of the environmental marker in the sample can be correlated with a general health of the environment. In such cases, the general health of the environment can be measured over a period of time, for example, such as a week, months, years, or decades.

In some embodiments, the devices, systems and methods of the present invention further include receiving or providing a report that indicates the safety or harmfulness for a subject to be exposed to the environment from which the sample was obtained based on information including the measured amount of the environmental marker. The information used to assess the safety risk or health of the environment can include data other than the type and measured amount of the environmental marker. These other data can include, for example, the location, altitude, temperature, time of day/month/year, pressure, humidity, wind direction and speed, weather, etc. The data can represent, for example, an average value or trend over a certain period (minutes, hours, days, weeks, months, years, etc.) or an instantaneous value over a shorter period (milliseconds, seconds, minutes, etc.).

In some embodiments, the report can be generated by the device configured to read the device, or can be generated at a remote location upon sending the data including the measured amount of the environmental marker. In some embodiments, an expert can be at the remote location or have access to the data sent to the remote location, and can analyze or review the data to generate the report. In some embodiments, the expert can be a scientist or administrator at a governmental agency, such as the US Centers for Disease Control (CDC) or the US Environmental Protection Agency (EPA), a research institution, such as a university, or a private company. In some embodiments, the expert can send to the user instructions or recommendations based on the data transmitted by the device and/or analyzed at the remote location.

A list of exemplary environmental markers is set forth in Table 8 of U.S. provisional application Ser. No. 62/234,538, filed on Sep. 29, 2015, which application is incorporated by reference herein.

Additional exemplary environmental markers are listed in Table 4.8.

TABLE 4.8

Environmental markers

| CLASS/SOURCE | MARKER |
|---|---|
| Synthetic hormone analogues | 17beta-estradiol (E2), estrone (EI), estrogen (ES: EI + E2 + estriol (E3)), 1 7alfa-ethynylestradiol (EE2), 4-nonylphenpol, testosterone |
| Halogenated hydrocarbons | p,p'-DDE, p,p'-DDD, p,p'-DDT, o,p'-DDE, o,p'-DDE, o,p'-DDT, o,p'-DDD, chlordane, nonachlor, oxychlordane, heptachlor, heptachlor epoxide, pentachloroanisole, hexachlorobenzene, heptachlorbenzene, o,p'-methoxychlor, p,p'-methoxychlor, Hexachlorocyclopentadiene |
| Pesticides | manganese ethylene-bis-dithiocarbamate, diazinon, chlorphyrifos, carbofuran, carbaryl, malathion, dieldrin, fipronil, desulfinylfipronil, fipronil sulfide, fipronil sulfone, aldicarb, aldicarb sulfone, aldicarb sulfoxide, carbaryl, 3-hydroxycarbofuran, methiocarb, methomyl, , oxamyl, propoxur, alpha-HCH, gamma-HCH, beta-HCH, delta-HCH, azinphos-methyl, chlorpyrifos, disulfoton, parathion, fonofos, ethoprop, parathion-methyl, phorate, terbufos, cis-permethrin, trans-permethrin, propargite, aldrin, chloroneb, endosulfan I, endrin, isodrin, mirex, toxaphene, lindane, O-ethyl O-4-nitrophenyl phenylphosphono-thioate (EPN), fenitrothion, pirimiphos-methyl, deltamethrin |
| Herbicide | acetochlor, alachlor, metolachlor, atrazine, deethylatrazine, cyanazine, terbuthylazine, terbutryn, metribuzin, bentazon, EPTC, triflualin, molinate norflurazon, simazine, prometon, promteryn, tebuthiuron, 2,4-D, diuron, dacthal, bromacil, deisopropyl atrazine, hydroxyatrazine, deethylhydroxyatrazine, deisopropylhydroxyatrazine, acetochlor ESA, acetochlor OA, alachlor ESA, alachlor OA, metolachlor ESA, metolachlor OA, 2,6-diethylaniline, napropamide, pronamide, propachlor, propanilm butylate, pebulate, propham, thiobencarb, triallate, dacthal, dacthal monoacid, 2,4-DB, dischlorprop, MCPA, MCPB, 2,4,5-T, 2,4,5-TP, benfluralin, ethalfluralin, oryzalin, pendimethalin, trifluralin, bentazon, norflurazon, acifluorfen, chloramben methyl ester, clopyralid, dicamba, picloram, dinoseb, DNOC, chlorothalonil, dichlobenil, 2,6-dichlorobenzamide (BAM), triclopyr, bromoxynil, bromacil, terbacil, fenuron, fluometuron, linuron, neburon, dalapon, diquat, endothall, Glyphosate, N-dealkylated triazines, mecoprop |
| Industrial material/waste | chromated copper arsenate, Carbon tetrachloride, Chlorobenzene, p-Dichlorobenzene, 1,2-Dichloroethanem, 1,1-Dichloroethylene, cis-1,2-Dichloroethylene, trans-1,2-Dichloroethylene, Dichloromethane, Di(2-ethylhexyl) adipate, Di(2-ethylhexyl) phthalate, Dibutyl phthalate (DBP), diethyl phthalate (DEP), dicyclohexyl phthalate (DCHP), Dioxin (2,3,7,8-TCDD), Epichlorohydrin, Ethylene dibromide, Polychlorinated biphenyls, Pentachlorophenol, styrene, Tetrachloroethylene, Toluene diisocyanate (TDI), 1,2,4-Trichlorobenzene, 1,1,1-Trichloroethane, 1,1,2-Trichloroethane, Trichloroethylene, perchloroethylene, Vinyl chloride, Xylenes, alkylphenol (AP), AP + APE, bisphenol A (BPA), benzene, Xylene, Toluene, Styrene, Toluidine, 2-(p-Tolyl)ethylamine, Ethylbenzene, 2-Methyl-naphthalene, and Propyl-benzene, PAH (polynuclear aromatic hydrocarbons) |
| Drinking water | Bromate, Chlorite, Haloacetic acids, Total Trihalomethanes, Chloramines, Chlorine, Chlorine dioxide, Benzo(a)pyrene, 4-tert-octylphenol |
| Household waste/Sewage runoff | Acrylamide, linear alkylbenzene sulfonates (LAS), alkyl ethoxylates (AE), alkylphenol ethoxylates (APE), triclosan |
| Poison/toxins | N-methylamino-L-alanine (BMAA), *Clostridium botulinum* neurotoxins, BoNT A, B, D , E, Ricin A, B, tetan TABLE 4.8-continued Environmental markers

| CLASS/SOURCE | MARKER |
| --- | --- |
| Pathogens/microbes (antigen in pretheses) | Anthrax (LF), *Giardia lamblia*, *Legionella*, Total Coliforms (including fecal coliform and *E. Coli*), Viruses (enteric) stapylococci (e.g., *Staphylococcus epidermidis* and *Staphylococcus aureus* (enterotoxin A, B, C, G, I, cells, TSST-1), *Enterrococcus faecalis*, *Pseudomonas aeruginosa*, *Escherichia coli* (Shiga-like toxin, F4, F5, H, K, O, bacteriophage K1, K5, K13), other gram-positive bacteria, and gram-negative bacilli. *Clostridium difficile* (Toxin A, B) *Bacteroidetes*, *Cryptosporidium parvum* (GP900, p68 or cryptopain, oocyst), *Candida albicans* *Bacillus anthracis*, *Bacillus stearothermophilus* Norovirus, *Listeria monocytogenes* (internalin), *Leptospira interrogans*, *Leptospira biflexa*, *Clostridium perfringens* (Epsilon toxin), *Salmonella typhimurium*, *Yersinia pestis* (F1, V antigens), *Aspergillus flavus* (aflatoxin), *Aspergillus parasiticus* (aflatoxin), avian influenza virus, Ebola virus (GP), *Histoplasma capsulatum*, *Blastomyces dermatitidis* (A antigen) Gram-positive bacteria (teichoic acid), Gram-ngative bacteria (such as *Pseudomonas aeruginosa*, *Klebsiella pneumoniae*, *Salmonella enteriditis*, *Enterobacter aerogenes*, *Enterobacter hermanii*, *Yersinia enterocolitica* and *Shigella sonnei*)(LPS), Polio virus, Influenza type A virus Disease specific prion (PrP-d) |
| Allergens | mite (Acas13, Blot1, Blot3, Blot4, Blot5, Blot6, Blot10, Blot11, Blot12, Blot13, Blot19); American house dust mite (Derf1, Derf2, Derf3, Derf7, Derf10, Derf11, Derf14, Derf15, Derf16, Derf17, Derf18w); house dust mite (Derm1); European house dust mite (Derp1, Derp2, Derp3, Derp4, Derp5, Derp6, Derp7, Derp8, Derp9, Derp10, Derp11, Derp14, Derp20, Derp21); mite (Eurm2; Eurm14); storage mite (Glyd2, Lepd2, Lepd5, Lepd7, Lepd10, Lepd13, Tyrp2, Tyrp13); *Dermatophagoides farinae* (Derf1.0101, Derf1.0102, Derf1.0103, Derf1.0104, Derf1.0105, Derf2.0101, Derf2.0102, Derf2.0103, Derf2.0104, Derf2.0105, Derf2.0106, Derf2.0107, Derf2.0108, Derf2.0109, Derf2.0110, Derf2.0111, Derf2.0112, Derf2.0113, Derf2.0114, Derf2.0115, Derf2.0116, Derf2.0117); *Dermatophagoides pteronyssinus* (Derp1.0101, Derp1.0102, Derp1.0103, Derp1.0104, Derp1.0105, Derp1.0106, Derp1.0107, Derp1.0108, Derp1.0109, Derp1.0110, Derp1.0111, Derp1.0112, Derp1.0113, Derp1.0114, Derp1.0115, Derp1.0116, Derp1.0117, Derp1.0118, Derp1.0119, Derp1.0120, Derp1.0121, Derp1.0122, Derp1.0123, Derp2.0101, Derp2.0102, Derp2.0103, Derp2.0104, Derp2.0105, Derp2.0106, Derp2.0107, Derp2.0108, Derp2.0109, Derp2.0110, Derp2.0111, Derp2.0112, Derp2.0113); *Euroglyphus maynei* (Eurm2.0101, Eurm2.0102); *Glycyphagus domesticus* (Glyd2.0101, Glyd2.0201); and *Lepidoglyphus destructor* (Lepd2.0101, Lepd2.0101, Lepd2.0101, Lepd2.0102, Lepd2.0201, Lepd2.0202) Pollen (Short Ragweed (*Ambrosia artemisiifolia*) allergen, Amb a 1, Amba2, Amba3, Amba5, Amba6, Amba7, Amba8, Amba9, Amba10; *Betula verrucosa* allergen, Bet v 1, *Phleum pratense* allergen, Phl p 5), giant ragweed (Ambt5); mugwort (Artv1, Artv2, Artv3, Artv4, Artv5, Artv6); sunflower (Hela1, Hela2, Hela3); *Mercurialis annua* (Mera1); lamb's-quarters, pigweed (Chea1); white goosefoot (Chea2, Chea3); Russian-thistle (Salk1); Rosy periwinkle (Catr1); English plantain (Plal1); Japanese hop (Humj1); *Parietaria judaica* (Parj1, Parj2, Parj3); *Parietaria officinalis* (Paro1); *Ambrosia artemisiifolia* (Amba8.0101, Amba8.0102, Amba9.0101, Amba9.0102); *Plantago lanceolata* (Plal1.0101, Plal1.0102, Plal1.0103); and *Parietaria judaica* (Parj1.0101, Parj1.0102, Parj1.0201, Par2.0101, Parj2.0102, Parj3.0101, Parj3.0102), Bermuda grass (Cynd1, Cynd7, Cynd12, Cynd15, Cynd22w, Cynd23, Cynd24); orchard grass (Dacg1, Dacg2, Dacg3, Dacg5); meadow fescue (Fesp4w); velvet grass (Holl1); rye grass (Lolp1, Lolp2, Lolp3, Lolp5, Lolp11); canary grass (Phaa1); Timothy (Phlp1, Phlp2, Phlp4, Phlp5, Phlp6, Phlp11, Phlp12, Phlp13); Kentucky blue grass (Poap1, Poap5); Johnson grass (Sorh1); *Cynodon dactylon* (Cynd1.0101, Cynd1.0102, Cynd1.0103, Cynd1.0104, Cynd1.0105, Cynd1.0106, Cynd1.0107, Cynd1.0201, Cynd1.0202, Cynd1.0203, Cynd1.0204); *Holcus lanatus* (Holl1.0101, Holl1.0102); *Lolium perenne* (Lolp1.0101, Lolp1.0102, Lolp1.0103, Lolp5.0101, Lolp5.0102); *Phleum pratense* (Phlp1.0101, Phlp1.0102, Phlp4.0101, Phlp4.0201, Phlp5.0101, Phlp5.0102, Phlp5.0103, Phlp5.0104, Phlp5.0105, Phlp5.0106, Phlp5.0107, Phlp5.0108, Phlp5.0201, Phlp5.0202); and *Secale cereale* (Secc20.0101, Secc20.0201), Alder (Alng1); Birch (Betv1, Betv2, Betv3, Betv4, Betv6, Betv7); hornbeam (Carb1); chestnut (Cass1, Cass5, Cass8); hazel (Cora1, Cora2, Cora8, Cora9, Cora10, Cora11); White oak (Quea1); Ash (Frae1); privet (Ligv1); olive (Olee1, Olee2, Olee3, Olee4, Olee5, Olee6, Olee7, Olee8, Olee9, Olee10); Lilac (Syrv1); Sugi (Cryj1, Cryj2); cypress (Cupa1); common cypress (Cups1, Cups3w); mountain cedar (Juna1, Juna2, Juna3); prickly juniper (Juno4); mountain cedar (Juns1); eastern red cedar (Junv1); London plane tree (Plaa1, Plaa2, Plaa3); date palm (Phod2); *Betula verrucosa* (Betv1.0101, Betv1.0102, Betv1.0103, Betv1.0201, Betv1.0301, Betv1.0401, Betv1.0402, Betv1.0501, Betv1.0601, Betv1.0602, Betv1.0701, Betv1.0801, Betv1.0901, Betv1.1001, Betv1.1101, Betv1.1201, Betv1.1301, Betv1.1401, Betv1.1402, Betv1.1501, Betv1.1502, Betv1.1601, Betv1.1701, Betv1.1801, Betv1.1901, Betv1.2001, Betv1.2101, Betv1.2201, Betv1.2301, Betv1.2401, Betv1.2501, Betv1.2601, Betv1.2701, |

TABLE 4.8-continued

Environmental markers

| CLASS/SOURCE | MARKER |
|---|---|
| | Betv1.2801, Betv1.2901, Betv1.3001, Betv1.3101, Betv6.0101, Betv6.0102); *Carpinus betulus* (Carb1.0101, Carb1.0102, Carb1.0103, Carb1.0104, Carb1.0105, Carb1.0106, Carb1.0106, Carb1.0106, Carb1.0106, Carb1.0107, Carb1.0107, Carb1.0108, Carb1.0201, Carb1.0301, Carb1.0302); *Corylus avellana* (Cora1.0101, Cora1.0102, Cora1.0103, Cora1.0104, Cora1.0201, Cora1.0301, Cora1.0401, Cora1.0402, Cora1.0403, Cora1.0404); *Ligustrum vulgare* (Ligv1.0101, Ligv1.01.02); *Olea europea* (Olee1.0101, Olee1.0102, Olee1.0103, Olee1.0104, Olee1.0105, Olee1.0106, Olee1.0107); *Syringa vulgaris* (Syrv1.0101, Syrv1.0102, Syrv1.0103); *Cryptomeria japonica* (Cryj2.0101, Cryj2.0102); and *Cupressus sempervirens* (Cups1.0101, Cups1.0102, Cups1.0103, Cups1.0104, Cups1.0105) |
| | mold (*Alternaria alternata* allergen, Alt a 1, Alta3, Alta4, Alta5, Alta6, Alta7, Alta8, Alta10, Alta12, Alta13, *Aspergillus fumigatus* allergen, Asp f 1, Aspf2, Aspf3, Aspf4, Aspf5, Aspf6, Aspf7, Aspf8, Aspf9, Aspf10, Aspf11, Aspf12, Aspf13, Aspf15, Aspf16, Aspf17, Aspf18, Aspf22w, Aspf23, Aspf27, Aspf28, Aspf29); *Aspergillus niger* (Aspn14, Aspn18, Aspn25); *Aspergillus oryzae* (Aspo13, Aspo21); *Penicillium brevicompactum* (Penb13, Penb26); *Penicillium chrysogenum* (Pench13, Pench18, Pench20); *Penicillium citrinum* (Penc3, Penc13, Penc19, Penc22w, Penc24); *Penicillium oxalicum* (Peno18); *Fusarium culmorum* (Fusc1, Fusc2); *Trichophyton rubrum* (Trir2, Trir4); *Trichophyton tonsurans* (Trit1, Trit4); *Candida albicans* (Canda1, Canda3); *Candida boidinii* (Candb2); *Psilocybe cubensis* (Psic1, Psic2); shaggy cap (Copc1, Copc2, Copc3, Copc5, Copc7); *Rhodotorula mucilaginosa* (Rhom1, Rhom2); *Malassezia furfur* (Malaf2, Malaf3, Malaf4); *Malassezia sympodialis* (Malas1, Malas5, Malas6, Malas7, Malas8, Malas9, Malas 10, Malas11, Malas12, Malas13); *Epicoccum purpurascens* (Epip1); and *Alternaria alternate* (Alta1.0101, Alta1.0102), *Aspergillus versicolor* antigen, *S. chartarum* antigen), *Cladosporium herbarum* (Clah2, Clah5, Clah6, Clah7, Clah8, Clah9, Clah10, Clah12); *Aspergillus flavus* (Aspf113); |
| | animals (*Bos domesticus* dander allergen, Bos d 2, Bosd3, Bosd4, Bosd5, Bosd6, Bosd7, Bosd8, Bosd2.0101, Bosd2.0102, Bosd2.0103, *Canis familiaris* allergen, Can f 1, Canf2, Canf3, Canf4, *Equus caballus* allergen, Equc1, Equc2, Equc3, Equc4, Equc5, *Felis domesticus* allergen, Fel d 1, Feld2, Feld3, Feld4, Feld5w, Feld6w, Feld7w, guinea pig (Cavp1, Cavp2); Mouse Urinary Protein (MUP, Musm1) allergen, Mus m 1, Rat Urinary Protein (RUP, Ratn1) allergen, Rat n 1., *Equus caballus* (Equc2.0101, Equc2.0102)) Mosquito (Aeda1, Aeda2); honey bee (Apim1, Apim2, Apim4, Apim6, Apim7); bumble bee (Bomp1, Bomp4); German cockroach (Blag1, Blag2, Blag4, Blag5, Blag6, Blag7, Blag8); American cockroach (Pera1, Pera3, Pera6, Pera7); midge (Chit1-9, Chit1.01, Chit1.02, Chit2.0101, Chit2.0102, Chit3, Chit4, Chit5, Chit6.01, Chit6.02, Chit7, Chit8, Chit9); cat flea (Ctef1, Ctef2, Ctef3); pine processionary moth (Thap1); silverfish (Leps1); white face hornet (Dolm1, Dolm2, Dolm5); yellow hornet (Dola5); wasp (Pola1, Pola2, Pola5, Pole1, Pole5, Polf5, Polg5, Polm5, Vesvi5); Mediterranean paper wasp (Pold1, Pold4, Pold5); European hornet (Vespc1, Vespc5); giant asian hornet (Vespm1, Vespm5); yellowjacket (Vesf5, Vesg5, Vesm1, Vesm2, Vesm5, Vesp5, Vess5, Vesv1, Vesv2, Vesv5); Australian jumper ant (Myrp1, Myrp2); tropical fire ant (Solg2, Solg4); fire ant (Soli2, Soli3, Soli4); Brazilian fire ant (Sols2); California kissing bug (Triap1); *Blattella germanica* (Blag1.0101, Blag1.0102, Blag1.0103, Blag1.02, Blag6.0101, Blag6.0201, Blag6.0301); *Periplaneta Americana* (Pera1.0101, Pera1.0102, Pera1.0103, Pera1.0104, Pera1.02, Pera3.01, Pera3.0201, Pera3.0202, Pera3.0203, Pera7.0101, Pera7.0102); *Vespa crabo* (Vespc5.0101, Vespc5.0101); and *Vespa mandarina* (Vesp m 1.01, Vesp m 1.02) |
| | Nematode (Anis1, Anis2, Anis3, Anis4); pigeon tick (Argr1); worm (Ascs1); papaya (Carp1); soft coral (Denn1); rubber (latex)(Hevb1, Hevb2, Hevb3, Hevb4, Hevb5, Hevb6.01, Hevb6.02, Hevb6.03, Hevb7.01, Hevb7.02, Hevb8, Hevb9, Hevb10, Hevb11, Hevb12, Hevb13); human autoallergens (Homs1, Homs2, Homs3, Homs4, Homs5); obeche (Trips1); and *Hevea brasiliensis* (Hevb6.01, Hevb6.0201, Hevb6.0202, Hevb6.03, Hevb8.0101, Hevb8.0102, Hevb8.0201, Hevb8.0202, Hevb8.0203, Hevb8.0204, Hevb10.0101, Hevb10.0102, Hevb10.0103, Hevb11.0101, Hevb11.0102) |

In some embodiments, the devices, systems and methods of the present invention can be used to detect or analyze a foodstuff sample. A foodstuff sample can be obtained from any suitable source, such as from raw food, processed food, cooked food, drinking water, etc. In some embodiments, an analyte that can be detected or analyzed using the devices, systems and methods of the invention is an foodstuff marker. A foodstuff marker can be any suitable marker, such as those shown in Table 4.9, that can be captured by a capturing agent that specifically binds the foodstuff marker in a device configured with the capturing agent. In some embodiments, the presence, absence, or the quantitative level of the foodstuff marker in the sample can be indicative of the safety or harmfulness to a subject if the foodstuff is consumed. In some embodiments, the foodstuff marker is a substance derived from a pathogenic or microbial organism that is indicative of the presence of the organism in the foodstuff from which the sample was obtained. In some embodiments, the foodstuff marker is a toxic or harmful substance if consumed by a subject. In some embodiments, the foodstuff marker is a bioactive compound that can unintentionally or unexpectedly alter the physiology if consumed by the subject.

In some embodiments, the foodstuff marker is indicative of the manner in which the foodstuff was obtained (for example, grown, procured, caught, harvested, processed, cooked, etc.). In some embodiments, the foodstuff marker is indicative of the nutritional content of the foodstuff. In some embodiments, the foodstuff marker is an allergen that can induce an allergic reaction if the foodstuff from which the sample is obtained is consumed by a subject.

In some embodiments, the devices, systems and methods in the present invention further includes receiving or providing a report that indicates the safety or harmfulness for a subject to consume the foodstuff from which the sample was obtained based on information including the measured level of the foodstuff marker. The information used to assess the safety of the foodstuff for consumption can include data other than the type and measured amount of the foodstuff marker. These other data can include any health condition associated with the consumer (allergies, pregnancy, chronic or acute diseases, current prescription medications, etc.).

The report can be generated by the device configured to read the device, or can be generated at a remote location upon sending the data including the measured amount of the foodstuff marker. In some embodiments, a food safety expert can be at the remote location or have access to the data sent to the remote location, and can analyze or review the data to generate the report. In some embodiments, the food safety expert can be a scientist or administrator at a governmental agency, such as the US Food and Drug Administration (FDA) or the CDC, a research institution, such as a university, or a private company. In some embodiments, the food safety expert can send to the user instructions or recommendations based on the data transmitted by the device and/or analyzed at the remote location.

A list of exemplary foodstuff markers is set forth in Table 9 of U.S. provisional application Ser. No. 62/234,538, filed on Sep. 29, 2015, which application is incorporated by reference herein.

Additional exemplary foodstuff markers are listed in Table 4.9.

TABLE 4.9

Foodstuff markers

| Source/Class | Marker/target |
|---|---|
| Pathogens/ microbes | *Bacillus anthracis* (LF), *Giardia lamblia*, *Legionella*, Total Coliforms (including fecal coliform and *E. Coli*), Viruses (enteric) stapylococci (e.g., *Staphylococcus epidermidis* and *Staphylococcus aureus* (enterotoxin A, B, C, G, I, cells, TSST-1), *Enterrococcus faecalis*, *Pseudomonas aeruginosa*, *Escherichia coli* (Shiga-like toxin, F4, F5, H, K, O, bacteriophage K1, K5, K13), other gram-positive bacteria, and gram-negative bacilli. *Clostridium difficile* (Toxin A, B), Bacteroidetes, *Cryptosporidium parvum* (GP900, p68 or cryptopain, oocyst), *Candida albicans*, *Bacillus anthracis*, *Bacillus stearothermophilus*, *Bacillus cereus*, *Bacillus licheniformis*, *Bacillus subtilis*, *Bacillus pumilus*, *Bacillus badius*, *Bacillus globigii*, *Salmonella typhimurium*, *Escherichia coli* O157:H7, Norovirus, *Listeria monocytogenes* (internalin), *Leptospira interrogans*, *Leptospira biflexa*, *Campylobacter jejuni*, *Campylobacter coli*, *Clostridium perfringens*, *Aspergillus flavus* (aflatoxins), *Aspergillus parasiticus* (aflatoxins), Ebola virus (GP), *Histoplasma capsulatum*, *Blastomyces dermatitidis* (A antigen), Gram-positive bacteria (teichoic acid), Gram-ngative bacteria (such as *Pseudomonas aeruginosa*, *Klebsiella pneumoniae*, *Salmonella enteriditis*, *Enterobacter aerogenes*, *Enterobacter hermanii*, *Yersinia enterocolitica* and *Shigella sonnei*)(LPS), Polio virus, Influenza type A virus, Disease specific prion (PrP-d), Hepatitis A virus, *Toxoplasma gondii*, *Vibrio cholera*, *Vibrio parahaemolyticus*, *Vibrio vulnificus*, *Enterococcus faecalis*, *Enterococcus faecium* |
| Toxins/ carcinogens | N-methylamino-L-alanine (BMAA), *Clostridium botulinum* neurotoxins, BoNT A, B, Ricin A, B; diphtheria toxin; Aristolochic acid; Colchicine, Ochratoxin A, Sterigmatocystin, Ergotamine, Fumonisins, Fusarin C, domoic acid, Brevetoxin, Mycotoxins |
| Halogenated hydrocarbons | Heptachlor, chlordane |
| Heavy metals | Lead, mercury, cadmium |
| Allergens | peanut (Ara h 1, Ara h 2, Ara h 6), fish, shellfish, mollusks, shrimp (*D. pteronyssinus* tropomyosin allergen, Der p 10) Cod (Gadc1); Atlantic salmon (Sals1); domestic cattle milk (Bosd4, Bosd5, Bosd6, Bosd7, Bosd8); chicken/egg (Gald1, Gald2, Gald3, Gald4, Gald5); shrimp (Mete1); shrimp (Pena1, Peni1); black tiger shrimp (Penm1, Penm2); squid (Todp1), brown garden snail (Helas1); abalone (Halm1); edible frog (Rane1, Rane2); oriental mustard (Braj1); rapeseed (Bran1); cabbage (Brao3); turnip (Brar1, Brar2); barley (Horv15, Horv16, Horv17, Horv21); rye (Secc20); wheat (Tria18, Tria19, Tria25, Tria26, gliadin); corn (Zeam14, Zeam25); rice (Orys1), celery (Apig1, Apig4, Apig5); carrot (Dauc1, Dauc4); hazelnut (Cora1.04, Cora2, Cora8); strawberry (Fraa1, Fraa3, Fraa4); apple (Mald1, Mald2, Mald3, Mald4); pear (Pyrc1, Pyrc4, Pyrc5); avocado (Persa1); apricot (Pruar1, Pruar3); sweet cherry (Pruav1, Pruav2, Pruav3, Pruav4); European plum (Prud3); almond (Prudu4); peach (Prup3, Prup4); asparagus (Aspao1); saffron crocus (Cros1, Cros2); lettuce (Lacs1); grape (Vitv1); banana (Musxp1); pineapple (Anac1, Anac2); lemon (Citl3); sweet orange (Cits1, Cits2, Cits3); litchi (Litc1); yellow mustard (Sina1); soybean (Glym1, Glym2, Glym3, Glym4); mung bean (Vigr1); peanut (Arah1, Arah2, Arah3, Arah4, Arah5, Arah6, Arah7, Arah8); lentil (Lenc1, Lenc2); pea (Piss1, Piss2); kiwi (Actc1, Actc2); bell pepper (Capa1w, Capa2); tomato (Lyce1, Lyce2, Lyce3); potato (Solat1, Solat2, Solat3, Solat4); Brazil nut |

TABLE 4.9-continued

Foodstuff markers

| Source/Class | Marker/target |
|---|---|
| | (Bere1, Bere2); black walnut (Jugn1, Jugn2); English walnut (Jugr1, Jugr2, Jugr3); Cashew (Anao1, Anao2, Anao3); Castor bean (Ricc1); sesame (Sesi1, Sesi2, Sesi3, Sesi4, Sesi5, Sesi6); muskmelon (Cucm1, Cucm2, Cucm3); Chinese-date (Zizm1); *Anacardium occidentale* (Anao1.0101, Anao1.0102); *Apium graveolens* (Apig1.0101, Apig1.0201); *Daucus carota* (Dauc1.0101, Dauc1.0102, Dauc1.0103, Dauc1.0104, Dauc1.0105, Dauc1.0201); *Citrus sinensis* (Cits3.0101, Cits3.0102); *Glycine max* (Glym1.0101, Glym1.0102, Glym3.0101, Glym3.0102); *Lens culinaris* (Lenc1.0101, Lenc1.0102, Lenc1.0103); *Pisum sativum* (Piss1.0101, Piss1.0102); *Lycopersicon esculentum* (Lyce2.0101, Lyce2.0102); *Fragaria ananassa* (Fraa3.0101, Fraa3.0102, Fraa3.0201, Fraa3.0202, Fraa3.0203, Fraa3.0204, Fraa3.0301); *Malus domestica* (Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302); *Prunus avium* (Pruav1.0101, Pruav1.0201, Pruav1.0202, Pruav1.0203); and *Prunus persica* (Prup4.0101, Prup4.0201) |
| Synthetic hormone analogues | 17beta-estradiol (E2), estrone (EI), estrogen (ES: EI + E2 + estradiol (E3)), 17alfa-ethynylestradiol (EE2), 4-nonylphenpol, testosterone, Diethylstilbestrol (DES), recombinant bovine growth hormone (rBGH) |
| Pesticides | Dieldrin, carbaryl, chlorpyrifos, parathion, aldrin, endosulfan I, endrin, toxaphene, O-ethyl O-4-nitrophenyl phenylphosphono-thioate (EPN), fenitrothion, pirimiphos-methyl, thiabendazole, methiocarb, Carbendazim, deltamethrin, Avermectin, Carbaryl, Cyanazine, Kresoxim, resmethrin, kadethrin, cyhalothrin, biphenthrin, fenpropathrin, allethrin and tralomethrin; aromatic-substituted alkanecarboxylic acid esters such as fenvarerate, flucythrinate, fluvalinate and cycloprothrin; and non-ester compounds such as etofenprox, halfenprox (MTI-732), 1-(3-phenoxyphenyl)-4-(4-ethoxyphenyl)-4-methylpentane (MTI-790), 1-(3-phenoxy-4-fluorophenyl)-4-(4-ethoxyphenyl)-4-methylpentane (MTI-800), dimethyl-(4-ethoxyphenyl)-(3-phenoxybenzyloxy)silane (SSI-116), silafluofen and PP-682, carbofuran, triazophos |
| Herbicide | atrazine, deethylatrazine, cyanazine, terbuthylazine, terbutryn, molinate, simazine, prometon, promteryn, hydroxyatrazine, 2,6-dichlorobenzamide (BAM), N-dealkylated triazines, mecoprop, thiram, acetochlor, alachlor, Chlorothalonil, Chlorsulfuron, Fenoxaprop ethyl, Linuron, monuron, diuron, Quizalofop-ethyl, Imazalil, Iprodione, Iprovalicarb, Myclobutanil |
| Industrial material/waste | Dioxin (2,3,7,8-TCDD), 4-tert-octylphenol, bisphenol A (BPA), Styrene, Di(2-ethylhexyl) phthalate, Dibutyl phthalate (DBP), benzophenone, benzene, trichloroethylene, polychlorinated biphenyl (PCB), nonylphenol, p-cresol, melamine, xylene |
| Antibiotics | 3-Amino-5-morpholinomethyl-2-oxazolidone (AMOZ; tissue bound metabolite of furaltadone), oxytetracycline, rolitetracycline, Actinomycin D, Amikacin sulfate, Aminoglycosides, nitrofuran (AOZ), Chloramphenicol, Doxycycline, Streptomycin, gentamicin, neomycin, kanamycin, sulfamethazine, enrofloxacin, sulfadiazine, enrofloxacin |
| Food coloring/ additive/ preservative | Tartrazine, ethoxyquin, erythritol, penicillin, Fluoroquinolone, Malachite Green/Leucomalachite Green, C.I. Solvent Yellow 14 (Sudan I), |
| Food preparation | Acrylamide, 2-amino-3-methylimidazo(4,5-f)quinolone, Benzo[a]pyrene |
| Nutritional content | Vitamins A (retinol), B12 (cobalmins), B6 (pyridoxine), B1 (thiamin), B2 (riboflavin), B3 (niacin), B5 (D-pantothenic acid), B7 (biotin), B9 (folic acid), C, D, E (alpha-tocopherol); |
| Other | Caffeine, Ovine myofibril proteins, Etodolac |

In some embodiments, the invention is directed to a kit containing a device of the invention. In some embodiments, the kit includes a device configured to specifically bind an analyte described herein. In some embodiments, the kit includes instructions for practicing the subject methods using a hand held device, e.g., a mobile phone. In some embodiments, the instructions can be present in the kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In some embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the device, or can be provided in the device.

In some embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

In some embodiments, the devices, systems and methods of the invention can be used for simple, rapid blood cell counting using a smartphone. In some embodiments, the first plate and the second plate are selected from a thin glass slide (e.g., 0.2 mm thick) or a thin plastic film (e.g., 15 mm thick) of a relative flat surface, and each have an areas with a length and width in about 0.5 cm to 10 cm. In some embodiments, the spacers are made of glass, plastics, or other materials that would not deform significantly under a pressing. In some embodiments, before the sample deposition, the spacers are placed on the first plate, the second plate or both; and the first plate, the second plate or both are optionally coated with reagent that facilitate the blood counting (staining dyes and/or anticoagulant). In some embodiments, the first plate and the second plate can be sealed in a bag for easy transport and longer shelf life-time.

In some embodiments of blood cell count testing, only about 1 uL (microliter) (or about 0.1 uL to 3 uL) of blood is needed for the sample, which can be taken, for example, from a finger or other human body location. In some embodiments, the blood sample can be directly deposited from human body (e.g., finger) onto the first plate and the second plate, without any dilution. In such embodiments, the first plate and the second plate can face each other, so that blood sample is between the inner surfaces of the first plate and the second plate. In some embodiments, reagents are pre-deposited (staining dyes or anticoagulant), they are deposited on the inner surface for mixing with the sample. The first plate and the second plate can then be pressed by fingers or a simple mechanical device (e.g. a clip that presses using a spring). Under the press, the inner spacing is reduced, the reduction will be eventually stopped at the value set by the spacers' height and the final sample thickness is reached, which generally is equal to the final inner spacing. Since the final inner spacing is known, the final sample thickness become known, namely being quantified (measured) by this method.

In some embodiments, if the blood sample is not diluted, after pressing (sample deformation) the spacers and hence the final sample thickness can be thin, e.g., less than 1 um, less than 2 um, less than 3 um, less than 4 um, less than 5 um, less than 7 um, less than 10 um, less than 15 um, less than 20 um, less than 30 um, less than 40 um, less than 50 um, less than 60 um, less than 80 um, less than 100 um, less than 150 um, or any ranges between any of the two numbers. A thin final sample can be useful because if the final sample thickness is thick, then many red cells can overlap during the imaging, which can make the cell counting inaccurate. For example, about 4 um thick of whole blood without dilution will give about one layer of blood red cells.

After the pressing, the sample can be imaged by a smartphone either directly or through an additional optical elements (e.g. lenses, filters, or light sources as needed). The image of the sample can be processed to identify the types of the cells as well as the cell number. The image processing can be done locally at the same smartphone that takes the image or remotely but the final result transmitted back to the smartphone (where the image is transmitted to a remote location and is processed there.) The smart phone will display the cell number for a particular cell. In some cases, certain advices will be displayed. The advices can stored on the smartphone before the test or come from a remote machines or professionals.

In certain embodiments, reagents are placed on the inner surfaces of the first plate and/or the second plate using the methods and devices described herein.

In some embodiments, a device or a method for the blood testing comprises (a) a device or a method described herein and (b) a plate spacing (i.e. the distance between the inner surfaces of the two plates) at the closed configuration or a use of such spacing, wherein a undiluted whole blood in the plate-spacing has an average inter-cell distance in the lateral direction for the red blood cells (RBC) larger than the average diameter of the disk shape of the RBC.

In some embodiments, a device or a method to arrange the orientation of a non-spherical cell comprises (a) a device or a method in as described herein and (b) a plate spacing (i.e. the distance between the inner surfaces of the two plates) at the closed configuration or a use of such spacing, wherein the spacing less than the average size of the cell in its long direction (the long direction is the maximum dimension direction of a cell).

Such arrangement can improve the measurements of the sample volume (e.g. red blood cell volume).

In some embodiments, the analytes in the blood tests include protein markers, a list of which can be found at the website of the American Association for Clinical Chemistry). Table 4.10 provides additional exemplary analytes that can be detected using the present invention at the point-of-care (POC) settings and/or at the point of use by non-professional users/subjects.

TABLE 4.10

POC analytes

| Disease/ Condition | Analyte |
|---|---|
| 1. Haematology | |
| Complete blood count (CBC) | RBCs, WBCs, Platelets |
| 2. Lipid panel | |
| Cholesterol level | Triglyceride, Total cholesterol, HDL cholesterol, LDL cholesterol |
| 3. Urinalysis | |
| Renal Diseases/ Kidney Function | pH, Protein, Glucose, Nitrites, Leukocyte esterase, Ketones, Blood cells, Casts, Crystals, Microorganisms, Squamous cells |

TABLE 4.10-continued

POC analytes

| Disease/Condition | Analyte |
|---|---|

4. Diabetes

| | |
|---|---|
| Diabetes | Glucose, HbA1c, 11-8, CTSS, ITGB2, HLA-DRA, CD53, PLAG27, or MMP9; RBP4; 8-iso-prostaglandin F2a (8-iso-PGF2a), 11-dehydro-thromboxane B2 (TXM), C-peptide, Advanced glycosylation end products (AGEs), 1,5-anhydroglucitol, NGPTL3 and 4, autoantibodies (Zn transporter 8, glutamic acid decarboxylase (GAD)), ATP-binding cassette, sub-family C (CFTR/MRP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, |

TABLE 4.10-continued

POC analytes

| Disease/Condition | Analyte |
|---|---|
| | mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta-melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in |

TABLE 4.10-continued

POC analytes

| Disease/ Condition | Analyte |
|---|---|
| | Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |

5. Sexually Transmitted Diseases

| Disease/ Condition | Analyte |
|---|---|
| Chlamydia | bacteria *Chlamydia trachomatis* |
| Gonorrhea | bacteria *Neisseria gonorrhoeae* |
| Syphilis | Antibodies, bacterial DNA |
| Trichomonas | protzoan *Trichomoniasis* |
| Human papillomavirus (HPV) | DNA or RNA of HPV virus |
| Genital herpes | Antibodies |
| Human Immunodeficiency Virus (HIV) | HIV antigen p24, Antibodies |

6. Other Infectious Diseases

| Disease/ Condition | Analyte |
|---|---|
| Ebola | Antigen, IgM and IgG antibodies, RNA |
| Malaria | Antigen, Nucleic acids, Antibodies |
| Hepatitis B and Hepatitis C | Viral proteins, Antibodies, Viral DNA |
| Influenza | Viral proteins, Antibodies, Viral DNA |

7. Cardiac testing

| Disease/ Condition | Analyte |
|---|---|
| Cardiac markers | Troponin (I or T), Creatine Kinase (CK) and CK-MB, Myoglobin, hs-CRP, BNP and NT-proBNP |

8. Female Reproduction testing

| Disease/ Condition | Analyte |
|---|---|
| Pregnancy test | HCG (human chorionic gonadotropin) |
| Ovulation test | LH (luteinizing hormone) |

9. Drugs of Abuse

| Disease/ Condition | Analyte |
|---|---|
| Alcohol | Ethanol, ethyl glucuronide |
| Cocaine | Cocaine, Benzolecgonine, Ecgonine, Ecgonine Methyl Ester |
| Heroine | Heroine, 6MAM, Morphine |
| PCP | PCP, Phencyclidine Thienylcyclohexylpiperidine (TCP) |
| Amphetamines | Amphetamines (such as D-Amphetamine, D-Methamphetamine, L-Amphetamine, L-Methamphetamine, 3,4-Methylenedioxy-methamphetamine (MDMA), 3,4-Methylenedioxyamphetamine (MDA), 3,4-Methylenedioxyethylamphetamine (MDEA), Paramethoxyamphetamine (PMA)) |
| Methamphetamine | D-Methamphetamine, D-Amphetamine, L-Methamphetamine, Chloroquine, (+/−) Ephedrine, 3,4-Methylenedioxy-methamphetamine (MDMA), 3,4-Methylenedioxyamphetamine (MDA), 3,4-Methylenedioxyethylamphetamine (MDEA), Procaine |
| MDMA (Ecstasy) | MDMA, MDA, MDEA, D-Amphetamine, D-Methamphetamine, Paramethoxyamphetamine (PMA) |
| Barbiturates | Secobarbital, Phenobarbital, Butalbital, Allobarbital, Alphenal, Amorbarbital, Aprobarbital, Hexobarbital, Butabarbital, Pentobarbital |
| Phenobarbital | Phenobarbital, Butalbital, Amobarbital, Secobarbital |
| Benzodiazepines | Oxazepam, Alprazolam, Bromazepam, Chlordiazepoxide, Clobazam, Clonazepam, Clorazepate, Delorazepam, Desalkyflurazepam, Diazepam, Estazolam, Fentanyl, Flunitrazepam (Rohypnol ®), Flurazepam, a-Hydroxyalprazolam, Lorazepam (Ativan ®), Lormetazepam, Medazepam, Midazolam, Nitrazepam, Nordiazepam, Prazepam, Temazepam, Tetrazepam |
| Cannabis (Marijuana, etc.) | Δ9-THC, 11-Nor-Δ8-THC-9-COOH, 11-Nor-Δ9-THC-9-COOH, 11-Hydroxy-Δ9-tetrahydrocannabinol, Δ8-Tetrahydrocannabinol, Δ9-Tetrahydrocannabinol, Cannabinol, Cannabidiol, pentanoic acid, butanoic acid, 4-hydroxybutyl, 4-hydroxypentyl |
| Codeine | Morphine, Codeine, Diacetyl morphine (heroine), Ethylmorphine, Hydromorphone, Meperidine, 6-Monoacetylmorphine, Morphine-3-glucuronide, Oxycodone, Oxymorphone, Promethazine, Rifampicine, Thebaine, Trimipamine |

TABLE 4.10-continued

POC analytes

| Disease/Condition | Analyte |
|---|---|
| Nicotine/Cotinine | Cotinine, Nicotine |
| Morphine | Morphine |
| Tricyclic antidepressants (TCA's) | Nortriptyline, Amitriptyline, Chlorpromazine, Clomipramine, Cyclobenzaprine, Desipramine, Diphenyldramine, Doxepine, Imipramine, Nordoxepine, Opipramol, Protriptyline, Perphenazine, Promazine, Promethazine, Trimipramine |
| LSD | LSD |
| Methadone | EDDP, Doxylamine, Methadone, Methadol |
| Methaqualone | Methaqualone, 3-hydroxy methaqualone, 4-hydroxy methaqualone, 2-hydroxy methaqualone, Amitriptyline, Carbamazepine, Nortriptyline, Phenytoin, Primidone, Theophyline |
| buprenorphine | Buprenorphine, Buprenorphine-3-B-d-gluconoride, Nor-Buprenorphine, Nor-Buprenorphine-3-B-d-gluconoride |
| Ketamine | Ketamine, Norketamine, Dextromethorphan, Dextrorphantartrate, EDDP, Phencyclidine, Promazine, Meperidine, D-Methamphetamine, Mephentermine h. s., MDEA, Nordoxepin hydrochloride, Promethazine, D-Norpropoxyphene, Methadone |
| MethCathinone | MethCathinone, 4-MMC (Mephedrone), 3-MMC (3-methylmethcathinone), 4-MEC (4-methylethcathinone), Methylone (MDMC, bk-MDMA), Cathinone, MDPV |
| MDPV | MDPV, Cathinone, MethCathinone |
| methylphenidate | methylphenidate |
| tramadol | Tramadol, N-demethyl-tramadol, O-demethyl-tramadol |
| oxycodone | Oxycodone, Oxymorphone, Codeine, Diacetyl Morphine (Heroine), Ethylmorphine, Hydrocodone, Hydromorphone, Merperidine, 6-Monoacetylmorphine, Morphine, Morphine-3-beta-D-glucuronide, Thebaine |
| propoxyphene | D-propoxyphene, D-norpropoxyphene |
| Fentanyl | Methaqualone, Mecloqualone, 3-hydroxy methaqualone, 4-hydroxy methaqualone, 2-hydroxy methaqualone, Amitriptyline, Carbamazepine, Nortriptyline, Phenytoin, Primidone, Theophyline |

10. Coagulation Disorders

| | |
|---|---|
| Congenital hemophilia; Von Willebrand disease; Acquired hemophilia | Platelet, Fibronogen, Factor V, Anti-Xa, Factor XIII screen, D-dimer |

11. Fecal Occult Blood Test

| | |
|---|---|
| Colon Cancer; colon polyps; crohn's disease; hemorrhoids; anal fissures; intestinal infections; Ulcers; Ulcerative colitis | Blood cells, Hemoglobin, Fecal DNA |

12. Blood Gas and Electrolytes pH, $pCO_2$, $pO_2$, Sodium (Na+), Potassium (K+), Calcium (Ca++), HCO3, TCO2, SBE In some embodiments, the devices, systems and methods of the invention can be used to detect or diagnose a health condition. In some embodiments, the health condition includes, but is not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause.

In some embodiments, relative levels of nucleic acids in two or more different nucleic acid samples can be obtained using such methods, and compared. In these embodiments, the results obtained from the methods described herein are usually normalized to the total amount of nucleic acids in the sample (e.g., constitutive RNAs), and compared. This can be done by comparing ratios, or by any other means. In particular embodiments, the nucleic acid profiles of two or more different samples can be compared to identify nucleic acids that are associated with a particular disease or condition.

In some embodiments, the devices, systems and methods in the present invention can include a) obtaining a sample, b) applying the sample to device containing a capture agent that binds to an analyte of interest, under conditions suitable for binding of the analyte in a sample to the capture agent, c) washing the device, and d) reading the device, thereby obtaining a measurement of the amount of the analyte in the sample. In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food. In some embodiments, the device can be placed in a microfluidic device and the applying step b) can include applying a sample to a microfluidic device comprising the device. In some embodiments, the reading step d) can include detecting a fluorescence or luminescence signal from the device. In some embodiments, the reading step d) can include reading the device with a handheld device configured to read the device. The handheld device can be a mobile phone, e.g., a smart phone. In some embodiments, the device can include a labeling agent that can bind to an analyte-capture agent complex on the device. In some embodiments, the devices, systems and methods in the present invention can further include, between steps c) and d), the steps of applying to the device a labeling agent that binds to an analyte-capture agent complex on the device, and washing the device. In any embodiment, the reading step d) can include reading an identifier for the device. The identifier can be an optical barcode, a radio frequency ID tag, or combinations thereof. In some embodiments, the devices, systems and methods in the present invention can further include applying a control sample to a control device containing a capture agent that binds to the analyte, wherein the control sample includes a known detectable amount of the analyte, and reading the control device, thereby obtaining a control measurement for the known detectable amount of the analyte in a sample. In some embodiments, the sample can be a diagnostic sample obtained from a subject, the analyte can be a biomarker, and the measured amount of the analyte in the sample can be diagnostic of a disease or a condition.

In some embodiments, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition. In some embodiments, the devices, systems and methods in the present invention can further include diagnosing the subject based on information including the measured amount of the biomarker in the sample. In some embodiments, the diagnosing step includes sending data containing the measured amount of the biomarker to a remote location and receiving a diagnosis based on information including the measurement from the remote location. In some embodiments, the biomarker can be selected from those listed in the Tables. In some embodiments, the device can contain a plurality of capture agents that each binds to a biomarker described herein, wherein the reading step d) includes obtaining a measure of the amount of the plurality of biomarkers in the sample, and wherein the amount of the plurality of biomarkers in the sample is diagnostic of a disease or condition. In some embodiments, the capture agent can be an antibody epitope and the biomarker can be an antibody that binds to the antibody epitope. In some embodiments, the antibody epitope includes a biomolecule, or a fragment thereof, selected from the Tables. In some embodiments, the antibody epitope includes an allergen, or a fragment thereof, selected from the Tables. In some embodiments, the antibody epitope includes an infectious agent-derived biomolecule, or a fragment thereof, selected from Tables. In some embodiments, the device can contain a plurality of antibody epitopes selected from the Tables, wherein the reading step d) includes obtaining a measure of the amount of a plurality of epitope-binding antibodies in the sample, and wherein the amount of the plurality of epitope-binding antibodies in the sample is diagnostic of a disease or condition.

In some embodiments, the sample can be an environmental sample, and wherein the analyte can be an environmental marker. In some embodiments, the environmental marker described herein. In some embodiments, the method can include receiving or providing a report that indicates the safety or harmfulness for a subject to be exposed to the environment from which the sample was obtained. In some embodiments, the method can include sending data containing the measured amount of the environmental marker to a remote location and receiving a report that indicates the safety or harmfulness for a subject to be exposed to the environment from which the sample was obtained. In any embodiment, the device can include a plurality of capture agents that each binds to an environmental marker described herein, and wherein the reading step d) can include obtaining a measure of the amount of the plurality of environmental markers in the sample.

In some embodiments, the sample can be a foodstuff sample, wherein the analyte can be a foodstuff marker, and wherein the amount of the foodstuff marker in the sample can correlate with safety of the foodstuff for consumption. In some embodiments, the foodstuff marker is an example described herein. In any embodiment, the method can include receiving or providing a report that indicates the safety or harmfulness for a subject to consume the foodstuff from which the sample is obtained. In any embodiment, the method can include sending data containing the measured amount of the foodstuff marker to a remote location and receiving a report that indicates the safety or harmfulness for a subject to consume the foodstuff from which the sample is obtained. In any embodiment, the device array can include a plurality of capture agents that each binds to a foodstuff marker described herein, wherein the obtaining can include obtaining a measure of the amount of the plurality of foodstuff markers in the sample, and wherein the amount of the plurality of foodstuff marker in the sample can correlate with safety of the foodstuff for consumption.

In some embodiments, the subject device is part of a microfluidic device. In some embodiments, the subject devices, systems, and methods are used to detect a fluorescence or luminescence signal. In some embodiments, the subject devices, systems, and methods include, or are used together with, a communication device, such as but not limited to:

mobile phones, tablet computers and laptop computers. In some embodiments, the subject devices, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

Various samples can be used in the assays conducted with the devices, apparatus, and systems herein described. In some embodiments, the sample comprises nucleic acids. In some embodiments, the sample comprises proteins. In some embodiments, the sample carbohydrates. The current devices, apparatus, and systems can be used to rapidly change the temperature of the sample and steadily maintain the temperature of the sample, providing a fast and cost-effective approach to process samples. In addition, various applications (e.g. assays) can be conducted with the devices, apparatus, and systems herein described. Such applications include but are not limited to diagnostic testing, health monitoring, environmental testing, and/or forensic testing. Such applications also include but are not limited to various biological, chemical, and biochemical assays (e.g. DNA amplification, DNA quantification, selective DNA isolation, genetic analysis, tissue typing, oncogene identification, infectious disease testing, genetic fingerprinting, and/or paternity testing).

In some embodiments, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

As used herein, "necessary reagents" or "reagents" include but are not limited to, primers, deoxynucleotides (dNTPs), bivalent cations (e.g. $Mg^{2+}$), monovalent cation (e.g. $K^+$), buffer solutions, enzymes, additives, and reporters. "Necessary reagents for nucleic acid amplification" or "reagents for nucleic acid amplification" can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase. Examples of suitable DNA-dependent polymerases include but not limited to Apta Taq polymerase, Kapa2G Fast polymerase, Kapa2G Robust, Z-Taq polymerase, Terra PCR Direct Polymerase, SpeedStar HS DNA polymerase, Phusion DNA polymerase, and High-Fidelity DNA polymerase.

As used herein, "additives", in some embodiments, include but not limited to, 7-deaza-2'-deoxyguanosine 7-deaza dGTP, BSA, gelatin, betaine, DMSO, formamide, Tween 20, NP-40, Triton X-100, tetramethylammonium chloride.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some other embodiments, as used herein, "necessary reagents" or "reagents" (e.g., for nucleic acid amplification reactions) can also include cell lysing reagent, which facilitates to break down cellular structures. Cell lysing reagents include but not limited to salts, detergents, enzymes, and other additives. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions. In some embodiments, for example when conducting isothermal amplification via LAMP, the sample is heated to 60-65° C. for about 1-70 min.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

As used herein, "cell lysing reagents", intend to include but not limited to salts, detergents, enzymes, and other additives, which facilitates to disrupt cellular structures. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

As used herein, "necessary reagent 2" include but not limited to, primers, deoxynucleotides (dNTPs), bivalent cations (e.g. $Mg^{2+}$), monovalent cation (e.g. $K^+$), buffer solutions, enzymes, and reporters. Necessary reagent 2 for nucleic acid amplification can be either in the dry form on the inner surface of the first or the second plate or both, or in a liquid form encased in, embedded in, or surrounded by, a material that melts with increasing temperatures, such as, for example, paraffin.

Figure 36A:
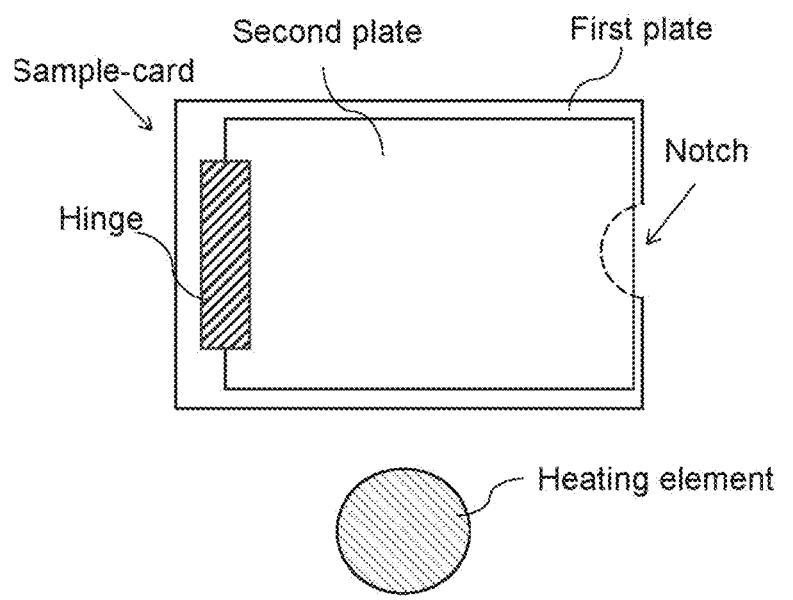
FIGS. 36A and 36B schematically illustrate a top view and side view, respectively, of a device having a separate heating element, in accordance with one or more embodiments.
Figure 36B:
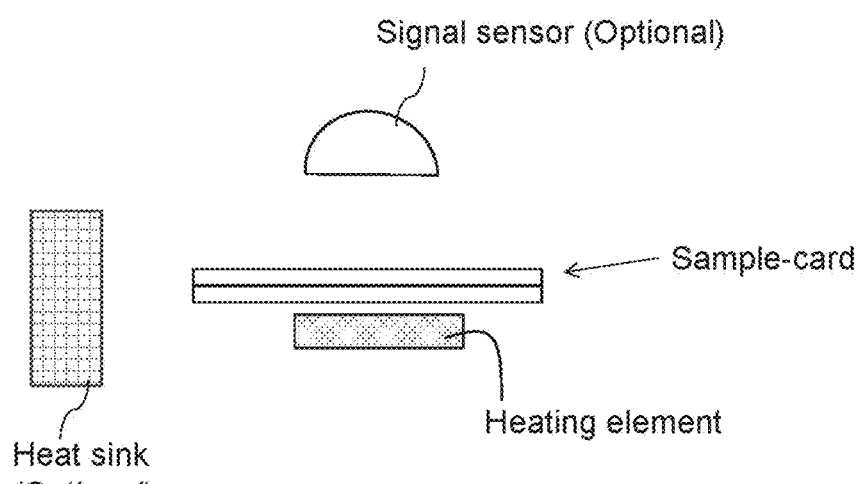
Figure 37A:
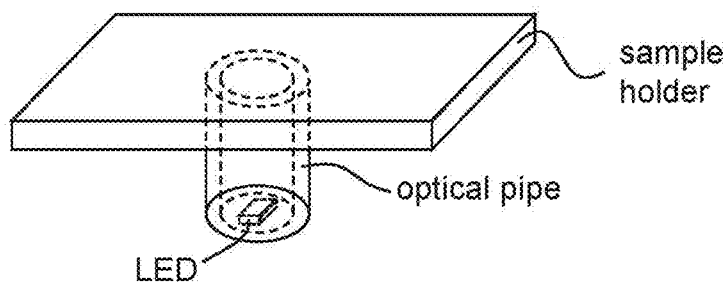
FIGS. 37A and 37B schematically illustrate a perspective view and a side view, respectively, of an optical pipe used to guide electromagnetic waves (e.g., light) from a heating source, in accordance with one or more embodiments.
Figure 37B:
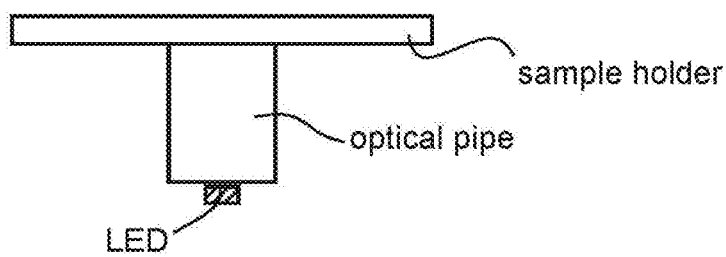

A Rapid Heating and Cooling Apparatus where a Separate Heating Element Outside QMAX-Card In some embodiments, the apparatus further comprises a separate heating element that is outside of RHC card and is configured to heat the RHC card when being placed near or in contact with the RHC card. The separate heating element is capable of attaching or detaching a RHC card, and gain energy from a heating source, in a similar fashion as the heating/cooling layer. The separate heating element allow a RHC card without a heating/cooling layer. For example, as shown in FIGS. 36A and 36B, the heating element is separate from the sample card.

The terms "CROF Card (or card)", "COF Card", "QMAX-Card", "Q-Card", "CROF device", "COF device", "QMAX-device", "CROF plates", "COF plates", and "QMAX-plates" are interchangeable and may be used to identify embodiments of the devices described herein. The term "X-plate" refers to one of the two plates in a CROF card, wherein the spacers are fixed to this plate. More descriptions of the COF Card, CROF Card, and X-plate are described in the provisional application Ser. Nos. 62/456, 065, filed on Feb. 7, 2017, which is incorporated herein in its entirety for all purposes.

A RHC card is a QMAX-care with or without spacer plus a heating/cooling layer on or inside of one of the plate.

Figure 26:
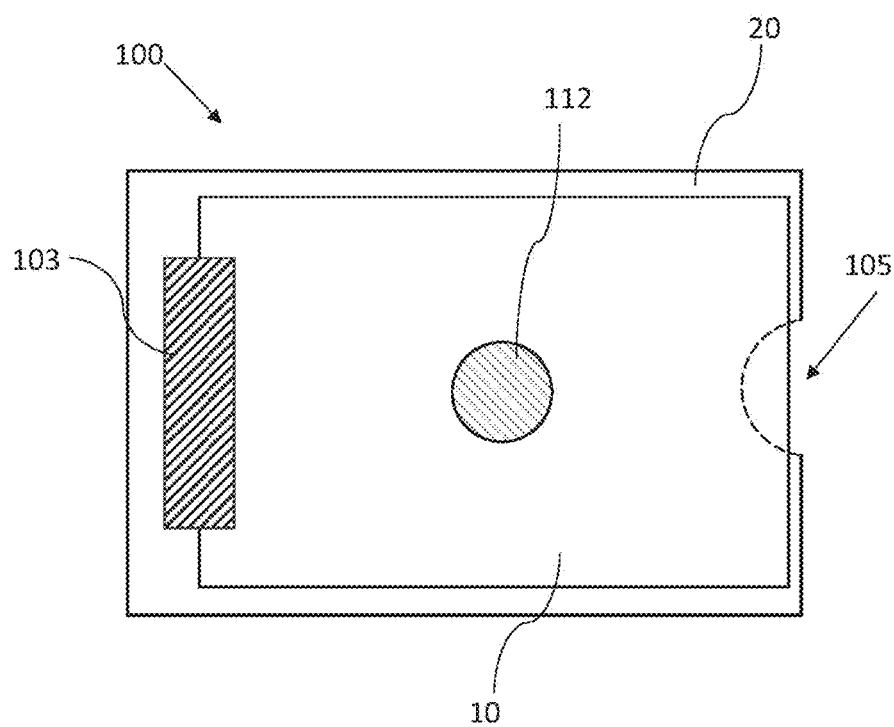
FIG. 26 schematically illustrates a top view of a device, in accordance with one or more embodiments.

FIG. 26 shows a device card 100, which comprises a first plate 10 and a second plate 20. In some embodiments, the first plate 10 and the second plate 20 are moveable against each other into different configurations, including an open configuration and a closed configuration. In certain embodiments, in the open configuration, the two plates are partially or completely separated apart and the average spacing between the plates is at least 300 um. In certain embodiments, the sample can be deposited on one or both the plates. In certain embodiments, in the closed configuration, at least part of the sample is compressed by the two plates into a layer, wherein the average sample thickness is 200 um or less.

In some embodiments, the QMAX card 100 comprises a hinge 103 that connects the first plate 10 and the second plate 20 so that the two plates can pivot against each other. In some embodiments, the QMAX card comprises a notch 105, which facilitates the switching of the card between the open configuration and the closed configuration. In some embodiments, one or both of the plates are transparent. In some embodiments, one or both of the plates are flexible. In some embodiments, the QMAX card 100 comprises a heating/cooling layer 190. In certain embodiments, the heating/cooling layer 190 is configured to absorb electromagnetic waves and convert the energy to increase the temperature of the sample.

FIGS. 25A and 25B show perspective and sectional views of an embodiment of the device of the present invention. FIG. 25A illustrates the device (also termed "sample holder" of the system) 100 in an open configuration. As shown in FIG. 25A, the sample holder 100 comprises a first plate 10, a second plate 20, and a spacing mechanism (not shown). The first plate 10 and second plate 20 respectively comprise an inner surface (11 and 21, respectively) and an outer surface (12 and 22, respectively). Each inner surface has a sample contact area (not indicated) for contacting a fluidic sample to be processed and/or analyzed by the device.

The first plate 10 and the second plate 20 are movable relative to each other into different configurations. One of the configurations is the open configuration, in which, as shown in FIG. 25A, the first plate 10 and the second plate 20 are partially or entirely separated apart, and the spacing between the first plate 10 and the second plate 20 (i.e. the distance between the first plate inner surface 11 and the second plate inner surface 21) is not regulated by the spacing mechanism. The open configuration allows a sample to be deposited on the first plate, the second plate, or both, in the sample contact area.

As shown in FIG. 25A, the second plate 20 further comprises a heating/cooling layer 112 in the sample contact area. It is also possible that the first plate 10 alternatively or additionally comprise the heating/cooling layer 112. In some embodiments, the heating/cooling layer 112 is configured to efficiently absorb radiation (e.g. electromagnetic waves) shed on it. The absorption percentage is 50% or more, 60% or more, 70% or more, 80% or more, 90% or more, 95% or more, 99% or more, 100% or less, 85% or less, 75% or less, 65% or less, or 55% or less, or in a range between any of the two values. The heating/cooling layer 112 is further configured to convert at least a substantial portion of the absorbed radiation energy into heat (thermal energy). For example, the heating/cooling layer 112 is configured to emit radiation in the form of heat after absorbing the energy from electromagnetic waves. The term "substantial portion" or "substantially" as used herein refers to a percentage that is 50% or more, 60% or more, 70% or more, 80% or more, 90% or more, 95% or more, 99% or more, 99% or more, or 99.9% or more.

FIGS. 24A and 24B illustrate the sample card in a closed configuration, where the heating/cooling layer comprises a heating zone that is directly being/to be heated by a heating source; FIG. 24A shows a prospective view and FIG. 24B shows a sectional view. In some embodiments, the heating/cooling layer comprises a heating zone that is being/to be directly heated by a heating source. In some embodiments, the heating sources emits electromagnetic radiation (waves) that, with or without modulation by lenses or other modulators, reaches the heating/cooling layer. The area that directly receives such radiation (waves) is referred to as the heating zone.

In some embodiments, the heating zone is smaller than the entire area of the heating/cooling layer. In some embodiments, the heating zone is about 1/1000, 1/500, 1/200, 1/100, 1/50, 1/20, 1/10, 1/5, 1/2, or 2/3 of the area of the heating/cooling layer, or in a range between any of the two values. In some embodiments, when the sample is loaded and compressed, by the two plates, into a thin layer, the volume of the sample directly in the path of the electromagnetic waves, or directly in contact with the area of the heating zone, is referred to as the heated volume. In some embodiments, since the sample layer is thin and/or due to the superior absorption properties of the heating/cooling layer, the sample in the heated volume can be rapidly heated to a desired temperature. In some embodiments, the sample in the heated volume can also be rapidly cooled to a desired temperature.

Biochemistry and Assays

The thermal cycler system and associated methods of the present invention can be used to facilitate a chemical, biological or medical assay or reaction. In some embodiments, the reaction requires temperature changes. In some embodiments, the reaction requires or prefers rapid temperature change in order to avoid non-specific reaction and/or reduce wait time. In certain embodiments, the system and methods of the present invention is used to facilitate a reaction that requires cyclical temperature changes for amplification of a nucleotide in a fluidic sample; such reactions include but are not limited to polymerase chain reaction (PCR). The descriptions below use PCR as an example to illustrate the capability and utilization of the thermal cycler system and method of the present invention. It is should be noted, however, some embodiments of the device, systems and method herein described also apply to other assays and/or reactions that require temperature control and change.

In some embodiments, the assays (e.g. PCR) can be conducted with a non-processed sample. For example, the template of a PCR reaction can be provided by a sample directed obtained from a subject without additional processing. In some embodiments, the sample can be whole blood from an individual. In some embodiments, such a "one-step" approach would allow for more convenient use of the devices herein described.

In some embodiments, the sample 90 is a pre-mixed reaction medium for polymerase chain reaction (PCR). For example, in certain embodiments, the reaction medium includes components such as but not limited to: DNA template, two primers, DNA polymerase (e.g. Taq polymerase), deoxynucleoside triphosphates (dNTPs), bivalent cations (e.g. $Mg^{2+}$), monovalent cation (e.g. $K^+$), and buffer solution. The specific components, the concentrations of each component, and the overall volume varies according to rational design of the reaction. In some embodiments, the PCR assay requires a number of changes/alterations in sample temperature between the following steps: (i) the optional initialization step, which requires heating the sample to 92-98° C.; (2) the denaturation step, which requires heating the sample to 92-98° C.; (3) the annealing step, which requires lowering the sample temperature to 50-65° C.; (4) extension (or elongation) step, which requires heating the sample to 75-80° C.; (5) repeating steps (2)-(4) for about 20-40 times; and (6) completion of the assay and lowering the temperature of the sample to ambient temperature (e.g. room temperature) or cooling to about 4° C. The specific temperature and the specific time period for each step varies and depends on a number of factors, including but not limited to length of the target sequence, length of the primers, the cation concentrations, and/or the GC percentage.

The thermal cycler system of the present invention provides rapid temperature change for the PCR assay. For example, referring to panels (A) and (B) of FIG. 24 and panel (B) of FIG. 25, in some embodiments, the sample 90 (e.g. pre-mixed reaction medium) is added to one or both of the plates 10 and 20 in the open configuration and the plates is switched to the closed configuration to compress the sample 90 into a thin layer which has a thickness 102 that is regulated by a spacing mechanism (not shown); the heating source 202 projects an electromagnetic wave 210 to the first plate 10 (e.g. specifically to the heating/cooling layer 112); the heating/cooling layer 112 is configured to absorb the electromagnetic wave 210 and convert at least a substantial portion of said electromagnetic wave 210 into heat, which increases the temperature of the sample; the removal of the electromagnetic wave 210 results in a temperature decrease in the sample 90.

In some embodiments, by projecting an electromagnetic wave 210 to the heating/cooling layer 112 or increasing the intensity of the electromagnetic wave, the thermal cycler systems provide rapid heating (increase temperature) for any or all of the initialization step, the denaturation step and/or the extension/elongation step; in some embodiments, with the removal of the electromagnetic wave projected from the heating source 202 or the decrease of the intensity of the electromagnetic wave, the cooling to the annealing step and/or the final cooling step is achieved with rapid speed. In some embodiments, the electromagnetic wave 210 or an increase of the intensity of the electromagnetic wave 210 creates an ascending temperature ramp rate of at least 80° C./s, 70° C./s, 60° C./s, 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average ascending temperature ramp rate in a PCR assay is 10° C./s or more. In some embodiments, the removal of the electromagnetic wave 210 or a reduction of the intensity of the electromagnetic wave 210 results in a descending temperature ramp rate of at least 80° C./s, 70° C./s, 60° C./s, 50° C./s, 45° C./s, 40° C./s, 35° C./s, 30° C./s, 25° C./s, 20° C./s, 18° C./s, 16° C./s, 1° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average descending temperature ramp rate in a PCR assay is 5° C./s or more. As used here, the term "ramp rate" refers to the speed of temperature change between two pre-set temperatures. In some embodiments, the average ascending or descending temperature to each step is different.

During a PCR, within any step after the target temperature has been reached, the sample needs to be maintained at the target temperature for a certain period of time. The thermal cycler system of the present invention provides the temperature maintenance function by (1) adjusting the intensity of the electromagnetic wave 210, lowering it if the temperature has been raised to the target or increasing it if the temperature has been decreased to the target, and/or (2) keep the target temperature by balancing the heat provided to the sample and the heat removed from the sample.

Figure 30:
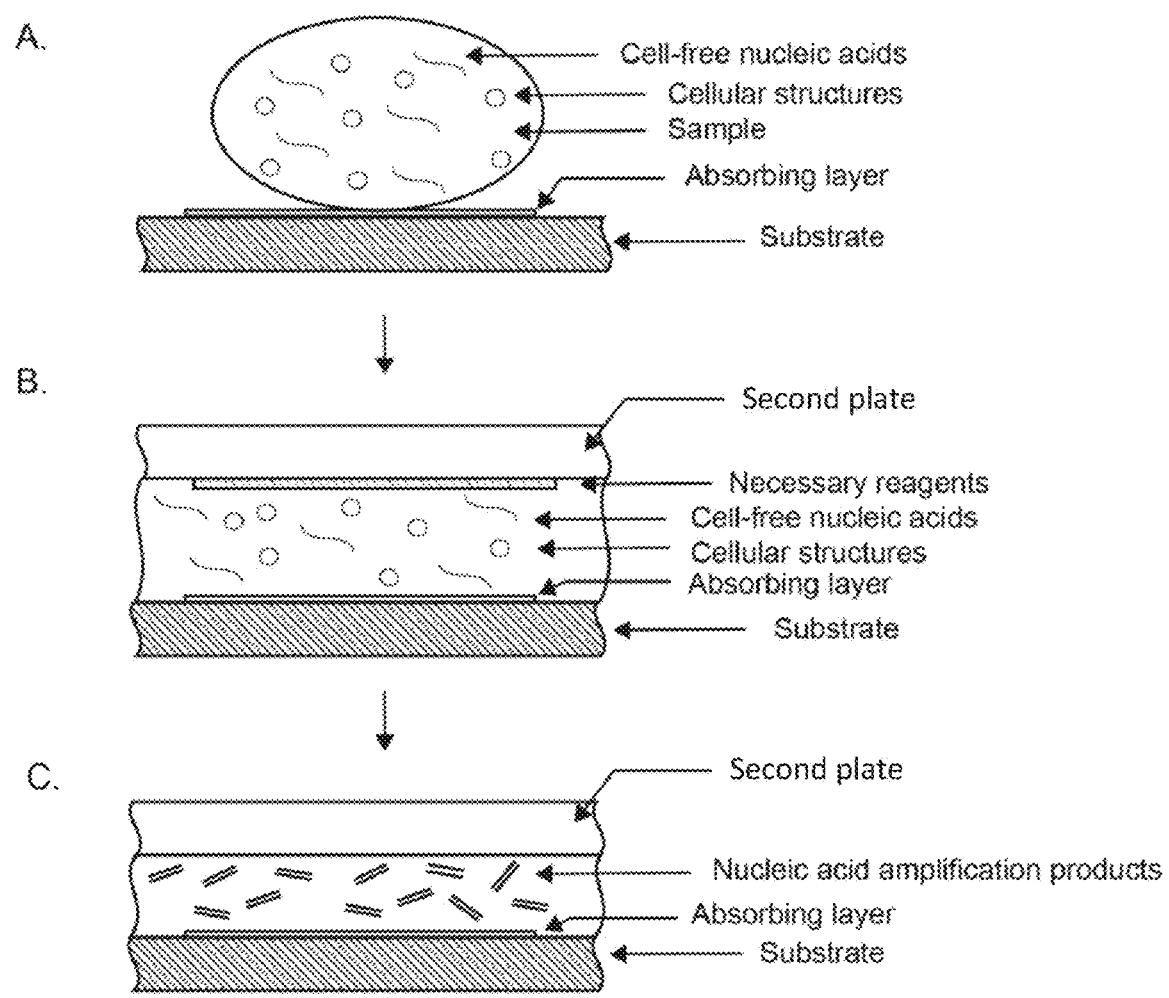
FIG. 30 schematically illustrates sectional views of a device, demonstrating how the sample is added and compressed, in accordance with one or more embodiments.

FIG. 30 illustrates a cross-sectional view of an exemplary procedure for nucleic acid amplification using a device, according to some embodiments. Examples of steps include (A) introducing sample containing nucleic acids onto the inner side of a first plate (substrate); (B) pressing a second plate onto the inner surface of the first plate to form a closed configuration of the device, where necessary reagents for nucleic acid amplification are dried on the inner surface of the second plate; (C) accumulating nucleic acid amplification products in the chamber enclosed by the first and the second plates.

The sample can be introduced onto either the first plate or the second plate, or even both when necessary. FIG. 30 herein provides an example of introducing sample onto the first plate inner surface.

More particularly, in step (B), a second plate is pressed onto the inner surface of the first plate, in contact with the sample, to form a closed configuration of the device. A "a second plate" may refer to a plate with periodic spacers on the inner surface contacting samples.

More particularly, in step (C), when the device is in the closed configuration, a heating source projects an electromagnetic wave to the heating/cooling layer on the inner or outer surface of the first plate, or the second plate or both. The heating/cooling layer is configured to absorb the electromagnetic wave and convert at least a substantial portion of the energy from the said electromagnetic wave into the form of heat, which transmitted to the sample in the closed chamber. In some embodiments, the heating source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65° C. for about 1-70 min.

Figure 31:
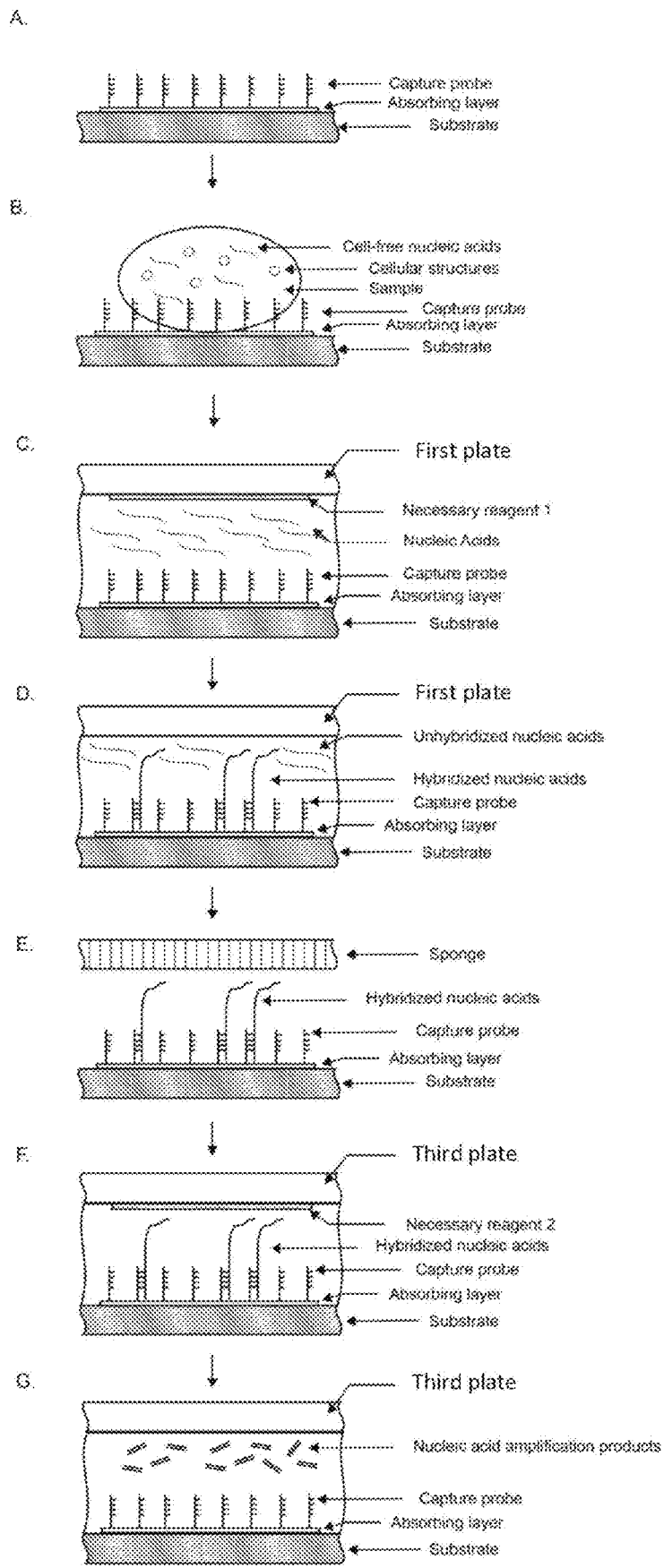
FIG. 31 schematically illustrates sectional views of a device, demonstrating a PCR process, in accordance with one or more embodiments.

FIG. 31 illustrates a cross-sectional view of an exemplary assay procedure combining nucleic acid extraction and amplification using a card device, according to some embodiments. Examples of steps include (A) immobilizing capture probes on the inner surface of a first plate (substrate); (B) introducing samples onto the inner surface of the first plate; (C) pressing a second plate onto the inner surface of the first plate to form a closed configuration of the device, where necessary reagents 1 to facilitate releasing and capturing nucleic acids are dried on the inner surface of the second plate; (D) capturing nucleic acids from the above said sample onto the inner surface of the first plate; (E) detaching the second plate and cleaning the inner surface of the first plate using sponge; (F) pressing a third plate onto the inner surface of the first plate, where necessary reagents 2 for nucleic acid amplification are dried on the inner surface of the third plate; (G) accumulating nucleic acid amplification products in the chamber enclosed by the first and the third plate.

In some embodiments, in step (a), capture probes are immobilized on the inner surface of the first plate. As used herein, "capture probes" may refer to oligonucleotides having the length between 1-200 bp, preferably between 5-50 bp, more preferably between 10-20 bp. Capture probes may have complementary sequence to nucleic acid sequences of interest in the sample. In some embodiments, identical capture probes may be immobilized on the surface of the first plate. In some other embodiments, different capture probes having different base pair compositions may be immobilized on the surface of the first plate. Capture probes can be DNA, or RNA, or both, but preferably to be single strand DNA. As used herein, "immobilize" refers to a process to anchor the capture probe on the plate surface. In some embodiments, capture probes are anchored through covalent bond, wherein, for example, either 5' or 3' end of the capture probe is modified to facilitate coating on the plate surface. Commonly used 3' end modifications include but not limited to thiol, dithiol, amine, biotin, etc. In some other embodiments, capture probes can be passively absorbed on the substrate surface.

After immobilized with capture probes, the plate surface may be blocked with blocker solutions. Suitable blockers include but not limited to 6-Mercapto-hexanol, bovine serum albumin, etc.

As shown in step (B) in FIG. 31, the "sample" can be any nucleic acid containing or not containing samples, including but not limited to human bodily fluids, such as whole blood, plasma, serum, urine, saliva, and sweat, and cell cultures (mammalian, plant, bacteria, fungi), according to some embodiments. The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The sample can be introduced onto either the first plate or the second plate, or even both when necessary. FIG. 31 herein provides an example of introducing sample onto the first plate inner surface.

In some embodiments, in step (C), a second plate is pressed onto the inner surface of the first plate (substrate), in contact with the sample, to form a closed configuration of the device. Necessary reagents 1 for nucleic acid amplification can be either in the dry form on the inner surface of the first or the second plate or both, or in a liquid form encased in, embedded in, or surrounded by, a material that melts with increasing temperatures, such as, for example, paraffin.

In some embodiments, in step (D), after in contact with the above said sample, dried necessary reagent 1 dissolves in the sample. Nucleic acids of interest, either released from disrupted cellular structures or presence as cell-free nucleic acids, or a combination thereof, hybridize to the complementary capture probes on the plate surface. Time used for hybridization varies, largely depending on the specifications of the spacers on the inner surface of the plate. In some embodiments, for example, when a plate having 30 um spacers in height is used, experimental data indicated after 2 min, hybridization between nucleic acids of interest and immobilized capture probes reached equilibrium. As used herein, "unhybridized nucleic acids" refer to nucleic acids that are not captured by the immobilized capture probes.

In some embodiments, in step (E) of FIG. 31, the second plate is detached from the first plate (substrate) and the surface of the first plate (substrate) is cleaned using sponge. As used herein, "sponge" refers to a class of flexible porous materials that change pore sizes under different pressures. Sponges containing washing buffer are in contact with the first plate surface to remove contaminates. In some embodiments, sponges are in contact with the first plate surface for one time. In some other embodiments, sponges are in contact with the first plate surface for twice, or more than twice. As used herein, "contaminates" refer to compounds including but not limited to cell debris, proteins, non-specific nucleic acid, etc. that are detrimental to the nucleic acid amplification reaction.

In some embodiments, in step (F) of FIG. 31, a third plate (QMAX card 2) is pressed onto the inner surface of the first plate, in contact with the sample, to form a closed configuration of the device. Necessary reagent 2 for nucleic acid amplification can be either in the dry form on the inner surface of the first or the third plate or both, or in a liquid form encased in, embedded in, or surrounded by, a material that melts with increasing temperatures, such as, for example, paraffin.

In some embodiments, in step (G) of FIG. 31, when the device is in the closed configuration, a heating source projects an electromagnetic wave to the heating/cooling layer on the inner or outer surface of the first plate, or the third plate or both. The heating/cooling layer is configured to absorb the electromagnetic wave and convert at least a substantial portion of the energy from the said electromagnetic wave into the form of heat, which transmitted to the sample in the closed chamber. In some embodiments, the heating source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65 oC for about 1-70 min.

In some embodiments, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be 1/1000, 1/100, 1/100, 1/5, 1/2 of the spacer height or in a range of any two values, and in either protrusion or well form.

Multiplexing

Figure 29A:
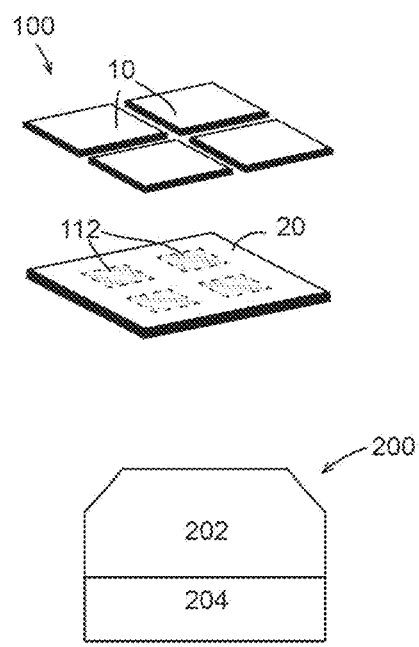
FIGS. 29A and 29B schematically illustrates a perspective view and a sectional view, respectively, of the device having multiple sample contact areas, according to some embodiments.
Figure 29B:
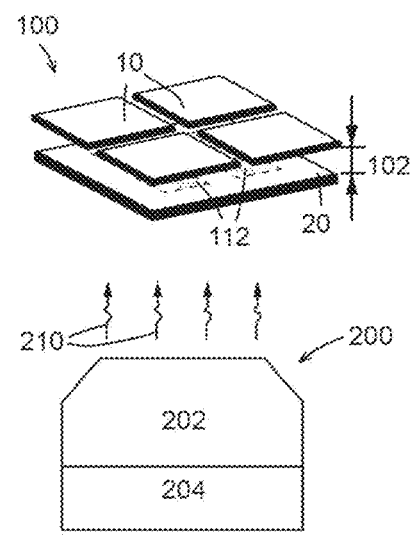

FIGS. 29A and 29B show perspective views of a sample holder 100 in an open configuration (FIG. 29A) and a closed configuration (FIG. 29B), where there are multiple sample contact areas on the plates, allowing the processing and analysis of multiple samples. As shown in FIGS. 29A and 29B, the thermal cycler system of the present invention comprises a sample holder 100 and a thermal control unit 200; the sample holder 100 comprises a plurality of first plates 10, a second plate 20, and a plurality of spacing mechanisms (not shown); the thermal control unit 200 comprises a heating source 202 and a controller 204.

Referring to FIG. 29A, one or both of the plates (e.g. the second plate 20) comprises a plurality of sample contact areas (not marked). In some embodiments, one or both of the plates (e.g. the second plate 20) comprises a plurality of heating/cooling layers 112. FIG. 29A shows the sample holder 100 in an open configuration, in which the first plates 10 and the second plate 20 are partially or entirely separated apart, allowing the deposition of one or more samples on one or both of the plates. In the open configuration, the spacing between the first plates 10 and the second plate 20 is not regulated by the spacing mechanisms.

FIG. 29B shows the sample holder 100 in a closed configuration, in which the inner surfaces of the two plates face each other and the spacing 102 between the two plates are regulated by the spacing mechanism (not shown). If one or more samples have been deposited on the plates, the plates are configured to compress each sample into a layer, the thickness of the layer is regulated by the spacing mechanism.

As shown in FIG. 29B, a plurality of first plates 10 is used to cover part of the second plate 20. For example, each first plate 10 covers a single sample contact area, onto which a sample is deposited. A spacing mechanism is present for each sample contact area and the spacing mechanisms have different heights, resulting in different spacing 102 for each sample contact area and for different thickness for each sample layer. For example, the spacing mechanism is pillar shaped spacers; each sample contact area has a set of spacers having a uniform height; different sets of spacers have the same or different heights, resulting in same or different sample layer thickness for the different samples.

Referring to FIGS. 29A and 29B, in some embodiments, the controller 204 directs the heating source 202 to project an electromagnetic wave 210 to the second plate 20 (and thus the heating/cooling layer 112), where the electromagnetic wave 210 is absorbed by the heating/cooling layer 112 and converted to heat, resulting in change of temperature in the samples. In some embodiments, when there are multiple sample contact areas, multiple samples are processed and analyzed. For example, in certain embodiments each of the sample is a pre-mixed PCR reaction medium having different components. One sample holder 100 is used to test different conditions for amplifying the same nucleotide and/or amplifying different nucleotides with the same or different conditions.

Additional Exemplary Embodiments

AAA-1.1 A device for rapidly changing the temperature of a fluidic sample, comprising:
a first plate (10), a second plate (20), a heating layer (112-1), and a cooling layer (112-2), wherein:
each of the first plate and the second plate has, on its respective inner surface, a sample contact area for contacting a fluidic sample; wherein the sample contact areas face each other, are separated by an average separation distance of 200 um or less between them, and are capable of contacting the sample and sandwiching the sample between them; the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger; and
wherein, in some embodiments, the heating layer and cooling layer are the same material layer that has a heating zone and a cooling zone, and wherein the heating zone and cooling zone can have the same area or different areas.

AAA-1.2 A device for rapidly changing the temperature of a fluidic sample, comprising:
A first plate (10), a second plate (20), a heating layer (112-1), and a cooling layer (112-2), wherein:
each of the first plate and the second plate has, on its respective inner surface, a sample contact area for contacting a fluidic sample; wherein the sample contact areas face each other, are separated by an average separation distance of 200 um or less from each other, and are capable of contacting the sample and sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger; and
wherein, in some embodiments, the heating layer and cooling layer are the same material layer that has a heating zone and a cooling zone, and wherein the heating zone and cooling zone can have the same area or different areas.

AAA-1.3 A device for rapidly changing the temperature of a fluidic sample, comprising:
a first plate (10), a second plate (20), a heating layer (112-1), and a cooling layer (112-2), wherein:
the first and second plates are movable relative to each other into different configurations;
each of the first plate and the second plate has, on its respective inner surface, a sample contact area for contacting a fluidic sample; wherein the sample contact areas face each other, are separated by an average separation distance of 200 um or less, and are capable of sandwiching the sample between them;
the heating layer is:
positioned on the inner surface, the outer surface, or inside of one of the plates, and
configured to heat a relevant volume of the sample, wherein the relevant volume of the sample is a portion or an entirety of the sample that is being heated to a desired temperature; and
the cooling layer is:
positioned on the inner surface, the outer surface, or inside of one of the plates; and
configured to cool the relevant sample volume; and
comprises a layer of material that that has a thermal conductivity to thermal capacity ratio of 0.6 cm$^2$/sec or larger;
wherein the distance between the cooling layer and a surface of the relevant sample volume is zero or less than a distance that is configured to make the thermal conductance per unit area between the cooling layer and the surface of the relevant sample volume equal to 70 W/(m$^2$·K) or larger;
wherein one of the configurations is an open configuration, in which: the two plates are partially or completely separated apart and the average spacing between the plates is at least 300 um;
wherein another of the configurations is a closed configuration which is configured after the fluidic sample is deposited on one or both of the sample contact areas in the open configuration; and in the closed configuration: at least part of the sample is confined by the two plates into a layer, wherein the average sample thickness is 200 um or less; and
wherein, in some embodiments, the heating layer and cooling layer are the same material layer that has a heating zone and a cooling zone, and wherein the heating zone and cooling zone can have the same area or different areas.

AAA-1.4 A device for rapidly changing the temperature of a fluidic sample, comprising:
a first plate (10), a second plate (20), spacers, a heating layer (112-1), and a cooling layer (112-2), wherein:
the first and second plates are movable relative to each other into different configurations;
each of the first plate and the second plate has, on its respective inner surface, a sample contact area for contacting a fluidic sample; wherein the sample contact areas face each other, are separated by an average separation distance of 200 um or less between them, and are capable of contacting the sample and sandwiching the sample between them;

one or both of the plates comprise the spacers and the spacers are fixed on the inner surface of a respective plate;

the spacers have a predetermined substantially uniform height that is equal to or less than 200 microns, and the inter-spacer-distance is predetermined;

the heating layer is:

positioned on the inner surface, the outer surface, or inside of one of the plates, and configured to heat a relevant volume of the sample, wherein the relevant volume of the sample is a portion or an entirety of the sample that is being heated to a desired temperature; and the cooling layer is:

positioned on the inner surface, the outer surface, or inside of one of the plates; and configured to cool the relevant sample volume; and comprises a layer of material that that has a thermal conductivity to thermal capacity ratio of 0.6 cm²/sec or larger;

wherein the distance between the cooling layer and a surface of the relevant sample volume is zero or less than a distance that is configured to make the thermal conductance per unit area between the cooling layer and the surface of the relevant sample volume equal to 70 W/(m²·K) or larger;

wherein one of the configurations is an open configuration, in which: the two plates are partially or completely separated apart, the spacing between the plates is not regulated by the spacers, and the sample is deposited on one or both of the plates; and wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers; and wherein, in some embodiments, the heating layer and cooling layer are the same material layer that has a heating zone and cooling zone, and wherein the heating zone and cooling zone can have the same area or different areas.

AAA-1.5 A device for rapidly changing the temperature of a fluidic sample, comprising:

a first plate (10), a second plate (20), and a heating/cooling layer (112), wherein:

the first plate (10) and the second plate (20) face each other, and are separated by a distance from each other;

each of the plates has, on its respective inner surface (11, 21), a sample contact area for contacting a fluidic sample; wherein the sample contact areas are facing each other, are in contact with the sample, sandwich a sample between them, and have an average separation distance (102) from each other, the heating/cooling layer (112) is on the outer surface (22) of the second plate (20);

and the heating/cooling layer is configured to comprise a heating zone and a cooling zone; wherein the heat zone is configured to heat the fluidic sample, the cooling zone is configured to cool the sample significantly by thermal radiative cooling;

wherein the heating zone is configured to receive a heating energy from a heating source and to have an area smaller than the total area of the heating/cooling layer; and wherein at least a part of a heating zone of the heating layer overlaps with the sample area.

AAA-1.6 A device for rapidly changing the temperature of a fluidic sample, comprising:

a first plate (10), a second plate (20), and a heating/cooling layer (112), wherein:

each of the first plate (10) and the second plate (20) has, on its respective inner surface (11, 21), a sample contact area for contacting a fluidic sample; wherein the sample contact areas are facing each other, are separated by an average separation distance (102) from each other, and are capable of contacting the sample and sandwiching the sample between them;

the heating/cooling layer (112) has a thermal conductivity of 50 W/(m·K) or larger and is on the outer surface (22), on the inner surface, or inside of the second plate (20); and the heating/cooling layer is configured to comprise a heating zone and a cooling zone; wherein the heating zone is configured to heat a portion of the sample and have an area smaller than the total area of the heating/cooling layer, and wherein the cooling zone is configured to cool the sample;

wherein the heating zone, the second plate, and the portion of the sample are configured to have a scaled thermal conduction ratio (STC ratio) of 2 or larger;

wherein the heating zone is configured to receive a heating energy from a heating source; and wherein at least a part of the heating zone of the heating layer overlaps with the sample area.

AAA-1.7 A device for rapidly changing the temperature of a fluidic sample, comprising:

a first plate (10), a second plate (20), and a heating/cooling layer (112), wherein:

each of the plates has, on its respective inner surface (11, 21), a sample contact area for contacting a fluidic sample; wherein the sample contact areas are facing each other, are in contact with the sample, sandwich the sample between them, and have an average separation distance (102) from each other;

the heating/cooling layer (112) has a thermal conductivity of 50 W/(m·K) or larger and is on the outer surface (22), on the inner surface, or inside of the second plate (20); and the heating/cooling layer is configured to comprise a heating zone and a cooling zone; wherein the heating zone is configured to heat a portion of the sample and have an area smaller than the total area of the heating/cooling layer, and wherein the cooling zone is configured to cool the sample;

wherein the heating zone, the second plate, and the portion of the sample are configured to have a scaled thermal conduction ratio (STC ratio) of 2 or larger;

wherein the heating/cooling layer has a thermal conductivity multiplying its thickness in the range of $6 \times 10^{-5}$ W/K to $3 \times 10^{-4}$ W/K.

wherein the heating zone is configured to receive a heating energy from a heating source; and wherein at least a part of the heating zone of the heating layer overlaps with the sample area.

AAA-2.1. The device of any prior embodiments, wherein the heating layer is configured to be heated by a heating source.

AAA-2.2. The device of any prior embodiments, wherein the heating layer is the same layer as the cooling layer, and the same layer comprises a heating zone area and a cooling zone area.

AAA-2.3. The device of any prior embodiments, wherein the heating layer (i.e. the heating zone) has an area smaller than the cooling layer (i.e. cooling zone).

AAA-2.4. The device of any prior embodiments, wherein the heating layer (i.e., the heating zone) has an area that is about 1/100, 1/50, 1/20, 1/10, 1/8, 1/6, 1/5, 1/4, 1/3, 1/2, 2/3, 3/4 or 5/6 of the cooling layer (i.e. cooling zone) area, or in a range between any of the two values.

AAA-2.5. The device of any prior embodiments, wherein the distance between the cooling layer and a surface of the relevant sample volume is zero or less than a distance that is configured to make the thermal conductance per unit area between the cooling layer and the surface of the relevant sample volume equal to 150 $W/(m^2 \cdot K)$ or larger.

AAA-2.6. The device of any prior embodiments, wherein the heating layer comprises metallic plasmonic materials, metamaterials, black silicon, graphite, carbon nanotube, silicon sandwich, graphene, or superlattice, or a combination thereof.

AAA-2.7. The device of any prior embodiments, wherein the heating layer comprises Al, Ag, or Au, with or without a paint layer.

AAA-2.8. The device of any prior embodiments, wherein the heating layer has a thermal conductance per unit area that is equal to or larger than 1000 $W/(m^2 \cdot K)$, 2000 $W/(m^2 \cdot K)$, 3000 $W/(m^2 \cdot K)$, 4000 $W/(m^2 \cdot K)$, 5000 $W/(m^2 \cdot K)$, 7000 $W/(m^2 \cdot K)$, 10000 $W/(m^2 \cdot K)$, 20000 $W/(m^2 \cdot K)$, 50000 $W/(m^2 \cdot K)$, 50000 $W/(m^2 \cdot K)$, 100000 $W/(m^2 \cdot K)$, or in range between any of the two values.

AAA-2.9. The device of any prior embodiments, wherein the heating layer has a thermal conductance per unit area that is in a range of 1000 $W/(m^2 \cdot K)$ to 2000 $W/(m^2 \cdot K)$, 2000 $W/(m^2 \cdot K)$ to 4000 $W/(m^2 \cdot K)$, 4000 $W/(m^2 \cdot K)$ to 10,000 $W/(m^2 \cdot K)$, or 10000 $W/(m^2 \cdot K)$ to 100000 $W/(m^2 \cdot K)$.

AAA3.1 The device of any prior embodiments, wherein the cooling layer has a thermal conductance per unit area that is equal to or larger than 1000 $W/(m^2 \cdot K)$, 2000 $W/(m^2 \cdot K)$, 3000 $W/(m^2 \cdot K)$, 4000 $W/(m^2 \cdot K)$, 5000 $W/(m^2 \cdot K)$, 7000 $W/(m^2 \cdot K)$, 10000 $W/(m^2 \cdot K)$, 20000 $W/(m^2 \cdot K)$, 50000 $W/(m^2 \cdot K)$, 50000 $W/(m^2 \cdot K)$, 100000 $W/(m^2 \cdot K)$, or in range between any of the two values.

AAA-3.2. The device of any prior embodiments, wherein the cooling layer has a thermal conductance per unit area that is in a range of 1000 $W/(m^2 \cdot K)$ to 2000 $W/(m^2 \cdot K)$, 2,000 $W/(m^2 \cdot K)$ to 4,000 $W/(m^2 \cdot K)$, 4,000 $W/(m^2 \cdot K)$ to 10,000 $W/(m^2 \cdot K)$, or 10,000 $W/(m^2 \cdot K)$ to 100,000 $W/(m^2 \cdot K)$.

AAA-3.3 The device of any prior embodiments, wherein the cooling layer cools the relevant sample primarily by thermal radiative cooling.

AAA-3.4 The device of any prior embodiments, wherein the cooling of the relevant sample through thermal radiative cooling is larger than the cooling through thermal conduction cooling in the direction lateral to the plates.

AAA-3.5 The device of any prior embodiments, wherein the cooling of the sample through thermal radiative cooling is at least 1.2 times, 1.5 times, 2 times, 5 times, 10 times, times, 50 times, 100 times, 200 times, 500 times, or 1000 times larger than the cooling through thermal conduction cooling, or in a range between any of the two values.

AAA4.1 The device of any prior embodiments, wherein the heating layer or the cooling layer has a thickness that is about 0.1 um, 0.2 um, 0.5 um, 1 um, 2 um, 5 um, 10 um, um, 30 um, 40 um, 50 um, 100 um, 200 um, 500 um, 1 mm, 2 mm, 5 mm, 10 mm, 20 mm, or 50 mm, or in a range between any of the two values.

AAA4.2 The device of any prior embodiments, wherein the heating layer or the cooling layer has an area that is less than 0.01 $mm^2$, 0.02 $mm^2$, 0.05 $mm^2$, 0.1 $mm^2$, 0.2 $mm^2$, 0.5 $mm^2$, 1 $mm^2$, 2 $mm^2$, 5 $mm^2$, 10 $mm^2$, 20 $mm^2$, 50 $mm^2$, 100 $mm^2$, 200 $mm^2$, 500 $mm^2$, or 1000 $mm^2$, or in a range between any of the two values.

AAA4.3 The device of any prior embodiments, wherein the heating layer or the cooling layer has an area dimension that is about 1 mm, 2 mm, 3 mm, 5 mm, 6 mm, 7 mm, 8 mm, 9 mm 10 mm, 12 mm, or 15 mm, or in a range between any two values.

AAA4.4 The device of any prior embodiments, wherein the heating layer or the cooling layer comprises metallic plasmonic materials, metamaterials, black silicon, graphite, carbon nanotube, silicon sandwich, graphene, or superlattice, or a combination thereof . . .

AAA5.1 The device of any prior embodiments, wherein the heating layer and the cooling layer are structurally separate layers, the heating layer has a heating zone, and the cooling layer has a cooling zone.

AAA6.1 The device of any prior embodiments, wherein the ratio of the cooling zone area to the heating zone area is larger than 1, 1.5, 2, 2.5, 3, 5, 10, 15, 20, 25, 50, 75, 100, 200, 500, or 1000, or in a range between any of the two values.

AAA6.2 The device of any prior embodiments, wherein the cooling zone area is larger than the lateral area of the relevant sample volume by a factor that is equal to or large than 1.2 times, 1.5 times, 2 times, 5 times, 10 times, 20 times, 50 times, 100 times, 200 times, 500 times, or 1000 times larger than the cooling through thermal conduction cooling, or in a range between any of the two values.

AAA6.3 The device of any prior embodiments, wherein the cooling of the device has a thermal radiation cooling that, during a thermal cycling, is equal to or larger than 50%, 55%, 60%, 65%, 70%, 75%, 80%, 85%, 90%, 95%, or 99% of the total cooling or in a range between any of the two values, wherein the total cooling is the sum of radiative cooling and conductive cooling.

AAA6.4 The device of any prior embodiments, wherein the cooling of the device by thermal radiation through a high K cooling layer, during a thermal cycling, is equal to or larger than.60%, 65%, 70%, 75%, 80%, 85%, 90%, 95%, or 99% of the total cooling or in a range between any of the two values, wherein the total cooling is the sum of radiative cooling and conductive cooling.

AAA7.1 The device of any prior embodiments, wherein at least one of the plates is flexible.

AAA8.1 The device of any prior embodiments, wherein the device comprises spacers that regulate the thickness of the sample when the sample is confined by the two plates into a thin layer.

AAA8.2 The device of any prior embodiments, wherein the spacers has an inter-spacer-distance (ISD), and wherein the fourth power of the inter-spacer-distance (ISD) divided by the thickness (h) and the Young's modulus (E) of the flexible plate ($ISD4/(hE)$) is $5 \times 10^6$ $um^3/GPa$ or less.

AAA8.3. The device of any prior embodiments, wherein the spacers has a contact filling factor, wherein the product of the contact filling factor and the Young's modulus of the spacers is 2 MPa or larger, and wherein the contact filling factor is, in the sample contact area, the ratio of the contact area between spacer and the plate to the total plate area.

AAA8.4. The device of any prior embodiments, wherein the spacers are in the sample contact area.

AAA8.5. The device of any prior embodiments, wherein the spacers have a shape of the pillars with substantially flat top.

AAA8.6. The device of any prior embodiments, wherein the spacers are fixed on either one or both of the plates.

AAA8.7. The device of any prior embodiments, wherein the spacers have a uniform height.

AAA8.8. The device of any prior embodiments, wherein the thickness of the sample is the same as the height of the spacers.

AAA9.1 The device of any prior embodiments, wherein the heating layer and/or the cooling layer is on the inner surface of one of the plates.

AAA9.2 The device of any prior embodiments, wherein the heating layer and/or the cooling layer is on the outer surface of one of the plates.

AAA9.3 The device of any prior embodiments, wherein the heating layer and the cooling layer are separate, the heating layer is on the outer surface of one of the plates, and the cooling layer is on the outer surface of the other plate.

AAA9.4 The device of any prior embodiments, wherein the heating layer and the cooling layer are separate, the heating layer is on the inner surface of one of the plates, and the cooling layer is on the inner surface of the other plate.

AAA9.5 The device of any prior embodiments, wherein the heating layer and the cooling layer are separate, the heating layer is on the inner or outer surface of one of the plates, and the cooling layer is on the inner or outer surface of the other plate.

AAA9.6 The device of any prior embodiments, wherein the heating layer and the cooling layer are inside one or both of the plates.

AAA9.7 The device of any prior embodiments, wherein the heating zone and the cooling zone are partly overlapping on the heating and/or cooling layer.

AAA10.1 The device of any prior embodiments, wherein the first plate or the second plate has a thickness that is less than 10 nm, 100 nm, 200 nm, 500 nm, 1000 nm, 2 μm (micron), 5 μm, 10 μm, 20 μm, 50 μm, 100 μm, 150 μm, 200 μm, 300 μm, 500 μm, 800 μm, 1 mm (millimeter), 2 mm, 3 mm, 5 mm, 10 mm, 20 mm, 50 mm, 100 mm, 500 mm, or in a range between any two of these values.

AAA10.2 The device of any prior embodiments, wherein the first plate or the second plate has an lateral area that is less than 1 mm$^2$ (square millimeter), 10 mm$^2$, 25 mm$^2$, 50 mm$^2$, 75 mm$^2$, 1 cm$^2$ (square centimeter), 2 cm$^2$, 3 cm$^2$, 4 cm$^2$, 5 cm$^2$, 10 cm$^2$, 100 cm$^2$, 500 cm$^2$, 1000 cm$^2$, 5000 cm$^2$, 10,000 cm$^2$, 10,000 cm$^2$, or in a range between any two of these values.

AAA10.3 The device of any prior embodiments, wherein the first plate or the second plate comprises acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

AAA10.3.1 The device of any prior embodiments, wherein the first plate or the second plate comprises PMMA.

AAA10.4 The device of any prior embodiments, wherein the plates are thermal-isolated from a structure that accommodate the plates.

AAA11.1 The device of any prior embodiments, wherein the relevant sample has a volume that is about 0.01 ul, 0.02 ul, 0.05 ul, 0.1 ul, 0.2 ul, 0.5 ul, 1 ul, 2 ul, 5 ul, 10 ul, 20 ul, 50 ul, 100 ul, 200 ul, 500 ul, 1 ml, 2 ml, 5 ml, 10 ml, 20 ml, or 50 ml, or in a range between any of the two values.

AAA11.2 The device of any prior embodiments, wherein ratio of the lateral average dimension of the relevant sample area to the sample thickness is greater than 1, 2, 3, 4, 5, 6, 7, 8, 9, 10, 20, 30, 40, 50, 60, 70, 80, 90,100,200, 500, 1000, 2000, 5000, 100,000, or in a range between any of the two values.

AAA12.1 The device of any prior embodiments, wherein the plates are configured to be operable directly by human hands.

AAA12.2 The device of any prior embodiments, wherein the plates are configured to be compressed directly by human hands with imprecise force, which is neither set to a precise level nor substantially uniform.

AAA12.3 The device of any prior embodiments, further comprising a hinge, which connects the first plate and the second plate and allows the two plates to pivot against each other into different configurations.

AAA12.4 The device of any prior embodiments, wherein at least one of the plates comprises one or more open notches on an edge or corners of the plate, and the notch(es) facilitates changing the plates between different configurations.

AAA12.5 The device of any prior embodiments, wherein at least one of the plates comprises one or more open notches on an edge or corners of the plate, and the notch(es) facilitates changing the plates from a configuration that is near or at closed configuration to an open configuration.

AAA13.1. A sample cartridge, comprising the device of any prior embodiments, and a sample support that is configured to support the device.

AAA13.2. The sample cartridge of any prior embodiments, wherein the sample support comprises one or more apertures that allow energy to reach the heating layer.

AAA14.1 An apparatus for rapidly changing temperature of a fluidic sample, comprising:
the device of any prior embodiments;
a heating source that is configured to supply energy to the device.

AAA14.2 The apparatus of any prior embodiments, wherein the heating source is configured to radiate electromagnetic waves in a range of wavelength that the heating/cooling layer has an absorption coefficient of 50% or higher.

AAA14.3. The apparatus of any prior embodiments, wherein the heating source comprises one or an array of light-emitting diodes (LEDs), one or an array of lasers, one or an array of lamps, or a combination of thereof.

AAA14.4. The apparatus of any prior embodiments, wherein the heating source comprises halogen lamp, halogen lamp with reflector, LED with focusing lens, laser with focusing lens, halogen lamp with coupling optical fiber, LED with coupling optical fiber, laser with coupling optical fiber.

AAA14.5 The apparatus of any prior embodiments, further comprising an optical pipe between the heating source and the device, wherein the optical pipe is configured to guide the energy from the heating source to the heating layer.

AAA15.1 An apparatus for rapidly changing temperature of a fluidic sample, comprising:
the device of any prior embodiments; and
an adaptor that is configured to accommodate the device.

AAA15.2 The apparatus of any prior embodiments, wherein the adaptor comprises a sample slot that is configured to accommodate the device and position the device to receive the electromagnetic waves from the heating source.

AAA15.3 The apparatus of any prior embodiments, wherein adaptor comprises a slider that is configured to allow the device to slide into the sample slot.

AAA16.1 An apparatus for rapidly changing temperature of a fluidic sample, comprising:
the device of any prior embodiments;
a heating source that is configured to supply energy the device; and
a control unit that is configured to control the heating unit.

AAA16.2 The apparatus of any prior embodiments, wherein the control unit is configured to control electromagnetic waves from the heating source.

AAA16.3 The apparatus of any prior embodiments, wherein the control unit is configured to control the presence, intensity, wavelength, frequency, and/or angle of the electromagnetic waves.

AAA16.2 The apparatus of any prior embodiments, wherein the control unit comprises a temperature sensor that is configured to detect the temperature of the sample.

A16.2.1 The apparatus of any prior embodiments, wherein the control unit controls the energy supplied by the heating source based on the temperature detected by the temperature sensor.

AAA17.1. A system for rapidly changing temperature of a fluidic sample, comprising:
a device of any prior embodiments;
a heating source that is configured to emit electromagnetic waves that can be received by the device; and
a control unit, which is configured to control heating and cooling of the sample, at least in part by changing the electromagnetic waves from the heating source.

AAA17.2 The system of any prior embodiments, further comprising an adaptor that is configured to accommodate the device.

AAA17.3 The system of any prior embodiments, further comprising an optical pipe that is configured to guide the electromagnetic waves from the heating source to the device.

AAA17.4 The system of any prior embodiments, further comprising a signal sensor that is configured to detect a signal from the sample.

AAA17.4.1. The system of any prior embodiments, wherein the signal sensor is an optical sensor that is configured to image the fluidic sample.

AAA18.1 A kit for rapidly changing temperature of a fluidic sample, comprising: a device of any prior embodiments; and reagents that configured to facilitate a chemical/biological reaction.

AAA18.2 The kit of any prior embodiments, wherein the reagents are configured for nucleic acid amplification:

AAA18.3 The kit of any prior embodiments, wherein the reagents comprises a pre-mixed polymerase chain reaction (PCR) medium:

AAA18.4 The kit of any prior embodiments, wherein the reagents are configured to detect nucleic acids by amplifying (generating numerous copies of) the target molecules in samples, wherein target molecule refers to a sequence, or partial sequence, of nucleic acid of interest.

AAA18.5 The kit of any prior embodiments, wherein the reagents comprise: primers, deoxynucleotides (dNTPs), bivalent cations (e.g. $Mg^{2+}$), monovalent cation (e.g. $K^+$), buffer solutions, enzymes, or reporters, or any combination or mixture thereof.

AAA18.6 The kit of any prior embodiments, wherein the reagents are either in the dry form on the inner surface of the first or the second plate or both, or in a liquid form encased in, embedded in, or surrounded by, a material that melts with increasing temperatures, such as, for example, paraffin.

AAA18.7 The kit of any prior embodiments, wherein the reagents comprise DNA-dependent polymerase, or RNA-dependent DNA polymerase, or DNA-dependent RNA polymerase.

AAA18.8 The kit of any prior embodiments, wherein the reagents comprise "reporters" that refer to any tag, label, or dye that can bind to, or intercalate within, the nucleic acid molecule or be activated by byproducts of the amplification process to enable visualization of the nucleic acid molecule or the amplification process.

AAA18.9 The kit of any prior embodiments, wherein the reagents comprise cell lysing reagent, which is configured to facilitate breaking down cellular structures.

AAA19.1 The device, apparatus, system, and/or kit of any prior embodiments, wherein the heating layer and/or the cooling layer are attached to the first plate and/or the second plate by e-beam evaporation.

AAA19.2. The device, apparatus, system, and/or kit of any prior embodiments, wherein the heating layer and/or the cooling layer comprise gold and the gold is attached to the first plate and/or the second plate by e-beam evaporation.

AA1. A device for rapidly changing a fluidic sample temperature, comprising:
a first plate, a second plate, and a heating/cooling layer, wherein:
the plates are movable relative to each other into different configurations;
each of the plates has, on its respective inner surface, a sample contact area for contacting a fluidic sample, and the heating/cooling layer is configured to heat the fluidic sample;
wherein the heating/cooling layer is (a) on (either the inner or outer surface) or inside one of the plates, and (b) capable of being heated by a heating source, wherein the heating source delivers heat energy to the heating/cooling layer optically, electrically, by radio frequency (RF) radiation, or a combination thereof;
wherein at least a part of a heating area of the heating/cooling layer overlaps with the sample area,
wherein one of the configurations is an open configuration, in which: the two plates are partially or completely separated apart and the average spacing between the plates is at least 300 um; and
wherein another of the configurations is a closed configuration which is configured after the fluidic sample is deposited on one or both of the sample contact areas in the open configuration; and in the closed configuration: at least part of the sample is compressed by the two plates into a layer, wherein the average sample thickness is 200 um or less.

AA2.1 A device for rapidly changing temperature of a fluidic sample, comprising:
a sample holder and a heating/cooling layer, wherein:
the sample holder comprises a first plate and a second plate, wherein each of the plates comprises, on its respective surface, a sample contact area for contacting the fluidic sample;

the first plate and the second plate are configured to confine the fluidic sample into a layer of highly uniform thickness of 0.1-200 um and substantially stagnant relative to the plates; and the heating/cooling layer: (1) has a thickness of less than 1 mm, (2) has an area that is substantially less than the area of either the first or the second plate, and (3) is configured to convert energy from electromagnetic waves into heat to raise the temperature of at least part of the fluidic sample in the layer of uniform thickness.

AA2.2 A device for rapidly changing temperature of a fluidic sample, comprising:

a sample holder and a heating/cooling layer, wherein:

the sample holder comprises a first plate and a second plate, wherein each of the plates comprises, on its respective surface, a sample contact area for contacting the fluidic sample;

the first plate and the second plate are configured to confine at least part of the sample into a layer of highly uniform thickness of 0.1-200 um and substantially stagnant relative to the plates, the first plate has a thickness of 500 um or less, and the second plate has a thickness of 5 mm or less; and the heating/cooling layer has a thickness of less than 1 mm and an area of less than 100 mm$^2$ and is configured to convert energy from electromagnetic waves into heat to raise the temperature of the at least part of the fluidic sample in the layer of uniform thickness.

AA2.3 A device for rapidly changing temperature of a fluidic sample, comprising:

a sample holder and a heating/cooling layer, wherein:

the sample holder comprises a first plate and a second plate, wherein each of the plates comprises, on its respective surface, a sample contact area for contacting the fluidic sample;

the first plate and the second plate are configured to confine at least part of the sample into a layer of highly uniform thickness of 0.1-200 um and substantially stagnant relative to the plates, the first plate has a thickness of 500 um or less, and the second plate has a thickness of 5 mm or less; and the heating/cooling layer: (1) has a thickness of less than 1 mm, (2) has an area of less than 100 mm$^2$ that is substantially less than the area of either the first or the second plate, and (3) is configured to convert energy from electromagnetic waves into heat to raise the temperature of at least part of the fluidic sample in the layer of uniform thickness.

AA3 A device for rapidly changing temperature of a fluidic sample, comprising:

a sample holder and a heating/cooling layer, wherein:

the sample holder comprises a first plate and a second plate, wherein each of the plates comprises, on its respective surface, a sample contact area for contacting the fluidic sample;

the first plate and the second plate are configured to confine at least part of the sample into a layer of highly uniform thickness of 500 um or less and substantially stagnant relative to the plates, the first plate is in contact with the heating/cooling layer and has a thickness of 1 um or less, and the second plate is not in contact with the heating/cooling layer and has a thickness of 5 mm or less; and the heating/cooling layer is configured to convert energy from electromagnetic waves into heat to raise the temperature of the at least part of the fluidic sample in the layer of uniform thickness, has an absorption coefficient of 50% or higher, and has a thickness of less than 3 mm.

AA4 A device for rapidly changing temperature of a fluidic sample, comprising:

a sample holder and a heating/cooling layer, wherein:

the sample holder comprises a first plate and a second plate, wherein each of the plates comprises, on its respective surface, a sample contact area for contacting the fluidic sample;

the first plate and the second plate are configured to confine at least part of the sample into a layer of highly uniform thickness of 500 um or less and substantially stagnant relative to the plates, the first plate is in contact with the heating/cooling layer and has a thickness of 1 um or less, and the second plate is not in contact with the heating/cooling layer and has a thickness of 0.1-2 mm; and the heating/cooling layer is configured to convert energy from electromagnetic waves into heat to raise the temperature of the at least part of the fluidic sample in the layer of uniform thickness, has an absorption coefficient of 60% or higher, and has a thickness of less than 2 mm.

AA6.1 The device of any prior embodiments, wherein the heating/cooling layer is on the inner surface of one of the plates.

AA6.2 The device of any prior embodiments, wherein the heating/cooling layer is on the outer surface of one of the plates.

AA6.3 The device of any prior embodiments, wherein the heating/cooling layer inside one of plates.

AA6.4 The device of any prior embodiments, wherein the heating/cooling layer is in contact with at least one of the plates.

AA6.5 The device of any prior embodiments, wherein the heating/cooling layer is not in contact with any of the plates.

AA6.6 The device of any prior embodiments, wherein the heating/cooling layer is in contact with the sample when the plates are in the closed configuration.

AA7. The device of any prior embodiments, wherein the heating/cooling layer is made from a single material or compound materials.

AA7.1 The device of any prior embodiments, wherein the heating/cooling layer comprises semiconductors or metallic materials with high absorbing surfaces.

AA7.2 The device of any prior embodiments, wherein the heating/cooling layer comprises Silicon, Ge, InP, GaAs, CdTe, CdS, aSi, metal including Au, Al, Ag, Ti, carbon coated Al, black painted Al, carbon (graphene, nanotube, nanowire) or a combination thereof.

AA7.3 The device of any prior embodiments, wherein the heating/cooling layer is acting as the fast heating conductive layer comprises Silicon, Ge, InP, GaAs, CdTe, CdS, aSi, metal including Au, Al, Ag, Ti, carbon coated Al, black painted Al, carbon (graphene, nanotube, nanowire) or a combination thereof.

AA8 The device of any prior embodiments, wherein the part of the heating area that overlaps the sample area is less than 1%, 5%, 10%, 20%, 30%, 40%, 50%, 60%, 70%, 80%, 90%, 95%, or 99% of the sample area, or in a range between any of the two values. AA8.1 The device of any prior embodiments, wherein the part of the heating area that overlaps the sample area is less than 0.1 mm$^2$, 0.5 mm$^2$, 1 mm$^2$, 5 mm$^2$, 10 mm$^2$, 25 mm$^2$, 50 mm$^2$, 75 mm$^2$, 1 cm$^2$ (square centimeter), 2 cm$^2$, 3 cm$^2$, 4 cm$^2$, 5 cm$^2$, 10 cm$^2$, or in a range between any of the two values.

AA9. The device of any prior embodiments, wherein the absorption coefficient of the heating/cooling layer is more than 30%, 40%, 50%, 60%, 70%, 80%, 90%, or in a range between any of the two values.

AA9.1. The device of any prior embodiments, wherein the absorption coefficient of the heating/cooling layer is more than 60%, 70%, 80%, 90%, or in a range between any of the two values.

AA9.2. The device of any prior embodiments, wherein the absorption coefficient of the heating/cooling layer is more than 60%.

AA10. The device of any prior embodiments, wherein the heating/cooling layer has an absorption wavelength range that is 100 nm to 300 nm, 400 nm to 700 nm (visible range), 700 nm to 1000 nm (IR range), 1 um to 10 um, 10 um to 100 um, or in a range between any of the two values.

AA11. The device of any prior embodiments, wherein the heating/cooling layer has a thickness equal to or less than 3 mm, 2 mm, 1 mm, 750 um, 500 um, 250 um, 100 um, 50 um, 25 um, 10 um, 500 nm, 200 nm, 100 nm, or 50 nm, or in a range between any of the two values.

AA12. The device of any prior embodiments, wherein the heating/cooling layer has an area of 0.1 mm$^2$ or less, 1 mm$^2$ or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, or in a range between any of the two values.

AA13. The device of any prior embodiments, wherein the first plate has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values.

AA13.1. The device of any prior embodiments, wherein the first plate has a thickness equal of 10-200 um.

AA14. The device of any prior embodiments, wherein the second plate has a thickness equal to or less than 5 mm, 4 mm, 3 mm, 2 mm, 1 mm, 750 um, 500 um, 250 um, 100 um, 75 um, 50 um, or 25 um, or in a range between any of the two values.

AA14.1. The device of any prior embodiments, wherein the second plate has a thickness equal of 10-1000 um.

AA15. The device of any prior embodiments, wherein the sample layer has a highly uniform thickness.

AA15.1 The device of any prior embodiments, wherein the sample layer has a thickness of equal to or less than 100 um, 50 um, 20 um, 10 um, 5 um, 1 um, 500 nm, 400 nm, 300 nm, 200 nm, or 100 nm, or in a range between any of the two values.

AA15.2. The device of any prior embodiments, wherein the sample layer has a thickness of 1-100 um.

AA16. The device of any prior embodiments, wherein the area of at least one of the plate is 1 mm$^2$ or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values.

AA17.1 The device of any prior embodiments, wherein the area of at least one of the plates is in the range of 500 to 1,000 mm$^2$; or around 750 mm$^2$.

AA18. The device of any prior embodiments, further comprising spacers that are configured to regulate the thickness of the sample layer.

AA18.1 The device of any prior embodiments, wherein the spacers are fixed on either one or both of the plates.

AA18.2 The device of any prior embodiments, wherein the spacers are fixed on the inner surface of either one or both of the plates.

AA18.3 The device of any prior embodiments, wherein the spacers have a uniform height.

AA18.4 The device of any prior embodiments, wherein at least one of the spacers is inside the sample contact area.

AA18.5 The device of any prior embodiments, wherein the thickness of the sample layer is the same as the height of the spacers.

AA19 The device any prior embodiments, wherein one or both plates are flexible.

AA20. The device of any prior embodiments, further comprising sealing structures that are attached to either one or both of the contact and second plates, wherein the sealing structures are configured to limit the evaporation of liquid inside the device.

AA21. The device of any prior embodiments, further comprising a clamping structure that is attached to either one or both of the first and second plates, wherein the clamp structure is configured to hold the device and regulate the thickness of the sample layer during the heating of the device.

AA22. The device of any prior embodiments, wherein the second plate is transparent for an electromagnetic wave from the sample.

AA23. The device of any prior embodiments, wherein the sample holder and the heating/cooling layer are connected by a thermal coupler.

AA24. The device of any prior embodiments, wherein the areas of the at least part of the sample and the heating/cooling layer are substantially larger than the uniform thickness.

AA25. The device of any prior embodiments, wherein the heating/cooling layer is configured to absorb electromagnetic waves selected from the group consisting of: radio waves, microwaves, infrared waves, visible light, ultraviolet waves, X-rays, gamma rays, and thermal radiation.

AA26. The device of any prior embodiments, wherein the sample is a pre-mixed polymerase chain reaction (PCR) medium.

AA27. The device of any prior embodiments, wherein the sample layer is laterally sealed to reduce sample evaporation.

AA28. The device of any prior embodiments, wherein the area of the radiation is smaller than the area of radiation absorption pad; The area of the radiation absorption pad is less than the area of sample liquid area; The area of sample liquid area is less than the first and second plate size.

AA29. The device of any prior embodiments, wherein the fluidic sample comprises a processed or unprocessed bodily fluid.

AA30. The device of any prior embodiments, wherein the fluidic sample comprises amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled condensate, or a mixture thereof.

AA31. The device of any prior embodiments, wherein the fluidic sample comprises nucleic acids or proteins, or a mixture thereof.

AA32. The device of any prior embodiments, wherein the fluidic sample comprises DNA or RNA, or a mixture thereof.

Apparatus with heating source

BB1. An apparatus for rapidly changing temperature of a fluidic sample, comprising:
- a holder that can hold a device of any AA embodiments; and
- a heating source that is configured to supply energy to the heating/cooling layer; and
- a controller that is configured to control the heating source.

BB1.1 The apparatus of any prior BB embodiments, wherein the heating source is configured to radiate electromagnetic waves in a range of wavelength that the heating/cooling layer has an absorption coefficient of 50% or higher.

BB2. The apparatus of any prior BB embodiments, wherein the heating source comprises one or an array of light-emitting diodes (LEDs), one or an array of lasers, one or an array of lamps, or a combination of thereof.

BB2.1. The apparatus of any prior BB embodiments, wherein the heating source comprises halogen lamp, halogen lamp with reflector, LED with focusing lens, laser with focusing lens, halogen lamp with coupling optical fiber, LED with coupling optical fiber, laser with coupling optical fiber.

BB3. The apparatus of any prior BB embodiments, wherein the wavelength is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values.

BB3.1 The apparatus of any prior BB embodiments, wherein the wavelength of the electromagnetic waves is 100 nm to 300 nm, 400 nm to 700 nm (visible range), 700 nm to 1,000 nm (IR range), 1 um to 10 um, 10 um to 100 um, or in a range between any of the two values.

BB4. The apparatus of any prior BB embodiments, further comprising a heat sink that is configured to absorb at least part of the heat radiated from the sample holder and/or the heating source.

BB4.1. The apparatus of any prior BB embodiments, wherein the heat sink is chamber that at least partially encloses the device.

BB4.2. The apparatus of any prior BB embodiments, wherein the chamber comprises a lower aperture configured to allow passage of electromagnetic waves from the heating source to the heating/cooling layer, and an upper aperture configured to allow imaging of the sample.

BB5. The apparatus of any prior BB embodiments, wherein the sample holder is heated optically, electrically, by RF, or a combination of thereof.

BB6. An apparatus for rapidly changing temperature of a fluidic sample, comprising: a device of any AA embodiments; and a heat sink that is configured to absorb at least part of the heat radiated from the sample holder and/or the heating source.

BB7. The apparatus of any prior BB embodiments, wherein the heat sink is a chamber that at least partially encloses the device, wherein the chamber comprises a radiation aperture configured to allow passage of electromagnetic waves from a heating source to the heating/cooling layer, and an optical aperture configured to allow imaging of the sample.

BB8. The apparatus of any prior BB embodiments, further comprising a cooling member attached to the chamber, wherein the cooling member is configured to reduce temperature in the chamber.

BB9. The apparatus of embodiment BB7, wherein the cooling member is a fan.

BB10. The apparatus of embodiment BB7, wherein the cooling member is a Peltier cooler.

BB11. The apparatus of any BB embodiments, wherein the chamber has a non-reflective inner surface.

BB11.1 The apparatus of any BB embodiments, wherein the chamber has an inner surface made of black metal.

BB12. The apparatus of any BB embodiments, wherein the device is suspended (i.e. has minimum) thermal conduction contact with the chamber wall.

BB13. The apparatus of any BB embodiments, wherein the heat sink is configured to connect the sample holder to a mobile device.

BB13.1 The apparatus of embodiment B13, wherein the mobile device is a smartphone comprising a camera.

BB14. The apparatus of any BB embodiments, wherein the heat sink comprises optical elements that optimizes capturing images of the sample in the sample card.

CC1. A system for rapidly changing temperature of a fluidic sample, comprising: a device of any AA embodiments or an apparatus of any BB embodiments; and a signal sensor that is configured to senses a signal from the sample on the device.

CC2. The system of any prior CC embodiments, wherein the signal sensor is an optical sensor that is configured to image the fluidic sample.

CC2.1 The system of any prior CC embodiments, wherein the optical sensor is a photodetector, camera, or a device capable of capturing images of the fluidic sample.

CC3. The system of any prior CC embodiments, wherein the signal sensor is an electrical sensor that is configured to detect electrical signals from the device.

CC4. The system of any prior CC embodiments, wherein the signal sensor is a mechanical sensor that is configured to detect mechanical signals from the device.

CC5. The system of any prior CC embodiments, wherein the signal sensor is configured to monitor the amount of an analyte in the sample.

CC6. The system of any prior CC embodiments, wherein signal sensor is outside the chamber and receive optical signals from the sample through an optical aperture on the chamber.

CC7. The system of any CC embodiment, further comprising a thermal coupler bound to the heating/cooling layer.

CC8. The system of any prior CC embodiments, further comprising a thermostat that monitor the temperature of the heating/cooling layer.

CC9. The system of any prior CC embodiments, further comprising a temperature monitoring dye that is configured to facilitate monitoring the temperature of the sample in the device.

CC9.1. The system of any prior CC embodiments, wherein the temperature monitoring dye is in liquid form.

CC9.2. The system of any prior CC embodiments, wherein the temperature monitoring dye comprises LDS 688, LDS 698, LDS 950, LD 390, LD 423, LD 425, or IR 144, or a combination thereof.

DD1. The device, apparatus, or system of any prior embodiments, wherein:
- there are spacers that are fixed on one of both of the plates, wherein at least one of the spacers is in the sample contact area;
- the sample layer has a thickness of 0.1-200 um;
- the first plate is in contact with the heating/cooling layer and has a thickness of 500 um or less, and the second pate is not in contact with the heating/cooling layer and has a thickness of 5 mm or less; and
- the heating/cooling layer: (1) has a thickness of less than 1 mm, (2) has an area of less than 100 mm$^2$ that is substantially less than the area of either the first or the second plate, and (3) is configured to convert energy from electromagnetic waves into heat to raise the temperature of at least part of the fluidic sample in the layer of uniform thickness.

DD2. The device, apparatus, or system of any prior embodiments, wherein:
- the heating/cooling layer is on the inner surface of the first plate and in contact with the sample when the plates are in the closed configuration;
- the heating/cooling layer is made from silicon; and
- there is a chamber that encloses the sample holder and the chamber has a non-reflective inner surface.

DD3. The device, apparatus, or system of any prior embodiments, wherein:
- there is a heating source that is configured to radiate electromagnetic waves in a range of wavelength that the heating/cooling layer has an absorption coefficient of 50% or higher;
- there is a chamber that comprises a lower aperture configured to allow passage of electromagnetic waves from the heating source to the heating/cooling layer, and an upper aperture configured to allow imaging of the sample; and
- there is an optical sensor that is configured to capture images of the fluidic sample in the sample holder.

EE1.1. A method for rapidly changing temperature of a fluidic sample, comprising:
- providing a device that comprises a first plate, a second plate, a heating layer, and a cooling layer, wherein:
- each of the plates comprises, on its respective inner surface, a sample contact area;
- the heating layer is positioned on the inner surface, the outer surface, or inside of one of the plates; and is configured to heat a relevant volume of the sample, wherein the relevant volume of the sample is a portion or an entirety of the sample that is being heated to a desired temperature; and
- the cooling layer is positioned on the inner surface, the outer surface, or inside of one of the plates; is configured to cool the relevant sample volume; and comprises a layer of material that that has a thermal conductivity to thermal capacity ratio of 0.6 cm$^2$/sec or larger, wherein the high thermal conductivity to thermal capacity ratio layer has an area larger than the lateral area of the sample volume;
- wherein the distance between the cooling layer and a surface of the relevant sample volume is zero or less than a distance that is configured to make the thermal conductance per unit area between the cooling layer and the surface of the relevant sample volume equal to 150 W/(m$^2$·K) or larger.
- depositing a fluidic sample on one or both of the sample contact areas of the respective plates;
- pressing the plates, by hand, to make the sample contact areas face each other, wherein the plates are separated by an average separation distance of 200 um or less, sandwiching the sample between them and pressing at least part of the sample into a thin layer:
- changing and/or maintaining the temperature of the relevant volume in the device.

EE1.2. A method for rapidly changing temperature of a fluidic sample, comprising:
- providing the device of the SC-A embodiments:
- depositing a fluidic sample on one or both of the sample contact areas of the respective plates;
- pressing the plates, by hand, to sandwich the sample between them and pressing at least part of the sample into a thin layer:
- changing and/or maintaining the temperature of the relevant volume in the device.

EE1.3. A method for rapidly changing temperature of a fluidic sample, comprising:
- obtaining the system of the CC embodiments;
- depositing the fluidic sample in the sample holder;
- pressing the first plate and the second plate to compress at least part of the sample into a layer of uniform thickness; and
- changing and maintaining the temperature of the sample layer by changing the presence, intensity, wavelength, frequency, and/or angle of the electromagnetic waves from the heating source.

EE2. The method of any prior EE embodiments, wherein changing the temperature of the sample layer comprises raising the temperature or lowering the temperature.

EE3. The method of any prior EE embodiments, further comprising imaging the sample layer with the optical sensor.

EE4. The method of any prior EE embodiments, further comprising monitoring the temperature of the sample layer and adjusting the step of changing and maintaining the temperature of the sample layer.

EE5. The method of any prior EE embodiments, wherein the step of changing and maintaining the temperature of the sample layer is conducted according to a pre-determined program.

EE6. The method of any prior EE embodiments, wherein the method is customized to facilitate polymerase chain reaction (PCR) assays for changing temperature of the sample according to a predetermined program EE7. The method of any prior EE embodiments, further comprising monitoring the amount of an analyte in the sample in real time.

FF1. The device, apparatus, system or method of any prior embodiments, wherein the sample comprises nucleic acids.

FF1.1 The device, apparatus, system or method of any prior embodiments, wherein the sample comprises DNA.

FF1.2 The device, apparatus, system or method of any prior embodiments, wherein the sample comprises RNA.

FF1.3 The device, apparatus, system or method of any prior embodiments, wherein the sample comprises DNA or RNA molecule, or a DNA/RNA hybrid, or mixtures of DNA and/or RNA.

FF1.4 The device, apparatus, system or method of any prior embodiments, wherein the sample comprises genomic or chromosomal DNA, plasmid DNA, amplified DNA, cDNA, total RNA, mRNA and small RNA.

FF1.5 The device, apparatus, system or method of any prior embodiments, wherein the sample comprises natural DNA and/or RNA molecule, or synthetic DNA and/or RNA molecule.

FF1.6 The device, apparatus, system or method of any prior embodiments, wherein the sample comprises cell-free nucleic acids, wherein "cell-free" refers to nucleic acids are not contained in any cellular structures.

FF1.7 The device, apparatus, system or method of any prior embodiments, wherein the sample comprises nucleic acids are contained within cellular structures, which include but not limited to human cells, animal cells, plant cells, bacterial cells, fungi cells, and/or viral particles.

FF1.8 The device, apparatus, system or method of any prior embodiments, wherein the sample comprises purified nucleic acids.

FF2. The device, apparatus, system or method of any prior embodiments, wherein the sample comprises proteins and/or lipids.

FF3. The device, apparatus, system or method of any prior embodiments, wherein the sample comprises reagents configured for nucleic acid amplification.

FF3.1. The device, apparatus, system or method of any prior embodiments, wherein the sample comprises a pre-mixed polymerase chain reaction (PCR) medium.

FF3.2. The device, apparatus, system or method of any prior embodiments, wherein the sample comprises reagents configured to detect nucleic acids by amplifying (generating numerous copies of) the target molecules in samples, wherein target molecule refers to a sequence, or partial sequence, of nucleic acid of interest.

FF3.3. The device, apparatus, system or method of any prior embodiments, wherein the nucleic acid amplification refers to nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

FF3.4. The device, apparatus, system or method of any prior embodiments, wherein the reagents comprise primers, deoxynucleotides (dNTPs), bivalent cations (e.g. $Mg^{2+}$), monovalent cation (e.g. $K^+$), buffer solutions, enzymes, or reporters, or any combination or mixture thereof.

FF3.5. The device, apparatus, system or method of any prior embodiments, wherein the reagents are either in the dry form on the inner surface of the first or the second plate or both, or in a liquid form encased in, embedded in, or surrounded by, a material that melts with increasing temperatures, such as, for example, paraffin.

FF3.6. The device, apparatus, system or method of any prior embodiments, wherein primers comprise one or more pairs of forward and reverse primers.

FF3.7. The device, apparatus, system or method of any prior embodiments, wherein the reagents comprise DNA-dependent polymerase, or RNA-dependent DNA polymerase, or DNA-dependent RNA polymerase.

FF3.8. The device, apparatus, system or method of any prior embodiments, wherein the reagents comprise "reporters" that refer to any tag, label, or dye that can bind to, or intercalate within, the nucleic acid molecule or be activated by byproducts of the amplification process to enable visualization of the nucleic acid molecule or the amplification process.

FF3.8.1 The device, apparatus, system or method of any prior embodiments, wherein the reports include but are not limited to fluorescent labels or dyes, intercalating agents, molecular beacon labels, or bioluminescent molecules, or a combination thereof.

FF3.9. The device, apparatus, system or method of any prior embodiments, wherein the reagents comprise cell lysing reagent, which is configured to facilitate breaking down cellular structures.

FF3.9.1. The device, apparatus, system or method of any prior embodiments, wherein the cell lysing reagent includes but not limited to salts, detergents, enzymes, and other additives.

FF3.9.2. The device, apparatus, system or method of any prior embodiments, wherein the salt includes but not limited to lithium salt (e.g. lithium chloride), sodium salt (e.g. sodium chloride), potassium (e.g. potassium chloride).

FF3.9.2. The device, apparatus, system or method of any prior embodiments, wherein the detergents are ionic, including anionic and cationic, non-ionic or zwitterionic.

FF3.9.3. The device, apparatus, system or method of any prior embodiments, wherein the ionic detergent includes any detergent which is partly or wholly in ionic form when dissolved in water.

FF3.9.4. The device, apparatus, system or method of any prior embodiments, wherein anionic detergents include but not limited to sodium dodecyl sulphate (SDS) or other alkali metal alkylsulphate salts or similar detergents, sarkosyl, or combinations thereof.

FF3.10. The device, apparatus, system or method of any prior embodiments, wherein enzymes includes but not limited to lysozyme, cellulose, and proteinase.

FF3.11. The device, apparatus, system or method of any prior embodiments, wherein chelating agents include but not limited to EDTA, EGTA and other polyamino carboxylic acids, and some reducing agents, such as dithiotreitol (dTT).

FF4. The device, apparatus, system or method of any prior embodiments, wherein the sample comprises an analyte the amount of which is changed with the temperature changes.

FF5. The device, apparatus, system or method of any prior embodiments, wherein the sample comprises human bodily fluids, such as but not limited to whole blood, plasma, serum, urine, saliva, and sweat, and cell cultures (mammalian, plant, bacteria, fungi), and a combination or mixture thereof.

FF6. The device, apparatus, system or method of any prior embodiments, wherein the sample is freshly obtained, stored or treated in any desired or convenient way, for example by dilution or adding buffers, or other solutions or solvents.

FF7. The device, apparatus, system or method of any prior embodiments, wherein the sample comprises cellular structures such as but not limited to human cells, animal cells, plant cells, bacteria cells, fungus cells, and virus particles, and a combination or mixture thereof.

GG1. The device, apparatus, system or method of any prior embodiments, wherein an analyte in the sample is stained.

GG2. The device, apparatus, system or method of any prior GG embodiments, wherein the amount of the analyte is measured by fluorescence intensity.

GG3. The device, apparatus, system or method of any prior GG embodiments, wherein the amount of the analyte is measured by colorimetric intensity.

GG4. The device, apparatus, system or method of any prior embodiments, wherein the analyte is nucleic acid, which is stained with ethidium bromide (EB), methylene blue, SYBR green I, SYBR green II, pyronin Y, DAPI, acridine orange, or Nancy-520, or a combination thereof.

GG5. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with fluorescence intensity.

GG6. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with colorimetric intensity.

GG7. The device, apparatus, system or method of any prior embodiments, wherein the analyte is RNA, which is stained with ethidium bromide (EB), methylene blue, SYBR green II, pyronin Y, or acridine orange, or a combination thereof, and measured with fluorescence intensity.

GG8. The device, apparatus, system or method of any prior embodiments, wherein the analyte is RNA, which is stained with ethidium bromide (EB), methylene blue, SYBR green II, pyronin Y, or acridine orange, or a combination thereof, and measured with colorimetric intensity.

GG9. The device, apparatus, system or method of any prior embodiments, wherein the analyte is nucleic acid to be detected by reporters.

GG9.1. The device, apparatus, system or method of any prior embodiments, wherein the reporters include but not limited to tag, label, or dye that can bind to, or intercalate within, the nucleic acid molecule or be activated by byproducts of the amplification process to enable visualization of the nucleic acid molecule or the amplification process.

GG9.2. The device, apparatus, system or method of any prior embodiments, wherein the reporters include but are not limited to fluorescent labels or tags or dyes, intercalating agents, molecular beacon labels, or bioluminescent molecules, or a combination thereof.

GG9.3. The device, apparatus, system or method of any prior embodiments, wherein the amount of reporter is measured by colorimetric intensity and/or by fluorescence intensity.

HH1. The device, apparatus, system or method of any prior embodiments, wherein the device, apparatus, system or method is configured to facilitate PCR assays for changing temperature of the sample according to a predetermined program.

HH2. The device, apparatus, system or method of any prior embodiments, wherein the device, apparatus, system or method is configured to conduct diagnostic testing, health monitoring, environmental testing, and/or forensic testing.

HH3. The device, apparatus, system or method of any prior embodiments, wherein the device, apparatus, system or method is configured to conduct DNA amplification, DNA quantification, selective DNA isolation, genetic analysis, tissue typing, oncogene identification, infectious disease testing, genetic fingerprinting, and/or paternity testing.

HH4. The device, apparatus, system or method of any prior embodiments, wherein the device, apparatus, system or method is configured to conduct real time PCR.

HH5. The device, apparatus, system or method of any prior embodiments, wherein the device, apparatus, system or method is configured to conduct nucleic acid amplification.

HH5.1 The device, apparatus, system or method of any prior embodiments, wherein nucleic acid amplification includes any techniques used to detect nucleic acids by amplifying (generating numerous copies of) the target molecules in samples, wherein target molecule refers to a sequence, or partial sequence, of nucleic acid of interest.

HH6 The device, apparatus, system or method of any prior embodiments, wherein the device, apparatus, system or method is configured to conduct nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

A1. A device for rapidly changing temperature of a thin fluidic sample layer, comprising:
a first plate, a second plate, and a heating/cooling layer, wherein:
the heating/cooling layer is on one of the plates,
each of the plates comprises, on its respective surface, a sample contact area for contacting a fluidic sample; and
the plates have a configuration for rapidly changing temperature of the sample, in which:
the sample contact areas face each other and are significant parallel,
the average spacing between the contact areas is equal to or less than 200 microns,
the two plates regulate (or confine) at least part of the sample into a layer of highly uniform thickness and substantially stagnant relative to the plates,
the heating/cooling layer is near the at least part of the sample of uniform thickness,
the area of the at least part of the sample and the heating/cooling layer are substantially larger than the uniform thickness.

A2. The device of embodiment A1, wherein the heating/cooling layer comprises a disk-coupled dots-on-pillar antenna (D2PA) array, silicon sandwich, graphene, back materials, superlattice or other plasmonic materials, other a combination thereof.

A3. The device of embodiment A1, wherein the heating/cooling layer comprises carbon or black nanostructures or a combination thereof.

A4. The device of any of embodiments A1-A3, wherein the heating/cooling layer is configured to absorb radiation energy.

A5. The device of any of embodiments A1-A4, wherein the heating/cooling layer is configured to radiate energy in the form of heat after absorbing radiation energy.

A6. The device of any of embodiments A1-A5, wherein the heating/cooling layer is positioned underneath the sample layer and in direct contact with the sample layer.

A7. The device of any of embodiments A1-A6, wherein the heating/cooling layer is configured to absorbing electromagnetic waves selected from the group consisting of: radio waves, microwaves, infrared waves, visible light, ultraviolet waves, X-rays, gamma rays, and thermal radiation.

A8. The device of any of embodiments A1-A7, wherein at least one of the plates does not block the radiation that the heating/cooling layer absorbs.

A9. The device of any of embodiments A1-A8, wherein one or both of the plates have low thermal conductivity.

A10. The device of any of embodiments A1-A9, wherein the uniform thickness of the sample layer is regulated by one or more spacers that are fixed to one or both of the plates.

A11. The device of any of embodiments A1-A10, wherein the sample is a pre-mixed polymerase chain reaction (PCR) medium.

A12. The device of embodiment A11, wherein the device is configured to facilitate PCR assays for changing temperature of the sample according to a predetermined program.

A13. The device of any of embodiments A1-A12, wherein the device is configured to conduct diagnostic testing, health monitoring, environmental testing, and/or forensic testing.

A14. The device of any of embodiments A1-A13, wherein the device is configured to conduct DNA amplification, DNA quantification, selective DNA isolation, genetic analysis, tissue typing, oncogene identification, infectious disease testing, genetic fingerprinting, and/or paternity testing.

A15. The device of any of embodiment A1-A14, wherein the sample layer is laterally sealed to reduce sample evaporation.

B1. A system for rapidly changing temperature of a thin fluidic sample layer, comprising:
  a first plate, a second plate, a heating/cooling layer, and a heating source, wherein:
  the heating/cooling layer is on one of the plates;
  the heating source is configured to radiate electromagnetic waves that the heating/cooling layer absorbs significantly;
  each of the plates comprises, on its respective surface, a sample contact area for contacting a fluidic sample; and
  the plates have a configuration for rapidly changing temperature of the sample, in which:
  the sample contact areas face each other and are significant parallel,
  the average spacing between the contact areas is equal to or less than 200 um,
  the two plates confine at least part of the sample into a layer of highly uniform thickness and substantially stagnant relative to the plates,
  the heating/cooling layer is near the at least part of the sample of uniform thickness,
  the area of the at least part of the sample and the heating/cooling layer are substantially larger than the uniform thickness.

B2. The system of embodiment B1, wherein the heating/cooling layer comprises a disk-coupled dots-on-pillar antenna (D2PA) array, silicon sandwich, graphene, superlattice or other plasmonic materials, other a combination thereof.

B3. The system of embodiment B1, wherein the heating/cooling layer comprises carbon or black nanostructures or a combination thereof.

B4. The system of any of embodiments B1-B3, wherein the heating/cooling layer is configured to absorb at least 80% of the radiation energy from the electromagnetic waves from the heating source.

B5. The system of any of embodiments B1-B4, wherein the heating/cooling layer is configured to radiate energy in the form of heat after absorbing radiation energy.

B6. The system of any of embodiments B1-B5, wherein the heating/cooling layer is positioned underneath the sample layer and in direct contact with the sample layer.

B7. The system of any of embodiments B1-B6, wherein the heating/cooling layer is configured to absorbing electromagnetic waves selected from the group consisting of: radio waves, microwaves, infrared waves, visible light, ultraviolet waves, X-rays, gamma rays, and thermal radiation.

B8. The system of any of embodiments B1-B7, wherein at least one of the plates does not block the radiation from the heating source.

B9. The system of any of embodiments B1-B8, wherein one or both of the plates have low thermal conductivity.

B10. The system of any of embodiments B1-B9, wherein the uniform thickness of the sample layer is regulated by one or more spacers that are fixed to one or both of the plates.

B11. The system of any of embodiments B1-B10, wherein the sample is a pre-mixed polymerase chain reaction (PCR) medium.

B12. The system of embodiment B11, wherein the system is configured to facilitate PCR assays for changing temperature of the sample according to a predetermined program.

B13. The system of any of embodiments B1-B12, wherein the system is configured to conduct diagnostic testing, health monitoring, environmental testing, and/or forensic testing.

B14. The system of any of embodiments B1-B15, wherein the system is configured to conduct DNB amplification, DNB quantification, selective DNB isolation, genetic analysis, tissue typing, oncogene identification, infectious disease testing, genetic fingerprinting, and/or paternity testing.

B15. The system of any of embodiments B1-B14, wherein the sample layer is laterally sealed to reduce sample evaporation.

B16. The system of any of embodiments B1-B15, further comprising a controller, which is configured to control the presence, intensity, wavelength, frequency, and/or angle of the electromagnetic waves.

B17. The system of any of embodiments B1-B16, further comprising a thermometer, which is configured to measure the temperature at or in proximity of the sample contact area and send a signal to the controller based on the measured temperature.

B18. The system of embodiment B17, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

C1. A system for facilitating a polymerase chain reaction (PCR) by rapidly changing temperature of a thin fluidic PCR sample layer, comprising:
  a first plate, a second plate, a heating/cooling layer, a heating source, and a controller wherein:
  the heating/cooling layer is on one of the plates;
  the heating source is configured to radiate electromagnetic waves that the heating/cooling layer absorbs significantly;
  each of the plates comprises, on its respective surface, a sample contact area for contacting a fluid PCR sample, which is a pre-mixed PCR medium;
  the controller is configured to control the heating source and rapidly change the temperature of the sample according to a predetermined program; and
  the plates have a configuration for rapidly changing temperature of the sample, in which:
  the sample contact areas face each other and are significant parallel,
  the average spacing between the contact areas is equal to or less than 200 um,
  the two plates confine at least part of the sample into a layer of highly uniform thickness and substantially stagnant relative to the plates,
  the heating/cooling layer is near the at least part of the sample of uniform thickness, and
  the area of the at least part of the sample and the heating/cooling layer are substantially larger than the uniform thickness.

C2. The system of embodiment C1, wherein the controller is configured to control the present, intensity, wavelength, frequency, and/or angle of the electromagnetic waves from the heating source.

C3. The system of embodiment C1 or C2, wherein the heating source and the heating/cooling layer are configured that the electromagnetic waves cause an average ascending temperature rate ramp of at least 10° C./s; and the removal of the electromagnetic waves results in an average descending temperature rate ramp of at least 5° C./s.

C4. The system of any of embodiments C1-C2, wherein the heating source and the heating/cooling layer are configured to create an average ascending temperature rate ramp of at least 10° C./s and an average descending temperature rate ramp of at least 5° C./s.

C5. The system of any of embodiments C1-C2, wherein the heating source and the heating/cooling layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

C6. The system of any of embodiments C1-C5, wherein the PCR sample comprises: template DNA, primer DNA, cations, polymerase, and buffer.

D1. A method for rapidly changing temperature of a thin fluidic sample layer, comprising:
providing a first plate a second plate, each of the plates comprising, on its respective inner surface, a sample contact area;
providing a heating/cooling layer and a heating source, wherein the heating/cooling layer is on one of the plates, and the heating source is configured to radiate electromagnetic waves that the heating/cooling layer absorbs significantly;
depositing a fludic sample on one or both of the plates;
pressing the plates into a closed configuration, in which:
the sample contact areas face each other and are significant parallel,
the average spacing between the contact areas is equal to or less than 200 um,
the two plates confine at least part of the sample into a layer of highly uniform thickness and substantially stagnant relative to the plates;
the heating/cooling layer is near the at least part of the sample of uniform thickness,
the area of the at least part of the sample and the heating/cooling layer are substantially larger than the uniform thickness; and
changing and maintaining the temperature of the sample layer by changing the presence, intensity, wavelength, frequency, and/or angle of the electromagnetic waves from the heating source.

D2. The method of embodiment D1, wherein the step of pressing the plates into a closed figuration comprises pressing the plates with an imprecise pressing force.

D3. The method of embodiment D1 or D2, wherein the step of pressing the plates into a closed figuration comprises pressing the plates directly with human hands.

D4. The method of any of embodiments D1-D3, wherein the layer of highly uniform thickness has a thickness variation of less than 10%.

D5. The method of any of embodiments D1-D4, wherein the heating/cooling layer comprises a disk-coupled dots-on-pillar antenna (D2PA) array, silicon sandwich, graphene, superlattice or other plasmonic materials, other a combination thereof.

D6. The method of any of embodiments D1-D5, wherein the heating/cooling layer comprises carbon or black nanostructures or a combination thereof.

D7. The method of any of embodiments D1-D6, wherein the heating/cooling layer is configured to absorb at least 80% of the radiation energy from the electromagnetic waves from the heating source.

D8. The method of any of embodiments D1-D7, wherein the heating/cooling layer is configured to radiate energy in the form of heat after absorbing radiation energy.

D9. The method of any of embodiments D1-D8, wherein the heating/cooling layer is positioned underneath the sample layer and in direct contact with the sample layer.

D10. The method of any of embodiments D1-D9, wherein the heating/cooling layer is configured to absorbing electromagnetic waves selected from the group consisting of: radio waves, microwaves, infrared waves, visible light, ultraviolet waves, X-rays, gamma rays, and thermal radiation.

D11. The method of any of embodiments D1-D10, wherein at least one of the plates does not block the radiation from the heating source.

D12. The method of any of embodiments D1-D11, wherein one or both of the plates have low thermal conductivity.

D13. The method of any of embodiments D1-D12, wherein the uniform thickness of the sample layer is regulated by one or more spacers that are fixed to one or both of the plates.

D14. The method of any of embodiments D1-D13, wherein the sample is a pre-mixed polymerase chain reaction (PCR) medium.

D15. The method of embodiment D14, wherein the method is used to facilitate PCR assays for changing temperature of the sample according to a predetermined program.

D16. The method of any of embodiments D1-D15, wherein the method is used to conduct diagnostic testing, health monitoring, environmental testing, and/or forensic testing.

D17. The method of any of embodiments D1-D16, wherein the method is used to conduct DNB amplification, DNB quantification, selective DNB isolation, genetic analysis, tissue typing, oncogene identification, infectious disease testing, genetic fingerprinting, and/or paternity testing.

D18. The method of any of embodiments D1-D17, wherein the sample layer is laterally sealed to reduce sample evaporation.

D19. The method of any of embodiments D1-D18, wherein the heating source is controlled by a controller, which is configured to control the presence, intensity, wavelength, frequency, and/or angle of the electromagnetic waves.

D20. The method of any of embodiments D1-D19, wherein the controller is configured to receive signals from a thermometer, which is configured to measure the temperature at or in proximity of the sample contact area and send a signal to the controller based on the measured temperature.

D21. The method of embodiment D20, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

E1. A method for facilitating a polymerase chain reaction (PCR) by rapidly changing temperatures in a fluidic PCR sample, comprising:
providing a first plate a second plate, each of the plates comprising, on its respective inner surface, a sample contact area;

providing a heating/cooling layer, a heating source and a controller, wherein the heating/cooling layer is on one of the plates, and the heating source is configured to radiate electromagnetic waves that the heating/cooling layer absorbs significantly;

depositing a fluidic PCR sample on one or both of the plates;

pressing the plates into a closed configuration, in which:

the sample contact areas face each other and are significant parallel, the average spacing between the contact areas is equal to or less than 200 µm, the two plates confine at least part of the PCR sample into a layer of highly uniform thickness and substantially stagnant relative to the plates;

the heating/cooling layer is near the at least part of the PCR sample of uniform thickness, the area of the at least part of the sample and the heating/cooling layer are substantially larger than the uniform thickness; and using the controller to control the heating source to conduct a PCR by changing and maintaining the temperature of the PCR sample layer according to a predetermined program, wherein when the temperatures are changed, the heating source creates an average ascending temperature rate ramp of at least 10° C./s and an average descending temperature rate ramp of at least 5° C./s during the PCR.

E2. The method of embodiment E1, wherein changing and maintaining the temperature of the PCR sample layer is achieved by adjusting the intensity, wavelength, frequency, and/or angle of the electromagnetic waves from the heating source.

E3. The system of any of embodiments E1-E2, wherein the heating source and the heating/cooling layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

E4. The method of any of embodiments E1-E3, wherein the PCR sample comprises: template DNA, primer DNA, cations, polymerase, and buffer.

NN1 A device for rapidly changing temperature of a thin fluidic sample layer, comprising:

a first plate, and a second plate, wherein:

each of the plates comprises, on its respective surface, a sample contact area for contacting a fluidic sample; and the plates have a configuration for rapidly changing temperature of the sample, in which:

the sample contact areas face each other and are significant parallel, the average spacing between the contact areas is equal to or less than 200 microns, the two plates regulate (or confine) at least part of the sample into a layer of highly uniform thickness and substantially stagnant relative to the plates, the heating/cooling layer is near the at least part of the sample of uniform thickness, the area of the at least part of the sample and the heating/cooling layer are substantially larger than the uniform thickness.

JJ1. The device of any prior embodiments, further comprising a hinge that connects the first plate and the second plate, and is configured to allow the two plates to rotate around the hinge into different configurations.

JJ2. The device of any prior embodiments, wherein after relative position of the plates are adjusted by an external force, the hinge maintains an angle between the two plates that is within 5 degrees from the angle just before the external force is removed.

JJ3. The device of any prior embodiments, wherein the wherein after relative position of the plates are adjusted by an external force, the hinge maintains an angle between the two plates that is within 10 degrees from the angle just before the external force is removed.

JJ4. The device of any prior embodiments, wherein the hinge is made of a piece of a piece of hinge material of a substantially uniform thickness, wherein the hinge material is attached to a part of the inner surface of the first plate and a part of the outer surface of the second plate, and the attachments do not completely separate using operation.

JJ5. The device of any prior embodiments, wherein the hinge is made of a piece of hinge material of a substantially uniform thickness, wherein the hinge material is attached a part of the outer surfaces of the first plate and the second plate, and the attachments do not completely separate using operation.

JJ6. The device of any prior embodiments, wherein the hinge material is a metal.

JJ7. The device of any prior embodiments, wherein the hinge materials is selected from a group consisting of: gold, silver, copper, aluminum, iron, tin, platinum, nickel, cobalt, and alloys thereof.

JJ8. The device of any prior embodiments, wherein the hinge comprises a first leaf, a second leaf, and a joint that connects the leaves and is configured for the leaves to rotate around the joint, wherein the first leaf is attached to the first plate inner surface without wrapping around any edge of the first plate, the second leaf is attached to the second plate outer surface, and the joint is positioned longitudinally parallel to the hinge edge of the second plate, allowing the two plates to rotate around the joint KK1. The device of any prior embodiments, wherein:

one of the plate comprises one or more open notches on an edge or corners of the plate, and at or near the closed configuration, an edge of the other plate is configured to overlap with the open notch KK2. The device of any prior embodiments, wherein the notch facilitates changing the plates from a configuration that is near or at closed configuration to an open configuration for sample deposition.

KK3. The device of any prior embodiments, wherein the the width of at least one notch is in the range of 1/6 to ⅔ of the width of the notched edge.

KK4. The device of any prior embodiments, wherein the opening edge of the plate without the notch is inside the notched edge except for the part over the notch.

KK5. The device of any prior embodiments, wherein the first plate comprises one or more notched edges, each of which has at least one notch; and the second plate comprises one or more corresponding opening edges juxtaposed over the notches, allowing a user to push against one of the opening edges over the notch to switch the two plates between the closed configuration and the open configuration or to change the angle formed by the first plate and the second plate KK6. The device of any prior embodiments, wherein the notch is positioned at an intersection of two neighboring notched edges.

LL1. The device of any prior embodiments, wherein any prior device embodiment, wherein each of the plate further comprises, on its respective outer surface, a force area for applying a pressing force that forces the plates together, and wherein the force is an imprecise force that has a magnitude which is, at the time that the force is applied, either (a) unknown and unpredictable, or (b) cannot be known and cannot be predicted within an accuracy equal or better than 30% of the force applied.

LL2. The device of any prior embodiments, wherein each of the plate further comprises, on its respective outer surface, a force area for applying a pressing force that forces the plates together, and wherein the force is an imprecise force that has a magnitude which cannot, at the time that the force is applied, be determined within an accuracy equal or better than 30%, 40%, 50%, 70%, 100%, 200%, 300%, 500%, 1000%, 2000%, or any range between the two values.

LL3. The device of any prior embodiments, wherein the imprecise force is provided by human hand.

MM1. The device, apparatus, system, or method of any prior embodiments, wherein the first plate and the second plate are flexible plastic film and/or thin glass film, that each has a substantially uniform thickness of a value selected from a range between 1 um to 25 um.

MM2. The device, apparatus, system, or method of any prior embodiments, wherein each plate has an area in a range of 1 cm^2 to 16 cm^2.

MM3. The device, apparatus, system, or method of any prior embodiments, wherein the sample sandwiched between the two plate has a thickness of 40 um or less.

MM4. The device, apparatus, system, or method of any prior embodiments, wherein the relevant sample to the entire sample ratio (RE ratio) is 12% or less.

MM5. The device, apparatus, system, or method of any prior embodiments, wherein the cooling zone is at least 9 times larger than the heating zone.

MM6. The device, apparatus, system, or method of any prior embodiments, wherein the sample to non-sample thermal mass ratio is 2.2 or lager.

MM7. The device, apparatus, system, or method of any prior embodiments, wherein the RHC card does not comprise spacer.

MM8. The device, apparatus, system, or method of any prior embodiments, wherein the RHC card comprises spacers that are fixed on one or both of the plates.

MM9. The device, apparatus, system, or method of any prior embodiments, wherein:
  the first plate and second plates are plastic or a thin glass. The first plate and second plate have a thickness of 100 nm, 500 nm, 1 um, 5 um, 10 um, in a range between any of the two values;
  the sample between the two plates has a thickness of 5 um, 10 um, 30 um, 50 um, 100 um, or in a range between any of the two values;
  the distance from the H/C layer to the sample is 10 nm, 100 nm, 500 nm, 1 um, 5 um, um, or in a range between any of the two values;
  the ratio of the cooling zone area to the relevant sample area is 16, 9, 4, 2, or in a range between any of the two values;
  the ratio of the cooling zone area to the heating area is 16, 9, 4, 2, or in a range between any of the two values; AND
  the distance between the H/C layer and the heating source (e.g. LED) is 5 mm, 10 mm, 20 mm, 30 mm, or in a range between any of the two values.

MM10. The device, apparatus, system, or method of any prior embodiments, wherein:
  the first plate and second plates are plastic or a thin glass. The first plate and second plate have a thickness of 100 nm, 500 nm, 1 um, 5 um, 10 um, in a range between any of the two values;
  the sample between the two plates has a thickness of 5 um, 10 um, 30 um, 50 um, 100 um, or in a range between any of the two values;
  the distance from the H/C layer to the sample is 10 nm, 100 nm, 500 nm, 1 um, 5 um, um, or in a range between any of the two values;
  the ratio of the cooling zone area to the relevant sample area is 16, 9, 4, 2, or in a range between any of the two values;
  the ratio of the cooling zone area to the heating area is 16, 9, 4, 2, or in a range between any of the two values; OR
  the distance between the H/C layer and the heating source (e.g. LED) is 5 mm, 10 mm, 20 mm, 30 mm, or in a range between any of the two values.

MM11. The device, apparatus, system, or method of any prior embodiments, wherein:
  the first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values;
  the sample between the two plates has a thickness of 5 um, 10 um, 30 um, 50 um, 100 um, or in a range between any of the two values;
  the distance between the H/C layer and the sample is 10 nm, 100 nm, 500 nm, 1 um, um, 10 um, or in a range between any of the two values;
  the ratio of the cooling zone area to the relevant sample area is 16, 9, 4, 2, or in a range between any of the two values;
  the ratio of the cooling zone area to the heating area is 16, 9, 4, 2, or in a range between any of the two values; AND
  the distance between the H/C layer and the heating source (e.g. LED) is 5 mm, 10 mm, 20 mm, 30 mm, or in a range between any of the two values.

MM12. The device, apparatus, system, or method of any prior embodiments, wherein:
  the first plate and second plates are plastic or a thin glass. The first plate has a thickness of 10 um, 25 um, 50 um, or in a range between any of the two values; while the second plate (that plate that has heating layer or cooling layer) has a thickness of 100 nm, 500 nm, 1 um, 5 um, 10 um, in a range between any of the two values;
  the sample between the two plates has a thickness of 5 um, 10 um, 30 um, 50 um, 100 um, or in a range between any of the two values;
  the distance between the H/C layer and the sample is 10 nm, 100 nm, 500 nm, 1 um, um, 10 um, or in a range between any of the two values;
  the ratio of the cooling zone area to the relevant sample area is 16, 9, 4, 2, or in a range between any of the two values;
  the ratio of the cooling zone area to the heating area is 16, 9, 4, 2, or in a range between any of the two values; OR
  the distance between the H/C layer and the heating source (e.g. LED) is 5 mm, 10 mm, 20 mm, 30 mm, or in a range between any of the two values.

MM13. The device, apparatus, system, or method of any prior embodiments, wherein:
- the first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values;
- the sample between the two plates has a thickness of 100 nm, 500 nm, 1 um, 5 um, um, 25 um, 50 um, 100 um, 250 um, or in a range between any of the two values;
- the distance between the H/C layer and the sample is 100 nm, 500 nm, 1 um, 5 um, um, 25 um, 50 um, 100 um, 175 um, 250 um, or in a range between any of the two values;
- the ratio of the cooling zone area to the relevant sample area is 100, 64, 16, 9, 4, 2, 1, 0.5, 0.1, or in a range between any of the two values;
- the ratio of the cooling zone area to the heating zone is 100, 64, 16, 9, 4, 2, 1, 0.5, 0.1, or in a range between any of the two values; AND
- the distance between the H/C layer and the heating source (e.g. LED) is 500 um, 1 mm, 3 mm, 5 mm, 10 mm, 20 mm, 30 mm, or in a range between any of the two values.

MM14. The device, apparatus, system, or method of any prior embodiments, wherein:
- the first plate and second plates are plastic or a thin glass. The first plate and second plate have a thickness of 100 nm, 500 nm, 1 um, 5 um, 10 um, 25 um, 50 um, 100 um, 175 um, 250 um, or in a range between any of the two values;
- the sample between the two plates has a thickness of 100 nm, 500 nm, 1 um, 5 um, um, 25 um, 50 um, 100 um, 250 um, or in a range between any of the two values;
- the distance between the H/C layer and the sample is 100 nm, 500 nm, 1 um, 5 um, um, 25 um, 50 um, 100 um, 175 um, 250 um, or in a range between any of the two values;
- the ratio of the cooling zone area to the relevant sample area is 100, 64, 16, 9, 4, 2, 1, 0.5, 0.1, or in a range between any of the two values;
- the ratio of the cooling zone area to the heating zone is 100, 64, 16, 9, 4, 2, 1, 0.5, 0.1, or in a range between any of the two values; OR
- the distance between the H/C layer and the heating source (e.g. LED) is 500 um, 1 mm, 3 mm, 5 mm, 10 mm, 20 mm, 30 mm, or in a range between any of the two values.

MM15. The device, apparatus, system, or method of any prior embodiments, wherein a light pipe collimates the light from a light source (e.g. LED) into the heating zone; the light pipe comprises a structure with a hollow hole (e.g. a tube or a structure milled a hole) with a reflective wall; and the light pipe has a lateral dimension for 1 mm to 8 mm and length of 2 mm to 50 mm.

MM16. The device, apparatus, system, or method of any prior embodiments, wherein:
- the first plate and second plates are plastic or a thin glass;
- the first plate and second plate have a thickness of 100 nm, 500 nm, 1 um, 5 um, 10 um, in a range between any of the two values;
- the sample between the two plates has a thickness in a range of 1 to 5 um, 5 um to um, 10 to 30 um, or 30 um to 50 um;
- the distance from the H/C layer to the sample is in a range of 10 nm to 100 nm, 100 nm to 500 nm, 500 nm to 1 um, 1 um to 5 um, 5 um to 10 um, or 10 um to 25 um;
- the ratio of the cooling zone area to the relevant sample area is 16, 9, 4, 2, or in a range between any of the two values;
- the ratio of the cooling zone area to the heating area is 16, 9, 4, 2, or in a range between any of the two values;
- the distance between the H/C layer and the heating source (e.g. LED) is 5 mm, 10 mm, 20 mm, 30 mm, or in a range between any of the two values;
- the KC ratio for the cooling layer is in a range of between 0.5 $cm^2$/sec and 0.7 $cm^2$/sec, 0.7 $cm^2$/sec and 0.9 $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and $cm^2$/sec, or 2 $cm^2$/sec and $cm^2$/sec; and
- the sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100.

MM17. The device, apparatus, system, or method of any prior embodiments, wherein:
- the first plate and second plates are plastic or a thin glass;
- the first plate and second plate have a thickness of 100 nm, 500 nm, 1 um, 5 um, 10 um, in a range between any of the two values;
- the sample between the two plates has a thickness in a range of 1 to 5 um, 5 um to um, 10 to 30 um, or 30 um to 50 um;
- the distance from the H/C layer to the sample is in a range of 10 nm to 100 nm, 100 nm to 500 nm, 500 nm to 1 um, 1 um to 5 um, 5 um to 10 um, or 10 um to 25 um;
- the ratio of the cooling zone area to the relevant sample area is 16, 9, 4, 2, or in a range between any of the two values;
- the ratio of the cooling zone area to the heating area is 16, 9, 4, 2, or in a range between any of the two values;
- the distance between the H/C layer and the heating source (e.g. LED) is 5 mm, 10 mm, 20 mm, 30 mm, or in a range between any of the two values;
- the KC ratio for the cooling layer is in a range of between 0.5 $cm^2$/sec and 0.7 $cm^2$/sec, 0.7 $cm^2$/sec and $cm^2$/sec, 0.9 $cm^2$/sec and 1 $cm^2$/sec, 1 $cm^2$/sec and 1.1 $cm^2$/sec, 1.1 $cm^2$/sec and 1.3 $cm^2$/sec, 1.3 $cm^2$/sec and 1.6 $cm^2$/sec, 1.6 $cm^2$/sec and 2 $cm^2$/sec, or 2 $cm^2$/sec and 3 $cm^2$/sec; OR
- the sample to non-sample thermal mass ratio is in a range of between 0.2 to 0.5, 0.5 to 0.7, 0.7 to 1, 1 to 1.5, 1.5 to 5, 5 to 10, 10 to 30, 30 to 50, or 50 to 100.

NN1. The device, apparatus, system or method of any prior embodiments, wherein the device comprises a heating layer and a cooling layer, where the cooling layer has an area larger than that heating zone.

NN2. The device, apparatus, system or method of any prior embodiments, wherein the device comprises one heating/cooling layer, where the cooling zone has an area larger than that heating zone.

NN3. The device, apparatus, system or method of any prior embodiments, wherein the device comprises a cooling layer that has a high thermal conductivity (50 W/($m^2$.-K)) and an area larger than lateral area of a relevant sample.

NN4. The device, apparatus, system or method of any prior embodiments, wherein the device comprises a cooling layer that has a high thermal conductivity (greater than 50 W/($m^2 \cdot K$) (m·K)) and an area larger than lateral area of a relevant sample by a factor of 2 to 40.

NN5. The device, apparatus, system or method of any prior embodiments, wherein the device comprises a cooling layer that has (i) a high thermal conductivity (greater than 50

W/(m·K)), and (ii) thermal radiation enhancement layer (specify the thermal radiation).

NN6. The device, apparatus, system or method of any prior embodiments, wherein the device comprises a cooling layer that has (i) a high thermal conductivity (greater than 50 W/(m·K)), and (ii) thermal radiation enhancement layer, and (iii) an area larger than lateral area of a relevant sample.

NN7. The device, apparatus, system or method of any prior embodiments, wherein the device comprises a cooling layer that has (i) a high thermal conductivity (greater than 50 W/(m·K)), and (ii) thermal radiation enhancement layer, and (iii) an area larger than lateral area of a relevant sample by a factor of 1.5 to 100.

NN8. The device, apparatus, system or method of any prior embodiments, wherein the device comprises a cooling zone has a thermal radiation enhancement layer that has an average light absorption coefficient of 70% over the wavelength range.

NN9. The device, apparatus, system or method of any prior embodiments, wherein the device comprises a cooling zone has a thermal conductivity multiplying its thickness in the range of $6 \times 10^{-5}$ W/K to $3 \times 10^{-4}$ W/K.

NN10. The device, apparatus, system or method of any prior embodiments, wherein the device comprises a cooling zone comprises a gold layer of a thickness in the range of 200 nm to 800 nm.

NN11. The device, apparatus, system or method of any prior embodiments, wherein the device comprises a thermal conductivity multiplying its thickness in the range of $6 \times 10^{-5}$ W/K to $3 \times 10^{-4}$ W/K.

NN12. The device, apparatus, system or method of any prior embodiments, wherein the device comprises a cooling layer that:
- has a high thermal conductivity (greater than 50 W/(m·K)),
- comprises thermal radiation enhancement layer that has an average light absorption coefficient of 70% over the wavelength range;
- has an area larger than lateral area of a relevant sample by a factor of 1.5 to 100; and
- has a thermal conductivity multiplying its thickness in the range of $6 \times 10^{-5}$ W/K to $3 \times 10{-4}$ W/K.

NN13. The device, apparatus, system or method of any prior embodiments, wherein the device comprises a cooling zone (layer) has thermal conductivity times its thickness of $6 \times 10^{-5}$ W/K, $9 \times 10^{-5}$ W/K, $1.2 \times 10^{-4}$ W/K, $1.5 \times 10^{-4}$ W/K, $1.8 \times 10^{-4}$ W/K, $2.1 \times 10^{-4}$ W/K, $2.7 \times 10^{-4}$ W/K, $3 \times 10^{-4}$ W/K, $1.5 \times 10^{-4}$ W/K, or in a range between any of the two values.

NN14. The device, apparatus, system or method of any prior embodiments, wherein the device comprises a cooling zone (layer) has thermal conductivity times its thickness in a range of $6 \times 10^{-5}$ W/K to $9 \times 10^{-5}$ W/K, $9 \times 10^{-5}$ W/K to $1.5 \times 10^{-4}$ W/K, $1.5 \times 10^{-4}$ W/K to $2.1 \times 10^{-4}$ W/K, $2.1 \times 10^{-4}$ W/K to $2.7 \times 10^{-4}$ W/K, $2.7 \times 10^{-4}$ W/K to $3 \times 10^{-4}$ W/K, or $3 \times 10^{-4}$ W/K to $1.5 \times 10^{-4}$ W/K.

NN15. The device, apparatus, system or method of any prior embodiments, wherein the device comprises cooling zone (layer) has thermal conductivity times its thickness in a range of $9 \times 10^{-5}$ W/K to $2.7 \times 10^{-4}$ W/K, $9 \times 10^{-5}$ W/K to $2.4 \times 10^{-4}$ W/K, $9 \times 10^{-5}$ W/K to $2.1 \times 10^{-4}$ W/K, or $9 \times 10^{-5}$ W/K to $1.8 \times 10^{-4}$ W/K.

NN16. The device, apparatus, system or method of any prior embodiments, wherein the device comprises cooling zone comprises a gold layer of a thickness in the range of 200 nm to 800 nm. In another embodiment, a cooling zone comprises a gold layer of a thickness in the range of 300 nm to 700 nm.

NN17. The device, apparatus, system or method of any prior embodiments, wherein in the device the materials between the heating zone and the relevant sample has a thermal conductivity and a thickness configured to have a conductance per unit area that is equal to or larger than 1,000 W/(m²·K), 2000 W/(m²·K), 3,000 W/(m²·K), 4000 W/(m²·K), 5000 W/(m²·K), 7,000 W/(m²·K), 10,000 W/(m²·K), 20,000 W/(m²·K), 50,000 W/(m²·K), 50,000 W/(m²·K), 100,000 W/(m²·K), or in a range of any the values.

NN18. The device, apparatus, system or method of any prior embodiments, wherein a preferred conductance per unit area of the material between the heating zone and the relevant sample is in a range of 1,000 W/(m²·K) to 2,000 W/(m²·K), 2,000 W/(m²·K) to 4000 W/(m²·K), 4,000 W/(m²·K) to 10,000 W/(m²·K), or 10,000 W/(m²·K) to 100,000 W/(m²·K).

NN19. The device, apparatus, system or method of any prior embodiments, wherein there is zero distance between the heating zone and the relevant sample, and hence an infinity for the conductance per unit area of the material between the heating zone and the relevant sample.

NN20. The device, apparatus, system or method of any prior embodiments, wherein the heating layer or the cooling layer is separated from a relevant sample by a thin plastics plate (or film) which has a thermal conductivity in the range of 0.1 to 0.3 W/(m·K), and the thin plastic layer has a thickness of 0 nm, 10 nm, 50 nm, 100 nm, 200 nm, 300 nm, 400 nm, 500 nm, 1 um, 2.5 um, 5 um, 10 um, 25 um, 50 um, 75 nm 100 um, 150 um, or in a range between any of the two values NN21. The device, apparatus, system or method of any prior embodiments, wherein the thin plastic plate (or film) that separate the relevant sample from the heating layer or the cooling layer has thickness in a range between 0 nm and 100 nm, 100 nm and 500 nm, 500 nm and 1 um, 1 um and 5 um, 5 um and 10 um, 10 um and 25 um, 25 um and 50 um, 50 um and 75 um, 75 um and 100 um, or 100 um and 150 um.

NN22. The device, apparatus, system or method of any prior embodiments, wherein the thin plastic plate (or film) that separates the relevant sample from the heating layer or the cooling layer has thickness of 0.1 um, 0.5 um, 1 um, 5 um, 10 um, 20 um, 25 um, or a range between any two values.

NN23. The device, apparatus, system or method of any prior embodiments, wherein the area of the heating zone is only a fraction of the area of the cooling zone or area, and the area of the cooling zone (layer) is larger than the area of the heating zone by a factor of 1.1, 1.5, 2, 3, 4, 5, 10, 20, 30, 40, 50, 70,100,200, 300, 400, 500, 600, 700, 800, 800, 1,000, 5000, 10,000, 100,000, or in a range between any of the two values.

NN24. The device, apparatus, system or method of any prior embodiments, wherein the cooling zone (layer) has an area that is larger than the lateral area of the hearing zone (layer) by a factor in a range of 1.1 to 1.5, 1.5 to 5, 5 to 10, 10 to 50, 50 to 100, 100 to 500, 500 to 1,000, 1000, to 10,000, or 10,000 to 100,000.

NN25. The device, apparatus, system or method of any prior embodiments, wherein the cooling zone (layer) has an area that is larger than the lateral area of the relevant sample by a factor of 1.5, 2, 3, 4, 5, 10, 20, 50, 70,100,200, 300, 400, 500, 600, 700, 800, 800, 1,000, 2000, 5000, 10,000, 100, 000, or in a range between any of the two values.

NN26. The device, apparatus, system or method of any prior embodiments, wherein the cooling zone (layer) has an area that is larger than the lateral area of the relevant sample by a factor in a range of 1.5 to 5, 5 to 10, 10 to 50, 50 to 100, 100 to 500, 500 to 1,000, 1000, to 10,000, or 10,000 to 100,000.

NN27. The device, apparatus, system or method of any prior embodiments, wherein the first plate or the second plate has a thickness of 10 nm, 100 nm, 200 nm, 300 nm, 400 nm, 500 nm, 1 um, 2.5 um, 5 um, 10 um, 25 um, 50 um, 100 um, 200 um, or 500 um, 1000 um, or in a range between any of the two values.

NN28. The device, apparatus, system or method of any prior embodiments, wherein the first plate and the second plate can have the same thickness or a different thickness, and can be made of the same materials or different materials.

NN29. The device, apparatus, system or method of any prior embodiments, wherein the first plate or the second plate has a thickness in a range of between 10 nm and 500 nm, 500 nm and 1 um, 1 um and 2.5 um, 2.5 um and 5 um, 5 um and 10 um, 10 um and 25 um, um and 50 um, 50 um and 100 um, 100 um and 200 um, or 200 um and 500 um, or 500 um and 1000 um.

NN30. The device, apparatus, system or method of any prior embodiments, wherein the first plate and second plates are plastic, a thin glass, or a material with similar physical properties. The first plate or second plate have a thickness of 100 nm, 500 nm, 1 um, 5 um, um, 25 um, 50 um, 100 um, 175 um, 250 um, or in a range between any of the two values.

NN31. The device, apparatus, system or method of any prior embodiments, wherein the ratio of the average lateral size of the relevant sample volume to the diffusion length of the reagent during the time for thermal cycling or a reaction is equal to or larger than 5, 6, 7, 10, 15, 20, 25, 30, 40, 50, 60, 70, 80, 90,100,150, 200, 500, 1,000, 5,000, 10,000, 100,000, or in a range between any two values.

NN32. The device, apparatus, system or method of any prior embodiments, wherein the ratio of the average lateral size of the relevant sample volume to the diffusion length of the reagent during the time for thermal cycling or a reaction is in a range of 5 to 10, 10 to 30, to 60, 6 to 100, 100 to 200, 200 to 500, 500 to 1,000, 1,000 to 5000, 5,000 to 10,000, or 10,000 to 100,000.

NN33. The device, apparatus, system or method of any prior embodiments, wherein the ratio of the average lateral size of the relevant sample volume to the diffusion length of the reagent during the time for thermal cycling or a reaction is in a range of 5 to 10, 10 to 30, to 60, 6 to 100, 100 to 200, 200 to 500, 500 to 1,000, 1,000 to 5,000, 5,000 to 10,000, or 10,000 to 100,000.

NN34. The device, apparatus, system or method of any prior embodiments, wherein the average lateral dimension of the relevant volume is 1 mm, 2 mm, 3 mm, 5 mm, 6 mm, 7 mm, 8 mm, 9 mm 10 mm, 12 mm, 15 mm, 20 mm, 30 mm, 40 mm, 50 mm, 70 mm, 100 mm, 200 mm, or in a range between any two values.

NN35. The device, apparatus, system or method of any prior embodiments, wherein the average lateral dimension of the relevant volume is in a range of 1 mm to 5 mm, 5 mm to 10 mm, 10 mm to 20 mm, 20 mm to 40 mm, 40 mm to 70 mm, 70 mm to 100 mm, or 100 mm to 200 mm.

NN36. The device, apparatus, system or method of any prior embodiments, wherein the average lateral dimension of the relevant volume is in a range of 1 mm to 5 mm, 1 mm to 10 mm, or 5 mm to 20 mm.

NN37. The device, apparatus, system or method of any prior embodiments, wherein the thermal radiation enhancement surface has a high average light absorptance (e.g. the black paint used in our experiments). In certain embodiments, the cooling zone has a surface that has an average light absorptance of 30%, 40%, 50%, 60%, 70%, 80%, 90%, 95%, 100%, or in a range between any of the two values.

NN38. The device, apparatus, system or method of any prior embodiments, wherein the cooling zone has a surface that has an average light absorptance in a range of 30% to 40%, 40% to 60%, 60% to 80% to 90%, or 90% to 100%.

NN39. The device, apparatus, system or method of any prior embodiments, wherein the cooling zone has a surface that has an average light absorptance in a range of 30% to 100%, 50% to 100%, 70% to 100%, or 80% to 100%.

NN40. The device, apparatus, system or method of any prior embodiments, wherein the cooling zone has a surface that has an average light absorptance of a value given above by averaging over a wavelength range 400 nm to 800 nm, 700 nm to 1500 nm, 900 nm to 2,000 nm, or 2,000 nm to 20,000 nm.

NN41. The device, apparatus, system or method of any prior embodiments, wherein the black paints are polymer mixtures that look black by human eyes. A black paint include, but not limited to, a mixture of polymers and nanoparticles. One example of the nanoparticles is black carbon nanoparticle, carbon, nanotubes, graphite particles, graphene, metal nanoparticles, semiconductor nanoparticles, or a combination thereof.

NN42. The device, apparatus, system or method of any prior embodiments, wherein the plasmonic structures include nanostructured plasmonic structures.

NN43. The device, apparatus, system or method of any prior embodiments, wherein a cooling plate comprise a layer of high thermal conductivity metal (50 W/(m·K) or higher) with a surface thermal radiation enhancement layer. In some embodiments, the surface thermal radiation enhancement layer has a low lateral thermal conductance, which is due to either ultrathin layer, low thermal conductivity, or both.

NN44. The device, apparatus, system or method of any prior embodiments, wherein thermal radiative cooling is achieved by increasing the area of radiative cooling layer (i.e. a high-K material, unless stated otherwise), and the radiative cooling layer area is larger than the lateral area of the relevant sample by a factor of 1.2, 1.5, 2, 3, 4, 5, 10, 20, 30, 40, 50, 60, 70, 80 100, 200, 300, 400, 500, 600, 700, 800, 800, 1,000, 2,000, 5,000, 10,000, 100,000, or in a range between any of the two values.

NN45. The device, apparatus, system or method of any prior embodiments, wherein the radiative cooling zone (layer) has an area that is larger than the lateral area of the relevant sample by a factor in a range of 1.2 to 3, 3 to 5, 5 to 10, 10 to 50, 50 to 100, 100 to 500, 500 to 1,000, 1000, to 10,000, or 10,000 to 100,000.

NN46. The device, apparatus, system or method of any prior embodiments, wherein the ratio of the thermal radiation cooling by the cooling zone (layer) to the total cooling of the sample and sample holder during a thermal cycling is 10%, 20%, 30%, 40%, 50%, 60%, 70%, 80%, 90%, 99%, or in a range between any of the two values.

NN47. The device, apparatus, system or method of any prior embodiments, wherein the ratio of the thermal radiation cooling by the cooling zone (layer) to the total cooling of the sample and sample holder during a thermal cycling is in a range of between 10% and 20%, 20% and 30%, 30% and 40%, 40% and50%, 50% and 60%, 60% and 70%, 70% and 80%, 80% and 90%, or 90% and 99%.

NN48. The device, apparatus, system or method of any prior embodiments, wherein the KC ratio materials for the heating layer is equal to or higher than 0.1 $cm^2$/sec, 0.2 cm²/sec, 0.3 cm²/sec, 0.4 cm²/sec, 0.5 cm²/sec, 0.6 cm²/sec, 0.7 cm²/sec, 0.8 cm²/sec, 0.9 cm²/sec, 1 cm²/sec, 1.1 cm²/sec, 1.2 cm²/sec, 1.3 cm²/sec, 1.4 cm²/sec, 1.5 cm²/sec, 1.6 cm²/sec, 2 cm²/sec, 3 cm²/sec, or in a range between any of the two values.

NN49. The device, apparatus, system or method of any prior embodiments, wherein the KC ratio for the heating layer is in a range of between 0.5 cm²/sec and 0. cm²/sec, 0.7 cm²/sec and 0.9 cm²/sec, 0.9 cm²/sec and 1 cm²/sec, 1 cm²/sec and 1.1 cm²/sec, 1.1 cm²/sec and 1.3 cm²/sec, 1.3 cm²/sec and 1.6 cm²/sec, 1.6 cm²/sec and 2 cm²/sec, or 2 cm²/sec and 3 cm²/sec.

NN50. The device, apparatus, system or method of any prior embodiments, wherein a thermal radiation enhancement surface(s) will be used (on one side or both side of the heating zone). A thermal radiation absorption enhancement surface can be achieved by directly modify the structures of the surface (e.g. patterning nanostructures), coating a high thermal radiation materials (e.g. coating a black paint), or both.

NN51. The device, apparatus, system or method of any prior embodiments, wherein the thermal radiation enhancement surface has a high average light absorptance (e.g. the black paint used in our experiments). In certain embodiments, the heating zone has a surface that has an average light absorptance of 30%, 40%, 50%, 60%, 70%, 80%, 90%, 95%, 100%, or in a range between any of the two values.

NN52. The device, apparatus, system or method of any prior embodiments, wherein the heating zone has a surface that has an average light absorptance in a range of 30% to 40%, 40% to 60%, 60% to 80% to 90%, or 90% to 100%.

NN53. The device, apparatus, system or method of any prior embodiments, wherein the heating zone has a surface that has an average light absorptance in a range of 30% to 100%, 50% to 100%, 70% to 100%, or 80% to 100%.

NN54. The device, apparatus, system or method of any prior embodiments, wherein the heating zone has a surface that has an average light absorptance of a value given above by averaging over a wavelength range 400 nm to 800 nm, 700 nm to 1,500 nm, 900 nm to 2,000 nm, or 2,000 nm to 20,000 nm.

NN55. The device, apparatus, system or method of any prior embodiments, wherein the LVS ratio for sample is 5, 10, 20, 50, 70,100,200, 300, 400, 500, 600, 700, 800, 800, 1,000, 2,000, 5,000, 10,000, 100,000, or in a range between any of the two values.

NN56. The device, apparatus, system or method of any prior embodiments, wherein the LVS ratio for sample is in a range of 5 to 10, 10 to 50, 50 to 100, 100 to 500, 500 to 1,000, 1,000, to 10,000, or 10,000 to 100,000, NN57. The device, apparatus, system or method of any prior embodiments, wherein the sample has a lateral dimension of 15 mm and a thickness of 30 um, hence an LVS for the sample of 500.

NN58. The device, apparatus, system or method of any prior embodiments, wherein the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

NN59. The device, apparatus, system or method of any prior embodiments, wherein the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

NN60. The device, apparatus, system or method of any prior embodiments, wherein the KC ratio materials for the cooling layer is equal to or higher than 0.1 cm²/sec, 0.2 cm²/sec, 0.3 cm²/sec, 0.4 cm²/sec, 0.5 cm²/sec, 0.6 cm²/sec, 0.7 cm²/sec, 0.8 cm²/sec, 0.9 cm²/sec, 1 cm²/sec, 1.1 cm²/sec, 1.2 cm²/sec, 1.3 cm²/sec, 1.4 cm²/sec, 1.5 cm²/sec, 1.6 cm²/sec, 2 cm²/sec, 3 cm²/sec, or in a range between any of the two values.

NN61. The device, apparatus, system or method of any prior embodiments, wherein the KC ratio for the cooling layer is in a range of between 0.5 cm²/sec and 0.7 cm²/sec, 0.7 cm²/sec and 0.9 cm²/sec, 0.9 cm²/sec and 1 cm²/sec, 1 cm²/sec and 1.1 cm²/sec, 1.1 cm²/sec and 1.3 cm²/sec, 1.3 cm²/sec and 1.6 cm²/sec.

NN62. The device, apparatus, system or method of any prior embodiments, wherein a high thermal conductivity (i.e. high-K) material is used for the cooling layer, and the high-K material has a thermal conductivity of equal to or larger than 50 W/(m·K), 80 W/(m·K), 100 W/(m·K), 150 W/(m·K), 200 W/(m·K), 250 W/(m·K), 300 W/(m·K), 350 W/(m·K), 400 W/(m·K), 450 W/(m·K), 500 W/(m·K), or in a range between any of the two values.

NN63. The device, apparatus, system or method of any prior embodiments, wherein the sample to non-sample thermal mass ratio (NSTM ratio) is 0.1, 0.2, 0.3, 0.4, 0.5, 0.6, 0.7, 1, 1.5, 2, 3, 4, 5, 10, 20, 30, 40, 50, 60, 70,100,200, 300, 1,000, 4,000, or in a range between any of the two values.

NN64. The device, apparatus, system or method of any prior embodiments, wherein the sample to non-sample thermal mass ratio (NSTM ratio) is in a range of between 0.1 to 0.2, 0.2 to 0.5, 0.5 to 0.7, 0.7 to 1, 1 to 1.5, 1.5 to 5, 5 to 10, 10 to 30, 30 to 50, 50 to 100, 100 to 300, 300 to 1,000, or 1,000 to 4,000.

NN65. The device, apparatus, system or method of any prior embodiments, wherein the device is configured to make the sample to non-sample thermal mass ratio high, one need to keep the area thermal mass of the non-sample low, which in turn, needs to make the plates and the heating/cooling layer thin, and/or the volume specific heat low.

NN66. The device, apparatus, system or method of any prior embodiments, wherein the device comprises a thin material that has multi-layers or mixed materials. For examples, a carbon fiber layer(s) with plastic sheets or carbon mixed with plastics, which can have a thickness of 0.1 um, 0.2 um, 0.5 um, 1 um, 2 um, 5 um, 10 um, 25 um, 50 um, or in a range between any of the two values.

NN67. The device, apparatus, system or method of any prior embodiments, wherein the relevant volume of the sample is 0.001 ul, 0.005 ul, 0.01 ul, 0.02 ul, 0.05 ul, 0.1 ul, 0.2 ul, 0.5 ul, 1 ul, 2 ul, 5 ul, 10 ul, 20 ul, 30 uL, 50 ul, 100 ul, 200 ul, 500 ul, 1 ml, 2 ml, 5 ml, or in a range between any of the two values.

NN68. The device, apparatus, system or method of any prior embodiments, wherein the relevant sample volume is in a range of 0.001 uL to 0.1 uL, 0.1 um to 2 uL, 2 uL to 10 uL, 10 uL to 30 uL, 30 uL to 100 uL, 100 uL to 200 uL, or 200 μl to 1 mL.

NN69. The device, apparatus, system or method of any prior embodiments, wherein the relevant sample volume is in a range of 0.001 uL to 0.1 uL, 0.1 um to 1 uL, 0.1 uL to 5 uL, or 0.1 uL to 10 uL.

NN70. The device, apparatus, system or method of any prior embodiments, wherein the ratio of the relevant sample to entire sample volume (RE ratio) is 0.01%, 0.05%, 0.1%, 0.5%, 0.1%, 0.5%, 1%, 5%, 10%, 20%, 30%, 40%, 50%, 60%, 70%, 80%, 90%, 100%, or in a range between any of the two values.

NN71. The device, apparatus, system or method of any prior embodiments, wherein the RE ratio is in a range of between 0.01% and 0.1%, 0.1% and 1%, 1% and 10%, 10% and 30%, 30% and 60%, 60% and 90%, or 90% and 100%.

NN72. The device, apparatus, system or method of any prior embodiments, wherein the area of the heating zone is only a fraction of the sample lateral area, and the fraction (i.e. the ratio of the heating zone to the sample lateral area) is 0.01%, 0.05%, 0.1%, 0.5%, 0.1%, 0.5%, 1%, 5%, 10%, 20%, 30%, 40%, 50%, 60%, 70%, 80%, 90%, 99%, or in a range between any of the two values.

NN73. The device, apparatus, system or method of any prior embodiments, wherein the ratio of the heating zone area to the sample lateral area is in a range of between 0.01% and 0.1%, 0.1% and 1%, 1% and 10%, 10% and 30%, 30% and 60%, 60% and 90%, or 90% and 99%.

NN74. The device, apparatus, system or method of any prior embodiments, wherein the scaled thermal conduction ratio (STM ratio) is 2 or larger, 5 or larger, 10 or larger, 20 or larger, 30 or larger, 40 or larger, 50 or larger, 100 or larger, 1,000 or larger, 10,000 or larger, 10,000 or larger, or in a range between any of the two values.

NN75.1 The device, apparatus, system or method of any prior embodiments, wherein the scaled thermal conduction ratio (STM ratio) is in a range of between 10 to 20, 30 to 50, 50 to 70, 70 to 100, 100 to 1,000, 1,000 to 10,000, or 10,000 to 1,000,000. NN75.2 The device, apparatus, system or method of any prior embodiments, wherein the scaled thermal conduction ratio (STM ratio) is in a range of between 10 to 20, 30 to 50, 50 to 70, 70 to 100, 100 to 1,000, 1,000 to 10,000, or 10,000 to 1,000,000; and the cooling zone (layer) has thermal conductivity times its thickness of $6\times10^{-5}$ W/K, $9\times10^{-5}$ W/K, $1.2\times10^{-4}$ W/K, $1.5\times10^{-4}$ W/K, $1.8\times10^{-4}$ W/K, $2.1\times10^{-4}$ W/K, $2.7\times10^{-4}$ W/K, $3\times10^{-4}$ W/K, $1.5\times10^{-4}$ W/K, or in a range between any of the two values.

NN75.3 The device, apparatus, system or method of any prior embodiments, wherein the scaled thermal conduction ratio (STM ratio) is in a range of between 20 to 80.

NN76. The device, apparatus, system or method of any prior embodiments, wherein the lateral to vertical size (LVS) ratio for relevant sample is 5, 10, 20, 50, 70, 100, 200, 300, 400, 500, 600, 700, 800, 800, 1,000, 2000, 5000, 10,000, 100,000, or in a range between any of the two values.

NN77. The device, apparatus, system or method of any prior embodiments, wherein the LVS ratio for relevant sample is in a range of 5 to 10, 10 to 50, 50 to 100, 100 to 500, 500 to 1,000, 1,000, to 10,000, or 10,000 to 100,000.

NN78. The device, apparatus, system or method of any prior embodiments, wherein the thickness of the relevant sample is reduced (which also can help sample heating speed), and the relevant sample has a thickness of 0.05 um, 0.1 um, 0.2 um, 0.5 um, 1 um, 2 um, 5 um, 10 um, 20 um, 30 um, 40 um, 50 um, 60 um, 70 um, 80 um, 90 um, 100 um, 200 um, 300 um, or in a range between any of the two values.

NN78. The device, apparatus, system or method of any prior embodiments, wherein the relevant sample has a thickness in a range between 0.05 um and 0.5 um, 0.5 um and 1 um, 1 um and 5 um, 5 um and 10 um, 10 um and 30 um, 30 um and 50 um, 50 um and 70 um, 70 um and 100 um, 100 um and 200 um, or 200 um and 300 um.

OO1. A device, comprising:
a first plate comprising a polymer material and having a thickness less than or equal to 100 μm;
a second plate comprising a polymer material and having a thickness less than or equal to 100 μm; and
a heating/cooling layer disposed on either the first plate or the second plate, the heating/cooling layer having a thermal conductivity between 6×10.5 W/K multiplied by the thickness of the heating/cooling layer and 1.5× $10^{-4}$ W/K multiplied by the thickness of the heating/cooling layer,
wherein the first plate and the second plate face each other in a parallel arrangement, and are separated from each other by a distance, and wherein the first plate and the second plate are configured to receive a fluid sample sandwiched between the first plate and the second plate.

OO2. A device, comprising:
a first plate;
a second plate having a thickness less than or equal to 100 um, wherein the second plate is separated from the first plate in a parallel arrangement by a distance less than or equal to the thickness of the second plate; and
a heating/cooling layer disposed on either the first plate or the second plate,
wherein the heating/cooling layer is configured to receive electromagnetic radiation such that at least a portion of a liquid sample sandwiched between the first plate and the second plate is heated at a rate of at least 30° C./sec.

OO3. A device, comprising:
a first plate;
a second plate having a thickness less than or equal to 100 um, wherein the second plate is separated from the first plate in a parallel arrangement by a distance less than or equal to the thickness of the second plate; and
a heating/cooling layer disposed on either the first plate or the second plate,
wherein at least a portion of a liquid sample sandwiched between the first plate and the second plate is cooled at a rate of at least 30° C./sec when the heating/cooling layer is not receiving electromagnetic radiation generated by an optical source.

OO4. A device, comprising:
a first plate;
a second plate having a thickness less than or equal to 100 um, wherein an inner surface of the second plate is separated from an inner surface of the first plate in a parallel arrangement by a distance less than or equal to the thickness of the second plate;
a heating/cooling layer disposed on the inner surface or on an outer surface of the second plate; and
a layer of reagents dried on the inner surface of the first plate.

OO5. The device of any of OO1-OO4 embodiments, further comprising a light absorbing layer disposed on the heating/cooling layer, wherein the light absorbing layer has an average light absorptance of at least 30%.

OO6. The device of OO5, wherein the light absorbing layer comprises black paint.

OO7. The device of any of OO1-OO6 embodiments, wherein the first plate is movable relative to the second plate.

OO8. The device of any of OO1-OO7 embodiments, wherein a thickness of the heating/cooling layer is less than or equal to 3 μm.

OO9. The device of any of OO1-OO8 embodiments, wherein at least one of the first plate and the second plate has an area across its major surface of about 400 $mm^2$.

OO10. The device of any of OO1-OO9 embodiments, further comprising a plurality of spherical spacers disposed between the first plate and the second plate.

OO11. The device of any of OO1-OO9 embodiments, further comprising a plurality of spacers having a height of about 10 um, wherein the plurality of spacers are disposed between the first plate and the second plate.

OO12. The device of any of OO1-OO11 embodiments, wherein the distance between the first plate and the second plate is less than or equal to 100 μm.

OO13. The device of any of OO1-OO12 embodiments, further comprising a hinge configured to connect the first plate with the second plate, and coupled to an edge of the first plate or the second plate.

OO14. The device of any of OO1-OO13 embodiments, wherein the at least a portion of the liquid sample comprises a volume of the sample along a path of the electromagnetic radiation.

OO15. The device of any of OO1-OO14 embodiments, wherein the at least a portion of the liquid sample comprises a volume of the sample that is adjacent to the heating/cooling layer.

OO16. The device of OO4, wherein the layer of dried reagents comprises reagents used for nucleic acid amplification.

PP1. A system, comprising:
a device, comprising:
a first plate comprising a polymer material and having a thickness less than or equal to 100 μm,
a second plate comprising a polymer material and having a thickness less than or equal to 100 μm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between $6 \times 10.5$ W/K multiplied by the thickness of the heating/cooling layer and $1.5 \times 10^{-4}$ W/K multiplied by the thickness of the heating/cooling layer, and a support frame configured to support at least one of the first plate and the second plate;
a housing having a first opening configured to receive the device and at least one other opening;
an optical source configured to direct electromagnetic radiation towards the heating/cooling layer,
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source, and
wherein the system consumes less than 500 mW of power.

PP2. A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate; and
an optical source configured to direct electromagnetic radiation towards the heating/cooling layer,
wherein at least a portion of a liquid sample sandwiched between the first plate and the second plate is cooled at a rate of at least 30° C./sec when the heating/cooling layer is not receiving the electromagnetic radiation generated by the optical source.

PP3. A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate; and
an optical source configured to direct electromagnetic radiation towards the heating/cooling layer, wherein the system consumes less than 500 mW of power.

PP4. A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate;
a housing having a first opening configured to receive the device and at least one other opening; and
an optical source configured to direct electromagnetic radiation through the at least one other opening of the housing and towards the heating/cooling layer,
wherein a liquid sample sandwiched between the first plate and the second plate is cooled at a rate of at least 30° C./sec when the heating/cooling layer is not receiving the electromagnetic radiation generated by the optical source.

PP5. The system of any one of PP1-PP4 embodiments, wherein the device further comprises a light absorbing layer disposed on the heating/cooling layer, wherein the light absorbing layer has an average light absorptance of at least 30%.

PP6. The system of PP5, wherein the light absorbing layer comprises black paint.

PP7. The system of any one of PP1-PP6 embodiments, wherein the first plate is movable relative to the second plate.

PP8. The system of any one of PP1-PP7 embodiments, wherein a thickness of the heating/cooling layer is less than or equal to 3 um.

PP9. The system of any one of PP1-PP8 embodiments, wherein at least one of the first plate and the second plate has an area across its major surface of about 400 mm$^2$.

PP10. The system of any one of PP1-PP9 embodiments, wherein the optical source comprises a light emitting diode (LED.)

PP11. The system of PP10, wherein the LED comprises a blue LED.

PP12. The system of any one of PP1-PP11 embodiments, further comprising an optical pipe configured to guide the electromagnetic radiation from the optical source to the heating/cooling layer.

PP13. The system of PP1 or PP4, wherein the at least one other opening of the housing is configured to be aligned over at least the portion of the liquid sample sandwiched between the first plate and the second plate when the device is placed within the housing via the first opening.

PP14. The system of any one of PP1-PP13 embodiments, wherein the support frame is configured to support at least the first plate or the second plate along a perimeter of the first plate or second plate.

QQ1. A method of using a device, comprising:
placing a second plate over a first plate such that a fluidic sample is sandwiched between the first plate and the second plate at a thickness determined by one or more spacers located on at least one of the first plate and the second plate;
activating a heat source configured to radiate electromagnetic radiation towards a heating layer located on either the first plate or the second plate; and
heating, using at least the heating layer, at least a portion of the fluidic sample at a rate of at least 30° C./sec.

QQ2. A method of using a device, comprising:
placing a second plate over the first plate such that a fluidic sample is sandwiched between the first plate and the second plate at a thickness determined by one or more spacers located on at least one of the first plate and the second plate;
activating, for a given time period, a heat source configured to radiate electromagnetic radiation towards a heating/cooling layer located on either the first plate or the second plate;
deactivating the heat source after the given time period, wherein at least a portion of the fluidic sample cools at a rate of at least 30° C./sec after the deactivating.

QQ3. A method of using a device, comprising:
placing a second plate over the first plate such that a fluidic sample is sandwiched between the first plate and the second plate at a thickness determined by one or more spacers located on at least one of the first plate and the second plate;
activating a heat source configured to radiate electromagnetic radiation towards a heating layer located on either the first plate or the second plate, wherein the heat source consumes less than 500 mW of power; and
heating, using at least the heating layer, at least a portion of the fluidic sample.

QQ4. The method of any one of QQ1-QQ3 embodiments, wherein the first plate or the second plate further comprises a light absorbing layer disposed on the heating layer, wherein the light absorbing layer has an average light absorptance of at least 30%.

QQ5. The method of QQ4, wherein the light absorbing layer comprises black paint.

QQ6. The method of any one of QQ1-QQ5 embodiments, further comprising closing the second plate over the first plate using a hinge connected between the first plate and the second plate.

QQ7. The method of any one of QQ1-QQ6 embodiments, wherein a thickness of the heating layer is less than or equal to 3 um.

QQ8. The method of any one of QQ1-QQ7 embodiments, wherein at least one of the first plate and the second plate has an area across its major surface of about 400 mm$^2$.

QQ9. The method of any one of QQ1-QQ8 embodiments, wherein activating a heat source comprises activating an LED to radiate light towards the heating layer.

QQ10. The method of QQ9, further comprising controlling an output of the LED based on a measured or estimated temperature of the portion of the fluidic sample.

QQ11. The method of any one of QQ1-QQ10 embodiments, further comprising expanding the electromagnetic radiation using a beam expander before the electromagnetic radiation reaches the heating layer.

QQ12. The method of any one of QQ1-QQ11 embodiments, further comprising supporting a perimeter of either the first plate or the second plate on a support frame.

RR1. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec; and
accumulating nucleic acid amplification products in at least the portion of the fluidic sample sandwiched between the first plate and the second plate.

RR2. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
amplifying nucleic acids in the sample by conducting one or more PCR cycles, wherein each PCR cycle comprises a denaturing step, an annealing step, and an elongation step;
wherein one or more of the denaturing step, the annealing step, and/or the elongation step comprises:
activating a heat source configured to radiate electromagnetic radiation towards a heating layer located on either the first plate or the second plate; and
heating, using at least the heating layer, at least a portion of the fluidic sample at a rate of at least 30° C./sec.

RR3. A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
accumulating nucleic acid amplification products in at least the portion of the fluidic sample sandwiched between the first plate and the second plate.

RR4. A method of amplifying nucleic acids, comprising:
depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate;

amplifying nucleic acids in the sample by conducting one or more PCR cycles, wherein each PCR cycle comprises a denaturing step, an annealing step, and an elongation step;

wherein one or more of the denaturing steps, the annealing step, and/or the elongation step comprises:

activating a heat source configured to radiate electromagnetic radiation towards a heating layer located on either the first plate or the second plate; and deactivating the heat source after the given time period, wherein at least a portion of the fluidic sample adjacent to the heating/cooling layer cools at a rate of at least 30° C./sec after the deactivating; and accumulating nucleic acid amplification products in at least the portion of the fluidic sample sandwiched between the first plate and the second plate.

RR5. A method of amplifying nucleic acids, comprising:

depositing a fluidic sample containing nucleic acids on a first plate of a fluidic device;

placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and accumulating nucleic acid amplification products in at least the portion of the fluidic sample sandwiched between the first plate and the second plate.

RR6. A method of amplifying nucleic acids, comprising:

depositing a fluidic sample containing nucleic acids on a first plate of a fluidic device;

placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;

amplifying nucleic acids in the sample by conducting one or more PCR cycles, wherein each PCR cycle comprises a denaturing step, an annealing step, and an elongation step;

wherein one or more of the denaturing step, the annealing step, and/or the elongation step comprises:

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and accumulating nucleic acid amplification products in at least the portion of the fluidic sample sandwiched between the first plate and the second plate.

RR7. The method of any one of RR1-RR6 embodiments, wherein the first plate or the second plate further comprises a light absorbing layer disposed on the heating/cooling layer, wherein the light absorbing layer has an average light absorptance of at least 30%.

RR8. The method of RR7, wherein the light absorbing layer comprises black paint.

RR9. The method of any one of RR1-RR8 embodiments, further comprising closing the second plate over the first plate using a hinge connected between the first plate and the second plate.

RR10. The method of any one of RR1-RR9 embodiments, wherein a thickness of the heating/cooling layer is less than or equal to 3 um.

RR11. The method of any one of RR1-RR10 embodiments, wherein at least one of the first plate and the second plate has an area across its major surface of about 400 mm$^2$.

RR12. The method of any one of RR1-RR11 embodiments, wherein activating a heat source comprises activating an LED to radiate light towards the heating/cooling layer.

RR13. The method of RR12, further comprising controlling an output of the LED based on a measured or estimated temperature of the portion of the fluidic sample.

RR14. The method of any one of RR1-RR13 embodiments, further comprising expanding the electromagnetic radiation using a beam expander before the electromagnetic radiation reaches the heating layer.

RR15. The method of any one of RR1-RR14 embodiments, further comprising supporting a perimeter of either the first plate or the second plate on a support frame.

SS1. A method for detecting whether a target nucleic acid sequence is present or absent in a sample, comprising:

depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;

activating a heat source configured to radiate electromagnetic radiation towards a heating layer located on either the first plate or the second plate;

heating, using at least the heating layer, at least a portion of the fluidic sample at a rate of at least 30° C./sec; and detecting whether the fluidic sample contains amplified product of the target nucleic acid sequence.

SS2. A method for detecting whether a target nucleic acid sequence is present or absent in a sample, comprising:

depositing a fluidic sample containing nucleic acids on a first plate of a fluidic device;

placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;

activating, for a given time period, a heat source configured to radiate electromagnetic radiation towards a heating/cooling layer located on either the first plate or the second plate;

deactivating the heat source after the given time period, wherein at least a portion of the fluidic sample adjacent to the heating/cooling layer cools at a rate of at least 30° C./sec after the deactivating; and detecting whether the fluidic sample contains amplified product of the target nucleic acid sequence.

SS3. A method for detecting whether a target nucleic acid sequence is present or absent in a sample, comprising:

depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
detecting whether the fluidic sample contains amplified product of the target nucleic acid sequence.

SS4. The method of any one of SS1-SS3 embodiments, wherein the first plate or the second plate further comprises a light absorbing layer disposed on the heating/cooling layer, wherein the light absorbing layer has an average light absorptance of at least 30%.

SS5. The method of SS4, wherein the light absorbing layer comprises black paint.

SS6. The method of any one of SS1-SS5 embodiments, further comprising closing the second plate over the first plate using a hinge connected between the first plate and the second plate.

SS7. The method of any one of SS1-SS6 embodiments, wherein a thickness of the heating/cooling layer is less than or equal to 3 um.

SS8. The method of any one of SS1-SS7 embodiments, wherein at least one of the first plate and the second plate has an area across its major surface of about 400 mm$^2$.

SS9. The method of any one of SS1-SS8 embodiments, wherein activating a heat source comprises activating an LED to radiate light towards the heating/cooling layer.

SS10. The method of SS9, further comprising controlling an output of the LED based on a measured or estimated temperature of the portion of the fluidic sample.

SS11. The method of any one of SS1-SS10 embodiments, further comprising expanding the electromagnetic radiation using a beam expander before the electromagnetic radiation reaches the heating layer.

SS12. The method of any one of SS1-SS11 embodiments, further comprising supporting a perimeter of either the first plate or the second plate on a support frame.

TT1. A method for detecting the presence or absence of an analyte in a sample, comprising:
depositing a fluidic sample on a first plate of a fluidic device;
placing a second plate over the first plate such that the fluidic sample is sandwiched between the first plate and the second plate, wherein reagents for detection of the analyte are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec; and
detecting whether the fluidic sample contains the analyte.

TT2. A method for detecting the presence or absence of an analyte in a sample, comprising:
depositing a fluidic sample containing on a first plate of a fluidic device;
placing a second plate over the first plate such that the fluidic sample is sandwiched between the first plate and the second plate, wherein reagents for detection of the analyte are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
detecting whether the fluidic sample contains the analyte.

TT3. A method for detecting the presence or absence of an analyte in a sample, comprising:
depositing a fluidic sample on a first plate of a fluidic device;
placing a second plate over the first plate such that the fluidic sample is sandwiched between the first plate and the second plate, wherein reagents for detection of the analyte are present on the inner surface of the second plate;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
detecting whether the fluidic sample contains the analyte.

UU1. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of an analyte are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec; and
detecting whether the fluidic sample contains the analyte;
wherein presence or absence of the analyte indicates that the subject has the condition.

UU2. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of the analyte are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
detecting whether the fluidic sample contains the analyte;
wherein presence or absence of the analyte indicates that the subject has the condition.

UU3. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of an analyte are present on the inner surface of the second plate;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
detecting whether the fluidic sample contains the analyte;
wherein presence or absence of the analyte indicates that the subject has the condition.

UU4. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of an analyte are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec;
quantifying the amount of the analyte in the fluidic sample; and
comparing the amount to a control or reference amount of the analyte;
wherein a greater or reduced amount of the analyte in the sample compared to the control or reference amount indicates that the subject has the condition.

UU5. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of an analyte are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating;
quantifying the amount of the analyte in the fluidic sample; and
comparing the amount to a control or reference amount of the analyte;
wherein a greater or reduced amount of the analyte in the sample compared to the control or reference amount indicates that the subject has the condition.

UU6. A method for diagnosing a condition in a subject, comprising:
depositing a fluidic sample from the subject on a first plate of a fluidic device;
placing a second plate over the first plate such that the fluidic sample is sandwiched between the first plate and the second plate, wherein reagents for detection of an analyte are present on the inner surface of the second plate;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
quantifying the amount of the analyte in the fluidic sample; and
comparing the amount to a control or reference amount of the analyte;
wherein a greater or reduced amount of the analyte in the sample compared to the control or reference amount indicates that the subject has the condition.

VV1. A kit, comprising:
a device of any one of OO embodiments; and
a pre-mixed polymerase chain reaction medium.

VV2. The kit of VV1, wherein the pre-mixed polymerase chain reaction medium comprises: a DNA template, two primers, a DNA polymerase, deoxynucleoside triphosphates (dNTPs), a bivalent cation, a monovalent cation, and a buffer solution.

PCR and Molecule Amplification

In some embodiments, the device, apparatus, system, and/or method herein described can be used for rapid molecule (e.g. nucleic acid) amplification. In certain embodiments, the device, apparatus, system, and method can be used for isothermal nucleic acid amplification. In certain embodiments, the device, apparatus, and system can be used for non-isothermal nucleic acid amplification.

Non-isothermal nucleic acid amplification generally requires the cycled addition and removal of thermal energy. Many non-isothermal strategies that can be used for nucleic acid amplification involve the heating and cooling, to precise temperatures at precise times, of a reaction mixture that includes one or several nucleic acids of interest (that can or cannot be chemically modified with additional agents) and reagents necessary to complete an amplification reaction. Non-limiting examples of such nucleic acid amplification reactions include PCR; variants of PCR (e.g., reverse transcriptase PCR (RT-PCR), quantitative PCR (Q-PCR), or realtime quantitative PCR (RTQ-PCR)); ligase-chain reaction (LCR); variants of LCR (e.g., reverse transcriptase LCR (RTLCR), quantitative LCR (Q-LCR), real-time quantitative LCR (RTQ-LCR)); and digital nucleic amplification reactions (e.g., digital PCR (dPCR), digital RT-PCR (dRT-PCR), digital Q-PCR (dQ-PCR), digital RTQ-PCR (dRTQ-PCR), digital LCR (dLCR), digital RT-LCR (dRT-LCR), digital Q-LCR (dQ-LCR), digital RTQ-LCR (dRTQ-LCR). These nucleic acid amplification reactions, and others, are described in more detail below.

PCR Reactions

The device, apparatus, system, and method of the current disclosure can include the completion of a PCR amplification reaction, or any step comprising a PCR amplification (e.g., denaturation, annealing, elongation, etc). In some embodiments, a sample can comprise reagents necessary to complete a PCR reaction. Nonlimiting examples of reagents for a PCR reaction include a template nucleic acid (e.g., DNA) molecule to be amplified, a set of two primers that can hybridize with a target sequence on the template nucleic acid, a polymerase (e.g., DNA polymerase), deoxynucleotide triphosphates (dNTPs), a buffer at a pH and concentration suitable for a desired PCR reaction, a monovalent cation, and a divalent cation. Generally, the ratio of each reagent in the sample can vary and depend upon, for example, the amount of nucleic acid to be amplified and/or the desired amount of amplification products. Methods to determine the ratio of each reagent necessary for a PCR amplification reaction are found in, for example, U.S. Pat. Nos. 4,683,202 and 4,683,195, which are entirely incorporated herein by reference for all purposes.

PCR generally involves the heating and cooling of a reaction mixture that includes several key reagents and a nucleic acid (e.g., DNA) template. Non-limiting examples of reagents that, in addition to a nucleic acid template, can be used for PCR include primers, a polymerase, deoxynucleoside triphosphates (dNTPs), buffer solution, divalent cations, and monovalent cations. In general, at least two different primers per nucleic acid template can be included in the reaction mixture, wherein each primer is complementary to a portion of (e.g., the 3' ends of) the nucleic acid template. The nucleic acid template is replicated by a polymerase.

Non-limiting examples of DNA polymerases that can be useful in PCR include Taq polymerase, Tma polymerase, and VentR polymerase, Kapa2g polymerase, KOD polymerase, HaqZ05 polymerase, Haqz05 polymerase, or combinations thereof.

dNTPs are nucleotides that include triphosphate groups and are generally the building-blocks from which amplified DNA is synthesized. Non-limiting examples of dNTPs useful in PCR include deoxyadenosine triphosphate (dATP), deoxyguanosine triphosphate (dGTP), deoxycytidine triphosphate (dCTP), and deoxythymidine triphosphate (dTTP).

A buffer solution can be generally used to provide a suitable chemical environment (e.g., pH, ionic strength, etc.) for optimum activity and stability of the DNA polymerase and/or other dependent components in the reaction mixture. For example, buffers of Tris-hydrochloride can be useful in PCR methods.

Divalent cations can also be required for DNA polymerase functionality, with non-limiting examples including magnesium ions ($Mg^{2+}$) and manganese ($Mn^{2+}$) ions. Monovalent cations, such as, for example, potassium ions ($K^+$) can be included and can be useful in minimizing the production of unwanted, non-specific amplification products.

In some embodiments, the reagents for a PCR reaction can be a component of an assay designed to test a blood or other liquid sample for the presence of an analyte. For example, chloride ions can be measured by any of the following protocols, and components of these assays can be present in a storage site: Colorimetric methods: chloride ions displace thiocyanate from mercuric thiocyanate. Free thiocyanate reacts with ferric ions to form a colored complex-ferric thiocyanate, which is measured photometrically. Coulometric methods: passage of a constant direct current between silver electrodes produces silver ions, which react with chloride, forming silver chloride. After all the chloride combines with silver ions, free silver ions accumulate, causing an increase in current across the electrodes and indicating the end point to the reaction. Mercurimetric methods: chloride is titrated with a standard solution of mercuric ions and forms $HgCl_2$ soluble complex. The end point for the reaction is detected colorimetrically when excess mercury ions combine with an indicator dye, diphenylcarbazon, to form a blue color. Likewise, magnesium can be measured colorimetrically using calmagite, which turns a red-violet color upon reaction with magnesium; by a formazan dye test; emits at 600 nm upon reaction with magnesium or using methylthymol blue, which binds with magnesium to form a blue colored complex. Likewise, calcium can be detected by a colorimetric technique using O-Cresolphtalein, which turns a violet color upon reaction of O-Cresolphtalein complexone with calcium. Likewise, Bicarbonate can be tested bichromatically because bicarbonate ($HCO3^-$) and phosphoenolpyruvate (PEP) are converted to oxaloacetate and phosphate in the reaction catalyzed by phosphoenolpyruvate carboxylase (PEPC). Malate dehydrogenase (MD) catalyzes the reduction of oxaloacetate to malate with the concomitant oxidation of reduced nicotinamide adenine dinucleotide (NADH). This oxidation of NADH results in a decrease in absorbance of the reaction mixture measured bichromatically at 380/410 nm proportional to the Bicarbonate content of the sample. Blood urea nitrogen can be detected in a colorimetric test in which diacetyl, or fearon develops a yellow chromogen with urea and can be quantified by photometry, or multiusing the enzyme urease, which converts urea to ammonia and carbonic acid, which can be assayed by, e.g., i) decrease in absorbance at 340 nm when the ammonia reacts with alpha-ketoglutaric acid, ii) measuring the rate of increase in conductivity of the solution in which urea is hydrolyzed. Likewise, creatinine can be measured colorimetrically, by treated the sample with alkaline picrate solution to yield a red complex. In addition, creatine can be measured using a non-Jaffe reaction that measures ammonia generated when creatinine is hydrolyzed by creatinine iminohydrolase. Glucose can be measured in an assay in which blood is exposed to a fixed quantity of glucose oxidase for a finite period of time to estimate concentration. After the specified time, excess blood is removed and the color is allowed to develop, which is used to estimate glucose concentration. For example, glucose oxidase reaction with glucose forms nascent oxygen, which converts potassium iodide (in the filter paper) to iodine, forming a brown color. The concentration of glycosylated hemoglobin as an indirect read of the level of glucose in the blood. When hemolysates of red cells are chromatographed, three or more small peaks named hemoglobin A1a, A1b, and A1c are eluted before the main hemoglobin A peak. These "fast" hemoglobins are formed by the irreversible attachment of glucose to the hemoglobin in a two-step reaction. Hexokinase can be measured in an assay in which glucose is phosphorylated by hexokinase (HK) in the presence of adenosine triphosphate (ATP) and magnesium ions to produce glucose-6-phosphate and adenosine diphosphate (ADP). Glucose-6-phosphate dehydrogenase (G6P-DH) specifically oxidises glucose-6-phosphate to gluconate-6-phosphate with the concurrent reduction of NAD+ to NADH. The increase in absorbance at 340 nm is proportional to the glucose concentration in the sample. HDL, LDL, triglycerides can be measured using the Abell-Kendall protocol that involves color development with Liebermann-Burchard reagent (mixed reagent of acetic anhydride, glacial acetic acid, and concentrated sulfuric acid) at 620 nm after hydrolysis and extraction of cholesterol. A fluorometric analysis can be used utilized to determine triglyceride reference values. Plasma high-density lipoprotein cholesterol (HDL-C) determination is measured by the same procedures used for plasma total cholesterol, after precipitation of apoprotein B-containing lipoproteins in whole plasma (LDL and VLDL) by heparin-manganese chloride. These compounds can also be detected colorimetrically in an assay that is based on the enzyme driven reaction that quantifies both cholesterol esters and free cholesterol. Cholesterol esters are hydrolyzed via cholesterol esterase into cholesterol, which is then oxidized by cholesterol oxidase into the ketone cholest-4-en-3-one plus hydrogen peroxide. The hydrogen peroxide is then detected with a highly specific colorimetric probe. Horseradish peroxidase catalyzes the reaction between the probe and hydrogen peroxide, which bind in a 1:1 ratio. Samples can be compared to a known concentration of cholesterol standard.

A single cycle of PCR typically comprises a series of steps that include a denaturation step, an annealing step, and an elongation step. During denaturation, a double-stranded DNA template can be melted into its individual strands, such that the hydrogen bonds formed between bases in each base-pair of the double-stranded DNA are broken. After denaturation, an annealing step is completed, wherein the reaction mixture is incubated under conditions at which the primers hybridize with complementary sequences present on each of the original individual strands. After annealing, the elongation step commences, wherein the primers are extended by a DNA polymerase, using dNTPs present in the reaction mixture. At the conclusion of elongation, two new double-stranded DNA molecules result, each comprising one of the original individual strands of the DNA template. Each step of PCR is generally initiated by a change in the temperature of the reaction mixture that results from the heating or cooling of the reaction mixture. At the completion of a single round of amplification, the thermal cycle can be repeated for further rounds of amplification. The generation of replicate amplification products is theoretically exponential with each subsequent thermal cycle. For example, for a single DNA template, each step n, can result in a total of r replicates.

Successful PCR amplification requires high yield, high selectivity, and a controlled reaction rate at each step. Yield, selectivity, and reaction rate also generally depend on temperature, and optimal temperatures depend on the composition and length of the polynucleotide, enzymes, and other components in the reaction mixture. In addition, different temperatures can be optimal for different steps or different nucleic acids to be amplified. Moreover, optimal reaction conditions can vary, depending on the sequence of the template DNA, sequence of a designed primer, and composition of the reaction mixture. Thermal cyders that can be used to perform a PCR reaction can be programmed by selecting temperatures to be maintained, time durations for each portion of a cycle, number of cycles, rate of temperature change, and the like.

Primers for PCR can be designed according to known algorithms. For example, algorithms implemented in commercially available or custom software can be used to design primers. In some examples, primers can consist of at least about 12 bases. In other examples, a primer can consist of at least about 15, 18, or 20 bases in length. In still other examples, a primer can be up to 50+ bases in length. Primers can be designed such that all of the primers participating in a particular reaction have melting temperatures that are within at least about 5° C., and more typically within about 2° C. of each other. Primers can be further designed to avoid selfhybridization or hybridization with other desired primers. Those of skill in the art will recognize that the amount or concentration of primer in a reaction mixture will vary, for example, according to the binding affinity of the primers for a given template DNA and/or the quantity of available template DNA. Typical primer concentrations, for example, can range from 0.01 uM to 0.5 uM.

In an example PCR reaction, a reaction mixture, including a double-stranded DNA template and additional reagents necessary for PCR, is heated to about 80-98° C. and held at that temperature for about 10-90 seconds, in order to denature the DNA template into its individual strands. Each individual strand, during the annealing step, is then hybridized to its respective primer included in the reaction mixture by cooling the reaction mixture to a temperature of about 30-65° C. and holding it at that temperature for about 1-2 minutes. The elongation step then commences, wherein elongation of the respective primers hybridized to each individual strand occurs by the action of a DNA polymerase adding dNTPs to the primers. Elongation is initiated by heating the reaction mixture to a temperature of about 70-75° C. and holding at that temperature for 30 seconds to 5 minutes. The reaction can be repeated for any desired number of cycles depending on, for example, the initial amount of DNA template, the length of the desired amplification product, the amount of dNTPs, the amount of primer, and/or primer stringency.

While general PCR methods can be useful for nucleic acid amplification, other more specialized forms of PCR can be even more useful for a given application. Nonlimiting examples of commonly used, more-specialized forms of PCR include reverse transcription PCR (RT-PCR) (e.g., U.S. Pat. No. 7,883,871), quantitative PCR (qPCR) (e.g., U.S. Pat. No. 6,180,349), real-time quantitative PCR (RTQ-PCR) (e.g., U.S. Pat. No. 8,058,054), allele-specific PCR (e.g., U.S. Pat. No. 5,595,890), assembly PCR (e.g. U.S. Patent Publication No. 20120178129), asymmetric PCR (e.g., European Patent Publication No. EP23 73 807), dial-out PCR (e.g., Schwartz J, NATURE METHODS, September 2012; 9 (9): 913-915), helicase-dependent PCR (e.g., Vincent M, EMBO REPORTS 5, 2004, 5 (8): 795-800), hot start PCR (e.g., European Patent Publication No. EP1419275), inverse PCR (e.g., U.S. Pat. No. 6,607,899), methylation-specific PCR (e.g., European Patent Publication No. EP1690948), miniprimer PCR (U.S. Patent Publication No. 20120264132), multiplex PCR (U.S. Patent Publication No. 20120264132), nested PCR (U.S. Patent Publication No. 20120264132), overlap-extension PCR (U.S. Patent Publication No. 20120264132), thermal asymmetric interlaced PCR (U.S. Patent Publication No. 20120264132), and touchdown PCR (U.S. Patent Publication No. 20120264132). The device, apparatus, system, and/or method herein disclosed can be utilized to conduct such more-specialized forms of PCR.

RT-PCR Reactions

The device, apparatus, system, and method of the current disclosure can include the completion of an RT-PCR amplification reaction, and, thus, a sample can comprise reagents necessary to complete a RT-PCR reaction. Non-limiting examples of such reagents include the reagents necessary to complete a PCR reaction, a reverse transcriptase, and a RNA template that can be used to synthesize a complementary DNA (cDNA) complement. In cases where reverse transcriptase must be removed prior to cDNA amplification, a sample supplied to a thermal cycler cannot contain reagents necessary to complete a PCR reaction and can require a separate amplification reaction. Generally, the ratio of each reagent in the sample can vary and depend upon, for example, the amount of nucleic acid to be amplified and/or the desired amount of amplification products. Methods to determine the ratio of each reagent necessary for an RT-PCR amplification reaction are generally known by those skilled in the art.

Reverse transcription refers to a process by which ribonucleic acid (RNA) is replicated to its single-stranded complementary DNA (cDNA) by a reverse transcriptase enzyme. Non-limiting examples of reverse transcriptase enzymes include Moloney murine leukemia virus (MMLV)

transcriptase, avian myeloblastosis virus (AMY) transcriptase, variants of AMV-transcriptase, or reverse transcriptases that have endo H activity. In reverse transcription PCR (RT-PCR), a reverse transcriptase, generally with endo H3 activity, is added to a reaction mixture that includes an RNA template and necessary reagents for PCR. The reverse transcriptase can complete RNA template replication to cDNA, by hybridizing dNTPs to the RNA template at proper conditions.

At the conclusion of replication, the reverse transcriptase can remove the single-stranded, cDNA replicated from the RNA template to permit additional replication of the cDNA with PCR methods described above. The cDNA and its amplification products that are produced from PCR can be used indirectly to garner information about the RNA, such as, for example, the sequence of the RNA. The cDNA product that is synthesized from an RNA by a reverse transcriptase can be removed from the reaction mixture to be used as a DNA template in a separate, subsequent set of PCR reactions or amplification via PCR can occur in situ where reverse transcriptase is included in the reaction mixture with reagents necessary for PCR.

Q-PCR or RTQ-PCR Reactions

The device, apparatus, system, and method of the current disclosure can include the completion of a Q-PCR or RTQ-PCR amplification reaction, and, thus a sample can comprise reagents necessary to complete a Q-PCR or RTQ-PCR amplification reaction. Non-limiting examples of such reagents include the reagents necessary to complete a PCR reaction and a reporter used to detect amplification products. Generally, the ratio of each reagent in the sample can vary and depend upon, for example, the amount of nucleic acid to be amplified and/or the desired amount of amplification products. Methods to determine the ratio of each reagent necessary for a Q-PCR or RTQ-PCR amplification reaction are generally known by those skilled in the art.

Quantitative PCR (Q-PCR) is a variation of PCR in which the amount of template DNA in a sample is quantified. Generally, amplification products produced by PCR methods are linked to a reporter, such as, for example, a fluorescent dye. At the end of a reaction, the reporter can be detected and the results back-calculated (based on the association ratio of reporter to DNA and the known number of thermal cycles) to determine the amount of original DNA template present. In some examples, the fluorescent dye can be detected in real time as amplification progresses. Such a variation of Q-PCR can be appropriately called real-time quantitative PCR (RTQ-PCR), real-time PCR, or kinetic PCR. Both Q-PCR and RTQ-PCR can be used to determine whether or not a specific DNA template is present in a sample. In general, due to the possible changes to reaction efficiency as the number of PCR cycles increases, however, RTQ-PCR methods can be generally more sensitive, more reliable, and thus, more frequently employed by those skilled in the art as measurements are made on amplification products as they are synthesized rather than on the aggregate of amplification products obtained at the completion of the desired number of thermal cycles. Q-PCR and RTQ-PCR can also be combined with other PCR methods, such as, for example, RT-PCR. As an example, utility of combining Q-PCR or RTQ-PCR with other PCR methods, reporters can be included in an RT-PCR reaction mixture to detect and/or quantify low levels of messenger RNA (mRNA) via replication of its associated cDNA, which can enable the quantification of relative gene expression in a particular cell or tissue.

One or more reporters can be used to quantify DNA amplified as part of Q-PCR and RTQ-PCR methods. Reporters can be associated with DNA both by covalent and/or non-covalent linkages (e.g., ionic interactions, Van der Waals forces, hydrophobic interactions, hydrogen bonding, etc.). For example, a fluorescent dye that non-covalently intercalates with double-stranded DNA can be used as a reporter. In another example, a DNA oligonucleotide probe that fluoresces when hybridized with a complementary DNA can be used as a reporter. In some examples, reporters can bind to initial reactants and changes in reporter levels can be used to detect amplified DNA. In other examples, reporters can only be detectable or non-detectable as DNA amplification progresses. Detection of reporters can be accomplished with one of many detection systems that are suitable in the art. Optical detectors (e.g., fluorimeters, ultra-violet/visible light absorbance spectrophotometers) or spectroscopic detectors (e.g., nuclear magnetic resonance (NMR), infrared spectroscopy) can be, for example, useful modalities of reporter detection. Gel based techniques, such as, for example, gel electrophoresis can also be used for detection.

A reporter used in a Q-PCR or RTQ-PCR reaction can be an intercalator that can be detected. An intercalator generally binds to DNA by disrupting hydrogen bonds between complementary bases, and, instead fits itself between the disrupted bases. An intercalator can form its own hydrogen bonds with one or more of the disrupted bases. Non-limiting examples of intercalators include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA.

A reporter used in a Q-PCR or RTQ-PCR reaction can be a minor groove binder that can be detected. Nonlimiting examples of minor grove binders include indoles and imidazoles (e.g., Hoechst 33258, Hoechst 33342, Hoechst 34580 and DAPI).

A reporter used in a Q-PCR or RTQ-PCR reaction can be a nucleic acid stain that can be detected. Non-limiting examples of nucleic acid stains include acridine orange (also capable of intercalating), 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

A reporter used in a Q-PCR or RTQ-PCR reaction can be a fluorescent dye that can be detected. Non-limiting examples of fluorescent dyes include fluorescein, fluorescein isothiocyanate (FITC), tetramethyl rhodamine isothiocyanate (TRITC), rhodamine, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5-(or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-aminomethyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-aminonaphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores known to those of skill in the art. For detailed listing of fluorophores that can be useful in Q-PCR and RTQ-PCR methods, see also Hermanson, G. T., BIOCONJUGATE TECHNIQUES (Academic Press, San Diego, 1996) and Lakowicz, J. R., PRINCIPLES OF FLUORESCENCE SPECTROSCOPY, (Plenum Pub Corp, 2nd edition (July 1999)), which are incorporated herein by reference.

A reporter used in a Q-PCR or RTQ-PCR reaction can be a radioactive species that can be detected. Nonlimiting examples of radioactive species that can be useful in Q-PCR and RTQ-PCR methods include 14C 1231 1241 1251 131 I, Tc99m, 35S, or 3H.

A reporter used in a Q-PCR or RTQ-PCR reaction can be an enzyme that can produce a detectable signal. Such signal can be produced by action of the enzyme on its given substrate. Non-limiting examples of enzymes that can be useful in Q-PCR or RTQ-PCR methods include alkaline phosphatase, horseradish peroxidase, 12-galactosidase, alkaline phosphatase, galactosidase, acetylcholinesterase, and luciferase.

A reporter used in a Q-PCR or RTQ-PCR reaction can be an affinity ligand-label that can be detected. A particular ligand can include a label, such as for example, a fluorescent dye, and binding of the labeled ligand to its substrate can produce a useful signal. Non-limiting examples of binding pairs that can be useful in Q-PCR or RTQ-PCR methods include streptavidin/biotin, avidin/biotin or an antigen/antibody complex, such as, for example, rabbit IgG and anti-rabbit IgG;

A reporter used in a Q-PCR or RTQ-PCR reaction can be a nanoparticle that can be detected via light scattering or surface plasmon resonance (SPR). Non-limiting examples of materials useful for SPR-based detection include gold and silver materials. Other nanoparticles that can be useful in Q-PCR or RTQ-PCR reactions can be quantum dots (Qdots). Qdots are generally constructed of semiconductor nanocrystals, described, for example in U.S. Pat. No. 6,207,392. Nonlimiting examples of semiconductor materials that can be used to produce a Qdot include MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe, GaAs, A reporter used in a Q-PCR or RTQ-PCR reaction can be a labeled oligonucleotide probe. Probe based quantitative methods rely on the sequence-specific detection of amplification products of a desired DNA template, using a labeled oligonucleotide. The oligonucleotide can be a primer or a longer, different type of oligonucleotide. The oligonucleotide can be DNA or RNA. As a result, unlike non-sequence specific reporters, a labeled, sequence-specific probe hybridizes with several bases in an amplification product, and, thus, results in increased specificity and sensitivity of detection. A label linked to a probe can be any of the various reporters mentioned above and can also include a quencher (a molecule used, for example, to inhibit fluorescence). Methods for performing probe-based quantitative amplification are described in U.S. Pat. No. 5,210,015, which is entirely incorporated herein by reference. Non-limiting examples of probes that can be useful in Q-PCR or RTQ-PCR reactions include TaqMan probes, TaqMan Tamara probes, TaqMan MGB probes, or Lion probes.

A variety of arrangements of quencher and fluorescent dye can be used when both are used. In the case of a molecular beacon, for example, a quencher is linked to one end of an oligonucleotide capable of forming a hairpin structure. At the other end of the oligonucleotide is a fluorescent dye. Unbound to a complementary sequence on an amplification product, the oligonucleotide inter-hybridizes with itself and assumes a hairpin configuration. In the hairpin configuration, the fluorescent dye and quencher are brought in close proximity which effectively prevents fluorescence of the dye. Upon hybridizing with an amplification product of a desired template DNA, however, the oligonucleotide hybridizes in a linear fashion, the fluorescence and quencher separate, and fluorescence from the dye can be achieved and subsequently detected. In other example, a linear, RNA based probe that includes a fluorescent dye and a quencher held in adjacent positions can be used for detection. The close proximity of the dye to the quencher prevents its fluorescence. Upon the breakdown of the probe with the exonuclease activity of a DNA polymerase, however, the quencher and dye are separated, and the free dye can fluoresce and be detected. As different probes can be designed for different sequences, multiplexing is possible. In a multiplexed detection, assaying for several DNA templates in the same reaction mixture can be possible by using different probes, each labeled with a different reporter, for each desired DNA template.

A Q-PCR or RTQ-PCR reaction can include a single reporter or can include multiple reporters. One or more detection methodologies can be used for quantification. Moreover, as Q-PCR and RT-PCR generally adds just a quantification step, it can be generally linked to any type of PCR reaction.

LCR Reactions

The device, apparatus, system, and method of the current disclosure can include the completion of a LCR amplification reaction (or any step of a LCR reaction-as described elsewhere herein), and, thus, a sample can comprise reagents necessary to complete a LCR amplification reaction. Non-limiting examples of such reagents include a template DNA molecule to be amplified, a set of oligonucleotide probes that can each hybridize with a different, but adjacent to the other, portion of a target sequence on the template DNA, a DNA ligase, a buffer at a pH and concentration suitable for a desired LCR reaction, a monovalent cation, and a divalent cation. Generally, the ratio of each reagent in the sample can vary and depend upon, for example, the amount of nucleic acid to be amplified and/or the desired amount of amplification products. Methods to determine the ratio of each reagent necessary for a LCR amplification reaction are generally known by those skilled in the art.

LCR is generally a method similar to PCR, with some important key distinctions. A key distinction of general LCR over PCR, is that LCR amplifies an oligonucleotide probe using a DNA ligase enzyme to produce amplification products instead of through polymerization of nucleotides with a DNA polymerase. In LCR, two complementary oligonucleotide probe pairs that are specific to a DNA template can be used. After denaturation of a to-be-replicated template DNA into its individual strands, each probe pair can hybridize to adjacent positions on its respective individual strand of the template. Primers are generally not used in LCR. Any gap and/or nick created by the joining of two probes can be sealed by the enzyme DNA ligase, in order to produce a continuous strand of DNA complementary to the template DNA. Similar to PCR, though, LCR generally requires thermal cycling, with each part of the thermal cycle driving a particular step of the reaction. Repeated temperature changes can result in the denaturation of the DNA template, annealing of the oligonucleotide probes, ligation of the oligonucleotide probes, and separation of the ligated unit from the original DNA template. Moreover, a ligated unit synthesized in one thermal cycle can be replicated in the next thermal cycle. Each thermal cycle can result in a doubling of the DNA template, resulting in exponential amplification of the template DNA in a fashion analogous to PCR.

Gap LCR Reactions

The device, apparatus, system, and method of the current disclosure can include the completion of a gap LCR amplification reaction, and, thus, a sample can comprise reagents necessary to complete a gap LCR amplification reaction. Non-limiting examples of such reagents include the reagents necessary to complete a LCR reaction, wherein the set of oligonucleotide probes can each hybridize with a different, non-adjacent portion of a target sequence on the template DNA, dNTPs, and a DNA polymerase. Generally, the ratio of each reagent in the sample can vary and depend upon, for example, the amount of nucleic acid to be amplified and/or the desired amount of amplification products. Methods to determine the ratio of each reagent necessary for a gap LCR amplification reaction are generally known by those skilled in the art.

Gap LCR is a specialized type of LCR that utilizes modified oligonucleotide probes that cannot be ligated if a specific sequence is not present on a DNA template. The probes can be designed in a way that when they hybridize to an individual strand of a DNA template, they do so discontinuously and are generally separated by a gap of one to several base pairs. The gap can be filled by with dNTPs using a DNA polymerase, which can result in adjacency of the two original probes. As in general LCR, DNA ligase can join the two resulting, adjacent probes in order to produce a continuous strand of DNA complementary to the original template. The newly synthesized strand can then be used for further thermal cycles of template amplification. Gap LCR generally has higher sensitivity than LCR as it minimizes ligation where a desired sequence is not present on a template DNA. Moreover, the combined use of both DNA ligase and DNA polymerase can also result in a more accurate identification of a sequence of interest, even in cases where low levels of DNA template are available.

Additionally, since LCR is a DNA replication method, analogous methods to RT-PCR, Q-PCR, and RTQPCR are possible. For example, any of the reporters specified above can be considered for use in a quantitative (Q-LCR) or real-time quantitative LCR (RTQ-LCR) reaction. Moreover, LCR methods can be combined with PCR or other nucleic amplification techniques.

Q-LCR and LTQ-LCR Reactions

The device, apparatus, system, and method of the current disclosure can include the completion of a Q-LCR or LTQ-PCR reaction, and, thus, a sample can comprise reagents necessary to complete a Q-LCR or RTQ-LCR reaction. Non-limiting examples of such reagents include the reagents necessary to complete a LCR reaction and a reporter used to detect amplification products. Generally, the ratio of each reagent in the sample can vary and depend upon, for example, the amount of nucleic acid to be amplified and/or the desired amount of amplification products. Methods to determine the ratio of each reagent necessary for a Q-LCR and RTQ-LCR amplification reaction are generally known by those skilled in the art.

Since LCR is a DNA replication method, analogous methods to RT-PCR, Q-PCR, and RTQPCR are possible. For example, any of the reporters specified above can be considered for use in a quantitative (Q-LCR) or real-time quantitative LCR (RTQ-LCR) reaction. Moreover, LCR methods can be combined with PCR or other nucleic amplification techniques.

Digital Nucleic Acid Amplification Reactions

The device, apparatus, system, and method of the current disclosure can include the completion of a digital nucleic acid amplification reaction, and, thus, a sample can comprise reagents necessary to complete a digital nucleic acid amplification reaction. In general, any of the example nucleic acid amplification reactions discussed herein can be conducted in digital form, upon proper separation of a sample and/or reagents necessary for nucleic acid amplification into smaller partitions. In some embodiments, such partitions can be droplets or can be larger aliquots of the original sample. Generally, the ratio of each reagent in partitions can vary and depend upon, for example, the amount of nucleic acid to be amplified in each droplet and/or the desired amount of amplification products. Methods to determine the ratio of each reagent necessary for a particular digital nucleic acid amplification reaction are generally known by those skilled in the art.

Digital nucleic acid amplification is a technique that allows amplification of a subset of nucleic acid templates fractioned into partitions obtained from a larger sample. In some cases, a partition can comprise a single nucleic acid template, such that amplification products generated from amplification of the template are exclusively derived from the template. Amplification products can be detected using a reporter, including any of those example reporters described herein. The amplification of a single nucleic acid template can be useful in discriminating genetic variations that include, for example, wild-type alleles, mutant alleles, maternal alleles, or paternal alleles of a gene. More comprehensive discussions of this technology, with respect to PCR, can be found elsewhere-see Pohl et al., Expert Rev. Mo!. Diagn., 4 (1): 41-7 (2004), and Vogelstein and Kinzler, Proc. Natl. Acad. Sci. USA 96:9236-9241 (1999), which are both incorporated herein in entirety by reference. So long as the proper thermal cycling of a partition comprising a complete reaction mixture (e.g., a reaction mixture comprising both the nucleic acid template to be amplified and the required reagents for the desired nucleic acid amplification reaction) is achieved, any of the example nucleic acid amplification reactions discussed herein can be conducted digitally. Indeed, digital nucleic acid amplification methods still require thermal cycling and accurate temperature control, as do their non-digital analogues.

In a digital nucleic acid amplification reaction, a large sample is fractioned into a number of smaller partitions, whereby the partitions can contain on average a single copy of a nucleic acid template or multiple copies of a template. Individual nucleic acid molecules can be partitioned with the aid of a number of devices and strategies with non-limiting examples that include micro-well plates, capillaries, dispersions that comprise emulsions, arrays of miniaturized chambers, nucleic acid binding surfaces, flow cells, droplet partitioning, or combinations thereof. Each partition can be thermal cycled to generate amplification products of its component template nucleic acid, using a nucleic acid amplification reaction of choice with non-limiting examples of such reactions that include a digital PCR (dPCR) nucleic acid amplification reaction, a digital LCR (dLCR) nucleic acid amplification reaction, a digital RT-PCR (dRT-PCR) nucleic acid amplification reaction, a digital (dRT-LCR) nucleic acid amplification reaction, a digital Q-PCR (dQ-PCR) nucleic acid amplification reaction, a digital Q-LCR (dQ-LCR) nucleic acid amplification reaction, a digital RTQ-PCR (dRTQ-PCR) nucleic acid amplification reaction, a digital LTQ-LCR (dLTQ-LCR) nucleic acid amplification reaction, or combinations thereof.

In cases where reporters are used, each partition can be considered "positive" or "negative" for a particular nucleic acid template of interest. The number of positives can be counted and, thus, one can deduce the starting amount of the template in the pre-partitioned sample based upon the count. In some examples, counting can be achieved by assuming that the partitioning of the nucleic acid template population in the original sample follows a Poisson distribution. Based on such an analysis, each partition is labeled as either containing a nucleic acid template of interest (e.g., labeled "positive") or not containing the nucleic acid template of interest (e.g., labeled "negative"). After nucleic acid amplification, templates can be quantified by counting the number of partitions that comprise "positive" reactions. Moreover, digital nucleic acid amplification is not dependent on the number of amplification cycles to determine the initial amount of nucleic acid template present in the original sample. This lack of dependency eliminates relying on assumptions with respect to uncertain exponential amplification, and, therefore, provides a method of direct, absolute quantification.

Most commonly, multiple serial dilutions of a starting sample are used to arrive at the proper concentration of nucleic acid templates in the partitions. The volume of each partition can depend on a host of factors that include, for example, the volume capacity of a thermal cycler used to generate amplification products. Furthermore, quantitative analyses conducted by digital nucleic acid amplification can generally require reliable amplification of single copies of nucleic acid template with low false positive rates. Such capability can require careful optimization in microliter-scale vessels. Moreover, the analytical precision of a nucleic acid amplification reaction can be dependent on the number of reactions.

In some embodiments, digital nucleic acid amplification reactions can be droplet digital nucleic acid amplification reactions. Non-limiting examples of such nucleic acid amplification reactions include droplet digital PCR (ddPCR), droplet digital RT-PCR (ddRT-PCR), droplet digital Q-PCR (ddQ-PCR), droplet digital RTQ-PCR (ddRTQ-PCR), droplet digital LCR (ddLCR), droplet digital RT-LCR (ddRT-LCR), droplet digital Q-LCR (ddQ-LCR), or droplet digital RTQ-LCR (ddRTQ-PCR), or combinations thereof.

In some cases, a digital nucleic acid amplification reaction can be a droplet digital nucleic acid amplification reaction. For example, such a nucleic acid amplification reaction can be a droplet digital PCR (ddPCR) nucleic acid amplification reaction. A ddPCR nucleic acid amplification reaction can be completed by first partitioning a larger sample comprising nucleic acids into a plurality of droplets. Each droplet comprises a random partition of nucleic acids in the original sample. The droplets can then be combined with different droplets that comprise the reagents necessary for a PCR reaction (e.g., a set of two primers that can hybridize with a target sequence on the template DNA, a DNA polymerase, deoxynucleotide triphosphates (dNTPs), a buffer at a pH and concentration suitable for a desired PCR reaction, a monovalent cation, and a divalent cation). The new combined droplet is then properly thermal cycled in a thermal cycler and PCR commences. Alternatively, a sample can already comprise reagents necessary for PCR prior to partitioning into droplets—droplet combination with other droplets would, thus, not be required.

Analogous procedures can be followed to complete a droplet digital RT-PCR (ddRT-PCR) nucleic acid amplification reaction, a droplet digital LCR (ddLCR) nucleic acid amplification reaction, a droplet digital RT-PCR (ddRT-LCR) nucleic acid amplification reaction, a droplet digital Q-PCR (ddQ-PCR) nucleic acid amplification reaction, a droplet digital RTQ-PCR (ddRTQ-PCR) nucleic acid amplification reaction, a droplet digital Q-LCR (ddQ-LCR) nucleic acid amplification reaction, or a droplet digital RTQ-LCR (ddRTQ-LCR) reaction.

In the case of a quantitative droplet digital nucleic acid amplification reaction (e.g., ddQ-PCR, ddRTQ-PCR, ddQ-LCR, or ddRTQ-LCR), droplets can also comprise a reporter used to detect amplification products. Such reporters can be contacted with nucleic acids by combining droplets or can already be included in a partition comprising nucleic acid templates to be amplified.

Droplet nucleic acid amplification can be completed using a variety of sample holders. In some examples, droplets can be applied to one or more wells of a sample holder and then thermal cycled. In other examples, a device comprising fluidic channels, such as, for example, a flow cell or microfluidic device can be used. Fluidic channels can be used to transport droplets through a sample holder (or other component of a thermal cycler) such that droplet thermal contact with different temperature regions of the sample holder (or other component of a thermal cycler) results in proper thermal cycling of the droplets.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

A RHC card (a sample holder) includes a Q-card.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, labeling an analyte includes using, for example, a labeling agent, such as an analyte specific binding member that includes a detectable label. Detectable labels include, but are not limited to, fluorescent labels, colorimetric labels, chemiluminescent labels, enzyme-linked reagents, multicolor reagents, avidin-streptavidin associated detection reagents, and the like. In some embodiments, the detectable label is a fluorescent label. Fluorescent labels are labeling moieties that are detectable by a fluorescence detector. For example, binding of a fluorescent label to an analyte of interest allows the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

In some embodiments, suitable fluorescent molecules (fluorophores) for labeling include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl) maleimide; anthranilamide; 4,4-difluoro-5-(2-thienyl)-4-bora-3a,4a diaza-5-indacene-3-propionic acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallolsulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino- -fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, 5 pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas 10 Red); N,N, N',N'-tetramethyl-6-carboxyrhodamine (TAMRA); tetramethyl rhodamine; tetramethyl rhodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In some embodiments, dyes that can be used to stain blood cells comprise Wright's stain (Eosin, methylene blue), Giemsa stain (Eosin, methylene blue, and Azure B), Can-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride).

In some embodiments, the labeling agent is configured to bind specifically to the analyte of interest. In some embodiments, a labeling agent can be present in the device before the sample is applied to the device. In some embodiments, the device can be washed after the labeling agent is bound to the analyte-capture agent complex to remove from the device any excess labeling agent that is not bound to an analyte-capture agent complex.

In some embodiments, the analyte is labeled after the analyte is bound to the device, e.g., using a labeled binding agent that can bind to the analyte simultaneously as the capture agent to which the analyte is bound in the CROF device, i.e., in a sandwich-type assay.

In some embodiments, a nucleic acid analyte can be captured on the device, and a labeled nucleic acid that can hybridize to the analyte simultaneously as the capture agent to which the nucleic acid analyte is bound in the device.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

Additional Exemplary Embodiments

A device, comprising:
a first plate comprising a polymer material and having a thickness less than or equal to 100 µm;
a second plate comprising a polymer material and having a thickness less than or equal to 100 um; and
a heating/cooling layer disposed on either the first plate or the second plate, the heating/cooling layer having a thermal conductivity between $6 \times 10^{-5}$ W/K multiplied by the thickness of the heating/cooling layer and $1.5 \times 10^{-4}$ W/K multiplied by the thickness of the heating/cooling layer,
wherein the first plate and the second plate face each other in a parallel arrangement, and are separated from each other by a distance, and wherein the first plate and the second plate are configured to receive a fluid sample sandwiched between the first plate and the second plate.

The device of any prior embodiment, further comprising a light absorbing layer disposed on the heating/cooling layer, wherein the light absorbing layer has an average light absorptance of at least 30%.

The device of any prior embodiment, wherein the light absorbing layer comprises black paint.

The device of any prior embodiment, wherein the first plate is movable relative to the second plate.

The device of any prior embodiment, wherein a thickness of the heating/cooling layer is less than or equal to 3 µm.

The device of any prior embodiment, wherein at least one of the first plate and the second plate has an area across its major surface of about 400 mm$^2$.

The device of any prior embodiment, further comprising a plurality of spherical spacers disposed between the first plate and the second plate.

The device of any prior embodiment, further comprising a plurality of spacers having a height of about 10 um, wherein the plurality of spacers are disposed between the first plate and the second plate.

The device of any prior embodiment, wherein the distance between the first plate and the second plate is less than or equal to 100 um. The device of any prior embodiment, further comprising a hinge configured to connect the first plate with the second plate, and coupled to an edge of the first plate or the second plate.

A device, comprising:
a first plate;
a second plate having a thickness less than or equal to 100 um, wherein the second plate is separated from the first plate in a parallel arrangement by a distance less than or equal to the thickness of the second plate; and a heating/cooling layer disposed on either the first plate or the second plate,
wherein the heating/cooling layer is configured to receive electromagnetic radiation such that at least a portion of a liquid sample sandwiched between the first plate and the second plate is heated at a rate of at least 30° C./sec.

The device of any prior embodiment, further comprising a light absorbing layer disposed on the heating/cooling layer, wherein the light absorbing layer has an average light absorptance of at least 30%.

The device of any prior embodiment, wherein the light absorbing layer comprises black paint.

The device of any prior embodiment, wherein the first plate is movable relative to the second plate.

The device of any prior embodiment, wherein a thickness of the heating/cooling layer is less than or equal to 3 μm.

The device of any prior embodiment, wherein at least one of the first plate and the second plate has an area across its major surface of about 400 mm².

The device of any prior embodiment, further comprising a plurality of spherical spacers disposed between the first plate and the second plate.

The device of any prior embodiment, further comprising a plurality of spacers having a height of about 10 um, wherein the plurality of spacers are disposed between the first plate and the second plate.

The device of any prior embodiment, wherein the at least a portion of the liquid sample comprises a volume of the sample along a path of the electromagnetic radiation.

The device of any prior embodiment, further comprising a hinge configured to connect the first plate with the second plate, and coupled to an edge of the first plate or the second plate.

A device, comprising:
a first plate;
a second plate having a thickness less than or equal to 100 um, wherein the second plate is separated from the first plate in a parallel arrangement by a distance less than or equal to the thickness of the second plate; and
a heating/cooling layer disposed on either the first plate or the second plate,
wherein at least a portion of a liquid sample sandwiched between the first plate and the second plate is cooled at a rate of at least 30° C./sec when the heating/cooling layer is not receiving electromagnetic radiation generated by an optical source.

The device of any prior embodiment, further comprising a light absorbing layer disposed on the heating/cooling layer, wherein the light absorbing layer has an average light absorptance of at least 30%.

The device of any prior embodiment, wherein the light absorbing layer comprises black paint.

The device of any prior embodiment, wherein the first plate is movable relative to the second plate.

The device of any prior embodiment, wherein a thickness of the heating/cooling layer is less than or equal to 3 μm.

The device of any prior embodiment, wherein at least one of the first plate and the second plate has an area across its major surface of about 400 mm².

The device of any prior embodiment, further comprising a plurality of spherical spacers disposed between the first plate and the second plate.

The device of any prior embodiment, further comprising a plurality of spacers having a height of about 10 um, wherein the plurality of spacers are disposed between the first plate and the second plate.

The device of any prior embodiment, wherein the at least a portion of the liquid sample comprises a volume of the sample that is adjacent to the heating/cooling layer.

The device of any prior embodiment, further comprising a hinge configured to connect the first plate with the second plate, and coupled to an edge of the first plate or the second plate.

A device, comprising:
a first plate;
a second plate having a thickness less than or equal to 100 um, wherein an inner surface of the second plate is separated from an inner surface of the first plate in a parallel arrangement by a distance less than or equal to the thickness of the second plate;
a heating/cooling layer disposed on the inner surface or on an outer surface of the second plate; and
a layer of reagents dried on the inner surface of the first plate.

The device of any prior embodiment, further comprising a light absorbing layer disposed on the heating/cooling layer, wherein the light absorbing layer has an average light absorptance of at least 30%.

The device of any prior embodiment, wherein the light absorbing layer comprises black paint.

The device of any prior embodiment, wherein the first plate is movable relative to the second plate.

The device of any prior embodiment, wherein a thickness of the heating/cooling layer is less than or equal to 3 μm.

The device of any prior embodiment, wherein at least one of the first plate and the second plate has an area across its major surface of about 400 mm².

The device of any prior embodiment, further comprising a plurality of spherical spacers disposed between the first plate and the second plate.

The device of any prior embodiment, further comprising a plurality of spacers having a height of about 10 um, wherein the plurality of spacers are disposed between the first plate and the second plate.

The device of any prior embodiment, wherein the layer of dried reagents comprises reagents used for nucleic acid amplification.

The device of any prior embodiment, further comprising a hinge configured to connect the first plate with the second plate, and coupled to an edge of the first plate or the second plate.

A system, comprising:
a device, comprising:
a first plate comprising a polymer material and having a thickness less than or equal to 100 μm,
a second plate comprising a polymer material and having a thickness less than or equal to 100 μm, wherein the second plate is separated from the first plate in a parallel arrangement by a distance less than or equal to the thickness of the second plate,
a heating/cooling layer disposed on either the first plate or the second plate, the heating/cooling layer having a thickness and a thermal conductivity between $6 \times 10^{-5}$ W/K multiplied by the thickness of the heating/cooling layer and $1.5 \times 10^{-4}$ W/K multiplied by the thickness of the heating/cooling layer, and
a support frame configured to support at least one of the first plate and the second plate;
a housing having a first opening configured to receive the device and at least one other opening;
an optical source configured to direct electromagnetic radiation towards the heating/cooling layer,
wherein the heating/cooling layer is configured to absorb at least a portion of the electromagnetic radiation such that at least a portion of a liquid sample sandwiched between the first plate and the second plate is heated at a rate of at least 30° C./sec, and
wherein at least the portion of the liquid sample sandwiched between the first plate and the second plate is cooled at a rate of at least 30° C./sec when the heating/cooling layer is not receiving the electromagnetic radiation generated by the optical source, and
wherein the system consumes less than 500 mW of power.

The system of any prior embodiment, wherein the device further comprises a light absorbing layer disposed on the heating/cooling layer, wherein the light absorbing layer has an average light absorptance of at least 30%.

The system of any prior embodiment, wherein the light absorbing layer comprises black paint.

The system of any prior embodiment, wherein the first plate is movable relative to the second plate.

The system of any prior embodiment, wherein a thickness of the heating/cooling layer is less than or equal to 3 µm.

The system of any prior embodiment, wherein at least one of the first plate and the second plate has an area across its major surface of about 400 mm².

The system of any prior embodiment, wherein the optical source comprises a light emitting diode (LED.)

The system of any prior embodiment, further comprising an optical pipe configured to guide the electromagnetic radiation from the optical source to the heating/cooling layer.

The system of any prior embodiment, wherein the at least one other opening of the housing is configured to be aligned over at least the portion of the liquid sample sandwiched between the first plate and the second plate when the device is placed within the housing via the first opening.

The system of any prior embodiment, wherein the support frame is configured to support at least the first plate or the second plate along a perimeter of the first plate or second plate.

A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate; and
an optical source configured to direct electromagnetic radiation towards the heating/cooling layer,
wherein at least a portion of a liquid sample sandwiched between the first plate and the second plate is cooled at a rate of at least 30° C./sec when the heating/cooling layer is not receiving the electromagnetic radiation generated by the optical source.

The system of any prior embodiment, wherein the device further comprises a light absorbing layer disposed on the heating/cooling layer, wherein the light absorbing layer has an average light absorptance of at least 30%.

The system of any prior embodiment, wherein the light absorbing layer comprises black paint.

The system of any prior embodiment, wherein the first plate is movable relative to the second plate.

The system of any prior embodiment, wherein a thickness of the heating/cooling layer is less than or equal to 3 µm.

The system of any prior embodiment, wherein at least one of the first plate and the second plate has an area across its major surface of about 400 mm².

The system of any prior embodiment, wherein the optical source comprises a light emitting diode (LED.)

The system of any prior embodiment, wherein the LED comprises a blue LED.

The system of any prior embodiment, further comprising an optical pipe configured to guide the electromagnetic radiation from the optical source to the heating/cooling layer.

The system of any prior embodiment, wherein the support frame is configured to support at least the first plate or the second plate along a perimeter of the first plate or second plate.

A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate; and
an optical source configured to direct electromagnetic radiation towards the heating/cooling layer, wherein the system consumes less than 500 mW of power.

The system of any prior embodiment, wherein the device further comprises a light absorbing layer disposed on the heating/cooling layer, wherein the light absorbing layer has an average light absorptance of at least 30%.

The system of any prior embodiment, wherein the light absorbing layer comprises black paint.

The system of any prior embodiment, wherein the first plate is movable relative to the second plate.

The system of any prior embodiment, wherein a thickness of the heating/cooling layer is less than or equal to 3 µm.

The system of any prior embodiment, wherein at least one of the first plate and the second plate has an area across its major surface of about 400 mm².

The system of any prior embodiment, wherein the optical source comprises a light emitting diode (LED.)

The system of any prior embodiment, wherein the LED comprises a blue LED.

The system of any prior embodiment, further comprising an optical pipe configured to guide the electromagnetic radiation from the optical source to the heating/cooling layer.

The system of any prior embodiment, further comprising a support frame configured to support at least the first plate or the second plate along a perimeter of the first plate or second plate.

A system, comprising:
a device, comprising:
a first plate,
a second plate having a thickness less than or equal to 100 um, wherein the second plate is separated from the first plate in a parallel arrangement by a distance less than or equal to the thickness of the second plate,
a heating/cooling layer disposed on either the first plate or the second plate, and
a support frame configured to support at least one of the first plate and the second plate;
a housing having a first opening configured to receive the device and at least one other opening; and
an optical source configured to direct electromagnetic radiation through the at least one other opening of the housing and towards the heating/cooling layer,
wherein a liquid sample sandwiched between the first plate and the second plate is cooled at a rate of at least 30° C./sec when the heating/cooling layer is not receiving the electromagnetic radiation generated by the optical source.

The system of any prior embodiment, wherein the device further comprises a light absorbing layer disposed on the heating/cooling layer, wherein the light absorbing layer has an average light absorptance of at least 30%.

The system of any prior embodiment, wherein the light absorbing layer comprises black paint.

The system of any prior embodiment, wherein the first plate is movable relative to the second plate.

The system of any prior embodiment, wherein a thickness of the heating/cooling layer is less than or equal to 3 μm.

The system of any prior embodiment, wherein at least one of the first plate and the second plate has an area across its major surface of about 400 mm².

The system of any prior embodiment, wherein the optical source comprises a light emitting diode (LED.)

The system of any prior embodiment, wherein the LED comprises a blue LED.

The system of any prior embodiment, further comprising an optical pipe configured to guide the electromagnetic radiation from the optical source to the heating/cooling layer.

The system of any prior embodiment, wherein the support frame is configured to support at least the first plate or the second plate along a perimeter of the first plate or second plate.

A method of using a device, comprising:
  placing a second plate over a first plate such that a fluidic sample is sandwiched between the first plate and the second plate at a thickness determined by one or more spacers located on at least one of the first plate and the second plate;
  activating a heat source configured to radiate electromagnetic radiation towards a heating layer located on either the first plate or the second plate; and
  heating, using at least the heating layer, at least a portion of the fluidic sample at a rate of at least 30° C./sec.

The method of any prior embodiment, wherein the first plate or the second plate further comprises a light absorbing layer disposed on the heating layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer . . .

The method of any prior embodiment, further comprising supporting a perimeter of either the first plate or the second plate on a support frame.

A method of using a device, comprising:
  placing a second plate over the first plate such that a fluidic sample is sandwiched between the first plate and the second plate at a thickness determined by one or more spacers located on at least one of the first plate and the second plate;
  activating, for a given time period, a heat source configured to radiate electromagnetic radiation towards a heating/cooling layer located on either the first plate or the second plate;
  deactivating the heat source after the given time period, wherein at least a portion of the fluidic sample cools at a rate of at least 30° C./sec after the deactivating.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of using a device, comprising:
  placing a second plate over the first plate such that a fluidic sample is sandwiched between the first plate and the second plate at a thickness determined by one or more spacers located on at least one of the first plate and the second plate;
  activating a heat source configured to radiate electromagnetic radiation towards a heating layer located on either the first plate or the second plate, wherein the heat source consumes less than 500 mW of power; and
  heating, using at least the heating layer, at least a portion of the fluidic sample.

The method of any prior embodiment, wherein the first plate or the second plate further comprises a light absorbing layer disposed on the heating layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer . . .

The method of any prior embodiment, further comprising supporting a perimeter of either the first plate or the second plate on a support frame.

A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating a heat source configured to radiate electromagnetic radiation towards a heating layer located on either the first plate or the second plate;
heating, using at least the heating layer, at least a portion of the fluidic sample at a rate of at least 30° C./sec; and
accumulating nucleic acid amplification products in at least the portion of the fluidic sample sandwiched between the first plate and the second plate.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
amplifying nucleic acids in the sample by conducting one or more PCR cycles, wherein each PCR cycle comprises a denaturing step, an annealing step, and an elongation step;
wherein one or more of the denaturing steps, the annealing step, and/or the elongation step comprises:
activating a heat source configured to radiate electromagnetic radiation towards a heating layer located on either the first plate or the second plate; and
heating, using at least the heating layer, at least a portion of the fluidic sample at a rate of at least 30° C./sec.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of amplifying nucleic acids, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
accumulating nucleic acid amplification products in at least the portion of the fluidic sample sandwiched between the first plate and the second plate.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of amplifying nucleic acids, comprising:
  depositing a fluidic sample containing nucleic acids on a first plate of a fluidic device;
  placing a second plate over the first plate such that the fluidic sample is sandwiched between the first plate and the second plate, wherein reagents for nucleic acid amplification are present on the inner surface of the second plate;
  amplifying nucleic acids in the sample by conducting one or more PCR cycles, wherein each PCR cycle comprises a denaturing step, an annealing step, and an elongation step;
  wherein one or more of the denaturing steps, the annealing step, and/or the elongation step comprises:
  activating a heat source configured to radiate electromagnetic radiation towards a heating layer located on either the first plate or the second plate; and
  deactivating the heat source after the given time period, wherein at least a portion of the fluidic sample adjacent to the heating/cooling layer cools at a rate of at least 30° C./sec after the deactivating; and
  accumulating nucleic acid amplification products in at least the portion of the fluidic sample sandwiched between the first plate and the second plate.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of amplifying nucleic acids, comprising:
  depositing a fluidic sample containing nucleic acids on a first plate of a fluidic device;
  placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;
  activating a heat source configured to radiate electromagnetic radiation towards a heating layer located on either the first plate or the second plate, wherein the heat source consumes less than 500 mW of power;
  heating, using at least the heating layer, at least a portion of the fluidic sample; and
  accumulating nucleic acid amplification products in at least the portion of the fluidic sample sandwiched between the first plate and the second plate.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method of amplifying nucleic acids, comprising:
  depositing a fluidic sample containing nucleic acids on a first plate of a fluidic device;
  placing a second plate over the first plate such that the fluidic sample is sandwiched between the first plate and the second plate at a thickness determined by one or more spacers located on at least one of the first plate and the second plate, wherein reagents for nucleic acid amplification are present on the inner surface of the second plate;

amplifying nucleic acids in the sample by conducting one or more PCR cycles, wherein each PCR cycle comprises a denaturing step, an annealing step, and an elongation step;
wherein one or more of the denaturing step, the annealing step, and/or the elongation step comprises;
activating a heat source configured to radiate electromagnetic radiation towards a heating layer located on either the first plate or the second plate, wherein the heat source consumes less than 500 mW of power;
heating, using at least the heating layer, at least a portion of the fluidic sample; and
accumulating nucleic acid amplification products in at least the portion of the fluidic sample sandwiched between the first plate and the second plate.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method for detecting whether a target nucleic acid sequence is present or absent in a sample, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;
activating a heat source configured to radiate electromagnetic radiation towards a heating layer located on either the first plate or the second plate;
heating, using at least the heating layer, at least a portion of the fluidic sample at a rate of at least 30° C./sec; and
detecting whether the fluidic sample contains amplified product of the target nucleic acid sequence.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method for detecting whether a target nucleic acid sequence is present or absent in a sample, comprising:
depositing a fluidic sample containing nucleic acids on a first plate of a fluidic device;
placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;
activating, for a given time period, a heat source configured to radiate electromagnetic radiation towards a heating/cooling layer located on either the first plate or the second plate;
deactivating the heat source after the given time period, wherein at least a portion of the fluidic sample adjacent to the heating/cooling layer cools at a rate of at least 30° C./sec after the deactivating; and
detecting whether the fluidic sample contains amplified product of the target nucleic acid sequence.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 µm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame A method for detecting whether a target nucleic acid sequence is present or absent in a sample, comprising:
- depositing a fluidic sample containing nucleic acids on a first plate of a fluidic device;
- placing a second plate over the first plate such that the fluidic sample is sandwiched between the first plate and the second plate, wherein reagents for nucleic acid amplification are present on the inner surface of the second plate, and wherein the reagents comprise primers that can hybridize with the target nucleic acid;
- activating a heat source configured to radiate electromagnetic radiation towards a heating layer located on either the first plate or the second plate, wherein the heat source consumes less than 500 mW of power;
- heating, using at least the heating layer, at least a portion of the fluidic sample; and
- detecting whether the fluidic sample contains amplified product of the target nucleic acid sequence.

The method of any prior embodiment, wherein the first plate or the second plate further comprises a light absorbing layer disposed on the heating/cooling layer, wherein the light absorbing layer has an average light absorptance of at least 30%.

The method of any prior embodiment, wherein the light absorbing layer comprises black paint.

The method of any prior embodiment, further comprising closing the second plate over the first plate using a hinge connected between the first plate and the second plate.

The method of any prior embodiment, wherein a thickness of the heating/cooling layer is less than or equal to 3 μm.

The method of any prior embodiment, wherein at least one of the first plate and the second plate has an area across its major surface of about 400 mm².

The method of any prior embodiment, wherein activating a heat source comprises activating an LED to radiate light towards the heating/cooling layer.

The method of any prior embodiment, further comprising controlling an output of the LED based on a measured or estimated temperature of the portion of the fluidic sample.

The method of any prior embodiment, further comprising expanding the electromagnetic radiation using a beam expander before the electromagnetic radiation reaches the heating layer.

The method of any prior embodiment, further comprising supporting a perimeter of either the first plate or the second plate on a support frame.

A method for detecting the presence or absence of an analyte in a sample, comprising:
- depositing a fluidic sample on a first plate of a fluidic device;
- placing a second plate over the first plate such that the fluidic sample is sandwiched between the first plate and the second plate, wherein reagents for detection of the analyte are present on the inner surface of the second plate;
- activating a heat source configured to radiate electromagnetic radiation towards a heating layer located on either the first plate or the second plate;
- heating, using at least the heating layer, at least a portion of the fluidic sample at a rate of at least 30° C./sec; and
- detecting whether the fluidic sample contains the analyte.

A method for detecting the presence or absence of an analyte in a sample, comprising:
- depositing a fluidic sample containing on a first plate of a fluidic device;
- placing a second plate over the first plate such that the fluidic sample is sandwiched between the first plate and the second plate, wherein reagents for detection of the analyte are present on the inner surface of the second plate;
- activating, for a given time period, a heat source configured to radiate electromagnetic radiation towards a heating/cooling layer located on either the first plate or the second plate;
- deactivating the heat source after the given time period, wherein at least a portion of the fluidic sample adjacent to the heating/cooling layer cools at a rate of at least 30° C./sec after the deactivating; and
- detecting whether the fluidic sample contains the analyte.

A method for detecting the presence or absence of an analyte in a sample, comprising:
- depositing a fluidic sample on a first plate of a fluidic device;
- placing a second plate over the first plate such that the fluidic sample is sandwiched between the first plate and the second plate, wherein reagents for detection of the analyte are present on the inner surface of the second plate;
- activating a heat source configured to radiate electromagnetic radiation towards a heating layer located on either the first plate or the second plate, wherein the heat source consumes less than 500 mW of power;
- heating, using at least the heating layer, at least a portion of the fluidic sample; and
- detecting whether the fluidic sample contains the analyte.

A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of an analyte are present on the inner surface of the second plate;
- activating a heat source configured to radiate electromagnetic radiation towards a heating layer located on either the first plate or the second plate;
- heating, using at least the heating layer, at least a portion of the fluidic sample at a rate of at least 30° C./sec; and
- detecting whether the fluidic sample contains the analyte;
- wherein presence or absence of the analyte indicates that the subject has the condition.

A method for diagnosing a condition in a subject, comprising:
- depositing a fluidic sample from the subject on a first plate of a fluidic device;
- placing a second plate over the first plate such that the fluidic sample is sandwiched between the first plate and the second plate, wherein reagents for detection of the analyte are present on the inner surface of the second plate;
- activating, for a given time period, a heat source configured to radiate electromagnetic radiation towards a heating/cooling layer located on either the first plate or the second plate;

deactivating the heat source after the given time period, wherein at least a portion of the fluidic sample adjacent to the heating/cooling layer cools at a rate of at least 30° C./sec after the deactivating; and detecting whether the fluidic sample contains the analyte;

wherein presence or absence of the analyte indicates that the subject has the condition.

A method for diagnosing a condition in a subject, comprising:

depositing a fluidic sample from the subject on a first plate of a fluidic device;

placing a second plate over the first plate such that the fluidic sample is sandwiched between the first plate and the second plate, wherein reagents for detection of an analyte are present on the inner surface of the second plate;

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and detecting whether the fluidic sample contains the analyte;

wherein presence or absence of the analyte indicates that the subject has the condition.

A method for diagnosing a condition in a subject, comprising:

depositing a fluidic sample from the subject on a first plate of a fluidic device;

placing a second plate over the first plate such that the fluidic sample is sandwiched between the first plate and the second plate, wherein reagents for detection of an analyte are present on the inner surface of the second plate;

activating a heat source configured to radiate electromagnetic radiation towards a heating layer located on either the first plate or the second plate;

heating, using at least the heating layer, at least a portion of the fluidic sample at a rate of at least 30° C./sec;

quantifying the amount of the analyte in the fluidic sample; and comparing the amount to a control or reference amount of the analyte;

wherein a greater or reduced amount of the analyte in the sample compared to the control or reference amount indicates that the subject has the condition.

A method for diagnosing a condition in a subject, comprising:

depositing a fluidic sample from the subject on a first plate of a fluidic device;

placing a second plate over the first plate such that the fluidic sample is sandwiched between the first plate and the second plate, wherein reagents for detection of an analyte are present on the inner surface of the second plate;

activating, for a given time period, a heat source configured to radiate electromagnetic radiation towards a heating/cooling layer located on either the first plate or the second plate;

deactivating the heat source after the given time period, wherein at least a portion of the fluidic sample adjacent to the heating/cooling layer cools at a rate of at least 30° C./sec after the deactivating;

quantifying the amount of the analyte in the fluidic sample; and comparing the amount to a control or reference amount of the analyte;

wherein a greater or reduced amount of the analyte in the sample compared to the control or reference amount indicates that the subject has the condition.

A method for diagnosing a condition in a subject, comprising:

depositing a fluidic sample from the subject on a first plate of a fluidic device;

placing a second plate over the first plate such that the fluidic sample is sandwiched between the first plate and the second plate, wherein reagents for detection of an analyte are present on the inner surface of the second plate;

activating a heat source configured to radiate electromagnetic radiation towards a heating layer located on either the first plate or the second plate, wherein the heat source consumes less than 500 mW of power;

heating, using at least the heating layer, at least a portion of the fluidic sample; and quantifying the amount of the analyte in the fluidic sample; and comparing the amount to a control or reference amount of the analyte;

wherein a greater or reduced amount of the analyte in the sample compared to the control or reference amount indicates that the subject has the condition.

A kit, comprising:

a device of any prior embodiment; and a pre-mixed polymerase chain reaction medium.

The kit of any prior embodiment, wherein the pre-mixed polymerase chain reaction medium comprises: a DNA template, two primers, a DNA polymerase, deoxynucleoside triphosphates (dNTPs), a bivalent cation, a monovalent cation, and a buffer solution.

The invention claimed is:

1. A method for rapidly changing a temperature of a fluidic sample, comprising:
   (a) obtaining a device, wherein the device comprises a first plate, a second plate, a plurality of spacers, and at least one clamp, wherein:
      (i) the first plate and the second plate are movable relative to each other into different configurations, including an open configuration and a closed configuration, wherein one or both of the first and second plates are flexible plates, wherein each of the first and second plates comprises, on its respective surface, a sample contact area for contacting a fluidic sample, and wherein at the closed configuration the first and second plates sandwich the fluidic sample into a layer of substantially uniform thickness of 200 µm or less;
      (ii) the plurality of spacers has a predetermined substantially uniform height that is equal to or less than 200 microns, wherein at least one of the plurality of spacers is inside the sample contact area;
      (iii) the at least one clamp comprises a top ring and a bottom ring, wherein the at least one clamp is configurable between:
         (a) a non-active mode, wherein the top ring and the bottom ring of the at least one clamp is configured to not push the first plate and second plate together; and
         (b) an active mode, wherein the top ring and the bottom ring of the at least one clamp are configured to exert a force to (i) squeeze the first plate and the second plate and deform an area of the flexible plates that is under a compression of the at least one clamp, and (ii) deform a portion of the plurality of spacers, wherein the portion of the plurality of spacers is under the compression of the at least one clamp, and the at least one clamp is configured to crush the portion of the plurality of spacers under the compression, thereby reducing the spacing between the two plates in the area of the flexible plates that is under the compression of the at least one clamp, and wherein the reduction of a spacing between the two plates is configured to reduce or prevent a fluidic flow between a sample portion encircled by the rings and a sample portion outside the rings, wherein in the open configuration, the two plates are partially or completely separated apart, the spacing between the two plates is not regulated by the plurality of spacers, and the at least one clamp is in non-active mode, and the sample is deposited on one or both of the two plates; and wherein in the closed configuration, the at least one clamp is in an active mode, at least a part of the sample deposited on the one or both of the first and second plates is compressed by the first and second plates to form the layer of substantially uniform thickness of 200 μm or less, wherein the two plates and plurality of spacers are configured to regulate the thickness of the layer;

(b) depositing a sample onto the sample contact area of at least one of the first and second plates of the device in the open configuration;

(c) closing the two plates into the closed configuration and placing the clamp in the active mode; and (d) rapidly changing the temperature of the sample portion encircled by the rings.

2. The method of claim 1, wherein the sample is a reaction mixture.

3. The method of claim 1, wherein the sample comprises deoxynucleoside triphosphates (dNTPs), a thermostable polymerase, a template, and primers.

4. The method of claim 2, wherein the method further comprises thermocycling the sample portion encircled by the rings through a plurality of cycles that comprise increasing the temperature of the reaction mixture to a temperature of at least 90° C. and then decreasing the temperature of the reaction mixture to one or more temperatures in the range of 40° C. to 80° C.

5. The method of claim 2, wherein the rapid changing of the temperature is for performing quantitative real-time polymerase chain reaction (qPCR), the method further comprises:

(a) thermocycling the reaction mixture, wherein the reaction mixture comprises a pair of PCR primers, a polymerase, a fluorescence-quencher probe oligonucleotide, deoxynucleoside triphosphates (dNTPs), and a template; and (b) in each cycle, measuring a fluorescent signal generated by cleavage of a label from the fluorescence-quencher probe oligonucleotide.

6. The method of claim 5, further comprising an imager for imaging the sample and/or signal.

7. The method of claim 5, wherein the fluorescence-quencher probe oligonucleotide comprises a fluorophore and a quencher, and the polymerase cleaves the fluorophore or quencher from the fluorescence-quencher probe oligonucleotide, thereby generating a fluorescent signal.

8. The method of claim 1, further comprising thermocycling the sample portion encircled by the rings.

9. The method of claim 2, wherein the method further comprises thermocycling the sample portion encircled by the rings through a plurality of cycles that comprise increasing the temperature of the reaction mixture to a temperature of at least 90° C. and then decreasing the temperature of the reaction mixture to one or more temperatures in the range of 40° C. to 65° C., then increasing the temperature of the reaction mix mixture to one or more temperatures in the range of 60° C. to 65° C.

10. The method of claim 1, wherein the sample portion encircled by the rings is thermocycled through 10 to 50 cycles.

11. The method of claim 5, wherein the thermocycling is done by activating a heat source configured to radiate electromagnetic radiation towards a heating layer located on either the first plate or the second plate of the device.

12. The method of claim 5, wherein the thermocycling comprises a plurality of cycles that comprise increasing the temperature of the reaction mixture to a temperature of at least 90° C. and then decreasing the temperature of the reaction mixture to one or more temperatures in the range of 40° C. to 80° C.

13. The method of claim 5, wherein the thermocycling comprises a plurality of cycles that comprise increasing the temperature of the reaction mixture to a temperature of at least 90° C. and then decreasing the temperature of the reaction mixture to one or more temperatures in the range of 40° C. to 65° C., then increasing the temperature of the reaction mixture to one or more temperatures in the range of 60° C. to 65° C.

14. The method of claim 5, wherein the sample is thermocycled through 10 to 50 cycles.

15. The method of claim 5, wherein the cleavage of the sample is measured by detecting fluorescence of the reaction mixture during at least some of the cycles.

16. The method of claim 5, further comprising plotting the fluorescent signal over time.

17. The method of claim 16, further comprising estimating the amount of the template in the sample using the plotted signal.

18. The method of claim 2, further comprising:

wherein the reaction mixture comprises a plurality of droplets, each droplet comprising a pair of polymerase chain rection (PCR) primers, a polymerase, a fluorescence-quencher probe, and deoxynucleoside triphosphates (dNTPs), and wherein only some of the droplets comprise a template;

emulsifying the reaction mixture to produce an emulsion;

applying the emulsion to the sample contact area of at least one of the first and second plates; and placing the second plate over the first plate such that the reaction mixture of the fluidic sample is sandwiched between the first plate and the second plate.

19. The method of claim 18, further comprising determining the number of droplets that fluoresce.

20. The method of claim 18, further comprising estimating the number of template molecules in the sample based on the number of droplets that fluoresce.

21. The method of claim 18, wherein the polymerase is a DNA polymerase.

22. The method of claim 1, wherein the sample contains an analyte, wherein the analyte is nucleic acid.

23. The method of claim 1, wherein the sample contains an analyte, wherein the analyte is RNA.

24. The method of claim 18, further comprising:
(a) thermocycling the emulsion; and
(b) determining which droplets fluoresce, wherein the fluorescence is generated by cleavage of a label from the fluorescence-quencher probe oligonucleotide by the polymerase.

* * * * *